US012655411B2

(12) United States Patent
Gamboa et al.

(10) Patent No.: US 12,655,411 B2
(45) Date of Patent: *Jun. 16, 2026

(54) MODIFIED STRAINS FOR THE PRODUCTION OF RECOMBINANT SILK

(71) Applicant: Bolt Threads, Inc., Emeryville, CA (US)

(72) Inventors: Matthew Scott Gamboa, Richmond, CA (US); Joshua Tyler Kittleson, Pleasant Hill, CA (US)

(73) Assignee: BOLT THREADS, INC., Emeryville, CA (US)

( * ) Notice: Subject to any disclaimer, the term of this patent is extended or adjusted under 35 U.S.C. 154(b) by 1038 days.

This patent is subject to a terminal disclaimer.

(21) Appl. No.: 17/527,429

(22) Filed: Nov. 16, 2021

(65) Prior Publication Data

US 2022/0251533 A1     Aug. 11, 2022

Related U.S. Application Data

(63) Continuation of application No. 16/842,498, filed on Apr. 7, 2020, now Pat. No. 11,214,785, which is a continuation of application No. 15/724,196, filed on Oct. 3, 2017, now Pat. No. 10,647,975.

(51) Int. Cl.
| | |
|---|---|
| *C12N 1/15* | (2006.01) |
| *C07K 14/435* | (2006.01) |
| *C12N 1/16* | (2026.01) |
| *C12N 9/60* | (2006.01) |
| *C12N 15/04* | (2006.01) |
| *C12N 15/57* | (2006.01) |
| *C12P 21/02* | (2006.01) |

(52) U.S. Cl.
CPC .......... *C12N 9/60* (2013.01); *C07K 14/43518* (2013.01); *C12Y 304/23041* (2013.01)

(58) Field of Classification Search
None
See application file for complete search history.

(56) References Cited

U.S. PATENT DOCUMENTS

| | | | |
|---|---|---|---|
| 7,262,287 B2 | 8/2007 | Kang et al. | |
| 8,440,456 B2 | 5/2013 | Callewaert et al. | |
| 10,647,975 B2* | 5/2020 | Gamboa .................. | C12N 9/60 |
| 11,214,785 B2* | 1/2022 | Gamboa .................. | C12N 9/60 |
| 11,634,729 B2* | 4/2023 | Stevens ................ | C12N 15/905 435/69.1 |
| 12,286,640 B2* | 4/2025 | Stevens ................ | C12N 15/905 |
| 2011/0021378 A1 | 1/2011 | Callewaert et al. | |
| 2012/0142895 A1 | 6/2012 | Jin et al. | |
| 2016/0222174 A1 | 8/2016 | Widmaier et al. | |

FOREIGN PATENT DOCUMENTS

| | | |
|---|---|---|
| CN | 102676563 A | 9/2012 |
| WO | 2010/135678 A1 | 11/2010 |
| WO | 2015/004241 A2 | 1/2015 |
| WO | 2015/042164 A2 | 3/2015 |

OTHER PUBLICATIONS

NCBI Reference Sequence XP_002490038.1, Jun. 2016, 2 pages (Year: 2016).*
Cho, E.Y. et al., "Multiple-Yapsin-Deficient Mutant Strains for High-Level Production of Intact Recombinant Proteins in *Saccharomyces cerevisiae*," Journal of Biotechnology, 2010, pp. 1-7, vol. 149.
Cregg, J., et al., "Recombinant Protein Expression in Pichia pastoris", Molecular Biotechnology, vol. 16, pp. 23-52 (2000).
De Schutter et al., "Genome sequence of the recombinant protein production host Pichia pastoris.," Nat. Biotechnol. 27 (6), 561-566 (2009).
Extended European Search Report for Application No. 17928005.2, 11 pages.
GenEmbl database Acc# FN392321 rom De Schutter et al, Genome sequence of the recombinant protein production host Pichia pastoris. Nat. Biotechnol. 27 (6), 561-566 (2009). Alignment with SID 2.
Guan, B. et al., "Absence of Yps7p, a Putative Glycosylphophatidylinositol-Linked Aspartyl Protease in Pichia pastoris, Results in Aberrant Cell Wall Composition and Increased Osmotic Stress Resistance," FEMS Yeast Res, 2012, pp. 969-979, vol. 12.
Issued_Patents_AA database Callewaert et al, U.S. Pat. No. 8,440,456 SID 63. Alignment with SID67.
Issued_Patents_AA database Callewaert et al, U.S. Pat. No. 8,440,456 SID 666. Alignment with SID68.
Issued_Patents_NA database Callewaert et al, U.S. Pat. No. 8,440,456 SID62. Alignment with SID 1.
Issued_Patents_NA database Callewaert et al, U.S. Pat. No. 8,440,456 SID664. Alignment with SID 2.
N_Geneseq database Acc# BBW42258 from Widmaier et al, 2015 WO2015042164. Alignment with SID 462.
NCBI gene database "PAS_chr3_1157". Downloaded Feb. 12, 2019.
NCBI gene database "PAS_chr4_0584". Downloaded Feb. 12, 2019.
PCT International Search Report and Written Opinion, PCT Application No. PCT/US2017/054997, dated Feb. 20, 2018, 15 pages.
Sazonova, E.A. et al., "Effect of Disruption of Pichia pastoris YPS1 Gene on Viability and Production of Recombinant Proteins," Russian Journal of Genetics, 2013, pp. 602-608, vol. 49, No. 6.

(Continued)

*Primary Examiner* — David Steadman
(74) *Attorney, Agent, or Firm* — MARSHALL, GERSTEIN & BORUN LLP

(57) ABSTRACT

Disclosed herein are modified strains for reducing degradation of recombinantly expressed products secreted from a host organism and methods of using the modified strains. In some embodiments, to attenuate a protease activity in *Pichia pastoris*, the genes encoding enzymes the degrade proteases are inactivated or mutated to reduce or eliminate activity. In preferred strains, the protease activity of proteases encoded by PAS_chr4_0584 (YPS1-1) and PAS_chr3_1157 (YPS1-2) (e.g., polypeptides comprising SEQ ID NO: 66 and 67) is attenuated.

27 Claims, 6 Drawing Sheets

Specification includes a Sequence Listing.

(56) References Cited

OTHER PUBLICATIONS

Silva, C.I.F et al., "Secreted Production of Collagen-Inspired Gel-Forming Polymers with High Thermal Stability in Pichia pastoris," Biotechnology and Bioengineering, Nov. 2011, pp. 2517-2525, vol. 108, No. 11.

UniProt database Acc# C4R3Q7 from De Schutter et al, Genome sequence of the recombinant protein production host Pichia pastoris. Nat. Biotechnol. 27 (6), 561-566 (2009). Alignment with SID 68.

Wu et al., "Disruption of YPS1 and PEP4 Genes Reduces Proteolytic Degradation of Secreted HAS/PTH in Pichia pastoris GS115," J. Ind. Microbiol. Biotechnol., Mar. 26, 2013, pp. 589-599, vol. 40.

Yao et al., "Degradation of HAS-AX15(R13K) When Expressed in Pichia pastoris Can Be Reduced Via the Disruption of YPS1 Gene in this Yeast," Journal of Biotechnology, Jan. 15, 2009, pp. 131-136, vol. 139, Iss. 2.

* cited by examiner

Homology Arm Insertion into Nourseothricin Marker Plasmid

Representative Single KO Western

PAS_chr4_0686
PAS_chr1-1_0127
PAS_chr3_0513
PAS_chr4_0874
PAS_chr1-4_0251
PAS_chr3_0299
PAS_chr3_0866
PAS_chr2-1_0172
PAS_chr1-1_0379
PAS_chr3_0633
PAS_chr3_0561
PAS_chr3_0896
PAS_chr4_0834
PAS_chr1-1_0274
PAS_chr1-4_0611
RMS464 (no knockout)

SEQUENCE LISTING

<160> NUMBER OF SEQ ID NOS: 522

<210> SEQ ID NO 1
<211> LENGTH: 1800
<212> TYPE: DNA
<213> ORGANISM: Pichia pastoris

<400> SEQUENCE: 1

```
atgttgaagg atcagttctt gttatgggtt gctttgatag cgagcgtacc ggtttccggc        60
gtgatggcag ctcctagcga gtccgggcat aacacggttg aaaaacgaga tgccaaaaac       120
gttgttggcg ttcaacagtt ggacttcagc gttctgaggg gtgattcctt cgaaagtgcc       180
tcttcagaga acgtgcctcg gcttgtgagg agagatgaca cgctagaagc tgagctaatc       240
aaccagcaat cattctactt gtcacgactg aaagttggat cacatcaagc ggatattgga       300
atcctagtgg acacaggatc ctctgattta tgggtaatgg actcggtaaa cccatactgc       360
agtagccgtt cccgcgtgaa gagagatata cacgatgaga agatcgccga atgggatccc       420
atcaatctca agaaaaatga aacttctcag aataaaaatt tttgggattg gctcgttgga       480
actagcacta gttctccttc caccgccacg gcaactggta gtggtagtgg tagtggtagt       540
ggtagtggta gtggtagtgc tgccacagcc gtatcggtaa gttctgcaca ggcaacattg       600
gattgctcta cgtatggaac gtttgatcac gctgattcct cgacgttcca tgacaataat       660
acagactttt tcatctcata cgctgatacc acttttgctt caggaatctg gggttatgac       720
gacgtcatta tcgacggcat agaggtgaaa gaactttcct tcgccgttgc agacatgacc       780
aattcctcta ttggtgtgtt aggtattgga ctgaaaggcc tagaatccac atatgctagt       840
gcatcttcgg tcagtgaaat gtatcagtat gacaatttgc cagccaagat ggtcaccgat       900
gggttgatca acaaaaatgc atactccttg tacttgaact ccaaggacgc ctcaagtggt       960
tccatcctct ttggaggtgt ggatcatgaa aaatattcgg gacaattgtt gacagttcca      1020
gtcatcaaca cactcgcttc cagtggttac agagaggcaa ttcgtttaca aattacttta      1080
aatggaatag atgtgaaaaa gggttctgac cagggaactc ttttacaagg gagatttgct      1140
gcattattgg actctggagc tacgctaacg tatgctcctt cttctgtttt aaattcaatt      1200
ggccggaacc tgggcggctc ctatgattcg tcaagacaag cttataccat tcgttgtgtt      1260
tctgcatcag ataccacttc tctggtattc aatttttgggg gtgctacagt ggaagtttcc      1320
ctgtacgatc tacagattgc aacatattac accgggggaa gtgccacgca atgtcttatt      1380
```

```
ggaatattca gctctggaag tgatgagttt gtgctcggtg ataccttctt gaggtcagcc    1440
tacgtggttt acgatcttga tgggcttgaa gtgtcgcttg cccaagccaa cttcaacgaa    1500
accgattctg atgttgaggc tattacctcc agtgtacctt ccgctactcg tgcatccgga    1560
tacagttcta catggtctgg ttctgccagc ggtacagttt acacttcggt tcagatggaa    1620
tccggtgctg cttccagctc caactcttct ggatcgaata tgggttcctc ttcctcatcg    1680
tcctcttcat cgtcctcgac ttccagtgga gacgaagaag gagggagctc cgccaacagg    1740
gtccccttca gctacctttc tctctgtttg gtagttattc tcggcgtgtg tatagtatag    1800
```

<210> SEQ ID NO 2
<211> LENGTH: 1781
<212> TYPE: DNA
<213> ORGANISM: Pichia pastoris

<400> SEQUENCE: 2

```
atgatcatca accacttggt attgacagcc ctcagcattg cactagcaag tgcgcaactc      60
caatcgcctt tcaaggctaa caagttgcca ttcaaaaagt ttatcattcc aacgacccaa     120
aggaccgttt aattaagaga gatgactacg agtccctcga cttgagacac atcggagtct     180
tgtacactgc agagatccaa attggatctg acgaaactga aattgaggtc attgtcgaca     240
ctggttctgc cgacttgtgg gtcatcgatt ccgacgctgc cgtctgtgag ttatcctacg     300
atgagattga ggccaatagc ttttcctcgg cttctgccaa attcatggac aagatagctc     360
ctccatcaca agagctcctg gatgggctga gtgagtttgg atttgctctc gatggtgaaa     420
tttctcaata cctagccgat aaatctggac gtgtttcgaa aagagaggaa aatcaacaag     480
atttcaacat taaccgtgac gagcctgtgt gtgaacagtt tggttccttc gattctagtt     540
cttccgacac tttccaaagc aacaattcag cttttggtat tgcttacctt gatggaacca     600
ctgctaacgg aacttgggtc agggacacag tccgcatcgg cgactttgcc atcagccaac     660
agagttttgc cttagtcaac atcacagata actacatggg aatcttgggt ctcggtcctg     720
ctacccaaca aaccaccaat agtaacccaa ttgcagcaaa cagatttact tatgatggtg     780
ttgtggattc attgcggtcc caaggattta tcaattcagc atcgttttct gtttacttgt     840
ctccagatga agataacgag cacgacgaat tcagcgacgg agaaatttta tttggtgcta     900
ttgatagggc caagatagac gggccattta gactttttccc atatgtcaat ccttacaaac     960
cagtttaccc cgatcaatat acttcctacg ttacagtgtc cacaattgcg gtgtcttcgt    1020
cagatgaaac tctcattatt gaaagacgtc ctcgtttggc attaatcgat acaggtgcca    1080
ccttctccta tttgccaacc tacccattga ttcgtttagc gttttccatc catggaggct    1140
ttgaatatgt ttctcaattg ggactatttg tcattcgtac aagttctctg tctgttgcta    1200
gaaataaggt gattgagttc aagtttggtg aagacgttgt gatccaatcc ccagtttctg    1260
atcatctatt ggacgtctca ggcctttttta ctgatggcca acaatactcc gcattaactg    1320
tacgtgaaag tcttgacgga ctttccattc taggtgatac attcatcaaa tcggcctact    1380
tattctttga caatgaaaac agccagctgg gtattggtca gatcaacgtc actgatgacg    1440
aggatattga ggtggtcggt gatttcacta ttgaacgaga cccagcctac tcctctactt    1500
ggtctagcga tttacctcat gaaacaccca ctagggcttt gagtactgct tcagggggag    1560
gccttggtac cggaataaac acggccacaa gtcgtgcaag ttctcgttcc acatctggct    1620
ctacttcacg aacttcttct acatctggct ctgcttctgg tacttcttca ggtgcatctt    1680
```

```
ctgctactca aaatgacgaa acatccactg atcttggagc tccagctgca tctttaagtg      1740
caacgccatg tcttttttgcc atcttgctgc tcatgttgta g                         1781

<210> SEQ ID NO 3
<211> LENGTH: 1584
<212> TYPE: DNA
<213> ORGANISM: Pichia pastoris

<400> SEQUENCE: 3 atgaaccccta gcagcttaat tctacttgca ctcagcattg gctactccat tgctgagtca       60
aatttctctt tcaaacccag caagttacct ctcaaaaaac atcgtgattc ttcttccccg      120
catgaacgat ttcttaaacg agatggaccc tatcatccgc tagaagccga cgcttacttt      180
tactacacta cgtctatatt ggttggatca gaagaagaaa aagttgaagt aacagttgat      240
ttaggaacct ctgatttatg ggtcgtcgat tacaacaccg gtttatgtga tagatccttt      300
gacgaaacct atcttaaacg tagtctggat acttctgagg aagattattc tgctggagat      360
cttggctcct cagtcggtgt acgcagcgct agaaaaattct tgcgcaaaag ggacaccaat      420
caaactgagg ttaatgaagc taactatggt gcttgtccaa attcgattac cttcaatcca      480
gaaaactcgt cttcttttcca gagtaatgat actgctttca atatcagcta ctttgatgga      540
accagtgcta gtggtttttg ggctactgat acaatttact ttggtgacct tgaggtcagc      600
gagcaatttt ttgggctggc aaacttaaca ataagttatg gaggagtctt aggtcttggc      660
ccttccaacc tacaaacaac caatgctaac cccaacggtg aggaattcat ttacagcgga      720
gtcttagatt ccatgcgtga tcaagggctt atcaactcgg cttctttctc aatctatctc      780
aatccagaga atttcagaga tgaagataac tattctaatg aaggagcgat tttgttcgga      840
gcaattgata atgcgaagat tgacgggtca ttgaagctgt taccatacgt gacttcaggt      900
ggacactctc agattgatgc taatttcact tacatcacct tgaataatat tgccgtggct      960
gacaatgata cagccctgat cgttgagacc aacccccaat tggcaatgtt gaatccaaag     1020
tttatataca cctattttcc aaacgaagta ttgacccggc tggtaaactc tattgacaat     1080
ctagaatatg atcctgttga ggggttatat aggataagga gaacaaacat tagggatatt     1140
aacaaaaaaa tcatagagtt tcaatttggt gacgagattg tgatacattc tcccttatca     1200
aattatctgt ctgatacatg ggttccaagc acaaactaca cctatttgga gattcaggat     1260
agcagagagg atttctttat ccttggtaat gcattttttca agtctgcgta tttgtttttt     1320
gacaatgata acagtgaagt cggtattggc caactaaagg ttaccgataa ggaggacatc     1380
gttccagttg gtgaattttc tttggatcaa gattcagggt actcgtcaac ctggtcaacg     1440
ttctcctatg aaactggttc agctcccttg ggtacgtcaa ctttcgaaac gagtacaaaa     1500
actagttcag atggagctgc cccgtcggtg tctcacatta acactagttc ctacttattt     1560
gcgtttgtac tacttttcct ttag                                             1584

<210> SEQ ID NO 4
<211> LENGTH: 1422
<212> TYPE: DNA
<213> ORGANISM: Pichia pastoris

<400> SEQUENCE: 4
atgttgccca tccgcttatc caaacttctg cttttgctct ccttaaagtt gaaattgggt       60
acagctgaag aaaaatacca aaagttggat ttaaaaagaa ttgacaaaga ctattatgcc      120
gtcgatgtca aagtcggctc cgatgagcag gagatcaaag aggtactaat agatacgggt      180
```

-continued

```
tcatctgatt tctggatctt ggacaaatcg ttctgtaatt ctccaacatc agaggaagaa        240
gagaacagta acgggcgtag caacaaggaa agctgtggag tctatggctc gttcgactcc        300
aacaagtcag agacatttca ggcaactggc caagtatttg acgctgctta cggtgacacc        360
acagccgagt cgacaggatc ttcaggagtt cgaggaattc atcagctacg ggtaggagat        420
attcatatag aagaactcta ttttggacta gtgacaaaca ctacaagttt accacccgtt        480
ttaggaattg cccagctttc cgaagagttc agcaacaact cttatcctaa cttttccatac       540 cagatgaaag aggaaggtct gattgatgtt gttgcatact ctctctcctt gggccaaagt        600
aaaggtgaac tactgttcgg ggctatggac cactcaaaat ataatggaac actattgaaa        660
gcccctatat tgcaggcggg cacaccagga atgcaagttc ttttaactgg agtggccctt        720
acaaatggtt catcaagcgt cttcaatgag acagacaata aaggttttat ctactttgac        780
agtgggacta ctgcttccac tctgccatca gagcactttg atgatctttt caaccatcac        840
ggatgggcgt acgatggtga tacattgaca tattcgattc aatgcgatag tgagggagaa        900
aaatctttac ttgacttcac tttagaatat accattgctg gtaatattgt catcaaagta        960
ccatttgaag acattattat gaagaatgaa aatgatggag aatgcctctc aaccgtaatg       1020
gtgtcgaacc agacttcttt ttcatattcc gatgacacac ccttttttcgt tgctggagac       1080 gaagttctgt tgaacgctta tgttgtttac aacctagaaa cacaagagct ggccattgct       1140
ccagcagtgg ataatccaga agatactgaa gaagatattg agattatctc cgcagacttt       1200
gatatttcag aagccagaga ttatagcgtt ggattagagt tcagaaatac cacaattcca       1260
gctacaactg attacttgcc ttcctcgatg tcgtcaggtt cagtcagcga agagactggt       1320
tccaagtctg agagctctac ttctgaggac tttgctgcag ccacgttgaa accatttaca       1380 ttttgggggtt tcgtcctttt tttctttcac tttttgattt ga                        1422
```

<210> SEQ ID NO 5
<211> LENGTH: 1839
<212> TYPE: DNA
<213> ORGANISM: Pichia pastoris

<400> SEQUENCE: 5

```
atgttagttg ctgttgccct agtgttgtta ctgtctacag gctatgctgg aatcgtcgcc         60
attgataccg aatatgagtt caccattggt tttcttagta cgatagaaat agggtttccc        120
ccacaaagca taacggctca atgggataca ggatcgtctg acctcttggt caattccgtg        180
acaaattcac agtgtgctca ggacggatgt agctttggtg cgttcgcctt caacaaatcc        240
accacttatt ccaatataac aaaccctaac aaccttcatg ttcagttctc ctttgcaagc        300
ggcagcgtgt tgatgacaa acttgtgagt gacactattt ttgtagattc caggtaatc         360 ccacggttca actttgcact ggtatcgaag ggagacctgt atggtgataa tatttttggt        420
attggaccga gagggaacca gggaacattc gattccaatg gaactccagc ttttctatgat       480 agctttcctt atcacttgaa ggccctcggt ttaatcaaac gactggctta ctcattttac        540
actgggccca cccagggaaa ggtagtattt ggaggggtgg atcatggaaa gtacgatggg        600
tgcctggaga aactcgagat tgtccatgac agtgcttttt acacactgct tgaggcaatt        660
gatgctgatg atacttccgt cttggatgag caaattcatg ttttgtttga tactggtacc        720
gccttgacac ttttttcccag ctttattgct gaacaactgg ctgatttttt gaaagctaca        780
tattcggacg aatacaatac gtttgtagtt ccctgcgacc aagattttga ttttgaatac        840
```

-continued

```
cttcattttg gttttcgaaa cattaagttg tcggtgcgct ttaaggatct gttttttagtc     900 attgacgata gtgtttgtgc tgtggggttt gatcaagggg cagatgcaaa caagataacc     960
tttgggtctt cacttttaag aaactactac acgctttatg atctagattc caaagaaatt    1020
ttgattgctg acgtcaagcc tgatggtcca gacgatattg aaatattatc gggtccagtt    1080
caacgaattt gtgatgaaaa gggtgtcagt agcacttcat tatggagtag tctgagtata    1140
gagtccacga tagaaccaga cacttttacc actaagcctt ctatttccca gacacggtat    1200
tcgactagct ccattggacc tcaaaacatt tctaactctt taggtgaata tccttcagtt    1260
tccgtcactc tttctgaaca ccataacact acttccatag cctcaaattc ctcattagaa    1320
gggaaaccag caactccaac tgttacagac cagtcgtacc agaataataa gactacctct    1380
accgtaattg ctgtgaattt gattacccat tcaaccactc attcaaccac tcattcaccc    1440
acctattcaa ccactcattc tagtaatgga tcacgctcaa ctttagagta cacttcaacc    1500
aaggaatcct cggtgaaaat gccctgtgcg ttgatcatct ccgacacaat tccgtacaat    1560
gcttccggtg ggaatagtag ttatggatcg ttaatttcaa catctacggt taacaatgtt    1620
gaagagaata attcaaacac tgttagacca agaaaaagac agaccttcgt ttcgggaacc    1680
acttccacga tactactcta ttcctcaact acgacccaag catatcagat gttgtcctca    1740
acttcaatcc cccgaccatc cataaaagcc agttcaaatg ctggtagccg caaaacttca    1800
aagacattat taacatttat catattgtat attttttag                           1839
```

```
<210> SEQ ID NO 6
<211> LENGTH: 1749
<212> TYPE: DNA
<213> ORGANISM: Pichia pastoris

<400> SEQUENCE: 6
atgtaccagg cgttgttggt tttgtctctg atatgctttt cgtcggctaa ttttgttaag      60
ctgcgaagca acgctggtat gttttatgat actatggctg gagttccacg ttcagatgaa     120
gagttctggt tgcgtttgga tattaaccaa ggtctctctt ggactctgga tagtagctac     180
tactcctgta atggctcaaa tgtttcgtct tccctgtgtt tcaattctgc tcaaaacgtt     240
tacgatgctt ccaatagtcc aactgcagat ttcgttgatg tctacgcaaa cacaactgta     300
aacaatacag atgaggcatc ggccgagaga gtaaatctta caaacaactt atttgctgat     360
ggcgtttata tggaagacaa ttttttacgtc acattgaata atggagcaag aatgactgct     420
acagatctga aattttttgaa tgcccacaat agtagcgccg ctgtggggtc tttggcgttg     480
gggagttaca cctcacagga cgtgccaact ttcttacaaa gactccaaag cggtggtctt     540
attgaatcca actcgttttc attggcatta aacgaaatcg attcttcata tggagagctc     600
tatttgggga caataaactc taccaagtat gtcgagcctc tggtagaatt cgattttatt     660
ccggtgtcag atcccaatgg agttttttgga ttcgattggg aagatacatt ccctacagtt     720
ccgatcagcg gattaagcat gtcttcgaat gacaaacaga gaactgtctt tttccccaat     780
gagtggaaca cacggtctt aacgggaaca tacccacttc caatgatgtt agattcaaga     840 aacatctta tccatcttcc attctcttca atcatacata tagcagtgca gcttaatgca     900
ctgtatcttg atacacttca taaatgggcc gtgaactgtt ctgttggtca actggacgca     960 actttaaaact ttcacatggg taaccttacc gttcatgctc ctatcaagga gttgattttat    1020 ccagcatacc aaggagacaa aaggctgagc tttgctaatg gagaagatgt ttgtattctt    1080
gccatggctc ctgatgttta cattggttat ccactgctag gaacccccctt tttaaggaat    1140
```

-continued

```
gcagtggttg ccgttaatca tgattcaaaa aaggtcgccg ttgccaatct taatagagat    1200
agcattcctc ccgcttcgaa cgtttctgtt tcggaatcaa tgggagttta tgttcctcca    1260
cctgtttcaa cttcaagaac atcggagaga ccgtccacac tagatgagac tagtacagcc    1320
aattttgaca aaagggaaga gtctgcaata tcatcaagtt cagtcactaa cagctcgtct    1380
agaaattctt caaccataac ttcttcagga actcaaaccg agcaaacatc aggcatagct    1440
accatcgaaa cagatagcat accaggagct ctagggaata atttaactga ttattcaacg    1500
ctgactctaa caatatacac caattccgaa gtggacgaac tcaatcctaa catagcaaca    1560
gcattcattt ccaatggttc tatttattca gagccttacc cctttccgg aactgcagtt     1620 gctgaatcat tcagtgcatc accttcacag gctgaaggat cgaactcatc gtcctcagga    1680
tcttctttag ttttgtgttt ctttacatca ttggccagtc tgttgactgt gagctgtcta    1740
ctactgtaa                                                            1749
```

```
<210> SEQ ID NO 7
<211> LENGTH: 1895
<212> TYPE: DNA
<213> ORGANISM: Pichia pastoris

<400> SEQUENCE: 7
atgtttgtga tccagctggc attcctatgt ctaggcgtca gcctaaccac tgcacaacct     60
agttcacctt tcaaggcaaa taagtttcct tttaaaaagg ttcactactc atcaaaccct    120
agcgatcgcc ttattaagcg agacaactat aagaagcttg acttgagaca tcttggcgtc    180
ttgtatactg cggaaattga aattggttca ggcaaaactg aaatcgaagt tattgttgac    240
accggatctg cagatttgtg ggtaattgac tcaaatgcag ccgtatgcga ttgtcctatc    300
ttgagataca aggtacaagt gtttccaccc ttagtcaaac tgccaacgta acacccctat    360
caggtaaact tttgaatgga cttcaagaaa ttggcattgt aactgatggc aaaatttcca    420
aaaagtttca ggaaaaccat ctttttgaaga gaaacgaggc cttgaatttt gatgtcgatc    480
tgaataagcc catttgtgat caatttggat ccttcaatcc acagtcatca agaactttc     540 aaagcaacga cacagcattt agtatcagat atctggacaa ctcttttgcc aatggatcgt    600
gggtgaggga tacggtttat gttggtgatt ttgaaattga ccagcaaagt tttgcattgg    660
ttgatatcac aaataactac atgggaattc tgggccttgg tccttctagt cagcagacaa    720
ccaatagtga tcctacagat aacagtttca cttatcttgg tattctggat tctttgcggg    780
cccaaggatt cattaattca gcctcgtact cggtttatct ggccccagat ggtaagactg    840
atgatactga tcacgatgat ggtgagatcc tgtttggtgc tatcgacgag gctaaaatta    900
atggacagtt gaagttgttt ccatatgtca atccttataa atcggtatac cctgaccaat    960
acgcttcata catcaccgtt tccagtatta ctgtagccag ttattttagt agccgcttgg    1020
ttgaaagaat ccctcaatta gctctttttag acactggtgc acattttct tacttgccaa    1080 cttatacgct gatacgtctc gcctatgcca tccatcctgg ttttgagtat gtccgacaac    1140
tgggtttatt tattatagag tcaaacgtac tctccagtgc gagacaaagt accattgact    1200
tccggtttgg caaagacgta gtaattcgat ccaatgtttc agaccatcta ctcgacgtat    1260
cacaatactt cacatctgga cattatcttg cacttaccat ccatgaaagt gtcgatgggc    1320
ttctcatttt gggtgacacg tttatcaagt ccacctactt attttcgac aatgataaca    1380 gtgaattggg tattggtcag atcaaaatta ccaatgacga ggatattcaa gaagttggtg    1440
```

-continued

```
aattcacctt agaacgcgat tcagactatt cttctacatg gtccatttac tcttatgaaa    1500
cttctttgga tcccttaagc actggcactg gtacggggtc aacctattct cctactcgca    1560
gtactacagc tagaagcgaa ccgactacgt ctcgacgctc caccaccctt caacccagaa    1620
caactgtgat tccttctatt gacaggcttt cattgaacag cataactagt catggttcct    1680
ctactaacgg aacctcccca actaatgaga cttcttttgc tgaggatgga ggaactttga    1740
cacccgaaga agcttctttg acaacttcac taaattctgc tactatttct gagactactt    1800
ttgtcgatgt tgaaacttct actaccaatg gtgcttcagt tgtatctttg agtgttggtc    1860
cctgcattat tgccttccta ctactcatct cttaa                              1895
```

```
<210> SEQ ID NO 8
<211> LENGTH: 3201
<212> TYPE: DNA
<213> ORGANISM: Pichia pastoris

<400> SEQUENCE: 8
```

```
atgagcatgg gagctactgt ttcaaaggag tccactgtag acctaacact gccgctgttg      60
cagctgagtc caagactgtt gttcctgcct ggagttgtct acaagacgac tttcaagttc     120
caggaggggg tcaacatctt gctacgtttt agagacctgt tcgatgagtc tttttctgaa     180
agaaatgacg ttctaggtga tattgcccgc tcgcagaagg aacaacagga aaacgattat     240
gaccatatcc cttttttgag cagcaatgct aagaagagca taggtgtcct gaaagaccaa     300
cttgaacttg gtgggtctga tgacaagtca cttccctggg ttattgcctg tctccctggg     360
ttcgaccagt cagaccagga ctccattgcc actacaattt gtcagataac tgaggtgtcc     420
gtcgttaacc aggatattgt actatccttc gaagcattaa ccagaggatc tttaaaatcc     480
aaaaagacca tctccatgaa tgaatcaacc atatctgtgg aagtggatat accatttact     540
gaggttgacc agaccatcag taacaagctc atcttgacaa atattgataa gggtctgcaa     600
ctactggaga atatcaaaca gtttctagtc acctatcaaa atgacatgat gaaccttgaa     660
gatactacca tggaaaagaa ctcccgtcta aagtctgcaa tgatgatttt ggctccgttg     720
tctcacttga tctacgccac tgtctcatct caagaatcca ctcatgctta tactagacta     780
tccaaccagt acaagtccgc taagaaggaa ttagattcaa ccaaaaacag aaagtcttta     840
ctcaagaaga tttttgaaaac taatgatatt ctcacttcag tgttcccctt cagtatggtt     900
caaaaggtgg atgtcttggg agctatttca agttctacag acaggatcca aacaactatc     960
gacgcgttgg actttgccaa tccacttttc gaaacatatt tgaacgttga ttatgttctg    1020
gagacatgga agatttttga cactaagaac ggcaaaattg ctgccaattt gaccaggtct    1080
caattagtat ctaaccactt gaagggcctc agagtactga ttgaagacat ccaaggaact    1140
tcaagaaggc gggtcagtcc ttctcagaga actcgtttgg cgccttcgcc aatacaaat     1200 tctgcaaatc aggcaccgaa agctggagaa tcagacgacg aaaataaaga attgcgtgat    1260
tttatcaaca acctctccaa attgaagatc tcagaggatg gaaagaggct cgttaccaaa    1320
gatttcaaca gaatgactca aatgcaacca agttcatcgg agtaccaact gctcagaact    1380
tatttagaga ttattatgga tatcccatgg gaaacaaaaa atattgtaaa acaacaaatt    1440
tttgatctag acaaggccaa agaaacacta gatcaggacc attacggaat ggactccgtc    1500
aaagatagga tcttagagta tttagcagtt cttaaactcc acgatcacat taaaacgtcc    1560
aaccccaagc aagaagacga ggaaatcaaa gccagagcac ccattctctt actaacaggt    1620
ccacctggtg ttggtaaaac ttcgttagga aaatctattg caaaggctct gaacaaaaag    1680
```

```
ttccagcgag taagtcttgg aggattgaag gatgagtccg aaattaaggg acatcgcaga      1740
acttacgttg gagcaatgcc aggactattg acccaagcac tgaggaaatc tcaatctttt      1800
gatccagtga tacttttgga tgaaattgac aaggttgtcg atggatccca aggccctggt      1860
agtcgtgtaa acggtgatcc agctgctgct ttgcttgaag tgttagaccc agagcaaaat      1920
tctaacttct ctgaccatta tatcgggttc ccacttgact tgtctcgtgt tgttttttatc     1980 tgtacgtcca acgatatgag catgatcagt gccccattaa gggatagaat ggaggttatt      2040
gaactgaatg gctacaatta tttcgaaaaa gtggagattg ttaaacaatt cttattacca      2100
aagcagatca aaagaaacgg actgcctacg aatgccgaat caccatcggt ggttattcct      2160
gacgaagtga ttatgtacat cgctgtcaat tatactcggg agccaggtat tcgtaatttg      2220
gaacggttaa tagggagtat ctgtcggggt aaggctattg aatactctag cttgatgagt      2280
agtactcaag ctccaggcga aattccaaag ggatacgttt ccaaggtcac ggtagataat      2340
ctttcaaagt acattggaat accccggaa ttgtctacag gcaagaatat gaggaatgat      2400
tcagctatct ctaaaaagta cggaatcgtg aacggcctca gttacaatag tagcggacat      2460
ggaagtaccc tagtctttga aatgaccggt atacctaata gtactaacac taacatgatt      2520
acgaccggca gattgggtga tgttcttaca gaaagtgtca agatcgcaag aacaattata      2580
agatcgatgt ttagtcacaa cttactacaa ttaaaggatg acgaaacttc aacttctggg      2640 gatctttttga agaggtttga cactactcag gttcacatgc atgtgcccgc tggtgctatt      2700
caaaaagacg gacccagtgc tggaatcacc attacgctgt gccttctgtc ggtgatgcta      2760
gagaaacctg taccaaggga tttggccatg actggagaga ttactttgag agggatggta      2820
ctgccaattg gaggtgttca tgagaagcta ctaggagcac atttaactgg aaccgttaaa      2880
agggtgatcc ttccaagaag taatcgaaga gatgtcattc aagactttat ctctaacttg      2940
gaagccaata acagaagttc tagggataag ctactggtag atcttatcaa agaggaggag      3000
tcattactgt ccaactcaaa taaatccgaa cgaattggag tgttcgggct tcctgaaaaa      3060
tgggttcaag agaagttggg acttcaagtg agctacgtgg aagaattttg ggatgttatc      3120
cagattgtct ggaacgatca ggttgaaatt gacagcacca aattacacga gctagctact      3180
aaagagttcg caaggctatg a                                                3201
```

<210> SEQ ID NO 9
<211> LENGTH: 1680
<212> TYPE: DNA
<213> ORGANISM: Pichia pastoris

<400> SEQUENCE: 9

```
atgcaattgc gtcattccgt tggattggct atcttatctg ccatagcagt ccaaggattg       60
ctaattccta acattgagtc attacccagc cagtttggtg ctaatggtga cagtgaacaa       120
ggtgtattag cccaccatgg taaacatcct aaagttgata tggctcacca tggaaagcat       180
cctaaaatcg ctaaggattc caagggacac cctaagcttt gccctgaagc tttgaagaag       240
atgaaagaag gccaccccttc ggctccagtc attactaccc attccgcttc taaaaactta       300
atcccttact cttatattat agtcttcaag aagggtgtca cttcagagga tatcgacttc       360
caccgtgacc ttatctccac tcttcatgaa gagtctgtga gcaaattaag agagtcagat       420
ccaaatcact cattttttcgt ttctaatgag aatggcgaaa caggttacac cggtgacttc       480
tccgttggtg acttgctcaa gggttacacc ggatacttca cggatgacac tttagagctt       540
```

-continued

```
atcagtaagc atccagcagt tgctttcatt gaaagggatt cgagagtatt tgccaccgat        600
tttgaaactc aaaacggtgc tccttggggt ttggccagag tctctcacag aaagcctctt        660
tccctaggca gcttcaacaa gtacttatat gatggagctg gtggtgaagg tgttacttcc        720
tatgttatcg atacaggtat ccacgtcact cacaaagaat tccagggtag agcatcttgg        780
ggtaagacca ttccagctgg agacgttgat gacgatggaa acggtcacgg aactcactgt        840
gctggtacca ttgcttctga aagctacggt gttgccaaga aggctaatgt tgttgccatc        900
aaggtcttga gatctaatgg ttctggttcg atgtcagatg ttctgaaggg tgttgagtat        960
gccacccaat cccacttgga tgctgttaaa aagggcaaca agaaatttaa gggctctacc       1020
gctaacatgt cactgggtgg tggtaaatct cctgctttgg accttgcagt caatgctgct       1080
gttaagaatg gtattcactt tgccgttgca gcaggtaacg aaaaccaaga tgcttgtaac       1140
acctcgccag cagctgctga gaatgccatc accgtcggtg catcaacctt atcagacgct       1200
agagcttact tttctaacta cggtaaatgt gttgacattt tcgctccagg tttaaacatt       1260
ctttctacct acactggttc ggatgacgca actgctacct tgtctggtac ttcaatggcc       1320
tctcctcaca ttgctggtct gttgacttac ttcctatcat tgcagcctgc tgctggatct       1380
ctgtactcta acggaggatc tgagggtgtc acacctgctc aattgaaaaa gaacctcctc       1440
aagtatgcat ctgtcggagt attagaggat gttccagaag acactccaaa cctcttggtt       1500
tacaatggtg gtgacaaaa cctttcttct ttctggggaa aggagacaga agacaatgtt       1560
gcttcctccg acgatactgg tgagtttcac tcttttgtga acaagcttga atcagctgtt       1620
gaaaacttgg cccaagagtt tgcacattca gtgaaggagc tggcttctga acttatttag       1680
```

```
<210> SEQ ID NO 10
<211> LENGTH: 1233
<212> TYPE: DNA
<213> ORGANISM: Pichia pastoris

<400> SEQUENCE: 10
atgatatttg acggtactac gatgtcaatt gccattggtt tgctctctac tctaggtatt         60
ggtgctgaag ccaaagttca ttctgctaag atacacaagc atccagtctc agaaacttta        120
aaagaggcca attttgggca gtatgtctct gctctggaac ataaatatgt ttctctgttc        180
aacgaacaaa atgctttgtc caagtcgaat tttatgtctc agcaagatgg ttttgccgtt        240
gaagcttcgc atgatgctcc acttacaaac tatcttaacg ctcagtattt tactgaggta        300
tcattaggta cccctccaca atcgttcaag gtgattcttg acacaggatc ctccaattta        360
tgggttccta gcaaagattg tggatcatta gcttgcttct tgcatgctaa gtatgaccat        420
gatgagtctt ctacttataa gaagaatggt agtagctttg aaattaggta tggatccggt        480
tccatggaag ggtatgtttc tcaggatgtg ttgcaaattg gggatttgac cattcccaaa        540
gttgattttg ctgaggccac atcggagccg gggttggcct tcgctttggg caaatttgac        600
ggaattttgg ggcttgctta tgattcaata tcagtaaata agattgttcc tccaatttac        660
aaggctttgg aattagatct ccttgacgaa ccaaaatttg ccttctactt gggggatacg        720
gacaaagatg aatccgatgg cggttttggc catttggtg tgtgtggacaa atctaagtat        780 gaaggaaaga tcacctggtt gcctgtcaga agaaaggctt actgggaggt ctcttttgat        840
ggtgtaggtt tgggatccga atatgctgaa ttgcaaaaaa ctggtgcagc catcgacact        900
ggaacctcat tgattgcttt gcccagtggc ctagctgaaa ttctcaatgc agaaattggt        960
gctaccaagg gttggtctgg tcaatacgct gtggactgtg acactagaga ctctttgcca       1020
```

-continued

```
gacttaactt taaccttcgc cggttacaac tttaccatta ctccatatga ctatactttg      1080
gaggtttctg ggtcatgtat tagtgctttc acccccatgg actttcctga accaataggt      1140
cctttggcaa tcattggtga ctcgttcttg agaaaatatt actcagttta tgacctaggc      1200
aaagatgcag taggtttagc caagtctatt tag                                    1233

<210> SEQ ID NO 11
<211> LENGTH: 942
<212> TYPE: DNA
<213> ORGANISM: Pichia pastoris

<400> SEQUENCE: 11
atgaagctct ccaccaattt gattctagct attgcagcag cttccgccgt tgtctcagct        60
gctccagttg ctccagccga agaggcagca aaccacttgc acaagcgtgc ttactacacc       120
gacacaacca agactcacac tttcactgag gttgttactg tctaccgaac tttgaaaccg       180
ggcgaaagta tcccaactga ctctccaagc cacggtggta aaagtactaa aaagggtaag       240
ggtagtacca ctcactctgg tgctccagga gctacctctg gtgctccaac tgacgacacc       300
acttcgacta gtggctcagt aggghttacca actagcgcaa cttcagttac ctcttctacc       360
tcctctgcaa gtacaacaag cagtggaact tcagccacta gcactggtac cggtactagc       420
actagcacta gcactggtac tggtactggt actacaggca caggaaccac tagttccagc       480
actagctctt ctgctacttc gactccaacc ggttctatcg acgctatcag ccagacactt       540
ctggatactc acaatgataa gcgtgctttg cacggcgtcc cagaccttac ttggtctacc       600
gaactcgctg actacgccca aggttacgcc gattcataca cttgtggctc ttcattagaa       660
cacacaggtg gaccatacgg tgaaaatttg gcctctggat actctcctgc tggcagtgta       720
gaagcatggt acaacgagat cagcgactac gatttctcta acccaggtta ttctgctggt       780
accggtcact tcacccaagt tgtctggaaa tcaactacac agctgggctg tggatacaag       840
gagtgcagta ccgacagata ctacatcatc tgcgaatacg cacctcgtgg aaatattgtt       900
tctgccggct acttcgaaga caacgtcctg cctcctgttt ga                         942

<210> SEQ ID NO 12
<211> LENGTH: 690
<212> TYPE: DNA
<213> ORGANISM: Pichia pastoris

<400> SEQUENCE: 12
atgactgtgc aaattttgat tgtagttacc agtgttgcta agtatgaaag cggaaagctg        60
ccaacaggct tgtggttaag tgagttgaca catatgtatc atagtgcaaa agagaacggc       120
tatgatgtga cgattgcgag tccgcaaggc ggaaacattc cgcttgaccc tgaaagcttg       180
aaatcaatgc tgattgacaa gctttcaaag gattatgaga caaaccaaga ctttatgaag       240
ttgttgcaaa acacaaaaag tttgggtgaa gtcacaggac aacagtttga cgttgtttat       300
ttggcaggtg gacacggaac aatgtatgac tttccgaaca cactgtttt acaaaacatc       360 atcaaagaac actatgaggc gggcaaaatt gttgccgctg tatgtcacgg agtttgtggg       420
cttttgaacg taaaactgtc tgatggcgag tatctaatca agacaaggc cattacagga       480 tttaattggt ttgaagaagc tatagcagga cgcagaaaag aagtaccgtt caaccttgaa       540
gcagaattga ataaaaaaac ttcaaaatac gagaaagctt ttatcccaat gacgtcaaaa       600
gtggtcgtgg acgggaactt aatcacagga cagaacccat tcagttcaaa agaaattgcg       660
```

-continued aaagtggtaa tggaacaact gaagcaataa                                        690

<210> SEQ ID NO 13
<211> LENGTH: 2517
<212> TYPE: DNA
<213> ORGANISM: Pichia pastoris

<400> SEQUENCE: 13
atgattgatg agaagcaatt gaatcaaccc aaaaggagcg tcttaagacg tctccatatg        60
ctgtttctgc cattactagc tatctccttt ttcctgatat atttaagtga tatcacacag       120
cctctcttcc gtgcccgaaa ggaagacgaa aacccgttgg aaatttactt gaaggcattg       180
gaaacgaatg aagctcacaa atggtcaaag gtgtacactt cgcagcctca tttggccgga       240
accaactacg gattggttga gtttactaag tccaaatttg aagaatatgg atttgaggcc       300
agtgtcgatg actacgatgt gtacctgagt taccctattg atcatagttt ggaattgtat       360
gagcattctg aggataaaaa tgacaagctc ttgtataagg cttcgctgca agaggacgtt       420
ctctctgaag acccaactac ttcaggcgac gacctgatcc ctaccttcct tggttacggt       480
gctaacggca atgtatctgc agaatacatc tacgctaact atggaaccaa agaggacttt       540
gaggatttgg tggcccgtgg tgttccaatc aaggggaaga tcgcagtcat tagatatggt       600
caaatattta gaggcttaaa ggtgaaattt gcccaagaat atggcgcaat cggtgctgtc       660
atatacagta cccaggcga cgattatggt atcacccctg aaaatggtta caagccttac       720
cctcatggta aagccagaaa cccaagctct gtgcaaagag ttctgcccca atttttgtct       780
gtttatcccg gtgacccaac cacgccagga gttggatcga agaagggagt agaaagagtt       840
gatcctcatg ctacaacccc ttccattcca gtcttgcctt tgagtttcaa agatgccttg       900
ccaattttga agaaacttaa taaggaagga ttgtctgttc ctgactcctg gaagggaggt       960
ctcgagggag ttgattacag taccggccca gctaaaaaca ttcatttgaa cctttatagc      1020
gaacaaaact ttactattac acctatttac aatgtctatg gagagatcaa aggtgagaat      1080
gctgacgaag ttatcattat tggtaaccat cgtgacgctt ggattaaggg aggtgcttct      1140
gaccctaaca gtggatctgc tgctttgatt gaacttagta gaggtttgca cgccctaacc      1200
aaaacaggat ggaagccaca ccgtactatt gtactagctt cctgggatgc tgaggaatat      1260
ggcttgattg gatctactga gtttggagaa cagtttgaga gttccttca gaagaaggtc      1320 gttgcctatt gaacgttga cgttgctgta gctggaactc atcttcattt gggtgcctcg      1380
ccatctttgt tcaaactatt gaaggataat gccaaagaaa tcactttcaa gaattcaacc      1440
gagactttgt atgacaacta tgttaaagat catggcaacg acattatttc gaccttagga      1500
agtggaagtg actacactgt ctttttggat catttgggaa ttccttcgct tgatattggt      1560
ttcattgctg gaaaaggtga cccagtatat cactatcatt caaactatga ttcgtaccac      1620
tggatcagta ctagtggtga tcctggattt gagtatcata atgtactggc caaatatttg      1680
ggttcgttgg ttttgaatct ctctgagaga gaggtgttgt acctgaagct tcatgattat      1740
gctaccgaat tgctcaagta cctcttggaa gcctacgccc aaatgccaga ggaatgggac      1800
gatgaagtaa ttggtttcag atcttcctcg tgtcatcgtg cgaaagcatc tcatcatggt      1860
aaggatcctc atcatgaggg aagacgccat cacggaaaag gattccattc taaaggaggg      1920
cctcatcatg gggaacgcca tcacggaaaa ggattccacg ctgaaggggg accccaccat      1980
gagaaaggac cgcatcacga aaaagggctc cacgtcgaag agagccccca tcatcagaaa      2040
ggacctcact ttgaaaaagg attccatcat gacatggaga tgtaccataa gaaattggct      2100

-continued

```
catcacggta aagaacccaa gacgaagcta aagcacttga agaaacaagt tgagagttta    2160
atcatcgatt tcgccaatac cactcaaaca tatgacgctt acactgactt ccttcagaag    2220
caacatgaga ttagggattc tctttcattc tgggagaaaa tcaagctaca ttttaagatc    2280
aaggcagcta acttcaaact aaatatttt gagcgagtt tccttcatga aaatggctta     2340
aagaacagag aatggttcaa acatattgta tatgctgcag gaaggaacac tggttacgcc    2400
ggacaaagac tgcctggtct tgtggaagcc attgaagaca agaatctgca tgatgcagta    2460
aaatggcttc acatcctttc caagaagatt gatagtctac agaagtcatt agagtag      2517
```

<210> SEQ ID NO 14
<211> LENGTH: 888
<212> TYPE: DNA
<213> ORGANISM: Pichia pastoris

<400> SEQUENCE: 14

```
atgagattac ttcacatttc attgctatca attatctcag tattgaccaa ggccaacgct      60
gaatgttgtt acaccaacac acatactacc actgaagtct ggtatactac agtatatgct     120
cgagatgtta gtgaagagac ttcttccaca ctggctggtg gaagtgcaac tgtcagctca     180
gaagtgagtt cgacaattga atctagcgtt gccacttccg ctaccaccga atcttcaagt     240
gagacatcag ggtccacatc tgggtccaca tctgccactg aatcatcaac tggtagtagc     300
tcgctagcaa ccagttcatc gataaccagt tcagagtctt ccaccattac acaaaccaca     360
ggacaagagt caacaagccc aaccccatcg tcctcagaga caggttcttc tactactact     420
ccctacgata taagtccaac ggcaagttcc gactttgatg cttttaaata tcaaattctt     480
gatgaacaca acataaaaag agctctacat ggagttgacg gattagagtg ggatgaagaa     540
gtatatgctg ccgcccaagc atatgctgac gcatacactt gtgacggaac cttggttcac     600
tctggaaata gtctgtacgg agaaaactta gcgtatggtt actcaaccag agggactgtt     660
gatgcctggt acagtgaaat tgaatattat gactttaata acccaggtta taccccaggt     720
gttggacatt tcactcaagt agtttggaaa agcaccacaa agctcggctg cgctttcaag     780
tactgcaatg actattacgg agcctacgtg gtatgcaact actcaccacc aggaaattat     840
gtcaacgagg gatacttcga agccaatgtg ttaccactgg tagattaa                 888
```

<210> SEQ ID NO 15
<211> LENGTH: 681
<212> TYPE: DNA
<213> ORGANISM: Pichia pastoris

<400> SEQUENCE: 15

```
atgagttatc ccctaggtct gggtcgtaca gcttataggt tcatcccgag gtcaatctgt      60
tcaagacgat ccatctcatc ccatgcatta cctccaacgc cctccaactc accaccagca     120
ggagatttat tcaccaaact gctgaacgaa cgcatcatat atttagcagg aggcattgat     180
gatgcgcaag caacatctat cacggctcaa ttgctgtatc tggaatcgca gtcaacgtcg     240
aaacaaatca acatttacat caactcacca ggaggttctg tcacggcagg gctggccatc     300
tacgacacaa tccagtatat ccgagcgcca gtttccacgg tttgcttagg acaggcatgc     360
tccatggcat ccctcttgct tgcaagcgga acgcatggca aacgtttgat cttgccaaac     420
gctaccataa tggtgcatca accatcttcg gcaaacggaa ttaagggaca ggccactgat     480
atcgagatat atgcccgtca tatcatcaat accaaacaga aattgcaaac tttataccta     540
```

-continued

```
aaacacatgt ctccaaccat gacggtggat gaaatcactg cacttttgga gagagatcgg      600
ttcatggagc cagaggaggc agtgtctctt ggactggcgg accgtgtatt agagaggaaa      660
cccccggttg tatctgacta a                                               681

<210> SEQ ID NO 16
<211> LENGTH: 1659
<212> TYPE: DNA
<213> ORGANISM: Pichia pastoris

<400> SEQUENCE: 16
atgacagata ccaaggagtt agccacgttg ctggagaact tgttgaaatt gcaaaaatca       60
ggaagtcttg gtgaaattgt gggtcaagca cagcgcattt atcatgacat ttctgacctc      120
tcagtcctat ctggattatc aaccccagaa gtgctctctc ctcacacatc tccagatgtc      180
cccgagagag ttccatctga agtcaactta gacaattcca atctggcaac tgatgtcaac      240
gaaaaggaga gtattttga cgattttgca aatgactaca tcgagtttac ctacaagaac      300
cccaccacct accatttggt gcaatctgtg gcggaattgt tgaagaaaag cggattcgaa      360
tatcttcctg aagcagctga ctggtccaaa ttattcgacc ctgaaaagac gggagcgtat      420
ttcacaatcc ggaatggaac ctctttagct gccttcacaa ttggtagttt ctggtcccca      480
gccaagggag taggagctat cggaagtcac atcgatgctc tcacaactaa gctgaagcca      540
gtctccaata agagtaaggt tgatggctac gagttgttgg gagtttcccc ctatgctggt      600
gctttgtctg acgtctggtg ggatagagat ttgggtattg gtggaagagt aatttacaaa      660
aatgaatctt ccggcaagct ttccaccact ttggttaaca gtacacctca tcctgttgct      720
catattccaa ctttggcccc tcattttggt actccctcca acggtccatt caacaaggaa      780
acccaagcag ttcccgttgt aggattttct gacggaaacg acgaggagaa acccactgag      840
gatgaacaaa agtctccttt gattggtaag cattctttaa aactactccg ctacatatct      900
aagctagcag gagtgccagt gtcctccttg attgatttcg atttggacat attcgatgtc      960
caaaaaggta ctaggggcgg tctttccaat gagttcattt acgccccaag agtggatgat     1020
cgtatttgtt cttactctgc tctacaagcg cttatcagac gtcacaagga tcccgaatcc     1080
tttgtcacag acgactcttt caatcttgtt gccctttatg acaacgagga tcggatct      1140 ctctccagac agggagccaa gggtggtcta cttgagtcga ccatttccag agcaatcgct     1200
gcattgaaaa tttcagagcc agggactctg caaagactat atgcaaattc agtgattctt     1260
tctgcagatg tcacacattt gttaaatccc aatttcaccg aagtgtactt ggagcaccac     1320
aagccactgc aaacacagg gattgcactt gcgctggatt cgaatggcca tatggccaca     1380
gatttgttag gcaaggtcgt tgttgagcag ctggctaaac tcaatgatga taaagtgcag     1440
tacttccaga ttcggaacga ttcaaggtct ggagggacca ttggacccag tatttccagt     1500
agtactggcg ctagaaccat tgatcttgga attccccaat gtccatgca cagtattcgt     1560 gctaccgtgg gatacaaaga tgttggcctc gctgtcaagt ttttccaagg gttctttaaa     1620
aattggagaa aagttgtcga cggcattgaa gagttttaa                           1659

<210> SEQ ID NO 17
<211> LENGTH: 3552
<212> TYPE: DNA
<213> ORGANISM: Pichia pastoris

<400> SEQUENCE: 17
atgacttcgg tattttggg tgtttataga gccctatttg attaccaagc tcaaaatgac       60
```

```
gaagaactaa ctgtgcatga gaatgatcta ctatacgtat tggaaaagtc cgaaattgat       120
gactggtgga aagttaaaca acgagttatc ggagttaatg tcgaggaacc aataggtctg       180
gtacccagta cttatattga gcctgctaca cctatcgggt cagctgttgc actgtatgat       240
tatgacagac aaacagaaga agaaaattact ttcaaggaga atgacacctt tgacgtgtac      300
gacaccgacg atcaggagtg gatcttggtt ggcctgaaca atatccattt tggtttcgtg       360
cctgcaaact acatacaaat ttctttgggt acgacggcac ctgcttctaa caatccacca       420
atacttagtc ccgccagctt ccctccacct cctcaacgga tcaacaactc ctctgttccc       480
tctctcaaag atgctgaacc agcaagaaat ctagaggacg ataatgctta tgaagaggag       540
gaagatgtac ctccaccaat gccaacgcga ccaactgcca ctacagctac atctaatatc       600
tctgctcctc aggactctga atccgaagag gaaccttcta gtagtagcag aaggccaagt       660
ggccgttcaa gggcggatga tgattttgta aaaggagact atttcacttg ggatgttcag       720
gaaattaatg gccgcaaaaa gaggaaagct gtcctgggta tcggaaatgg tagtatttat       780
gtccaagcag agggacattc ttctaagaaa tgggatatca ggaatttgac aaatttcagt       840
aacgaaaaaa agcacgtctt ttttgacttt accaacccct cggcatccta tgaacttcat       900
gcaggctcca aggacgcagc agatgccatc ctgtcaattg ttggtgattt gaaaggtgct       960
tcttcaatgc gtgctttgaa agaggtgaag gctgcatctt ctgccccaaa aaccaagact      1020
ggtaaagtca gttacaactt cgatgctgaa agtcccgatg agttgtcgat tagggagggt      1080
gatgttgtct acatattgaa cgataaagaa tcctctgagt ggtggatagt tcaggacgtt      1140
aatactaaca agaaaggtgt tgttccagct agctacatag agttgattag cgggggtgga      1200
tctactttag ccagcattgg ctcttctatt tccaaaggtt ctaagaaagc ttttggatcc      1260
tccagaaaac gtaaggaaaa agagcgtaag catttggaag agcaacgtgc cgctaaaaga      1320
gaaaccgaaa gggaacgtca aagacttcga tccaaggaag aaagggatag gctaagaaag      1380
ttagatgaaa aggaaagaag gaaaaagcaa aaagctactc cacaggatga agaccaaccc      1440
gagactagca aacctaatcc tcatagagtg cgtacctgga ttgacagttc aggatccttc      1500
aaagttgaag cagagtattt gggagttgtt gacggtaaga ttcatctgca taaaacaaac      1560
ggtgtaaaga ttgccgtagc ggctcctaag ttgtcactag aggatttaga gtatgtggaa      1620
agaatcactg gaatgtcgtt agaaaaatac aagccaaagc caaatctag tggttcctat       1680 tccagacctt ccaaaaagcc atcctctaga gaatcttcac caaaggagtc cagccgctcc      1740
ggagttaaac aatcagttcc caagattgat cctcccaaag acccagatta tgattggttt      1800
caatttttct tgggttgcga tattgatccg aataattgtc agcgatacag tgtggttttc      1860
attaatgaac aactggatga gagtagtttg caagacctca ctccatccct actaagatcg      1920
ctagggttaa gagaaggtga tattttgaga gttcaaaaat tcttggataa caagtttggt      1980
cgaaccaaag ctcaagaatc tgctaccaat ggtggtttat ttaccaagag tgatggtaca      2040
ttgaagaaca ataggtccac tgatgttcta acaagtacag ttgtaacgcg agaaactta     2100 agtcctacta aggccgaggc taagagcaaa agaattgatg acgaagcatg ggctctcaaa      2160
cccgctgccg aatctagctc tcaaatggat caattctcca gacctgtcag tgcaatgagc      2220
aaacaattga ctggatccat acaagatctc gtcaacttga aacctttggg ggacaatgca      2280
aacaacgctt cggtagccca caaagctgaa acaccaaaca ctacccagga caaaccttct      2340
gctcctgtct tggaacctgt gaagactgga gctgcaaggg gacctgtgca agcgcaacca      2400
```

-continued

```
acaagtggtg gtttcgtcac tgcacaacct actggtgctc tagttgcaat gcctacaggt    2460
ttcatgccca ttacgatggt gcccgtaaag acaggaggaa ctatagctct tcaacccact    2520
ggtggattcg tttcgttgca aagaactggt ggggtacttc cgcaggttac aggggggactt    2580 gttcccgttc agactggtgg gttagtaatg cctcagacct catttggtgt aactccaact    2640
ttgcagccaa caggagggat tctacctgct cagaggacag gtggattggt tcctgttcaa    2700
aggacggggg ggctaattcc cgtccaacaa actggaagat tagttcctgt tcaacaaact    2760
ggaggattga ttcctgttca aaggactgga ggattagttc ccgttcagag aactggaaac    2820
ttacaacctg tacctacaac ctcttttgga agtcaaccaa caggaacttt tgtgcctcaa    2880
tcttcctttg gtaatcagtt ggccaccaat ttgaataacc cgcaaaccac attcggctct    2940
caaccaacag gaggtttccc tcagacatca tttgcacaaa atcagtttag acaatcgaca    3000
ggaggtttcc agcagacccc aattgtgcaa caaacagggg gattcccca atactccgct    3060 ggacaacaga cggtaggatt ccctcagaac tcttttggac agcagacagg aggaattgcc    3120
caaaactcat ttggacaaca gacaggaggt tatcaaacag gttttcaagg aaatggatcg    3180
attccaatgc cccagtcctc attcggtgct tcaaatctgg gattcaatgg tgctacgcag    3240
cagaactaca acattggcat gggccaatct ttgccagcag cttctatccc tccccttcaa    3300
ccctcttaca cctcatcact caatggaatg tcaaacatgc ttcagaacgt aagcatctct    3360
cagcagccac aacaagccca gccaatgacg acttttggag cacctgtggc ccagcctccg    3420
ttacaggctc aaccaactgg ctttggtttt ggtaactcgc cctatggagg tcagaaccca    3480
ctccaatctc agccaacagg taaaagagcc aacttatcag cagctaccgc agacaaccca    3540
ttcggcttct ag    3552
```

<210> SEQ ID NO 18
<211> LENGTH: 1662
<212> TYPE: DNA
<213> ORGANISM: Pichia pastoris

<400> SEQUENCE: 18

```
atgaccaacc aatcaacagt ggtggattta cgcctttcat ccaagagagt tgttggcaaa      60
ccagtcaagt tgcccacagt cctagcgtgc tcagggtcag attcttccgg tggtgcaggg     120
atcgaagcag atatcaaatc catcacggct tttgggtgct atgcgctaac agcaattaca     180
tctttaactg cccagaatac caaaggtgtc accagtatag aaaacaccga cccaaagttt     240
ttcgaagaga ttttagaggc aaattttgag gacattgaaa tcgatgtggt gaaaactgga     300
ctgttaaacc ctgagtcatc tcgtttattg ctgaaatttt tagataaata ccacaaagga     360
aagccatttg tcctggatcc ggtcttagtg gctacgtctg gttcaatgct tgcagatcaa     420
cacgaattag ggttcaccat tgattctcat tttaagaaag ctactatcat tactccaaat     480
ttcgaagagg catgtgtgat ctactcttac ttgaaaaagc tgaagactgt agatgagttg     540
ggtgaaatag aaactttaga ggatttgaaa ggaatggcca agttcatcca gcaaactaca     600
cattgcaact ctgttcttct taaaggtggc catattccct ggaatagaaa cgagcagttg     660
gttaaaaaaa agggaggaga tccagcatac attactgata ttctttatca gggtcatttg     720
gataaattca cggtaatcaa gacagattac ttgacaagtt ctggaactca tggttctggg     780
tgtacgattg ctgcctcaat tgctgcaaac attgcccgtt cgttgaagat tgaggatgct     840
gtaatttctt cgattagata cgttcatcag gcaatttttg agcagatgaa gacgctagga     900
caaggaaaag gccctttgaa tcatgtgttt catatttctc ctcccattaa cggcacaagt     960
```

-continued

```
gctgagaata actttcttcc gttctatcca ggtcacttct tagattactt actggagcat      1020
cctttggtga gtcccatctg gaagaactac atcaaccacc cattttttaga aaacgtagca      1080 acaaataagc tggctaagaa cagattcatc cactacattt gtcaagatta cgtgtatcta      1140
gcttcttatg cccgtgtcca cggcttagct gccggagttg cacctgatat tgaaagcata      1200
aaggcagaag cccatataat cgactccatc atggaagaaa tgcatagaca taaagacgta      1260
ttgaactctc gtggaattgt gaaactggat gaattaagac cctccaaggc ctgcaaacag      1320
tattccgact acctcctaaa cattgcgaag acatcagact gggtggccat aaaaaatcgcc     1380 ttagcaccat gcatctttgg ctactattac gctgccattt atgctcggtc gtttatcaag      1440
gatgaagctg acgtggacga agaattcttg aattggatca atacgtatac cggtgattgg      1500
tacaaagatg ctgttgacga ggccagacag tcgctagaaa gccatatgca agctgtttct      1560
cccgtccagt tagcagagct agtcaagatc tttgcagatg tctgtcaatt ggaggtgaac      1620
ttctggactt cgccaatgga actaccagaa caagatctat ga                       1662
```

<210> SEQ ID NO 19
<211> LENGTH: 1008
<212> TYPE: DNA
<213> ORGANISM: Pichia pastoris

<400> SEQUENCE: 19

```
atgcctacag tggtgactaa cgagtcctct ctcttgcaaa caaccgtgag tgttgcacca       60
ttggtgcttt tatctgttgt tgatcactac gaacgagtgg tgcaggcacc caacgcccca      120
actaattcaa acgacaaaag agtcgtgggg gtcattttgg gagacaatac aaacaagaac      180
ttgatcaagg taaccaactc atttgccatc ccgtttgaag aagacgaaaa gaacagggat      240
atttggtttt tggatcacga cttcatcgaa tcgatgatgg aaatgttcaa gaagattaat      300
gccaaagaaa gacttattgg atggtaccac tctggaccaa agttaaagtc atctgatcta      360
caaatcaacg agttattcaa gagattcact ccaaatcctt tgcttttgat tgtggatgta      420
aattccaccg atatagtcga tattcctaca gactcatatt tggcaattga agaaattaga      480
gacgatggct caagtgcaga aaaaacgttt atccatttac catccatcat ccaggccgaa      540
gaagcagaag aaattggagt ggagcatctt ctgagggata tccgagacca ggcgtgcgga      600
aatctgtcca taagattgac taacaatttc aaatcgctga agtctttaaa cgatcgcata      660
gccaacattg tccaatattt gcgcaagatt ttaagtggag aattaccaat aaataatgta      720
attcttggaa aattacagga catattcaac ttattgccca acttggttgc cgttcaaggt      780
gatcccacaa aaccagccac tgcaagtgct aaccaactag ccacatcatt caatgtgaag      840
accaatgatg aattaatgat ggtttacatc tccagtttag taagatccat cttggctttc      900
catgatttga tcgacaataa gatcgagaac aagaagaaca acgagaaaga taaggaattc      960
acaccaacag aggaagaacc ccaacaagcg gctatagaat cgaaataa                 1008
```

<210> SEQ ID NO 20
<211> LENGTH: 969
<212> TYPE: DNA
<213> ORGANISM: Pichia pastoris

<400> SEQUENCE: 20

```
atgacaatgt caaccgaaga tatcatcgcc aggcatagga aggagaaaag ggaccaaatt       60
gcacttatta caaggatgaa gaagcagagc actaagtcaa ccaaaaagga aatcatgaaa      120
```

-continued

```
caatgctctc tcttggaaga agagctacag gcaagacata agaaggagtt aggtgagtgc      180
aagactgaaa attccgtcga gagaagtagt gagcctactg acgaaaaatc aaatggtgga      240
gaactttttt cccctgaaaa gttattatca atgatgactt taaaacagca aggaactcca      300
agtgagaatc aaggaaacgc aactgttcca aagagaaaac gcaataggca gaaggacaga      360
ttagctagaa gggaagttgc cattaaagag atgcaagcag cagcagcaaa agaggctaac      420
ctccaaacaa atttcaaaga gatagaattg aacaacataa gccaactgtg ccaagttgct      480
cacctggaac catatgatat ccgacctgat gggcattgct tgtttgcatc tataaaagat      540
cagttggagg ttcggcacaa aattgaaaat ataagtatac aagatcttcg gtctctggct      600
gcgagtcata ttaaaaatga tcccgagact tatactcctt tccttttttga tgagaatact      660 atgaaaatca gggacattga tgactatgca aacgagctgg aaaccacggc tttatgggga      720
ggtgatatgg aaattttggc attgagcaaa gagtttgatt gtccaatcag tgtaatgatt      780
agtggaagac ctattcatct tgtcaatgcc gacggttcta aagaggagtt gaagttggtt      840
tattaccgtc atgcatatgg cctaggtgag cattacaact ctttaagaga tagatcagag      900
ataagggagt cttgtatagt tgagcaagag gaaaaagaag cggtagacga tggaaaatca      960
tcttcttga                                                            969
```

```
<210> SEQ ID NO 21
<211> LENGTH: 939
<212> TYPE: DNA
<213> ORGANISM: Pichia pastoris

<400> SEQUENCE: 21
atgagactta agatcaagcg ttcaaatgaa cagcggctaa taacattgcc tgacggggct       60
acagtatcgg atttacttaa tgaaattgga tcagcttcta tcaatataaa ggttgggttt      120
cctcctcaga caattgatat ctcagatacc agcaagttgc ttactgatag tggaatcaag      180
aatggtgaaa tgatcattgt cactgatacc attgaaacag aagtgcctgt caacaagaat      240
gaggttgcaa ttgccactgt ctcaaaccag aatgatgcgc cctacgttca aatagacgac      300
atcttcctag tcttgcggaa gattcccgat gataattctt gtttcttcaa ctctgtcggc      360
tactgtatat ttggtcctga ttcaatcaag tatccggatt ctcaacaaga actaagacag      420
gccgtcgcta atgtaatcag agagaacaac caaggtattt ataactccgc catcttgggt      480
ggaaagtcaa tcacagagta ttctcagtgg atccaaagca gtaattcctg gggaggagcc      540
atcgaagcac agatattggc agaatacctt gatatcagta tctggacagt ggatattgag      600
tctcttcaag tctacaaatt taatgatgaa atggcttcaa ggttttgcgt tattatgtat      660
agtggtattc attacgacgc tatggctctc aagctggaca catcattaga tgaggaggac      720
tcacaaattt gtgtgtttga taagttcagt gagttgggga ctttgattga agacaacgtt      780
ctcaaattaa ccaaccatct taagaaccag ggctattata cgaatacttc cacattcata      840
ctccaatgtc aaatatgtct cgcaacattg caaggagaaa agaagcaaa tagccacgca      900 aagaaaactg ccacacaaa ttttggtgaa gtcaattga                              939
```

```
<210> SEQ ID NO 22
<211> LENGTH: 5528
<212> TYPE: DNA
<213> ORGANISM: Pichia pastoris

<400> SEQUENCE: 22
atgtcattgt ctgatcctga ggacagccta agacgtctac ttgtgagttt accctccaat       60
```

-continued

```
gttaagtacg atgcggagtc ttcggtattg aaaagccgac tgaaccttgc tctatatttc      120
tcgctgacaa agagaggtga atatctgggt tccttggtaa cggacttgcc aatggatttg      180
ccatcatctt attccgaaat cttagaggct gaagatgatt cctactcaag attggctgaa      240
tcaatgtaca aatgccctaa ctataagcat catggaagac cttgtgcaag gcagttcaag      300
caaggagagc cgatataccg gtgctacgaa tgtggttttg acgagacttg tgtaatgtgc      360
atgcattgtt ttaataggga gcaacatcga gaccacgagg tttccatttc aattgcttcg      420
tcctccaacg atggtatctg tgattgtgga gatcctcagg catggaatat cgaattacac      480
tgccagagtg aactggaaca agatgaccat tcaagttcag aagttaatcc agattttaaa      540
tctgctataa gggaaacaat ggatattatt ttagattaca ttttggattg tactattcat      600
tctgcatcta tgcttcctgc tgttcaggac atgatgaagg aagacccatc cgactatgaa      660
atggctattc aatatgcttc agatagttct tctctgccca ttgaaagata tggagtggaa      720
gacacgaatg ttcagtcctg gaacgtagtc ctgtggaacg acgaattcca taattatgat      780
gaggctattg attgcatcca gcaagttagt agatgttcat tgtctaaagg acaagctgac      840
gctcaaaaga ttaatgattt tggattttcc atcataagaa gaagtgaatc cttgccttta      900
ctgatagaaa ggtgcgccaa ggttgaagaa tccgggttta ctattacgat tctttctgat      960
agagatgtta cccgattgat tattattgat actatttttg attggttatt gactctgtta     1020
gaaatttcaa ggccggaaat tcagactgct attagagaaa gtttgtgtga atctcttttg     1080
gaagagtttc atgccgacat tcacgaagga gattttttct accgggaaga tgaatattca     1140
gacacacggg gtttgctgga tttcaaaaac agaattccag ccccattggt ggaggatgta     1200
atgaacgagt tgtctattga tgacttgaag aacagaaaac tatccagttt tcttaatgaa     1260
caaccttcag ctctagtcgg ctcaagagta cagtatttct tctatatgga tctgcggttc     1320
tggaaaaagg caagaaaatc tttgaaattg ctaacgacat ctgttttggt ttcaaacttg     1380
gaatacaaaa agacttttttc tgaacagttt gtgaaaatat actcgcatct gttgatattg     1440
atggcaaagg aagatagaga gtggcttctc agcaatgcgg gcaatgctgt agtacaactc     1500
tttacatgtc ctaaaacatc tctccattta ttacaaccac aatatttcag aagcatcatc     1560
gtccccatca ttttgttgtt cgaatcttat actggaaacc atttgctgtg gaaacgacca     1620
tatcaactct tatcacgtaa gaaaggtctc aaatttggtt taatgcgttc tttaactgat     1680
ctagtgacgt taatcaccac tgcccatcaa tcagaagaac atttggtact ttttcagggt     1740
aagaacttca tttacataat catgcttttt aggatgttcc agagtgccct gacattggtc     1800
agaaaggaag gagaacatat taccagggaa tccactgaat ttttaaccta cctgcaaata     1860
tcttactacc ttaatgatgt catcaaaggt attgttgaaa ttgcgcaggt tcctgaaata     1920
cgtaaacctg aacattggaa agttgtggaa acaaacatac aaatattggc cactttaatt     1980
tcatcagaac cttataagtt tcatatggtg cacgaaaaac aacttattga ccatgacgta     2040
acaaagaaac caacctctct tattaatcca ttgaatggat tactgtctaa catgttaaca     2100
accgtaaggg ccaattcttt ttcattttta actcgtcaag tttctcagat taattttttgg     2160 agtatcaatc ccgaagtctc attttcagat gatttagact atctgaaact ctcatcgaag     2220
agtttagaag caattacttt gagttcacag ataaaaattg gccactggat tagaaatgga     2280
tccatgacta gtaaacaagc gcaattgtac tgcacgaggt tcactcaata tggttacata     2340
gccgacgttc atttgaacca acttgctata ctcgaagaac gcgacgatga tcgtctatta     2400
```

-continued

```
ttaaacattt tggatagatt caatctaata gattggttct ataacgatca ggacgtgctt      2460
ggtactgttt tcgaagaacg atcttttac ctaatgaatg aattggttaa gtttcttat        2520 aatatgtttt cacacagagt taacttccag tttgaatcaa atttcacaga gaaaacccag      2580
tatgaggtaa cgcaatacat tttatacacg ctttgtaaag gatctttgtc attttcagat     2640
ctgacagccg actttcctat ctccgtggaa gttactgttt ttgacaagat ccttgatgag      2700
gttgctgttt acgaagagcc caaaactatg aatgattctg gaaagtattc tatcaagaaa      2760
agttattaca aaaagatgga tccaatgtct atttatgtgg actcgggtga tttcgatgat      2820
gtatcaacag cgatagtaaa ggaactttca attttaggaa aaataaaaga ggagaatgtt      2880
gtaattgaac ctcagatcag tggaccgaat gaatccaaca gccgtgtctt gagcagattg      2940
aaacggttct tcattagcaa atctgtagtc aaactgtttt ataaattgtt acaatctgct     3000
ctttctgaga gcaatgagac ctacgtcatt gaacttttac atttgattca agcagtttta      3060
ttagatgaac atgaattgta cagaatcgaa gatccagtgc aatactttat tcaaattcct      3120
gtgtgtgatc tactgttatc agttgttgag cacaatgatt tttcacgacc tgtctgcaaa      3180
aaactgaagt tctattgaat tggttgatcc agcgggacga gtcaatcatt gactcattgg      3240
ttgattcttt tggtgaaaag cacattgaaa actttaaaaa atctaaggga tctcaagttc      3300
tggagactaa acgagctaaa caaaagcgtt tagccaagga gagacaagag aagatcaaat      3360
cacgatttgc taaacagcaa aagtctttca tgaagcagaa tttggacgca aaaaagagtg      3420
cggaacatgt aactacacat ttatccaaag acaatgaagg attaggtagt tcctcccagg      3480 actctttca tgagtgcatt ctttgtcaac gtgctcagga gggcaacgag atgtttggaa       3540
tccctgcata tgttgaaaaa gtttccacgt tttgggattt tcaacctaag gatgagtcaa      3600
cctatacgga aagatgctta acaaccattg aaaatcaaat gaaacaattg catgaagaaa      3660
cggatgccaa caatgaggtt agagaacatc tttattatca aaaagatact cctgtaaaaa      3720
gcatggcacc gatatcttca agacacattg ttaagtcatg cgggcaccac atgcattata      3780 aatgttttc tgagttacta gaaaacagca ggaagtttag cacttgtccg ctttgtcgct       3840
ctgccattaa tgcttttgtt ccacaatttg ccatgaaaaa cgatgctagc cctgctttc       3900 aggaggctgc ttcgaatatt agtcactttg aaaagttgaa tttgaatcaa attgtatcga      3960
aatatcttct caatgattcc ttcttgaaat ttattgcgga agaaagtaag gaccagttca      4020
tgtatttgaa tgagtttaaa gacattttga aagacgcccc agatgcttct gaccacatgt      4080
tgagtgaagg gttatttccc tcattttgg ccatgtcaac attattgggt aataccctag       4140
caaatactga aattcgtctc agattatccc ccgagaagat tccccagaaa ggaaacttga      4200
agagaaaaga ttcggaatta ataacctcat tacttcaatg tgtctcggtt atctcaatct      4260
tattgaaaca atcttatcct gaagagcagt atctgtctcc atttttgaat aaaccaaatt      4320
cattaattat tgattttgcc atttcacttc tacttggaaa agaagactca cttcaagaaa      4380
ctattgtggg catttacaag caaacaattc tgcattcatt gaatttacta ttgactaacg      4440
ttggagataa tgagcatttc agaaggatgc tgagcggtgc aaactctatt attaatgatt      4500
cagaactggc cattttcaaa aagtttgtgt caacggccac ttttacctct gatgtttcat      4560
tcattacttg caacgaacaa ttattggttg gactgtatat tcttttggag aaaaccacca      4620
cagtgtatct taaacagttg tttctgataa tcagcatgtg cagacccttg gacttatgcc      4680
taaatcgtga ctacgagaat tccaatgatt acgaccacta tttgtttggc caactgtgca      4740 aatttttaa cctttccagt ataatcagtt atttgggatc tggaattcct ggtggaaacc       4800
```

```
tattggagga gcaaaatgat cttatattaa aaggacaatc cactctccct tcaacaattg    4860
agtatccagg tctcgtttat cttgtgaatt tgcctagaga actgaacact tttacttttt    4920
caaaatatga cacccaagat gcagttaatc taaacttttc tgtttgttta acgtgtggca    4980
aaagagtgaa acatagcggt gattctgaaa atgaaattga aaacttccct gggtacaatg    5040
gtgttcctct tactttgttt caccatcata agaattgtcc tttctctgga tatggagaag    5100
cacaatgtat cttcttaacc ccaaagttga ataaattgac tgccttacta aagattcagc    5160
ctccacgagg aatttctgat cgctcgctat atcacagtac atttgcattc ccattgagca    5220
gcccatatct aaccacacat ggagagtcac attctggtca tggaggcttg atacgcaaag    5280
cgttcctgaa tagagatcga tttcgaaatc tgaatgagct atggttggat ggtgaactag    5340
ctttgtatat ttcccgaagc cttggggatt ctcaaattgt agcggaacca atcaaccctg    5400
ttatgattac aatgccggga ggtattcagg aggcattaaa tcttgcgttc accactttcc    5460
tcggtgacca agaacccggg gatgatgact tggaagatta tgagtatgac atactgttaa    5520
atagatga                                                           5528

<210> SEQ ID NO 23
<211> LENGTH: 3168
<212> TYPE: DNA
<213> ORGANISM: Pichia pastoris

<400> SEQUENCE: 23
atgtctgcct ttggtgtggt tccgagtgta ttaaacactg gaaaccagat caagcagaaa      60
aacggaacgc ttttcaagaa atcttctgga gtttacaata aacagcagcg ggatcacaat     120
tccagggata aaaagcgatc agctcgtaaa acaaatacac cgccaacacc gactgagagt     180
acttccgcaa agaagtcatc aactcaatca gacgacaaag tgagtcctga tattttacaa     240
ttgtcgcata ttgagattca atatgtgggc ccacttcttt ccaacccaga atctttggga     300
tatgtgaaac aaaacaataa taccaaaatc aagactccga atatttagt ggatacagat      360 tcaaacctgg tttttggtcc tgatacaact aataaatggg atattgagaa ccagcacaaa     420
atgatcgaaa tggaatcttc ccatcaaggt gactggcaag gtatttatga acaatttcaa     480
gaaatgaata aagtggagcg tcaaaaaatg gaagatctgg gcttggtggc aaaagaggga     540
caaagcatgg acctgacaaa tgctatctca ttcaaaggta gctgcgtgga tatgtgtccc     600
gtttatgata gagtcaagag ggaggtacag agagatgttg atccattgga gagagatcct     660
gccactggta agatatctcg agagagagct ttaaagaaat ttgtgcgtcc ttcaggccaa     720
gcaccgcctc ttccttctga cgtaagacct cctcatattc tggtaaaaag tttaaactat     780
attgtggata atttgctgga taaattaccg caaagtcatt cattaatttg ggatagaacc     840
cgtagtatca gacaagattt tacactacag agctactctg gcttggaagc aattgagtgt     900
aacgaaagaa tttgtcgcat acatctactt tgtgctcata taatgccggg ttctgatcaa     960
tctgacttct ccaagcagca agaaattgaa caattcacaa aatcattgaa aacattaaca    1020
gacatatatg atgttgtcag atccaaagga ggaaaatgtg ccaacgaagc tgaattcagg    1080
gcttataatt tgctggtgca ttttcgggac ccaaatctaa ttcatgaaat ccagaactta    1140
cctactcgaa ttcttaagga cgaacgagtt caacttgctt taatgtttcg aagtctacta    1200
ttgaataata atttcaaaga ataccagagg aacattcctg gttgcttggg ggttttttcag   1260 cagtttttca atatgtgttt tgatccagcc accccattct taatcggatg tgtgctggaa    1320
```

```
cttaattttg aagagataag attttacgct ttgaaatcga tctcacgttc ttatcacaag    1380
aaatctgccc ctctaacgac ccagaagtta gcatctatgc tcggatttga ttccgaggat    1440
aagctcctaa cttttcactaa ttatttcaag actcctacgt gtactaattc tagaaatgaa    1500
acgtgcattg atatctcaaa acttagatac gagagtttta cggatttggc tgctccaaag    1560
cagatttaca cttcaagatt agacaacaaa ttaaaaggat tcacctataa ggatgttgtt    1620
gatcaaggat taaataacac atccttgcac atagctaatt tgaaagaaac aatggctcag    1680
aatcaacata ttgcagtgga gaaattaccc aatatctcat ttccacaaca tgctttgtct    1740 tctaccccctt tcgaagtaga atcaaagtca gacatagtca gatcttcttc cggatcggct    1800
ccgcccagaa ctttgatccc accgattcaa gaaaaagtaa taacttctca aatacagcca    1860
ccaataactc ccgtcgttcc cactgaagaa atccaaactc ttccaaaaat agaggagccc    1920
aggttcaaag atcttccaaa ttttgaaaat gcatgcaaag aggtttcctc tattttaatc    1980
aagaagacta tatctccttt gattgctccc atagtgaaca atcagctaga agagtacaac    2040
cggcgacaaa cggtttttaag ggatcaggag agacaaaatc aaagaagaca acttttgatt    2100
tcatcccttc aggaagaatt gtactctgct tttatacgag aacaagtgta tattcaagtg    2160
gttgatactc aagccaaaga gtgctttaac aagaatctga aacggcgaat atttcagaaa    2220
ttcatcgggg gtttaattac attgaaaaac aaacaaatga ataagagaag aaaacttgat    2280
gaaattcaag tcttcaagaa taaggttgtt tcctcaagtc aacttcggta ttcagtttca    2340
agaagtcaaa cggaggacaa ttcaacgtca aactcgagtg acgaggaagc atcagctgtt    2400
cagatgaata ttactctttc accatctgtg gatccacttt ggtcacccat agatattaag    2460
tttatattag actccaattt aaagttgttt gaggataaca aggataaata ctggaatttc    2520
atgtttgcga ttgccgattg gactattcta ccaagcaaat ggcttcgtta caaattccaa    2580
cttcaaaacc ccagtctcat aaatactgtt gaatcctcaa attacaaagc caaattacgg    2640
gctctaccca gtgacaaact tcttacaagg gaatacatgg agcactgtcg atttttggta    2700
tttcaagtcg gaaaggttga tgaatcatca aacctgaaag aatctttgtt cagagactca    2760
cagtttatta accgattaat gaaatatgcc aagaagtact cgcaatacca gattggagta    2820
cttgtcttat attatcatga ggatgactct tttgataaac agaaaattat tgatcttttg    2880
ttattagaac aatacacaaa taagttagtc aactcactcg agatagttga catgaacaaa    2940
ctcacaaatg atgaactgat aaaagcattg accacgctag tccacaacta taaggataaa    3000
ggtatcaaca aatcggtacc aacatcttcc accaaaggac acaccactag cattatggaa    3060
caggatatga cagtatacag ctacagcacg tccaattcca gggatgctaa gcttaattat    3120
attttgaagc aagcctaccc ccgcaggggg tttcacttga aacaatga                 3168
```

```
<210> SEQ ID NO 24
<211> LENGTH: 1401
<212> TYPE: DNA
<213> ORGANISM: Pichia pastoris

<400> SEQUENCE: 24
atgtcagaat ggccctcagc tttggaaaat tttgtaagtc attgtttcca gcgtgccaac      60
attgagagct ttccacccgg caaaaaaaaa gaactccaaa aacagttgac gcaaatcatc     120
aatttagcaa ttcttgaaaa caaacttaat tctaataact ggtccaaaca aaagctacca     180
atatttggag aagcaagaga gttagaattg gagcagaaaa tgggaaatgt ttatccaatt     240
actgtttcta gtcgaagaag tgacttgatg catcaagagg cagttcaacc atctgagcct     300
```

-continued

```
ttagttccct ccgaaagcca acaaaagaaa aagtctagag aattgcgatt taagatcact      360
aaaaaaagtt ctgtatcacc cgcaaataaa atacaagttg cttgtgactt gaattgtaaa      420
cttgtgggaa ctaacacctc tatcgagaaa gattattata gacttacatc tcatccggat      480
ccttccatgg taagaccttt gcctatttta aagaaatcgt tgcagcatct ttacgccaaa      540
tatcaaagtc tagaacgttt caaagctctc agcaaggcag agtacagcta ttttttgaat      600
caactgaaat ccctaaggca agacctcaca gtgcaagaca ttcagaatca gttcactgtt      660
aaagtttacg aatttaatac tcaattggcg attcaaaatg aagattttgg tgagcttaat      720
caatgtttga ctcagctggc gcaattgtac actgtatcaa ctatgggtca tacttattac      780
tattctgata ctggcaaata caaccaagag cacaactgtt ttcttgccaa ggatctttgt      840
gaggatcgaa accatatcaa tatgttcaaa tttacgagtt atagaatttt atattttctt      900
ctcatagacg cccctggga attgctaaaa ataaggcagg atttattcaa ccgtggtcaa      960
cagtatgcaa ttcgtcacaa caaatttctt ttgaagtcat tcaagctttc ggatctcata     1020
accgccatgg attatattca tatcaaggac gaatattcat tcctcgtgaa tatggactca     1080
gatgtctgca atttaaggac agtgtttgat gacgaacata tgactttgaa ccaagacgac     1140 tggttttttct ataagatact ctaccataag attttcttac gagaacagct gaaggccctg     1200
ataactataa gcaaatctta tcgacagata tccctctact acttgaaaaa tctactgatg     1260
gatttagtat tcttggaaaa gaataagtta tctcgtttca ttgagaatgg tgaggtattt     1320
aactgcacga gcgcaagatc attactgctt caaatagaga agaagcagct atcaaagata     1380
gatatcaagg gtcaggtatg a                                              1401
```

<210> SEQ ID NO 25
<211> LENGTH: 1075
<212> TYPE: DNA
<213> ORGANISM: Pichia pastoris

<400> SEQUENCE: 25

```
atggttgact cagagactat caacaaattc atagaagtaa cgggagcctc tgccttccaa       60
gcaattcagt acctagagga gactgatgac tttgaagcgg cagtcaatga ttattattcc      120
tctcaactgg agaatgagaa gggcaagggt aaatcagaac gtccagtcaa tcaaacaaag      180
gcttctgcag ggcccaagat cagaactttc aacgacctaa atagcaactc aaatggggac      240
aacaatcttt tcacaggtgg tgaaaagtcc ggtcttcaag ttgagaaccc agacaaacgt      300
ggggacccct ttgggttggt caatgatctt ttgaagaaag ctgaggaaac tggccaacaa      360
ccagatacaa ggccccatga agaagctcct gctagacaat ttgttggaac tggccacaag      420
ctgggcagta cggacagtcc ctccgaagtt agtgtctgac cctgcctcaa gaataagaag      480
agctcagaaa gtcagccgac agataacatt ttggaaggac ggattccaag ttggagacgg      540
agatttatac agatatgatg accctgcaaa cgcaagatat ctagccgact tgaacgctgg      600
aagggcacca ctggctcttc tagatgtcga gattgggcaa gaggtagatg tcacagtgca      660
taaaaagata gaaaaaaatt tcactcctcc taagaaagcc cgagttggct ttcaaggtaa      720
aggtcagaga ttagggtctc cagtaccggg cgacataaag ctcagtcaat ctcctgaggt      780
gcaacaagaa acacaagagg aagctgagga ggaaaagcaa aaggaggagg ccgagcagct      840
gggaactggg gattctcccg ttcagattag actcgccaat ggtcagagaa ttgttcatag      900
attcaattct actgattctg ttgctcaatt atatgcattt gtcaatgaac atagtccctc      960
```

-continued

```
cgccagagaa tttgtgcttt ctctagcttt cccggtgaaa cctattgaga acaatgagga     1020
cacactcaag gatgctggac tcataaacgc tgttgttgtc caaagatgga aataa          1075

<210> SEQ ID NO 26
<211> LENGTH: 897
<212> TYPE: DNA
<213> ORGANISM: Pichia pastoris

<400> SEQUENCE: 26
atgggcgtga tacttccaga cgatggtaag caatcgggag gccaaccaaa tagaagggct       60
aaagtcctga gccgattttt accaccagaa catcaaagac cttcaatcgg cctcttcctg      120
ggacttttta ctccagcagc tgataatgag attgccctgt ggacttgcat tggcgctcag      180
ctctttagtg ggctggcatt gcttagaatg agccgaagat ttgttttttc gcccgatcaa      240
tctgtaagaa ggtttctctt taagactttt cataatgtgg taggtgcagc cctgatattt      300
gggagcggat tagaagggac taggatgctt ctacctgagg atccttggaa agaagaagct      360
agaaaagcaa gaatattggc ccaattgaaa ggtgagcccg ttagttggtg gtatggaccc      420
aagagtttta ttccttctgg aaggttagaa tacacaaaac agatgcagtt tcacaacttt      480
gaagtcatgc ataaatcacc cgaaaaaata gcccgagctc tcatgattaa ggacaaactc      540
aaggaggaaa caaataccct ttattcgtcc attcatgaga aagcggaaca acagactatt      600
cgactctcta aagatctaca gaacaacgtt cccctcaaag gggtaacgtc atatgttcct      660
caatttagca cttcaaatac ggacaccaag ttatatttga aaaatgttag cttgaagacc      720
catgccgacc tggaaaaggt ctgggcagaa cacaatcctt gggacatcct ggaagagaaa      780
atttctccaa tttccgtaat tgcactgcca aagtttaacc caattatatc tgaggttgaa      840
cctgacaagc agcaaccatc tacgggtgat atcaaataca ttagtgacag aaaataa       897

<210> SEQ ID NO 27
<211> LENGTH: 1530
<212> TYPE: DNA
<213> ORGANISM: Pichia pastoris

<400> SEQUENCE: 27
atgaaatatt tgccactcgt tgctaccctg gcctcttcgg ccctcgctgc tggcatcaac       60
ttcgcccaat tactggacca gaagccactg gacattgccg ataatgttaa atgggaattg      120
aagcctgagg tcgactctgc tgctcttcaa agtgcagtca atgagctaga cttgaaaatc      180
gaagccagct atttgtttaa agttgcacat ggttccgtct ttgaatacgg acatcctacc      240
agagtcatcg gttctcctgg tcactggtcc acaatcaacc atgtcctcga cacattacat      300
aacttcaaac actactacga cgttgacgtt cagccatttg aagcctttac cggtatcctt      360
aagtctttct cattgaccat taacggagtt gcaccaaagt ctgcagaagc tttagattta      420
actcctccta ctcctggcgg ttttccagtg accggtccag tcgttttagt tgataattat      480
ggttgtcaag cttctgacta tccattcaac gtgactaacg gaattgcctt aattcaaagg      540
ggttcttgtt cattcggtca aaaatcagaa cttgctggtc tccgtggagc caaagccgct      600
ctcatttaca caacgtgcc aggtagtgct aagggaacct taggtgcccc aactcctcat      660
caggtaccat cgttgtcact ttctcaggaa gatggagagg ccgtcaagcg tcagcttctg      720
acttctggaa gcgtaattgc aactgtcgct gtcgattcct acgttaagaa gttcaaaacc      780
aagaatgtga ttgctaccac tcgttacggt aatgatagca acattgtgat gctaggtgca      840
cattcagact ctgttgctgc tggaccaggt atcaatgacg atggttctgg taccatctct      900
```

```
cttttgaacg tggccaaata cctaactaaa ttcaaagtta ataacaaggt tcgtttcgct     960
tggtgggcag ctgaagaaga aggattactt ggatccgact actacgtttc aaagttaacc    1020
cccaaggaga aatctcagat tcgtttgttt atggactacg atatgatggc ttcccctaac    1080
tacgcctacc aggtctataa tgccactaac agcgagaacc cagttggatc tgaggagctt    1140
aagaatttat acattgactg gtacgttgaa cagggtctga actacactct agttccattt    1200
gatggccgat ccgactatga tggattcatc aagagcggta ttcccggagg tggtattgct    1260
accggagcag aaggtttgaa gaccgaagag gaggctgaac tatttggtgg tgaagctgga    1320
gttgcatatg acccatgtta ccactctctt tgtgacgatt tggccaaccc tgactatgtt    1380
ccatgggttg tcaatactaa attaattgcc cacagtgtcg ccacttatgc aaagagcttg    1440
gacggattcc cattgcgtga ggagcctagc ccattcaaga tgactgccca gtcaaacttc    1500
aagtaccacg gtccaaaact tgtcctttag                                      1530

<210> SEQ ID NO 28
<211> LENGTH: 513
<212> TYPE: DNA
<213> ORGANISM: Pichia pastoris

<400> SEQUENCE: 28
atgctcaaac actccttaaa aacagggttg gtctttctca cttggatacc ggtgatttat      60
acggtaaagg aacacctgat atacgttgga aaggtggaag gatcctcaat gtcacccact     120
ttgaatcccg ttaaaggtta ttctgactat gtgattttat ggaagttaaa cttcaaagag     180
tcactcaaag tgggagacgt ggtttttata aggtctcctg tagatccaga gaagttatat     240
gctaaacgta taaaggctgt tcaaggggat accgtggtga ctaggcatcc ataccccaaa     300
gacaaagtgt ccattccaag aaaccatctt tgggtagaag gagacaatat acacagcgtg     360
gatagtaaca actttggtcc gatatcgttg ggccttgtat taggaagagc aactcacgta     420 attttttcccc tgaacaggat aggtaatatc tctggtgaag ggggtagaga agttagggag     480
gattatttaa gagcggagga cagtccgatg taa                                   513

<210> SEQ ID NO 29
<211> LENGTH: 915
<212> TYPE: DNA
<213> ORGANISM: Pichia pastoris

<400> SEQUENCE: 29
atggtttctg aaattcagct tagattagct gttattattt atgatatact ctgttcggcg      60
tcttatgttc tagtcatcca tttgagacca accagagccc ttccgcatca acccatagac     120
cgtaacaatc tctaacgat taaagaaagg tgccagcgag ccagtgtgtt gactgctaca     180
catgtattat tattgcctat tcttttaaaa gtgttgagac tgtcagaaat tgcggaaact     240
acggcgaaac ttggaatagt ggtgggatat cacaaccaga gctggtcttt ctctaacctc     300
caagatgata ttgtcagcat tttcaaagct ttaggtttga ccatgattct cttttctggt     360
cctattgtag attatttta ctattcaaac tcaacagaag taatcaagca agatctggcg     420
tatgtcgtta gcctcgaggg tatgcgtgat ctacttgtgg gacccatcac tgaggaactt     480
ctttatcggt catgttccat ttcattaatg ctagtagcta acgattacgc caacaaattt     540
ctgttcggcc aacactggtt aataatggta tcatcactct acttcggtat agcacatctt     600
catcatgctg ttgaactgta tcattgtaaa agatattcat taactaccat aaccatatca     660
```

-continued

```
actgccttcc aatggtcata tacaacgtta tttggaatat atgcaagctt tctatacttg      720
cgaacaggat ctgtatggtc agcaatagtt gttcattcat tttgcaacat gatggggttt      780
ccccggttga catttggacg tgatgaagcg agagattgga aagtgggtta ctatgtgttg      840
ctcgctctag gttccgtcct attcaaaaag tttctttact ctctaacaga atctaaccat      900
acgcttcttc tataa                                                       915

<210> SEQ ID NO 30
<211> LENGTH: 2451
<212> TYPE: DNA
<213> ORGANISM: Pichia pastoris

<400> SEQUENCE: 30
atgtatcccg aacacaagta tcgggagtat caacggaggg tgcccttatg gcagtactcc       60
ctgttggtga ttgtactgct atacgggtct catttgctta tcagcaccat caacttgata      120
cactataacc acaaaaatta tcatgcacac ccagtcaata gtggtatcgt tcttaatgag      180
tttgctgatg acgattcatt ctctttgaat ggcactctga acttggagaa ctggagaaat      240
ggtacctttt cccctaaatt tcattccatt cagtggaccg aaataggtca ggaagatgac      300
cagggatatt acattctctc ttccaattcc tcttacatag taaagtcttt atccgaccca      360
gactttgaat ctgttctatt caacgagtct acaatcactt acaacggtga agaacatcat      420
gtggaagacg tcatagtgtc caataatctt caatatgcat tggtagttac ggataagaga      480
cataattggc gccattcttt ttttgcgaat tactggctgt ataaagtcaa caatcctgaa      540
caggttcagc ctttgtttga tacagatcta tcgttgaatg gtcttattag ccttgtccat      600
tggtctccgg attcttccca agttgcattt gtgttggaaa ataacatata tttgaagcat      660
cttaacaact tttctgattc aaggattgat caactaactt atgatggagg cgaaaacata      720
ttttatggca aaccagattg ggtttatgaa gaagaagtgt ttgaaagcaa ctctgctatg      780
tggtggtctc caaatggaaa gttttttatca atattgcgaa ctaatgacac ccaagtgcct      840
gtctatccta ttccatattt tgttcagtct gatgctgaaa cagctatcga tgaataccct      900
cttctgaaac acataaaata cccaaaggca ggatttccca atccagttgt tgatgtgatt      960
gtatacgatg ttcaacgcca gcacatatct aggttacctg ctggtgatcc tttctacaac     1020
gatgagaaca ttaccaatga ggacagactt atcactgaga tcatctgggt tggtgattca     1080
cggttcctga ccaagattac gaacagggaa agtgacttgt tagcatttta tctggtagac     1140
gctgaggcta acaatagtaa gctggtaaga ttccaagatg ctaagagcac caagtcttgg     1200
tttgaaattg aacacaacac attgtatatt cctaaggata cttcagtggg aagggcacaa     1260
gatggctaca tcgacaccat agatgttaac ggctacaacc atttagccta tttctcacca     1320
ccagacaacc cagaccccaa ggtcattctt acgcgtggtg attgggaagt cgttgacagt     1380
ccatctgcat ttgacttcaa aagaaatttg gtttacttta cagcaaccaa gaaatcctca     1440
atagaaagac atgtttattg tgttgggata gacgggaaac aattcaacaa tgtaactgat     1500
gtttcatcag atggatacta cagtacaagc ttttcccctg gagcaagata tgtattgcta     1560
tcacaccaag gtccccgtgt aaccttatcaa aagatgatag atcttgtcaa aggcaccgaa     1620
gaaataatcg aatctaacga agatttgaaa gactccgttg ctttatttga tttacctgat     1680
gtcaagtacg cgaaatcga gcttgaaaaa ggtgtcaagt caaactacgt tgagatcagg     1740
cctaagaact tcgatgaaag caaaaagtat ccggtttat tttttgtgta tgggggggcca     1800 ggttcccaat tggtaacaaa gacatttct aagagtttcc agcatgttgt atcctctgag     1860
```
cttgacgtca ttgttgtcac ggtggatgga agagggactg gatttaaagg tagaaaatat    1920
agatccatag tgcgggacaa cttgggtcat tatgaatccc tggaccaaat cacggcagga    1980
aaaatttggg cagcaaagcc ttacgttgat gagaatagac tggccatttg gggttggtct    2040
tatggaggtt acatgacgct aaaggtttta gaacaggata aaggtgaaac attcaaatat    2100
ggaatgtctg ttgcccctgt gacgaattgg aaattctatg attctatcta cacagaaaga    2160
tacatgcaca ctcctcagga caatccaaac tattataatt cgtcaatcca tgagattgat    2220
aatttgaagg gagtgaagag gttcttgcta atgcacggaa ctggtgacga caatgttcac    2280
ttccaaaata cactcaaagt tctagattta tttgatttac atggtcttga aaactatgat    2340
atccacgtgt tccctgatag tgatcacagt attagatatc acaacggtaa tgttatagtg    2400
tatgataagc tattccattg gattaggcgt gcattcaagg ctggcaaata a           2451

<210> SEQ ID NO 31
<211> LENGTH: 1866
<212> TYPE: DNA
<213> ORGANISM: Pichia pastoris

<400> SEQUENCE: 31
atgaaaccgt atcaccatgc aaaaagccgc ccaataggca gctacctgta ttttggggtg     60
tttaccgtag cattgacatt tctgacgtgg cttaaatatg acgcagagct gtttgctcag    120
caggttcact cgaaagacat ttatgaccca cagttcaaca ttacgttgcc aattgatggc    180
ccaacattta ccccatcaaa gaactattca attagtgttc aaaatgcagc agtggcgtcc    240
gatatagaac aatgttcaaa attaggtgta tctattctgc agcaaggtgg caatgcggcc    300
gattcagcag tcaccgtggc cctgtgtatc ggaacaatca attcgtattc gtccggtata    360
gggggaggag gattcattgt ctctaagtta attgataatc ctaccgctct gagttttgat    420
tgtcgagaaa tggctccttc taaaagtttc aaagaaatgt tcaactatca tgaggagaag    480
gccagagtag gtggtttggc tgtcgccatt ccaggagagt taaagggact ctatgaactg    540
tttcagcacc atggttctgg taatgttgag tggaaagatt tgattttgcc cgttgctgag    600
ttggctgagg tgggatggac tgtcgatccg ctgtttttcta gtgcattgaa atctattgag    660
caccatattt acgagcattc atatgattgg gcctttgcat tgaatgaaga cggaaaaatt    720
aaaaaaagag gtgactggat taatcgtccc atgttggcta ctacgttgag gagaaatagct    780 gaaagtggca acgttgatct attctatgac ccagagagcg atatagtaca aagcatggtg    840
aatgctacta gaaagtatgg aggaatcctt gaagcctcag actttgcaaa atatagagtt    900
cgaattgaag aatcgttgac attgcataac tttacatctg acggccttac ggtttatacg    960
tccaatgggc atcctcagg gttggtgctc cttgctgggt tgaagctcat ggacttattc    1020
gaagatttca aggaatttca taatgatttc ggggctgttg agtctcaaag gcttgttgaa    1080
acgatgaagt ggatggcttc agtaagaagc aaccttggag atttgaacat ttactccacc    1140
aacgaaactg aaattgacga tcataggaag aggtacgaca gatacaaatc agatgagtgg    1200
gcaatagaaa ctcatgccaa aattaatgat tcccacacac ttccttcttg gaaagattat    1260
gctccagcct ttctacctaa tgatcctcat ggtacatctc atttcagtat cgttgaccaa    1320
tacggtaatg cggtggctat gacaaccact gttaaccttg gatttggatc taaaatacac    1380
gatcctatat caggattat tctaaatgat gaaatggacg atttttcagt tccaacatca    1440
tctaatgcat ttggtttgca tccatcaatc tataattggg tagagcctta caaaagacct    1500

-continued

```
ctctcttcat gtgctcctac cgtaattgtt gattctctgg gagtacctca ttttgtcatc   1560
ggggcagcag gagggtccaa gatcactacc acagttttac aagcaattat aagagtttac   1620
cattatcacc tggatctttt agacgtcatt gcatatccac gctttcatca tcaactactt   1680
ccggaagaag ttcttctgga gtttccacga gataataaac taatacgcca tctaaaagaa   1740
agagggcatg atgttagagt ccaagcacca atatccacca tgaatggtat cctacgaaaa   1800
agaggtggaa gcctgatagc agttagtgat cactggagaa agcttggtcg accttggggc   1860
ttttga                                                              1866

<210> SEQ ID NO 32
<211> LENGTH: 1605
<212> TYPE: DNA
<213> ORGANISM: Pichia pastoris

<400> SEQUENCE: 32
atgaaatcgg ttatttggag ccttctatct ttgctagcat tgtcgcaggc attgactatt     60
ccattgctgg aagagcttca acagcaaaca tttttttagca agaaaaccgt tcctcaacaa    120
gttgctgaat tggtgggcac ccattactct aaggatgaga taatcagtct atggaaggac    180
attgagctga atgtacccag ggaaaagatc caagaggcct tcgataagtt cgtaaaacaa    240
tcaactgcca cttcccccgt tagaaatgaa tttcccttgt ctcagcaaga ttgggtgaca    300
gtgaccaaca ccaagtttga taattatcaa ttgagggtta aaaaatccca ccctgaaaag    360
ctaaacattg ataaggtaaa gcaatcttcg ggatacctgg atatcattga tcaagataag    420
catcttttct attggttttt tgaatcccga aatgatccgt ccacagaccc aatcatccta    480
tggttgaatg gtggacccgg ctgctcttct attacagggt tgctattcga aaagattggc    540
cccagttaca tcaccaaaga gattaagccg gaacataatc cttattcatg gaacaacaat    600
gctagtgtta tcttccttga gcaaccggtt ggagtaggat tttcttactc ttctaagaaa    660
gtcggtgata ctgcaactgc tgccaaagat acatatgtgt ttttggagct tttcttccaa    720
aagtttcctc agttcctgac ctctaatctg cacattgctg gggaatcgta tgctggccat    780
tatttgccca agattgcttc tgagattgtg tctcacgcag acaagacgtt tgaccttttca    840 ggagtcatga tcggtaatgg tcttactgat cctctaattc agtataagta ctatcagcca    900
atggcctgtg aaaaggtgg ctacaagcag gtcatttcgg acgaggaatg tgatgaattg    960
gatagggtct atccaagatg tgaacgttta acgcgggcat gttatgagtt ccaaaattca   1020
gttacttgtg ttccggcaac actttattgc gaccaaaagc tactgaagcc gtacactgac   1080
actggcttga atgtctatga tattcgtaca atgtgcgatg aagggactga tttgtgttac   1140
aaagaactgg aatacgtgga gaagtacatg aaccagcctg aagtgcagga agccgtgggc   1200
tctgaagtca gttcttacaa aggttgtgac gatgatgtct tcttaagatt tttgtactct   1260
ggcgatggat ctaagccttt ccaccagtat atcacggatg ttctcaatgc aagtattccg   1320
gttctgattt acgcaggtga taagattat atctgtaatt ggctaggaaa ccaagcttgg   1380
gtcaatgagc tagaatggaa cttgtctgag gaattccagg caactccgat tcgaccgtgg   1440
ttcactttgg acaataacga ttatgcagga aacgtacaaa cttatggaaa ctttttcctt   1500
ctaagagtat ttgatgctgg tcacatggtt ccttacaatc aaccagtcaa cgcacttgac   1560
atggttgtca gatggacaca cggtgatttc tcatttggtt attaa               1605

<210> SEQ ID NO 33
<211> LENGTH: 2520
```

<212> TYPE: DNA
<213> ORGANISM: Pichia pastoris

<400> SEQUENCE: 33

```
atgactcaat tagatgtcga atcattgatt caagaactca cactaaatga aaaggttcaa      60
cttctgtccg gatcagactt ttggcacacc accccagtta gacgtctagg aattccaaag     120
atgagattat ctgacggtcc taacggcgtc cgaggaacca agtttttcaa tggagttcca     180
accgcatgtt ttccttgtgg tactggatta ggtgccactt tcgataaaga acttctaaaa     240
gaagctggct ccttgatggc agacgaagct aaagcaaaag ctgcctcggt agttttgggt     300
cctacagcta acattgctcg aggccccaac ggaggaagag gcttcgaatc ttttggagag     360
gatccagtgg ttaatggatt atctagtgct gcaatgatta atggattgca aggtaaatat     420
attgcggcta ccatgaaaca ttatgtttgt aacgatttag agatggatcg taattgcatt     480
gatgcacagg tgtctcacag agctctaaga gaagtgtacc ttcttccatt ccaaattgcg     540
gtaagagatg caaatcctcg cgctatcatg actgcttata ataaagcaaa cggtgaacat     600
gtatctcagt caaagtttct tctagatgag gttttgagaa aagaatgggg ctgggatggt     660
ttgttaatgt ccgattggtt cggtgtgtac gatgcaaagt cttctatcac taatggtctt     720
gacctggaaa tgcctggtcc acctcagtgc agagtccatt cggcaaccga tcatgccatc     780
aattctgggg agatacacat aaatgatgtc gatgagcggg tgcgaagcct cttaagttta     840
attaactatt gtcaccagag tggcgtcact gaggaggatc cggagacatc cgataacaac     900
accccagaga ccatcgaaaa actcagaaaa atcagtagag aatcaatcgt cttgctgaag     960
gatgatgaca ggaacagaag tatccttcct ctgaagaagt cagataaaat tgccgtgatt    1020
ggaaacaatg ctaagcaggc tgcatattgc ggaggaggtt ctgcttctgt tctctcgtac    1080
catactacaa ctcctttcga ctctatcaaa tcacgattgg aagattcaaa cactccagct    1140
tacaccatcg gtgctgatgc ttacaagaac cttccgcctt tgggccctca gatgacagac    1200
agcgatggaa aaccggggtt cgacgccaaa ttttttgttg gctcgcctac atctaaagat    1260
agaaagctga ttgatcactt tcagttgacc aattcacaag tcttcctggt tgactactat    1320
aatgaacaga tccctgaaaa caaagagttt tacgtagacg ttgaagggca attcattcct    1380
gaggaagatg gaacctataa ctttggcttg accgtattcg gaacgggaag attattcgtg    1440
gatgataagc tggtttccga tagtagccaa aaccagaccc ctggagattc cttttttgga    1500
ctagcagctc aagaggttat cgggtccatt catttggtca gggtaaagc atataaaata    1560 aaggttcttt atggatccag tgtcaccaga acatatgaaa ttgcagccag tgttgctttt    1620
gaaggaggag catttacttt tggtgcagca aaacaaagaa atgaagatga agaaattgct    1680
agagctgtgg aaattgctaa ggcaaatgat aaagtggtgt tgtgcatagg tctaaatcaa    1740
gactttgaaa gtgagggatt cgacaggccg gatatcaaaa ttcctggagc aaccaacaag    1800
atggtaagtg ctgtttttgaa ggctaaccct aacactgtga tcgtcaacca aacaggaacc    1860
ccagtcgaga tgccatgggc cagtgacgct ccagtgatct tgcaggcttg gtttgggggg    1920
tctgaggcag ggaccgctat agctgatgta ctattcggtg actacaaccc tagcggaaaa    1980
ctaacggtta cttttccctt gagatttgag gataaccctg catatctcaa cttccaatcc    2040
aataagcaag catgttggta tggggaagac gtttatgtgg gctacagata ttacgagacc    2100
atagacaggc ctgtgttatt cccatttggc cacggattgt cattcaccga atttgatttt    2160
accgacatgt ttgtcaggct tgaagaagaa aaccttgaag ttgaggttgt agtcagaaac    2220
```

-continued

```
acaggaaagt atgatggtgc tgaagttgtg cagttgtacg tagcaccagt atccccatcc    2280
ctgaaaaggc ccatcaaaga actcaaggaa tatgctaaga ttttcttagc cagtggtgag    2340
gcaaaaacag ttcacctgag cgttcctatt aagtatgcca cttcgttctt tgacgaatat    2400
cagaagaaat ggtgctccga aaaggagag tacacaatct tactgggatc cagctcagca    2460
gatattaaag tttcgcaatc tattactta gaaaaaacaa cttttggaa aggtttatag    2520

<210> SEQ ID NO 34
<211> LENGTH: 5004
<212> TYPE: DNA
<213> ORGANISM: Pichia pastoris

<400> SEQUENCE: 34
atgttcctca aaagtctcct tagttttgcg tctatcctaa cgctttgcaa ggcctgggat      60
ctggaagatg tacaagatgc accaaagatc aaaggtaatg aagtacccgg tcgctatatc     120
attgagtatg aagaagcttc cacttcagca tttgctaccc aactgagagc tgggggatat     180
gactttaaca tccaatacga ctactcaact ggttcccttt tcaacggagc atctgttcaa     240
atcagcaacg ataacaaaac cactttccag gatttgcaaa gtttgcgtgc agtcaaaaat     300
gtttacccag ctactctcat tacattagat gaaacatttg agcttgctga cacgaagcca     360
tggaaccctc atggaattac cggtgtcgat tctttgcatg agcaaggata tactggtagt     420
ggtgttgtta ttgcagttat cgatactggt gttgactata cacaccctgc tctgggtggt     480
ggtatcggag ataatttccc tatcaaagct ggttatgatt tgtcttccgg tgatggtgtc     540
atcacgaatg atcctatgga ttgtgacggt catggtacct ttgtatcctc catcattgtt     600
gcaaataaca aagatatggt tggtgttgca ccagatgctc agattgtcat gtacaaagtg     660
ttcccctgtt ctgatagtac ttcgactgac atagttatgg cgggtatgca aaaggcctat     720
gatgatggtc acaagattat ttcgctatca ctgggatctg actcggggtt ttccagtact     780
ccagcttcct taatggccag caggattgct caagacagag ttgtttttggt ggctgctggt     840 aactctggag aacttggtcc attctatgcc tcctcccctg cttctgggaa acaagtcatt     900
tcagttggat ctgttcaaaa cgaacaatgg acaaccttc cagtaacctt tacctcttca     960
aacggtgaat caagggtttt tccttacctc gcttacaatg gtgcacagat tggatttgat    1020
gccgagcttg aggttgattt taccgaagaa agaggatgcg tctatgaacc agagatctcc    1080
gcagataatg cgaataaagc tattttgtta agaaggggcg tcggctgtgt tgaaaacttg    1140
gaattcaatt tattgtctgt ggctggttac aaggcttact tcttgtacaa ctcattttca    1200
agaccatgga gtctcttgaa tatttctcca ctgattgagc tagacaacgc ttactctctt    1260
gttgaagagg aagttggaat atgggtgaaa acccaaatcg acgccggtaa caccgtcaag    1320
ttaaaggtga gcacgagtga ccaaatgttg ccatctgata aagagtattt gggagttgga    1380
aagatggatt attactcctc tcaaggacct gcttatgagc ttgaattttt cccaacgata    1440
tccgctccag gtggagacag ttggggcgct tggcccggtg ggcaatacgg tgttgcctca    1500
ggaacaagtt ttgcttgccc ctatgttgca ggtcttacag ctctttatga atcgcagttt    1560
ggaattcaag atcccaggga ctatgtgaga aaattagtct ccacagctac cgatcttcaa    1620
ttatttgact ggaacgcagt gaaacttgag acctctatga atgctccact tattcaacag    1680
ggagctggtc tagtgaacgc tcttggtttg tttgagacta agactgtgat cgtgtctgct    1740
ccttatttgg agctcaatga caccatcaat agagccagtg agtataccat tcaaattaag    1800
aatgagaact ctgagactat tacctatcaa gttgttcacg ttccgggaac tactgtctac    1860
```

-continued

```
tctagatcag cttctgggaa catcccatac ctggtcaatc aagattttgc accttacggt    1920
gatagtgatg ctgcgacagt tgctctatcc acagaagagt tggttttggg accaggagaa    1980
gttggtgaag tcactgtgat cttctctaca gaagaaattg atcaagaaac tgctccaatt    2040
attcagggta agattacatt ttatggtgat gtcataccga ttgctgttcc ttatatggga    2100
gttgaagttg atattcattc ctgggagcct ctcattgaga ggcctttatc agtgagaatg    2160
tatttggatg atggttcctt agcatatgtt gatgatgatc ctgattatga gttcaatgtg    2220
tatgactggg attctcctag attttatttt aacctgagat atgcaaccaa agaagtatcg    2280
attgacttgg tgcaccctga ttatagcatt gagaacgact acgaatggcc tttagtttcc    2340
ggacacaaca actattatgg tcccgtggga tacgactacg attatacctc gggtcaagcc    2400
tttttgcctc gttactttca acaacgtatt aacgaacttg gatatctttc tttttccaga    2460
tttgctaact tttctgtagt tcctgctggt gaatacaaag ctctatttag agttttgcta    2520
ccatatggag acttttggaa caaagaagac tggcaattgt ttgaatcccc agtgtttaac    2580
gtcctcgctc caccgaatga agaaacact actgaagagc caactgagga atccagcgag    2640
gagcctaccg aagagtcaac gtctgagtca actgaagagc cctcttctga gtcaactgag    2700
aaatctagcg aggtgccaac tgaagaaatt actgaagatg caacatccac aattgatgat    2760
gatgaagcat ccaccgaaag ctctactgaa gaaccaagtg ctcagcccac cggtccttac    2820
tctgatttga ctgtcggtga ggccattacc gacgttagtg tcaccagttt gaggacaact    2880
gaagcatttg gatacacttc cgactggttg gttgtgtctt tcactttcaa cactactgac    2940
agagatatta ctctcccacc ttacgctgtt gtacaagtaa ctatcccaaa tgaacttcaa    3000
ttcattgctc atccagaata cgccccatac cttgagccct cattgcaagt tttctacact    3060
aagaatgaaa gattaattat gactagtcag ttcaactacg acaccagagt catcgacttc    3120
aagtttgaca atcgagacca agtaataact caagtggagg gagttgttta tttcacgatg    3180
aaactagaac aagatttcat ttctgcattg gccccaggtg aatacgattt tgaatttcat    3240
acatccgttg attcttatgc ttcgaccttt gactttattc cattgattag atccgagcca    3300
atcaaattga tagcaggtgc accagacgaa gttgaatggt ttattgatat tccaagtgca    3360
tacagcgatt tggcaacgat agatattagt tctgatatcg atactaatga taatttgcag    3420
cagtacttct atgattgctc aaagctcaag tacactattg gaaaagagtt tgatcagtgg    3480
ggtaatttta cagctggatc agatggtaac caatacagca ataccaccga tgggtatgtt    3540
ccaattactg attctaccgg ctctccagta gctgaagttc aatgtttaat ggaaagtatc    3600
tcattgagtt tcacaaatac tcttgctgag gatgaagtat tgagagttgt tcttcactct    3660
tctgcgttta gacgtggttc attcaccatg gccaacgtgg taaacgttga cattacagct    3720
ggtggattgg caaaaagaga actcttctct tatatattgg atgaaaatta ctatgctagt    3780
actggatctg aggggttggc atttgacgta tttgaagttg ctgatcaggt cgaggagcca    3840
actgaggagt caacctcaga ggaatctact gaacaggaaa cttccaccga ggaacctacc    3900
gaggaatcaa ctgaacctac tgaggaatct acccaggaac ctactgaaga gcccaccgac    3960
gagcctactt ctgagtcaac tgaggaacct tctgaggagc caacttctga cgatctctca    4020
attgacccaa ctgctgtacc taccgatgaa cctactgaag agccaactga ggagcctact    4080
tctgagtcaa ctgaggaacc ttctgaggag ccaacttctg acgatctctc aattgaccca    4140
actgctgtac ctaccgatga acctactgaa gagccaactg aggagccgac ctctgagact    4200
```

-continued

```
accgatgatc catcgatagc acctactgct gtgccaactt ccgacacatc ttctggacaa    4260
tcggtggtta ctcaaaacac tacagtcact cagactacca tcacttcagt ctgtaatgtt    4320
tgtgctgaga cccctgtaac aatcacttac actgcaccag ttgtgactaa gccagtttct    4380
tacaccaccg ttacttcagt ttgccatgta tgtgcagaga caccaatcac agttaccttg    4440
acgttgccat gtgaaaccga agacgtgaca aagactgccg gccctaagac tgtcacttac    4500
accgaagttt gcaactcctg tgctgacaag cctatcactt acacctacat cgctccagag    4560
tacactcaag gtgccgaacg tacaacagtt acatcggttt gcaacgtttg tgctgagaca    4620
cctgtaacgc taacatacac tgcgccgaaa gccagtcgtc atacagttcc ttcacaatat    4680
tcaagtgccg gagagctcat ttcatccaag gggatcacga ttcctactgt tcctgcccgt    4740
ccaactggta cttatagtaa gtctgttgac actagccaac gtacactcgc taccattaca    4800
aaatcttcag atgagtctaa cactgttacc actactcaag ccacacaagt tttgagcggt    4860
gaatccagtg gaattcaagc tgcttcaaac agcacgagca tctcagctcc aactgtcact    4920
acagctggga acgagaactc tggatctaga ttttcgtttg ctggactatt cacagttctg    4980
cctcttatct tgttcgttat ataa                                           5004
```

```
<210> SEQ ID NO 35
<211> LENGTH: 1335
<212> TYPE: DNA
<213> ORGANISM: Pichia pastoris

<400> SEQUENCE: 35
```

```
atgcagtttg cttccttact gcttctcttg tatattttct tggggcaaat ttatcctact     60
gaagcagcaa aatattttgt tcgtctgaag aagcctcaca cactagacct cttgttcaaa    120
caggatgaag cagatgcatc tgctgagaac cgaatctctc ttcatggttt aagggaccga    180
atcaaaaaaa agatctcttt tggaacgttc gaaggttttg ttggtgaatt cacaacagaa    240
cttgtagaaa aactaaaaaa gaattcgttg attgcagaca taactcctga cattatcgtc    300
tcatcttgcg atatcgaatt gcagtccccc gctcctgatc acctggctag gttatccaaa    360
gaaggtgccg taagagcaca agatcgtctt cttggaccgg aattttttcta cgatggtgac    420 tggactggag aaggcgtcaa tgtatacgtg atagacacgg gtatcagggt aaatctagat    480
gaatttgagg gcagagcatc atttggtgct gattttacag gcactgggaa agatgactct    540
gttggtcatg aacccacgt agctggtctt attggctcca aaacttttgg agtggccaaa    600
aatatcaact tgtatatccgt aaaagctctc tctggtaatg ggagcggttc gctttcagag    660
gtcctacagg cgattgaatt cgcagtcaag catatgaaag ccagtcgtaa gccaggtgtt    720
gctaacttgt ctctaggtgc accaaaaaat tcaatccttg aaaaagcgat tgaagaggca    780
ttcaagaacg gtttagtcat agtagcagca gctggcaatg ccttcgtgga tgcctgtaac    840
acatcccctg caaactctcc atatgcaatc accgttggag ctataggtga tcacaacgat    900
gaaataacta gattttccaa ctggggagcc tgtgtcgatc tttttgcagg aggggacaca    960
attgtaagtg taggacttct caatggagtc gctgtccgca tgtctggaac ttcgatgtct   1020
gctccaatag tcgcaggctt agccggaata ttacttgacc agggtgtggc cccagaagat   1080
gtaaaaggta agttaatacga gctctcagat gaagggaaga tcaacgataa tactggaatt   1140
ctaaagccgg gaactccaaa ccgaatagcc aacaatggaa ttcgaaaaag tgattatgaa   1200
gatcaaaaag aaaatgacaa tgatgaagac gatgaagacg gggaagacaa tctagaagac   1260
attgaagagg acgaggatta ttgggatgaa gagagaaggt ataggggaata tgcggtatct   1320
```

-continued

```
agtttagtct tctaa                                                   1335

<210> SEQ ID NO 36
<211> LENGTH: 546
<212> TYPE: DNA
<213> ORGANISM: Pichia pastoris

<400> SEQUENCE: 36
atgttcaaca ttatccaacg gatacagagt ttgagcaatt tttatttaac ggtttccatt     60
ctattatgta ttgttacaac agttgtctca attattagta tgttcttgga tgaaacgtcc    120
agtattcctg cccaattaag caatgttgta atatcaacaa atttaaagta tagcagatcg    180
tttggttcag tcggtggtag acctaaagaa aactccaaga ttttatttga tcttgatatg    240
gatctggctc cattattcaa ttggaatact aaacaactgt ttgtacaatt ggtagcagag    300
taccctacct ctgttgccga tgatggtgcg aaggtgacct attgggatag cataaattact   360 gagaaaaagt acgcaagagt gcatgtcaat aagcagaggg gaaaatactc agtttgggac    420
gtgtcggact ccttttcaagg ccgcaatgct acggttaaac tgaaatggaa cttacagccc   480
tatgtcggct ttctattctt tggacaaact aagggagaga ttgaggtggc ctatcctgca    540
acataa                                                              546

<210> SEQ ID NO 37
<211> LENGTH: 870
<212> TYPE: DNA
<213> ORGANISM: Pichia pastoris

<400> SEQUENCE: 37
atgagtgtca tagtgcatcc tcttgcacta ttgacaataa tcgacgagtt ccagagacga     60
ggtcgcaaca acgattccat aatattcggt gggttacttg gtaaacatga tgaatccacc    120
aaccaaatat ctgttgttaa cagctttgtg ataccattga tcgataatca gtttttgaat    180
aaagagtact tgcaggacat gctactcaaa ttttctatca ttaattccaa ctttcgattc    240
gtaggttact atcacgttca atctttaaac ggtaccgaaa ctcaacagta tgacttgaac    300
gctattaacc tagtatgcca agatgataat aggccttcgt cctttgtcca ttggatagta    360
acagatccaa aagagttcaa atcattctcg atgtattact tggatgattc aatggttcaa    420
ctcgtcaatt ccaatattca acattacatt tctaaaccat gccctatga atttaaaaac     480 cttctgtctg agaaaattgc tatcgacaca atcctcaagc aatccaggct agaaaaagac    540
ttatccacca aaaactcact gaagaaatta aacaatagtt atatcgacat tcattcctca    600
ctgaacgttc tctataaatc agtcaatagg cttattcgtt acctcaaaaa atgctcaaaa    660
tcagaagttt caattgacta tgacacagtt caggaaatga atactgtaat actgaaaatt    720
gaaaggctta aattgatacc ccaagtcaag gaggagtttg acttagtgac tctttcacta    780
ctggtagaca atcttgatca gatggatcat cttttgtatc tccggaaaca agtggaacag    840
tacaaaatat ctgaatcaat gtatagttag                                    870

<210> SEQ ID NO 38
<211> LENGTH: 1167
<212> TYPE: DNA
<213> ORGANISM: Pichia pastoris

<400> SEQUENCE: 38
atgaaatttc actcgattgt cttcacattt tcactcgttt tgagttcact ggcgttgtcg     60
```

-continued

```
ataccatggg tgtctgacca catggtccag catctttttg ccgacccttc aatcagtaaa        120
ggtcctgatg tagatctcgt tgggctacat aagcatttgg tcagcatcaa atctctttcg        180
ggctatgaac aagaagtagt atcgtggttg gccgattatc tagccagtag gggtcttact        240
gtggagttga acaaggtcga ggacgaaact gaacgttaca atttgtatgc ttatttggga        300
accacccgca acactaaggt tgtgctaact tctcacttag acacagttcc cccttatctt        360
ccctacaaag ttgaggaagg tggctatatc tttggcagag gaagctgtga tgctaaggga        420
tcagttgcgg cacaagtgat tgccttccta aatctcttgg aagagggctc catcaaagaa        480
ggtgatgtca gtcttttgta cgtcgttggt gaagagattg gaggtgatgg aatgcgcaca        540
gctagcaaga ccttgggtgc taaatgggac actgccattt ttggagaacc taccgagaac        600
aagcttgcca ttggacacaa gggaattgca ctgtttgacc tgaagattac aggaaaatcc        660
tgtcattctg gatacctga gctgggaatt gatgccgacg ctatgttggt ccagattttg        720
cacaagttgc tttttgagac ttcttggcct gtcagtgatt tgctgggaaa ctccacagtc        780
aacgcgggac agatcaacgg aggagtagct gctaatgtta tttcttcgga agcacatgcc        840
aaggttttaa tccgcgtggc taaagacatt gacgctgtag agaagctgat ctacgaggcc        900
attgccccct tcgaggagta tacagacatt acctttcact ccaaagaaga tgctactttc        960
ttggattaca aggttgaagg gttcgagaac tacattgcag cctacagtac cgatgtacca       1020
ttcctagtga cgggctccaa tttgaccaga tatttgtacg gaccaggaag catcatggtg       1080
gctcatgggc ctgatgaaat ggtcaaggtt tcagacctgc aggatagtgt tgacggatac       1140
aagcgattag tctccgtctc actttag                                           1167
```

```
<210> SEQ ID NO 39
<211> LENGTH: 1776
<212> TYPE: DNA
<213> ORGANISM: Pichia pastoris

<400> SEQUENCE: 39
atgccagaga aaagaaaca aaaaaaagag tcgacatctc cattcaaggg taacctagtt         60
gggatctcat tggtagctgt ggcattgttt gccatctacc agtacctcta cccaagctcg        120
ttttcctctc agcctgaaac cccagcccca gttttcgatc tgagcagtga attagaagca        180
ttgtgtcccg tgtaccctgc agtcagatct tccgacttcg aaaaggatcg ccccatctta        240
gagagaattc tgaacgatcc ctcatttaga atcgcttctg ctcaaaaact gagtaaggct        300
gttcagatcg atacccaagt gttcgacgaa caattggacg tggctcaaga ccctgaagtt        360
tggaccaaat tcgtcaagtt ccatgaatat ttggaggcaa ctttccccac cgtttactcc        420
caattgaagg tcgacaaaat caacacctat ggcttggttt tcacttggga aggctcagac        480
cctagtctga aaccactcat gttcttggct caccaagacg tggttccagt ccagaaagat        540
actcttcagg attggtcata tccccctttc gaaggacgta tcgccgatga cagagtttgg        600
ggacgtggat cagctgattg caagagttta ctgattgcat tactggaaac cgtagaattg        660
ctggtagatg aagggtactc accaaagaga ggtgtcatcc tcgcatttgg attcgacgaa        720
gaagcttcag gtacctacgg tgctcacaat atctccaagt ttttgcttga aaatatgggg        780
ccagatagta ttgccctcat tttggatgaa ggtgaggctg tcagttacgt ggacaagaaa        840
caaactaccc tcgttgcaaa gattgctacg caggaaaagg gttaccttga cctagaggtc        900
gcattgacca ctgtaggagg ccattcttct gtcccccta agcacactgc aattggcctt        960
atttccaagt tggtcacaca tatcgaagat catccattgg acccagaaat tagtaccaga       1020
```

-continued

```
aatcctctgg tacagttttc gaactgtctt ggtgcagctg gggctttgag agatgacttc      1080
aagactgctc ttgttgcata cagcaaggat ccgtcgaaca acattgtcaa acaaggtgtg      1140
attaaaggta tttccaagat tgcatttttc ttcggttctt tgattaccac aacacaagcc      1200
accgatctta ttttcggtgg agagaagatc aatgctttgc ctgaaagtgc tagagtagtt      1260
atcaaccata gagtggacgt tgagcgtgat tcagcccaaa tcatagacag attgattcac      1320
ttccacgttg ttcctattgc caaggagcac ggtttcaagg tcacttacag tgactatggt      1380
agtgacaaag ttgaaactgt ctacgagcca gaaggagttg cctcattggg agaattccac      1440
gtttctcctt tctccagagt ctgggagcct gctccagaat ctccatccga cgacaatgtc      1500
tggtccatca tttctggtac cactcgtacg atatttgagg agtttgtgga cccctcggct      1560
aaacttattg caagtccata catgatgcct ggtaacaccg acactcgaca ctactggccg      1620
ctgacaaaga atatctatag atacgttcca ggtattgtag atatttacaa ggctaagata      1680
cactcggtag atgaatctac cgaggttgat gcccacttgc aagttatagc tttctaccac      1740
gagttcatca aggttgccag cgaatgggag ctttga                                1776
```

<210> SEQ ID NO 40
<211> LENGTH: 1275
<212> TYPE: DNA
<213> ORGANISM: Pichia pastoris

<400> SEQUENCE: 40

```
atgaaatcct ctaaagaact atacaaggag gctctcaact atgaatactc ttccgcggtt        60
tctttcaagg cctgggttcg aagtgctcaa atcattttgc gacatgcccg gcagtttgct       120
gaacaaagat acatcagtga gtgctataag ttgtctgttc gttttgtaga cttgattgtg       180
aacaagatgg ccacgcataa agagctcaag caattgaaga aaataaatgc accagtatat       240
ctcacctatt tggatttggc tacgaagaaa gtcccagatg tcatcaagga atgtgaggcc       300
ttgaagacaa ttttggatga tgagtaccaa agctacctca aactgcaaca attgaaacga       360
cagaagcaga aagaccaatt gatccatcat cagaatcagg ctcaaacgca taaattacgt       420
agatcttcat caatattgaa agatcatatc aacgctgttg atgaaagagc gctgttgaaa       480
caactacagc agttgacata ccatgatcgt gaattcgcaa ccgcaataac ggagatgcca       540
aattatccag agatcccca gctgagtatt tcaacgaatc agaacactag atcagaggca       600
cccccacttc caccaagagt atcgcaggaa cagtcattag caccagtatc actagattca       660
tcacaggcag atttacaaca caaaactgtt aacttcaccg aagctgggca accattacga       720
acagtattta tttcagatag actccaatct gagttcctta gactagcgga accaaacacg       780
atacaaaagc tagagacttg tggcatcctt tgtggaaagc tcgtcagaaa tgcattcttc       840
atcacccatt tggttatacc agatcaagag tcgacaccaa acacatgtaa tacaagaaat       900
gaggaaaagt tattcgacac tatagatcag cttgatttat ttgtccttgg atggatacat       960
acccacccaa cacaatcatg cttcctgtct tccatagact tacatacaca gaattcgtac      1020
cagatcatgt taagcgaagc aattgccatt gtgtgtgcac cagcacctca gttttctcat      1080
cattcttttg gatgttttcg gctaacccat cctccgggaa ttccaaccat tacacaatgc      1140
actaggacgg gatttcatcc tcatgaggaa cccaatctgt atgtgacttg taatcgaaag      1200
aacatgggcg acgtgcaagg cggacacgtt gtgatcaaga tcatttacc gtttgaaaag      1260 cttgatctaa gataa                                                       1275
```

```
<210> SEQ ID NO 41
<211> LENGTH: 1347
<212> TYPE: DNA
<213> ORGANISM: Pichia pastoris

<400> SEQUENCE: 41
atgactagtt ctgtagataa agtgagtcag aaggtcgctg acgtaaaact gggctcctcc        60
aagtcaacaa agaataacaa gagcaaaggt aaaggaaaat ccaacaagaa tcaagtggtt       120
gaggatgatg atgaggatga ttttgaaaag gccttggagc ttgcaatgca attagatgca       180
caaaaactag ctcagaaaaa agctgatgat gtgcctcttg ttgaagaaga agagaaaaaa       240
gttgaggaaa agattgaaca gcaatatgac cccatttcca cttttttaccc tgatggaaac       300 tatccccaag agaagttgt gggattacaaa gatgacaact tgtaccgtac tactgatgaa       360
gaaaagcgag ctttggatcg agagaagaat aacaagtgga atgaatttcg taaaggtgct       420
gaaattcata ggagagttcg aaaactggca aaggatgaga tcaaaccggg aatgtcaatg       480
atcgagatcg ccgaactaat cgaaaacgca gttcgtggat atagtggtga agacggactc       540
aagggtggta tgggatttcc ttgtggtctt tctttgaacc attgtgctgc gcactattct       600
cctaatgcta acgacaaact tgtcttaaat tatgaagacg tcatgaaagt agattttggt       660
gtccatgtga acggtcacat tatcgatagt gcattcacgt taacattcga tgacaaatat       720
gatgatctgt tgaaagctgt caaggatgct accaatactg gtattcgtga agcaggtatt       780
gatgtgagat tgaccgacat tggtgaagcc atccaagaag taatggagtc ctacgaagtt       840
actttagacg gagaaacata ccaagttaaa cctatcaaga tctttgtgg ccataacatc       900 ggccagtata gaattcatgg tggtaagtct gttcccatag tgaagaattt tgacaacacc       960
aagatggagg aaggtgaaac ctttgcaatt gaaacctttg gcagtacagg aaggggtcat      1020
gtgataggac aaggtgaatg ctctcactac gccaagaatc cagatgcccc cgccaatgct      1080
atctccagca ttcgtgtgaa ccgtgctaaa caattgctaa agactatcga tgagaacttt      1140
ggtactcttc cattctgtcg tcgctacata gatcgtcttg gagaagaaaa gtacttattg      1200
gcattgaacc agttggttaa atctggagtt gttagcgatt atccacccctt ggtagatgtc      1260 aagggggtcat acactgccca atacgagcac accatccttt tgagacctaa tgttaaggaa      1320
gttgtatccc gcggtgaaga ctactag                                          1347

<210> SEQ ID NO 42
<211> LENGTH: 1119
<212> TYPE: DNA
<213> ORGANISM: Pichia pastoris

<400> SEQUENCE: 42
atgattcaca gctgtgctag tgctgagtgc tcaaaagcga ctgaatctac cttaaaatgt        60
cccttgtgtc taaaacaagg tcagatccaa tattttgta accaaaaatg tttcaagaat       120
ggatggaaga tccacaaagc ggttcacgcc aaagatggtg atatagatgg ttcgtacaac       180 cccttttccca actttgccta caccggtgag ctcagaccag catatccctt gtctgtgaga       240
cgagaggttc cagagaacat tactctccca gattatgctc ttgatggagt accagtctca       300
gaaatcaaaa ataacagaat gaacaagatc aatttggtaa cggagccaga agacctggcc       360
aagctaaaaa atgtttgccg tttagcacga gaggttctag atgctgcggc tgcatctatc       420
aaaccaggag ttaccactga tgagatagat gaaatcgttc atagtgaaac aatcaagaga       480
gaagcatacc cctcccctttt aaattacttc aattttccca aatctgtttg cacatccgtt       540
```

-continued

```
aatgaagtca tctgccacgg tatacctgat cgtagaccgc tccaggatgg tgacatcgtg      600
aacctggatg ttacccttta taaagatgga tttcatgcag atctgaatga aacgtactat      660
gttggagaga aggccaagac taacaaagat ctggtcaacc tcgtcgagac aaccagagaa      720
gctcttgctg aagctatccg tttagtgaaa cccggcatgc cgttccgtca aattggtact      780
gttatcgaaa actatgtgac tgaaagaggc tgtgaaactg ttcgttctta cactggtcat      840
ggtatcaata ctttgttcca cactgaacca accattccgc attacgctcg taacaaagct      900
gttggagtag ccaaaccagg agtggtattc actatcgaac caatgttgac tctgggcact      960
catcgtgacg tggtttggcc cgacaactgg accgccgtta ccgctgatgg aggaccaagt     1020
gcccaatttg aacataccct tttggttacg gaagatggtg tggagattct cactggcaga     1080
acggaaactt cgccaggcgg tgccatctca agactataa                           1119
```

<210> SEQ ID NO 43
<211> LENGTH: 1605
<212> TYPE: DNA
<213> ORGANISM: Pichia pastoris

<400> SEQUENCE: 43

```
atgctctata agaccacctt gtcaatagca cacacgagtg tgatattgtt gtcattgata       60
accgccataa gttgctttga gttgcatctt cctcagaagg tttctcatat agtagacagt      120
ttacaatata cttgcggcca attttttgcaa aagcagcaga tctttgcact ctataacaag     180
caaaatttca ccgaaatagt gaaccagaat atcaagggaa tagaggagag agttttgtct      240
gagttgcttg aagaaagatt agagaatgaa tcccagaatg attattatac cgccaattct      300
caaaattggc ctatcgactt ggatcagtac tcagaatcat ttgtaataag gatcacatct      360
gaagatgagt ttatcaagta cttgatcttc aaggaagcta aagctttgca tatttccata      420
tgggagcaat ctgttggttt gatagatttg aaggttgacc gtgatcagat gcaccgccta      480
ctttacaacg tggagtcacg catactggaa cgaagaacga gaagtgttga cagtccagtt      540
tctgaatata aagtacaatt gatgattgga gatcttccac agcgaatcta cgaaacatat      600
ccttcgacaa aagtgacatc tttgcaagcc ctaggagagt tcccttcttt ccagaaccta      660
agtaatgctt ttttttgagga ttttagaacg ctggaaacta tatacgactg gttcgaagaa      720
atacagaagg aatttcctaa gctagtgtcg atcaactgga ttgggcaaac ttatgaaggt      780
cgtgatctga aggctcttca cgttagaggg aagcactctg gcaacaaaac agtagtcgtt      840
acaggtggaa tgcatgcgcg tgaatggata tcagtaacca gtgcatgcta tgccgttcac      900
aaactgctcc aaaactatgc tgacggacac cacaaggaag cgaaatacct ggacaagttg      960
gactttttgt ttgttccagt tttgaatcct gatggatacg aatatagctt taacgaagac     1020
aggttgtgga ggaagaacag acaagaaact tatatgcccc gatgtttttgg tatagacatt     1080 gaccattcat ttgattatca tttcgtgaaa tcagaagact tacctgtgg agaggaatat      1140 tcgggtgagt ccccttttcga aagtatagaa agtgaagtgt ggaataattt cctgaacaga     1200
accaaagaag aacataagat ctacggctat atcgacttac actcgtattc gcaaacggtg     1260
ctgtatccct atgcgtactc atgcgaaatc ttaccaaggg acgaggaaaa cctgattgag     1320
ctaggttacg gtattgcaag ggccataaga aagagtacag ggaaaaaata tcaagtgttg     1380
aaggcatgcg aagacaggga tgcagatcta ttgcctgatt tgggaggagg aaccgcttta     1440
gattatatgt accacaaccg tgcatactgg gcgtttcaga tcaaattgag ggattccggt     1500
```

-continued

```
aatcatggct ttctccttcc caaaaagttt atatacccag ttggaacaga ggtttatgcc    1560
tcaattcagt acttttgttc ttttgtgctg aatttagaag gctaa               1605

<210> SEQ ID NO 44
<211> LENGTH: 1191
<212> TYPE: DNA
<213> ORGANISM: Pichia pastoris

<400> SEQUENCE: 44
atgaaattga ccataacatt agcccataac gatcaaatct tggacattga tgtgtccagt      60
gaaatgctac tatctgacct caaagtcctg ttggagttgg aaacttccgt acttaaaaac     120
gaccaacaat tattttacaa taacaacctg ctcactggag atgactcgcc actggaagat     180
ttaggactca aagataatga actcataatt ctgagcaaag tcgaagcaca tagtgatgtc     240
aattcacact tgaactctgt tagagaacag ttgatacaaa acccgctata ccaggccagt     300
ttacctccaa gtcttagaga taagctcgac gaccctcaag gcttcaaaga agaagtggaa     360
aaactaatcc aattggggca gtttggacaa tacgggcctt cccgtacttc cgtccaacag     420
gaattagaca gactacaaag agatcctgac aatccacaaa atcagaaacg aattatggag     480
ctcattaacg aacaagctat agaggaaaat atgaatactg cttttgaaat ctcacctgaa     540
tctttcgttt ccgtgaatat gctctatata aatgtggaaa ttaatggtgt ccattgtaaa     600
gcattcgtcg atagtggagc ccaaacgacc ataatgtccc ctaaactcgc agagaaatgc     660
aaccttgcga atctaattga taaaaaggttc cgaggagtcg cacagggtgt aggaagttct     720
gaaatcattg tcgtatcca ttctgctccc ataaaaatcg aagatattat tgttccctgc      780
tcattcactg ttttggatac caaggttgac cttctattcg gacttgatat gttgagaaga     840
catcagtgtg tgattgacct taagaacaac tgtttacaaa ttgcagacag aaagacagaa     900
tttttaggag aagcagacat cccaaaggaa ttctttaacc aaccaatgga agctccatcc     960
acagctcctg tcccaaaacc tgtacaacct cctcaacaac tcggtcagcg gccggctgga    1020
agccctccct ccacaattca aagaccagca gtacaaccgc cacctgtgga tatacctcca    1080
gaaaaaatcc agcagttgat caaccttgga ttcggagaag aggagtcgaa agaagcactt    1140
attagatcta gaggaaatgt ggaagttgca gcggctttgt tattcaacta g           1191

<210> SEQ ID NO 45
<211> LENGTH: 1553
<212> TYPE: DNA
<213> ORGANISM: Pichia pastoris

<400> SEQUENCE: 45
atgccaaacc ttccttctag cttgaacaag atgactgctc aagccgtgaa atacgcaaac      60
ggtatgtcat ctgccctctc ccgtgtttga gactctatcc actaacttta gattttatca     120
ccttcctgaa caattcacct actccatacc atgctgtcga ctccgtaaag tccaaattgg      180
tagagtcggg gtttaacgag ctcagtgaga gagttaattg ggccggaaaa gtcaagaaga      240
atggcgctta ctttgtgact cgtaacaatt cgtccattat agccttcact gttggcgggc      300
actggcagcc aggtaacgga gtgtcaattg ttggagccca tactgattcc ccaaccttga      360
gaatcaaacc catatcccat tcgactaagg agggatttaa ccaagttgga attgaaactt      420
atggtggagg cttgtggcat acgtggtttg acagagattt aggagtagct ggacgagtgt      480
ttattgaaga agaagaatct ggtaacattg tgtccaagtt agtcaagatc gataaaccag      540
tattgagaat ccccacacta gccatacacc ttaccaaaga gagagctaag tttgagttta     600
```

```
ataaggaaac tcaattccat ccaatctcat cgcttgaaaa ctcctctgaa aaggagaaaa      660
acaaagatga ggaacatgac gcttgtgcag gagaagattt gactacggag gagtttaagt      720
caattcaatc tgttgtggag agacacaaca aacaattgct tgatctggtg gctgcagatc      780
ttgattgctc tatatcccag atagtggact ttgaattgat tcttttcgac cacaacaaac      840
cagtactcgg aggtttgaat gaagaatttg tgttctcagg aagattggac aacctaactt      900
cttgtttctg tgccactgaa gcgcttataa atgccagtaa agataccaac aggttagatc      960
tggatactaa tattcaactg atctctctgt ttgaccacga agagattgga tcagtttctg     1020
ctcaaggagc tgattcttca tttctacctg acatacttca gcgtataaca agactaactg     1080
gtaatgaggt tagcaccgat ctggaaggac aaccaaattc tttcttttta gagtcaatgg     1140
ccaaatcttt cctactatct tcagatatgg cacatggtgt gcatcccaac tatgggggaag     1200 tctatgagaa gctaaatagg ccaagaatca acgagggacc agtgatcaaa ataaacgcta     1260
atcaaaggta cagcaccaat tccccaggta ttgtttttgct caagaagatt ggtgagttgg     1320
gaaaggtccc cttgcaattg tttgttgtta gaaacgactc tccctgtggg tcaacaattg     1380
gtccaatgtt gagtgctaaa cttggacttc gaacgctgga cctcgggaac ccccagctct     1440
ccatgcattc tatcagagaa actggaggtg ctcgtgacgt taaaaagttg gtcgatcttt     1500
tcgaaagcta ttttgagaat tattacacct tggagcctaa gattaaggta taa           1553
```

<210> SEQ ID NO 46
<211> LENGTH: 1413
<212> TYPE: DNA
<213> ORGANISM: Pichia pastoris

<400> SEQUENCE: 46

```
atgaacaaag gtccgaaaga attggagggc cgcaagtatc cagcaagagc ccatgcactg       60
acggtcaaaa atcactttat ccaaaagaag gctgacattt caagtcgttc tgcaatcttt      120
attagtggcg aagatctcaa gttgtatcct tactgtgacc aaacagctcc tctcagacag      180
aatcgttatt tcttttatct gtcaggttgt aatatccctg atcccatgt ccttttttgac      240 ttggacgccg aattgttaat tctggtgcta ccagaaattg attgggatga tgtcatgtgg      300
agtgggatgc ctctttcgat tgaagatgcc tacaagacgt ttgatgtgga caaggtggta      360
tatcttaaag atttgcaagg cttttttgtcg tcgtttggaa aaatatatac aactgacatc      420
aatgatgaaa attctaagtt tggcaatcta ctaacagaga aagatcctga cttgttctgg      480
gctctggatg aatccagatt gatcaaagac gactatgaac tcactctaat gagacatgcg      540
tcaaaaattt ctgacaattc ccattacgct gtcatgtcgg ctcttccaat tgaaactgac      600
gaaggccata ttcacgctga gtttgtttat cattcgttaa gacagggatc taaatttcaa      660
agttatgacc cgatttgttg cagtggacca aactgtagta cccttcatta tgttaagaat      720
gacgattcta tggagaataa acacaccgtt ctaatcgatg ctggtgcaga atggaacaac      780
tatgctagtg acgttacaag atgttttccc atcaatggag attggacgaa agagcatctt      840
gagatctata atgctgtttt ggatatgcag gaccaagtta tgaagaagat taagcctgaa      900
gcccattggg atgagctaca ccttttggca catcgtgttc tcattaagca ttttttgagc      960
ctcggcatat ttcataacgg aacagaggat gagatatttg agagtggagt ctcagtatca     1020
ttctttcctc atgggctggg tcacctttta ggaatggata tcatgatgt tggtgggcac     1080 cccaactatg atgatccaaa ccctctattg agatacctaa gattgagaag agtgttgaaa     1140
```

-continued

```
gaaaatatgg tagttacgaa cgaacctgga atctacttct ctccctatct tgttgaattg      1200
ggactgaagg atgataataa ggcaaaatat gtcaacaagg atgtactgga aaagtattgg      1260
tatgtcggag gtgtgagaat tgaagacgat attcttgtta cgaaagatgg gtatgaaaac      1320
ttcaccaaga ttactagcga ccccgaagaa atttccaaaa tcgttaaaaa ggggttggag      1380
aagggtaaag acgggttcca taatgttgta tga      1413

<210> SEQ ID NO 47
<211> LENGTH: 2612
<212> TYPE: DNA
<213> ORGANISM: Pichia pastoris

<400> SEQUENCE: 47
atgacatctc ggacagctga gaacccgttc gatatagagc ttcaagagaa tctaagtcca        60
cgttcttcca attcgtccat attggaaaac attaatgagt atgctagaag acatcgcaat       120
gattcgcttt cccaagaatg tgataatgaa gatgagaacg aaaatctcaa ttatactgat       180
aacttggcca agttttcaaa gtctggagta tcaagaaaga gctgtatgct aatatttggt       240
atttgctttg ttatctggct gtttctcttt gaccttgtat gcgagggaca atcgattttc       300
caatttgaac gagtacgttc cagattcaaa cagccacgga actgcttctg ccaccacgtc       360
taatcgttga accaaaacag actgaattac ctgaaagcaa agattctaac actgattatc       420
aaaaaggagc taaattgagc cttagcggct ggagatcagg tctgtacaat gtctatccaa       480
aactgatctc tcgtggtgaa gatgacatat actatgaaca cagtttttcat cgtatagatg       540 aaaagaggat tacagactct caacacggtc gaactgtatt taactatgag aaaattgaag       600
taaatggaat cacgtataca gtgtcatttg tcaccatttc tccttacgat tctgccaaat       660
tcttagtcgc atgcgactat gaaaaacact ggagacattc tacgtttgca aaatatttca       720
tatatgataa ggaaagcgac caagaggata gctttgtacc tgtctacgat gacaaggcat       780
tgagcttcgt tgaatggtcg ccctcaggtg atcatgtagt attcgttttt gaaaacaatg       840
tatacctcaa acaactctca actttagagg ttaagcaggt aacttttgat ggtgatgaga       900
gtatttacaa tggtaagcct gactggatct atgaagagga agttttaagt agcgacagag       960
ccatatggtg gaatgacgat ggatcgtact ttacgttctt gagacttgat gacagcaatg      1020
tcccaacctt caacttgcag catttttttg aagaaacagg ctctgtgtcg aaatatccgg      1080
tcattgatcg attgaaatat ccaaaaccag gatttgacaa ccccctggtt tctttgttta      1140
gttacaacgt tgccaagcaa aagttagaaa agctaaatat tggagcagca gtttctttgg      1200
gagaagactt cgtgctttac agtttaaaat ggatagacaa ttctttttc ttgtcgaagt      1260 tcacagaccg cacttcgaaa aaaatggaag ttactctagt ggacattgaa gccaattctg      1320
cttcggtggt gagaaaacat gatgcaactg agtataacgg ctggttcact ggagaatttt      1380
ctgtttatcc tgtcgttgga gataccattg gttacattga tgtaatctat tatgaggact      1440
acgatcactt ggcttattat ccagactgca catccgataa gtatattgtg cttacagatg      1500
gttcatggaa tgttgttgga cctggagttt tagaagtgct tgaagataga gtctacttta      1560
tcggcaccaa agaatcatca atggaacatc acttgtatta tacatcatta acgggaccca      1620
aggttaaggc tgttatggat atcaaagaac tgggtactt tgatgtaaac attaagggaa      1680
aatatgcttt actatcttac agaggcccca aactcccata ccagaaattt attgatcttt      1740
ctgaccctag tacaacaagt cttgatgaca ttttatcgtc aatagagga attgtcgagg      1800 ttagtttagc aactcacagc gttcctgttt ctacctatac taatgtaaca cttgaggacg      1860
```

-continued

```
gcgtcacact gaacatgatt gaagtgttgc ctgccaattt taatcctagc aagaagtacc    1920
cactgttggt caacatttat ggtggaccgg gctcccagaa gttagatgtg cagttcaaca    1980
ttgggtttga gcatattatt tcttcgtcac tggatgcaat agtgctttac atagatccga    2040
gaggtactgg aggtaaaagc tgggctttta aatcttacgc tacagagaaa ataggctact    2100
gggaaccacg agacatcact gcagtagttt ccaagtggat ttcagatcac tcatttgtga    2160
atcctgacaa aactgcgata tggggtggt cttacggtgg gttcactacg cttaagacat    2220
tggaatatga ttctggagag gttttcaaat atggtatggc tgttgctcca gtaactaatt    2280
ggcttttgta tgactccatc tacactgaaa gatacatgaa ccttccaaag gacaatgttg    2340
aaggctacag tgaacacagc gtcattaaga aggtttccaa ttttaagaat gtaaaccgat    2400
tcttggtttg tcacgggact actgatgata acgtgcattt tcagaacaca ctaaccttac    2460
tggaccagtt caatattaat ggtgttgtga attacgatct tcaggtgtat cccgacagtg    2520
aacatagcat tgcccatcac aacgcaaata aagtgatcta cgagaggtta ttcaagtggt    2580
tagagcgggc atttaacgat agattttgt aa    2612
```

<210> SEQ ID NO 48
<211> LENGTH: 2127
<212> TYPE: DNA
<213> ORGANISM: Pichia pastoris

<400> SEQUENCE: 48

```
atgacctgcc aaagtgtaga agagctggat gctattgttg aatcaaagct tagggaggtt      60
gataataaag tttcgaacgg aaatgttgac ttcatcaaac aatatctgat tcaggcgatg     120
aactattatg acaagtatag atctgaaatc aaaaaaattg acccacaga aaagaaccct      180 aaatactatt gttttcaaga ggcagcgtat gttaactaca aagcttccca agctttacta     240
agagagagaa tacccaagct gcctggcttt ggaggatata aatctgcgta ttcaaaaatc     300
tatcgtgaac tgatagaaat ggtagagggg caagaacatg agattgccca gataaaaagc     360
ggcttaagga aaaactttg tgatgataca ttagttcttc gactgagaag tttaaaatca     420
ccatctgcta ctcagcccaa aagtttaccg gattctacac ccacttcaca atttaaacca     480
aaaccttcaa agccttttag tatcacaatc aatgaggaat acatttcggt tgaccaattg     540
tcacgccttc ttaaaacgaa cccgaatgac atactcctca ttgatctacg gtctcgtcaa     600
gagtacgacg tgtatcacat tgaagatggc tccggggtgg acatgtcaat atgtatagaa     660
ccaatgagta tcagaaacgg atacacagca gaggatcttt atcaactttc aatggccgtc     720
aatccagatt atgaaggag attgttcaag aatcggtctc agtatgaact gttggtatgt     780
tatggtaatt atgacaacga ggctactgtt caaatgttca tgactatcat gaataaagat     840
acttccctca gaggcggag cgtctatttg aaatccggaa ttaagggctg gaatcaggat     900
ctgagttttc aagattcgaa accgaatggg tacttaacta gtacgactga ctacttcagt     960
aacactccga acacacaat tacgcccaaa tcatcaaaat caagttcaaa acctacttta    1020
aaaactactg tcaactctgg gcctgccac actgttggga tcaataatct aggaaataca    1080
tgttacatga attgcatact tcaatgccta ttagaaagtg ataagtttgt ttcatttttt    1140
ttacaaggcg attataagaa acatatcaat attaatagcc gattaggctc gagaggtata    1200
ttggctacag gatttcattt gttagtgcta ttaatatcca gatcatctgg taaaacagtg    1260
actccttctt catttgccaa agatgtttca acagtgaata agaattttaa gttaggagag    1320
```

-continued

```
caacaggatt gttttgaatt tttagatttt ctcctggata gtttacatga agacctgaat        1380
gaatgtggga atgaaccacc aatcgcagaa ctcacacctg aagaggaaaa gcttagggaa        1440
gctttaccta tcaggattgc ttcgaccatt gaatgggaaa ggtatttaaa aaacaatttt        1500
agcatagtag aagatgtgtt tcaagggcag tacttctcca gattggaatg tacagtctgt        1560
aaaagcactt caactactta taactcattc agttcactgt ccttgccaat cccattagat        1620
cgacaaaatg tcacactaga tgactgtttc caggcttttt gttctgtaga agaattgaac        1680
ggagatgaca gatggcattg tccaagctgt aaaaaaaagc aggtcgcttt taagaaactt        1740
ggtatctcta gactaccaag tgttctgatc gttcacttta aaaggtttca ggtcaagtgg        1800
gaaacaggtc atataatcaa gatagacaag tttatcagtt atccgttcaa gctatcaatg        1860
gacaaatatt ggcccaaagc tcaatcagaa gaagaactaa gaaacttgga gaagctacca        1920
tcgagaaatc agaatccccc tttcaattat cgattgacag gggtggctaa tcattttggg        1980
accagaacat catctggtca ctacacatca tatgttcaaa aaggtggcca atggtattac        2040
tttgacgata gtgctgtgac tagcaatgtt gatcgtcata aaatcgtaaa tgggaacgcc        2100 tatgtttat tttatcgacg tagttag                                            2127
```

```
<210> SEQ ID NO 49
<211> LENGTH: 669
<212> TYPE: DNA
<213> ORGANISM: Pichia pastoris

<400> SEQUENCE: 49
atggaagccg tgaatttaca aattgaatgg attagacagg tgcctccagt tactgtggct         60
cttgtagcat ccatgtcaat gacctatttt ttgcaacgca tagatgtatt atcctcaaat        120
atgttcgtgt ttgaaagaca tcgtgtgttt aatgagatgg cctattctcg tttgatacta        180
agtttcttct tcagcgccca ttcgtttgtt ggattcttt ggacattgta cacattattt         240
cagaattcac aggcactcga gctgacctat gaaaactcaa tcgattacct ctactcattg        300
gtgataatag caggtttgat cgtggcatgg gcctcatact tggggggtcc gttcatgctg        360
ggatgggttc tagctgacgt cttgagaacc atatggtgca aacagaatcc caacgaaaga        420
atgtctattt tggggctagt ttccttcaag gcaggatact ttccatttgt aatacttgcc        480
atttcatggc tagaaggaag ttcaagaaat cttctattaa tgctaattag ccaaactgtc        540
agtcaggctt atatttttgg acaccatatg atgcccgaac tacacgggat cgatctgttt        600
ctgcctatat ggaaattcca gtgtttcaga cgtcagagac aaccaccaat tcatcagcat        660
caagactaa                                                               669
```

```
<210> SEQ ID NO 50
<211> LENGTH: 927
<212> TYPE: DNA
<213> ORGANISM: Pichia pastoris

<400> SEQUENCE: 50
atgtcaaagg tggtggtatt cctaaatgga ttattggcaa taacctttac gtttgaactt         60
ctctctgttt taagcgtgcc aatcaccaag catatccaac tttgttctta tcaaggatat        120
aagtttggcg tgtttggata ttgcaccgag aataatatct gcacaacgat aggaatcggt        180
tatcatcgaa attcaataga cgaattgaga ggcttttcat taccaagtaa tgcaagaagc        240
tctatatcaa gcttgttggt ggttcatttg attggctgtg tttgcacctt tattttatgg        300
gttctaagtc tcatgttgaa tatggataga tttcacagat cattatggtt cttattaacg        360
```

-continued

```
tgtctagtat ggacttgtgc tttctttttt tttacattat tctccttcct ggtagacgtg        420
ttactatttg tgccacacgt tgcgtttgga ggttggttga tgttggtaag tactgtattt        480
ttggcattta caggaaccat tttttgcatc atgcgaagaa ctgtcagctc aagaaaaact        540
catttgaaga actacaacgg gggaagtaca agtttgatgc ggctgcagac gtatatctcc        600
aatagctcta gaggaagctc tgtaaccaat gatgaatacg tctggtttca agaaactcca        660
ttacaagacc tctacccccc agacaatccc aattacgacg acatctacgg aacgactgaa        720
cacgaactaa cccgcttgga cacaatatct cttgaaaggc caagaatagg ccttatcaca        780
aacgaaaatg ccagcggcga tggtgggggta gtttccccac cacagaatga cagtacactt        840
ctggaatctt cgggcagaat taggaatggg ccactgggag accgaagtga atttcccaac        900
ggatcaacaa gcgaactttc tgcataa                                            927
```

<210> SEQ ID NO 51
<211> LENGTH: 714
<212> TYPE: DNA
<213> ORGANISM: Pichia pastoris

<400> SEQUENCE: 51

```
atgaaataca gtgaccaatt aatagaagag tacaaagaat tatggttaac agcgacatct         60
aatgagctta ctagagaatg gtgccaggga actctccacc tgagcaaatt atacgtttac        120
ttgacacaag acttaaagta ttttgggggat ggatttcgac tttttaggcaa aaccatttcg      180 ttatgtcgcc gtaggcaatc gcttgtgtca ttaggcaaac atgtggggat gctcagtaat        240
agtgagaaca cgtacttcgt ggattgtatt aacgatctta ctgaacagtt attaagagat        300
gggatgtaca atgctgaaga attagaagaa atcagtggtt taacgttacc tgccgtggaa        360
aggtaccttt tattcatgag atcgatggta gagtcttcta caataactta tgcagaaatg        420
attactgtga tgtttgtaat ggaacaagtc tatctggatt ggtcaaataa tggactgaga        480
agtaaacctg acaacttgca ttggtggttc aatgaatgga ttgatataca tagtgggggag       540 aactttgaaa gctggtgcca gttttttaaag gatgaggtag accgctgtat acaggagttg       600
aaggatgcta atagagatga tctcgtggcg aggggttgagg agattttttag agaaacatta     660 gaacttgaag tcgaattctt taaaagttgt tacgatatca cggacgatga atga              714
```

<210> SEQ ID NO 52
<211> LENGTH: 357
<212> TYPE: DNA
<213> ORGANISM: Pichia pastoris

<400> SEQUENCE: 52

```
atgcactcga aatttaggtg ggtatgtgtc gatactcaat tctgcacaca ccaccaaaat         60
ctgtcgcctt tctcttatat ctccaacccg agtccaatgt cattttctta ccttgaaggc        120
aacatcgatt ttaaaggaca ggaacttgca aacaggatca ctaaaaaact aatcacattt        180
ggtgcaatta ttagttttct ggtaggattt ttgagtgaca acatcttata cactgtatac       240
actttcgcag cttttggtttt attgactgct tctttggtta ttccccctttt tagcttctac       300 aaaaagaacc ctgtaacatg gttaccaaag aaatccaaaa tagagattca gcattga          357
```

<210> SEQ ID NO 53
<211> LENGTH: 3423
<212> TYPE: DNA
<213> ORGANISM: Pichia pastoris -continued

```
<400> SEQUENCE: 53
atgacagact ctgttaactc tgatgattct gatctggaaa tcatagaggt gactgagcct      60
actccaaaag tggacctttt ggcccccaat ccagcattta attttactgc ccccataagc     120
aacagtaacg gcacaactcc aataaggaga aaacttgatg accaatccaa ctccaattct     180
tttgccagac tggaatcgtt acgggaatca tcagtgaaac cacaagctag tacgttcaat     240
agtagtaggt tcatccccca agccgaccaa ttttccaata atcagaataa tgaacttgat     300
aacaacaatg gattcgccga ctggatttct aagtcccaac ctgaatttcc ctttccactt     360
aatgatggac caaaaaagtc cagcaatcaa cctacaaact caaattttga agagatcatc     420
gatttaactg aagatatcga dataaataca tctgtccccg catctacatc atcttctacc     480
ccagttccct ccagcacaca gaatcagagc catcatatag ccaacaacaa cacagcacaa     540
gatgcgcata tcttccaagg gaaacgacct ctccaatcat attcagatga tgaagacgaa     600
gatttgcaaa ttgtaggatc caatattgtt cagcagcctc taggaattat gccaggaact     660
ttcaacgccc ctgcaaacat actccatttt gacggttcaa accagaatga acaagccaga     720
tggctggact tgcggataaa agatttgtta gataatcttc acaatcttcg agttcatgct     780
cagtcgaata ttatggagat caataggttc atttccactt tggggcattt aaacagagaa     840
gtttcagagc tcaatctaag atatcaatct atcgtgaaca atcctcaggc gaccgctaat     900
aatcaaggat acctcactca gcttttgaac aggattcagg agcttactaa tgaaaaagcg     960
cacatattta gagagatgga tacatccaag ataaaacagc aggagattca cagaagaatc    1020
catgctctct cgtcaacaat tgacaaactg aaaaaagatc gtgaacttat ctttcgaaat    1080
gctcaaaatg cttttcacgg tgatatgaag aatgaagttt tggaaggcca gtctttcatg    1140
gatgcaattc atagggcaaa tagcttgggt tatgcttcaa atatttattc tcgttctgat    1200
gaagacgctg gaagcttaca acggcttctt gaaaatatcc agcccgatat ggaggacaaa    1260
gacgatgatg aattggctaa aactccgaag gagttcaata ttcaactgct gaagcatcag    1320
agagttgggt tagattggct acttcggatg gagaagtcaa ccaacaaagg aggcatttta    1380
gcagatgcca tgggcctggg aaaaaccatc caggctatta gtattattta cgcaaacaaa    1440
tggaaaacac aagaagaagc cgaagaggag gcaaaacttg aagagaaggt tagatccgaa    1500
aagtctacat cagaaacgaa tggagaggtc agcaaaacgt caacggcaaa gtcggaaaag    1560
aaacccatcc aaggagacga aggatatttc aaaactacgt taataatagc accagtttct    1620
cttctacatc agtgggagtc tgaaatcttg ttaaagacga aaccagaata caggctaaaa    1680
gttttcattt atcacaagca aaaaatgtcc tcgtttgaag agctccaaca gtatgatata    1740
gtattaacat cgtatggaac tctgtcttct caaatgaaga agcattttga agaggcaatt    1800
aaggaggcag acctacagcc caactcttca tccataccag cagaagactc tggaggcata    1860
tctttcaagt caccattttt tgcaaaagaa acaaagtttc ttcgagtcat tctagacgaa    1920
gcccataaga tcaaaggaaa aaatacaatc acttcgaagg cagtcgcttt ggtgaagtct    1980
aaatacagat ggtgtttaac gggcacaccg ctacaaaata aaattgaaga actatggcct    2040
ctacttcgat tcttgagaat taagccatat tatgatgaaa agcgatttag aactggcata    2100
gtattaccta taaagagttc catgtcaggc aaatatgatt ccacagacaa gaagattgct    2160
atgaggaaac ttcatgccct acttaaagca atcttgttga aacgaaacaa agattcgaag    2220
attgatggag agcccattct caagttaccc aagaagcata tcattgacac attcatagaa    2280
atggaagcaa aagagttaga cttttacaag gatctggaag gacagacagc caaaaaagcc    2340
```

-continued

```
gaaaagatgc taaacgctgg aaagggacaa ggaaatcatt attctggtat tcttatcttg      2400
ctattgagac tgagacaaac ttgttgccac catttcctcg tgaagttatc tgagatgaag      2460
caagaagcca aattgaaaca ggaagttgct accaagatgc cacaattggc cacacaacta      2520
tctcctgctg tggtaaggag aattaacatt gaagcagagg ccggatttac gtgtcctata      2580
tgtttggata acatcataaa tgagaatgct tgtatattat acaaatgtgg acatgttgtt      2640
tgtcaagatt gcaaagacga tttcttcacc aattatcaag agaatgaaac tgatgacggt      2700
cttagagtgt ccaaatgtgt gacctgtcgt ttgcctgtca acgaaagcaa tgtaatcagt      2760
ttcccagtct acgacaagat tgtgaaccag catatttcag tgatggatat agttaaaagt      2820
gagtctccag tgttgtcaaa aattgaaatg attcaacaac tgatccggga gaacaaaggc      2880
gtcttcgaat cgtctgccaa gatcgataaa gcagtggaaa tgatacaaga gttactgaga      2940
gacaatccag gggagaagat catagttttt agtcaattca caactctctt cgatgtcata      3000
gaggtaatac tcaaagagaa caacattaaa ttcattagat atgacgggtc aatgtctctt      3060
agcaatagag atgctgccat tcaagagttt tatgagagta cggagaaaaa cgtaatgctt      3120
ctttctttga aagcagggaa cgtgggggttg acattgactt gcgcctcccg tgtcataata      3180
atggacccat tttggaaccc atatgtggaa gaccaggcca tggatagagc ccatagaatt      3240
ggccagttaa gagaagtttt cgtctatcga atgttgatca agaacaccgt cgaagataga      3300
attttgacca ttcaaaatac gaaaagagaa atagttgaaa acgctctgga taaccagagt      3360
ttgaatacga tatccaagct tggcaggaac gagttggctt tcttatttgg tatcggcaat      3420
tga                                                                     3423

<210> SEQ ID NO 54
<211> LENGTH: 1080
<212> TYPE: DNA
<213> ORGANISM: Pichia pastoris

<400> SEQUENCE: 54
atggagtgta aaaaagtcaa agatcgccta gtcacggaat acttaaagat tgaatgtagt       60
cgacttaacc gaaggatacg ctccctgaaa aatccaaaag ttgagcaagc cctactgcaa      120
ttcaagaact cacgtttggc tcacatgaga aaggctcatc tggatggaat aagaaaccca      180
cagtatacgg atgacgccat ctttcaggca ttggaaacca tggatttgga ccacatattt      240
gagaaggcag gtagtcttta caactcacag caacaagatg aatcaaaaaa agattccctg      300
gatgaaacag atttcaccgt ggtggcgttg ctagattggt tcaagaatga cttcttcaaa      360
tgggtaaaca agccaccttg tcctgtttgc catagtgaag atgaaagccg cataagaatg      420
gtcggatctg caaggcccac tagtgaagaa ttgtcgtacg gagcaggggt cgtagaggtg      480
tttaattgtg accattgtag ctgtgcaatc agatttccaa gatataacga ccctaagaag      540
ctcctgagaa ctagagctgg acgatgtggg gaatggaata actgtttttct gttgtgtcta      600 aaagccttgg gtctgaaagc tagatgtgtg aggaatgtgg aagatcatgt atggagtgaa      660
tactactcgg aacatctcaa gcggtgggtc catctggata gttgcgagaa tgcctttgat      720
caaccagaac tatactgcaa aggttggggg aaaaagatga gctattgttt tgcttttgat      780
gacactctca tagaagatgt gagtgccaag tacattactc aaggtagact gcctaaaatg      840
ctagacgacg aaaccatcag aatatgcttg tatttttttca accaggaagc tcttaagatg      900
gtgagtgaaa tccagaggc attctactcc gctttggtta agtatcacag atgtctgtct      960
```

-continued

```
gcgaatagaa aagagagcgg gtcaaaatca cgagccgtga atgctagttt gacttcattg      1020
ttaccacgac aatctggtag cgcatcctgg acgtctgaga gaggcgaaaa cggactttag      1080

<210> SEQ ID NO 55
<211> LENGTH: 819
<212> TYPE: DNA
<213> ORGANISM: Pichia pastoris

<400> SEQUENCE: 55
atgcctataa aggggcggtt caccaaaaag aagccaaaaa ggaaagatga gccaaatcga        60
ccgtccccca cccagttcat caaaaaaata gcctcattga aaaagcagac caggagagat       120
gaggccctgg atgtgctaca cgaactagca gttgttgtgt cacctttgat gaaagagaac       180
ggtttcactg ttggattatt atgcgaaatg ttcccgaaga atgcctcttt attggggctg       240
aatgtgaata tgggttcaaa gatcatgatc cgattgagac ctagccacaa catgaacttg       300
tttttgccaa aaagagagat catcggtaca atgctccatg agttaaccca taatcgcttt       360
tcggcccatg atgtaaggtt ttatgacttt cttgagggtc tcaagagcag gttttttgag       420
attcaggtga aaggatcttt acaaactaca gggtatgtta actttagtga agttctatct       480
ggtaatgcgg cgagagggca actgattcaa aaggaaaaag agaaaggaca aagattgggt       540
ggtaataagc atgcaaaacc tatgagagtc ctaatcttgg aggcggccga aaagagaatg       600
atagactcta aatggtgcgg aggagctagc aatgaagtag gccttccaaa aattgaagat       660
ctaatggacg atgaagaagc tcaacactct gaactaaagg aagagaatac aaagaaggtc       720
agaaaaattg ttcaacctag caaaaagaaa attgtagatt tggaaaacct accgaatggc       780
aagtccatta ttattgatct aactaatgac gatgactaa                              819

<210> SEQ ID NO 56
<211> LENGTH: 1719
<212> TYPE: DNA
<213> ORGANISM: Pichia pastoris

<400> SEQUENCE: 56
atggaacaca attgtctgaa agtcaatgaa ttggcgctcc agttggctca atcactgcag        60
aacagcaaag tcagcacagc tgatcctcta aagaagagga caagcagcta cagaggcctg       120
agtagcgagc ctataatcac agaggaagaa ccaacaatca agggcgacta ataatagattt       180 tacagtcagt cttcagataa gcaagtattg gacaataaac catggttgca ggatggaaac       240
tatttcaaga ctgtatacat ttcaacgata gcactactga agatgatgtc tcatgcccgg       300
tccggtggtt caattgagat tatgggcatg ctgacaggta aggtgtttgc caacacatta       360
gtcgtaatgg attgctactt acttccggtt gaaggtacag agacacgagt gaatgctcaa       420
gcggaaggat atgagttcat ggtctcttat ttggataact taaaggaaat caagcataac       480
gagaatatca taggatggta tcactctcat cctggttatg ggtgctggtt gagtggaatt       540
gatgttgcca ctcagaattt aaaccaaaag tttcaagatc cctacctggc gatagtgatt       600
gatcctgaaa gatcagtcag acaaggattt gttgagattg gagcattcag aacgtttgct       660
gagccagccg ttggaagatc gtcgtcgtca gtttcctctg caagtggtgc aggaattagt       720
gatgttgcgt tttcttccgg tagaaacagt gcatctggaa tgtcctcagt tctgagtgca       780
agtaatatta gcattgccga gagctaagc aaacaatcga tcacccaaaa tgttttttgac       840 agaactacta caaagattcc caagggcaaa atgactgatt ttggagctca ttcaggaaaa       900
tattactcgc tagaggttaa ggttttcaga tctccactgg aggagaaact actggatacg       960
```

-continued

```
tttggttcta aaacctggat taaaggttta acgaactact ccaacgttgt taatgccgag     1020
gaaactcaag tggagttaat gcataaaata atggaagcca cggagaactt acggaaggaa     1080
tctccttcta aattgccatc tttggtgatg gggaacctga tttattcagg tgcctctcaa     1140
ggaacaacag ggaaccgcaa gcgctcaatg tccaaatctt ctatttattc gggtttacaa     1200
gcttcatcgg gtatacccag ttctaggtat cctacgaagg gaaaaaatat gagtggatct     1260
caattcaatg atgacccgct agcaagatca ctggataaaa taccgccaga tagtccagat     1320
caacagtacg atggcgcatt atccattcaa caaccgaaaa gagcatataa tacacatact     1380
tctagagcag gtgggttggc cagcgttctg tcctctggga gtatggatcc tcaaagttac     1440
tccatggtag gacgaatgag tctaactaat caatcgccgg ggacagctct gagaggccta     1500
aatacacctc ccaacaaacg accgcagaga aaccctggtc atacaagctc aggtcaagga     1560
ggaacgcctg gaggagtcag tcggtccaaa gagaaaatta acaagccaat aggtataagc     1620
atgattagca aggatttcaa ggttgtcatc tcacaacagg tcaaccagat gctacgtcgt     1680
cacgtccaga atgacctttt tggatccaat agtccctaa                            1719
```

```
<210> SEQ ID NO 57
<211> LENGTH: 2181
<212> TYPE: DNA
<213> ORGANISM: Pichia pastoris

<400> SEQUENCE: 57
```

```
atggatcatg cccaacgatt gctagaacta agtttttaca atcaaagtct gggcaaatca      60
gtgatagcaa agaaatacag aatagaatcc tctcgatatt tgaatgaaca actggacaag     120
tccttgacaa gagataatga tctgattgga ttatgccgta tagcattaga caacaagttg     180
accatatcag ataagattat atggatgagc tctcaagttg aagacaactt ctttccgcca     240 gttttcaag gcttgaagac gtatattgat agcgacgaga tttatcaaga gaaacttta      300 agcgtaccag cggattttga accaatagtt gaatggaaga gttgcacaga gttgcccaat     360
gaatggtcaa acaatggtgt ggacaattta tttcaggatt cttttagatga ctgttcgttt     420 gtagcttcat ttctatcctg caacaatatt ggtatccctc tcatggataa agtcattccc     480
cacaaaaact cgttcaaata tgcggttaga ctgactttca atggttgcga aaggttggtg     540
tttattgata gccgtttgcc tttgcttagg aatacttcca agactttacg agtgtcaagt     600
ttttctaaca aagatctctt atggcctagc atcatcgaaa aagctttcct gaaaatgtgt     660
gatgatgggt acaagtttc aggatcaaat tcagccattg caaactatgc tttgactggc      720
tggatccctg aagtcattaa aacttcttca tgtacaatag cagatattag ccgattgcat     780
gaggattttc ggaacggaaa cgtagtacta tgcttgggaa cgggcaatct gaccgagcga     840
gaatgcaaac agtatggatt gatccccaat catgactatg ctgtcactaa actatcattt     900
acgaatgatt cagaatacaa gtttgacatt cgtaatccgt ggactaaagg gcagaaagca     960
gtgacaatta cagatctttc aacctttgaa gttatctacg caaacagaaa tcctataatg    1020
ttttcgcaca tgaaccagct aagcggtatc tgtcaaagtc aggttaatga agagttcata    1080
gatctaattc ttaaccattc gcagtatacc ctaggcaatg acggtaattc tacaattgat    1140
gtgattcttt tctttgaaag acattcgtta agaaagaaaa tcagtgcaga gtctcgtatt    1200
gagattttcc aatcagaagg cgaaagacta atctccagaa gaaataaagc aagcaaggaa    1260
tgtgtttcta ataataccaa ctttcatttc ataacaatcg aactgaaacc gttagaaaag    1320
```

```
gtaactgtgg taatagatat cggcgagtct tcgattcgaa gccatccatt tactctaaag      1380
gcttttgcca atgattcaac tataactttg aacaaagcac tttctagacc tggttgtttc      1440
aagcaaatgg acctagagct aacgcccta aactctggtg ggaattggga taattatgct       1500
tattacaaaa atccacaact catagtcact cttcacggag attcaacgga tgaagctcca      1560
tttgaatctg ctgttttcag caaaagtgat aagaccctat ttacgtatac agtgtttggg      1620
aaaagtgacg atccagactt tcctttcatc actgacgcaa gcaagaacaa gctcgtaagc      1680
acagacaata agtataaata cagatcatgt acaagatcaa gagttgtttc ttgcgacaaa      1740
agctatttgt tcgtgctgag ctcctacgaa cctgatgcaa ttgagtcttt caaagtattt      1800
tttcaatgtt cccacgattt ttctatagag tgggctgaga cgtcgcttgg gcttttcaca      1860
aaggaagaaa ctttctcctg gaaggaccaa ttagtcaagg agttcattat tcaagtctat      1920 aaccccttcaa agttgaaagt tcacgcagta aacaccaaca acaaacgcag atcaaaacta     1980
aattgctctc tctcattcca aaacacatta atcagctctt tgcaagacta cacagacaat      2040
ctctatggat gctttattag cgggaacttg gagattcccg gcaagtatct attacaagtt      2100
cataaaaaca ttatatctaa cgaagaatgt ttggtcgaaa ttggatctag ttcgtcattt      2160
gagttatggg aacatcatta a                                                2181

<210> SEQ ID NO 58
<211> LENGTH: 1137
<212> TYPE: DNA
<213> ORGANISM: Pichia pastoris

<400> SEQUENCE: 58
atgttgaaaa ctcgatttca ttccagaaag ggttttgtaa tctacagtgg agatgatgaa        60
gagagtgacg aagagagtaa acaatggatg tttcccgagt cgacctttgt aaccaatggg       120
tttgaccaat tgttcaaggt gagaaatgtc aataccatta tgacgacga tgacggctac        180 caatcgttcg atcaaccgga ttgggcgcaa gatttaaccg cagatactca gtatcttgct       240
ttaggtgacg aaggggagaa tcatcgttca caacaagaga taggcaacag gaaaagagcc       300
aacaaaaagc aaaagaagcc aactaaagca aagacaaaac gtcaacaaag acgcacagcc       360
aaaaatgatc aatccacgga acgatctgcc atttcacaac cttctaactt aagtacactg       420
aactccttac tcaaatctgt tcggtctgaa cttttccaatt ctgatgggag tccccacaca      480
ttctacgatg tatctctcta tgaagaagat ctgaacaacc tagctgatga cgaatggttg       540
aacgataata acgtctcgtt tatctacgag tacattgaaa gattttacat taccccgttgt      600 ttgagcgaca agcttcaatt ttcatcaaag aagatggtca attctcaaat aatactcctc       660
cgaccttcta tggttttttt gctggcacat tcaactccaa aagatatcca ggattttctc       720
ccaccgttgg ataagtctgg ctttatattc cttcctctga acgacaatga tgatctggaa       780
atggctgaag gtggatccca ttggtgtctt ttagttgtag ctgttcacga taacaaatgt       840
ttcctctatg actcattaga gaatgccaat ctcacagagt ctgttgcgct tgtgtctaag       900
ctgtccactc tgctaaacag gcgaatacaa ctcgttgaaa atacacattg tcctcaacaa       960
ctcaatggca gtgattgtgg agtaatcaca acccaaatta cagcactact ggtatcccga      1020
ctgctttgtg ttttgccggg acatcctata aatttggatc ttcaaaatgt agctatcaac      1080
gcaataagcg ggagaatctt catgttaaaa ctcctccaac atgttctgaa caattaa        1137

<210> SEQ ID NO 59
<211> LENGTH: 408
```

-continued

```
<212> TYPE: DNA
<213> ORGANISM: Pichia pastoris

<400> SEQUENCE: 59
atggcaccac cagtccctgt atatacgaga gatgaagtca agatgcaatt tccacagtac        60
atgatgaaat ttttgccttc aaactgtgag ctgtactcca tcatccagaa ccaatgtacc       120
ttctctgctg acgagataat atgtgtgccc ttcaagaggg tgtttgccaa atgccggagg       180
ggaaaccaag aagccaagag gaacataata ccagagaatg gaggactgaa tttaactgga       240
aagaaactaa tcccaagaga atacacagtc attgaagtta cggactccct aacgaacaag       300
tacgacaata gtagcctcat ggacagattt tttgaggcag aaagagattt aatgataagg       360
tttcaagaat atgaggaacg gaacagtaag gaaggagaaa taaagtag                    408

<210> SEQ ID NO 60
<211> LENGTH: 1449
<212> TYPE: DNA
<213> ORGANISM: Pichia pastoris

<400> SEQUENCE: 60
atgctcagac agtttgctgg aagggagttc aagcgtcggt tttctacggg aatcaagacg        60
atgccaacaa agcttaccaa actgccaaat ggtattcgtg tcgtaacgga cgaagctccg       120
ggccatttta gtgccatggg catttttcgtt gatgctggtt caagatatga gagccagttt      180
ccagaattaa ccggccactc tcacatcatc gatagacttg cattcaaatc aacatccaaa       240
ttcgatggga aatctatggt agaaaacacc aatcatttag gtggcaactt tatgtgtgcc       300
tcttcaagag agtcattgat ataccaggct tcagtgttca caaagatgt ggacaagatg        360 gctgaaatcc tcagttctac agtcaaagaa cctttatta ctgaggagga agtttctaat         420
cagatagcaa cagcagatta tgagttggat gagttatggc tgcaacctga cctaattctt       480
cccgaattgt ctcaacaggt agcttatgga tcaaaaaatt tgggttcccc gctgctctgt       540
ccgaaggagt ctttagcaaa catctcaaga gaatcccttt tgaagtatcg tgaaatattt       600
tttagacctg agaacttggt cgttgctatg ttgggagttc cccacgagaa ggccttggaa       660
cttgttgata aaaatttagg cgatatgaaa tctgtcggtt ccagtccagt ggtcaaagaa       720
cctgctaaat atacaggagg agaacttct ttgcctccag ttcctcctat gggtgggctt        780
cccgagtttc atcacatata tcttacattt gaaggtgtcc ccgtggactc tgacgatgtc       840
tactcactgg ctactttgca gatgctcgtc ggtggtggtg gatctttctc tgctggtggt       900
ccaggaaaag gaatgtatgc cagagcatac acgcgagttc tgaatcagta cggttttatt       960
gaaagttgca attcatatat acacaatttc tcagactcgg ggctgtttgg tctctcaatt      1020
tcaagcattc cgcaggcaaa taaagttgtt gcagaactct taggtcatga actgagctgc      1080 ttgtttttctg aaaatccggg caaaggtgct cttaccaatg ccgaagtaaa ccgtgccaaa      1140
aatcagctac ggtcttcttt gttgatgaac ttggagagca gatggttca attagaagaa       1200 ctaggaagac acattcaagt ttatggcaga aaagttgatg tcacagagat gtgtgataaa      1260
atcagcaaag ttacaaagga agatctagtt gcaattgcaa agaaagtctt gaccggaagc      1320
aacccgacta tagttgttca aggtgacaga gaatcttatg gagacattga gggtactttg      1380 gcatctttg gagttggttt agatgccgct tccaaagctt caaagaaaaa aacgagaggt      1440
tggttctaa                                                            1449

<210> SEQ ID NO 61
```

```
<211> LENGTH: 390
<212> TYPE: DNA
<213> ORGANISM: Pichia pastoris

<400> SEQUENCE: 61
atggcaatta tcaagttcaa cgcaggcaaa gtcaagattg acgaggaaac caagctttgt      60
acacccttgg caacaagagg agaaataatc gtccaattgt cggctgaggg cgaagagttt     120
tatgatttca aatgggtccc tactgagaac acagctggtg aaggtaacca gtcagagaca     180
ttcttggtca ttccgggcga tgtgacgtgg aaacacgtca aaagttgtaa agatggtaga     240
gttttcaaat tgacattttt gagtagtggg gcaaagagtt tgttctggat gcaagatgat     300
aatggaaacg aggatgaccc atcagagttg acaaccaaag ataaggaaat tagtgaaaaa     360
attaccaagt tgttcgacga agaagagtga                                       390

<210> SEQ ID NO 62
<211> LENGTH: 2184
<212> TYPE: DNA
<213> ORGANISM: Pichia pastoris

<400> SEQUENCE: 62
atgaaacact tggctgtcca taagtacaag gtaggagcca tcgcagctgg cttggttgtc      60
tcctataaaa tctttgccta ccgcgctgcg tcttcctcct cctcaaacgt catcaacttg     120
accaatatgg caaaaactcc aatcacttta aaacccctc aggctccact ccgctgggac      180
catactccag agcagatcct tgccgaaact gataagtata tatctaccag tcaagaggtt     240
gacgattggg tggcaaacag ctttgccact gccaatgtgg acaccatcaa gaaaatagcc     300
gccgctgaga tgaacaata cttgccactg tgtcaattga gttttttatca acatatctcg     360 gataaccagg acgttcgtaa tgccagtact gttagtgagg agaaaattga taagttctcc     420
atcgaatcca accttagaga agatgtgttc aaaacagtga acaaagtgtt caaacaggtt     480
caagaagatt cggaactcca aaagaccttg gacccagaat ttaggcgttt actagaaaaa     540
ttgaacctag gttacgtgag atctggttta gatttatccc aggagaagag agaccaagtc     600
aagagtttga acaagaact atcaaccatt tcaatcaagt ttaataagaa cttgggagag     660
gaaactgaac acatttggtt caccactgag gagttaaaag gtgttccaga atcagttgtt     720
gagcagtttg aaactaagaa tgagaatgat gttacttacc acaagatgac atacaagtat     780
cctgacctgt tcccggtact aaaaatatgcc gttaatccag ctacgagaca aagagctttt     840
gtcggggatc aaaacaagat acctgaaaat tcaggattac ttgtgaaagc cgtcaatttg     900
agaaacgaac ttgcaaaagt tttgggttat gataccctatg ctgactatat cctggaagtg     960
aagatggcca agaactccaa gaatgttttt gaatttcttg atgatgtaag ggaaaaaactc    1020 agacctctcg gagagaagga actgcaaaga atgttgactc tcaaggctaa cgacccaaat    1080
gctgttgata aggaaaatta ctacgtctgg gatcatcgtt actatgataa caagcttctt    1140
gaatctgaat acaaagtgga tgagcaaaag ctggctgaat actttccaat ggagtccacc    1200
attgaaaaaa tgcttgccat ttacgagcac ttgttcaatt tgcagtttca acaagttgac    1260
gattcggaga acaagtttg gcatccagat gtaaaacaat tctccgtttg gaaaatcgat    1320
aaccctgatt ctcctgaatt tgtgggctgg atctatttg atttgcatcc aagagaagga    1380
aaatacggtc acgctgctaa ttttggaatc ggtcctagtt acatcaaaga agatgggagt    1440
aaaaattatc ctgtcactgc tttggtttgc aactttctca aaccatcaaa ggataagcca    1500 tcctattga agcacaatga agtcactaca ttcttccatg agctaggaca tggtatccat    1560
```

-continued

```
gatttaattg ggcaaactag gtatgctcgt ttccatggta cttcagttgc tcgtgatttc     1620
gttgaatgtc cttcacagat tctagagtac tggacctgga ctagagatca actcaagtct     1680
ctttcccaac attacaagac aggagaagcc ctctccgatg aactcattga ttcgctagtc     1740
aagtccaagc atgtcaatgg cgccattttc aatcttaggc agttacactt tggtctcttt     1800
gacatgaaac tacatactgc caaagagcct gaatctttag atgtgacaag gttgtggaac     1860
gaattacgtg aggaagtcgc tctggttaag aatggtgacc aaattacgaa aggatacggt     1920
tcatttggac acctaatggg cggttatgct gctggttact acggatacct gtattctcaa     1980
gtgtttgcca gtgacattta ttacaccttt ttcaaagctg atccaatgag tacagctcaa     2040
ggtatcaagt accgtgatat cattcttgcc agaggtggat caagagagga gctagataat     2100
ctcaaggaat tacttggaag agagcctaca tctgatgcct ttatgactga gcttggagta     2160
gaaaatggtg cgtccaagtt gtaa                                            2184
```

<210> SEQ ID NO 63
<211> LENGTH: 2766
<212> TYPE: DNA
<213> ORGANISM: Pichia pastoris

<400> SEQUENCE: 63

```
atgcgttttt tggtctcatc ctttcggccc ttcagacata caatttcgtc gcatatctca       60
atgggccagg ctctgtctgc cattcgtgta tttcataaaa attctcactc acgtacccaa      120
ggtttaaggc gccactctca ctactgttgc caccgcaaga tagatatgag tacttctact      180
aaacttccag agcgtcaatt gctaccagcc aatgttaggc ctaccaaata tgatttgaca      240
ttggagccct tattttctac cttcaagttt aacggagaag agactataca tttagatgtt      300
caggaggact ccagttctat tacgctacac gctctagaca tcgatctcca agattcacta      360
ttgataactt caaacaagtc taagactccc ccgcttcatg tgacaagcaa tgatgatgac      420
caatcgctca cttttcaatt caaagagggt actctagtaa agggagataa ggtgcagctg      480
cagttgaaat ttgttggtga attgaatgat aagatggccg gttttttaccg ctcttcatat      540 gaagagaatg gagaaactaa atatttggca actacccaga tggagccaac agattgtcgt      600
cgtgctttcc cttcctttga tgagccatcg ctaaaagccg tattcaacat tgccctcatt      660
gctgatcaga aacttacttg tctctcaaac atggacgtga agaggaaca atctctcgga      720 gatagaagga agaaggtgat attcaatccc actccactaa tttctactta cctaattgct      780
tttattgttg gtgatttaaa atatattgaa gccgactata actatcgcat tcctgtcaga      840
gtttatgcca cccctggttt agagaagcag ggtcgttttt ctgtcgagct tgctgctaaa      900
acattagaat tctttgagca acagtttgat attgattatc ctcttccaaa gatggacatg      960
gtggcgattc atgatttcag tgcaggagct atggaaaact ttgggcttgt tacctataga     1020
gttgttgatt tgctgtacga tgaaaaaaat tcaaatttgg ctactaagca acgtgttgca     1080
gaagttgtcc aacacgaatt ggcgcatcag tggtttggta atcttgtcac aatggagtgg     1140
tgggagggcc tttggctgaa tgaaggcttt gctacatgga tgtcttggta ctcttgtgac     1200
aagtttttcc ctgattggaa agtatgggaa caatatgtta cagattcttt acaacaggct     1260
ctggctctgg acgctctacg tgcttctcac cctattgaag ttcctgtgaa aagggccgac     1320
gagatcaatc aaattttga cgcaatttcc tattctaaag atcctccctt gctaaaaatg     1380
atctccaaat ggctcggaga ggatgtgttc attaagggag tctccagtta tttaaaaaag     1440
```

```
cacaggtatg gtaatacgaa aaccaccgat ttgtgggaat cgctttctga ggtgtctgga    1500
aaagatgtgg tcaaagttat gagtatctgg actggtaaaa ttggatttcc aatcatctca    1560
gtaactgaaa atgcaaaccg tatcactttt actcagaaca gatatttaac tactggtgat    1620
gtaactcctg aagaggatac gacgatttat cctgtttttt tgggactcaa aacagaaagc    1680
tcaactgatg agtcgctggt ccttgactca aggtcaatgt cagtagatat ccagaattct    1740
gactttttca aagttaatgc tgaacaagcc ggtatttaca ggaccaatta tgcaccagag    1800
agatggatca aacttggaaa gcaacctcac cttctaagtg tagaagaccg tgctggtttg    1860
gttgcggatg cgggcgctct ggctagttct ggtcactcat ctacaaggaa cttttttgaac   1920 cttgtaaatt catggaaaga tgagtctagc tttgttgtct gggacgaaat aacttcccgt    1980
gttgcagctt taaaagcagc ttggttattt gaatcccaat ctgacattga cgccctgaat    2040
gctttcgtaa gagaccttat ttctacgaag atcaaaagta tcggatggtc attcaatgat    2100
aatgaaccat ccttgaaca aagactaaag agccttctat atgctactgc tgctggtgca    2160
aaagtaccag gagtagttaa atcagcattg ataaactttc aaaaatacgt tgctggtgat    2220
aagactgcca ttcaccctaa cataaaggca gttacgtttc aaactgttgc ggcccaagga    2280
tctgaaaagg aatgggatca gttactcgac atctacaaga accctgtatc tattgatgag    2340
aaaattattg ctcttaggtc tctcggaagg tttgaagatc ccatcttgat cgcaaagacc    2400
ctggcactgt tatttgatgg ttccgtaagg tcacaagata tttacgtacc aatgcaaggc    2460
cttcgtgcga ctaagatagg agtagagtca cttttcaagt ggttgactct taattgggac    2520
aagatttata aattgcttcc acctggtctg tcaatgcttg gttctgtggt tactatcagt    2580
acttctgggt tcacttcctt ggatgatcaa aagcgtgtca aagatttctt tgcatcaaag    2640
gataccaaag gcttcgacca gggtttggcc caggcgttag acaccatcca atccaaggca    2700
agttgggtac aacgtgactc taggaatgta tccgattggc tacgtgagca gggatacaaa    2760
aaatag                                                              2766
```

<210> SEQ ID NO 64
<211> LENGTH: 1803
<212> TYPE: DNA
<213> ORGANISM: Pichia pastoris

<400> SEQUENCE: 64

```
atgataagga tatccttgct gaaaagagca ctgtttccct acgggcgact accaatgcat      60
aatggtaggt ggtattcaga cataggtggc ggaaattcaa ggaatcggaa cgaacagaaa     120
ccaaaattgc ctgtaccaac tagtaatgaa gttaaggaca atgagtcaaa cccggacttc     180
tttattaaaa acggctttag atcagctgat attgcagaga catcctttgt gaaagacaag     240
ggtgctacag tcgaagagga acgtaataca tcggacagtt cacacgaatc tcctcaactt     300
aattttaagg aaaccaacga cgaaacgaat tcaacgatcc aaccaccagt ggcaaaatta     360
cccaccccaa agcaattgaa acaatacctg gataggttca tcgtgggaca agagaagtgc     420
aagaagataa tgtcggtcgc agtttacact cattatgttc gaataaataa ccaggctcag     480
aaacggaatc agaaggtcga ttcctctgaa gaaaatgttg agaatgggtt tccaaatgtt     540
actaaagaat ttgaggacga aaatgaccca gattatgttc cggatttgga gaaatcaaat     600
gttcttttgc tgggaccgtc tggatcaggc aagaccctga ttgctaagac tctcgctaaa     660
tgtctgcagg ttccatttat aattcaagat tgtacctcct tgacccaggc tggttatgtt     720
ggcgaggata ttgagagctg tattgaaaag ttgctaattg attcagacta cgatattgaa     780
```

```
aggtgtgaaa agggaattat tgtgctggat gaaatagaca agttggccaa gccctctgtc      840
tatacaggaa ccaaagatat tgcaggagag ggtgttcaac aaggcctttt aaaactggtt      900
gaaggtacta cagttacggt tcaatgcaag aggagcaatg ctcctgatca taatcagttc      960
ggattgaatg gcaaagctac aaatcaggac aaggaaaatt atatcgttga cactacaaat     1020
atcttatttt taaccctggg agcgtttgtg aacctagata agattgttgc ttataggctg     1080
aagcagaact ctattggatt cgatactgat gagtcgaaag atatttctga aacagactca     1140
gtttccgaca aatctacatt agaatatgtt acacttccag atggatcaaa agtttcagct     1200
ctggaacttg tgtcttctac ggatctacag aattatgggt tgattccaga actgatcggc     1260
aggcttccga ttgtatcttc actttctcct ttaacagttg atgatcttgt ggctgtcctg     1320
actgagccca ggaactcgat actaaagcaa tatgtgcatt tctttgacac tgtcaatgtc     1380
aaacttgcta tcacttccaa ggcaatcaga aggatagccg agatctcgat caagaatggt     1440
acaggtgcaa gaggtctcag agccattttg gagaaactgc tactcaatgc caagtatgat     1500
tgccctggta gtagtatttc atttgtgtta gttgatacag atgttataag taagtctatc     1560
gatgagaata aggaaacggg ggaattcgtc ttcaaagatg gtgagccaaa gtattactcg     1620
cgtggagaat attttteett tttcaatgag ttatcaaaag aagacgaaaa actcaagaca     1680
tcaattgaaa agatgtgcca aataccactt tccaagaatc gcatagttta ctccgaagag     1740
gagcaggcaa ggttggattc ttctaaacct ctcgccgtga agcactatga acctttcatt     1800
tga                                                                   1803

<210> SEQ ID NO 65
<211> LENGTH: 2322
<212> TYPE: DNA
<213> ORGANISM: Pichia pastoris

<400> SEQUENCE: 65
atgagcttca acctgctaag tgttcctttta cgaacgtcaa agccgatacc gttaggcgaa       60
agcctaaaag agcttatcaa caatcagtac taccagacat ctgctgcgtt caaatcggat      120
atcgaagaga tcgaccaact aagaaatgat gtcctatcaa tagaaccaaa caatgatgga      180
cttgcattgc tcaagagata ctatgtacag ttagccagca ttagccaaaa actccctgat      240
tattttatgg agtatccctg gtttggaaca ttaggatacc aagtaactgg ccccgtagct      300
ctaaaatccc tctatttcga aagaatcaat atagcgtaca acatcgcagc gacgtattca      360
atcataggtt taaacgagcc cagagctaca ggagaaggct tgaaaaaatc atgcatttat      420
tttcagtata gtagtggggc attcgaaagt gtactgaagc tagtggagca aaaaccgaaa      480
gagctgacac ttcccattga tcttagtgtt aacattatga aaaccctggc taaactcatg      540
ctggctcagg cccaggaatg ttttttggcaa aaggctgttt ctaacacttt aaaagataac      600
gttattgcaa ggttggcctt tcaagtatct caattttacg atgaagctct gtctatggct      660
tacaagtgcg atattttaaa gtctgaatgg atagaacata tgagttgcaa gaagctgcat      720
tttaaggctg cggcccaatt tagacttgct tgtgtggcag tcgctgcttc tagacatgga      780
gaggaaatag caagattaag gattgcaaat accatttgcg aaacagcatc tagagaagcc      840
aagtatcacc ttccctctgt atcttccgat ttggagagtc tttcgaagat aatcaaagac      900
tctttaagaa gaagtgaacg tgataatgat ctaatatatc tgcaggaagt tcctaatgaa      960
tcagatcttc ctccaattgt tgcagcatct atggttgaac ctaagccaat agttgagtta     1020
```

-continued

```
aattcagctg aatgtgcgaa agatacaaag aaatacggca aaatcctttt ccatgatctt   1080
atgccatact tagtgattga aattgcacag gcatttagag agaggcagga ttcttatgtt   1140
gtaaagcata tcaaggagcc catggagatg ctgacaaaga ttcttcacac aatccttgct   1200
gaaaatggac ttccggcgtt gatagatacc atacaaaggc ctcaaagatt gccaaccaac   1260
atccttgaac attgtcaaat actcaatgaa aggggtggca tggacaaact taaggtattt   1320
ttcgaagata tcagcaagct aagacacaaa agtgagcaag ttctccaaaa ctgtgtcgaa   1380
ttgctacaaa tggaagagtc cgaaaatgag gaaatgagaa ggaagcatgg atcacagagg   1440
tggaattttg ctgactctag ggaggcatca gcagatgtca ggaaaagtgt acaggcacta   1500
gagggctatt tgaaacaggc ccatgatggt gatcaagtga tctggaatga cttcgaacaa   1560
ttgaagccac tactaagcat gatgagtgct cctaattcaa ctaaattact ggaagaattt   1620
gtaccaaatt caaaattcgt cagacttcct ccagaattga accgaatcgt taacgaatta   1680
agagctgatg ttaatcaggt caaaaagctc gcatcgcaaa gggaaacttt tattaataca   1740
gttaaagtaa aaagcaccga cctgtccata ttgcccttgg tagtttccca ttataagaaa   1800
ttacaacaaa acaacattaa tacgatcacg acggaattgt tcgaagaagt gttcagacga   1860
caggttagca acttcgattc tgatatcaga tttgttcaaa aacacaggga caaccaaatc   1920
gagttagaga agcatattaa atctttggtc caacaattca atcagcttag agggaatata   1980
gatgcctcgc aagaacgcca aaatgcactt cagttgttgg acgatgccta aacggatac   2040 cttgatttgg taaacaacct cacacaggga cttagttttt acaatgattt cactggaaag   2100
gcaaatgatg tctatttgag atgtcaagaa ttctacaact ttcgtaaaca agaagccatg   2160
aagctggagc aggaaatata tgctgtattt gaacaaggta aatctcctca gaaaaaacaa   2220
ctagaagatc aggtttcaga tcaaccaaaa agtgaagtca agtcttcaaa gggttattct   2280
aatgagctgt ggaaccccga cgttggaatt aaatttggct ag                      2322
```

<210> SEQ ID NO 66
<211> LENGTH: 960
<212> TYPE: DNA
<213> ORGANISM: Pichia pastoris

<400> SEQUENCE: 66

```
atggtggcct ctcttcacat tgtcaatccg aatttggcct ccgctttcag tttgcctccc     60
aggtcaaaca ctttgagcgt ttccatacac gcttcggctt tgttacagat cctggaatca    120
agttacttcg accagaataa gaatggtcgt atcataggaa ccctcctagg ttctaggtct    180
gaagagacaa cggaggttca agtcaaagac tctttcatag tttcccacac ggaggacgga    240
gacgagttta ccattgattc ttctcaacgt gaatttgtcg ccatccacaa gaagtctagc    300
ccaagagact cagtcgtagg atggtttttcc attaactcta aggtcgacag ctttatcgga    360
ctggtccatg acttttttctc aaagggtcca gatagcacac accgtaccc tgccatatat    420 ttgagtatcc agttatgtga cgagagcgga tccttcgtag agccagtttt caaggcgtac    480
gttgcctccc cagtgggatg ttatggagct ctggcaagtc acttagacct tgaaaaagct    540
ggctcttttg tcttctctga agtcccaacc aaggtcatat actctgctaa cgaaaaaagt    600
ctgctggctc atttcaagaa caacgttgtg aacccaaag ttccaatacc acaaaacgac    660
acaaatcaac taatttcaca actcaacaaa ctcgacgttt ccattgacca gttaatagac    720
tacgttgaca aagtcatttc aggatctctg gatgaaatg atgtgaagaa tgatgagatt    780
ggccgtttcc tgttgaccaa cttagtttcc cttccaactt ctccttcaaa ggaagagctt    840
```

```
tcatcttcca taagctctca tatccaggac tcactgatga tcgactactt ggcctccgcc    900
gtgaaaactc aattagatgt tagctccaaa ttaatgaacc tggtacaaga tgataaatag    960
```

<210> SEQ ID NO 67
<211> LENGTH: 599
<212> TYPE: PRT
<213> ORGANISM: Pichia pastoris

<400> SEQUENCE: 67

```
Met Leu Lys Asp Gln Phe Leu Leu Trp Val Ala Leu Ile Ala Ser Val
1               5                   10                  15

Pro Val Ser Gly Val Met Ala Ala Pro Ser Glu Ser Gly His Asn Thr
                20                  25                  30

Val Glu Lys Arg Asp Ala Lys Asn Val Val Gly Val Gln Gln Leu Asp
            35                  40                  45

Phe Ser Val Leu Arg Gly Asp Ser Phe Glu Ser Ala Ser Ser Glu Asn
        50                  55                  60

Val Pro Arg Leu Val Arg Arg Asp Asp Thr Leu Glu Ala Glu Leu Ile
65                  70                  75                  80

Asn Gln Gln Ser Phe Tyr Leu Ser Arg Leu Lys Val Gly Ser His Gln
                85                  90                  95

Ala Asp Ile Gly Ile Leu Val Asp Thr Gly Ser Ser Asp Leu Trp Val
            100                 105                 110

Met Asp Ser Val Asn Pro Tyr Cys Ser Ser Arg Ser Arg Val Lys Arg
        115                 120                 125

Asp Ile His Asp Glu Lys Ile Ala Glu Trp Asp Pro Ile Asn Leu Lys
    130                 135                 140

Lys Asn Glu Thr Ser Gln Asn Lys Asn Phe Trp Asp Trp Leu Val Gly
145                 150                 155                 160

Thr Ser Thr Ser Ser Pro Ser Thr Ala Thr Ala Thr Gly Ser Gly Ser
                165                 170                 175

Gly Ser Gly Ser Gly Ser Gly Ser Gly Ser Ala Ala Thr Ala Val Ser
            180                 185                 190

Val Ser Ser Ala Gln Ala Thr Leu Asp Cys Ser Thr Tyr Gly Thr Phe
        195                 200                 205

Asp His Ala Asp Ser Ser Thr Phe His Asp Asn Asn Thr Asp Phe Phe
    210                 215                 220

Ile Ser Tyr Ala Asp Thr Thr Phe Ala Ser Gly Ile Trp Gly Tyr Asp
225                 230                 235                 240

Asp Val Ile Ile Asp Gly Ile Glu Val Lys Glu Leu Ser Phe Ala Val
                245                 250                 255

Ala Asp Met Thr Asn Ser Ser Ile Gly Val Leu Gly Ile Gly Leu Lys
            260                 265                 270

Gly Leu Glu Ser Thr Tyr Ala Ser Ala Ser Ser Val Ser Glu Met Tyr
        275                 280                 285

Gln Tyr Asp Asn Leu Pro Ala Lys Met Val Thr Asp Gly Leu Ile Asn
    290                 295                 300

Lys Asn Ala Tyr Ser Leu Tyr Leu Asn Ser Lys Asp Ala Ser Ser Gly
305                 310                 315                 320

Ser Ile Leu Phe Gly Gly Val Asp His Glu Lys Tyr Ser Gly Gln Leu
                325                 330                 335

Leu Thr Val Pro Val Ile Asn Thr Leu Ala Ser Ser Gly Tyr Arg Glu
            340                 345                 350
```

-continued
_____

```
Ala Ile Arg Leu Gln Ile Thr Leu Asn Gly Ile Asp Val Lys Lys Gly
        355                 360                 365

Ser Asp Gln Gly Thr Leu Leu Gln Gly Arg Phe Ala Ala Leu Leu Asp
        370                 375                 380

Ser Gly Ala Thr Leu Thr Tyr Ala Pro Ser Ser Val Leu Asn Ser Ile
385                 390                 395                 400

Gly Arg Asn Leu Gly Gly Ser Tyr Asp Ser Ser Arg Gln Ala Tyr Thr
                405                 410                 415

Ile Arg Cys Val Ser Ala Ser Asp Thr Thr Ser Leu Val Phe Asn Phe
                420                 425                 430

Gly Gly Ala Thr Val Glu Val Ser Leu Tyr Asp Leu Gln Ile Ala Thr
        435                 440                 445

Tyr Tyr Thr Gly Gly Ser Ala Thr Gln Cys Leu Ile Gly Ile Phe Ser
        450                 455                 460

Ser Gly Ser Asp Glu Phe Val Leu Gly Asp Thr Phe Leu Arg Ser Ala
465                 470                 475                 480

Tyr Val Val Tyr Asp Leu Asp Gly Leu Glu Val Ser Leu Ala Gln Ala
                485                 490                 495

Asn Phe Asn Glu Thr Asp Ser Asp Val Glu Ala Ile Thr Ser Ser Val
                500                 505                 510

Pro Ser Ala Thr Arg Ala Ser Gly Tyr Ser Ser Thr Trp Ser Gly Ser
        515                 520                 525

Ala Ser Gly Thr Val Tyr Thr Ser Val Gln Met Glu Ser Gly Ala Ala
        530                 535                 540

Ser Ser Ser Asn Ser Ser Gly Ser Asn Met Gly Ser Ser Ser Ser Ser
545                 550                 555                 560

Ser Ser Ser Ser Ser Ser Thr Ser Ser Gly Asp Glu Glu Gly Gly Ser
                565                 570                 575

Ser Ala Asn Arg Val Pro Phe Ser Tyr Leu Ser Leu Cys Leu Val Val
                580                 585                 590

Ile Leu Gly Val Cys Ile Val
        595
```

```
<210> SEQ ID NO 68
<211> LENGTH: 562
<212> TYPE: PRT
<213> ORGANISM: Pichia pastoris

<400> SEQUENCE: 68
```

```
Met Ile Ile Asn His Leu Val Leu Thr Ala Leu Ser Ile Ala Leu Ala
1               5                   10                  15

Asn Asp Tyr Glu Ser Leu Asp Leu Arg His Ile Gly Val Leu Tyr Thr
                20                  25                  30

Ala Glu Ile Gln Ile Gly Ser Asp Glu Thr Glu Ile Glu Val Ile Val
        35                  40                  45

Asp Thr Gly Ser Ala Asp Leu Trp Val Ile Asp Ser Asp Ala Ala Val
        50                  55                  60

Cys Glu Leu Ser Tyr Asp Glu Ile Glu Ala Asn Ser Phe Ser Ser Ala
65                  70                  75                  80

Ser Ala Lys Phe Met Asp Lys Ile Ala Pro Pro Ser Gln Glu Leu Leu
                85                  90                  95

Asp Gly Leu Ser Glu Phe Gly Phe Ala Leu Asp Gly Glu Ile Ser Gln
                100                 105                 110

Tyr Leu Ala Asp Lys Ser Gly Arg Val Ser Lys Arg Glu Glu Asn Gln
        115                 120                 125
```

-continued

```
Gln Asp Phe Asn Ile Asn Arg Asp Glu Pro Val Cys Glu Gln Phe Gly
    130             135             140

Ser Phe Asp Ser Ser Ser Ser Asp Thr Phe Gln Ser Asn Asn Ser Ala
145             150             155             160

Phe Gly Ile Ala Tyr Leu Asp Gly Thr Thr Ala Asn Gly Thr Trp Val
                165             170             175

Arg Asp Thr Val Arg Ile Gly Asp Phe Ala Ile Ser Gln Gln Ser Phe
            180             185             190

Ala Leu Val Asn Ile Thr Asp Asn Tyr Met Gly Ile Leu Gly Leu Gly
        195             200             205

Pro Ala Thr Gln Gln Thr Thr Asn Ser Asn Pro Ile Ala Ala Asn Arg
    210             215             220

Phe Thr Tyr Asp Gly Val Val Asp Ser Leu Arg Ser Gln Gly Phe Ile
225             230             235             240

Asn Ser Ala Ser Phe Ser Val Tyr Leu Ser Pro Asp Glu Asp Asn Glu
            245             250             255

His Asp Glu Phe Ser Asp Gly Glu Ile Leu Phe Gly Ala Ile Asp Arg
            260             265             270

Ala Lys Ile Asp Gly Pro Phe Arg Leu Phe Pro Tyr Val Asn Pro Tyr
        275             280             285

Lys Pro Val Tyr Pro Asp Gln Tyr Thr Ser Tyr Val Thr Val Ser Thr
    290             295             300

Ile Ala Val Ser Ser Ser Asp Glu Thr Leu Ile Ile Glu Arg Arg Pro
305             310             315             320

Arg Leu Ala Leu Ile Asp Thr Gly Ala Thr Phe Ser Tyr Leu Pro Thr
            325             330             335

Tyr Pro Leu Ile Arg Leu Ala Phe Ser Ile His Gly Gly Phe Glu Tyr
            340             345             350

Val Ser Gln Leu Gly Leu Phe Val Ile Arg Thr Ser Ser Leu Ser Val
        355             360             365

Ala Arg Asn Lys Val Ile Glu Phe Lys Phe Gly Glu Asp Val Val Ile
    370             375             380

Gln Ser Pro Val Ser Asp His Leu Leu Asp Val Ser Gly Leu Phe Thr
385             390             395             400

Asp Gly Gln Gln Tyr Ser Ala Leu Thr Val Arg Glu Ser Leu Asp Gly
            405             410             415

Leu Ser Ile Leu Gly Asp Thr Phe Ile Lys Ser Ala Tyr Leu Phe Phe
            420             425             430

Asp Asn Glu Asn Ser Gln Leu Gly Ile Gly Gln Ile Asn Val Thr Asp
        435             440             445

Asp Glu Asp Ile Glu Val Val Gly Asp Phe Thr Ile Glu Arg Asp Pro
    450             455             460

Ala Tyr Ser Ser Thr Trp Ser Ser Asp Leu Pro His Glu Thr Pro Thr
465             470             475             480

Arg Ala Leu Ser Thr Ala Ser Gly Gly Gly Leu Gly Thr Gly Ile Asn
            485             490             495

Thr Ala Thr Ser Arg Ala Ser Ser Arg Ser Thr Ser Gly Ser Thr Ser
            500             505             510

Arg Thr Ser Ser Thr Ser Gly Ser Ala Ser Gly Thr Ser Ser Gly Ala
        515             520             525

Ser Ser Ala Thr Gln Asn Asp Glu Thr Ser Thr Asp Leu Gly Ala Pro
    530             535             540
```

```
Ala Ala Ser Leu Ser Ala Thr Pro Cys Leu Phe Ala Ile Leu Leu Leu
545                 550                 555                 560

Met Leu
```

<210> SEQ ID NO 69
<211> LENGTH: 207
<212> TYPE: PRT
<213> ORGANISM: Pichia pastoris

<400> SEQUENCE: 69

```
Met Val Ala Ser His Val Asn Asn Ala Ser Ala Ser Arg Ser Asn Thr
1               5                   10                  15

Ser Val Ser His Ala Ser Ala Ser Ser Tyr Asp Asn Lys Asn Gly Arg
                20                  25                  30

Gly Thr Gly Ser Arg Ser Thr Thr Val Val Lys Asp Ser Val Ser His
            35                  40                  45

Thr Asp Gly Asp Thr Asp Ser Ser Arg Val Ala His Lys Lys Ser Ser
        50                  55                  60

Arg Asp Ser Val Val Gly Trp Ser Asn Ser Lys Val Asp Ser Gly Val
65                  70                  75                  80

His Asp Ser Lys Gly Asp Ser Thr His Tyr Ala Tyr Ser Cys Asp Ser
                85                  90                  95

Gly Ser Val Val Lys Ala Tyr Val Ala Ser Val Gly Cys Tyr Gly Ala
            100                 105                 110

Ala Ser His Asp Lys Ala Gly Ser Val Ser Val Thr Lys Val Tyr Ser
        115                 120                 125

Ala Asn Lys Ser Ala His Lys Asn Asn Val Val Lys Val Asn Asp Thr
        130                 135                 140

Asn Ser Asn Lys Asp Val Ser Asp Asp Tyr Val Asp Lys Val Ser Gly
145                 150                 155                 160

Ser Asp Arg Asn Asp Val Lys Asn Asp Gly Arg Thr Asn Val Ser Thr
                165                 170                 175

Ser Ser Lys Ser Ser Ser Ser Ser His Asp Ser Met Asp Tyr Ala Ser
            180                 185                 190

Ala Val Lys Thr Asp Val Ser Ser Lys Met Asn Val Asp Asp Lys
        195                 200                 205
```

<210> SEQ ID NO 70
<211> LENGTH: 20
<212> TYPE: DNA
<213> ORGANISM: Artificial Sequence
<220> FEATURE:
<223> OTHER INFORMATION: Description of Artificial Sequence: Synthetic
     primer

<400> SEQUENCE: 70

```
acctattgtt taccttcctg                                                   20
```

<210> SEQ ID NO 71
<211> LENGTH: 40
<212> TYPE: DNA
<213> ORGANISM: Artificial Sequence
<220> FEATURE:
<223> OTHER INFORMATION: Description of Artificial Sequence: Synthetic
     primer

<400> SEQUENCE: 71

```
gaattctctc acttaatctt tagctcccat gctcatcttg                             40
```

-continued

<210> SEQ ID NO 72
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 72
gcggccgcaa gaagttgatt gtttatttgt aggcggtgcc                               40

<210> SEQ ID NO 73
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 73
gggctatccg ccttatcttg                                                     20

<210> SEQ ID NO 74
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 74
aataacttca tgactgcatt                                                     20

<210> SEQ ID NO 75
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 75
gaattctctc acttaatctt agtttaaata atatggagat                               40

<210> SEQ ID NO 76
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 76
gcggccgcaa gaagttgatt attggagaaa aggaatacac                               40

<210> SEQ ID NO 77
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 77
ggcatctccg tctggtgcag                                                     20

<210> SEQ ID NO 78

-continued

<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 78
caaggttcga aactgcagct                                                                               20

<210> SEQ ID NO 79
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 79
ctcacttaat cttctgtact ctgaagagag agcaaaccaa tggcaa                               46

<210> SEQ ID NO 80
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 80
agaagttgat tgagactttc aacgagggtc ctttggcaat cattggt                            47

<210> SEQ ID NO 81
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 81
accccaggac caggtatttc                                                                               20

<210> SEQ ID NO 82
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 82
tactacaggc tggctgttcc                                                                               20

<210> SEQ ID NO 83
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 83
ctcacttaat cttctgtact ctgaagaagt ccaactgttg aacgcc                               46

<210> SEQ ID NO 84
<211> LENGTH: 46

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 84
agaagttgat tgagactttc aacgagggtc cccttcagct accttt                    46

<210> SEQ ID NO 85
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 85
tccctgctaa gccctaatcg                                                 20

<210> SEQ ID NO 86
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 86
aagttgtatg gccgtcctca                                                 20

<210> SEQ ID NO 87
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 87
ctcacttaat cttctgtact ctgaagtgag tcttggttgt gtcggt                    46

<210> SEQ ID NO 88
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 88
agaagttgat tgagactttc aacgaggcct cctgtttgat cggttc                    46

<210> SEQ ID NO 89
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 89
gtgccatggt gacgttacag                                                 20

<210> SEQ ID NO 90
<211> LENGTH: 20
<212> TYPE: DNA
```

<213> ORGANISM: Artificial Sequence
<220> FEATURE:
<223> OTHER INFORMATION: Description of Artificial Sequence: Synthetic
      primer

<400> SEQUENCE: 90
cggagttata ggggacgctt                                              20

<210> SEQ ID NO 91
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 91
ctcacttaat cttctgtact ctgaagcgtc acatcatagc cgttctc                47

<210> SEQ ID NO 92
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 92
agaagttgat tgagactttc aacgagcgtc aaaagtggtc gtggac                 46

<210> SEQ ID NO 93
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 93
tggcccagtt acacggaata                                              20

<210> SEQ ID NO 94
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 94
gtcgatcgtt ggtgtgtgac                                              20

<210> SEQ ID NO 95
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 95
ctcacttaat cttctgtact ctgaaggagc cgactttgac atcgac                 46

<210> SEQ ID NO 96
<211> LENGTH: 46
<212> TYPE: DNA
<213> ORGANISM: Artificial Sequence -continued

```
<220> FEATURE:
<223> OTHER INFORMATION: Description of Artificial Sequence: Synthetic
      primer

<400> SEQUENCE: 96
agaagttgat tgagactttc aacgagagcg aagagactgg ttccaa                    46

<210> SEQ ID NO 97
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 97
agctgttcta accgtcctca                                                 20

<210> SEQ ID NO 98
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 98
cttggaatat ctgtgggcgc                                                 20

<210> SEQ ID NO 99
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 99
ctcacttaat cttctgtact ctgaagtcat gaccagcagt tgttca                    46

<210> SEQ ID NO 100
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 100
agaagttgat tgagactttc aacgagatgc tgcaggaagg aacact                    46

<210> SEQ ID NO 101
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 101
caaactctgc acctccaagc                                                 20

<210> SEQ ID NO 102
<211> LENGTH: 20
<212> TYPE: DNA
<213> ORGANISM: Artificial Sequence
<220> FEATURE:
```

-continued

<223> OTHER INFORMATION: Description of Artificial Sequence: Synthetic
      primer

<400> SEQUENCE: 102
ctctgattgc acgagaaggc                                               20

<210> SEQ ID NO 103
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 103
ctcacttaat cttctgtact ctgaagtgaa aggcgattgg agttgc                  46

<210> SEQ ID NO 104
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 104
agaagttgat tgagactttc aacgagctgg ctctgcttct ggtact                  46

<210> SEQ ID NO 105
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 105
gatgttgagg cgggcataag                                               20

<210> SEQ ID NO 106
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 106
tttcaacggg gttctacgga                                               20

<210> SEQ ID NO 107
<211> LENGTH: 48
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 107
ctcacttaat cttctgtact ctgaaggtgg tagtatgtgt gttggtgt               48

<210> SEQ ID NO 108
<211> LENGTH: 46
<212> TYPE: DNA
<213> ORGANISM: Artificial Sequence
<220> FEATURE:
<223> OTHER INFORMATION: Description of Artificial Sequence: Synthetic -continued primer

<400> SEQUENCE: 108
agaagttgat tgagactttc aacgagctgc gctttcaagt actgca                          46

<210> SEQ ID NO 109
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 109
tgtcttcctc gtcttcctcg                                                       20

<210> SEQ ID NO 110
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 110
cgggcaataa tcagtggagc                                                       20

<210> SEQ ID NO 111
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 111
ctcacttaat cttctgtact ctgaagcgtt ggaggtaatg catggg                          46

<210> SEQ ID NO 112
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 112
agaagttgat tgagactttc aacgagggcg gaccgtgtat tagaga                          46

<210> SEQ ID NO 113
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 113
tcagagaagc cagtggaagg                                                       20

<210> SEQ ID NO 114
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 114
ttcctcggcc tctttatgct                                              20

<210> SEQ ID NO 115
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 115
ctcacttaat cttctgtact ctgaagcaac gtggctaact ccttgg                 46

<210> SEQ ID NO 116
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 116
agaagttgat tgagactttc aacgaggttg tcgacggcat tgaaga                 46

<210> SEQ ID NO 117
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 117
tcggttcaaa gcccctaagt                                              20

<210> SEQ ID NO 118
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 118
aggtgtgaaa tgcgctgatc                                              20

<210> SEQ ID NO 119
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 119
ctcacttaat cttctgtact ctgaagaaac caacaacgcc tggtac                 46

<210> SEQ ID NO 120
<211> LENGTH: 46
<212> TYPE: DNA
<213> ORGANISM: Artificial Sequence
<220> FEATURE:
<223> OTHER INFORMATION: Description of Artificial Sequence: Synthetic
      primer
```

-continued

<400> SEQUENCE: 120
agaagttgat tgagactttc aacgagtcac aggctgaagg atcgaa                              46

<210> SEQ ID NO 121
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 121
ccatggtgtg ttttccggtt                                                          20

<210> SEQ ID NO 122
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 122
tgagggacaa agtaatgggg t                                                        21

<210> SEQ ID NO 123
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 123
ctcacttaat cttctgtact ctgaagaccg aagtcatggt tggaaa                             46

<210> SEQ ID NO 124
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 124
agaagttgat tgagactttc aacgagctac cgcagacaac ccattc                             46

<210> SEQ ID NO 125
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 125
cgctccctca tcgagtactt                                                          20

<210> SEQ ID NO 126
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 126
cagacatcgt ggaaactgcc                                                                    20

<210> SEQ ID NO 127
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 127
ctcacttaat cttctgtact ctgaagtatc tgcttcgatc cctgca                                     46

<210> SEQ ID NO 128
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 128
agaagttgat tgagactttc aacgagttct cccgtccagt tagcag                                     46

<210> SEQ ID NO 129
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 129
atttcagaag ctccgcatcc                                                                    20

<210> SEQ ID NO 130
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 130
acaaaagcac gcgattgaga                                                                    20

<210> SEQ ID NO 131
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 131
ctcacttaat cttctgtact ctgaagacac tcacggttgt ttgcaa                                     46

<210> SEQ ID NO 132
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 132

-continued agaagttgat tgagactttc aacgagaacc ccaacaagcg gctata                46

<210> SEQ ID NO 133
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 133
acccggatct gctagtgaag                                             20

<210> SEQ ID NO 134
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 134
cgtatgctcg tgtgactgtg                                             20

<210> SEQ ID NO 135
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 135
ctcacttaat cttctgtact ctgaagttcc tatgcctggc gatgat               46

<210> SEQ ID NO 136
<211> LENGTH: 49
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 136
agaagttgat tgagactttc aacgagaggg agtcttgtat agttgagca            49

<210> SEQ ID NO 137
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 137
agcaggggta ttttcacgga                                             20

<210> SEQ ID NO 138
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 138
agcatgattg tgttgggtgg                                             20

```
<210> SEQ ID NO 139
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 139
ctcacttaat cttctgtact ctgaagaatc cgatactgta gccccg                      46

<210> SEQ ID NO 140
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 140
agaagttgat tgagactttc aacgaggcaa agaaaactgg ccacac                      46

<210> SEQ ID NO 141
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 141
ggaaggccct attcacgact                                                   20

<210> SEQ ID NO 142
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 142
caccatttcc ctgctgtgtc                                                   20

<210> SEQ ID NO 143
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 143
ctcacttaat cttctgtact ctgaagtcaa taccgaagac tccgca                      46

<210> SEQ ID NO 144
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 144
agaagttgat tgagactttc aacgagggga ggtattcagg aggcat                      46
```

-continued

<210> SEQ ID NO 145
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 145
gctcgatcag atattgtccg c                                                 21

<210> SEQ ID NO 146
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 146
agcagctctc caatcagtgt                                                   20

<210> SEQ ID NO 147
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 147
ctcacttaat cttctgtact ctgaagctgg aattgtgatc ccgctg                      46

<210> SEQ ID NO 148
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 148
agaagttgat tgagactttc aacgagtttt gaagcaagcc tacccc                      46

<210> SEQ ID NO 149
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 149
caggatccag ccgctaaaac                                                   20

<210> SEQ ID NO 150
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 150
tgaacaagca gccacatcac                                                   20

-continued

```
<210> SEQ ID NO 151
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 151
ctcacttaat cttctgtact ctgaagtgag ggccattctg acatact                  47

<210> SEQ ID NO 152
<211> LENGTH: 48
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 152
agaagttgat tgagactttc aacgaggtga ggtatttaac tgcacgag                 48

<210> SEQ ID NO 153
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 153
tcgcctacat agtctgcaca                                                20

<210> SEQ ID NO 154
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 154
acctcatgcc atgtctgtca                                                20

<210> SEQ ID NO 155
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 155
ctcacttaat cttctgtact ctgaagttga ctgccgcttc aaagtc                   46

<210> SEQ ID NO 156
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 156
agaagttgat tgagactttc aacgagccgc cagagaattt gtgctt                   46

<210> SEQ ID NO 157
```

```
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 157
tagaggtgaa cgtttggcct                                              20

<210> SEQ ID NO 158
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 158
aatccatcac ctccacccag                                              20

<210> SEQ ID NO 159
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 159
ctcacttaat cttctgtact ctgaaggctg ctggagtaaa aggtcc                 46

<210> SEQ ID NO 160
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 160
agaagttgat tgagactttc aacgagcaag cagcaaccat ctacgg                 46

<210> SEQ ID NO 161
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 161
aacctcatcc actgtcagca                                              20

<210> SEQ ID NO 162
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 162
ggaagacaaa gttcgctccg                                              20

<210> SEQ ID NO 163
<211> LENGTH: 48
```

-continued

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 163
ctcacttaat cttctgtact ctgaagtcat agttgagagc ctccttgt                     48

<210> SEQ ID NO 164
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 164
agaagttgat tgagactttc aacgagacaa tgcactagga cgggat                       46

<210> SEQ ID NO 165
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 165
cttgaatcag gcgacgtacc                                                    20

<210> SEQ ID NO 166
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 166
cccagctctc tttcactcca                                                    20

<210> SEQ ID NO 167
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 167
ctcacttaat cttctgtact ctgaagttga agagcagcag agtcga                       46

<210> SEQ ID NO 168
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 168
agaagttgat tgagactttc aacgagttaa ttgcccacag tgtcgc                       46

<210> SEQ ID NO 169
<211> LENGTH: 20
<212> TYPE: DNA
```

-continued

<213> ORGANISM: Artificial Sequence
<220> FEATURE:
<223> OTHER INFORMATION: Description of Artificial Sequence: Synthetic
       primer

<400> SEQUENCE: 169
accttccaca gtcgacgaat                                                                  20

<210> SEQ ID NO 170
<211> LENGTH: 21
<212> TYPE: DNA
<213> ORGANISM: Artificial Sequence
<220> FEATURE:
<223> OTHER INFORMATION: Description of Artificial Sequence: Synthetic
       primer

<400> SEQUENCE: 170
acaaacagtc aaatgcacgg a                                                                21

<210> SEQ ID NO 171
<211> LENGTH: 46
<212> TYPE: DNA
<213> ORGANISM: Artificial Sequence
<220> FEATURE:
<223> OTHER INFORMATION: Description of Artificial Sequence: Synthetic
       primer

<400> SEQUENCE: 171
ctcacttaat cttctgtact ctgaagtcct tccacctttc caacgt                                     46

<210> SEQ ID NO 172
<211> LENGTH: 47
<212> TYPE: DNA
<213> ORGANISM: Artificial Sequence
<220> FEATURE:
<223> OTHER INFORMATION: Description of Artificial Sequence: Synthetic
       primer

<400> SEQUENCE: 172
agaagttgat tgagactttc aacgaggggg tagagaagtt agggagg                                    47

<210> SEQ ID NO 173
<211> LENGTH: 20
<212> TYPE: DNA
<213> ORGANISM: Artificial Sequence
<220> FEATURE:
<223> OTHER INFORMATION: Description of Artificial Sequence: Synthetic
       primer

<400> SEQUENCE: 173
ggaactacaa ctggaggcct                                                                  20

<210> SEQ ID NO 174
<211> LENGTH: 20
<212> TYPE: DNA
<213> ORGANISM: Artificial Sequence
<220> FEATURE:
<223> OTHER INFORMATION: Description of Artificial Sequence: Synthetic
       primer

<400> SEQUENCE: 174
tagtgccggt tccatggatt                                                                  20

<210> SEQ ID NO 175
<211> LENGTH: 46
<212> TYPE: DNA
<213> ORGANISM: Artificial Sequence

```
<220> FEATURE:
<223> OTHER INFORMATION: Description of Artificial Sequence: Synthetic
      primer

<400> SEQUENCE: 175
ctcacttaat cttctgtact ctgaagggtc tatgggttga tgcgga                      46

<210> SEQ ID NO 176
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 176
agaagttgat tgagactttc aacgagatgt gttgctcgct ctaggt                      46

<210> SEQ ID NO 177
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 177
cgacaaacac accaaggtcc                                                   20

<210> SEQ ID NO 178
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 178
gttgttggag tgagcgatgg                                                   20

<210> SEQ ID NO 179
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 179
ctcacttaat cttctgtact ctgaagcctc cgttgatact cccgat                      46

<210> SEQ ID NO 180
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 180
agaagttgat tgagactttc aacgagtgca ttcaaggctg gcaaat                      46

<210> SEQ ID NO 181
<211> LENGTH: 20
<212> TYPE: DNA
<213> ORGANISM: Artificial Sequence
<220> FEATURE:
```

<223> OTHER INFORMATION: Description of Artificial Sequence: Synthetic
      primer

<400> SEQUENCE: 181
gcatatggag tggtgtgcag                                              20

<210> SEQ ID NO 182
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 182
cgggtagcat tgaacgtacg                                              20

<210> SEQ ID NO 183
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 183
ctcacttaat cttctgtact ctgaagatgc tacggtaaac acccca               46

<210> SEQ ID NO 184
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 184
agaagttgat tgagactttc aacgagactg gagaaagctt ggtcga               46

<210> SEQ ID NO 185
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 185
aggcaccaga agaaagagct                                              20

<210> SEQ ID NO 186
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 186
ggacacgttt ggagcttctt                                              20

<210> SEQ ID NO 187
<211> LENGTH: 46
<212> TYPE: DNA
<213> ORGANISM: Artificial Sequence
<220> FEATURE:
<223> OTHER INFORMATION: Description of Artificial Sequence: Synthetic -continued

```
      primer

<400> SEQUENCE: 187
ctcacttaat cttctgtact ctgaaggccc accaattcag caactt                      46

<210> SEQ ID NO 188
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 188
agaagttgat tgagactttc aacgaggatg ctggtcacat ggttcc                      46

<210> SEQ ID NO 189
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 189
aaccgccaat agtttcagcc                                                    20

<210> SEQ ID NO 190
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 190
ggatgagaaa gcggcttctg                                                    20

<210> SEQ ID NO 191
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 191
ctcacttaat cttctgtact ctgaaggtgc caaaagtctg atccgg                      46

<210> SEQ ID NO 192
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 192
agaagttgat tgagactttc aacgagtgcc acttcgttct ttgacg                      46

<210> SEQ ID NO 193
<211> LENGTH: 20
<212> TYPE: DNA
<213> ORGANISM: Artificial Sequence
<220> FEATURE:
<223> OTHER INFORMATION: Description of Artificial Sequence: Synthetic
      primer
```

-continued

<400> SEQUENCE: 193
acggatcagt gatggcgtat                                              20

<210> SEQ ID NO 194
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 194
atgggatctg gacgacgttt                                              20

<210> SEQ ID NO 195
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 195
ctcacttaat cttctgtact ctgaagagct ggatcacaaa cattcgg                47

<210> SEQ ID NO 196
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 196
agaagttgat tgagactttc aacgagcttt gagtgttggt ccctgc                 46

<210> SEQ ID NO 197
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 197
cggctaccaa gtcagacctt                                              20

<210> SEQ ID NO 198
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 198
gttgcccatt acgtcctgtg                                              20

<210> SEQ ID NO 199
<211> LENGTH: 49
<212> TYPE: DNA
<213> ORGANISM: Artificial Sequence
<220> FEATURE:
<223> OTHER INFORMATION: Description of Artificial Sequence: Synthetic
      primer -continued

```
<400> SEQUENCE: 199
ctcacttaat cttctgtact ctgaagcctt tgatctttgg tgcatcttg              49

<210> SEQ ID NO 200
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 200
agaagttgat tgagactttc aacgagcact acagctggga acgaga               46

<210> SEQ ID NO 201
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 201
acgggttgga aaagttgagc                                            20

<210> SEQ ID NO 202
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 202
agtggggttg gagattggag                                            20

<210> SEQ ID NO 203
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 203
ctcacttaat cttctgtact ctgaagacga ttccagcata gcctgt               46

<210> SEQ ID NO 204
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 204
agaagttgat tgagactttc aacgagctgg tagccgcaaa acttca               46

<210> SEQ ID NO 205
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 205
```
gcgttgaatc ctcctcgttc                                              20

<210> SEQ ID NO 206
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 206
ctgtggggtc tgaacatcct                                              20

<210> SEQ ID NO 207
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 207
ctcacttaat cttctgtact ctgaagagct gctagggttc attgagt               47

<210> SEQ ID NO 208
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 208
agaagttgat tgagactttc aacgagctcc cttgggtacg tcaact                46

<210> SEQ ID NO 209
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 209
tggcagtctt cacatgtcct                                              20

<210> SEQ ID NO 210
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 210
agctggtcaa gtctggtacc                                              20

<210> SEQ ID NO 211
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 211
ctcacttaat cttctgtact ctgaaggagg tctagtgtgt gaggct                      46

<210> SEQ ID NO 212
<211> LENGTH: 49
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 212
agaagttgat tgagactttc aacgagagaa ggtataggga atatgcggt                   49

<210> SEQ ID NO 213
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 213
tagccacaac cctgatgacg                                                   20

<210> SEQ ID NO 214
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 214
tacactggga cgcagatgtt                                                   20

<210> SEQ ID NO 215
<211> LENGTH: 48
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 215
ctcacttaat cttctgtact ctgaagtgct caaactctgt atccgttg                    48

<210> SEQ ID NO 216
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 216
agaagttgat tgagactttc aacgagcttt caaggccgca atgcta                      46

<210> SEQ ID NO 217
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 217
cttcctttgc agttggtggt                                                   20

<210> SEQ ID NO 218
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 218
gggtctttgg ctttggtgag                                                                 20

<210> SEQ ID NO 219
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 219
ctcacttaat cttctgtact ctgaagcgtc tctggaactc gtcgat                                     46

<210> SEQ ID NO 220
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 220
agaagttgat tgagactttc aacgagcccc aagtcaagga ggagtt                                     46

<210> SEQ ID NO 221
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 221
gagtccaatc acggccaatc                                                                 20

<210> SEQ ID NO 222
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 222
tgcttcttcg gacagatcgt                                                                 20

<210> SEQ ID NO 223
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 223
ctcacttaat cttctgtact ctgaagtact gattgaaggg tcggca                                     46

-continued

```
<210> SEQ ID NO 224
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 224
agaagttgat tgagactttc aacgagttgt acggaccagg aagcat                      46

<210> SEQ ID NO 225
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 225
ttcctctgcc tcttccttgg                                                   20

<210> SEQ ID NO 226
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 226
agcatgcaaa cacgaggtac                                                   20

<210> SEQ ID NO 227
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 227
ctcacttaat cttctgtact ctgaagagag gaaaacgagc ttgggt                      46

<210> SEQ ID NO 228
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 228
agaagttgat tgagactttc aacgagatca aggttgccag cgaatg                      46

<210> SEQ ID NO 229
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 229
accctacaga accgcaatga                                                   20
```

```
<210> SEQ ID NO 230
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 230
acagcccaaa tagagacgca                                                  20

<210> SEQ ID NO 231
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 231
ctcacttaat cttctgtact ctgaagagga gcccagtttt acgtca                     46

<210> SEQ ID NO 232
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 232
agaagttgat tgagactttc aacgagtatc ccgcggtgaa gactac                     46

<210> SEQ ID NO 233
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 233
gtgttgctaa gcctgtggac                                                  20

<210> SEQ ID NO 234
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 234
tcctcctttc gacgcttctt                                                  20

<210> SEQ ID NO 235
<211> LENGTH: 49
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 235
ctcacttaat cttctgtact ctgaagacag ctgtgaatca tgaagtttt                  49

<210> SEQ ID NO 236
```

```
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 236
agaagttgat tgagactttc aacgagattc tcactggcag aacgga                    46

<210> SEQ ID NO 237
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 237
ttttcacgtt gaggccactg                                                 20

<210> SEQ ID NO 238
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 238
agctccgcag taacaggaat                                                 20

<210> SEQ ID NO 239
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 239
ctcacttaat cttctgtact ctgaagtcaa agcaacttat ggcggt                    46

<210> SEQ ID NO 240
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 240
agaagttgat tgagactttc aacgagctct tcgcagcacc agaaag                    46

<210> SEQ ID NO 241
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 241
tcgttgttgc tggtgttctg                                                 20

<210> SEQ ID NO 242
<211> LENGTH: 20
```

-continued

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 242
agtttgaagg cacgttggtc                                              20

<210> SEQ ID NO 243
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 243
ctcacttaat cttctgtact ctgaagactc caacaggact ttgaggt                47

<210> SEQ ID NO 244
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 244
agaagttgat tgagactttc aacgagaaat gtggaagttg cagcgg                 46

<210> SEQ ID NO 245
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 245
aggttgatcg ccgtcttgta                                              20

<210> SEQ ID NO 246
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 246
tcttcatgag gtggtaggcg                                              20

<210> SEQ ID NO 247
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 247
ctcacttaat cttctgtact ctgaagagag ggcagatgac ataccg                 46

<210> SEQ ID NO 248
<211> LENGTH: 46
<212> TYPE: DNA
```

-continued

```
<213> ORGANISM: Artificial Sequence
<220> FEATURE:
<223> OTHER INFORMATION: Description of Artificial Sequence: Synthetic
      primer

<400> SEQUENCE: 248
agaagttgat tgagactttc aacgaggaga aactggaggt gctcgt                    46

<210> SEQ ID NO 249
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 249
caaggcattc agttgaccgt                                                 20

<210> SEQ ID NO 250
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 250
accaacgagc cttacagaca                                                 20

<210> SEQ ID NO 251
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 251
ctcacttaat cttctgtact ctgaagtttt gaccgtcagt gcatgg                    46

<210> SEQ ID NO 252
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 252
agaagttgat tgagactttc aacgaggtcg gaggtgtgag aattga                    46

<210> SEQ ID NO 253
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 253
tgggaactat gtggctcctc                                                 20

<210> SEQ ID NO 254
<211> LENGTH: 20
<212> TYPE: DNA
<213> ORGANISM: Artificial Sequence
```

-continued

```
<220> FEATURE:
<223> OTHER INFORMATION: Description of Artificial Sequence: Synthetic
      primer

<400> SEQUENCE: 254
cgagctatca gtactcccgg                                             20

<210> SEQ ID NO 255
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 255
ctcacttaat cttctgtact ctgaaggggtt ctcagctgtc cgagat             46

<210> SEQ ID NO 256
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 256
agaagttgat tgagactttc aacgagtagc attgcccatc acaacg              46

<210> SEQ ID NO 257
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 257
gtgggaagac tattgatgcg a                                          21

<210> SEQ ID NO 258
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 258
gggaaatcgc tgaggtgtac                                            20

<210> SEQ ID NO 259
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 259
ctcacttaat cttctgtact ctgaagaggt catctggaag ctttgc              46

<210> SEQ ID NO 260
<211> LENGTH: 49
<212> TYPE: DNA
<213> ORGANISM: Artificial Sequence
<220> FEATURE:
```

<223> OTHER INFORMATION: Description of Artificial Sequence: Synthetic
     primer

<400> SEQUENCE: 260
agaagttgat tgagactttc aacgagggtg gccaatggta ttactttga                49

<210> SEQ ID NO 261
<211> LENGTH: 20
<212> TYPE: DNA
<213> ORGANISM: Artificial Sequence
<220> FEATURE:
<223> OTHER INFORMATION: Description of Artificial Sequence: Synthetic
     primer

<400> SEQUENCE: 261
ataagagccc cgatacaggc                                                20

<210> SEQ ID NO 262
<211> LENGTH: 21
<212> TYPE: DNA
<213> ORGANISM: Artificial Sequence
<220> FEATURE:
<223> OTHER INFORMATION: Description of Artificial Sequence: Synthetic
     primer

<400> SEQUENCE: 262
cttgacacac tttgctcctg a                                              21

<210> SEQ ID NO 263
<211> LENGTH: 46
<212> TYPE: DNA
<213> ORGANISM: Artificial Sequence
<220> FEATURE:
<223> OTHER INFORMATION: Description of Artificial Sequence: Synthetic
     primer

<400> SEQUENCE: 263
ctcacttaat cttctgtact ctgaagagta gctgacctgt tgtgcc                  46

<210> SEQ ID NO 264
<211> LENGTH: 46
<212> TYPE: DNA
<213> ORGANISM: Artificial Sequence
<220> FEATURE:
<223> OTHER INFORMATION: Description of Artificial Sequence: Synthetic
     primer

<400> SEQUENCE: 264
agaagttgat tgagactttc aacgagggac accatatgat gcccga                  46

<210> SEQ ID NO 265
<211> LENGTH: 20
<212> TYPE: DNA
<213> ORGANISM: Artificial Sequence
<220> FEATURE:
<223> OTHER INFORMATION: Description of Artificial Sequence: Synthetic
     primer

<400> SEQUENCE: 265
cagatcaagt ccaagtccgc                                                20

<210> SEQ ID NO 266
<211> LENGTH: 20
<212> TYPE: DNA
<213> ORGANISM: Artificial Sequence
<220> FEATURE:
<223> OTHER INFORMATION: Description of Artificial Sequence: Synthetic -continued primer

<400> SEQUENCE: 266
agagactttg cgagagtccc                                                                  20

<210> SEQ ID NO 267
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 267
ctcacttaat cttctgtact ctgaagtgca atatccaaac acgcca                                     46

<210> SEQ ID NO 268
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 268
agaagttgat tgagactttc aacgagactt ctggaatctt cgggca                                     46

<210> SEQ ID NO 269
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 269
ggatgtttgg gccattgtga                                                                  20

<210> SEQ ID NO 270
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 270
caatctctcg cttcatcacg                                                                  20

<210> SEQ ID NO 271
<211> LENGTH: 49
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 271
ctcacttaat cttctgtact ctgaagtcgc tgttaaccat aattctttg                                  49

<210> SEQ ID NO 272
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 272
agaagttgat tgagactttc aacgaggcga gggttgagga gatttt                46

<210> SEQ ID NO 273
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 273
ggccatggca ctattttgtt                                             20

<210> SEQ ID NO 274
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 274
acgtacttcc cgcccaataa                                             20

<210> SEQ ID NO 275
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 275
ctcacttaat cttctgtact ctgaagccca cctaaatttc gagtgca               47

<210> SEQ ID NO 276
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 276
agaagttgat tgagactttc aacgagacac tttcgcagct tttggt                46

<210> SEQ ID NO 277
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 277
tcctccttgc catgaagagg                                             20

<210> SEQ ID NO 278
<211> LENGTH: 20
<212> TYPE: DNA
<213> ORGANISM: Artificial Sequence
<220> FEATURE:
<223> OTHER INFORMATION: Description of Artificial Sequence: Synthetic
      primer -continued

<400> SEQUENCE: 278
gcctgatgaa gatgatgccg                                              20

<210> SEQ ID NO 279
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 279
ctcacttaat cttctgtact ctgaagaggc tcagtcacct ctatga                 46

<210> SEQ ID NO 280
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 280
agaagttgat tgagactttc aacgagtgat caagaacacc gtcgaag               47

<210> SEQ ID NO 281
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 281
tccctttgtt ggtcgtacga                                              20

<210> SEQ ID NO 282
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 282
tggttcaact tgtagcgcat                                              20

<210> SEQ ID NO 283
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 283
ctcacttaat cttctgtact ctgaaggggc ttgctcaact tttgga                 46

<210> SEQ ID NO 284
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 284

-continued agaagttgat tgagactttc aacgagcgac aatctggtag cgcatc                    46

<210> SEQ ID NO 285
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 285
atgctcgtac aaagacccca                                                 20

<210> SEQ ID NO 286
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 286
tgagatctcc aagtgcagca                                                 20

<210> SEQ ID NO 287
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 287
ctcacttaat cttctgtact ctgaaggacg gtcgatttgg ctcatc                    46

<210> SEQ ID NO 288
<211> LENGTH: 49
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 288
agaagttgat tgagactttc aacgagtgaa gaagctcaac actctgaac                 49

<210> SEQ ID NO 289
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 289
tgattgacgg caccctgtat                                                 20

<210> SEQ ID NO 290
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 290

-continued caataattca gctgcgccct                                                    20

<210> SEQ ID NO 291
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 291
ctcacttaat cttctgtact ctgaagcctc tgtagctgct tgtcct                       46

<210> SEQ ID NO 292
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 292
agaagttgat tgagactttc aacgagagga gtcagtcggt ccaaag                       46

<210> SEQ ID NO 293
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 293
tgtgggctgg gatgtgtaat                                                    20

<210> SEQ ID NO 294
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 294
agcacggtca agtaaatcgc                                                    20

<210> SEQ ID NO 295
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 295
ctcacttaat cttctgtact ctgaagtgct atcactgatt tgccca                       46

<210> SEQ ID NO 296
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 296
agaagttgat tgagactttc aacgagggag attcccggca agtatc                       46

-continued

```
<210> SEQ ID NO 297
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 297
ggctttctga ctacctgggt                                               20

<210> SEQ ID NO 298
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 298
aaagggaaga agggtgcagt                                               20

<210> SEQ ID NO 299
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 299
ctcacttaat cttctgtact ctgaagaagg tcgactcggg aaacat                  46

<210> SEQ ID NO 300
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 300
agaagttgat tgagactttc aacgagtggt atcccgactg ctttgt                  46

<210> SEQ ID NO 301
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 301
tggaatggct cgagaatggt                                               20

<210> SEQ ID NO 302
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 302
accaacaggc tgaacactag a                                             21
```

-continued

```
<210> SEQ ID NO 303
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 303
ctcacttaat cttctgtact ctgaagtcgt cagcagagaa ggtaca                    46

<210> SEQ ID NO 304
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 304
agaagttgat tgagactttc aacgagacgg actccctaac gaacaa                    46

<210> SEQ ID NO 305
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 305
tctgatggtt ggctttgctt                                                 20

<210> SEQ ID NO 306
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 306
cggtttgtgg cccatctatg                                                 20

<210> SEQ ID NO 307
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 307
ctcacttaat cttctgtact ctgaagaaaa ccgacgcttg aactcc                    46

<210> SEQ ID NO 308
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 308
agaagttgat tgagactttc aacgagaagt cttgaccgga agcaac                    46
```

<210> SEQ ID NO 309
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 309
gggccttaac aaacaccaca                                                  20

<210> SEQ ID NO 310
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 310
tagaggcgga aaggaacgag                                                  20

<210> SEQ ID NO 311
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 311
ctcacttaat cttctgtact ctgaagttgc caagggtgta caaagc                     46

<210> SEQ ID NO 312
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 312
agaagttgat tgagactttc aacgagacca agttgttcga cgaaga                     46

<210> SEQ ID NO 313
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 313
caacacatac caggcgaagg                                                  20

<210> SEQ ID NO 314
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 314
ccctcctccg ccatcattat                                                  20

<210> SEQ ID NO 315

```
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 315
ctcacttaat cttctgtact ctgaagtagg agacaaccaa gccagc                   46

<210> SEQ ID NO 316
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 316
agaagttgat tgagactttc aacgagggag tagaaaatgg tgcgtcc                  47

<210> SEQ ID NO 317
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 317
aatggctcca aatcacaggc                                                20

<210> SEQ ID NO 318
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 318
gctttgagga atgcgtgaag a                                              21

<210> SEQ ID NO 319
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 319
ctcacttaat cttctgtact ctgaaggtag tgagagtggc gcctta                   46

<210> SEQ ID NO 320
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 320
agaagttgat tgagactttc aacgagtggg tacaacgtga ctctagg                  47

<210> SEQ ID NO 321
<211> LENGTH: 20
```

-continued

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 321
acactcttaa ggctcgtcgt                                                  20

<210> SEQ ID NO 322
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 322
ctcctccact tcagtatccg t                                                21

<210> SEQ ID NO 323
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 323
ctcacttaat cttctgtact ctgaagttcc ttgaatttcc gccacc                     46

<210> SEQ ID NO 324
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 324
agaagttgat tgagactttc aacgaggagc aggcaaggtt ggattc                     46

<210> SEQ ID NO 325
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 325
ctgggcagca ataacggtt                                                   20

<210> SEQ ID NO 326
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 326
ccaaagttgg ctccgagtag                                                  20

<210> SEQ ID NO 327
<211> LENGTH: 46
<212> TYPE: DNA
```

-continued

```
<213> ORGANISM: Artificial Sequence
<220> FEATURE:
<223> OTHER INFORMATION: Description of Artificial Sequence: Synthetic
      primer

<400> SEQUENCE: 327
ctcacttaat cttctgtact ctgaagccta acggtatcgg ctttga                    46

<210> SEQ ID NO 328
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 328
agaagttgat tgagactttc aacgagggca aaatcctttt ccatga                    46

<210> SEQ ID NO 329
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 329
gaagaaggcc aagtgtgata                                                 20

<210> SEQ ID NO 330
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 330
gacgagacgc tgttcctttc                                                 20

<210> SEQ ID NO 331
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 331
ctcacttaat cttctgtact ctgaagtgtg aagagaggcc accatt                    46

<210> SEQ ID NO 332
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 332
agaagttgat tgagactttc aacgagtgat cgactacttg gcctcc                    46

<210> SEQ ID NO 333
<211> LENGTH: 20
<212> TYPE: DNA
<213> ORGANISM: Artificial Sequence
```

-continued

```
<220> FEATURE:
<223> OTHER INFORMATION: Description of Artificial Sequence: Synthetic
      primer

<400> SEQUENCE: 333
aacaacattc aagctgccgt                                                        20

<210> SEQ ID NO 334
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 334
atcggcaaag atgaagcgac                                                        20

<210> SEQ ID NO 335
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 335
gctggacact tctgagctca                                                        20

<210> SEQ ID NO 336
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 336
acttgtcagg acgatacgga                                                        20

<210> SEQ ID NO 337
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 337
ccggtctccc tggaaataga                                                        20

<210> SEQ ID NO 338
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 338
gcgaggtcct tgtcaatgag                                                        20

<210> SEQ ID NO 339
<211> LENGTH: 20
<212> TYPE: DNA
<213> ORGANISM: Artificial Sequence
<220> FEATURE:
```

-continued

<223> OTHER INFORMATION: Description of Artificial Sequence: Synthetic
     primer

<400> SEQUENCE: 339
acaagaactc gggctccttt                                                    20

<210> SEQ ID NO 340
<211> LENGTH: 20
<212> TYPE: DNA
<213> ORGANISM: Artificial Sequence
<220> FEATURE:
<223> OTHER INFORMATION: Description of Artificial Sequence: Synthetic
     primer

<400> SEQUENCE: 340
ttgcagcgct ccataatgtc                                                    20

<210> SEQ ID NO 341
<211> LENGTH: 20
<212> TYPE: DNA
<213> ORGANISM: Artificial Sequence
<220> FEATURE:
<223> OTHER INFORMATION: Description of Artificial Sequence: Synthetic
     primer

<400> SEQUENCE: 341
gctgattctg agaacgctgg                                                    20

<210> SEQ ID NO 342
<211> LENGTH: 20
<212> TYPE: DNA
<213> ORGANISM: Artificial Sequence
<220> FEATURE:
<223> OTHER INFORMATION: Description of Artificial Sequence: Synthetic
     primer

<400> SEQUENCE: 342
gccattcttc ggtgcagtag                                                    20

<210> SEQ ID NO 343
<211> LENGTH: 20
<212> TYPE: DNA
<213> ORGANISM: Artificial Sequence
<220> FEATURE:
<223> OTHER INFORMATION: Description of Artificial Sequence: Synthetic
     primer

<400> SEQUENCE: 343
tagagttgtc ccaaacggca                                                    20

<210> SEQ ID NO 344
<211> LENGTH: 20
<212> TYPE: DNA
<213> ORGANISM: Artificial Sequence
<220> FEATURE:
<223> OTHER INFORMATION: Description of Artificial Sequence: Synthetic
     primer

<400> SEQUENCE: 344
cgtggttctc gaggctctat                                                    20

<210> SEQ ID NO 345
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 345
ggagttggaa cgtcgtagga                                            20

<210> SEQ ID NO 346
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 346
agttgtccgt cattagccct                                            20

<210> SEQ ID NO 347
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 347
tgttcccttt cggctagaca                                            20

<210> SEQ ID NO 348
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 348
acggttgagg gcattacgta                                            20

<210> SEQ ID NO 349
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 349
ttgtcttcca ccccttcgtt                                            20

<210> SEQ ID NO 350
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 350
ggttggcctt ggacattgtt                                            20

<210> SEQ ID NO 351
<211> LENGTH: 20
<212> TYPE: DNA
<213> ORGANISM: Artificial Sequence
<220> FEATURE:
<223> OTHER INFORMATION: Description of Artificial Sequence: Synthetic
      primer -continued

```
<400> SEQUENCE: 351
tgctcttcgg tactcatgct                                           20

<210> SEQ ID NO 352
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 352
tttggccatg ctgagctttt                                           20

<210> SEQ ID NO 353
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 353
aagcccgatc acttgcattt                                           20

<210> SEQ ID NO 354
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 354
cacctaatgt ttggcacccc                                           20

<210> SEQ ID NO 355
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 355
atcccagact gacatcgcaa                                           20

<210> SEQ ID NO 356
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 356
ccgccagaaa ttcatgccat                                           20

<210> SEQ ID NO 357
<211> LENGTH: 20
<212> TYPE: DNA
<213> ORGANISM: Artificial Sequence
<220> FEATURE:
<223> OTHER INFORMATION: Description of Artificial Sequence: Synthetic
      primer
```

-continued

```
<400> SEQUENCE: 357
tcgtttcact gtaccatgca                                            20

<210> SEQ ID NO 358
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 358
accagtccgc attttcactg                                            20

<210> SEQ ID NO 359
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 359
gtggacagct gcaatcgtag                                            20

<210> SEQ ID NO 360
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 360
caactgggaa gcctgcattt                                            20

<210> SEQ ID NO 361
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 361
ccttgcatat ccgtttgcca                                            20

<210> SEQ ID NO 362
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 362
ggaggttcag gagcaggaat                                            20

<210> SEQ ID NO 363
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 363
```

-continued cggtttcatc tgttgcctcc                                                        20

<210> SEQ ID NO 364
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 364
gtcgcccatg ttctttcgat                                                        20

<210> SEQ ID NO 365
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 365
caaacaggct ggaaaccaca                                                        20

<210> SEQ ID NO 366
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 366
aatctccacg ttcagttgcg                                                        20

<210> SEQ ID NO 367
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 367
tcatcccttg aaaaccccga                                                        20

<210> SEQ ID NO 368
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 368
ttgtggaggg agattcaggc                                                        20

<210> SEQ ID NO 369
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 369

-continued

```
aaggtaagga acgtgcttgc                                         20

<210> SEQ ID NO 370
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 370
gttctactgt tcacgtgctc t                                       21

<210> SEQ ID NO 371
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 371
accggttaga atacatgctg c                                       21

<210> SEQ ID NO 372
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 372
cgaaaagaag ctggactccg                                         20

<210> SEQ ID NO 373
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 373
ttccatcgta cgaccagtgt                                         20

<210> SEQ ID NO 374
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 374
agcgatgagg ccaacagtat                                         20

<210> SEQ ID NO 375
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 375
tgtccagccc aaaagactga                                         20
```

```
<210> SEQ ID NO 376
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 376
ctcctggggc tcgtactaag                                                20

<210> SEQ ID NO 377
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 377
cctcaataac gacggccttg                                                20

<210> SEQ ID NO 378
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 378 cctttcctg atcagtgggg                                                 20

<210> SEQ ID NO 379
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 379
tgttggggaa tgaaacacga                                                20

<210> SEQ ID NO 380
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 380
gaaggacgag tagggttgct                                                20

<210> SEQ ID NO 381
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 381
tcctgatctg gctcgtttgt                                                20
```

-continued

```
<210> SEQ ID NO 382
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 382
acctccaact cctgaaagca                                                     20

<210> SEQ ID NO 383
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 383
cctcgagtct gggctttaca                                                     20

<210> SEQ ID NO 384
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 384
ggagagatgc cagaccaagt                                                     20

<210> SEQ ID NO 385
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 385
agcctgttct actgcatacg t                                                   21

<210> SEQ ID NO 386
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 386
ccatttcttg taccctgggc                                                     20

<210> SEQ ID NO 387
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 387
gcagaaaagg cgcgaatttc                                                     20
```

-continued

```
<210> SEQ ID NO 388
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 388
gggaaaggat gtggaccaac                                                   20

<210> SEQ ID NO 389
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 389
tggccaagag tgtccaattg                                                   20

<210> SEQ ID NO 390
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 390
taacagatgg cgcacgtaga                                                   20

<210> SEQ ID NO 391
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 391
ccttgcgttc ccaggtaaag                                                   20

<210> SEQ ID NO 392
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 392
tgtggtatgg tttggggcta                                                   20

<210> SEQ ID NO 393
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 393
actcccgttc ctccatgttc                                                   20

<210> SEQ ID NO 394
```

-continued

```
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 394
acggtacaaa aggcgtttca                                                 20

<210> SEQ ID NO 395
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 395
agtcaaactc ggtggtaggt                                                 20

<210> SEQ ID NO 396
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 396
cggttatcat gtgcctgctc                                                 20

<210> SEQ ID NO 397
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 397
atgttgctgc tccgaaatcc                                                 20

<210> SEQ ID NO 398
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 398
gatctgctgg ccttgagagt                                                 20

<210> SEQ ID NO 399
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 399
ctatgtcctg gtgtttgccg                                                 20

<210> SEQ ID NO 400
<211> LENGTH: 20
```

-continued

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 400
gccaatgatg atctcgcagg                                                    20

<210> SEQ ID NO 401
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 401
gcctttgata tgccgtcgtt                                                    20

<210> SEQ ID NO 402
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 402
tcgagtaatg cttcccacca                                                    20

<210> SEQ ID NO 403
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 403
agctttcaca acagcgatcg                                                    20

<210> SEQ ID NO 404
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 404
tgattgcttc tgggttgctg                                                    20

<210> SEQ ID NO 405
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 405
caaaaccggc gtaaaatggc                                                    20

<210> SEQ ID NO 406
<211> LENGTH: 20
<212> TYPE: DNA
```

-continued

```
<213> ORGANISM: Artificial Sequence
<220> FEATURE:
<223> OTHER INFORMATION: Description of Artificial Sequence: Synthetic
      primer

<400> SEQUENCE: 406
ttgtgctgca tctgtgtgag                                                    20

<210> SEQ ID NO 407
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 407
agcctacaag tggttacagg t                                                  21

<210> SEQ ID NO 408
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 408
ggaaaccgac cagcctaaag                                                    20

<210> SEQ ID NO 409
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 409
agtcgcacca ggttatcaca                                                    20

<210> SEQ ID NO 410
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 410
ggaaagctgc ccagaaactc                                                    20

<210> SEQ ID NO 411
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 411
tgagaggatt cgttgtggct                                                    20

<210> SEQ ID NO 412
<211> LENGTH: 20
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 412
ctatgtcgaa gtagcggtgc                                              20

<210> SEQ ID NO 413
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 413
agagtggcac tgctatcgaa                                              20

<210> SEQ ID NO 414
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 414
cgtacaaact tggcagctgt                                              20

<210> SEQ ID NO 415
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 415
gctgtgttgt aaattccggc                                              20

<210> SEQ ID NO 416
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 416
acaacccgga agacaactct                                              20

<210> SEQ ID NO 417
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 417
tgtcgttgcc ttcccgatat                                              20

<210> SEQ ID NO 418
<211> LENGTH: 20
<212> TYPE: DNA
<213> ORGANISM: Artificial Sequence
<220> FEATURE:
```

<223> OTHER INFORMATION: Description of Artificial Sequence: Synthetic
      primer

<400> SEQUENCE: 418
gaagatggga gagggtgctt                                              20

<210> SEQ ID NO 419
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 419
cttgttgacg acggtagcag                                              20

<210> SEQ ID NO 420
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 420
ccctagtctc gttcgaaggg                                              20

<210> SEQ ID NO 421
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 421
ggcacagcag gttttcgtat                                              20

<210> SEQ ID NO 422
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 422
ggagattctg atgctacccc a                                            21

<210> SEQ ID NO 423
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 423
tggagccatc agatcaggac                                              20

<210> SEQ ID NO 424
<211> LENGTH: 20
<212> TYPE: DNA
<213> ORGANISM: Artificial Sequence
<220> FEATURE:
<223> OTHER INFORMATION: Description of Artificial Sequence: Synthetic -continued

```
        primer

<400> SEQUENCE: 424
cctgttcttg caagccttca                                    20

<210> SEQ ID NO 425
<211> LENGTH: 20
<212> TYPE: DNA
<213> ORGANISM: Artificial Sequence
<220> FEATURE:
<223> OTHER INFORMATION: Description of Artificial Sequence: Synthetic
        primer

<400> SEQUENCE: 425
taagacatgc gaccaccaga                                    20

<210> SEQ ID NO 426
<211> LENGTH: 20
<212> TYPE: DNA
<213> ORGANISM: Artificial Sequence
<220> FEATURE:
<223> OTHER INFORMATION: Description of Artificial Sequence: Synthetic
        primer

<400> SEQUENCE: 426
catggccaat gtcgaactgt                                    20

<210> SEQ ID NO 427
<211> LENGTH: 20
<212> TYPE: DNA
<213> ORGANISM: Artificial Sequence
<220> FEATURE:
<223> OTHER INFORMATION: Description of Artificial Sequence: Synthetic
        primer

<400> SEQUENCE: 427
agctggctga aaaggtgttg                                    20

<210> SEQ ID NO 428
<211> LENGTH: 20
<212> TYPE: DNA
<213> ORGANISM: Artificial Sequence
<220> FEATURE:
<223> OTHER INFORMATION: Description of Artificial Sequence: Synthetic
        primer

<400> SEQUENCE: 428
ctcagtgttg gaaagcaccc                                    20

<210> SEQ ID NO 429
<211> LENGTH: 20
<212> TYPE: DNA
<213> ORGANISM: Artificial Sequence
<220> FEATURE:
<223> OTHER INFORMATION: Description of Artificial Sequence: Synthetic
        primer

<400> SEQUENCE: 429
tagggaatct ttggtggcgt                                    20

<210> SEQ ID NO 430
<211> LENGTH: 20
<212> TYPE: DNA
<213> ORGANISM: Artificial Sequence
<220> FEATURE:
<223> OTHER INFORMATION: Description of Artificial Sequence: Synthetic
        primer
```

-continued

```
<400> SEQUENCE: 430
ggaacctaga gcgagcaaca                                              20

<210> SEQ ID NO 431
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 431
caggctctat tgtcgacgtg                                              20

<210> SEQ ID NO 432
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 432
ggaggtgatg acaatgccac                                              20

<210> SEQ ID NO 433
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 433
ctgtgaagct cctcctacgt                                              20

<210> SEQ ID NO 434
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 434
ggacactgct ggacaagaga                                              20

<210> SEQ ID NO 435
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 435
tactgacgcc gaagagctag                                              20

<210> SEQ ID NO 436
<211> LENGTH: 20
<212> TYPE: DNA
<213> ORGANISM: Artificial Sequence
<220> FEATURE:
<223> OTHER INFORMATION: Description of Artificial Sequence: Synthetic
      primer
```

-continued

```
<400> SEQUENCE: 436
ccgatcgcaa aatagtggca                                                  20

<210> SEQ ID NO 437
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 437
gttgtggttg tatgcggtca                                                  20

<210> SEQ ID NO 438
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 438
caataactcc actggtgccg                                                  20

<210> SEQ ID NO 439
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 439
tcgttatact ccagcgtgct                                                  20

<210> SEQ ID NO 440
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 440
gggctcaaaa tctggaacca                                                  20

<210> SEQ ID NO 441
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 441
caatgcagta ctcaccggtg                                                  20

<210> SEQ ID NO 442
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 442
```

-continued

```
aagctgacga ccccttagac                                           20

<210> SEQ ID NO 443
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 443
ctatcgtgtc tgggctgcta                                           20

<210> SEQ ID NO 444
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 444
aaggagattg ccgcaactct                                           20

<210> SEQ ID NO 445
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 445
gtggagtcag agtcgagagg                                           20

<210> SEQ ID NO 446
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 446
cccagctttt atacggcttg g                                         21

<210> SEQ ID NO 447
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 447
cagcaaaagc tcgtgatcca                                           20

<210> SEQ ID NO 448
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 448
```

-continued tgcgggtagt cgattgatgt                                    20

<210> SEQ ID NO 449
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 449
tcacgtatct cagcaacagg a                                  21

<210> SEQ ID NO 450
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 450
ggacctagga aatacgccca                                    20

<210> SEQ ID NO 451
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 451
actccagttc cacaagtcca                                    20

<210> SEQ ID NO 452
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 452
actgccaacc gtttactcca                                    20

<210> SEQ ID NO 453
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 453
gcgcggaaga ttaaagtcgt                                    20

<210> SEQ ID NO 454
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 454
ttggactcga tcgatgaggg                                    20

```
<210> SEQ ID NO 455
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 455
tgatgacttc caagatgcgc                                                        20

<210> SEQ ID NO 456
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 456
tcacctggag caactgatgt                                                        20

<210> SEQ ID NO 457
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 457
gtttggtacg cttgtaggcc                                                        20

<210> SEQ ID NO 458
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 458
gatgagcaag catccattca                                                        20

<210> SEQ ID NO 459
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 459
aaagacagga gcgtgagcat                                                        20

<210> SEQ ID NO 460
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 460
ctcaacttcg cttgcccttt                                                        20
```

-continued

```
<210> SEQ ID NO 461
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 461
tgggaaacag aacgatgaac t                                              21

<210> SEQ ID NO 462
<211> LENGTH: 2835
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 462
ggtggttacg gtccaggcgc tggtcaacaa ggtccaggaa gtggtggtca acaaggacct      60
ggcggtcaag gaccctacgg tagtggccaa caaggtccag gtggagcagg acagcagggt     120
ccgggaggcc aaggacctta cggaccaggt gctgctgctg ccgccgctgc cgctgccgga     180
ggttacggtc caggagccgg acaacagggt ccaggtggag ctggacaaca aggtccagga     240
tcacaaggtc ctggtggaca aggtccatac ggtcctggtg ctggtcaaca gggaccaggt     300
agtcaaggac ctggttcagg tggtcagcag ggtccaggag acagggtcc ttacggccct      360 tctgccgctg cagcagcagc cgctgccgca ggaggatacg gacctggtgc tggacaacga     420
tctcaaggac caggaggaca aggtccttat ggacctggcg ctggccaaca aggacctggt     480
tctcagggtc caggttcagg aggccaacaa ggcccaggag gtcaaggacc atacggacca     540
tccgctgcgg cagctgcagc tgctgcaggt ggatatggcc caggagccgg acaacagggt     600
cctggttcac aaggtccagg atctggtggt caacagggac caggcggcca gggaccttat     660
ggtccaggag ccgctgcagc agcagcagct gttggaggtt acggccctgg tgccggtcaa     720
caaggcccag atctcagggg tcctggatct ggaggacaac aaggtcctgg aggtcagggt     780
ccatacggac cttcagcagc agctgctgct gcagccgctg gtggttatgg acctggtgct     840
ggtcaacaag gaccgggttc tcagggtccg ggttcaggag gtcagcaggg ccctggtgga     900
caaggacctt atggacctag tgcggctgca gcagctgccg ccgcaggtgg ttacggtcca     960
ggcgctggtc aacaaggtcc aggaagtggt ggtcaacaag gacctggcgg tcaaggaccc    1020
tacggtagtg gccaacaagg tccaggtgga gcaggacagc agggtccggg aggccaagga    1080
ccttacggac caggtgctgc tgctgccgcc gctgccgctg ccggaggtta cggtccagga    1140
gccggacaac agggtccagg tggagctgga caacaaggtc caggatcaca aggtcctggt    1200
ggacaaggtc catacggtcc tggtgctggt caacagggac caggtagtca aggacctggt    1260
tcaggtggtc agcagggtcc aggaggacag ggtccttacg gcccttctgc cgctgcagca    1320
gcagccgctg ccgcaggagg atacggacct ggtgctggac aacgatctca aggaccagga    1380
ggacaaggtc cttatggacc tggcgctggc caacaaggac ctggttctca gggtccaggt    1440
tcaggaggcc aacaaggccc aggaggtcaa ggaccatacg gaccatccgc tgcggcagct    1500
gcagctgctg caggtggata tggcccagga gccggacaac agggtcctgg ttcacaaggt    1560
ccaggatctg gtggtcaaca gggaccaggc ggccagggac cttatggtcc aggagccgct    1620
gcagcagcag cagctgttgg aggttacggc cctggtgccg gtcaacaagg cccaggatct    1680
```

-continued

```
cagggtcctg gatctggagg acaacaaggt cctggaggtc agggtccata cggaccttca    1740
gcagcagctg ctgctgcagc cgctggtggt tatggacctg gtgctggtca acaaggaccg    1800
ggttctcagg gtccgggttc aggaggtcag cagggccctg gtggacaagg accttatgga    1860
cctagtgcgc ctgcagcagc tgccgccgca ggtggttacg gtccaggcgc tggtcaacaa    1920
ggtccaggaa gtggtggtca acaaggacct ggcggtcaag accctacgg tagtggccaa     1980 caaggtccag gtggagcagg acagcagggt ccgggaggcc aaggacctta cggaccaggt    2040
gctgctgctg ccgccgctgc cgctgccgga ggttacggtc aggagccgg acaacagggt     2100 ccaggtggag ctggacaaca aggtccagga tcacaaggtc ctggtggaca aggtccatac    2160
ggtcctggtg ctggtcaaca gggaccaggt agtcaaggac ctggttcagg tggtcagcag    2220
ggtccaggag acagggtcc ttacggccct tctgccgctg cagcagcagc cgctgccgca     2280
ggaggatacg gacctggtgc tggacaacga tctcaaggac caggaggaca aggtccttat    2340
ggacctggcg ctggccaaca aggacctggt tctcagggtc caggttcagg aggccaacaa    2400
ggcccaggag gtcaaggacc atacggacca tccgctgcgg cagctgcagc tgctgcaggt    2460
ggatatggcc caggagccgg acaacagggt cctggttcac aaggtccagg atctggtggt    2520
caacagggac caggcggcca gggaccttat ggtccaggag ccgctgcagc agcagcagct    2580
gttggaggtt acggccctgg tgccggtcaa caaggcccag gatctcaggg tcctggatct    2640
ggaggacaac aaggtcctgg aggtcaggt ccatacggac cttcagcagc agctgctgct     2700
gcagccgctg gtggttatgg acctggtgct ggtcaacaag accgggttc tcagggtccg     2760 ggttcaggag gtcagcaggg ccctggtgga caaggacctt atggacctag tgcggctgca    2820
gcagctgccg ccgca                                                     2835
```

<210> SEQ ID NO 463
<211> LENGTH: 945
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 463

```
Gly Gly Tyr Gly Pro Gly Ala Gly Gln Gln Gly Pro Gly Ser Gly Gly
1               5                   10                  15

Gln Gln Gly Pro Gly Gly Gln Gly Pro Tyr Gly Ser Gly Gln Gln Gly
                20                  25                  30

Pro Gly Gly Ala Gly Gln Gln Gly Pro Gly Gly Gln Gly Pro Tyr Gly
            35                  40                  45

Pro Gly Ala Ala Ala Ala Ala Ala Ala Ala Ala Gly Gly Tyr Gly Pro
        50                  55                  60

Gly Ala Gly Gln Gln Gly Pro Gly Gly Ala Gly Gln Gln Gly Pro Gly
65                  70                  75                  80

Ser Gln Gly Pro Gly Gly Gln Gly Pro Tyr Gly Pro Gly Ala Gly Gln
                85                  90                  95

Gln Gly Pro Gly Ser Gln Gly Pro Gly Ser Gly Gly Gln Gln Gly Pro
            100                 105                 110

Gly Gly Gln Gly Pro Tyr Gly Pro Ser Ala Ala Ala Ala Ala Ala Ala
        115                 120                 125

Ala Ala Gly Gly Tyr Gly Pro Gly Ala Gly Gln Arg Ser Gln Gly Pro
        130                 135                 140
```

-continued

```
Gly Gly Gln Gly Pro Tyr Gly Pro Gly Ala Gly Gln Gln Gly Pro Gly
145                 150                 155                 160

Ser Gln Gly Pro Gly Ser Gly Gly Gln Gln Gly Pro Gly Gly Gln Gly
                165                 170                 175

Pro Tyr Gly Pro Ser Ala Ala Ala Ala Ala Ala Ala Gly Gly Tyr
            180             185             190

Gly Pro Gly Ala Gly Gln Gln Gly Pro Gly Ser Gln Gly Pro Gly Ser
            195             200             205

Gly Gly Gln Gln Gly Pro Gly Gln Gly Pro Tyr Gly Pro Gly Ala
        210                 215                 220

Ala Ala Ala Ala Ala Val Gly Gly Tyr Gly Pro Gly Ala Gly Gln
225                 230                 235                 240

Gln Gly Pro Gly Ser Gln Gly Pro Gly Ser Gly Gly Gln Gln Gly Pro
            245                 250                 255

Gly Gly Gln Gly Pro Tyr Gly Pro Ser Ala Ala Ala Ala Ala Ala Ala
            260                 265                 270

Ala Gly Gly Tyr Gly Pro Gly Ala Gly Gln Gln Gly Pro Gly Ser Gln
            275                 280                 285

Gly Pro Gly Ser Gly Gly Gln Gln Gly Pro Gly Gln Gly Pro Tyr
        290                 295                 300

Gly Pro Ser Ala Ala Ala Ala Ala Ala Ala Gly Gly Tyr Gly Pro
305                 310                 315                 320

Gly Ala Gly Gln Gln Gly Pro Gly Ser Gly Gln Gln Gly Pro Gly
                325                 330                 335

Gly Gln Gly Pro Tyr Gly Ser Gly Gln Gln Gly Pro Gly Gly Ala Gly
            340                 345                 350

Gln Gln Gly Pro Gly Gly Gln Gly Pro Tyr Gly Pro Gly Ala Ala Ala
            355                 360                 365

Ala Ala Ala Ala Ala Ala Gly Gly Tyr Gly Pro Gly Ala Gly Gln Gln
            370                 375                 380

Gly Pro Gly Gly Ala Gly Gln Gln Gly Pro Gly Ser Gln Gly Pro Gly
385                 390                 395                 400

Gly Gln Gly Pro Tyr Gly Pro Gly Ala Gly Gln Gln Gly Pro Gly Ser
            405                 410                 415

Gln Gly Pro Gly Ser Gly Gly Gln Gln Gly Pro Gly Gly Gln Gly Pro
            420                 425                 430

Tyr Gly Pro Ser Ala Ala Ala Ala Ala Ala Ala Ala Gly Gly Tyr
            435                 440                 445

Gly Pro Gly Ala Gly Gln Arg Ser Gln Gly Pro Gly Gly Gln Gly Pro
            450                 455                 460

Tyr Gly Pro Gly Ala Gly Gln Gln Gly Pro Gly Ser Gln Gly Pro Gly
465                 470                 475                 480

Ser Gly Gly Gln Gln Gly Pro Gly Gly Gln Gly Pro Tyr Gly Pro Ser
                485                 490                 495

Ala Ala Ala Ala Ala Ala Ala Ala Gly Gly Tyr Gly Pro Gly Ala Gly
            500                 505                 510

Gln Gln Gly Pro Gly Ser Gln Gly Pro Gly Ser Gly Gly Gln Gln Gly
            515                 520                 525

Pro Gly Gly Gln Gly Pro Tyr Gly Pro Gly Ala Ala Ala Ala Ala Ala
            530                 535                 540

Ala Val Gly Gly Tyr Gly Pro Gly Ala Gly Gln Gln Gly Pro Gly Ser
545                 550                 555                 560

Gln Gly Pro Gly Ser Gly Gly Gln Gln Gly Pro Gly Gly Gln Gly Pro
```

-continued

```
                565                 570                 575

Tyr Gly Pro Ser Ala Ala Ala Ala Ala Ala Ala Gly Gly Tyr Gly
            580                 585                 590

Pro Gly Ala Gly Gln Gln Gly Pro Gly Ser Gln Gly Pro Gly Ser Gly
            595                 600                 605

Gly Gln Gln Gly Pro Gly Gly Gln Gly Pro Tyr Gly Pro Ser Ala Ala
    610                 615                 620

Ala Ala Ala Ala Ala Ala Gly Gly Tyr Gly Pro Gly Ala Gly Gln Gln
625                 630                 635                 640

Gly Pro Gly Ser Gly Gly Gln Gln Gly Pro Gly Gly Gln Gly Pro Tyr
            645                 650                 655

Gly Ser Gly Gln Gln Gly Pro Gly Gly Ala Gly Gln Gln Gly Pro Gly
            660                 665                 670

Gly Gln Gly Pro Tyr Gly Pro Gly Ala Ala Ala Ala Ala Ala Ala
            675                 680                 685

Ala Gly Gly Tyr Gly Pro Gly Ala Gly Gln Gln Gly Pro Gly Gly Ala
    690                 695                 700

Gly Gln Gln Gly Pro Gly Ser Gln Gly Pro Gly Gly Gln Gly Pro Tyr
705                 710                 715                 720

Gly Pro Gly Ala Gly Gln Gln Gly Pro Gly Ser Gln Gly Pro Gly Ser
            725                 730                 735

Gly Gly Gln Gln Gly Pro Gly Gly Gln Gly Pro Tyr Gly Pro Ser Ala
            740                 745                 750

Ala Ala Ala Ala Ala Ala Ala Gly Gly Tyr Gly Pro Gly Ala Gly
            755                 760                 765

Gln Arg Ser Gln Gly Pro Gly Gly Gln Gly Pro Tyr Gly Pro Gly Ala
    770                 775                 780

Gly Gln Gln Gly Pro Gly Ser Gln Gly Pro Gly Ser Gly Gly Gln Gln
785                 790                 795                 800

Gly Pro Gly Gly Gln Gly Pro Tyr Gly Pro Ser Ala Ala Ala Ala Ala
            805                 810                 815

Ala Ala Ala Gly Gly Tyr Gly Pro Gly Ala Gly Gln Gln Gly Pro Gly
            820                 825                 830

Ser Gln Gly Pro Gly Ser Gly Gly Gln Gln Gly Pro Gly Gly Gln Gly
            835                 840                 845

Pro Tyr Gly Pro Gly Ala Ala Ala Ala Ala Ala Ala Val Gly Gly Tyr
    850                 855                 860

Gly Pro Gly Ala Gly Gln Gln Gly Pro Gly Ser Gln Gly Pro Gly Ser
865                 870                 875                 880

Gly Gly Gln Gln Gly Pro Gly Gly Gln Gly Pro Tyr Gly Pro Ser Ala
            885                 890                 895

Ala Ala Ala Ala Ala Ala Gly Gly Tyr Gly Pro Gly Ala Gly Gln
            900                 905                 910

Gln Gly Pro Gly Ser Gln Gly Pro Gly Ser Gly Gly Gln Gln Gly Pro
            915                 920                 925

Gly Gly Gln Gly Pro Tyr Gly Pro Ser Ala Ala Ala Ala Ala Ala Ala
    930                 935                 940

Ala
945
```

<210> SEQ ID NO 464
<211> LENGTH: 315
<212> TYPE: PRT
<213> ORGANISM: Artificial Sequence

```
<220> FEATURE:
<223> OTHER INFORMATION: Description of Artificial Sequence: Synthetic
      polypeptide

<400> SEQUENCE: 464

Gly Gly Tyr Gly Pro Gly Ala Gly Gln Gln Gly Pro Gly Ser Gly Gly
1               5                   10                  15

Gln Gln Gly Pro Gly Gly Gln Gly Pro Tyr Gly Ser Gly Gln Gln Gly
                20                  25                  30

Pro Gly Gly Ala Gly Gln Gln Gly Pro Gly Gly Gln Gly Pro Tyr Gly
            35                  40                  45

Pro Gly Ala Ala Ala Ala Ala Ala Ala Ala Ala Gly Gly Tyr Gly Pro
        50                  55                  60

Gly Ala Gly Gln Gln Gly Pro Gly Gly Ala Gly Gln Gln Gly Pro Gly
65                  70                  75                  80

Ser Gln Gly Pro Gly Gly Gln Gly Pro Tyr Gly Pro Gly Ala Gly Gln
                85                  90                  95

Gln Gly Pro Gly Ser Gln Gly Pro Gly Ser Gly Gly Gln Gln Gly Pro
            100                 105                 110

Gly Gly Gln Gly Pro Tyr Gly Pro Ser Ala Ala Ala Ala Ala Ala Ala
        115                 120                 125

Ala Ala Gly Gly Tyr Gly Pro Gly Ala Gly Gln Arg Ser Gln Gly Pro
    130                 135                 140

Gly Gly Gln Gly Pro Tyr Gly Pro Gly Ala Gly Gln Gln Gly Pro Gly
145                 150                 155                 160

Ser Gln Gly Pro Gly Ser Gly Gly Gln Gln Gly Pro Gly Gly Gln Gly
                165                 170                 175

Pro Tyr Gly Pro Ser Ala Ala Ala Ala Ala Ala Ala Gly Gly Tyr
            180                 185                 190

Gly Pro Gly Ala Gly Gln Gln Gly Pro Gly Ser Gln Gly Pro Gly Ser
        195                 200                 205

Gly Gly Gln Gln Gly Pro Gly Gly Gln Gly Pro Tyr Gly Pro Gly Ala
    210                 215                 220

Ala Ala Ala Ala Ala Ala Val Gly Gly Tyr Gly Pro Gly Ala Gly Gln
225                 230                 235                 240

Gln Gly Pro Gly Ser Gln Gly Pro Gly Ser Gly Gly Gln Gln Gly Pro
            245                 250                 255

Gly Gly Gln Gly Pro Tyr Gly Pro Ser Ala Ala Ala Ala Ala Ala Ala
        260                 265                 270

Ala Gly Gly Tyr Gly Pro Gly Ala Gly Gln Gln Gly Pro Gly Ser Gln
        275                 280                 285

Gly Pro Gly Ser Gly Gly Gln Gln Gly Pro Gly Gly Gln Gly Pro Tyr
    290                 295                 300

Gly Pro Ser Ala Ala Ala Ala Ala Ala Ala Ala
305                 310                 315

<210> SEQ ID NO 465
<211> LENGTH: 4324
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 465
ggagttgaat cacatcttac tggatagcga gctttttgac gaagtgaaaa tttctaattt      60
```

-continued

```
taaacaagag gaaggggtca aaaacggaga tatcttatac ttggaaaaag agatgacaat      120
cagtgatttc atcaattttg tatctagttg gccttctgtg ttttcgtgga agcagcaacg      180
aggaaaggag ggtatcctag atgattttta caacgaactg aacgactgct ttgaggggggg     240 taacatgaaa gtaatatgga actccgtcct agtatttgcc aggaggaagc aaagggttgt      300
ataggcttta gtacttatag aggaaacggg gttacgtgca agcgcgcatg cctgagcttt      360
gagggggggg actttcacat ctcttcttct cacacttagc cctaacacag agaataataa      420
aaagcattgc aagatgagtg ttgtcagcaa gcaatacgac atccacgaag gcattatctt      480
tgtaattgaa ttgaccccgg agcttcacgc gccggcttca gaagggaaat ctcagctcca      540
gatcatctta gagaatgtca gtgaggttat ttctgagcta atcattacct tgcccggtac      600
aggaataggg tgttacctta ttaattacga cggtggtcaa aacgacgaaa tttaccccat      660
ttttgagtta caagacctga atttggaaat gatgaaacaa ttgtaccaag tcttggagga      720
ccatgtaagt gggcttaatc ctctcgagaa gcaattccca attgaacaca gtaaaccgtt      780
atcagccact ctgttctttc acttaaggtc tcttttttac atggcgaaga ctcataagcg      840
tactggaaga cattacaact tgaaaaagat tttcttgttc actaataacg ataaacctta      900
caatggaaac tctcagctga gagttccctt gaagaaaacc ctggctgatt acaatgacgt      960
agacattact ttgattccgt ttcttctgaa caagccttca ggtgtcaagt ttgacaagac     1020
ggaatactca gaaattttgt tctatgataa agatgcttgt tcgatgtcaa ttgaggagat     1080
ccgccaacga atttctagac ataaggagat caagcgggtt tacttcacct gtcctttgaa     1140
aatcgcaaat aacttgtgca tttctgtgaa aggttattct atgttttatc atgaaactcc     1200
aaggaagatc aaatttgtcg tcaatgaggg ttcaactttc aaagatgtgg agacaaaatc     1260
tcagtttgtc gatccaacat ccggaaaaga gtttttccagt gaacagctga tcaaagcata     1320
tcctctaggt gccgatgctt acattccttt aaactcagag caagtcaaaa caataaatcg     1380
atttaatgat atcatcaata tcccctcttt ggaaattcta ggtttcaggg atatatctaa     1440
ttggttgcca cagtatcagt ttggcaaagc atcgtttta tccctaata actatggtga      1500 ttttacacat tcgcagagaa catttagttg tcttcagtaa tgtcttgttt cttttgttgc     1560
agtggtgagc cattttgact tcgtgaaagt ttctttagaa tagttgtttc cagaggccaa     1620
acattccacc cgtagtaaag tgcaagcgta ggaagaccaa gactggcata aatcaggtat     1680
aagtgtcgag cactggcagg tgatcttctg aaagtttcta ctagcagata agatccagta     1740
gtcatgcata tggcaacaat gtaccgtgtg gatctaagaa cgcgtcctac taaccttcgc     1800
attcgttggt ccagtttgtt gttatcgatc aacgtgacaa ggttgtcgat tccgcgtaag     1860
catgcatacc caaggacgcc tgttgcaatt ccaagtgagc cagttccaac aatctttgta     1920
atattagagc acttcattgt gttgcgcttg aaagtaaaat gcgaacaaat taagagataa     1980
tctcgaaacc gcgacttcaa acgccaatat gatgtgcggc acacaataag cgttcatatc     2040
cgctgggtga ctttctcgct ttaaaaaatt atccgaaaaa atttttgacg gctagctcag     2100
tcctaggtac gctagcatta aagaggagaa aatggctaaa ctgacctctg ctgttccggt     2160
tctgaccgct cgtgacgttg ctggtgctgt tgagttctgg accgaccgtc tgggtttctc     2220
tcgtgacttc gttgaagacg acttcgctgg tgttgttcgt gacgacgtta ccctgttcat     2280
ctctgctgtt caggaccagg ttgttccgga caacaccctg gcttgggttt gggttcgtgg     2340 tctgacgaa ctgtacgctg aatggtctga agttgtttct accaacttcc gtgacgcttc      2400
tggtccggct atgaccgaaa tcggtgaaca gccgtggggt cgtgagttcg ctctgcgtga     2460
```

-continued

```
cccggctggt aactgcgttc acttcgttgc tgaagaacag gactaacacg tccgacggcg    2520
gcccacgggt cccaggcctc ggagatccgt ccccctttc ctttgtcgat atcatgtaat     2580
tagttatgtc acgcttacat tcacgccctc cccccacatc cgctctaacc gaaaaggaag    2640
gagttagaca acctgaagtc taggtccta tttattttt tatagttatg ttagtattaa      2700
gaacgttatt tatatttcaa attttctt ttttctgta cagacgcgtg tacgcatgta      2760
acattatact gaaaaccttg cttgagaagg ttttgggacg ctcgaaggct ttaatttgca    2820
agctgtatta gtttcacttt tcagcaacct ggtcggaaag atccacatca agaatggata    2880
ccaaccccaa gagtatgaaa atccttccct acaatggcac ttcaaaatgt tacgtgacga    2940
ttaccttcaa ttggaacacg atatcgacat cagtgacccc cttgagaaac aaaagtacat    3000
aaacagcctc gatgagacaa aaaccaagat catgaaacta cgggactatg tcaaggaaac    3060
tgccgatgat gacgacccct cacggcttgc caacactctc aaagagctca accaagagct    3120
gaacaaaatt tccaactttg atatcatcgc caataagaag ccaaagaccc ccacgacagt    3180
agaccctgtt cctactgatg atgacatcat caacgcctgg aaggcaggaa ctctgaacgg    3240
tttcaaggtg gatcaattac gaaaatacgt aaggtcacga aacaactttc tggagacggc    3300
ctccaaaaag gcagatctca tcgccaacat tgacaagtac tttcagcaga agttcaaaga    3360
gactaaggcc tgattcgtgt tccttactt ttcctcgcaa cgtgttttt tcccaccaca     3420 ttgcctatgt tgtaatgcaa tgcagatgct ggcccagttt ttgacgattc tcgaaaattg    3480
gcattttcgt cgatgccatt ggccaaactg aaaattcaag acaaaataga ttggatttta    3540
tctgcaacgt cttccaccta cacaaccact ctacaaactt cagacaaaca tgtttataaa    3600
agcagctact agatccaaaa tgacaagttc gttattctct actacgtttg ttgtggcatt    3660
tggattggtg gctagcaaca acctcttgcc atgtcctgtt gaccactcta tgaataacga    3720
gactccgcaa gaattgaaac cattgcaggc tgaatcttct actagaaagt tgaactcttc    3780
cgcttaagtc aaataaaact actgacacag atgatgcaca gaaacaacgg atcacgctct    3840
tgactgatta gtcccgtcat tttggttctc attttcttca cagtcaccta tcaatgtatg    3900
atcacctgga aggatttccc tacgatactt caaatctttt acttgataat attactcatt    3960
atggctcagg aatgcagact gcctgattca agacgctgct cttcttattt aacacttgta    4020
cactaacccc atggaagcca gggaagggaa taaccatctc tctggtaata aatcggtctt    4080
tatttatgca tagaaaagga atctattata tttcgttcat ttggcactct gctaactgta    4140
gattaacggg tctcgtaaat tcaaaatctt cttccgatca aaccggggtg aaatattact    4200
tctcgtgcat agctaatttt caaataaccg tcctaaaatg aacggtcatt tacctggact    4260
ctcttgccaa atgggcaaca aaacataaag ctgatcagaa cgtaactagt ctctcggaat    4320
ccat                                                                 4324
```

```
<210> SEQ ID NO 466
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 466
ggagttgaat cacatcttac tg                                               22
```

-continued

```
<210> SEQ ID NO 467
<211> LENGTH: 1099
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 467
gacaactaaa tgttctctgc gaatgtgtaa aatcaccata gttattaggg gataaaaacg      60
atgctttgcc aaactgatac tgtggcaacc aattagatat atccctgaaa cctagaattt     120
ccaaagaggg gatattgatg atatcattaa atcgatttat tgttttgact tgctctgagt     180
ttaaaggaat gtaagcatcg gcacctagag gatatgcttt gatcagctgt tcactggaaa     240
actcttttcc ggatgttgga tcgacaaact gagattttgt ctccacatct ttgaaagttg     300
aaccctcatt gacgacaaat ttgatcttcc ttggagtttc atgataaaac atagaataac     360
ctttcacaga aatgcacaag ttatttgcga ttttcaaagg acaggtgaag taaacccgct     420
tgatctcctt atgtctagaa attcgttggc ggatctcctc aattgacatc gaacaagcat     480
ctttatcata gaacaaaatt tctgagtatt ccgtcttgtc aaacttgaca cctgaaggct     540
tgttcagaag aaacggaatc aaagtaatgt ctacgtcatt gtaatcagcc agggttttct     600
tcaagggaac tctcagctga gagtttccat tgtaaggttt atcgttatta gtgaacaaga     660
aaatcttttt caagttgtaa tgtcttccag tacgcttatg agtcttcgcc atgtaaaaaa     720
gagaccttaa gtgaaagaac agagtggctg ataacggttt actgtgttca attgggaatt     780
gcttctcgag aggattaagc ccacttacat ggtcctccaa gacttggtac aattgtttca     840
tcatttccaa attcaggtct tgtaactcaa aaatggggta aatttcgtcg ttttgaccac     900
cgtcgtaatt aataaggtaa caccctattc ctgtaccggg caaggtaatg attagctcag     960
aaataacctc actgacattc tctaagatga tctggagctg agatttccct tctgaagccg    1020
gcgcgtgaag ctccggggtc aattcaatta caaagataat gccttcgtgg atgtcgtatt    1080
gcttgctgac aacactcat                                                 1099

<210> SEQ ID NO 468
<211> LENGTH: 549
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 468
tcaggcctta gtctctttga acttctgctg aaagtacttg tcaatgttgg cgatgagatc      60
tgcctttttg gaggccgtct ccagaaagtt gtttcgtgac cttacgtatt ttcgtaattg     120
atccaccttg aaaccgttca gagttcctgc cttccaggcg ttgatgatgt catcatcagt     180
aggaacaggg tctactgtcg tggggtctt tggcttctta ttggcgatga tatcaaagtt     240
ggaaattttg ttcagctctt ggttgagctc tttgagagtg ttggcaagcc gtgaagggtc     300
gtcatcatcg gcagtttcct tgacatagtc ccgtagtttc atgatcttgg tttttgtctc     360
atcgaggctg tttatgtact tttgtttctc aaggggtca ctgatgtcga tatcgtgttc     420
caattgaagg taatcgtcac gtaacatttt gaagtgccat tgtagggaag gattttcata     480
ctcttggggt tggtatccat tcttgatgtg gatctttccg accaggttgc tgaaaagtga     540
aactaatac                                                             549
```

<210> SEQ ID NO 469
<211> LENGTH: 552
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 469
ttcagtaatg tcttgtttct tttgttgcag tggtgagcca ttttgacttc gtgaaagttt        60
ctttagaata gttgtttcca gaggccaaac attccacccg tagtaaagtg caagcgtagg       120
aagaccaaga ctggcataaa tcaggtataa gtgtcgagca ctggcaggtg atcttctgaa       180
agtttctact agcagataag atccagtagt catgcatatg gcaacaatgt accgtgtgga       240
tctaagaacg cgtcctacta accttcgcat tcgttggtcc agtttgttgt tatcgatcaa       300
cgtgacaagg ttgtcgattc cgcgtaagca tgcatccca  aggacgcctg ttgcaattcc       360
aagtgagcca gttccaacaa tctttgtaat attagagcac ttcattgtgt tgcgcttgaa       420
agtaaaatgc gaacaaatta agagataatc tcgaaaccgc gacttcaaac gccaatatga       480
tgtgcggcac acaataagcg ttcatatccg ctgggtgact ttctcgcttt aaaaaattat       540
ccgaaaaaat tt                                                          552

<210> SEQ ID NO 470
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 470
cagaggccaa acattccacc                                                   20

<210> SEQ ID NO 471
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 471
ttaaagagga gaaa                                                         14

<210> SEQ ID NO 472
<211> LENGTH: 375
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 472
atggctaaac tgacctctgc tgttccggtt ctgaccgctc gtgacgttgc tggtgctgtt        60
gagttctgga ccgaccgtct gggtttctct cgtgacttcg ttgaagacga cttcgctggt       120
gttgttcgtg acgacgttac cctgttcatc tctgctgttc aggaccaggt tgttccggac       180
aacacccctg gcttgggtttg ggttcgtggt ctggacgaac tgtacgctga atggtctgaa       240
gttgtttcta ccaacttccg tgacgcttct ggtccggcta tgaccgaaat cggtgaacag       300
ccgtggggtc gtgagttcgc tctgcgtgac ccggctggta actgcgttca cttcgttgct       360

-continued gaagaacagg actaa                                                                                          375

<210> SEQ ID NO 473
<211> LENGTH: 318
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 473
cacgtccgac ggcggcccac gggtcccagg cctcggagat ccgtcccct tttcctttgt      60 cgatatcatg taattagtta tgtcacgctt acattcacgc cctcccccca catccgctct     120
aaccgaaaag gaaggagtta gacaacctga agtctaggtc cctatttatt tttttatagt     180
tatgttagta ttaagaacgt tatttatatt tcaaattttt cttttttttc tgtacagacg     240
cgtgtacgca tgtaacatta tactgaaaac cttgcttgag aaggtttggg gacgctcgaa     300
ggctttaatt tgcaagct                                                                                      318

<210> SEQ ID NO 474
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 474
aggagttaga caacctgaag                                                                                    20

<210> SEQ ID NO 475
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 475
gtaactagtc tctcggaatc cat                                                                                23

<210> SEQ ID NO 476
<211> LENGTH: 1623
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 476
cttcagagta cagaagatta agtgagagaa ttctaccgtt cgtatagcat acattatacg      60
aagttatttc agtaatgtct tgtttctttt gttgcagtgg tgagccattt tgacttcgtg     120
aaagtttctt tagaatagtt gtttccagag gccaaacatt ccaccgtag taaagtgcaa      180 gcgtaggaag accaagactg gcataaatca ggtataagtg tcgagcactg gcaggtgatc     240
ttctgaaagt ttctactagc agataagatc cagtagtcat gcatatggca acaatgtacc     300
gtgtggatct aagaacgcgt cctactaacc ttcgcattcg ttggtccagt ttgttgttat     360
cgatcaacgt gacaaggttg tcgattccgc gtaagcatgc atacccaagg acgcctgttg     420
caattccaag tgagccagtt ccaacaatct ttgtaatatt agagcacttc attgtgttgc     480

-continued

```
gcttgaaagt aaaatgcgaa caaattaaga gataatctcg aaaccgcgac ttcaaacgcc      540
aatatgatgt gcggcacaca ataagcgttc atatccgctg ggtgactttc tcgctttaaa      600
aaattatccg aaaaaatttt tgacggctag ctcagtccta ggtacgctag cattaaagag      660
gagaaaatga ctactcttga tgacacagcc tacagatata ggacatcagt tccgggtgac      720
gcagaggcta tcgaagcctt ggacggttca ttcactactg atacggtgtt tagagtcacc      780
gctacaggtg atggcttcac cttgagagag gttcctgtag acccacccctt aacgaaagtt      840 ttccctgatg acgaatcgga tgacgagtct gatgctggtg aggacggtga ccctgattcc      900
agaacatttg tcgcatacgg agatgatggt gacctggctg gctttgttgt ggtgtcctac      960
agcggatgga atcgtagact cacagttgag gacatcgaag ttgcacctga acatcgtggt     1020
cacggtgttg tcgtgcact gatgggactg gcaacagagt ttgctagaga aagaggagcc     1080
ggacatttgt ggttagaagt gaccaatgtc aacgctcctg ctattcacgc atataggcga     1140
atgggtttca ctttgtgcgg tcttgatact gctttgtatg acggaactgc ttctgatggt     1200
gaacaagctc tttacatgag tatgccatgt ccatagcacg tccgacggcg gcccacgggt     1260
cccaggcctc ggagatccgt ccccctttc ctttgtcgat atcatgtaat tagttatgtc     1320
acgcttacat tcacgccctc cccccacatc cgctctaacc gaaaaggaag gagttagaca     1380
acctgaagtc taggtcccta tttatttttt tatagttatg ttagtattaa gaacgttatt     1440
tatatttcaa atttttcttt tttttctgta cagacgcgtg tacgcatgta acattatact     1500
gaaaaccttg cttgagaagg ttttgggacg ctcgaaggct ttaatttgca agctataact     1560
tcgtatagca tacattatac cttgttatgc ggccgcaaga agttgattga gactttcaac     1620
gag                                                                  1623
```

<210> SEQ ID NO 477
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 477

```
cttcagagta cagaagatta agtgaga                                          27
```

<210> SEQ ID NO 478
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 478

```
taccgttcgt atagcataca ttatacgaag ttat                                  34
```

<210> SEQ ID NO 479
<211> LENGTH: 552
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 479

```
ttcagtaatg tcttgtttct tttgttgcag tggtgagcca ttttgacttc gtgaaagttt      60
```

-continued

```
ctttagaata gttgtttcca gaggccaaac attccacccg tagtaaagtg caagcgtagg      120
aagaccaaga ctggcataaa tcaggtataa gtgtcgagca ctggcaggtg atcttctgaa      180
agtttctact agcagataag atccagtagt catgcatatg gcaacaatgt accgtgtgga      240
tctaagaacg cgtcctacta accttcgcat tcgttggtcc agtttgttgt tatcgatcaa      300
cgtgacaagg ttgtcgattc cgcgtaagca tgcataccca aggacgcctg ttgcaattcc      360
aagtgagcca gttccaacaa tctttgtaat attagagcac ttcattgtgt tgcgcttgaa      420
agtaaaatgc gaacaaatta agagataatc tcgaaaccgc gacttcaaac gccaatatga      480
tgtgcggcac acaataagcg ttcatatccg ctgggtgact ttctcgcttt aaaaaattat      540
ccgaaaaaat tt                                                          552
```

```
<210> SEQ ID NO 480
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 480
ttaaagagga gaaa                                                         14
```

```
<210> SEQ ID NO 481
<211> LENGTH: 570
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 481
atgactactc ttgatgacac agcctacaga tataggacat cagttccggg tgacgcagag       60
gctatcgaag ccttggacgg ttcattcact actgatacgg tgtttagagt caccgctaca      120
ggtgatggct tcaccttgag agaggttcct gtagacccac ccttaacgaa agtttccct       180 gatgacgaat cggatgacga gtctgatgct ggtgaggacg gtgaccctga ttccagaaca      240
tttgtcgcat acggagatga tggtgacctg gctggctttg ttgtggtgtc ctacagcgga      300
tggaatcgta gactcacagt tgaggacatc gaagttgcac ctgaacatcg tggtcacggt      360
gttggtcgtg cactgatggg actggcaaca gagtttgcta gagaaagagg agccggacat      420
ttgtggttag aagtgaccaa tgtcaacgct cctgctattc acgcatatag gcgaatgggt      480
ttcactttgt gcggtcttga tactgctttg tatgacggaa ctgcttctga tggtgaacaa      540
gctctttaca tgagtatgcc atgtccatag                                      570
```

```
<210> SEQ ID NO 482
<211> LENGTH: 318
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 482
cacgtccgac ggcggcccac gggtcccagg cctcggagat ccgtcccct tttcctttgt       60 cgatatcatg taattagtta tgtcacgctt acattcacgc cctcccccca catccgctct      120
aaccgaaaag gaaggagtta gacaacctga agtctaggtc cctatttatt tttttatagt      180
```

-continued

```
tatgttagta ttaagaacgt tatttatatt tcaaattttt cttttttttc tgtacagacg      240
cgtgtacgca tgtaacatta tactgaaaac cttgcttgag aaggttttgg gacgctcgaa      300
ggctttaatt tgcaagct                                                   318

<210> SEQ ID NO 483
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 483
ataacttcgt atagcataca ttataccttg ttat                                  34

<210> SEQ ID NO 484
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 484
gcggccgcaa gaagttgatt gagactttca acgag                                 35

<210> SEQ ID NO 485
<211> LENGTH: 3869
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 485
tactacaggc tggctgttcc tcgcatggtg tttaatgtcc tgactgggtt ttcgtttatc       60
ggtattaccg gagccacctt gactgtaagg gaacgatact ggactaagag agtaatgcga      120
aaggcaacag cgtttctggc gaacctaatc aatgacggtt acgagtttac tactcctaaa      180
gccagtctta ttttgctaga gcgagtcaac gcttacttaa agggccaggg acctaattat      240
gacatcgatt ttgacgagca ggaggcgttc attaaagaaa tggaggagtt gaggacctct      300
ggtggatatg agaacagata ctcatattca ggaaccgatg aaacacccag agatccgggt      360
tgcctgtttc ttcccattgc tttaaataaa tggcactttg atgtgctaga ctgcctgagg      420
atatacggta ctcaggaaga tctggaatct aaattattaa gtgttcagca attggtgtta      480
caatgttgca tgaagcacag tggcatgact ccagacatgg tctttgcaac ggaagtagct      540
cagaagccga ccttcgaaga cgacatagtt tgtgatgata ttgacgctta tgcccagggg      600
ggtgattgtc tagattattg ttacacgcca agcaattact ccagaacttt agaaattcat      660
ggcaagattg ctaccttaca acgagagctg gggctatgct ataatattct cggaattttg      720
gaccgttttt ccgattaagg tttttagctc cattgcgcca accccgctc tccagactcc       780 ttcgttatcc agcattcagc atggacaggt tcaaaaaata aaatttcttg atatgggtcc       840
acttcaaaca tgcgcctacc tgtaggaaaa aaaagagaa cataaatatg ccgcgaacag       900
aaaacgtaat gtactgttct atatataaac tgttcagatc aatcataaat tctcagtttc      960
aaactttccg ctcagccaga ttttattcgt aaagaacgca tcattggctc tatgttgaag     1020
gatcagttct tgttatgggt tgctttgata gcgagcgtac cggtttccgg cgtgatggca     1080
```

-continued

```
gctcctagcg agtccgggca taacacggtt gaaaaacgag atgccaaaaa cgttgttggc   1140
gttcaacagt tggacttctt cagagtacag aagattaagt gagagaattc taccgttcgt   1200
atagcataca ttatacgaag ttatttcagt aatgtcttgt ttcttttgtt gcagtggtga   1260
gccattttga cttcgtgaaa gtttctttag aatagttgtt tccagaggcc aaacattcca   1320
cccgtagtaa agtgcaagcg taggaagacc aagactggca taaatcaggt ataagtgtcg   1380
agcactggca ggtgatcttc tgaaagtttc tactagcaga taagatccag tagtcatgca   1440
tatggcaaca atgtaccgtg tggatctaag aacgcgtcct actaaccttc gcattcgttg   1500
gtccagtttg ttgttatcga tcaacgtgac aaggttgtcg attccgcgta agcatgcata   1560
cccaaggacg cctgttgcaa ttccaagtga gccagttcca acaatctttg taatattaga   1620
gcacttcatt gtgttgcgct tgaaagtaaa atgcgaacaa attaagagat aatctcgaaa   1680
ccgcgacttc aaacgccaat atgatgtgcg gcacacaata agcgttcata tccgctgggt   1740
gactttctcg ctttaaaaaa ttatccgaaa aaatttttga cggctagctc agtcctaggt   1800
acgctagcat taaagaggag aaaatgacta ctcttgatga cacagcctac agatatagga   1860
catcagttcc gggtgacgca gaggctatcg aagccttgga cggttcattc actactgata   1920
cggtgtttag agtcaccgct acaggtgatg gcttcacctt gagagaggtt cctgtagacc   1980 caccccttaac gaaagttttc cctgatgacg aatcggatga cgagtctgat gctggtgagg   2040
acggtgaccc tgattccaga acatttgtcg catacgagga tgatggtgac ctggctggct   2100
ttgttgtggt gtcctacagc ggatggaatc gtagactcac agttgaggac atcgaagttg   2160
cacctgaaca tcgtggtcac ggtgttggtc gtgcactgat gggactggca acagagtttg   2220
ctagagaaag aggagccgga catttgtggt tagaagtgac caatgtcaac gctcctgcta   2280
ttcacgcata taggcgaatg ggtttcactt tgtgcggtct tgatactgct ttgtatgacg   2340
gaactgcttc tgatggtgaa caagctcttt acatgagtat gccatgtcca tagcacgtcc   2400
gacggcggcc cacgggtccc aggcctcgga gatccgtccc cctttccctt tgtcgatatc   2460
atgtaattag ttatgtcacg cttacattca cgccctcccc ccacatccgc tctaaccgaa   2520
aaggaaggag ttagacaacc tgaagtctag gtccctattt atttttttat agttatgtta   2580
gtattaagaa cgttatttat atttcaaatt tttctttttt ttctgtacag acgcgtgtac   2640
gcatgtaaca ttatactgaa aaccttgctt gagaaggttt tgggacgctc gaaggcttta   2700
atttgcaagc tataacttcg tatagcatac attatacctt gttatgcggc cgcaagaagt   2760
tgattgagac tttcaacgag ggtccccttc agctaccttt ctctctgttt ggtagttatt   2820
ctcggcgtgt gtatagtata gtataaaagg gcctacattg ataggcttc aacattcctc   2880 aataaacaaa catccaacat cgcgcattcc gcatttcgca tttcacattt cgcgcctgcc   2940
ttcctttagg ttctttgaat catcatcaat cgtcgccgtc tacatcagag caggacttat   3000
ctttgccttc cccaaaaatt gccactccgt caaatagatt cttttgaatc cttgactatt   3060
tttgcctaaa taggtttttg ttagtttttc ttcaaagccc aaaagaaact ctatttagat   3120
tcatccagaa acaatctttt tctcacccca tttcgaagtg ccgtggagca cagacataaa   3180
aagatgacta ccgttcaacc tacagggcca gacaggctca ccctgccgca tattctactg   3240
gaattcaacg atggctcctc gcagcatgca gtgatcgagc taagcatgaa cgaggggatt   3300
aatatatcca cccatgagtg gaatccatcc actaatgagc aatcgccacg ggaagagaga   3360
gcaccacccc aacaatccaa tccatcgcat catccagaat catcgaacat agctactcaa   3420
agtcccgctc aggaaaccga gactcagccc ggcattccag gactagatag gcctgccttt   3480
```

-continued

```
gatacctcgg caacggggtc gtcagaacag gttgacccag tacagggaag gatcctggat      3540
gatattatag gccaatcatt aaggacttcc gaagaagacg ataccgaatc ccgccagaga      3600
ccacgagacc agaagaacat tatgatcacc gtgaattact tgtacgcaga cgacacaaat      3660
tccagaagtg ctaatacaaa caaccagacg cccaataaca cttctagaac ttccgacagt      3720
gaacgtgtgg gctccttatc gttgcacgtt ccggatctac cagataatgc cgacgattac      3780
tatatcgatg tactcattaa actaaccaca agcattgccc tcagcgtcat cacgtccatg      3840
atcaagaaac gattagggct tagcaggga                                        3869
```

<210> SEQ ID NO 486
<211> LENGTH: 1157
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 486

```
tactacaggc tggctgttcc tcgcatggtg tttaatgtcc tgactgggtt ttcgtttatc        60
ggtattaccg gagccacctt gactgtaagg gaacgatact ggactaagag agtaatgcga       120
aaggcaacag cgtttctggc gaacctaatc aatgacggtt acgagtttac tactcctaaa       180
gccagtctta ttttgctaga gcgagtcaac gcttacttaa agggccaggg acctaattat       240
gacatcgatt ttgacgagca ggaggcgttc attaaagaaa tggaggagtt gaggacctct       300
ggtggatatg agaacagata ctcatattca ggaaccgatg aaacacccag agatccgggt       360
tgcctgtttc ttcccattgc tttaaataaa tggcactttg atgtgctaga ctgcctgagg       420
atatacggta ctcaggaaga tctggaatct aaattattaa gtgttcagca attggtgtta       480
caatgttgca tgaagcacag tggcatgact ccagacatgg tctttgcaac ggaagtagct       540
cagaagccga ccttcgaaga cgacatagtt tgtgatgata ttgacgctta tgcccagggg       600
ggtgattgtc tagattattg ttacacgcca agcaattact ccagaacttt agaaattcat       660
ggcaagattg ctaccttaca acgagagctg gggctatgct ataatattct cggaattttg       720
gaccgttttt ccgattaagg ttttttagctc cattgcgcca accccgctc tccagactcc       780 ttcgttatcc agcattcagc atggacaggt tcaaaaaata aaatttcttg atatgggtcc       840
acttcaaaca tgcgcctacc tgtaggaaaa aaaaagagaa cataaatatg ccgcgaacag       900
aaaacgtaat gtactgttct atatataaac tgttcagatc aatcataaat tctcagtttc       960
aaactttccg ctcagccaga tttttattcgt aaagaacgca tcattggctc tatgttgaag      1020
gatcagttct tgttatgggt tgctttgata gcgagcgtac cggtttccgg cgtgatggca      1080
gctcctagcg agtccgggca taacacggtt gaaaaacgag atgccaaaaa cgttgttggc      1140
gttcaacagt tggactt                                                     1157
```

<210> SEQ ID NO 487
<211> LENGTH: 1089
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 487

```
ggtcccctto agctaccttt ctctctgttt ggtagttatt ctcggcgtgt gtatagtata        60
```

-continued

```
gtataaaagg gcctacattg gataggcttc aacattcctc aataaacaaa catccaacat    120
cgcgcattcc gcatttcgca tttcacattt cgcgcctgcc ttcctttagg ttctttgaat    180
catcatcaat cgtcgccgtc tacatcagag caggacttat ctttgccttc cccaaaaatt    240
gccactccgt caaatagatt cttttgaatc cttgactatt tttgcctaaa taggtttttg    300
ttagtttttc ttcaaagccc aaaagaaact ctatttagat tcatccagaa acaatctttt    360
tctcacccca tttcgaagtg ccgtggagca cagacataaa aagatgacta ccgttcaacc    420
tacagggcca gacaggctca ccctgccgca tattctactg gaattcaacg atggctcctc    480
gcagcatgca gtgatcgagc taagcatgaa cgaggggatt aatatatcca cccatgagtg    540
gaatccatcc actaatgagc aatcgccacg ggaagagaga gcaccacccc aacaatccaa    600
tccatcgcat catccagaat catcgaacat agctactcaa agtcccgctc aggaaaccga    660
gactcagccc ggcattccag gactagatag gcctgccttt gatacctcgg caacggggtc    720
gtcagaacag gttgacccag tacagggaag gatcctggat gatattatag gccaatcatt    780
aaggacttcc gaagaagacg ataccgaatc ccgccagaga ccacgagacc agaagaacat    840
tatgatcacc gtgaattact tgtacgcaga cgacacaaat tccagaagtg ctaatacaaa    900
caaccagacg cccaataaca cttctagaac ttccgcacgt gaacgtgtgg gctccttatc    960
gttgcacgtt ccggatctac cagataatgc cgacgattac tatatcgatg tactcattaa   1020
actaaccaca agcattgccc tcagcgtcat cacgtccatg atcaagaaac gattagggct   1080
tagcaggga                                                           1089
```

```
<210> SEQ ID NO 488
<211> LENGTH: 3964
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 488
gccttctcgt gcaatcagag ctgttgaaag agagaagagg gcacacggaa gctgctgttc     60
aattgtgtga attgaccgga ttacaacctg ctggagtgat aggagagctg gttcgtgacg    120
aggacggctc tatgatgcga ttagacgact gtgttcagtt tggtctccgc cacaacgtaa    180
aaattatcaa ccttgaccag atcattgaat acatggattc caagaacagc tagatacgat    240
ggataggaat acagagatat catgattgag gaacgtaaga gctttttcga aagtgtgagt    300
ttgtggtgag ggccaggcgg tggggaggtg gtggggagcc tccttggtcg aatgtagata    360
tagtaagcaa gacacaagag cgcgcgaagt cttcaacgag gcggcgttgg gtcttgtacg    420
caacgtaatg actacacagt tgagcttgtc gcgaaccggt cgacattttg atcatgcata    480
ctatgttgag acaccatctc gtactattgc ggcaaccagc tgtaaatttg actaattaaa    540
gctgatgaag gatgcaggc gtcgtcaatt ttttgattga ttgcatttaa ttgtttgagc    600
cattcaaggc tgaatgcccg gcaccctaga cccttcttgt gagtactata aacccgcagg    660
cagggtaccc ttggccttct gcgagactac cagtcataac gtatatccac aatgtactag    720
taatagcccg ggaaaactct aatcccacag aacgtctaac gcctcctatg tcatcgatac    780
ccattcgcac tactgccatg gcccccctta cgtgatcatt tcacttactc ccgcctaagc    840
ttcgcccaca tgcctgcgtt ttgccaagat ttactgacga gtttggttta ctcatcctct    900
atttataact actagacttt caccattctt caccaccctc gtgccaatga tcatcaacca    960
```

-continued

```
cttggtattg acagccctca gcattgcact agcaagtgcg caactccaat cgcctttcac      1020
ttcagagtac agaagattaa gtgagagaat tctaccgttc gtatagcata cattatacga      1080
agttatttca gtaatgtctt gtttctttg ttgcagtggt gagccatttt gacttcgtga      1140
aagtttcttt agaatagttg tttccagagg ccaaacattc cacccgtagt aaagtgcaag      1200
cgtaggaaga ccaagactgg cataaatcag gtataagtgt cgagcactgg caggtgatct      1260
tctgaaagtt tctactagca gataagatcc agtagtcatg catatggcaa caatgtaccg      1320
tgtggatcta agaacgcgtc ctactaacct tcgcattcgt tggtccagtt tgttgttatc      1380
gatcaacgtg acaaggttgt cgattccgcg taagcatgca tacccaagga cgcctgttgc      1440
aattccaagt gagccagttc caacaatctt tgtaatatta gagcacttca ttgtgttgcg      1500
cttgaaagta aaatgcgaac aaattaagag ataatctcga aaccgcgact tcaaacgcca      1560
atatgatgtg cggcacacaa taagcgttca tatccgctgg gtgactttct cgctttaaaa      1620
aattatccga aaaaattttt gacggctagc tcagtcctag gtacgctagc attaaagagg      1680
agaaaatgac tactcttgat gacacagcct acagatatag gacatcagtt ccgggtgacg      1740
cagaggctat cgaagccttg gacggttcat tcactactga tacggtgttt agagtcaccg      1800
ctacaggtga tggcttcacc ttgagagagg ttcctgtaga cccaccctta acgaaagttt      1860
tccctgatga cgaatcggat gacgagtctg atgctggtga ggacggtgac cctgattcca      1920
gaacatttgt cgcatacgga gatgatggtg acctggctgg ctttgttgtg gtgtcctaca      1980
gcggatggaa tcgtagactc acagttgagg acatcgaagt tgcacctgaa catcgtggtc      2040
acggtgttgg tcgtgcactg atgggactgg caacagagtt tgctagagaa agaggagccg      2100
gacatttgtg gttagaagtg accaatgtca acgctcctgc tattcacgca tataggcgaa      2160
tgggtttcac tttgtgcggt cttgatactg ctttgtatga cggaactgct tctgatggtg      2220
aacaagctct ttacatgagt atgccatgtc catagcacgt ccgacggcgg cccacgggtc      2280
ccaggcctcg gagatccgtc ccccttttcc tttgtcgata tcatgtaatt agttatgtca      2340
cgcttacatt cacgccctcc ccccacatcc gctctaaccg aaaaggaagg agttagacaa      2400
cctgaagtct aggtccctat ttattttttt atagttatgt tagtattaag aacgttattt      2460
atatttcaaa ttttttcttt ttttctgtac agacgcgtgt acgcatgtaa cattatactg      2520
aaaaccttgc ttgagaaggt tttgggacgc tcgaaggctt taatttgcaa gctataactt      2580
cgtatagcat acattatacc ttgttatgcg gccgcaagaa gttgattgag actttcaacg      2640
agctggctct gcttctggta cttcttcagg tgcatcttct gctactcaaa atgacgaaac      2700
atccactgat cttggagctc cagctgcatc tttaagtgca acgccatgtc tttttgccat      2760
cttgctgctc atgttgtagt agactttttt tttcactgag tttttatgta ctactgatta      2820
cattgtgtag gtgtaatgat gtgcactata atactaatat agtcaaaatg ctacagagga      2880
aagtgcaggt tgcctgtggt ggtttttctt attagcaccc tctgaacact ctttacctct      2940
aacatcctca gccatgctaa tcgcgcataa aataaatctt cgaacttttt tccattttat      3000
gctcataaag cttccttact gtcaccttat caaaagagct tttgccacta aagtagtcac      3060
acccagaatt gctcccgaat atcgtccaac aatgctagga tctgtggaaa gtttgacaaa      3120
taatttgaac accttgagct tgaagcttcc tgaagttaat atccaaggct cctttccaga      3180
aagtaaccca gtggaccttt tgagaaacta catcactcaa gaacttagta aaatttctgg      3240
agttgacaaa gaattgattt tcccagcctt ggaatggggt accacactgg aaaaaggtga      3300
tcttttgatc ccagttcctc gtctgagaat aaagggtgct aatcctaaag atttagccga      3360
```

-continued

```
acaatgggct gctgcattcc caaagggtgg atatcttaaa gacgttattg cgcaaggacc       3420
tttcttgcag ttctttttta acacatcggt tctgtacaag ttggtgatat ctgatgctct       3480
ggagagaggc gatgactttg gtgcacttcc tctaggaaag ggacaaaaag ttatagtgga       3540
gttttcttct ccaaatattg ccaaaccttt ccacgctggc catcttagaa gtacaatcat       3600
cggtggtttt atttccaatc tgtatgaaaa gctgggtcat gaagttatga ggatgaatta       3660
tttgggagac tggggaaaac aatttggtgt tcttgcagta ggatttgagc gttacggtga       3720
tgaggcaaaa ttaaagactg atccaatcaa ccatttgttt gaggtctatg ttaaaatcaa       3780
ccaagatatt aaggctcaat cagagtctac tgaggagatt gcagaagggc aatcattaga       3840
tgaccaggca agagcttttt tcaagaaaat ggaaaatggc gacgaatcgg ctgtaagctt       3900
gtggaaaaga ttccgtgagt tatccattga gaagtacatt gatacttatg cccgcctcaa       3960
catc                                                                    3964
```

<210> SEQ ID NO 489
<211> LENGTH: 1019
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 489

```
gccttctcgt gcaatcagag ctgttgaaag agagaagagg gcacacggaa gctgctgttc         60
aattgtgtga attgaccgga ttacaacctg ctggagtgat aggagagctg gttcgtgacg        120
aggacggctc tatgatgcga ttagacgact gtgttcagtt tggtctccgc cacaacgtaa        180
aaattatcaa ccttgaccag atcattgaat acatggattc caagaacagc tagatacgat        240
ggataggaat acagagatat catgattgag gaacgtaaga gctttttcga aagtgtgagt        300
ttgtggtgag ggccaggcgg tggggaggtg gtggggagcc tccttggtcg aatgtagata        360
tagtaagcaa gacacaagag cgcgcgaagt cttcaacgag gcggcgttgg gtcttgtacg        420
caacgtaatg actacacagt tgagcttgtc gcgaaccggt cgacattttg atcatgcata        480
ctatgttgag acaccatctc gtactattgc ggcaaccagc tgtaaatttg actaattaaa        540
gctgatgaag gatgcaggc gtcgtcaatt ttttgattga ttgcatttaa ttgtttgagc        600
cattcaaggc tgaatgcccg gcaccctaga cccttcttgt gagtactata aacccgcagg        660
cagggtaccc ttggccttct gcgagactac cagtcataac gtatatccac aatgtactag        720
taatagcccc ggaaaactct aatcccacag aacgtctaac gcctcctatg tcatcgatac        780
ccattcgcac tactgccatg gcccccctta cgtgatcatt tcacttactc ccgcctaagc        840
ttcgcccaca tgcctgcgtt ttgccaagat ttactgacga gtttggttta ctcatcctct        900
atttataact actagacttt caccattctt caccaccctc gtgccaatga tcatcaacca        960
cttggtattg acagccctca gcattgcact agcaagtgcg caactccaat cgcctttca       1019
```

<210> SEQ ID NO 490
<211> LENGTH: 1322
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 490

-continued

```
ctggctctgc ttctggtact tcttcaggtg catcttctgc tactcaaaat gacgaaacat        60
ccactgatct tggagctcca gctgcatctt taagtgcaac gccatgtctt tttgccatct       120
tgctgctcat gttgtagtag actttttttt tcactgagtt tttatgtact actgattaca       180
ttgtgtaggt gtaatgatgt gcactataat actaatatag tcaaaatgct acagaggaaa       240
gtgcaggttg cctgtggtgg ttttttcttat tagcaccctc tgaacactct ttacctctaa       300
catcctcagc catgctaatc gcgcataaaa taaatcttcg aacttttttc cattttatgc       360
tcataaagct tccttactgt caccttatca aaagagcttt tgccactaaa gtagtcacac       420
ccagaattgc tcccgaatat cgtccaacaa tgctaggatc tgtggaaagt ttgacaaata       480
atttgaacac cttgagcttg aagcttcctg aagttaatat ccaaggctcc tttccagaaa       540
gtaacccagt ggacctttg agaaactaca tcactcaaga acttagtaaa atttctggag       600
ttgacaaaga attgattttc ccagccttgg aatggggtac cacactggaa aaaggtgatc       660
ttttgatccc agttcctcgt ctgagaataa agggtgctaa tcctaaagat ttagccgaac       720
aatgggctgc tgcattccca aagggtggat atcttaaaga cgttattgcg caaggacctt       780
tcttgcagtt cttttttaac acatcggttc tgtacaagtt ggtgatatct gatgctctgg       840
agagaggcga tgactttggt gcacttcctc taggaaaggg acaaaaagtt atagtggagt       900
tttcttctcc aaatattgcc aaaccttttcc acgctggcca tcttagaagt acaatcatcg       960
gtggttttat ttccaatctg tatgaaaagc tgggtcatga agttatgagg atgaattatt      1020
tgggagactg gggaaaacaa tttggtgttc ttgcagtagg atttgagcgt tacggtgatg      1080
aggcaaaatt aaagactgat ccaatcaacc atttgtttga ggtctatgtt aaaatcaacc      1140
aagatattaa ggctcaatca gagtctactg aggagattgc agaagggcaa tcattagatg      1200
accaggcaag agcttttttc aagaaaatgg aaaatggcga cgaatcggct gtaagcttgt      1260
ggaaaagatt ccgtgagtta tccattgaga agtacattga tacttatgcc cgcctcaaca      1320
tc                                                                     1322
```

<210> SEQ ID NO 491
<211> LENGTH: 3932
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 491

```
gacgagacgc tgttcctttc aacttgtcca cttggactga caagtcaaca cctgttacta        60
attcttttgt catctctcag tatgaagaca cgcgtgttcc tcaatcagcc accagttcta       120
cacatccaaa cataccctaaa cacgccaaag agtatccgtt agcaaatggg ccacctgggt       180
ggtgttggaa ttcccattcc agtatgtcga cagaccaacc aatatatcca ggacaccaat       240
atccaccacc gcttcagcag cactaccact ttgcttcacc caggcaacta tcaaactcta       300
gctctgggac gtcatccgtt cctttccaac cacccctgc tggtcaatta caaccacaag       360
gtaattctat gttcatacac atgccatttt cgctaaatgg cccaccagct gctggacagc       420
aattgatacc accccaagga ctagcctcaa tacctgtcgg ccccggcaac aacagttccc       480
tattggttag ccaaggtgca cctggcggct attctttagc ttcaccagcg ttgtcaccgg       540
tagatgcgac cttcgaagat cccgtcaaga gactgcccaa aaagcggaca aaaactggat       600
gtctcacttg ccgtaagaga cgaatcaaat gtgacgaacg caagccgttc tgtttcaact       660
```

-continued

```
gtgaaaaaag caaaaaggtg tgtactggtt ttacgcatct attcaaagat cccctagca      720 aatcctaccc tcccagttca gatggtgcct cccctgttgc caatgaccac cctgtccccc      780
caaggcaaaa ctttggtgaa ttgaggggca gtctgaatta catcatcaac tagaagaatg      840
cttattcctt ttctctactg tataatcacg acgttatgtc cttttaatata agaaacgaca      900 attaaaccac tttaggtgga cataatccat ttctggatgc tgttcgatgt gtagtgtcta      960
aaccgatact gagatttctc tttctctttc tcttttttttt ttttttcctta ccattttcctt    1020 caagaaaata caccttttcga cagatcatca taaatggtgg cctctcttca cacttcagag    1080
tacagaagat taagtgagag aattctaccg ttcgtatagc atacattata cgaagttatt     1140
tcagtaatgt cttgtttctt ttgttgcagt ggtgagccat tttgacttcg tgaaagtttc     1200
tttagaatag ttgtttccag aggccaaaca ttccacccgt agtaaagtgc aagcgtagga     1260
agaccaagac tggcataaat caggtataag tgtcgagcac tggcaggtga tcttctgaaa     1320
gtttctacta gcagataaga tccagtagtc atgcatatgg caacaatgta ccgtgtggat     1380
ctaagaacgc gtcctactaa ccttcgcatt cgttggtcca gtttgttgtt atcgatcaac     1440
gtgacaaggt tgtcgattcc gcgtaagcat gcatacccaa ggacgcctgt tgcaattcca     1500
agtgagccag ttccaacaat ctttgtaata ttagagcact tcattgtgtt gcgcttgaaa     1560 gtaaatgcg aacaaattaa gagataatct cgaaaccgcg acttcaaacg ccaatatgat      1620
gtgcggcaca caataagcgt tcatatccgc tgggtgactt tctcgcttta aaaaattatc     1680
cgaaaaaatt tttgacggct agctcagtcc taggtacgct agcattaaag aggagaaaat     1740
gactactctt gatgacacag cctacagata taggacatca gttccgggtg acgcagaggc     1800
tatcgaagcc ttggacggtt cattcactac tgatacggtg tttagagtca ccgctacagg     1860
tgatggcttc accttgagag aggttcctgt agacccaccc ttaacgaaag ttttccctga     1920
tgacgaatcg gatgacgagt ctgatgctgg tgaggacggt gaccctgatt ccagaacatt     1980
tgtcgcatac ggagatgatg gtgacctggc tggctttgtt gtggtgtcct acagcggatg     2040
gaatcgtaga ctcacagttg aggacatcga agttgcacct gaacatcgtg gtcacggtgt     2100
tggtcgtgca ctgatgggac tggcaacaga gtttgctaga aaagaggag ccggacattt      2160 gtggttagaa gtgaccaatg tcaacgctcc tgctattcac gcatataggc gaatgggttt     2220
cactttgtgc ggtcttgata ctgctttgta tgacggaact gcttctgatg gtgaacaagc     2280
tctttacatg agtatgccat gtccatagca cgtccgacgg cggcccacgg gtcccaggcc     2340
tcggagatcc gtcccccttt tcctttgtcg atatcatgta attagttatg tcacgcttac     2400
attcacgccc tccccccaca tccgctctaa ccgaaaagga aggagttaga caacctgaag     2460
tctaggtccc tatttatttt tttatagtta tgttagtatt aagaacgtta tttatatttc     2520
aaatttttct tttttttctg tacagacgcg tgtacgcatg taacattata ctgaaaacct     2580
tgcttgagaa ggttttggga cgctcgaagg ctttaatttg caagctataa cttcgtatag     2640
catacattat accttgttat gcggccgcaa gaagttgatt gagactttca acgagtgatc     2700
gactacttgg cctccgccgt gaaaactcaa ttagatgtta gctccaaatt aatgaacctg     2760
gtacaagatg ataaatagga actcaaatac aaagcctacc attaatgact gttttatttt     2820
tatactaaag tagctaaagg gtgattatca aggagtggtt aacgatctat tcctagcagg     2880
gcactcagct catcgatctt tccaatatcg gcgtataacg cttccacttc tatcaacgta     2940
tcttcgttaa aaagaccacc tctggtggga actaatcctt ctgctgccgc ctctgctaaa     3000
ctctgtcttc gaatccgttt cttactaaca tcagcttcga cagataagcc actcttcttt     3060
```

-continued

```
atctttttct tagatcctgt tttgaatctc agggacttta ctggtgccat aacaacttcc    3120
tgttccagta ccttgttctt cttactcttt tttggtatta aagaatgtcc cgccttgagt    3180
cctcgatcat ccttggccat actcaatcgt ctagtagtgc tgttgaaatg ctgtaaagaa    3240
gaggaatatc ttcttaaatg gttggtatct ttttcagcaa ccacaccttt gtttcggaaa    3300
gcggataatg gcacattgct tggattgata gaagaagcta taaaagccca tcctgcgttt    3360
ggagcagttt gattgctctg agttactatg ttcaactgtg tattggcaaa agccttagag    3420
tcgctgtctg attcgcttat attgagtaaa tcatccaggt ccaatagagg aacagaacca    3480
gtctgcttcc cttttggttt tgtacgatcc ctaattgcac ccttcacaga aagttctacc    3540
cgtttggact ttatactgtc tttgttctct gatactgatc gcattgaaaa cccatcaata    3600
atctcaaagg gtttgccaca gtccgaggtg gtccaaattc caatcactgg agggatagga    3660
tccactttgg aagatgccag aacttctttt gcaattttgg taccaatttt tttattggat    3720
gttttgggaa gagcttcatc ttcatcagtg gagttgctgc tttcgttgtc atctactttt    3780
tggtcatctt ctagttcgtc gtcgtctgaa gcaatagcat ctgaggagga cgcatctcct    3840
tcacctttga aaaagtaatt aaataggtag gagtcatcat cagaatcttg ttcttggtct    3900
gatccccttt cgacggcagc ttgaatgttg tt    3932
```

```
<210> SEQ ID NO 492
<211> LENGTH: 1072
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 492
```

```
gacgagacgc tgttcctttc aacttgtcca cttggactga caagtcaaca cctgttacta     60 attctttgt catctctcag tatgaagaca cgcgtgttcc tcaatcagcc accagttcta    120
cacatccaaa catacctaaa cacgccaaag agtatccgtt agcaaatggg ccacctgggt    180
ggtgttggaa ttcccattcc agtatgtcga cagaccaacc aatatatcca ggacaccaat    240
atccaccacc gcttcagcag cactaccact ttgcttcacc caggcaacta tcaaactcta    300
gctctgggac gtcatccgtt cctttccaac caccccctgc tggtcaatta caaccacaag    360
gtaattctat gttcatacac atgccatttt cgctaaatgg cccaccagct gctggacagc    420
aattgatacc accccaagga ctagcctcaa tacctgtcgg ccccggcaac aacagttccc    480
tattggttag ccaaggtgca cctggcggct attctttagc ttcaccagcg ttgtcaccgg    540
tagatgcgac cttcgaagat cccgtcaaga gactgcccaa aaagcggaca aaaactggat    600
gtctcacttg ccgtaagaga cgaatcaaat gtgacgaacg caagccgttc tgtttcaact    660
gtgaaaaaag caaaaaggtg tgtactggtt ttacgcatct attcaaagat cccctagca    720 aatcctaccc tcccagttca gatggtgcct ccctgttgc caatgaccac cctgtccccc    780
caaggcaaaa ctttggtgaa ttgaggggca gtctgaatta catcatcaac tagaagaatg    840
cttattcctt ttctctactg tataatcacg acgttatgtc ctttaatata agaaacgaca    900
attaaaccac tttaggtgga cataatccat ttctggatgc tgttcgatgt gtagtgtcta    960
aaccgatact gagatttctc tttctctttc tcttttttt tttttccta ccatttcctt   1020 caagaaaata caccttcga cagatcatca taaatggtgg cctctcttca ca    1072
```

-continued

```
<210> SEQ ID NO 493
<211> LENGTH: 1237
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 493
tgatcgacta cttggcctcc gccgtgaaaa ctcaattaga tgttagctcc aaattaatga      60
acctggtaca agatgataaa taggaactca aatacaaagc ctaccattaa tgactgtttt     120
atttttatac taaagtagct aaagggtgat tatcaaggag tggttaacga tctattccta     180
gcagggcact cagctcatcg atctttccaa tatcggcgta taacgcttcc acttctatca     240
acgtatcttc gttaaaaaga ccacctctgg tgggaactaa tccttctgct gccgcctctg     300
ctaaactctg tcttcgaatc cgtttcttac taacatcagc ttcgacagat aagccactct     360
tctttatctt tttcttagat cctgttttga atctcaggga ctttactggt gccataacaa     420
cttcctgttc cagtaccttg ttcttcttac tcttttttgg tattaaagaa tgtcccgcct     480
tgagtcctcg atcatccttg gccatactca atcgtctagt agtgctgttg aaatgctgta     540
aagaagagga atatcttctt aaatggttgg tatctttttc agcaaccaca cctttgtttc     600
ggaaagcgga taatggcaca ttgcttggat tgatagaaga agctataaaa gcccatcctg     660
cgtttggagc agtttgattg ctctgagtta ctatgttcaa ctgtgtattg gcaaaagcct     720
tagagtcgct gtctgattcg cttatattga gtaaatcatc caggtccaat agaggaacag     780
aaccagtctg cttcccttt ggttttgtac gatccctaat tgcacccttc acagaaagtt     840
ctacccgttt ggactttata ctgtctttgt tctctgatac tgatcgcatt gaaaacccat     900
caataatctc aaagggtttg ccacagtccg aggtggtcca aattccaatc actggaggga     960
taggatccac tttggaagat gccagaactt cttttgcaat tttggtacca atttttttat    1020
tggatgtttt gggaagagct tcatcttcat cagtggagtt gctgctttcg ttgtcatcta    1080 cttttttggtc atcttctagt tcgtcgtcgt ctgaagcaat agcatctgag gaggacgcat    1140
ctccttcacc tttgaaaaag taattaaata ggtaggagtc atcatcagaa tcttgttctt    1200
ggtctgatcc cctttcgacg gcagcttgaa tgttgtt                             1237

<210> SEQ ID NO 494
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 494

Ser Gly Ala Gly Gly
1               5

<210> SEQ ID NO 495
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 495

Gly Ser Gly Ala Gly
1               5
```

<210> SEQ ID NO 496
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 496

Gly Gly Ser Gly Ala
1               5

<210> SEQ ID NO 497
<211> LENGTH: 181
<212> TYPE: PRT
<213> ORGANISM: Aliatypus gulosus

<400> SEQUENCE: 497

Gly Ala Ala Ser Ser Ser Ser Thr Ile Ile Thr Thr Lys Ser Ala Ser
1               5                   10                  15

Ala Ser Ala Ala Ala Asp Ala Ser Ala Ala Ala Thr Ala Ser Ala Ala
            20                  25                  30

Ser Arg Ser Ser Ala Asn Ala Ala Ala Ser Ala Phe Ala Gln Ser Phe
        35                  40                  45

Ser Ser Ile Leu Leu Glu Ser Gly Tyr Phe Cys Ser Ile Phe Gly Ser
        50                  55                  60

Ser Ile Ser Ser Ser Tyr Ala Ala Ala Ile Ala Ser Ala Ala Ser Arg
65                  70                  75                  80

Ala Ala Ala Glu Ser Asn Gly Tyr Thr Thr His Ala Tyr Ala Cys Ala
                85                  90                  95

Lys Ala Val Ala Ser Ala Val Glu Arg Val Thr Ser Gly Ala Asp Ala
            100                 105                 110

Tyr Ala Tyr Ala Gln Ala Ile Ser Asp Ala Leu Ser His Ala Leu Leu
        115                 120                 125

Tyr Thr Gly Arg Leu Asn Thr Ala Asn Ala Asn Ser Leu Ala Ser Ala
        130                 135                 140

Phe Ala Tyr Ala Phe Ala Asn Ala Ala Ala Gln Ala Ser Ala Ser Ser
145                 150                 155                 160

Ala Ser Ala Gly Ala Ala Ser Ala Ser Gly Ala Ala Ser Ala Ser Gly
                165                 170                 175

Ala Gly Ser Ala Ser
            180

<210> SEQ ID NO 498
<211> LENGTH: 126
<212> TYPE: PRT
<213> ORGANISM: Plectreurys tristis

<400> SEQUENCE: 498

Gly Ala Gly Ala Gly Ala Gly Ala Gly Ala Gly Ala Gly Ala Gly Ala
1               5                   10                  15

Gly Ser Gly Ala Ser Thr Ser Val Ser Thr Ser Ser Ser Ser Gly Ser
            20                  25                  30

Gly Ala Gly Ala Gly Ala Gly Ser Gly Ala Gly Ser Gly Ala Gly Ala
        35                  40                  45

Gly Ser Gly Ala Gly Ala Gly Ala Gly Ala Gly Gly Ala Gly Ala Gly
    50                  55                  60

-continued

```
Phe Gly Ser Gly Leu Gly Leu Gly Tyr Gly Val Gly Leu Ser Ser Ala
65                  70                  75                  80

Gln Ala Gln Ala Gln Ala Gln Ala Ala Ala Gln Ala Gln Ala Gln Ala
                    85                  90                  95

Gln Ala Gln Ala Tyr Ala Ala Ala Gln Ala Gln Ala Gln Ala Gln Ala
                100                 105                 110

Gln Ala Gln Ala Ala Ala Ala Ala Ala Ala Ala Ala Ala
        115                 120                 125
```

<210> SEQ ID NO 499
<211> LENGTH: 239
<212> TYPE: PRT
<213> ORGANISM: Plectreurys tristis

<400> SEQUENCE: 499

```
Gly Ala Ala Gln Lys Gln Pro Ser Gly Glu Ser Ser Val Ala Thr Ala
1                   5                   10                  15

Ser Ala Ala Ala Thr Ser Val Thr Ser Gly Gly Ala Pro Val Gly Lys
                    20                  25                  30

Pro Gly Val Pro Ala Pro Ile Phe Tyr Pro Gln Gly Pro Leu Gln Gln
            35                  40                  45

Gly Pro Ala Pro Gly Pro Ser Asn Val Gln Pro Gly Thr Ser Gln Gln
        50                  55                  60

Gly Pro Ile Gly Gly Val Gly Gly Ser Asn Ala Phe Ser Ser Ser Phe
65                  70                  75                  80

Ala Ser Ala Leu Ser Leu Asn Arg Gly Phe Thr Glu Val Ile Ser Ser
                    85                  90                  95

Ala Ser Ala Thr Ala Val Ala Ser Ala Phe Gln Lys Gly Leu Ala Pro
                100                 105                 110

Tyr Gly Thr Ala Phe Ala Leu Ser Ala Ala Ser Ala Ala Ala Asp Ala
            115                 120                 125

Tyr Asn Ser Ile Gly Ser Gly Ala Asn Ala Phe Ala Tyr Ala Gln Ala
        130                 135                 140

Phe Ala Arg Val Leu Tyr Pro Leu Val Gln Gln Tyr Gly Leu Ser Ser
145                 150                 155                 160

Ser Ala Lys Ala Ser Ala Phe Ala Ser Ala Ile Ala Ser Ser Phe Ser
                165                 170                 175

Ser Gly Thr Ser Gly Gln Gly Pro Ser Ile Gly Gln Gln Gln Pro Pro
            180                 185                 190

Val Thr Ile Ser Ala Ala Ser Ala Ser Ala Gly Ala Ser Ala Ala Ala
        195                 200                 205

Val Gly Gly Gly Gln Val Gly Gln Gly Pro Tyr Gly Gly Gln Gln Gln
    210                 215                 220

Ser Thr Ala Ala Ser Ala Ser Ala Ala Ala Thr Ala Thr Ser
225                 230                 235
```

<210> SEQ ID NO 500
<211> LENGTH: 182
<212> TYPE: PRT
<213> ORGANISM: Araneus gemmoides

<400> SEQUENCE: 500

```
Gly Asn Val Gly Tyr Gln Leu Gly Leu Lys Val Ala Asn Ser Leu Gly
1                   5                   10                  15

Leu Gly Asn Ala Gln Ala Leu Ala Ser Ser Leu Ser Gln Ala Val Ser
            20                  25                  30
```

-continued

```
Ala Val Gly Val Gly Ala Ser Ser Asn Ala Tyr Ala Asn Ala Val Ser
        35              40              45

Asn Ala Val Gly Gln Val Leu Ala Gly Gln Gly Ile Leu Asn Ala Ala
    50              55              60

Asn Ala Gly Ser Leu Ala Ser Ser Phe Ala Ser Ala Leu Ser Ser Ser
65              70              75              80

Ala Ala Ser Val Ala Ser Gln Ser Ala Ser Gln Ser Gln Ala Ala Ser
            85              90              95

Gln Ser Gln Ala Ala Ala Ser Ala Phe Arg Gln Ala Ala Ser Gln Ser
            100             105             110

Ala Ser Gln Ser Asp Ser Arg Ala Gly Ser Gln Ser Ser Thr Lys Thr
        115             120             125

Thr Ser Thr Ser Thr Ser Gly Ser Gln Ala Asp Ser Arg Ser Ala Ser
    130             135             140

Ser Ser Ala Ser Gln Ala Ser Ala Ser Ala Phe Ala Gln Gln Ser Ser
145             150             155             160

Ala Ser Leu Ser Ser Ser Ser Ser Phe Ser Ser Ala Phe Ser Ser Ala
            165             170             175

Thr Ser Ile Ser Ala Val
            180
```

```
<210> SEQ ID NO 501
<211> LENGTH: 180
<212> TYPE: PRT
<213> ORGANISM: Argiope aurantia

<400> SEQUENCE: 501

Gly Ser Leu Ala Ser Ser Phe Ala Ser Ala Leu Ser Ala Ser Ala Ala
1               5               10              15

Ser Val Ala Ser Ser Ala Ala Ala Gln Ala Ala Ser Gln Ser Gln Ala
            20              25              30

Ala Ala Ser Ala Phe Ser Arg Ala Ala Ser Gln Ser Ala Ser Gln Ser
        35              40              45

Ala Ala Arg Ser Gly Ala Gln Ser Ile Ser Thr Thr Thr Thr Thr Ser
    50              55              60

Thr Ala Gly Ser Gln Ala Ala Ser Gln Ser Ala Ser Ser Ala Ala Ser
65              70              75              80

Gln Ala Ser Ala Ser Ser Phe Ala Arg Ala Ser Ser Ala Ser Leu Ala
            85              90              95

Ala Ser Ser Ser Phe Ser Ser Ala Phe Ser Ser Ala Asn Ser Leu Ser
            100             105             110

Ala Leu Gly Asn Val Gly Tyr Gln Leu Gly Phe Asn Val Ala Asn Asn
        115             120             125

Leu Gly Ile Gly Asn Ala Ala Gly Leu Gly Asn Ala Leu Ser Gln Ala
    130             135             140

Val Ser Ser Val Gly Val Gly Ala Ser Ser Ser Thr Tyr Ala Asn Ala
145             150             155             160

Val Ser Asn Ala Val Gly Gln Phe Leu Ala Gly Gln Gly Ile Leu Asn
            165             170             175

Ala Ala Asn Ala
            180
```

```
<210> SEQ ID NO 502
<211> LENGTH: 199
<212> TYPE: PRT
<213> ORGANISM: Deinopis spinosa
```

```
<400> SEQUENCE: 502

Gly Ala Ser Ala Ser Ala Tyr Ala Ser Ala Ile Ser Asn Ala Val Gly
1               5                   10                  15

Pro Tyr Leu Tyr Gly Leu Gly Leu Phe Asn Gln Ala Asn Ala Ala Ser
            20                  25                  30

Phe Ala Ser Ser Phe Ala Ser Ala Val Ser Ser Ala Val Ala Ser Ala
        35                  40                  45

Ser Ala Ser Ala Ala Ser Ser Ala Tyr Ala Gln Ser Ala Ala Ala Gln
    50                  55                  60

Ala Gln Ala Ala Ser Ser Ala Phe Ser Gln Ala Ala Ala Gln Ser Ala
65                  70                  75                  80

Ala Ala Ala Ser Ala Gly Ala Ser Ala Gly Ala Gly Ala Ser Ala Gly
                85                  90                  95

Ala Gly Ala Val Ala Gly Ala Gly Ala Val Ala Gly Ala Gly Ala Val
            100                 105                 110

Ala Gly Ala Ser Ala Ala Ala Ser Gln Ala Ala Ala Ser Ser Ser
            115                 120                 125

Ala Ser Ala Val Ala Ser Ala Phe Ala Gln Ser Ala Ser Tyr Ala Leu
    130                 135                 140

Ala Ser Ser Ser Ala Phe Ala Asn Ala Phe Ala Ser Ala Thr Ser Ala
145                 150                 155                 160

Gly Tyr Leu Gly Ser Leu Ala Tyr Gln Leu Gly Leu Thr Thr Ala Tyr
            165                 170                 175

Asn Leu Gly Leu Ser Asn Ala Gln Ala Phe Ala Ser Thr Leu Ser Gln
            180                 185                 190

Ala Val Thr Gly Val Gly Leu
        195

<210> SEQ ID NO 503
<211> LENGTH: 171
<212> TYPE: PRT
<213> ORGANISM: Nephila clavipes

<400> SEQUENCE: 503

Gly Ala Thr Ala Ala Ser Tyr Gly Asn Ala Leu Ser Thr Ala Ala Ala
1               5                   10                  15

Gln Phe Phe Ala Thr Ala Gly Leu Leu Asn Ala Gly Asn Ala Ser Ala
            20                  25                  30

Leu Ala Ser Ser Phe Ala Arg Ala Phe Ser Ala Ser Ala Glu Ser Gln
        35                  40                  45

Ser Phe Ala Gln Ser Gln Ala Phe Gln Gln Ala Ser Ala Phe Gln Gln
    50                  55                  60

Ala Ala Ser Arg Ser Ala Ser Gln Ser Ala Ala Glu Ala Gly Ser Thr
65                  70                  75                  80

Ser Ser Ser Thr Thr Thr Thr Thr Ser Ala Ala Arg Ser Gln Ala Ala
                85                  90                  95

Ser Gln Ser Ala Ser Ser Ser Tyr Ser Ser Ala Phe Ala Gln Ala Ala
            100                 105                 110

Ser Ser Ser Leu Ala Thr Ser Ser Ala Leu Ser Arg Ala Phe Ser Ser
            115                 120                 125

Val Ser Ser Ala Ser Ala Ala Ser Ser Leu Ala Tyr Ser Ile Gly Leu
    130                 135                 140

Ser Ala Ala Arg Ser Leu Gly Ile Ala Asp Ala Ala Gly Leu Ala Gly
145                 150                 155                 160
```

-continued

```
Val Leu Ala Arg Ala Ala Gly Ala Leu Gly Gln
            165                 170

<210> SEQ ID NO 504
<211> LENGTH: 268
<212> TYPE: PRT
<213> ORGANISM: Argiope trifasciata

<400> SEQUENCE: 504

Gly Gly Ala Pro Gly Gly Gly Pro Gly Gly Ala Gly Pro Gly Gly Ala
1               5                   10                  15

Gly Phe Gly Pro Gly Gly Gly Ala Gly Phe Gly Pro Gly Gly Gly Ala
            20                  25                  30

Gly Phe Gly Pro Gly Gly Ala Ala Gly Gly Pro Gly Gly Pro Gly Gly
        35                  40                  45

Pro Gly Gly Pro Gly Gly Ala Gly Gly Tyr Gly Pro Gly Gly Ala Gly
    50                  55                  60

Gly Tyr Gly Pro Gly Gly Val Gly Pro Gly Gly Ala Gly Gly Tyr Gly
65                  70                  75                  80

Pro Gly Gly Ala Gly Gly Tyr Gly Pro Gly Gly Ser Gly Pro Gly Gly
            85                  90                  95

Ala Gly Pro Gly Gly Ala Gly Gly Glu Gly Pro Val Thr Val Asp Val
            100                 105                 110

Asp Val Thr Val Gly Pro Glu Gly Val Gly Gly Gly Pro Gly Gly Ala
        115                 120                 125

Gly Pro Gly Gly Ala Gly Phe Gly Pro Gly Gly Ala Gly Phe Gly
    130                 135                 140

Pro Gly Gly Ala Pro Gly Ala Pro Gly Gly Pro Gly Gly Pro Gly Gly
145                 150                 155                 160

Pro Gly Gly Pro Gly Gly Pro Gly Gly Val Gly Pro Gly Gly Ala Gly
            165                 170                 175

Gly Tyr Gly Pro Gly Gly Ala Gly Gly Val Gly Pro Ala Gly Thr Gly
        180                 185                 190

Gly Phe Gly Pro Gly Gly Ala Gly Gly Phe Gly Pro Gly Gly Ala Gly
        195                 200                 205

Gly Phe Gly Pro Gly Gly Ala Gly Gly Phe Gly Pro Ala Gly Ala Gly
    210                 215                 220

Gly Tyr Gly Pro Gly Gly Val Gly Pro Gly Gly Ala Gly Gly Phe Gly
225                 230                 235                 240

Pro Gly Gly Val Gly Pro Gly Gly Ser Gly Pro Gly Gly Ala Gly Gly
            245                 250                 255

Glu Gly Pro Val Thr Val Asp Val Asp Val Ser Val
            260                 265

<210> SEQ ID NO 505
<211> LENGTH: 420
<212> TYPE: PRT
<213> ORGANISM: Nephila clavipes

<400> SEQUENCE: 505

Gly Val Ser Tyr Gly Pro Gly Gly Ala Gly Gly Pro Tyr Gly Pro Gly
1               5                   10                  15

Gly Pro Tyr Gly Pro Gly Gly Glu Gly Pro Gly Gly Ala Gly Gly Pro
            20                  25                  30

Tyr Gly Pro Gly Gly Val Gly Pro Gly Gly Ser Gly Pro Gly Gly Tyr
        35                  40                  45
```

-continued

```
Gly Pro Gly Gly Ala Gly Pro Gly Gly Tyr Gly Pro Gly Gly Ser Gly
    50                  55                  60

Pro Gly Gly Tyr Gly Pro Gly Gly Ser Gly Pro Gly Gly Tyr Gly Pro
65                  70                  75                  80

Gly Gly Ser Gly Pro Gly Gly Tyr Gly Pro Gly Gly Ser Gly Pro Gly
                85                  90                  95

Gly Tyr Gly Pro Gly Gly Tyr Gly Pro Gly Gly Ser Gly Pro Gly Gly
                100                 105                 110

Ser Gly Pro Gly Gly Ser Gly Pro Gly Gly Tyr Gly Pro Gly Gly Thr
                115                 120                 125

Gly Pro Gly Gly Ser Gly Pro Gly Gly Tyr Gly Pro Gly Gly Ser Gly
    130                 135                 140

Pro Gly Gly Ser Gly Pro Gly Gly Tyr Gly Pro Gly Gly Ser Gly Pro
145                 150                 155                 160

Gly Gly Phe Gly Pro Gly Gly Ser Gly Pro Gly Gly Tyr Gly Pro Gly
            165                 170                 175

Gly Ser Gly Pro Gly Gly Ala Gly Pro Gly Gly Val Gly Pro Gly Gly
            180                 185                 190

Phe Gly Pro Gly Gly Ala Gly Pro Gly Gly Ala Ala Pro Gly Gly Ala
            195                 200                 205

Gly Pro Gly Gly Ala Gly Pro Gly Gly Ala Gly Pro Gly Gly Ala Gly
    210                 215                 220

Pro Gly Gly Ala Gly Pro Gly Gly Ala Gly Pro Gly Gly Ala Gly Gly
225                 230                 235                 240

Ala Gly Gly Ala Gly Gly Ser Gly Gly Ala Gly Gly Ser Gly Gly Thr
            245                 250                 255

Thr Ile Ile Glu Asp Leu Asp Ile Thr Ile Asp Gly Ala Asp Gly Pro
            260                 265                 270

Ile Thr Ile Ser Glu Glu Leu Pro Ile Ser Gly Ala Gly Gly Ser Gly
            275                 280                 285

Pro Gly Gly Ala Gly Pro Gly Gly Val Gly Pro Gly Gly Ser Gly Pro
    290                 295                 300

Gly Gly Val Gly Pro Gly Gly Ser Gly Pro Gly Gly Val Gly Pro Gly
305                 310                 315                 320

Gly Ser Gly Pro Gly Gly Val Gly Pro Gly Gly Ala Gly Gly Pro Tyr
            325                 330                 335

Gly Pro Gly Gly Ser Gly Pro Gly Gly Ala Gly Gly Ala Gly Gly Pro
            340                 345                 350

Gly Gly Ala Tyr Gly Pro Gly Gly Ser Tyr Gly Pro Gly Gly Ser Gly
            355                 360                 365

Gly Pro Gly Gly Ala Gly Gly Pro Tyr Gly Pro Gly Gly Glu Gly Pro
    370                 375                 380

Gly Gly Ala Gly Gly Pro Tyr Gly Pro Gly Gly Ala Gly Gly Pro Tyr
385                 390                 395                 400

Gly Pro Gly Gly Ala Gly Gly Pro Tyr Gly Pro Gly Gly Glu Gly Gly
            405                 410                 415

Pro Tyr Gly Pro
        420
```

```
<210> SEQ ID NO 506
<211> LENGTH: 376
<212> TYPE: PRT
<213> ORGANISM: Latrodectus hesperus
```

-continued

```
<400> SEQUENCE: 506

Gly Ile Asn Val Asp Ser Asp Ile Gly Ser Val Thr Ser Leu Ile Leu
1               5                   10                  15

Ser Gly Ser Thr Leu Gln Met Thr Ile Pro Ala Gly Gly Asp Asp Leu
                20                  25                  30

Ser Gly Gly Tyr Pro Gly Gly Phe Pro Ala Gly Ala Gln Pro Ser Gly
            35                  40                  45

Gly Ala Pro Val Asp Phe Gly Gly Pro Ser Ala Gly Gly Asp Val Ala
        50                  55                  60

Ala Lys Leu Ala Arg Ser Leu Ala Ser Thr Leu Ala Ser Ser Gly Val
65                  70                  75                  80

Phe Arg Ala Ala Phe Asn Ser Arg Val Ser Thr Pro Val Ala Val Gln
                85                  90                  95

Leu Thr Asp Ala Leu Val Gln Lys Ile Ala Ser Asn Leu Gly Leu Asp
            100                 105                 110

Tyr Ala Thr Ala Ser Lys Leu Arg Lys Ala Ser Gln Ala Val Ser Lys
            115                 120                 125

Val Arg Met Gly Ser Asp Thr Asn Ala Tyr Ala Leu Ala Ile Ser Ser
        130                 135                 140

Ala Leu Ala Glu Val Leu Ser Ser Ser Gly Lys Val Ala Asp Ala Asn
145                 150                 155                 160

Ile Asn Gln Ile Ala Pro Gln Leu Ala Ser Gly Ile Val Leu Gly Val
                165                 170                 175

Ser Thr Thr Ala Pro Gln Phe Gly Val Asp Leu Ser Ser Ile Asn Val
            180                 185                 190

Asn Leu Asp Ile Ser Asn Val Ala Arg Asn Met Gln Ala Ser Ile Gln
            195                 200                 205

Gly Gly Pro Ala Pro Ile Thr Ala Glu Gly Pro Asp Phe Gly Ala Gly
        210                 215                 220

Tyr Pro Gly Gly Ala Pro Thr Asp Leu Ser Gly Leu Asp Met Gly Ala
225                 230                 235                 240

Pro Ser Asp Gly Ser Arg Gly Gly Asp Ala Thr Ala Lys Leu Leu Gln
            245                 250                 255

Ala Leu Val Pro Ala Leu Leu Lys Ser Asp Val Phe Arg Ala Ile Tyr
            260                 265                 270

Lys Arg Gly Thr Arg Lys Gln Val Val Gln Tyr Val Thr Asn Ser Ala
        275                 280                 285

Leu Gln Gln Ala Ala Ser Ser Leu Gly Leu Asp Ala Ser Thr Ile Ser
    290                 295                 300

Gln Leu Gln Thr Lys Ala Thr Gln Ala Leu Ser Ser Val Ser Ala Asp
305                 310                 315                 320

Ser Asp Ser Thr Ala Tyr Ala Lys Ala Phe Gly Leu Ala Ile Ala Gln
            325                 330                 335

Val Leu Gly Thr Ser Gly Gln Val Asn Asp Ala Asn Val Asn Gln Ile
            340                 345                 350

Gly Ala Lys Leu Ala Thr Gly Ile Leu Arg Gly Ser Ser Ala Val Ala
        355                 360                 365

Pro Arg Leu Gly Ile Asp Leu Ser
    370                 375

<210> SEQ ID NO 507
<211> LENGTH: 200
<212> TYPE: PRT
<213> ORGANISM: Argiope trifasciata
```

<400> SEQUENCE: 507

Gly Ala Gly Tyr Thr Gly Pro Ser Gly Pro Ser Thr Gly Pro Ser Gly
1               5                   10                  15

Tyr Pro Gly Pro Leu Gly Gly Gly Ala Pro Phe Gly Gln Ser Gly Phe
                20                  25                  30

Gly Gly Ser Ala Gly Pro Gln Gly Gly Phe Gly Ala Thr Gly Gly Ala
        35                  40                  45

Ser Ala Gly Leu Ile Ser Arg Val Ala Asn Ala Leu Ala Asn Thr Ser
    50                  55                  60

Thr Leu Arg Thr Val Leu Arg Thr Gly Val Ser Gln Gln Ile Ala Ser
65                  70                  75                  80

Ser Val Val Gln Arg Ala Ala Gln Ser Leu Ala Ser Thr Leu Gly Val
                85                  90                  95

Asp Gly Asn Asn Leu Ala Arg Phe Ala Val Gln Ala Val Ser Arg Leu
                100                 105                 110

Pro Ala Gly Ser Asp Thr Ser Ala Tyr Ala Gln Ala Phe Ser Ser Ala
            115                 120                 125

Leu Phe Asn Ala Gly Val Leu Asn Ala Ser Asn Ile Asp Thr Leu Gly
    130                 135                 140

Ser Arg Val Leu Ser Ala Leu Leu Asn Gly Val Ser Ser Ala Ala Gln
145                 150                 155                 160

Gly Leu Gly Ile Asn Val Asp Ser Gly Ser Val Gln Ser Asp Ile Ser
                165                 170                 175

Ser Ser Ser Ser Phe Leu Ser Thr Ser Ser Ser Ser Ala Ser Tyr Ser
            180                 185                 190

Gln Ala Ser Ala Ser Ser Thr Ser
        195                 200

<210> SEQ ID NO 508
<211> LENGTH: 357
<212> TYPE: PRT
<213> ORGANISM: Uloborus diversus

<400> SEQUENCE: 508

Gly Ala Ser Ala Ala Asp Ile Ala Thr Ala Ile Ala Ala Ser Val Ala
1               5                   10                  15

Thr Ser Leu Gln Ser Asn Gly Val Leu Thr Ala Ser Asn Val Ser Gln
                20                  25                  30

Leu Ser Asn Gln Leu Ala Ser Tyr Val Ser Ser Gly Leu Ser Ser Thr
        35                  40                  45

Ala Ser Ser Leu Gly Ile Gln Leu Gly Ala Ser Leu Gly Ala Gly Phe
    50                  55                  60

Gly Ala Ser Ala Gly Leu Ser Ala Ser Thr Asp Ile Ser Ser Ser Val
65                  70                  75                  80

Glu Ala Thr Ser Ala Ser Thr Leu Ser Ser Ser Ala Ser Ser Thr Ser
                85                  90                  95

Val Val Ser Ser Ile Asn Ala Gln Leu Val Pro Ala Leu Ala Gln Thr
                100                 105                 110

Ala Val Leu Asn Ala Ala Phe Ser Asn Ile Asn Thr Gln Asn Ala Ile
            115                 120                 125

Arg Ile Ala Glu Leu Leu Thr Gln Gln Val Gly Arg Gln Tyr Gly Leu
    130                 135                 140

Ser Gly Ser Asp Val Ala Thr Ala Ser Ser Gln Ile Arg Ser Ala Leu
145                 150                 155                 160

```
Tyr Ser Val Gln Gln Gly Ser Ala Ser Ser Ala Tyr Val Ser Ala Ile
                165                 170                 175

Val Gly Pro Leu Ile Thr Ala Leu Ser Ser Arg Gly Val Val Asn Ala
            180                 185                 190

Ser Asn Ser Ser Gln Ile Ala Ser Ser Leu Ala Thr Ala Ile Leu Gln
            195                 200                 205

Phe Thr Ala Asn Val Ala Pro Gln Phe Gly Ile Ser Ile Pro Thr Ser
    210                 215                 220

Ala Val Gln Ser Asp Leu Ser Thr Ile Ser Gln Ser Leu Thr Ala Ile
225                 230                 235                 240

Ser Ser Gln Thr Ser Ser Ser Val Asp Ser Ser Thr Ser Ala Phe Gly
                245                 250                 255

Gly Ile Ser Gly Pro Ser Gly Pro Ser Pro Tyr Gly Pro Gln Pro Ser
            260                 265                 270

Gly Pro Thr Phe Gly Pro Gly Pro Ser Leu Ser Gly Leu Thr Gly Phe
            275                 280                 285

Thr Ala Thr Phe Ala Ser Ser Phe Lys Ser Thr Leu Ala Ser Ser Thr
    290                 295                 300

Gln Phe Gln Leu Ile Ala Gln Ser Asn Leu Asp Val Gln Thr Arg Ser
305                 310                 315                 320

Ser Leu Ile Ser Lys Val Leu Ile Asn Ala Leu Ser Ser Leu Gly Ile
                325                 330                 335

Ser Ala Ser Val Ala Ser Ser Ile Ala Ala Ser Ser Ser Gln Ser Leu
                340                 345                 350

Leu Ser Val Ser Ala
        355

<210> SEQ ID NO 509
<211> LENGTH: 32
<212> TYPE: PRT
<213> ORGANISM: Euprosthenops australis

<400> SEQUENCE: 509

Gly Gly Gln Gly Gly Gln Gly Gln Gly Arg Tyr Gly Gln Gly Ala Gly
1               5                   10                  15

Ser Ser Ala Ala Ala Ala Ala Ala Ala Ala Ala Ala Ala Ala Ala Ala
            20                  25                  30

<210> SEQ ID NO 510
<211> LENGTH: 42
<212> TYPE: PRT
<213> ORGANISM: Tetragnatha kauaiensis

<400> SEQUENCE: 510

Gly Gly Leu Gly Gly Gly Gln Gly Ala Gly Gln Gly Gly Gln Gln Gly
1               5                   10                  15

Ala Gly Gln Gly Gly Tyr Gly Ser Gly Leu Gly Gly Ala Gly Gln Gly
            20                  25                  30

Ala Ser Ala Ala Ala Ala Ala Ala Ala Ala
        35                  40

<210> SEQ ID NO 511
<211> LENGTH: 42
<212> TYPE: PRT
<213> ORGANISM: Argiope aurantia

<400> SEQUENCE: 511
```

-continued

```
Gly Gly Tyr Gly Pro Gly Ala Gly Gln Gln Gly Pro Gly Ser Gln Gly
1               5                   10                  15

Pro Gly Ser Gly Gly Gln Gln Gly Pro Gly Gly Leu Gly Pro Tyr Gly
                20                  25                  30

Pro Ser Ala Ala Ala Ala Ala Ala Ala Ala
        35                  40

<210> SEQ ID NO 512
<211> LENGTH: 46
<212> TYPE: PRT
<213> ORGANISM: Deinopis spinosa

<400> SEQUENCE: 512

Gly Pro Gly Gly Tyr Gly Gly Pro Gly Gln Gln Gly Pro Gly Gln Gly
1               5                   10                  15

Gln Tyr Gly Pro Gly Thr Gly Gln Gln Gly Gln Gly Pro Ser Gly Gln
                20                  25                  30

Gln Gly Pro Ala Gly Ala Ala Ala Ala Ala Ala Ala Ala
        35                  40                  45

<210> SEQ ID NO 513
<211> LENGTH: 42
<212> TYPE: PRT
<213> ORGANISM: Nephila clavata

<400> SEQUENCE: 513

Gly Pro Gly Gly Tyr Gly Leu Gly Gln Gln Gly Pro Gly Gln Gln Gly
1               5                   10                  15

Pro Gly Gln Gln Gly Pro Ala Gly Tyr Gly Pro Ser Gly Leu Ser Gly
                20                  25                  30

Pro Gly Gly Ala Ala Ala Ala Ala Ala Ala
        35                  40

<210> SEQ ID NO 514
<211> LENGTH: 1800
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MISC_FEATURE
<222> LOCATION: (7)..(11)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (15)..(19)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (23)..(27)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (31)..(35)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (39)..(43)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (47)..(51)
```

```
<223> OTHER INFORMATION: This region may encompass "SGGQQ,"  "GAGQQ,"
      "GQGPY,"  "AGQQ" or "SQ," wherein some positions may be absent
<220> FEATURE:
<221> NAME/KEY: MISC_FEATURE
<222> LOCATION: (55)..(59)
<223> OTHER INFORMATION: This region may encompass "SGGQQ,"  "GAGQQ,"
      "GQGPY,"  "AGQQ" or "SQ," wherein some positions may be absent
<220> FEATURE:
<221> NAME/KEY: MISC_FEATURE
<222> LOCATION: (63)..(67)
<223> OTHER INFORMATION: This region may encompass "SGGQQ,"  "GAGQQ,"
      "GQGPY,"  "AGQQ" or "SQ," wherein some positions may be absent
<220> FEATURE:
<221> NAME/KEY: MISC_FEATURE
<222> LOCATION: (4)..(67)
<223> OTHER INFORMATION: This region may encompass 4-8 repeating
      "GPG-X1" repeating units, wherein X1 is "SGGQQ,"  "GAGQQ,"
      "GQGPY,"  "AGQQ" or "SQ," and some positions may be absent
<220> FEATURE:
<221> NAME/KEY: MISC_FEATURE
<222> LOCATION: (71)..(90)
<223> OTHER INFORMATION: This region may encompass 6-20 residues
<220> FEATURE:
<221> NAME/KEY: MISC_FEATURE
<222> LOCATION: (97)..(101)
<223> OTHER INFORMATION: This region may encompass "SGGQQ,"  "GAGQQ,"
      "GQGPY,"  "AGQQ" or "SQ," wherein some positions may be absent
<220> FEATURE:
<221> NAME/KEY: MISC_FEATURE
<222> LOCATION: (105)..(109)
<223> OTHER INFORMATION: This region may encompass "SGGQQ,"  "GAGQQ,"
      "GQGPY,"  "AGQQ" or "SQ," wherein some positions may be absent
<220> FEATURE:
<221> NAME/KEY: MISC_FEATURE
<222> LOCATION: (113)..(117)
<223> OTHER INFORMATION: This region may encompass "SGGQQ,"  "GAGQQ,"
      "GQGPY,"  "AGQQ" or "SQ," wherein some positions may be absent
<220> FEATURE:
<221> NAME/KEY: MISC_FEATURE
<222> LOCATION: (121)..(125)
<223> OTHER INFORMATION: This region may encompass "SGGQQ,"  "GAGQQ,"
      "GQGPY,"  "AGQQ" or "SQ," wherein some positions may be absent
<220> FEATURE:
<221> NAME/KEY: MISC_FEATURE
<222> LOCATION: (129)..(133)
<223> OTHER INFORMATION: This region may encompass "SGGQQ,"  "GAGQQ,"
      "GQGPY,"  "AGQQ" or "SQ," wherein some positions may be absent
<220> FEATURE:
<221> NAME/KEY: MISC_FEATURE
<222> LOCATION: (137)..(141)
<223> OTHER INFORMATION: This region may encompass "SGGQQ,"  "GAGQQ,"
      "GQGPY,"  "AGQQ" or "SQ," wherein some positions may be absent
<220> FEATURE:
<221> NAME/KEY: MISC_FEATURE
<222> LOCATION: (145)..(149)
<223> OTHER INFORMATION: This region may encompass "SGGQQ,"  "GAGQQ,"
      "GQGPY,"  "AGQQ" or "SQ," wherein some positions may be absent
<220> FEATURE:
<221> NAME/KEY: MISC_FEATURE
<222> LOCATION: (153)..(157)
<223> OTHER INFORMATION: This region may encompass "SGGQQ,"  "GAGQQ,"
      "GQGPY,"  "AGQQ" or "SQ," wherein some positions may be absent
<220> FEATURE:
<221> NAME/KEY: MISC_FEATURE
<222> LOCATION: (94)..(157)
<223> OTHER INFORMATION: This region may encompass 4-8 repeating
      "GPG-X1" repeating units, wherein X1 is "SGGQQ,"  "GAGQQ,"
      "GQGPY,"  "AGQQ" or "SQ," and some positions may be absent
<220> FEATURE:
<221> NAME/KEY: MISC_FEATURE
<222> LOCATION: (161)..(180)
<223> OTHER INFORMATION: This region may encompass 6-20 residues
<220> FEATURE:
<221> NAME/KEY: MISC_FEATURE
<222> LOCATION: (187)..(191)
<223> OTHER INFORMATION: This region may encompass "SGGQQ,"  "GAGQQ,"
      "GQGPY,"  "AGQQ" or "SQ," wherein some positions may be absent
<220> FEATURE:
<221> NAME/KEY: MISC_FEATURE
```

-continued

```
<222> LOCATION: (195)..(199)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (203)..(207)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (211)..(215)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (219)..(223)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (227)..(231)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (235)..(239)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (243)..(247)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (184)..(247)
<223> OTHER INFORMATION: This region may encompass 4-8 repeating
      "GPG-X1" repeating units, wherein X1 is "SGGQQ," "GAGQQ,"
      "GQGPY," "AGQQ" or "SQ," and some positions may be absent
<220> FEATURE:
<221> NAME/KEY: MISC_FEATURE
<222> LOCATION: (251)..(270)
<223> OTHER INFORMATION: This region may encompass 6-20 residues
<220> FEATURE:
<221> NAME/KEY: MISC_FEATURE
<222> LOCATION: (277)..(281)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (285)..(289)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (293)..(297)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (301)..(305)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (309)..(313)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (317)..(321)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (325)..(329)
<223> OTHER INFORMATION: This region may encompass "SGGQQ," "GAGQQ,"
      "GQGPY," "AGQQ" or "SQ," wherein some positions may be absent
<220> FEATURE:
```

```
<221> NAME/KEY: MISC_FEATURE
<222> LOCATION: (333)..(337)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (274)..(337)
<223> OTHER INFORMATION: This region may encompass 4-8 repeating
      "GPG-X1" repeating units, wherein X1 is "SGGQQ," "GAGQQ,"
      "GQGPY," "AGQQ" or "SQ," and some positions may be absent
<220> FEATURE:
<221> NAME/KEY: MISC_FEATURE
<222> LOCATION: (341)..(360)
<223> OTHER INFORMATION: This region may encompass 6-20 residues
<220> FEATURE:
<221> NAME/KEY: MISC_FEATURE
<222> LOCATION: (367)..(371)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (375)..(379)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (383)..(387)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (391)..(395)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (399)..(403)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (407)..(411)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (415)..(419)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (423)..(427)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (364)..(427)
<223> OTHER INFORMATION: This region may encompass 4-8 repeating
      "GPG-X1" repeating units, wherein X1 is "SGGQQ," "GAGQQ,"
      "GQGPY," "AGQQ" or "SQ," and some positions may be absent
<220> FEATURE:
<221> NAME/KEY: MISC_FEATURE
<222> LOCATION: (431)..(450)
<223> OTHER INFORMATION: This region may encompass 6-20 residues
<220> FEATURE:
<221> NAME/KEY: MISC_FEATURE
<222> LOCATION: (457)..(461)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (465)..(469)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (473)..(477)
<223> OTHER INFORMATION: This region may encompass "SGGQQ," "GAGQQ,"
      "GQGPY," "AGQQ" or "SQ," wherein some positions may be absent
```

```
<220> FEATURE:
<221> NAME/KEY: MISC_FEATURE
<222> LOCATION: (481)..(485)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (489)..(493)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (497)..(501)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (505)..(509)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (513)..(517)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (454)..(517)
<223> OTHER INFORMATION: This region may encompass 4-8 repeating
      "GPG-X1" repeating units, wherein X1 is "SGGQQ," "GAGQQ,"
      "GQGPY," "AGQQ" or "SQ," and some positions may be absent
<220> FEATURE:
<221> NAME/KEY: MISC_FEATURE
<222> LOCATION: (521)..(540)
<223> OTHER INFORMATION: This region may encompass 6-20 residues
<220> FEATURE:
<221> NAME/KEY: MISC_FEATURE
<222> LOCATION: (547)..(551)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (555)..(559)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (563)..(567)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (571)..(575)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (579)..(583)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (587)..(591)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (595)..(599)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (603)..(607)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (544)..(607)
<223> OTHER INFORMATION: This region may encompass 4-8 repeating
```

-continued

```
     "GPG-X1" repeating units, wherein X1 is "SGGQQ," "GAGQQ,"
     "GQGPY," "AGQQ" or "SQ," and some positions may be absent
<220> FEATURE:
<221> NAME/KEY: MISC_FEATURE
<222> LOCATION: (611)..(630)
<223> OTHER INFORMATION: This region may encompass 6-20 residues
<220> FEATURE:
<221> NAME/KEY: MISC_FEATURE
<222> LOCATION: (637)..(641)
<223> OTHER INFORMATION: This region may encompass "SGGQQ," "GAGQQ,"
     "GQGPY," "AGQQ" or "SQ," wherein some positions may be absent
<220> FEATURE:
<221> NAME/KEY: MISC_FEATURE
<222> LOCATION: (645)..(649)
<223> OTHER INFORMATION: This region may encompass "SGGQQ," "GAGQQ,"
     "GQGPY," "AGQQ" or "SQ," wherein some positions may be absent
<220> FEATURE:
<221> NAME/KEY: MISC_FEATURE
<222> LOCATION: (653)..(657)
<223> OTHER INFORMATION: This region may encompass "SGGQQ," "GAGQQ,"
     "GQGPY," "AGQQ" or "SQ," wherein some positions may be absent
<220> FEATURE:
<221> NAME/KEY: MISC_FEATURE
<222> LOCATION: (661)..(665)
<223> OTHER INFORMATION: This region may encompass "SGGQQ," "GAGQQ,"
     "GQGPY," "AGQQ" or "SQ," wherein some positions may be absent
<220> FEATURE:
<221> NAME/KEY: MISC_FEATURE
<222> LOCATION: (669)..(673)
<223> OTHER INFORMATION: This region may encompass "SGGQQ," "GAGQQ,"
     "GQGPY," "AGQQ" or "SQ," wherein some positions may be absent
<220> FEATURE:
<221> NAME/KEY: MISC_FEATURE
<222> LOCATION: (677)..(681)
<223> OTHER INFORMATION: This region may encompass "SGGQQ," "GAGQQ,"
     "GQGPY," "AGQQ" or "SQ," wherein some positions may be absent
<220> FEATURE:
<221> NAME/KEY: MISC_FEATURE
<222> LOCATION: (685)..(689)
<223> OTHER INFORMATION: This region may encompass "SGGQQ," "GAGQQ,"
     "GQGPY," "AGQQ" or "SQ," wherein some positions may be absent
<220> FEATURE:
<221> NAME/KEY: MISC_FEATURE
<222> LOCATION: (693)..(697)
<223> OTHER INFORMATION: This region may encompass "SGGQQ," "GAGQQ,"
     "GQGPY," "AGQQ" or "SQ," wherein some positions may be absent
<220> FEATURE:
<221> NAME/KEY: MISC_FEATURE
<222> LOCATION: (634)..(697)
<223> OTHER INFORMATION: This region may encompass 4-8 repeating
     "GPG-X1" repeating units, wherein X1 is "SGGQQ," "GAGQQ,"
     "GQGPY," "AGQQ" or "SQ," and some positions may be absent
<220> FEATURE:
<221> NAME/KEY: MISC_FEATURE
<222> LOCATION: (701)..(720)
<223> OTHER INFORMATION: This region may encompass 6-20 residues
<220> FEATURE:
<221> NAME/KEY: MISC_FEATURE
<222> LOCATION: (727)..(731)
<223> OTHER INFORMATION: This region may encompass "SGGQQ," "GAGQQ,"
     "GQGPY," "AGQQ" or "SQ," wherein some positions may be absent
<220> FEATURE:
<221> NAME/KEY: MISC_FEATURE
<222> LOCATION: (735)..(739)
<223> OTHER INFORMATION: This region may encompass "SGGQQ," "GAGQQ,"
     "GQGPY," "AGQQ" or "SQ," wherein some positions may be absent
<220> FEATURE:
<221> NAME/KEY: MISC_FEATURE
<222> LOCATION: (743)..(747)
<223> OTHER INFORMATION: This region may encompass "SGGQQ," "GAGQQ,"
     "GQGPY," "AGQQ" or "SQ," wherein some positions may be absent
<220> FEATURE:
<221> NAME/KEY: MISC_FEATURE
<222> LOCATION: (751)..(755)
<223> OTHER INFORMATION: This region may encompass "SGGQQ," "GAGQQ,"
     "GQGPY," "AGQQ" or "SQ," wherein some positions may be absent
<220> FEATURE:
<221> NAME/KEY: MISC_FEATURE
<222> LOCATION: (759)..(763)
```

```
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (767)..(771)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (775)..(779)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (783)..(787)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (724)..(787)
<223> OTHER INFORMATION: This region may encompass 4-8 repeating
      "GPG-X1" repeating units, wherein X1 is "SGGQQ," "GAGQQ,"
      "GQGPY," "AGQQ" or "SQ," and some positions may be absent
<220> FEATURE:
<221> NAME/KEY: MISC_FEATURE
<222> LOCATION: (791)..(810)
<223> OTHER INFORMATION: This region may encompass 6-20 residues
<220> FEATURE:
<221> NAME/KEY: MISC_FEATURE
<222> LOCATION: (817)..(821)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (825)..(829)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (833)..(837)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (841)..(845)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (849)..(853)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (857)..(861)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (865)..(869)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (873)..(877)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (814)..(877)
<223> OTHER INFORMATION: This region may encompass 4-8 repeating
      "GPG-X1" repeating units, wherein X1 is "SGGQQ," "GAGQQ,"
      "GQGPY," "AGQQ" or "SQ," and some positions may be absent
<220> FEATURE:
<221> NAME/KEY: MISC_FEATURE
<222> LOCATION: (881)..(900)
<223> OTHER INFORMATION: This region may encompass 6-20 residues
<220> FEATURE:
<221> NAME/KEY: MISC_FEATURE
```

```
<222> LOCATION: (907)..(911)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (915)..(919)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (923)..(927)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (931)..(935)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (939)..(943)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (947)..(951)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (955)..(959)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (963)..(967)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (904)..(967)
<223> OTHER INFORMATION: This region may encompass 4-8 repeating
      "GPG-X1" repeating units, wherein X1 is "SGGQQ," "GAGQQ,"
      "GQGPY," "AGQQ" or "SQ," and some positions may be absent
<220> FEATURE:
<221> NAME/KEY: MISC_FEATURE
<222> LOCATION: (971)..(990)
<223> OTHER INFORMATION: This region may encompass 6-20 residues
<220> FEATURE:
<221> NAME/KEY: MISC_FEATURE
<222> LOCATION: (997)..(1001)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (1005)..(1009)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (1013)..(1017)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (1021)..(1025)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (1029)..(1033)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (1037)..(1041)
<223> OTHER INFORMATION: This region may encompass "SGGQQ," "GAGQQ,"
      "GQGPY," "AGQQ" or "SQ," wherein some positions may be absent
<220> FEATURE:
```

```
<221> NAME/KEY: MISC_FEATURE
<222> LOCATION: (1045)..(1049)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (1053)..(1057)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (994)..(1057)
<223> OTHER INFORMATION: This region may encompass 4-8 repeating
      "GPG-X1" repeating units, wherein X1 is "SGGQQ," "GAGQQ,"
      "GQGPY," "AGQQ" or "SQ," and some positions may be absent
<220> FEATURE:
<221> NAME/KEY: MISC_FEATURE
<222> LOCATION: (1061)..(1080)
<223> OTHER INFORMATION: This region may encompass 6-20 residues
<220> FEATURE:
<221> NAME/KEY: MISC_FEATURE
<222> LOCATION: (1087)..(1091)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (1095)..(1099)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (1103)..(1107)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (1111)..(1115)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (1119)..(1123)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (1127)..(1131)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (1135)..(1139)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (1143)..(1147)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (1084)..(1147)
<223> OTHER INFORMATION: This region may encompass 4-8 repeating
      "GPG-X1" repeating units, wherein X1 is "SGGQQ," "GAGQQ,"
      "GQGPY," "AGQQ" or "SQ," and some positions may be absent
<220> FEATURE:
<221> NAME/KEY: MISC_FEATURE
<222> LOCATION: (1151)..(1170)
<223> OTHER INFORMATION: This region may encompass 6-20 residues
<220> FEATURE:
<221> NAME/KEY: MISC_FEATURE
<222> LOCATION: (1177)..(1181)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (1185)..(1189)
<223> OTHER INFORMATION: This region may encompass "SGGQQ," "GAGQQ,"
      "GQGPY," "AGQQ" or "SQ," wherein some positions may be absent
```

```
<220> FEATURE:
<221> NAME/KEY: MISC_FEATURE
<222> LOCATION: (1193)..(1197)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (1201)..(1205)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (1209)..(1213)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (1217)..(1221)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (1225)..(1229)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (1233)..(1237)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (1174)..(1237)
<223> OTHER INFORMATION: This region may encompass 4-8 repeating
      "GPG-X1" repeating units, wherein X1 is "SGGQQ," "GAGQQ,"
      "GQGPY," "AGQQ" or "SQ," and some positions may be absent
<220> FEATURE:
<221> NAME/KEY: MISC_FEATURE
<222> LOCATION: (1241)..(1260)
<223> OTHER INFORMATION: This region may encompass 6-20 residues
<220> FEATURE:
<221> NAME/KEY: MISC_FEATURE
<222> LOCATION: (1267)..(1271)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (1275)..(1279)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (1283)..(1287)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (1291)..(1295)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (1299)..(1303)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (1307)..(1311)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (1315)..(1319)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (1323)..(1327)
<223> OTHER INFORMATION: This region may encompass "SGGQQ," "GAGQQ,"
```

```
      "GQGPY," "AGQQ" or "SQ," wherein some positions may be absent
<220> FEATURE:
<221> NAME/KEY: MISC_FEATURE
<222> LOCATION: (1264)..(1327)
<223> OTHER INFORMATION: This region may encompass 4-8 repeating
      "GPG-X1" repeating units, wherein X1 is "SGGQQ," "GAGQQ,"
      "GQGPY," "AGQQ" or "SQ," and some positions may be absent
<220> FEATURE:
<221> NAME/KEY: MISC_FEATURE
<222> LOCATION: (1331)..(1350)
<223> OTHER INFORMATION: This region may encompass 6-20 residues
<220> FEATURE:
<221> NAME/KEY: MISC_FEATURE
<222> LOCATION: (1357)..(1361)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (1365)..(1369)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (1373)..(1377)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (1381)..(1385)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (1389)..(1393)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (1397)..(1401)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (1405)..(1409)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (1413)..(1417)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (1354)..(1417)
<223> OTHER INFORMATION: This region may encompass 4-8 repeating
      "GPG-X1" repeating units, wherein X1 is "SGGQQ," "GAGQQ,"
      "GQGPY," "AGQQ" or "SQ," and some positions may be absent
<220> FEATURE:
<221> NAME/KEY: MISC_FEATURE
<222> LOCATION: (1421)..(1440)
<223> OTHER INFORMATION: This region may encompass 6-20 residues
<220> FEATURE:
<221> NAME/KEY: MISC_FEATURE
<222> LOCATION: (1447)..(1451)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (1455)..(1459)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (1463)..(1467)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (1471)..(1475)
```

-continued

```
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (1479)..(1483)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (1487)..(1491)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (1495)..(1499)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (1503)..(1507)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (1444)..(1507)
<223> OTHER INFORMATION: This region may encompass 4-8 repeating
      "GPG-X1" repeating units, wherein X1 is "SGGQQ," "GAGQQ,"
      "GQGPY," "AGQQ" or "SQ," and some positions may be absent
<220> FEATURE:
<221> NAME/KEY: MISC_FEATURE
<222> LOCATION: (1511)..(1530)
<223> OTHER INFORMATION: This region may encompass 6-20 residues
<220> FEATURE:
<221> NAME/KEY: MISC_FEATURE
<222> LOCATION: (1537)..(1541)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (1545)..(1549)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (1553)..(1557)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (1561)..(1565)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (1569)..(1573)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (1577)..(1581)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (1585)..(1589)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (1593)..(1597)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (1534)..(1597)
<223> OTHER INFORMATION: This region may encompass 4-8 repeating
      "GPG-X1" repeating units, wherein X1 is "SGGQQ," "GAGQQ,"
      "GQGPY," "AGQQ" or "SQ," and some positions may be absent
<220> FEATURE:
```

```
<221> NAME/KEY: MISC_FEATURE
<222> LOCATION: (1601)..(1620)
<223> OTHER INFORMATION: This region may encompass 6-20 residues
<220> FEATURE:
<221> NAME/KEY: MISC_FEATURE
<222> LOCATION: (1627)..(1631)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (1635)..(1639)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (1643)..(1647)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (1651)..(1655)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (1659)..(1663)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (1667)..(1671)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (1675)..(1679)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (1683)..(1687)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (1624)..(1687)
<223> OTHER INFORMATION: This region may encompass 4-8 repeating
      "GPG-X1" repeating units, wherein X1 is "SGGQQ," "GAGQQ,"
      "GQGPY," "AGQQ" or "SQ," and some positions may be absent
<220> FEATURE:
<221> NAME/KEY: MISC_FEATURE
<222> LOCATION: (1691)..(1710)
<223> OTHER INFORMATION: This region may encompass 6-20 residues
<220> FEATURE:
<221> NAME/KEY: MISC_FEATURE
<222> LOCATION: (1717)..(1721)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (1725)..(1729)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (1733)..(1737)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (1741)..(1745)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (1749)..(1753)
<223> OTHER INFORMATION: This region may encompass "SGGQQ," "GAGQQ,"
      "GQGPY," "AGQQ" or "SQ," wherein some positions may be absent
<220> FEATURE:
```

```
<221> NAME/KEY: MISC_FEATURE
<222> LOCATION: (1757)..(1761)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (1765)..(1769)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (1773)..(1777)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (1714)..(1777)
<223> OTHER INFORMATION: This region may encompass 4-8 repeating
      "GPG-X1" repeating units, wherein X1 is "SGGQQ," "GAGQQ,"
      "GQGPY," "AGQQ" or "SQ," and some positions may be absent
<220> FEATURE:
<221> NAME/KEY: MISC_FEATURE
<222> LOCATION: (1781)..(1800)
<223> OTHER INFORMATION: This region may encompass 6-20 residues
<220> FEATURE:
<221> NAME/KEY: MISC_FEATURE
<222> LOCATION: (1)..(1800)
<223> OTHER INFORMATION: This sequence may encompass 2-20
      "GGY-[GPG-X1]n1-GPS-(A)n2" repeating units, wherein X1 is "SGGQQ,"
      "GAGQQ," "GQGPY," "AGQQ" or "SQ," n1 is 4-8 and n2 is 6-20 and
      some positions may be absent

<400> SEQUENCE: 514

Gly Gly Tyr Gly Pro Gly Xaa Xaa Xaa Xaa Xaa Gly Pro Gly Xaa Xaa
1               5                   10                  15

Xaa Xaa Xaa Gly Pro Gly Xaa Xaa Xaa Xaa Xaa Gly Pro Gly Xaa Xaa
            20                  25                  30

Xaa Xaa Xaa Gly Pro Gly Xaa Xaa Xaa Xaa Xaa Gly Pro Gly Xaa Xaa
        35                  40                  45

Xaa Xaa Xaa Gly Pro Gly Xaa Xaa Xaa Xaa Xaa Gly Pro Gly Xaa Xaa
    50                  55                  60

Xaa Xaa Xaa Gly Pro Ser Ala Ala Ala Ala Ala Ala Ala Ala Ala Ala
65                  70                  75                  80

Ala Ala Ala Ala Ala Ala Ala Ala Ala Ala Gly Gly Tyr Gly Pro Gly
                85                  90                  95

Xaa Xaa Xaa Xaa Xaa Gly Pro Gly Xaa Xaa Xaa Xaa Xaa Gly Pro Gly
            100                 105                 110

Xaa Xaa Xaa Xaa Xaa Gly Pro Gly Xaa Xaa Xaa Xaa Xaa Gly Pro Gly
        115                 120                 125

Xaa Xaa Xaa Xaa Xaa Gly Pro Gly Xaa Xaa Xaa Xaa Xaa Gly Pro Gly
    130                 135                 140

Xaa Xaa Xaa Xaa Xaa Gly Pro Gly Xaa Xaa Xaa Xaa Xaa Gly Pro Ser
145                 150                 155                 160

Ala Ala Ala Ala Ala Ala Ala Ala Ala Ala Ala Ala Ala Ala Ala Ala
                165                 170                 175

Ala Ala Ala Ala Gly Gly Tyr Gly Pro Gly Xaa Xaa Xaa Xaa Xaa Gly
            180                 185                 190

Pro Gly Xaa Xaa Xaa Xaa Xaa Gly Pro Gly Xaa Xaa Xaa Xaa Xaa Gly
        195                 200                 205

Pro Gly Xaa Xaa Xaa Xaa Xaa Gly Pro Gly Xaa Xaa Xaa Xaa Xaa Gly
    210                 215                 220

Pro Gly Xaa Xaa Xaa Xaa Xaa Gly Pro Gly Xaa Xaa Xaa Xaa Xaa Gly
225                 230                 235                 240
```

-continued

```
Pro Gly Xaa Xaa Xaa Xaa Xaa Gly Pro Ser Ala Ala Ala Ala Ala Ala
        245                 250                 255

Ala Ala Ala Ala Ala Ala Ala Ala Ala Ala Ala Ala Ala Gly Gly
        260                 265                 270

Tyr Gly Pro Gly Xaa Xaa Xaa Xaa Xaa Gly Pro Gly Xaa Xaa Xaa Xaa
        275                 280                 285

Xaa Gly Pro Gly Xaa Xaa Xaa Xaa Xaa Gly Pro Gly Xaa Xaa Xaa Xaa
        290                 295                 300

Xaa Gly Pro Gly Xaa Xaa Xaa Xaa Xaa Gly Pro Gly Xaa Xaa Xaa Xaa
305                 310                 315                 320

Xaa Gly Pro Gly Xaa Xaa Xaa Xaa Xaa Gly Pro Gly Xaa Xaa Xaa Xaa
        325                 330                 335

Xaa Gly Pro Ser Ala Ala Ala Ala Ala Ala Ala Ala Ala Ala Ala
        340                 345                 350

Ala Ala Ala Ala Ala Ala Ala Ala Gly Gly Tyr Gly Pro Gly Xaa Xaa
        355                 360                 365

Xaa Xaa Xaa Gly Pro Gly Xaa Xaa Xaa Xaa Xaa Gly Pro Gly Xaa Xaa
        370                 375                 380

Xaa Xaa Xaa Gly Pro Gly Xaa Xaa Xaa Xaa Xaa Gly Pro Gly Xaa Xaa
385                 390                 395                 400

Xaa Xaa Xaa Gly Pro Gly Xaa Xaa Xaa Xaa Xaa Gly Pro Gly Xaa Xaa
        405                 410                 415

Xaa Xaa Xaa Gly Pro Gly Xaa Xaa Xaa Xaa Xaa Gly Pro Ser Ala Ala
        420                 425                 430

Ala Ala Ala Ala Ala Ala Ala Ala Ala Ala Ala Ala Ala Ala Ala
        435                 440                 445

Ala Ala Gly Gly Tyr Gly Pro Gly Xaa Xaa Xaa Xaa Xaa Gly Pro Gly
        450                 455                 460

Xaa Xaa Xaa Xaa Xaa Gly Pro Gly Xaa Xaa Xaa Xaa Xaa Gly Pro Gly
465                 470                 475                 480

Xaa Xaa Xaa Xaa Xaa Gly Pro Gly Xaa Xaa Xaa Xaa Xaa Gly Pro Gly
        485                 490                 495

Xaa Xaa Xaa Xaa Xaa Gly Pro Gly Xaa Xaa Xaa Xaa Xaa Gly Pro Gly
        500                 505                 510

Xaa Xaa Xaa Xaa Xaa Gly Pro Ser Ala Ala Ala Ala Ala Ala Ala
        515                 520                 525

Ala Ala Ala Ala Ala Ala Ala Ala Ala Ala Ala Gly Gly Tyr Gly
        530                 535                 540

Pro Gly Xaa Xaa Xaa Xaa Xaa Gly Pro Gly Xaa Xaa Xaa Xaa Xaa Gly
545                 550                 555                 560

Pro Gly Xaa Xaa Xaa Xaa Xaa Gly Pro Gly Xaa Xaa Xaa Xaa Xaa Gly
        565                 570                 575

Pro Gly Xaa Xaa Xaa Xaa Xaa Gly Pro Gly Xaa Xaa Xaa Xaa Xaa Gly
        580                 585                 590

Pro Gly Xaa Xaa Xaa Xaa Xaa Gly Pro Gly Xaa Xaa Xaa Xaa Xaa Gly
        595                 600                 605

Pro Ser Ala Ala Ala Ala Ala Ala Ala Ala Ala Ala Ala Ala Ala
        610                 615                 620

Ala Ala Ala Ala Ala Ala Gly Gly Tyr Gly Pro Gly Xaa Xaa Xaa Xaa
625                 630                 635                 640

Xaa Gly Pro Gly Xaa Xaa Xaa Xaa Xaa Gly Pro Gly Xaa Xaa Xaa Xaa
        645                 650                 655

Xaa Gly Pro Gly Xaa Xaa Xaa Xaa Xaa Gly Pro Gly Xaa Xaa Xaa Xaa
```

-continued

```
            660                 665                 670

Xaa Gly Pro Gly Xaa Xaa Xaa Xaa Xaa Gly Pro Gly Xaa Xaa Xaa Xaa
        675                 680                 685

Xaa Gly Pro Gly Xaa Xaa Xaa Xaa Xaa Gly Pro Ser Ala Ala Ala Ala
        690                 695                 700

Ala Ala Ala Ala Ala Ala Ala Ala Ala Ala Ala Ala Ala Ala Ala Ala
705                 710                 715                 720

Gly Gly Tyr Gly Pro Gly Xaa Xaa Xaa Xaa Gly Pro Gly Xaa Xaa
            725                 730                 735

Xaa Xaa Xaa Gly Pro Gly Xaa Xaa Xaa Xaa Gly Pro Gly Xaa Xaa
            740                 745                 750

Xaa Xaa Xaa Gly Pro Gly Xaa Xaa Xaa Xaa Gly Pro Gly Xaa Xaa
            755                 760                 765

Xaa Xaa Xaa Gly Pro Gly Xaa Xaa Xaa Xaa Gly Pro Gly Xaa Xaa
            770                 775                 780

Xaa Xaa Xaa Gly Pro Ser Ala Ala Ala Ala Ala Ala Ala Ala Ala
785                 790                 795                 800

Ala Ala Ala Ala Ala Ala Ala Ala Ala Ala Gly Gly Tyr Gly Pro Gly
            805                 810                 815

Xaa Xaa Xaa Xaa Xaa Gly Pro Gly Xaa Xaa Xaa Xaa Xaa Gly Pro Gly
            820                 825                 830

Xaa Xaa Xaa Xaa Xaa Gly Pro Gly Xaa Xaa Xaa Xaa Xaa Gly Pro Gly
            835                 840                 845

Xaa Xaa Xaa Xaa Xaa Gly Pro Gly Xaa Xaa Xaa Xaa Xaa Gly Pro Gly
        850                 855                 860

Xaa Xaa Xaa Xaa Xaa Gly Pro Gly Xaa Xaa Xaa Xaa Xaa Gly Pro Ser
865                 870                 875                 880

Ala Ala Ala Ala Ala Ala Ala Ala Ala Ala Ala Ala Ala Ala Ala
            885                 890                 895

Ala Ala Ala Ala Gly Gly Tyr Gly Pro Gly Xaa Xaa Xaa Xaa Xaa Gly
            900                 905                 910

Pro Gly Xaa Xaa Xaa Xaa Xaa Gly Pro Gly Xaa Xaa Xaa Xaa Xaa Gly
        915                 920                 925

Pro Gly Xaa Xaa Xaa Xaa Xaa Gly Pro Gly Xaa Xaa Xaa Xaa Xaa Gly
        930                 935                 940

Pro Gly Xaa Xaa Xaa Xaa Xaa Gly Pro Gly Xaa Xaa Xaa Xaa Xaa Gly
945                 950                 955                 960

Pro Gly Xaa Xaa Xaa Xaa Xaa Gly Pro Ser Ala Ala Ala Ala Ala Ala
            965                 970                 975

Ala Ala Ala Ala Ala Ala Ala Ala Ala Ala Ala Ala Ala Gly Gly
            980                 985                 990

Tyr Gly Pro Gly Xaa Xaa Xaa Xaa Xaa Gly Pro Gly Xaa Xaa Xaa Xaa
        995                 1000                1005

Xaa Gly Pro Gly Xaa Xaa Xaa Xaa Xaa Gly Pro Gly Xaa Xaa Xaa
    1010                1015                1020

Xaa Xaa Gly Pro Gly Xaa Xaa Xaa Xaa Xaa Gly Pro Gly Xaa Xaa
    1025                1030                1035

Xaa Xaa Xaa Gly Pro Gly Xaa Xaa Xaa Xaa Xaa Gly Pro Gly Xaa
    1040                1045                1050

Xaa Xaa Xaa Xaa Gly Pro Ser Ala Ala Ala Ala Ala Ala Ala Ala
    1055                1060                1065

Ala Ala Ala Ala Ala Ala Ala Ala Ala Ala Ala Ala Gly Gly Tyr
    1070                1075                1080
```

-continued

```
Gly Pro  Gly Xaa Xaa Xaa Xaa  Xaa Gly Pro Gly Xaa  Xaa Xaa Xaa
    1085                1090                1095

Xaa Gly  Pro Gly Xaa Xaa Xaa  Xaa Xaa Gly Pro Gly  Xaa Xaa Xaa
    1100                1105                1110

Xaa Xaa  Gly Pro Gly Xaa Xaa  Xaa Xaa Xaa Gly Pro  Gly Xaa Xaa
    1115                1120                1125

Xaa Xaa  Xaa Gly Pro Gly Xaa  Xaa Xaa Xaa Xaa Gly  Pro Gly Xaa
    1130                1135                1140

Xaa Xaa  Xaa Xaa Gly Pro Ser  Ala Ala Ala Ala Ala  Ala Ala Ala
    1145                1150                1155

Ala Ala  Ala Ala Ala Ala Ala  Ala Ala Ala Ala Ala  Gly Gly Tyr
    1160                1165                1170

Gly Pro  Gly Xaa Xaa Xaa Xaa  Xaa Gly Pro Gly Xaa  Xaa Xaa Xaa
    1175                1180                1185

Xaa Gly  Pro Gly Xaa Xaa Xaa  Xaa Xaa Gly Pro Gly  Xaa Xaa Xaa
    1190                1195                1200

Xaa Xaa  Gly Pro Gly Xaa Xaa  Xaa Xaa Xaa Gly Pro  Gly Xaa Xaa
    1205                1210                1215

Xaa Xaa  Xaa Gly Pro Gly Xaa  Xaa Xaa Xaa Xaa Gly  Pro Gly Xaa
    1220                1225                1230

Xaa Xaa  Xaa Xaa Gly Pro Ser  Ala Ala Ala Ala Ala  Ala Ala Ala
    1235                1240                1245

Ala Ala  Ala Ala Ala Ala Ala  Ala Ala Ala Ala Ala  Gly Gly Tyr
    1250                1255                1260

Gly Pro  Gly Xaa Xaa Xaa Xaa  Xaa Gly Pro Gly Xaa  Xaa Xaa Xaa
    1265                1270                1275

Xaa Gly  Pro Gly Xaa Xaa Xaa  Xaa Xaa Gly Pro Gly  Xaa Xaa Xaa
    1280                1285                1290

Xaa Xaa  Gly Pro Gly Xaa Xaa  Xaa Xaa Xaa Gly Pro  Gly Xaa Xaa
    1295                1300                1305

Xaa Xaa  Xaa Gly Pro Gly Xaa  Xaa Xaa Xaa Xaa Gly  Pro Gly Xaa
    1310                1315                1320

Xaa Xaa  Xaa Xaa Gly Pro Ser  Ala Ala Ala Ala Ala  Ala Ala Ala
    1325                1330                1335

Ala Ala  Ala Ala Ala Ala Ala  Ala Ala Ala Ala Ala  Gly Gly Tyr
    1340                1345                1350

Gly Pro  Gly Xaa Xaa Xaa Xaa  Xaa Gly Pro Gly Xaa  Xaa Xaa Xaa
    1355                1360                1365

Xaa Gly  Pro Gly Xaa Xaa Xaa  Xaa Xaa Gly Pro Gly  Xaa Xaa Xaa
    1370                1375                1380

Xaa Xaa  Gly Pro Gly Xaa Xaa  Xaa Xaa Xaa Gly Pro  Gly Xaa Xaa
    1385                1390                1395

Xaa Xaa  Xaa Gly Pro Gly Xaa  Xaa Xaa Xaa Xaa Gly  Pro Gly Xaa
    1400                1405                1410

Xaa Xaa  Xaa Xaa Gly Pro Ser  Ala Ala Ala Ala Ala  Ala Ala Ala
    1415                1420                1425

Ala Ala  Ala Ala Ala Ala Ala  Ala Ala Ala Ala Ala  Gly Gly Tyr
    1430                1435                1440

Gly Pro  Gly Xaa Xaa Xaa Xaa  Xaa Gly Pro Gly Xaa  Xaa Xaa Xaa
    1445                1450                1455

Xaa Gly  Pro Gly Xaa Xaa Xaa  Xaa Xaa Gly Pro Gly  Xaa Xaa Xaa
    1460                1465                1470
```

```
Xaa Xaa  Gly Pro Gly Xaa Xaa  Xaa Xaa Xaa Gly Pro  Gly Xaa Xaa
    1475             1480             1485

Xaa Xaa  Xaa Gly Pro Gly Xaa  Xaa Xaa Xaa Xaa Gly  Pro Gly Xaa
    1490             1495             1500

Xaa Xaa  Xaa Xaa Gly Pro Ser  Ala Ala Ala Ala Ala  Ala Ala Ala
    1505             1510             1515

Ala Ala  Ala Ala Ala Ala Ala  Ala Ala Ala Ala Ala  Gly Gly Tyr
    1520             1525             1530

Gly Pro  Gly Xaa Xaa Xaa Xaa  Xaa Gly Pro Gly Xaa  Xaa Xaa Xaa
    1535             1540             1545

Xaa Gly  Pro Gly Xaa Xaa Xaa  Xaa Xaa Gly Pro Gly  Xaa Xaa Xaa
    1550             1555             1560

Xaa Xaa  Gly Pro Gly Xaa Xaa  Xaa Xaa Xaa Gly Pro  Gly Xaa Xaa
    1565             1570             1575

Xaa Xaa  Xaa Gly Pro Gly Xaa  Xaa Xaa Xaa Xaa Gly  Pro Gly Xaa
    1580             1585             1590

Xaa Xaa  Xaa Xaa Gly Pro Ser  Ala Ala Ala Ala Ala  Ala Ala Ala
    1595             1600             1605

Ala Ala  Ala Ala Ala Ala Ala  Ala Ala Ala Ala Ala  Gly Gly Tyr
    1610             1615             1620

Gly Pro  Gly Xaa Xaa Xaa Xaa  Xaa Gly Pro Gly Xaa  Xaa Xaa Xaa
    1625             1630             1635

Xaa Gly  Pro Gly Xaa Xaa Xaa  Xaa Xaa Gly Pro Gly  Xaa Xaa Xaa
    1640             1645             1650

Xaa Xaa  Gly Pro Gly Xaa Xaa  Xaa Xaa Xaa Gly Pro  Gly Xaa Xaa
    1655             1660             1665

Xaa Xaa  Xaa Gly Pro Gly Xaa  Xaa Xaa Xaa Xaa Gly  Pro Gly Xaa
    1670             1675             1680

Xaa Xaa  Xaa Xaa Gly Pro Ser  Ala Ala Ala Ala Ala  Ala Ala Ala
    1685             1690             1695

Ala Ala  Ala Ala Ala Ala Ala  Ala Ala Ala Ala Ala  Gly Gly Tyr
    1700             1705             1710

Gly Pro  Gly Xaa Xaa Xaa Xaa  Xaa Gly Pro Gly Xaa  Xaa Xaa Xaa
    1715             1720             1725

Xaa Gly  Pro Gly Xaa Xaa Xaa  Xaa Xaa Gly Pro Gly  Xaa Xaa Xaa
    1730             1735             1740

Xaa Xaa  Gly Pro Gly Xaa Xaa  Xaa Xaa Xaa Gly Pro  Gly Xaa Xaa
    1745             1750             1755

Xaa Xaa  Xaa Gly Pro Gly Xaa  Xaa Xaa Xaa Xaa Gly  Pro Gly Xaa
    1760             1765             1770

Xaa Xaa  Xaa Xaa Gly Pro Ser  Ala Ala Ala Ala Ala  Ala Ala Ala
    1775             1780             1785

Ala Ala  Ala Ala Ala Ala Ala  Ala Ala Ala Ala Ala
    1790             1795             1800

<210> SEQ ID NO 515
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 515

Ser Gly Gly Gln Gln
1               5
```

-continued

```
<210> SEQ ID NO 516
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 516

Gly Ala Gly Gln Gln
1               5

<210> SEQ ID NO 517
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 517

Gly Gln Gly Pro Tyr
1               5

<210> SEQ ID NO 518
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 518

Ala Gly Gln Gln
1

<210> SEQ ID NO 519
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (1)..(10)
<223> OTHER INFORMATION: This sequence may encompass 2-10 residues

<400> SEQUENCE: 519

Ala Ala Ala Ala Ala Ala Ala Ala Ala Ala
1               5                   10

<210> SEQ ID NO 520
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (1)..(8)
<223> OTHER INFORMATION: This sequence may encompass 6-8 residues

<400> SEQUENCE: 520

His His His His His His His His
1               5
```

-continued

```
<210> SEQ ID NO 521
<211> LENGTH: 70
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MISC_FEATURE
<222> LOCATION: (7)..(11)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (15)..(19)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (23)..(27)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (31)..(35)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (39)..(43)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (47)..(51)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (55)..(59)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (63)..(67)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (4)..(67)
<223> OTHER INFORMATION: This region may encompass 4-8 "GPG-X1"
      repeating units, wherein X1 is "SGGQQ," "GAGQQ," "GQGPY," "AGQQ"
      or "SQ," and some positions may be absent

<400> SEQUENCE: 521

Gly Gly Tyr Gly Pro Gly Xaa Xaa Xaa Xaa Xaa Gly Pro Gly Xaa Xaa
1               5                   10                  15

Xaa Xaa Xaa Gly Pro Gly Xaa Xaa Xaa Xaa Xaa Gly Pro Gly Xaa Xaa
            20                  25                  30

Xaa Xaa Xaa Gly Pro Gly Xaa Xaa Xaa Xaa Xaa Gly Pro Gly Xaa Xaa
        35                  40                  45

Xaa Xaa Xaa Gly Pro Gly Xaa Xaa Xaa Xaa Xaa Gly Pro Gly Xaa Xaa
    50                  55                  60

Xaa Xaa Xaa Gly Pro Ser
65                  70

<210> SEQ ID NO 522
<211> LENGTH: 20
<212> TYPE: PRT
<213> ORGANISM: Artificial Sequence
<220> FEATURE:
<223> OTHER INFORMATION: Description of Artificial Sequence: Synthetic
```

-continued

```
     peptide
<220> FEATURE:
<221> NAME/KEY: MISC_FEATURE
<222> LOCATION: (1)..(20)
<223> OTHER INFORMATION: This sequence may encompass 6-20 residues

<400> SEQUENCE: 522

Ala Ala Ala Ala Ala Ala Ala Ala Ala Ala Ala Ala Ala Ala Ala
1               5                   10                  15

Ala Ala Ala Ala
          20
```

MODIFIED STRAINS FOR THE PRODUCTION OF RECOMBINANT SILK

CROSS-REFERENCE TO RELATED APPLICATIONS

This application is a continuation of U.S. Non-Provisional application Ser. No. 16/482,498, filed Apr. 7, 2020, which is a continuation of U.S. Non-Provisional application Ser. No. 15/724,196, now U.S. Pat. No. 10,647,975, filed Oct. 3, 2017, the contents of which is incorporated by reference in its entirety.

SEQUENCE LISTING

The instant application contains a Sequence Listing which has been submitted electronically in ASCII format and is hereby incorporated by reference in its entirety. Said ASCII copy, created on Nov. 16, 2021, is named BTT-012C2_CRF_sequencelisting.txt and is 388,959 bytes in size.

FIELD OF THE INVENTION

The present disclosure relates to methods of strain optimization to produce or enhance production of proteins or metabolites from cells. The present disclosure also relates to compositions resulting from those methods. In particular, the disclosure relates to yeast cells selected or genetically engineered to reduce degradation of recombinant proteins expressed by the yeast cells, and to methods of cultivating yeast cells for the production of useful compounds.

BACKGROUND OF THE INVENTION

The methylotrophic yeast *Pichia pastoris* is widely used in the production of recombinant proteins. *P. pastoris* grows to high cell density, provides tightly controlled methanol-inducible trans gene expression and efficiently secretes heterologous proteins in defined media.

However, during culture of a strain of *P. pastoris*, recombinantly expressed proteins may be degraded before they can be collected, resulting in a mixture of proteins that includes fragments of recombinantly expressed proteins and a decreased yield of full-length recombinant proteins. What is needed, therefore, are tools and engineered strains to mitigate protein degradation in *P. pastoris*.

SUMMARY OF THE INVENTION

In some embodiments, provided herein is a *Pichia pastoris* microorganism, in which the activity of a YPS1-1 protease and a YPS1-2 protease has been attenuated or eliminated, wherein said microorganism expresses a recombinant polypeptide.

In some embodiments, the YPS1-1 protease comprises a polypeptide sequence at least 95% identical to SEQ ID NO: 67. In some embodiments, the YPS1-1 protease comprises SEQ ID NO: 67. In some embodiments, the YPS1-1 protease is encoded by a YPS1-1 gene. In some embodiments, the YPS1-1 gene comprises a polynucleotide sequence at least 95% identical to SEQ ID NO: 1. In some embodiments, the YPS1-1 gene comprises at least 15, 20, 25, 30, 40, or 50 contiguous nucleotides of SEQ ID NO: 1. In some embodiments, the YPS1-1 gene comprises SEQ ID NO: 1. In some embodiments, the YPS1-1 gene is at locus PAS_chr4_0584 of said microorganism.

In some embodiments, the YPS1-2 protease comprises a polypeptide sequence at least 95% identical to SEQ ID NO: 68. In some embodiments, the YPS1-2 protease comprises SEQ ID NO: 68. In some embodiments, the YPS1-2 protease is encoded by a YPS1-2 gene. In some embodiments, the YPS1-2 gene comprises a polynucleotide sequence at least 95% identical to SEQ ID NO: 2. In some embodiments, the YPS1-2 gene comprises at least 15, 20, 25, 30, 40, or 50 contiguous nucleotides of SEQ ID NO: 2. In some embodiments, the YPS1-2 gene comprises SEQ ID NO: 2. In some embodiments, the YPS1-2 gene is at locus PAS_chr3_1157 of said microorganism.

In some embodiments, the YPS1-1 gene or said YPS1-2 gene, or both, has been mutated or knocked out.

In some embodiments, the microorganism expresses a recombinant protein. In some embodiments, the recombinant protein comprises at least one block polypeptide sequence from a silk protein. In some embodiments, the recombinant protein comprises a silk-like polypeptide. In some embodiments, the silk-like polypeptide comprises one or more repeat sequences $\{GGY\text{-}[GPG\text{-}X_1]n_1\text{-}GPS\text{-}(A) n_2\}n_3$ (SEQ ID NO: 514), wherein $X_1$=SGGQQ (SEQ ID NO: 515) or GAGQQ (SEQ ID NO: 516) or GQGPY (SEQ ID NO: 517) or AGQQ (SEQ ID NO: 518) or SQ; $n_1$ is from 4 to 8; $n_2$ is from 6 to 20; and $n_3$ is from 2 to 20. In some embodiments, the silk-like polypeptide comprises a polypeptide sequence encoded by SEQ ID NO: 462.

In some embodiments, the activity of one or more additional proteases in the microorganism has been attenuated or eliminated. In some embodiments, the one or more additional proteases comprises YPS1-5, MKC7, or YPS1-3.

In some embodiments, the YPS1-5 gene is at locus PAS_chr3_0688 of said microorganism.

In some embodiments, the MKC7 protease is encoded by a MKC7 gene comprising a polynucleotide sequence at least 95% identical to SEQ ID NO: 7. In some embodiments, the MKC7 gene comprises at least 15, 20, 25, 30, 40, or 50 contiguous nucleotides of SEQ ID NO: 7. In some embodiments, the MKC7 gene comprises SEQ ID NO: 7. In some embodiments, the MKC7 gene is at locus PAS_chr1-1_0379 of said microorganism.

In some embodiments, the YPS1-3 protease is encoded by a YPS1-3 gene comprising a polynucleotide sequence at least 95% identical to SEQ ID NO: 3. In some embodiments, the YPS1-3 gene comprises at least 15, 20, 25, 30, 40, or 50 contiguous nucleotides of SEQ ID NO: 3. In some embodiments, the YPS1-3 gene comprises SEQ ID NO: 3. In some embodiments, the YPS1-3 gene is at locus PAS_chr3_0299 of said microorganism.

In some embodiments, the one or more additional proteases comprise a polypeptide sequence at least 95% identical to a polypeptide sequence selected from the group consisting of: SEQ ID NO: 68-130. In some embodiments, the one or more additional proteases comprise a polypeptide sequence selected from the group consisting of: SEQ ID NO: 68-130. In some embodiments, the one or more additional proteases are encoded by a polynucleotide sequence at least 95% identical to a polynucleotide sequence selected from the group consisting of: SEQ ID NO: 3-66. In some embodiments, the one or more additional proteases are encoded by a polynucleotide sequence comprising at least 15, 20, 25, 30, 40, or 50 contiguous nucleotides of a polynucleotide sequence selected from the group consisting of: SEQ ID NO: 3-66.

In some embodiments, the microorganism comprises a 3×, 4× or 5× protease knockout.

Also provided herein, according to some embodiments of the invention, is a *Pichia pastoris* engineered microorganism comprising YPS1-1 and YPS1-2 activity reduced by a mutation or deletion of the YPS1-1 gene comprising SEQ ID NO: 1 and the YPS1-2 gene comprising SEQ ID NO: 2, wherein said microorganism further comprises a recombinantly expressed protein comprising a polypeptide sequence encoded by SEQ ID NO: 462.

In some embodiments, also provided herein is cell culture comprising a protease mitigated microorganism as described herein.

Also provided herein, according to some embodiments, is a cell culture comprising a microorganism whose YPS1-1 and YPS1-2 activity has been attenuated or eliminated as described herein, wherein the microorganism recombinantly expresses a protein, wherein said recombinantly expressed protein is less degraded than a cell culture comprising an otherwise identical *Pichia pastoris* microorganism whose YPS1-1 and YPS1-2 activity has not been attenuated or eliminated.

In some embodiments, provided herein is a method of producing a recombinant protein with a reduced degradation, comprising: culturing whose YPS1-1 and YPS1-2 activity has been attenuated or eliminated as described herein in a culture medium under conditions suitable for expression of the recombinantly expressed protein; and isolating the recombinant protein from the microorganism or the culture medium.

In some embodiments, the recombinant protein is secreted from said microorganism, and wherein isolating said recombinant protein comprises collecting a culture medium comprising said secreted recombinant protein. In some embodiments, the recombinant protein has a decreased level of degradation as compared to said recombinant protein produced by an otherwise identical microorganism wherein said YPS1-1 and said YPS1-2 protease activity has not been attenuated or eliminated.

Also provided herein is a method of modifying *Pichia pastoris* to reduce the degradation of a recombinantly expressed protein, comprising knocking out or mutating a gene encoding a YPS1-1 protein and a YPS1-2 protein. In some embodiments, the method of modifying *Pichia pastoris* to reduce the degradation of a recombinantly expressed protein further comprises knocking out or mutating one or more additional genes encoding a YPS1-3 protein, a YPS1-5 protein, or an MKC7 protein. In some embodiments, the method of modifying *Pichia pastoris* to reduce the degradation of a recombinantly expressed protein further comprises knocking out one or more genes encoding a protein comprising a polypeptide selected from the group consisting of SEQ ID NO: 68-130.

In some embodiments, the recombinantly expressed protein comprises a polyA sequence comprising at least at least 2, 3, 4, 5, 6, 7, 8, 9, or 10 contiguous alanine residues (SEQ ID NO: 519). In some embodiments, the recombinantly expressed protein comprises a silk-like polypeptide. In some embodiments, the silk-like polypeptide comprises one or more repeat sequences $\{GGY\text{-}[GPG\text{-}X_1]n_1\text{-}GPS\text{-}(A)\ n_2\}n_3$ (SEQ ID NO: 514), wherein $X_1$=SGGQQ (SEQ ID NO: 515) or GAGQQ (SEQ ID NO: 516) or GQGPY (SEQ ID NO: 517) or AGQQ (SEQ ID NO: 518) or SQ; $n_1$ is from 4 to 8; $n_2$ is from 6 to 20; and $n_3$ is from 2 to 20. In some embodiments, the recombinantly expressed protein comprises a polypeptide sequence encoded by SEQ ID NO: 462.

BRIEF DESCRIPTION OF THE DRAWINGS

The foregoing and other objects, features and advantages will be apparent from the following description of particular

Figure 1:
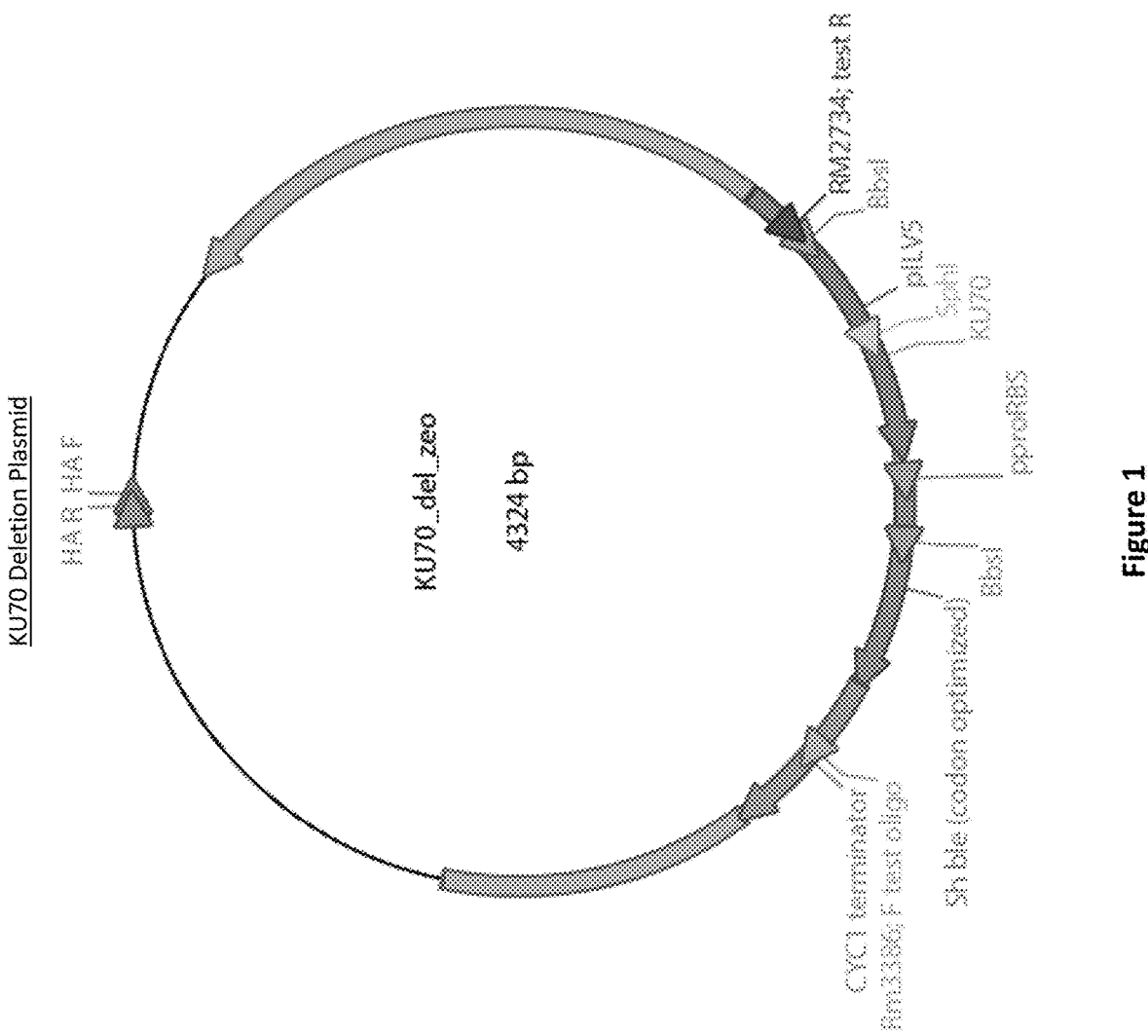

4 embodiments of the invention, as illustrated in the accompanying drawings in which like reference characters refer to the same parts throughout the different views. The drawings are not necessarily to scale, emphasis instead placed upon illustrating the principles of various embodiments of the invention.

FIG. 1 is a plasmid map for KU 70 deletion with a zeocin resistance marker.

Figure 2:
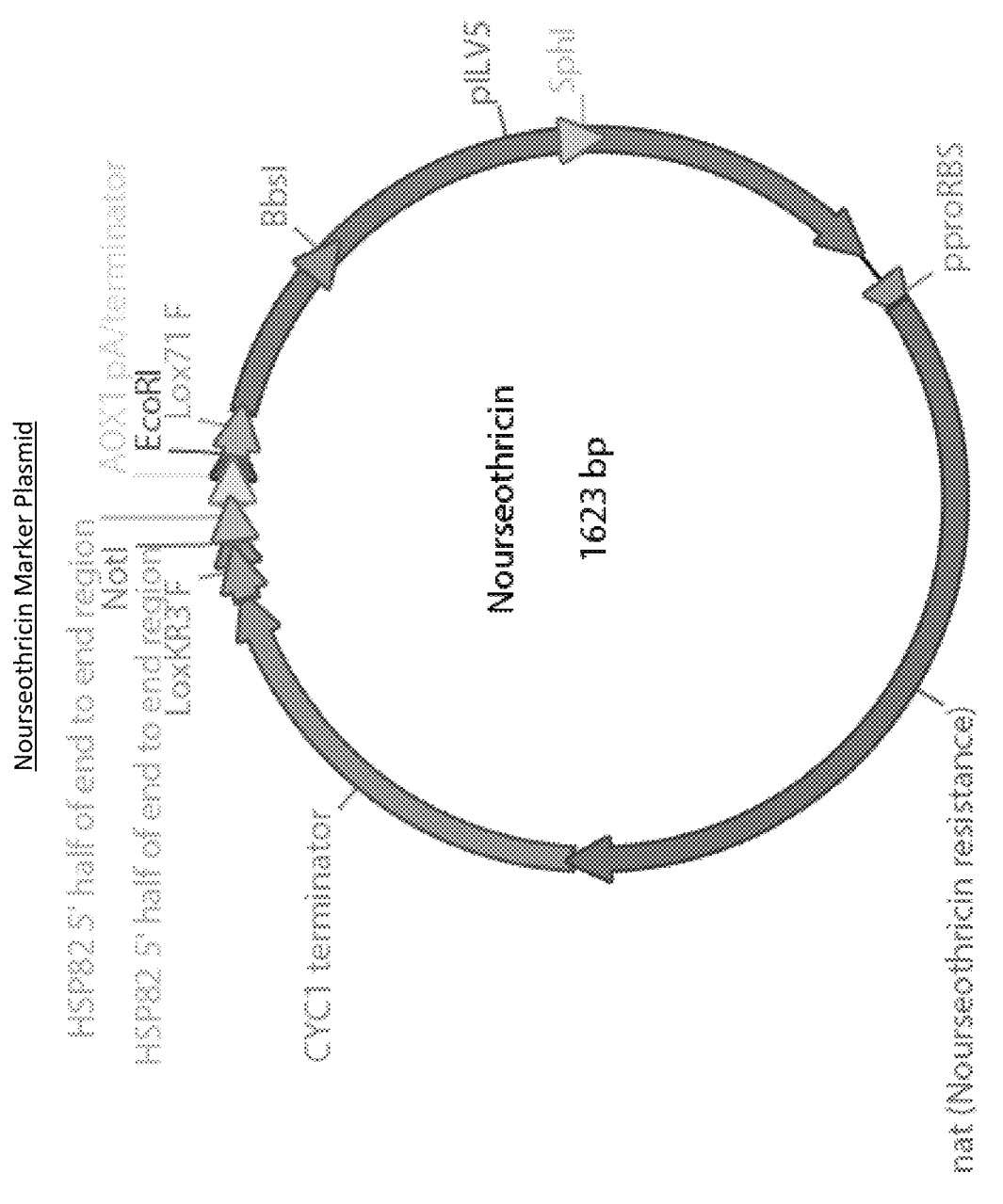

FIG. 2 is a plasmid map of a plasmid comprising a nourseothricin marker used with homology arms for targeted protease gene deletion.

Figures 3A, 3B:
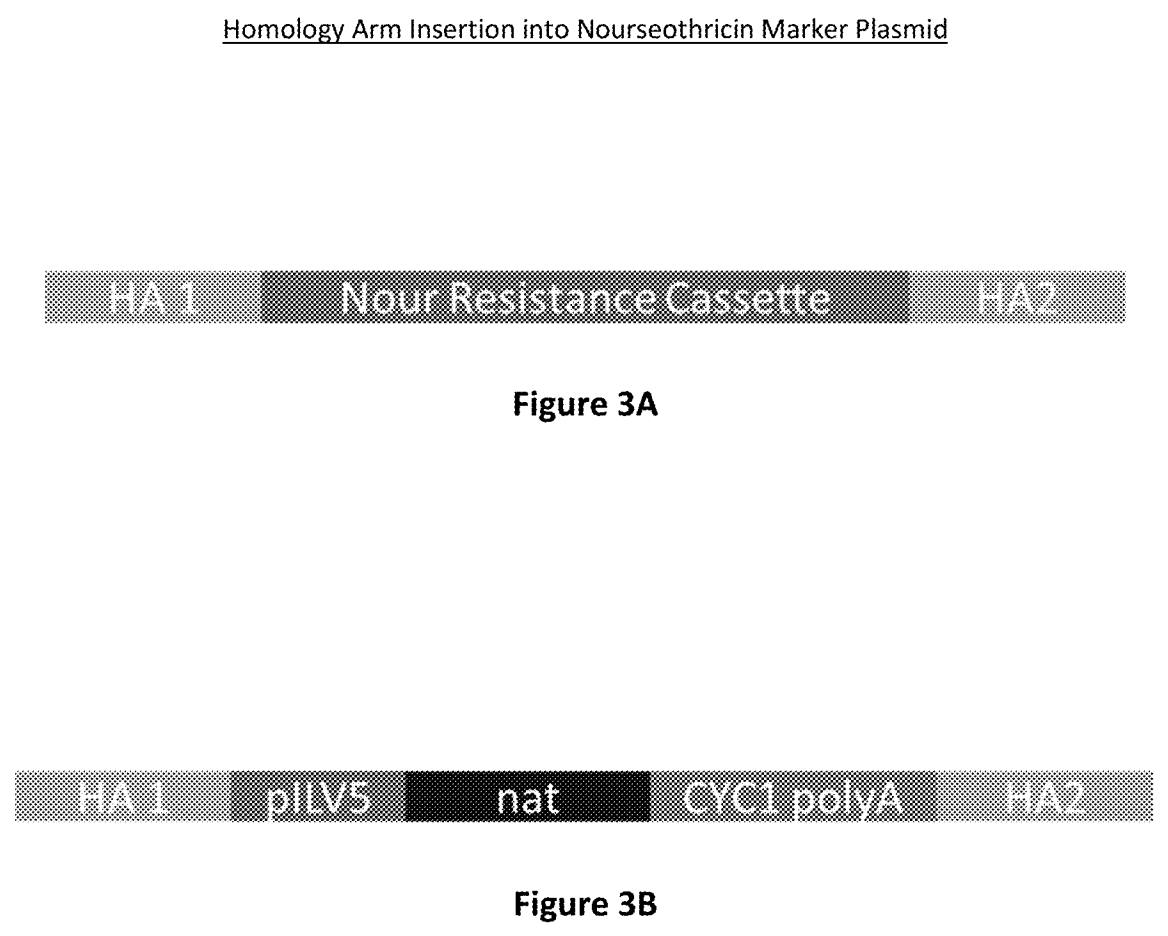

FIG. 3A and FIG. 3B are cassettes for protease knockout with homology arms targeting the desired protease gene flanking a nourseothricin resistance marker.

Figure 4:
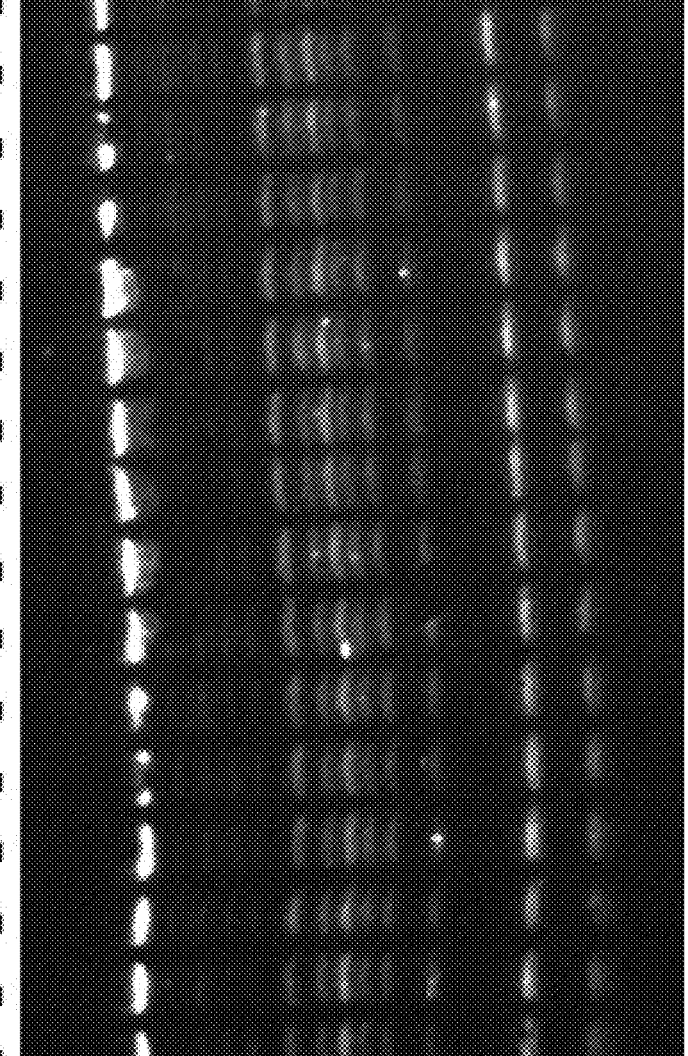

FIG. 4 is a representative western blot of protein isolated from single KO strains to show protein degradation from these strains.

Figure 5:
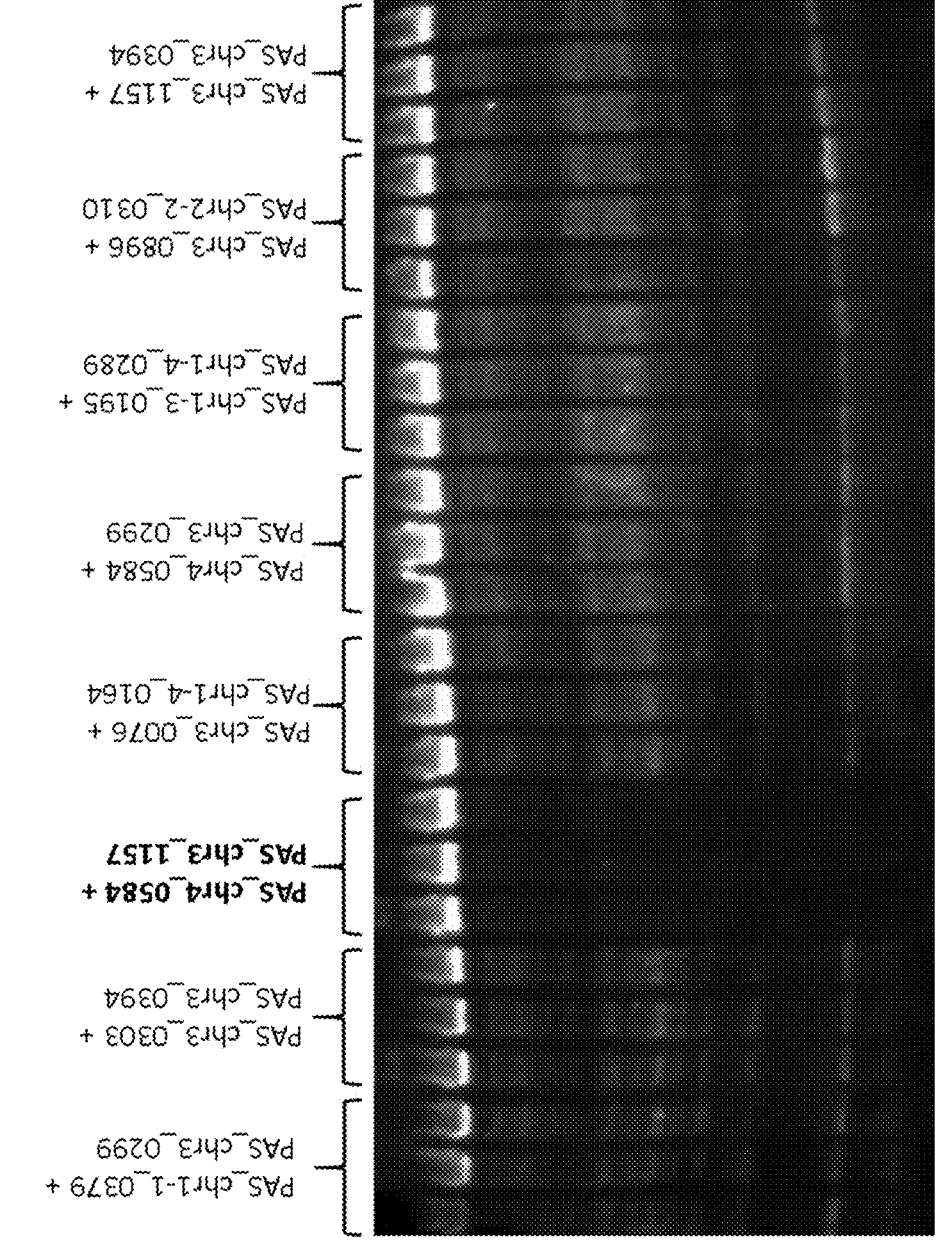

FIG. 5 is a representative western blot of protein isolated from double KO strains to show protein degradation from these strains.

Figure 6:
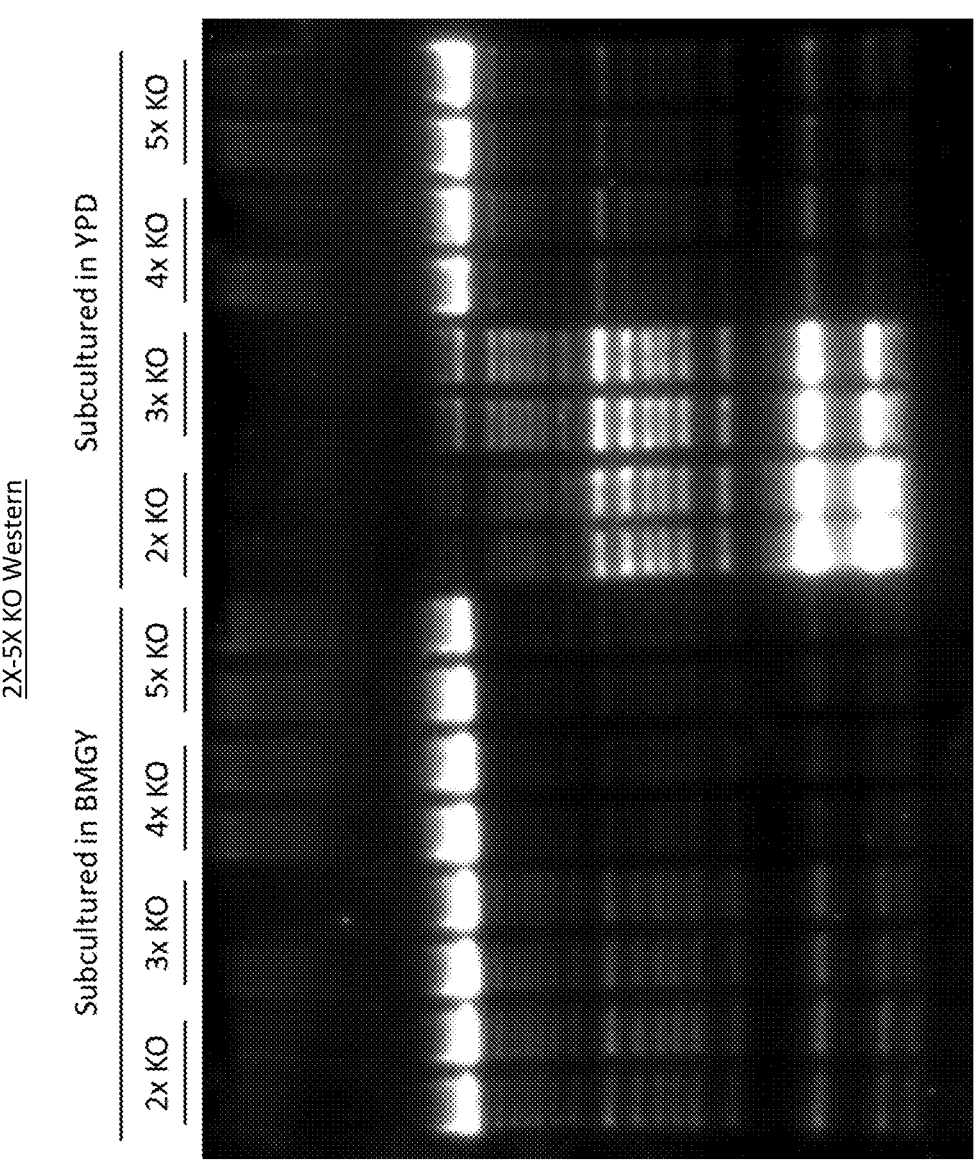

FIG. 6 is a representative western blot of protein isolated from 2×, 3×, 4×, and 5× protease KO strains subcultured in BMGY or YPD to show protein degradation in these strains.

DETAILED DESCRIPTION

The details of various embodiments of the invention are set forth in the description below. Other features, objects, and advantages of the invention will be apparent from the description and the drawings, and from the claims.

Definitions

Unless otherwise defined herein, scientific and technical terms used in connection with the present invention shall have the meanings that are commonly understood by those of ordinary skill in the art. Further, unless otherwise required by context, singular terms shall include the plural and plural terms shall include the singular. The terms "a" and "an" includes plural references unless the context dictates otherwise. Generally, nomenclatures used in connection with, and techniques of, biochemistry, enzymology, molecular and cellular biology, microbiology, genetics and protein and nucleic acid chemistry and hybridization described herein are those well-known and commonly used in the art.

The following terms, unless otherwise indicated, shall be understood to have the following meanings:

The term "polynucleotide" or "nucleic acid molecule" refers to a polymeric form of nucleotides of at least 10 bases in length. The term includes DNA molecules (e.g., cDNA or genomic or synthetic DNA) and RNA molecules (e.g., mRNA or synthetic RNA), as well as analogs of DNA or RNA containing non-natural nucleotide analogs, non-native internucleoside bonds, or both. The nucleic acid can be in any topological conformation. For instance, the nucleic acid can be single-stranded, double-stranded, triple-stranded, quadruplexed, partially double-stranded, branched, hairpinned, circular, or in a padlocked conformation.

Unless otherwise indicated, and as an example for all sequences described herein under the general format "SEQ ID NO:", "nucleic acid comprising SEQ ID NO:1" refers to a nucleic acid, at least a portion of which has either (i) the sequence of SEQ ID NO:1, or (ii) a sequence complementary to SEQ ID NO:1. The choice between the two is dictated by the context. For instance, if the nucleic acid is used as a probe, the choice between the two is dictated by the requirement that the probe be complementary to the desired target.

An "isolated" RNA, DNA or a mixed polymer is one which is substantially separated from other cellular components that naturally accompany the native polynucleotide in its natural host cell, e.g., ribosomes, polymerases and genomic sequences with which it is naturally associated.

An "isolated" organic molecule (e.g., a silk protein) is one which is substantially separated from the cellular components (membrane lipids, chromosomes, proteins) of the host cell from which it originated, or from the medium in which the host cell was cultured. The term does not require that the biomolecule has been separated from all other chemicals, although certain isolated biomolecules may be purified to near homogeneity.

The term "recombinant" refers to a biomolecule, e.g., a gene or protein, that (1) has been removed from its naturally occurring environment, (2) is not associated with all or a portion of a polynucleotide in which the gene is found in nature, (3) is operatively linked to a polynucleotide which it is not linked to in nature, or (4) does not occur in nature. The term "recombinant" can be used in reference to cloned DNA isolates, chemically synthesized polynucleotide analogs, or polynucleotide analogs that are biologically synthesized by heterologous systems, as well as proteins and/or mRNAs encoded by such nucleic acids.

An endogenous nucleic acid sequence in the genome of an organism (or the encoded protein product of that sequence) is deemed "recombinant" herein if a heterologous sequence is placed adjacent to the endogenous nucleic acid sequence, such that the expression of this endogenous nucleic acid sequence is altered. In this context, a heterologous sequence is a sequence that is not naturally adjacent to the endogenous nucleic acid sequence, whether or not the heterologous sequence is itself endogenous (originating from the same host cell or progeny thereof) or exogenous (originating from a different host cell or progeny thereof). By way of example, a promoter sequence can be substituted (e.g., by homologous recombination) for the native promoter of a gene in the genome of a host cell, such that this gene has an altered expression pattern. This gene would now become "recombinant" because it is separated from at least some of the sequences that naturally flank it.

A nucleic acid is also considered "recombinant" if it contains any modifications that do not naturally occur to the corresponding nucleic acid in a genome. For instance, an endogenous coding sequence is considered "recombinant" if it contains an insertion, deletion or a point mutation introduced artificially, e.g., by human intervention. A "recombinant nucleic acid" also includes a nucleic acid integrated into a host cell chromosome at a heterologous site and a nucleic acid construct present as an episome.

As used herein, the phrase "degenerate variant" of a reference nucleic acid sequence encompasses nucleic acid sequences that can be translated, according to the standard genetic code, to provide an amino acid sequence identical to that translated from the reference nucleic acid sequence. The term "degenerate oligonucleotide" or "degenerate primer" is used to signify an oligonucleotide capable of hybridizing with target nucleic acid sequences that are not necessarily identical in sequence but that are homologous to one another within one or more particular segments.

The term "percent sequence identity" or "identical" in the context of nucleic acid sequences refers to the residues in the two sequences which are the same when aligned for maximum correspondence. The length of sequence identity comparison may be over a stretch of at least about nine nucleotides, usually at least about 20 nucleotides, more usually at least about 24 nucleotides, typically at least about 28 nucleotides, more typically at least about 32 nucleotides, and preferably at least about 36 or more nucleotides. There are a number of different algorithms known in the art which can be used to measure nucleotide sequence identity. For instance, polynucleotide sequences can be compared using FASTA, Gap or Bestfit, which are programs in Wisconsin Package Version 10.0, Genetics Computer Group (GCG), Madison, Wis. FASTA provides alignments and percent sequence identity of the regions of the best overlap between the query and search sequences. Pearson, Methods Enzymol. 183:63-98 (1990) (hereby incorporated by reference in its entirety). For instance, percent sequence identity between nucleic acid sequences can be determined using FASTA with its default parameters (a word size of 6 and the NOPAM factor for the scoring matrix) or using Gap with its default parameters as provided in GCG Version 6.1, herein incorporated by reference. Alternatively, sequences can be compared using the computer program, BLAST (Altschul et al., J. Mol. Biol. 215:403-410 (1990); Gish and States, Nature Genet. 3:266-272 (1993); Madden et al., Meth. Enzymol. 266:131-141 (1996); Altschul et al., Nucleic Acids Res. 25:3389-3402 (1997); Zhang and Madden, Genome Res. 7:649-656 (1997)), especially blastp or tblastn (Altschul et al., Nucleic Acids Res. 25:3389-3402 (1997)).

The term "substantial homology" or "substantial similarity," when referring to a nucleic acid or fragment thereof, indicates that, when optimally aligned with appropriate nucleotide insertions or deletions with another nucleic acid (or its complementary strand), there is nucleotide sequence identity in at least about 75%, 80%, 85%, preferably at least about 90%, and more preferably at least about 95%, 96%, 97%, 98% or 99% of the nucleotide bases, as measured by any well-known algorithm of sequence identity, such as FASTA, BLAST or Gap, as discussed above.

Alternatively, substantial homology or similarity exists when a nucleic acid or fragment thereof hybridizes to another nucleic acid, to a strand of another nucleic acid, or to the complementary strand thereof, under stringent hybridization conditions. "Stringent hybridization conditions" and "stringent wash conditions" in the context of nucleic acid hybridization experiments depend upon a number of different physical parameters. Nucleic acid hybridization will be affected by such conditions as salt concentration, temperature, solvents, the base composition of the hybridizing species, length of the complementary regions, and the number of nucleotide base mismatches between the hybridizing nucleic acids, as will be readily appreciated by those skilled in the art. One having ordinary skill in the art knows how to vary these parameters to achieve a particular stringency of hybridization.

In general, "stringent hybridization" is performed at about 25° C. below the thermal melting point (Tm) for the specific DNA hybrid under a particular set of conditions. "Stringent washing" is performed at temperatures about 5° C. lower than the Tm for the specific DNA hybrid under a particular set of conditions. The Tm is the temperature at which 50% of the target sequence hybridizes to a perfectly matched probe. See Sambrook et al., Molecular Cloning: A Laboratory Manual, 2d ed., Cold Spring Harbor Laboratory Press, Cold Spring Harbor, N.Y. (1989), page 9.51, hereby incorporated by reference. For purposes herein, "stringent conditions" are defined for solution phase hybridization as aqueous hybridization (i.e., free of formamide) in 6×SSC (where 20×SSC contains 3.0 M NaCl and 0.3 M sodium citrate), 1% SDS at 65° C. for 8-12 hours, followed by two washes in 0.2×SSC, 0.1% SDS at 65° C. for 20 minutes. It will be appreciated by the skilled worker that hybridization at 65° C. will occur at different rates depending on a number of factors including the length and percent identity of the sequences which are hybridizing.

The nucleic acids (also referred to as polynucleotides) of this present invention may include both sense and antisense strands of RNA, cDNA, genomic DNA, and synthetic forms and mixed polymers of the above. They may be modified chemically or biochemically or may contain non-natural or derivatized nucleotide bases, as will be readily appreciated by those of skill in the art. Such modifications include, for example, labels, methylation, substitution of one or more of the naturally occurring nucleotides with an analog, inter-nucleotide modifications such as uncharged linkages (e.g., methyl phosphonates, phosphotriesters, phosphoramidates, carbamates, etc.), charged linkages (e.g., phosphorothioates, phosphorodithioates, etc.), pendent moieties (e.g., polypep-tides), intercalators (e.g., acridine, psoralen, etc.), chelators, alkylators, and modified linkages (e.g., alpha anomeric nucleic acids, etc.) Also included are synthetic molecules that mimic polynucleotides in their ability to bind to a designated sequence via hydrogen bonding and other chemi-cal interactions. Such molecules are known in the art and include, for example, those in which peptide linkages sub-stitute for phosphate linkages in the backbone of the mol-ecule. Other modifications can include, for example, analogs in which the ribose ring contains a bridging moiety or other structure such as the modifications found in "locked" nucleic acids.

The term "mutated" when applied to nucleic acid sequences means that nucleotides in a nucleic acid sequence may be inserted, deleted or changed compared to a reference nucleic acid sequence. A single alteration may be made at a locus (a point mutation) or multiple nucleotides may be inserted, deleted or changed at a single locus. In addition, one or more alterations may be made at any number of loci within a nucleic acid sequence. A nucleic acid sequence may be mutated by any method known in the art including but not limited to mutagenesis techniques such as "error-prone PCR" (a process for performing PCR under conditions where the copying fidelity of the DNA polymerase is low, such that a high rate of point mutations is obtained along the entire length of the PCR product: see, e.g., Leung et al., Technique. 1:11-15 (1989) and Caldwell and Joyce, *PCR Methods Applic.* 2:28-33 (1992)); and "oligonucleotide-directed mutagenesis" (a process which enables the genera-tion of site-specific mutations in any cloned DNA segment of interest; see, e.g., Reidhaar-Olson and Sauer, *Science* 241:53-57 (1988)).

The term "attenuate" as used herein generally refers to a functional deletion, including a mutation, partial or complete deletion, insertion, or other variation made to a gene sequence or a sequence controlling the transcription of a gene sequence, which reduces or inhibits production of the gene product, or renders the gene product non-functional. In some instances a functional deletion is described as a knockout mutation. Attenuation also includes amino acid sequence changes by altering the nucleic acid sequence, placing the gene under the control of a less active promoter, down-regulation, expressing interfering RNA, ribozymes or antisense sequences that target the gene of interest, or through any other technique known in the art. In one example, the sensitivity of a particular enzyme to feedback inhibition or inhibition caused by a composition that is not a product or a reactant (non-pathway specific feedback) is lessened such that the enzyme activity is not impacted by the presence of a compound. In other instances, an enzyme that has been altered to be less active can be referred to as attenuated.

The term "deletion" as used herein refers to the removal of one or more nucleotides from a nucleic acid molecule or one or more amino acids from a protein, the regions on either side being joined together.

The term "knock-out" as used herein is intended to refer to a gene whose level of expression or activity has been reduced to zero. In some examples, a gene is knocked-out via deletion of some or all of its coding sequence. In other examples, a gene is knocked-out via introduction of one or more nucleotides into its open reading frame, which results in translation of a non-sense or otherwise non-functional protein product.

The term "vector" as used herein is intended to refer to a nucleic acid molecule capable of transporting another nucleic acid to which it has been linked. One type of vector is a "plasmid." which generally refers to a circular double stranded DNA loop into which additional DNA segments may be ligated, but also includes linear double-stranded molecules such as those resulting from amplification by the polymerase chain reaction (PCR) or from treatment of a circular plasmid with a restriction enzyme. Other vectors include cosmids, bacterial artificial chromosomes (BAC) and yeast artificial chromosomes (YAC). Another type of vector is a viral vector, wherein additional DNA segments may be ligated into the viral genome (discussed in more detail below). Certain vectors are capable of autonomous replication in a host cell into which they are introduced (e.g., vectors having an origin of replication which functions in the host cell). Other vectors can be integrated into the genome of a host cell upon introduction into the host cell, and are thereby replicated along with the host genome. Moreover, certain preferred vectors are capable of directing the expression of genes to which they are operatively linked. Such vectors are referred to herein as "recombinant expres-sion vectors" (or simply "expression vectors").

"Operatively linked" or "operably linked" expression control sequences refers to a linkage in which the expression control sequence is contiguous with the gene of interest to control the gene of interest, as well as expression control sequences that act in trans or at a distance to control the gene of interest.

The term "expression control sequence" refers to poly-nucleotide sequences which are necessary to affect the expression of coding sequences to which they are opera-tively linked. Expression control sequences are sequences which control the transcription, post-transcriptional events and translation of nucleic acid sequences. Expression con-trol sequences include appropriate transcription initiation, termination, promoter and enhancer sequences; efficient RNA processing signals such as splicing and polyade-nylation signals; sequences that stabilize cytoplasmic mRNA; sequences that enhance translation efficiency (e.g., ribosome binding sites); sequences that enhance protein stability; and when desired, sequences that enhance protein secretion. The nature of such control sequences differs depending upon the host organism; in prokaryotes, such control sequences generally include promoter, ribosomal binding site, and transcription termination sequence. The term "control sequences" is intended to include, at a mini-mum, all components whose presence is essential for expression, and can also include additional components whose presence is advantageous, for example, leader sequences and fusion partner sequences.

The term "regulatory element" refers to any element which affects transcription or translation of a nucleic acid molecule. These include, by way of example but not limitation: regulatory proteins (e.g., transcription factors), chaperones, signaling proteins, RNAi molecules, antisense RNA molecules, microRNAs and RNA aptamers. Regulatory elements may be endogenous to the host organism. Regulatory elements may also be exogenous to the host organism. Regulatory elements may be synthetically generated regulatory elements.

The term "promoter," "promoter element." or "promoter sequence" as used herein, refers to a DNA sequence which when ligated to a nucleotide sequence of interest is capable of controlling the transcription of the nucleotide sequence of interest into mRNA. A promoter is typically, though not necessarily, located 5' (i.e., upstream) of a nucleotide sequence of interest whose transcription into mRNA it controls, and provides a site for specific binding by RNA polymerase and other transcription factors for initiation of transcription. Promoters may be endogenous to the host organism. Promoters may also be exogenous to the host organism. Promoters may be synthetically generated regulatory elements.

Promoters useful for expressing the recombinant genes described herein include both constitutive and inducible/repressible promoters. Where multiple recombinant genes are expressed in an engineered organism of the invention, the different genes can be controlled by different promoters or by identical promoters in separate operons, or the expression of two or more genes may be controlled by a single promoter as part of an operon.

The term "recombinant host cell" (or simply "host cell"), as used herein, is intended to refer to a cell into which a recombinant vector has been introduced. It should be understood that such terms are intended to refer not only to the particular subject cell but to the progeny of such a cell. Because certain modifications may occur in succeeding generations due to either mutation or environmental influences, such progeny may not, in fact, be identical to the parent cell, but are still included within the scope of the term "host cell" as used herein. A recombinant host cell may be an isolated cell or cell line grown in culture or may be a cell which resides in a living tissue or organism.

The term "peptide" as used herein refers to a short polypeptide, e.g., one that is typically less than about 50 amino acids long and more typically less than about 30 amino acids long. The term as used herein encompasses analogs and mimetics that mimic structural and thus biological function.

The term "polypeptide" encompasses both naturally-occurring and non-naturally-occurring proteins, and fragments, mutants, derivatives and analogs thereof. A polypeptide may be monomeric or polymeric. Further, a polypeptide may comprise a number of different domains each of which has one or more distinct activities.

The term "isolated protein" or "isolated polypeptide" is a protein or polypeptide that by virtue of its origin or source of derivation (1) is not associated with naturally associated components that accompany it in its native state, (2) exists in a purity not found in nature, where purity can be adjudged with respect to the presence of other cellular material (e.g., is free of other proteins from the same species) (3) is expressed by a cell from a different species, or (4) does not occur in nature (e.g., it is a fragment of a polypeptide found in nature or it includes amino acid analogs or derivatives not found in nature or linkages other than standard peptide bonds). Thus, a polypeptide that is chemically synthesized or synthesized in a cellular system different from the cell from which it naturally originates will be "isolated" from its naturally associated components. A polypeptide or protein may also be rendered substantially free of naturally associated components by isolation, using protein purification techniques well known in the art. As thus defined, "isolated" does not necessarily require that the protein, polypeptide, peptide or oligopeptide so described has been physically removed from its native environment.

The term "polypeptide fragment" refers to a polypeptide that has a deletion, e.g., an amino-terminal and/or carboxy-terminal deletion compared to a full-length polypeptide. In a preferred embodiment, the polypeptide fragment is a contiguous sequence in which the amino acid sequence of the fragment is identical to the corresponding positions in the naturally-occurring sequence. Fragments typically are at least 5, 6, 7, 8, 9 or 10 amino acids long, preferably at least 12, 14, 16 or 18 amino acids long, more preferably at least 20 amino acids long, more preferably at least 25, 30, 35, 40 or 45, amino acids, even more preferably at least 50 or 60 amino acids long, and even more preferably at least 70 amino acids long.

A protein has "homology" or is "homologous" to a second protein if the nucleic acid sequence that encodes the protein has a similar sequence to the nucleic acid sequence that encodes the second protein. Alternatively, a protein has homology to a second protein if the two proteins have "similar" amino acid sequences. (Thus, the term "homologous proteins" is defined to mean that the two proteins have similar amino acid sequences.) As used herein, homology between two regions of amino acid sequence (especially with respect to predicted structural similarities) is interpreted as implying similarity in function.

When "homologous" is used in reference to proteins or peptides, it is recognized that residue positions that are not identical often differ by conservative amino acid substitutions. A "conservative amino acid substitution" is one in which an amino acid residue is substituted by another amino acid residue having a side chain (R group) with similar chemical properties (e.g., charge or hydrophobicity). In general, a conservative amino acid substitution will not substantially change the functional properties of a protein. In cases where two or more amino acid sequences differ from each other by conservative substitutions, the percent sequence identity or degree of homology may be adjusted upwards to correct for the conservative nature of the substitution. Means for making this adjustment are well known to those of skill in the art. See, e.g., Pearson, 1994, *Methods Mol. Biol.* 24:307-31 and 25:365-89 (herein incorporated by reference).

The twenty conventional amino acids and their abbreviations follow conventional usage. See *Immunology—A Synthesis* (Golub and Gren eds., Sinauer Associates, Sunderland, Mass., 2$^{nd}$ ed. 1991), which is incorporated herein by reference. Stereoisomers (e.g., D-amino acids) of the twenty conventional amino acids, unnatural amino acids such as α-, α-disubstituted amino acids, N-alkyl amino acids, and other unconventional amino acids may also be suitable components for polypeptides of the present invention. Examples of unconventional amino acids include: 4-hydroxyproline, γ-carboxyglutamate, ε-N,N,N-trimethyllysine, ε-N-acetyllysine, O-phosphoserine, N-acetylserine, N-formylmethionine, 3-methylhistidine, 5-hydroxylysine, N-methylarginine, and other similar amino acids and imino acids (e.g., 4-hydroxyproline). In the polypeptide notation used herein, the left-hand end corresponds to the amino terminal end and the right-hand end corresponds to the carboxy-terminal end, in accordance with standard usage and convention.

The following six groups each contain amino acids that are conservative substitutions for one another: 1) Serine(S), Threonine (T); 2) Aspartic Acid (D), Glutamic Acid (E); 3) Asparagine (N), Glutamine (Q): 4) Arginine (R), Lysine (K); 5) Isoleucine (I), Leucine (L), Methionine (M), Alanine (A), Valine (V), and 6) Phenylalanine (F), Tyrosine (Y), Tryptophan (W).

Sequence homology for polypeptides, which is sometimes also referred to as percent sequence identity, is typically measured using sequence analysis software. See, e.g., the Sequence Analysis Software Package of the Genetics Computer Group (GCG), University of Wisconsin Biotechnology Center, 910 University Avenue, Madison, Wis. 53705. Protein analysis software matches similar sequences using a measure of homology assigned to various substitutions, deletions and other modifications, including conservative amino acid substitutions. For instance, GCG contains programs such as "Gap" and "Bestfit" which can be used with default parameters to determine sequence homology or sequence identity between closely related polypeptides, such as homologous polypeptides from different species of organisms or between a wild-type protein and a mutein thereof. See, e.g., GCG Version 6.1.

A useful algorithm when comparing a particular polypeptide sequence to a database containing a large number of sequences from different organisms is the computer program BLAST (Altschul et al., *J. Mol. Biol.* 215:403-410 (1990); Gish and States, *Nature Genet.* 3:266-272 (1993); Madden et al., *Meth. Enzymol.* 266:131-141 (1996); Altschul et al., *Nucleic Acids Res.* 25:3389-3402 (1997); Zhang and Madden, *Genome Res.* 7:649-656 (1997)), especially blastp or tblastn (Altschul et al., *Nucleic Acids Res.* 25:3389-3402 (1997)).

Preferred parameters for BLASTp are: Expectation value: 10 (default); Filter: seg (default); Cost to open a gap: 11 (default); Cost to extend a gap: 1 (default); Max. alignments: 100 (default); Word size: 11 (default); No. of descriptions: 100 (default); Penalty Matrix: BLOWSUM62.

Preferred parameters for BLASTp are: Expectation value: 10 (default); Filter: seg (default); Cost to open a gap: 11 (default); Cost to extend a gap: 1 (default); Max. alignments: 100 (default); Word size: 11 (default); No. of descriptions: 100 (default); Penalty Matrix: BLOWSUM62. The length of polypeptide sequences compared for homology will generally be at least about 16 amino acid residues, usually at least about 20 residues, more usually at least about 24 residues, typically at least about 28 residues, and preferably more than about 35 residues. When searching a database containing sequences from a large number of different organisms, it is preferable to compare amino acid sequences. Database searching using amino acid sequences can be measured by algorithms other than blastp known in the art. For instance, polypeptide sequences can be compared using FASTA, a program in GCG Version 6.1. FASTA provides alignments and percent sequence identity of the regions of the best overlap between the query and search sequences. Pearson, Methods Enzymol. 183:63-98 (1990) (incorporated by reference herein). For example, percent sequence identity between amino acid sequences can be determined using FASTA with its default parameters (a word size of 2 and the PAM250 scoring matrix), as provided in GCG Version 6.1, herein incorporated by reference.

Throughout this specification and claims, the word "comprise" or variations such as "comprises" or "comprising,"

will be understood to imply the inclusion of a stated integer or group of integers but not the exclusion of any other integer or group of integers.

Exemplary methods and materials are described below, although methods and materials similar or equivalent to those described herein can also be used in the practice of the present invention and will be apparent to those of skill in the art. All publications and other references mentioned herein are incorporated by reference in their entirety. In case of conflict, the present specification, including definitions, will control. The materials, methods, and examples are illustrative only and not intended to be limiting.

Overview

Provided herein are recombinant strains and methods of producing recombinant strains to increase production of a full-length desired product in a target cell, e.g., by reducing protease degradation.

In some embodiments, to attenuate a protease activity in *Pichia pastoris*, the genes encoding these enzymes are inactivated or mutated to reduce or eliminate activity. This can be done through mutations or insertions into the gene itself of through modification of a gene regulatory element. This can be achieved through standard yeast genetics techniques. Examples of such techniques include gene replacement through double homologous recombination, in which homologous regions flanking the gene to be inactivated are cloned in a vector flanking a selectable maker gene (such as an antibiotic resistance gene or a gene complementing an auxotrophy of the yeast strain).

Alternatively, the homologous regions can be PCR-amplified and linked through overlapping PCR to the selectable marker gene. Subsequently, such DNA fragments are transformed into *Pichia pastoris* through methods known in the art, e.g., electroporation. Transformants that then grow under selective conditions are analyzed for the gene disruption event through standard techniques, e.g. PCR on genomic DNA or Southern blot. In an alternative experiment, gene inactivation can be achieved through single homologous recombination, in which case, e.g. the 5' end of the gene's ORF is cloned on a promoterless vector also containing a selectable marker gene. Upon linearization of such vector through digestion with a restriction enzyme only cutting the vector in the target-gene homologous fragment, such vector is transformed into *Pichia pastoris*. Integration at the target gene site is confirmed through PCR on genomic DNA or Southern blot. In this way, a duplication of the gene fragment cloned on the vector is achieved in the genome, resulting in two copies of the target gene locus: a first copy in which the ORF is incomplete, thus resulting in the expression (if at all) of a shortened, inactive protein, and a second copy which has no promoter to drive transcription.

Alternatively, transposon mutagenesis is used to inactivate the target gene. A library of such mutants can be screened through PCR for insertion events in the target gene.

The functional phenotype (i.e., deficiencies) of an engineered/knockout strain can be assessed using techniques known in the art. For example, a deficiency of an engineered strain in protease activity can be ascertained using any of a variety of methods known in the art, such as an assay of hydrolytic activity of chromogenic protease substrates, band shifts of substrate proteins for the selected protease, among others.

Attenuation of a protease activity described herein can be achieved through mechanisms other than a knockout mutation. For example, a desired protease can be attenuated via amino acid sequence changes by altering the nucleic acid sequence, placing the gene under the control of a less active promoter, down-regulation, expressing interfering RNA, ribozymes or antisense sequences that target the gene of interest, or through any other technique known in the art. In preferred strains, the protease activity of proteases encoded at PAS_chr4_0584 (YPS1-1) and PAS_chr3_1157 (YPS1-2) (e.g., polypeptides comprising SEQ ID NO: 67 and 68) is attenuated by any of the methods described above. In some aspects, the invention is directed to methylotrophic yeast strains, especially *Pichia pastoris* strains, wherein a YPS1-1 and a YPS1-2 gene (e.g., as set forth in SEQ ID NO: 1 and SEQ ID NO: 2) have been inactivated. In some embodiments, additional protease encoding genes may also be knocked-out in accordance with the methods provided herein to further reduce protease activity of a desired protein product expressed by the strain.

Production of Recombinant Strains

Provided herein are methods of transforming a strain to reduce activity, e.g., using vectors to deliver recombinant genes or to knock-out or otherwise attenuate endogenous genes as desired. These vectors can take the form of a vector backbone containing a replication origin and a selection marker (typically antibiotic resistance, although many other methods are possible), or a linear fragment that enables incorporation into the target cell's chromosome. The vectors should correspond to the organism and insertion method chosen.

Once the elements of a vector are selected, construction of the vector can be performed in many different ways. In an embodiment, a DNA synthesis service or a method to individually make every vector may be used.

Once the DNA for each vector (including the additional elements required for insertion and operation) is acquired, it must be assembled. There are many possible assembly methods including (but not limited to) restriction enzyme cloning, blunt-end ligation, and overlap assembly [see, e.g., Gibson, D. G., et al., Enzymatic assembly of DNA molecules up to several hundred kilobases. Nature methods, 6 (5), 343-345 (2009), and GeneArt Kit (tools.invitrogen.com/content/sfs/manuals/geneart_seamless_cloning_and_assembly_man.pdf)]. Overlap assembly provides a method to ensure all of the elements get assembled in the correct position and do not introduce any undesired sequences.

The vectors generated above can be inserted into target cells using standard molecular biology techniques, e.g., molecular cloning. In an embodiment, the target cells are already engineered or selected such that they already contain the genes required to make the desired product, although this may also be done during or after further vector insertion.

Depending on the organism and library element type (plasmid or genomic insertion), several known methods of inserting the vector comprising DNA to incorporate into the cells may be used. These may include, for example, transformation of microorganisms able to take up and replicate DNA from the local environment, transformation by electroporation or chemical means, transduction with a virus or phage, mating of two or more cells, or conjugation from a different cell.

Several methods are known in the art to introduce recombinant DNA in bacterial cells that include but are not limited to transformation, transduction, and electroporation, see Sambrook, et al., Molecular Cloning: A Laboratory Manual (1989), Second Edition, Cold Spring Harbor Press, Plainview, N.Y. Non-limiting examples of commercial kits and bacterial host cells for transformation include NovaBlue Singles™ (EMD Chemicals Inc., NJ, USA), Max Efficiency® DH5α™, One Shot® BL21 (DE3) *E. coli* cells, One Shot® BL21 (DE3) pLys *E. coli* cells (Invitrogen Corp., Carlsbad, Calif., USA), XL1-Blue competent cells (Stratagene, CA, USA). Non limiting examples of commercial kits and bacterial host cells for electroporation include Zappers™ electrocompetent cells (EMD Chemicals Inc., NJ, USA), XL1-Blue Electroporation-competent cells (Stratagene, CA, USA), ElectroMAX™ *A. tumefaciens* LBA4404 Cells (Invitrogen Corp., Carlsbad, Calif., USA).

Several methods are known in the art to introduce recombinant nucleic acid in eukaryotic cells. Exemplary methods include transfection, electroporation, liposome mediated delivery of nucleic acid, microinjection into to the host cell, see Sambrook, et al., Molecular Cloning: A Laboratory Manual (1989), Second Edition, Cold Spring Harbor Press, Plainview, N.Y. Non-limiting examples of commercial kits and reagents for transfection of recombinant nucleic acid to eukaryotic cell include Lipofectamine™ 2000. Optifect™ Reagent, Calcium Phosphate Transfection Kit (Invitrogen Corp., Carlsbad, Calif., USA), GeneJammer® Transfection Reagent, LipoTAXI® Transfection Reagent (Stratagene, CA, USA). Alternatively, recombinant nucleic acid may be introduced into insect cells (e.g. sf9), sf21, High Five™) by using baculo viral vectors.

Transformed cells are isolated so that each clone can be tested separately. In an embodiment, this is done by spreading the culture on one or more plates of culture media containing a selective agent (or lack of one) that will ensure that only transformed cells survive and reproduce. This specific agent may be an antibiotic (if the library contains an antibiotic resistance marker), a missing metabolite (for auxotroph complementation), or other means of selection. The cells are grown into individual colonies, each of which contains a single clone.

Colonies are screened for desired production of a protein, metabolite, or other product, or for reduction in protease activity. In an embodiment, screening identifies recombinant cells having the highest (or high enough) product production titer or efficiency. This includes a decreased proportion of degradation products or an increased total amount of full-length desired polypeptides collected from a cell culture.

This assay can be performed by growing individual clones, one per well, in multi-well culture plates. Once the cells have reached an appropriate biomass density, they are induced with methanol. After a period of time, typically 24-72 hours of induction, the cultures are harvested by spinning in a centrifuge to pellet the cells and removing the supernatant. The supernatant from each culture can then be tested for protease activity and/or protein degradation.

Silk Sequences

In some embodiments, the modified strains with reduced protease activity described herein recombinantly express a silk-like polypeptide sequence. In some embodiments, the silk-like polypeptide sequences are 1) block copolymer polypeptide compositions generated by mixing and matching repeat domains derived from silk polypeptide sequences and/or 2) recombinant expression of block copolymer polypeptides having sufficiently large size (approximately 40 kDa) to form useful fibers by secretion from an industrially scalable microorganism. Large (approximately 40 kDa to approximately 100 kDa) block copolymer polypeptides engineered from silk repeat domain fragments, including sequences from almost all published amino acid sequences of spider silk polypeptides, can be expressed in the modified microorganisms described herein. In some embodiments, silk polypeptide sequences are matched and designed to produce highly expressed and secreted polypeptides capable of fiber formation. In some embodiments, knock-out of protease genes or reduction of protease activity in the host modified strain reduces degradation of the silk like polypeptides.

Provided herein, in several embodiments, are compositions for expression and secretion of block copolymers engineered from a combinatorial mix of silk polypeptide domains across the silk polypeptide sequence space, wherein the block copolymers have minimal degradation. In some embodiments provided herein are methods of secreting block copolymers in scalable organisms (e.g., yeast, fungi, and gram positive bacteria) with minimal degradation. In some embodiments, the block copolymer polypeptide comprises 0 or more N-terminal domains (NTD), 1 or more repeat domains (REP), and 0 or more C-terminal domains (CTD). In some aspects of the embodiment, the block copolymer polypeptide is >100 amino acids of a single polypeptide chain. In some embodiments, the block copolymer polypeptide comprises a domain that is at least 80%, 81%, 82%, 83%, 84%, 85%, 86%, 87%, 88%, 89%, 90%, 91%, 92%, 93%, 94%, 95%, 96%, 97%, 98%, or 99% identical to a sequence of a block copolymer polypeptide as disclosed in International Publication No. WO/2015/042164, "Methods and Compositions for Synthesizing Improved Silk Fibers," incorporated by reference in its entirety.

Several types of native spider silks have been identified. The mechanical properties of each natively spun silk type are believed to be closely connected to the molecular composition of that silk. See, e.g., Garb, J. E., et al., Untangling spider silk evolution with spidroin terminal domains, *BMC Evol. Biol.*, 10:243 (2010); Bittencourt, D., et al., Protein families, natural history and biotechnological aspects of spider silk. *Genet. Mol. Res.*, 11:3 (2012); Rising, A., et al., Spider silk proteins: recent advances in recombinant production, structure-function relationships and biomedical applications, *Cell. Mol. Life Sci.*, 68:2, pg. 169-184 (2011); and Humenik, M., et al., Spider silk: understanding the structure-function relationship of a natural fiber, *Prog. Mol. Biol. Transl. Sci.*, 103, pg. 131-85 (2011). For example:

Aciniform (AcSp) silks tend to have high toughness, a result of moderately high strength coupled with moderately high extensibility. AcSp silks are characterized by large block ("ensemble repeat") sizes that often incorporate motifs of poly serine and GPX. Tubuliform (TuSp or Cylindrical) silks tend to have large diameters, with modest strength and high extensibility. TuSp silks are characterized by their poly serine and poly threonine content, and short tracts of poly alanine. Major Ampullate (MaSp) silks tend to have high strength and modest extensibility. MaSp silks can be one of two subtypes: MaSp1 and MaSp2. MaSp1 silks are generally less extensible than MaSp2 silks, and are characterized by poly alanine, GX, and GGX motifs. MaSp2 silks are characterized by poly alanine, GGX, and GPX motifs. Minor Ampullate (MiSp) silks tend to have modest strength and modest extensibility. MiSp silks are characterized by GGX. GA, and poly A motifs, and often contain spacer elements of approximately 100 amino acids. Flagelliform (Flag) silks tend to have very high extensibility and modest strength. Flag silks are usually characterized by GPG, GGX, and short spacer motifs.

The properties of each silk type can vary from species to species, and spiders leading distinct lifestyles (e.g. sedentary web spinners vs. vagabond hunters) or that are evolutionarily older may produce silks that differ in properties from the above descriptions (for descriptions of spider diversity and classification, see Hormiga, G., and Griswold, C. E., Systematics, phylogeny, and evolution of orb-weaving spiders, *Annu. Rev. Entomol.* 59, pg. 487-512 (2014); and Blackedge, T. A. et al., Reconstructing web evolution and spider diversification in the molecular era, *Proc. Natl. Acad. Sci. U.S.A.*, 106:13, pg. 5229-5234 (2009)). However, synthetic block copolymer polypeptides having sequence similarity and/or amino acid composition similarity to the repeat domains of native silk proteins can be used to manufacture on commercial scales consistent silk-like fibers that recapitulate the properties of corresponding natural silk fibers.

In some embodiments, a list of putative silk sequences can be compiled by searching GenBank for relevant terms, e.g. "spidroin" "fibroin" "MaSp", and those sequences can be pooled with additional sequences obtained through independent sequencing efforts. Sequences are then translated into amino acids, filtered for duplicate entries, and manually split into domains (NTD, REP, CTD). In some embodiments, candidate amino acid sequences are reverse translated into a DNA sequence optimized for expression in *Pichia (Komagataella) pastoris*. The DNA sequences are each cloned into an expression vector and transformed into *Pichia (Komagataella) pastoris*. In some embodiments, various silk domains demonstrating successful expression and secretion are subsequently assembled in combinatorial fashion to build silk molecules capable of fiber formation.

Silk polypeptides are characteristically composed of a repeat domain (REP) flanked by non-repetitive regions (e.g., C-terminal and N-terminal domains). In an embodiment, both the C-terminal and N-terminal domains are between 75-350 amino acids in length. The repeat domain exhibits a hierarchical architecture. The repeat domain comprises a series of blocks (also called repeat units). The blocks are repeated, sometimes perfectly and sometimes imperfectly (making up a quasi-repeat domain), throughout the silk repeat domain. The length and composition of blocks varies among different silk types and across different species. Table 1 lists examples of block sequences from selected species and silk types, with further examples presented in Rising, A. et al., Spider silk proteins: recent advances in recombinant production, structure-function relationships and biomedical applications, *Cell Mol. Life Sci.*, 68:2, pg 169-184 (2011); and Gatesy, J. et al., Extreme diversity, conservation, and convergence of spider silk fibroin sequences, *Science,* 291: 5513, pg. 2603-2605 (2001). In some cases, blocks may be arranged in a regular pattern, forming larger macro-repeats that appear multiple times (usually 2-8) in the repeat domain of the silk sequence. Repeated blocks inside a repeat domain or macro-repeat, and repeated macro-repeats within the repeat domain, may be separated by spacing elements. In some embodiments, block sequences comprise a glycine rich region followed by a polyA region. In some embodiments, short (~1-10) amino acid motifs appear multiple times inside of blocks. For the purpose of this invention, blocks from different natural silk polypeptides can be selected without reference to circular permutation (i.e., identified blocks that are otherwise similar between silk polypeptides may not align due to circular permutation). Thus, for example, a "block" of SGAGG (SEQ ID NO: 494) is, for the purposes of the present invention, the same as GSGAG (SEQ ID NO: 495) and the same as GGSGA (SEQ ID NO: 496); they are all just circular permutations of each other. The particular permutation selected for a given silk sequence can be dictated by convenience (usually starting with a G) more than anything else. Silk sequences obtained from the NCBI database can be partitioned into blocks and non-repetitive regions.

TABLE 1

Samples of Block Sequences

| Species | Silk Type | Representative Block Amino Acid Sequence |
|---------|-----------|------------------------------------------|
| *Aliatypus gulosus* | Fibroin 1 | GAASSSSTIITTKSASASAA ADASAAATASAASRSSANAA ASAFAQSFSSILLESGYFCS IFGSSISSSYAAAIASAASR AAAESNGYTTHAYACAKAVA SAVERVTSGADAYAYAQAIS DALSHALLYTGRLNTANANS LASAFAYAFANAAAQASASS ASAGAASASGAASASGAGSA S (SEQ ID NO: 497) |
| *Plectreurys tristis* | Fibroin 1 | GAGAGAGAGAGAGAGAGSGA STSVSTSSSSGSGAGAGAGS GAGSGAGAGSGAGAGAGAGG AGAGFGSGLGLGYGVGLSSA QAQAQAQAAAQAQAQAQAQA YAAAQAQAQAQAQAQAAAAA AAAAAA (SEQ ID NO: 498) |
| *Plectreurys tristis* | Fibroin 4 | GAAQKQPSGESSVATASAAA TSVTSGGAPVGKPGVPAPIF YPQGPLQQGPAPGPSNVQPG TSQQGPIGGVGGSNAFSSSF ASALSLNRGFTEVISSASAT AVASAFQKGLAPYGTAFALS AASAAADAYNSIGSGANAFA YAQAFARVLYPLVQQYGLSS SAKASAFASAIASSFSSGTS GQGPSIGQQQPPVTISAASA SAGASAAAVGGGQVGQGPYG GQQQSTAASASASAAAATATS (SEQ ID NO: 499) |
| *Araneus gemmoides* | TuSp | GNVGYQLGLKVANSLGLGNA QALASSLSQAVSAVGVGASS NAYANAVSNAVGQVLAGQGI LNAANAGSLASSFASALSSS AASVASQSASQSQAASQSQA AASAFRQAASQSASQSDSRA GSQSSTKTTSTSTSGSQADS RSASSSASQASASAFAQQSS ASLSSSSSFSSAFSSATSIS AV (SEQ ID NO: 500) |
| *Argiope aurantia* | TuSp | GSLASSFASALSASAASVAS SAAAQAASQSQAAASAFSRA ASQSASQSAARSGAQSISTT TTTSTAGSQAASQSASSAAS QASASSFARASSASLAASSS FSSAFSSANSLSALGNVGYQ LGFNVANNLGIGNAAGLGNA LSQAVSSVGVGASSSTYANA VSNAVGQFLAGQGILNAANA (SEQ ID NO: 501) |
| *Deinopis spinosa* | TuSp | GASASAYASAISNAVGPYLY GLGLFNQANAASFASSFASA VSSAVASASASAASSAYAQS AAAQAQAASSAFSQAAAQSA AAASAGASAGAGASAGAGAV AGAGAVAGAGAVAGASAAAA SQAAASSSASAVASAFAQSA SYALASSSAFANAFASATSA GYLGSLAYQLGLTTAYNLGL SNAQAFASTLSQAVTGVGL (SEQ ID NO: 502) |
| *Nephila clavipes* | TuSp | GATAASYGNALSTAAAQFFA TAGLLNAGNASALASSFARA FSASAESQSFAQSQAFQQAS AFQQAASRSASQSAAEAGST SSSTTTTTSAARSQAASQSA |

TABLE 1-continued

Samples of Block Sequences

| Species | Silk Type | Representative Block Amino Acid Sequence |
|---------|-----------|------------------------------------------|
| | | SSSYSSAFAQAASSSLATSS ALSRAFSSVSSASAASSLAY SIGLSAARSLGIADAAGLAG VLARAAGALGQ (SEQ ID NO: 503) |
| *Argiope trifasciata* | Flag | GGAPGGGPGGAGPGGAGFGP GGGAGFGPGGGGAGFGPGGAA GGPGGPGGPGGPGGAGGYGP GGAGGYGPGGVGPGGAGGYG PGGAGGYGPGGSGPGGAGPG GAGGEGPVTVDVDVTVGPEG VGGGPGGAGPGGAGFGPGGG AGFGPGGAPGAPGPGGPGG PGGPGGPGGVGPGGAGGYGP GGAGGVGPAGTGGFGPGGAG GFGPGGAGGFGPGGAGGFGP AGAGGYGPGGVGPGGAGGFG PGGVGPGGSGPGGAGGEGPV TVDVDVSV (SEQ ID NO:504) |
| *Nephila clavipes* | Flag | GVSYGPGGAGGPYGPGGPYG PGGEGPGGAGGPYGPGGVGP GGSGPGGYGPGGAGPGGYGP GGSGPGGYGPGGSGPGGYGP GGYGPGGSGPGGSGPGGSGP GGYGPGGTGPGGSGPGGYGP GGSGPGGSGPGGYGPGGSGP GGFGPGGSGPGGYGPGGSGP GGAGPGGVGPGGFGPGGAGP GGAAPGGAGPGGAGPGGAGP GGAGPGGAGPGGAGPGGAGG AGGAGGSGGAGGSGGTTIIE DLDITIDGADGPITISEELP ISGAGGSGPGGAGPGGVGPG GSGPGGVGPGGSGPGGVGPG GSGPGGVGPGGAGGPYGPGG SGPGGAGGAGGPGGAYGPGG SYGPGGSGPGGAGGPYGPGG GEGPGGAGGPYGPGGAGGPY GPGGAGGPYGPGGEGGPYGP (SEQ ID NO: 505) |
| *Latrodectus hesperus* | AcSp | GINVDSDIGSVTSLILSGST LQMTIPAGGDDLSGGYPGGF PAGAQPSGGAPVDFGGPSAG GDVAAKLARSLASTLASSGV FRAAFNSRVSTPVAVQLTDA LVQKIASNLGLDYATASKLR KASQAVSKVRMGSDTNAYAL AISSALAEVLSSSGKVADAN INQIAPQLASGIVLGVSTTA PQFGVDLSSINVNLDISNVA RNMQASIQGGPAPITAEGPD FGAGYPGGAPTDLSGLDMGA PSDGSRGGDATAKLLQALVP ALLKSDVFRAIYKRGTRKQV VQYVTNSALQQAASSLGLDA STISQLQTKATQALSSVSAD SDSTAYAKAFGLAIAQVLGT SGQVNDANVNQIGAKLATGI LRGSSAVAPRLGIDLS (SEQ ID NO: 506) |
| *Argiope trifasciata* | AcSp | GAGYTGPSGPSTGPSGYPGP LGGGAPFGQSGFGBGSAGPQG GFGATGGASAGLISRVANAL ANTSTLRTVLRTGVSQQIAS SVVQRAAQSLASTLGVDGNN LARFAVQAVSRLPAGSDTSA YAQAFSSALFNAGVLNASNI DTLGSRVLSALLNGVSSAAQ GLGINVDSGSVQSDISSSSS |

TABLE 1-continued

Samples of Block Sequences

| Species | Silk Type | Representative Block Amino Acid Sequence |
|---|---|---|
| | | FLSTSSSSASYSQASASSTS (SEQ ID NO: 507) |
| *Uloborus diversus* | AcSp | GASAADIATAIAASVATSLQ SNGVLTASNVSQLSNQLASY VSSGLSSTASSLGIQLGASL GAGFGASAGLSASTDISSSV EATSASTLSSSASSTSWSSI NAQLVPALAQTAVLNAAFSN INTQNAIRIAELLTQQVGRQ YGLSGSDVATASSQIRSALY SVQQGSASSAYVSAIVGPLI TALSSRGWNASNSSQIASSL ATAILQFTANVAPQFGISIP TSAVQSDLSTISQSLTAISS QTSSSVDSSTSAFGGISGPS GPSPYGPQPSGPTFGPGPSL SGLTGFTATFASSFKSTLAS STQFQLIAQSNLDVQTRSSL ISKVLINALSSLGISASVAS SIAASSSQSLLSVSA (SEQ ID NO: 508) |
| *Euprosthenops australis* | MaSp1 | GGQGGQGQGRYGQGAGSSAA AAAAAAAAAAAA (SEQ ID NO:509) |
| *Tetragnatha kauaiensis* | MaSp1 | GGLGGGQGAGQGGQQGAGQG GYGSGLGGAGQGASAAAAAA AA (SEQ ID NO: 510) |
| *Argiope aurantia* | MaSp2 | GGYGPGAGQQGPGSQGPGSG GQQGPGGLGPYGPSAAAAAA AA (SEQ ID NO: 511) |
| *Deinopis spinosa* | MaSp2 | GPGGYGGPGQQGPGQGQYGP GTGQQGQGPSGQQGPAGAAA AAAAAA (SEQ ID NO: 512) |
| *Nephila clavata* | MaSp2 | GPGGYGLGQQGPGQQGPGQQ GPAGYGPSGLSGPGGAAAAA AA (SEQID NO: 513) |

Fiber-forming block copolymer polypeptides from the blocks and/or macro-repeat domains, according to certain embodiments of the invention, is described in International Publication No. WO/2015/042164, incorporated by reference. Natural silk sequences obtained from a protein database such as GenBank or through de novo sequencing are broken up by domain (N-terminal domain, repeat domain, and C-terminal domain). The N-terminal domain and C-terminal domain sequences selected for the purpose of synthesis and assembly into fibers include natural amino acid sequence information and other modifications described herein. The repeat domain is decomposed into repeat sequences containing representative blocks, usually 1-8 depending upon the type of silk, that capture critical amino acid information while reducing the size of the DNA encoding the amino acids into a readily synthesizable fragment. In some embodiments, a properly formed block copolymer polypeptide comprises at least one repeat domain comprising at least 1 repeat sequence, and is optionally flanked by an N-terminal domain and/or a C-terminal domain.

In some embodiments, a repeat domain comprises at least one repeat sequence. In some embodiments, the repeat sequence is 150-300 amino acid residues. In some embodiments, the repeat sequence comprises a plurality of blocks. In some embodiments, the repeat sequence comprises a plurality of macro-repeats. In some embodiments, a block or a macro-repeat is split across multiple repeat sequences.

In some embodiments, the repeat sequence starts with a Glycine, and cannot end with phenylalanine (F), tyrosine (Y), tryptophan (W), cysteine (C), histidine (H), asparagine (N), methionine (M), or aspartic acid (D) to satisfy DNA assembly requirements. In some embodiments, some of the repeat sequences can be altered as compared to native sequences. In some embodiments, the repeat sequences can be altered such as by addition of a serine to the C terminus of the polypeptide (to avoid terminating in F, Y, W, C, H, N, M, or D). In some embodiments, the repeat sequence can be modified by filling in an incomplete block with homologous sequence from another block. In some embodiments, the repeat sequence can be modified by rearranging the order of blocks or macrorepeats.

In some embodiments, non-repetitive N- and C-terminal domains can be selected for synthesis. In some embodiments, N-terminal domains can be by removal of the leading signal sequence, e.g., as identified by SignalP (Peterson, T. N., et. Al., SignalP 4.0: discriminating signal peptides from transmembrane regions, *Nat. Methods*, 8:10, pg. 785-786 (2011).

In some embodiments, the N-terminal domain, repeat sequence, or C-terminal domain sequences can be derived from *Agelenopsis aperta, Aliatypus gulosus, Aphonopelma seemanni, Aptostichus* sp. AS217, *Aptostichus* sp. AS220, *Araneus diadematus, Araneus gemmoides, Araneus ventricosus, Argiope amoena, Argiope argentata, Argiope bruennichi, Argiope trifasciata, Atypoides riversi, Avicularia juruensis, Bothriocyrtum californicum, Deinopis Spinosa, Diguetia canities, Dolomedes tenebrosus, Euagrus chisoseus. Euprosthenops australis, Gasteracantha mammosa, Hypochilus thorelli, Kukulcania hibernalis, Latrodectus hesperus, Megahexura fulva, Metepeira grandiosa, Nephila antipodiana, Nephila clavata, Nephila clavipes, Nephila madagascariensis, Nephila pilipes, Nephilengys cruentata, Parawixia bistriata, Peucetia viridans, Plectreurys tristis, Poecilotheria regalis, Tetragnatha kauaiensis,* or *Uloborus diversus.*

In some embodiments, the silk polypeptide nucleotide coding sequence can be operatively linked to an alpha mating factor nucleotide coding sequence. In some embodiments, the silk polypeptide nucleotide coding sequence can be operatively linked to another endogenous or heterologous secretion signal coding sequence. In some embodiments, the silk polypeptide nucleotide coding sequence can be operatively linked to a 3×FLAG nucleotide coding sequence. In some embodiments, the silk polypeptide nucleotide coding sequence is operatively linked to other affinity tags such as 6-8 His residues (SEQ ID NO: 520).

Silk-Like Polypeptides

In some embodiments, the *P. pastoris* strains disclosed herein have been modified to express a silk-like polypeptide. Methods of manufacturing preferred embodiments of silk-like polypeptides are provided in WO 2015/042164, especially at Paragraphs 114-134, incorporated herein by reference. Disclosed therein are synthetic proteinaceous copolymers based on recombinant spider silk protein fragment sequences derived from MaSp2, such as from the species *Argiope bruennichi.* Silk-like polypeptides are described that include two to twenty repeat units, in which a molecular weight of each repeat unit is greater than about 20 kDa. Within each repeat unit of the copolymer are more than about 60 amino acid residues that are organized into a number of "quasi-repeat units." In some embodiments, the repeat unit of a polypeptide described in this disclosure has at least 95% sequence identity to a MaSp2 dragline silk protein sequence.

In some embodiments, each "repeat unit" of a silk-like polypeptide comprises from two to twenty "quasi-repeat" units (i.e., $n_3$ is from 2 to 20). Quasi-repeats do not have to be exact repeats. Each repeat can be made up of concatenated quasi-repeats. Equation 1 shows the composition of a repeat unit according the present disclosure and that incorporated by reference from WO 2015/042164. Each silk-like polypeptide can have one or more repeat units as defined by Equation 1.

$$\text{(Equation 1)}$$
$$\text{(SEQ ID NO: 514)}$$
$$\{GGY\text{-}[GPG\text{-}X1]_{n1}\text{-}GPS\text{-}(A)_{n2}\}_{n3}.$$

The variable compositional element $X_1$ (termed a "motif") is according to any one of the following amino acid sequences shown in Equation 2 and $X_1$ varies randomly within each quasi-repeat unit.

$$\text{(Equation 2)}$$
$$\text{(SEQ ID NO: 515)}$$
$$X_1 = SGGQQ$$
or $$\text{(SEQ ID NO: 516)}$$
GAGQQ
or $$\text{(SEQ ID NO: 517)}$$
GQGPY
or $$\text{(SEQ ID NO: 518)}$$
AGQQ
or

SQ

Referring again to Equation 1, the compositional element of a quasi-repeat unit represented by "GGY-[GPG-X$_1$]$_{n1}$-GPS" (SEQ ID NO: 521) in Equation 1 is referred to a "first region." A quasi-repeat unit is formed, in part by repeating from 4 to 8 times the first region within the quasi-repeat unit. That is, the value of n1 indicates the number of first region units that are repeated within a single quasi-repeat unit, the value of n1 being any one of 4, 5, 6, 7 or 8. The compositional element represented by "(A)$_{n2}$" (SEQ ID NO: 522) (i.e., a polyA sequence) is referred to as a "second region" and is formed by repeating within each quasi-repeat unit the amino acid sequence "A" $n_2$ times (SEQ ID NO: 522). That is, the value of $n_2$ indicates the number of second region units that are repeated within a single quasi-repeat unit, the value of $n_2$ being any one of 6, 7, 8, 9, 10, 11, 12, 13, 14, 15, 16, 17, 18, 19, or 20. In some embodiments, the repeat unit of a polypeptide of this disclosure has at least 95% sequence identity to a sequence containing quasi-repeats described by Equations 1 and 2. In some embodiments, the repeat unit of a polypeptide of this disclosure has at least 80%, or at least 90%, or at least 95%, or at least 99% sequence identity to a sequence containing quasi-repeats described by Equations 1 and 2.

In additional embodiments, 3 "long" quasi repeats are followed by 3 "short" quasi-repeat units. Short quasi-repeat units are those in which n$_1$=4 or 5. Long quasi-repeat units are defined as those in which n$_1$=6, 7 or 8. In some embodiments, all of the short quasi-repeats have the same $X_1$ motifs in the same positions within each quasi-repeat unit of a repeat unit. In some embodiments, no more than 3 quasi-repeat units out of 6 share the same $X_1$ motifs.

In additional embodiments, a repeat unit is composed of quasi-repeat units that do not use the same $X_1$ more than two occurrences in a row within a repeat unit. In additional embodiments, a repeat unit is composed of quasi-repeat units where at least 1, 2, 3, 4, 5, 6, 7, 8, 9, 10, 11, 12, 13, 14, 15, 16, 17, 18, 19 or 20 of the quasi-repeats do not use the same X; more than 2 times in a single quasi-repeat unit of the repeat unit.

Thus, in some embodiments, provided herein are strains of yeast that recombinantly express silk-like polypeptides with a reduced degradation to increase the amount of full-length polypeptides present in the isolated product from a cell culture. In some embodiments, the strain expressing a silk-like polypeptide is a *P. pastoris* strain comprises a PAS_chr4_0584 knock-out and a PAS_chr3_1157 knock-out.

EQUIVALENTS AND SCOPE

Those skilled in the art will recognize, or be able to ascertain using no more than routine experimentation, many equivalents to the specific embodiments in accordance with the invention described herein. The scope of the present invention is not intended to be limited to the above Description, but rather is as set forth in the appended claims.

In the claims, articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or all of the group members are present in, employed in, or otherwise relevant to a given product or process.

It is also noted that the term "comprising" is intended to be open and permits but does not require the inclusion of additional elements or steps. When the term "comprising" is used herein, the term "consisting of" is thus also encompassed and disclosed.

Where ranges are given, endpoints are included. Furthermore, it is to be understood that unless otherwise indicated or otherwise evident from the context and understanding of one of ordinary skill in the art, values that are expressed as ranges can assume any specific value or subrange within the stated ranges in different embodiments of the invention, to the tenth of the unit of the lower limit of the range, unless the context clearly dictates otherwise.

All cited sources, for example, references, publications, databases, database entries, and art cited herein, are incorporated into this application by reference, even if not expressly stated in the citation. In case of conflicting statements of a cited source and the instant application, the statement in the instant application shall control.

Section and table headings are not intended to be limiting.

Examples

Below are examples of specific embodiments for carrying out the present invention. The examples are offered for illustrative purposes only, and are not intended to limit the scope of the present invention in any way. Efforts have been made to ensure accuracy with respect to numbers used (e.g., amounts, temperatures, etc.), but some experimental error and deviation should, of course, be allowed for.

The practice of the present invention will employ, unless otherwise indicated, conventional methods of protein chemistry, biochemistry, recombinant DNA techniques and pharmacology, within the skill of the art. Such techniques are explained fully in the literature. See, e.g., T. E. Creighton, Proteins: Structures and Molecular Properties (W.H. Freeman and Company, 1993); A. L. Lehninger, Biochemistry (Worth Publishers, Inc., current addition); Sambrook, et al., Molecular Cloning: A Laboratory Manual (2nd Edition, 1989); Methods In Enzymology (S. Colowick and N. Kaplan eds., Academic Press, Inc.); Remington's Pharmaceutical Sciences, 18th Edition (Easton, Pennsylvania: Mack Publishing Company, 1990); Carey and Sundberg Advanced Organic Chemistry 3rd Ed. (Plenum Press) Vols A and B (1992).

Example 1: Production of Recombinant Yeast Expressing 18B

First, we transformed a strain of *P. pastoris* to abrogate KU70 function to facilitate further editing and engineering. A HIS+ derivative of *Pichia pastoris* (*Komagataella* phaffii) strain GS115 (NRRL Y15851) was electroporated with a DNA cassette consisting of homology arms flanking a zeocin resistance marker and targeting the KU70 locus. A map of the cassette is shown in FIG. 1, and sequences are provided in Table 10. Transformants were plated on YPD agar plates supplemented with zeocin. This resulted in abrogation of KU70 function.

Then, we modified this strain to express a recombinant gene encoding a silk-like polypeptide. A HIS+ derivative of *Pichia pastoris* (*Komagataella phaffii*) strain GS115 (NRRL Y15851) was transformed with a recombinant vector (SEQ ID NO: 462) to cause expression and secretion of a silk-like polypeptide ("18B") (SEQ ID NO: 463). Transformation was accomplished by electroporation as described in PMID 15679083, incorporated by reference herein.

Each vector includes an 18B expression cassette with the polynucleotide sequence encoding the silk-like protein in the recombinant vectors flanked by a promoter (pGCW14) and a terminator (tAOX1 pA signal). The recombinant vectors further comprised dominant resistance markers for selection of bacterial and yeast transformants, and a bacterial origin of replication. The first recombinant vector included targeting regions that directed integration of the 18B polynucleotide sequences immediately 3' of the AOX2 loci in the *Pichia pastoris* genome. The resistance marker in the first vector conferred resistance to G418 (aka geneticin). The second recombinant vector included targeting regions that directed integration of the 18B polynucleotide sequences immediately 3' of the TEF1 loci in the *Pichia pastoris* genome. The resistance marker in the second vector conferred resistance to Hygromycin B.

Example 2: Generating a Library of Single Protease KO Mutants

After successful transformation and secretion of 18B in a recombinant *Pichia pastoris* strain, 65 open reading frames (ORFs) encoding proteases were individually targeted for deletion (Table 2). Cells were transformed with vector comprising a DNA cassette with ~1150 bp homology arms flanking a nourseothricin resistance marker. A plasmid map comprising the nourseothricin resistance marker is shown in FIG. 2, and sequences provided in Table 11.

Homology arms used for each target were amplified by the primers provided in Table 7, and inserted into the nourseothricin resistance plasmid. Homology arms were inserted into the nourseothricin plasmid to generate cassettes comprising a nourseothricin resistance marker flanded by 3' and 5' homology arms to the target protease as shown in FIG. 3A and FIG. 3B. In FIG. 3A, the resistance cassette (Nour Resistance Cassette) is shown flanked by homology arms (HA1 and HA2). In FIG. 3B, details of the nourseothricin marker are shown, including the promoter from ILV5 gene from *Saccharomyces cerevisiae* (pILV5), the Nourseothricin acetyltransferase gene from *Streptomyces noursei* (nat), and the polyA signal from CYC1 gene from *Saccharomyces cerevisiae*.

The homology arms in each vector targeted one of the 65 desired protease loci as provided in Table 2. Transformants were plated on YPD agar plates supplemented with nourseothricin, and incubated for 48 hours at 30° C.

TABLE 2

| Proteases targeted for deletion in *P. Pastoris* strain | | |
| --- | --- | --- |
| Protease Gene Symbol | Protease ORF Sequence (SEQ ID NO:) | Protease polypeptide sequence (SEQ ID NO:) |
| PAS_chr4_0584 (YPS1-1) | 1 | 67 |
| PAS_chr3_1157 (YPS1-2) | 2 | 68 |
| PAS_chr3_0299 (YPS1-3) | 3 | |
| PAS_chr3_0303 | 4 | |
| PAS_chr3_0866 | 5 | |
| PAS_chr3_0394 | 6 | |
| PAS_chr1-1_0379 (MCK7) | 7 | |
| PAS chr1-1 0174 | 8 | |
| PAS chr1-1 0226 | 9 | |
| PAS_chr3_1087 | 10 | |
| PAS_chr3_0076 | 11 | |
| PAS_chr3_0691 | 12 | |
| PAS_chr3_0815 | 13 | |
| PAS_chr1-4_0164 | 14 | |
| PAS_chr3_0979 | 15 | |
| PAS_chr3_0803 | 16 | |
| PAS_chr2-1_0366 | 17 | |
| PAS_chr3_0842 | 18 | |
| PAS_chr1-3_0195 | 19 | |
| PAS_chr1-4_0052 | 20 | |
| PAS_chr2-2_0057 | 21 | |
| PAS_chr1-3_0150 | 22 | |
| PAS_chr1-3_0221 | 23 | |
| PAS_FragD_0022 | 24 | |
| PAS_chr2-1_0159 | 25 | |
| PAS_chr2-1_0326 | 26 | |
| PAS_chr1-4_0611 | 27 | |
| PAS_chr1-1_0274 | 28 | |
| PAS_chr4_0834 | 29 | |
| PAS_chr3_0896 | 30 | |
| PAS_chr3_0561 | 31 | |
| PAS_chr3_0633 | 32 | |
| PAS_chr4_0013 | 33 | |
| PAS_chr2-1_0172 | 34 | |
| PAS_chr1-4_0251 | 35 | |
| PAS_chr4_0874 | 36 | |
| PAS_chr3_0513 | 37 | |
| PAS_chr1-1_0127 | 38 | |
| PAS_chr4_0686 | 39 | |
| PAS_chr2-2_0056 | 40 | |
| PAS_chr2-2_0159 | 41 | |
| PAS_chr3_0388 | 42 | |
| PAS_chr3_0419 | 43 | |
| PAS_chr1-3_0258 | 44 | |

TABLE 2-continued

| | Proteases targeted for deletion in *P. Pastoris* strain | |
|---|---|---|
| Protease<br>Gene<br>Symbol | Protease<br>ORF<br>Sequence<br>(SEQ ID<br>NO:) | Protease<br>polypeptide<br>sequence<br>(SEQ ID<br>NO:) |
| PAS_chr4_0913 | 45 | |
| PAS_chr1-1_0066 | 46 | |
| PAS_chr2-2_0310 | 47 | |
| PAS_chr1-3_0261 | 48 | |
| PAS_chr2-1_0546 | 49 | |
| PAS_chr2-2_0398 | 50 | |
| PAS_chr4_0835 | 51 | |
| PAS_chr1-1_0491 | 52 | |
| PAS_chr2-1_0447 | 53 | |
| PAS_chr1-3_0053 | 54 | |
| PAS_chr3_0200 | 55 | |
| PAS_chr1-3_0105 | 56 | |
| PAS_chr3_0635 | 57 | |
| PAS_chr4_0503 | 58 | |
| PAS_chr2-1_0569 | 59 | |
| PAS_chr3_1223 | 60 | |
| PAS_chr2-1_0597 | 61 | |
| PAS_chr1-1_0327 | 62 | |
| PAS_chr2-2_0380 | 63 | |
| PAS_chr3_0928 | 64 | |
| PAS_chr1-3_0184 | 65 | |

Example 3: Testing Single Protease Knockout Clones for Reduced Protein Degradation Resulting clones were inoculated into 400 µL of Buffered Glycerol-complex Medium (BMGY) in 96-well blocks, and incubated for 48 hours at 30° C. with agitation at 1,000 rpm. Following the 48-hour incubation, 4 µL of each culture was used to inoculate 400 µL of BMGY in 96-well blocks, which were then incubated for 48 hours at 30° C. Guanidine thiocyanate was added to a final concentration of 2.5M to the cell cultures to extract the recombinant protein. After a 5 minute incubation, solutions were centrifuged and the supernatant was sampled and analyzed by western blot.

Western blot data for a representative clone of each protease knock-out is shown in FIG. 4. Single protease deletions showed no discernable impact on the distribution of 18B silk fragments detected via western blot.

Example 4: Generating a Library of Protease Double Knock-Outs

In addition to the individual KOs, different pair-wise combinations of proteases were knocked out. These proteases were selected, in part, because they were paralogs that may have compensatory function with respect to each other.

To generate double knockouts, nourseothricin resistance was eliminated from the single protease knock-out strains produced in Example 2, and a second protease deleted by transformation with a second nourseothricin resistance cassette as provided in Example 2. Transformants were plated on YPD agar plates supplemented with nourseothricin, and incubated for 48 hours at 30° C. Double protease knock-outs tested are provided in Table 3.

TABLE 3

| | Protease double KO strains of *P. Pastoris* expressing silk-like polypeptide | | | |
|---|---|---|---|---|
| Double<br>KO<br>Strain | Protease<br>KO 1 | ORF<br>SEQ<br>ID NO: | Protease<br>KO 2 | ORF<br>SEQ<br>ID NO: |
| 1 | PAS_chr1-1_0379 | 7 | PAS_chr3_0299 | 3 |
| 2 | PAS_chr3_0394 | 6 | PAS_chr3_0303 | 4 |
| 3 | PAS_chr4_0584 | 1 | PAS_chr3_1157 | 2 |
| 4 | PAS_chr3_0076 | 11 | PAS_chr1-4_0164 | 14 |
| 5 | PAS_chr4_0584 | 1 | PAS_chr3_0299 | 3 |
| 6 | PAS_chr1-3_0195 | 19 | PAS_chr1-4_0289 | 66 |
| 7 | PAS_chr3_0896 | 30 | PAS_chr2-2_0310 | 47 |
| 8 | PAS_chr3_0394 | 6 | PAS_chr3_1157 | 2 |

Example 5: Testing Double Protease Knockout Clones for Reduced Protein Degradation Resulting clones were inoculated into 400 µL of Buffered Glycerol-complex Medium (BMGY) in 96-well blocks, and incubated for 48 hours at 30° C. with agitation at 1,000 rpm. Following the 48-hour incubation, 4 µL of each culture was used to inoculate 400 µL of BMGY in 96-well blocks, which were then incubated for 48 hours at 30° C. Guanidine thiocyanate was added to a final concentration of 2.5M to the cell cultures to extract the recombinant protein. After a 5 min incubation, solutions were centrifuged and the supernatant was sampled and analyzed by western blot.

FIG. 5 shows representative results from different protease double knockout strains. As shown, despite the presence of protein degradation in all single knockout strains tested, the combination of PAS_chr4_0584+PAS_chr3_1157 protease knockout (Strain 3 from Table 3) resulted in the near-complete elimination of 18B degradation products. None of the other combinations of proteases resulted in the elimination of degradation products.

Example 6: Additional Protease Knock-Out Strains

As shown in Examples 4 and 5, a modified *Pichia pastoris* cell capable of producing a desired protein (e.g., 18B) was transformed to delete proteases at PAS_chr4_0584 and PAS-_chr3_1157 to mitigate degradation of the desired protein. We further knocked out one or more additional proteases to enhance the production of full-length products and minimize degradation.

For each additional knockout, an additional protease gene was deleted from a single protease KO (1×KO), double protease KO (2×KO), triple protease KO (3×KO), or quadruple protease KO (4×KO) by transformation with a nourseothricin resistance cassette with homology arms targeting the desired gene as provided in Example 2. The protease genes knocked out in each strain are shown in Table 4:

TABLE 4

| | 2X-5X KO Strains |
|---|---|
| KO Strain | Protease Genes Knocked Out |
| 2X KO | PAS_chr4_0584 (YPS1-1)<br>PAS_chr3_1157 (YPS1-2) |
| 3X KO | PAS_chr4_0584 (YPS1-1)<br>PAS_chr3_1157 (YPS1-2)<br>PAS_chr3_0688 (YPS1-5) |
| 4X KO | PAS_chr4_0584 (YPS1-1)<br>PAS_chr3_1157 (YPS1-2) |

TABLE 4-continued 2X-5X KO Strains

| KO Strain | Protease Genes Knocked Out |
|---|---|
| 5X KO | PAS_chr3_0688 (YPS1-5) |
| | PAS_chr1-1_0379 (MCK7) |
| | PAS_chr4_0584 (YPS1-1) |
| | PAS_chr3_1157 (YPS1-2) |
| | PAS_chr3_0688 (YPS1-5) |
| | PAS_chr1-1_0379 (MCK7) |
| | PAS_chr3_0299 (YPS1-3) |

The resulting cells were isolated on selective media plates (by auxotrophy or antibiotic resistance marker) and individual clones were isolated for further testing. Individual clones were tested by liquid culture assay under product protein producing conditions as follows: Isolated colonies of each strain were inoculated into 400 μL of Buffered Glycerol-complex Medium (BMGY) in 96-well blocks, and incubated for 48 hours at 30° C.' with agitation at 1,000 rpm. Following the 48-hour incubation, 4 μL of each culture was used to inoculate either 400 μL of BMGY or 400 μL of YPD (Yeast Extract Peptone Dextrose Medium) in 96-well blocks, which were then incubated for 48 hours at 30° C. with agitation at 1,000 rpm.

Protein expressed by the cells was isolated and analyzed for degradation as follows: Guanidine thiocyanate was added to a final concentration of 2.5M to the cell cultures to extract the recombinant protein. After a 5 min incubation, solutions were centrifuged and the supernatant was sampled and analyzed by western blot.

FIG. 6 shows the results of a Western Blot of purified protein from the 2×KO, 3×KO, 4×KO and 5×KO strains inoculated in BMGY or YPD. As shown, the deletion of additional protease genes from the strain having the PAS_chr4_0584+PAS_chr3_1157 protease knockout (Strain 3 from Table 3) resulted in the further elimination of 18B degradation products.

Other Embodiments

It is to be understood that the words which have been used are words of description rather than limitation, and that changes may be made within the purview of the appended claims without departing from the true scope and spirit of the invention in its broader aspects.

While the present invention has been described at some length and with some particularity with respect to the several described embodiments, it is not intended that it should be limited to any such particulars or embodiments or any particular embodiment, but it is to be construed with references to the appended claims so as to provide the broadest possible interpretation of such claims in view of the prior art and, therefore, to effectively encompass the intended scope of the invention.

All publications, patent applications, patents, and other references mentioned herein are incorporated by reference in their entirety. In case of conflict, the present specification, including definitions, will control. In addition, section headings, the materials, methods, and examples are illustrative only and not intended to be limiting.

Sequence Listing

TABLE 5

SEQUENCE LISTING
Open reading frame nucleotide sequence for proteases targeted for deletion in *P. pastoris*

| Protease Gene Symbol/ Locus tag | SEQ ID NO: | Open reading frame nucleotide sequence (5' to 3') |
|---|---|---|
| PAS_chr4_0584 | 1 | atgttgaaggatcagttcttgttatgggttgctttgatagcgagcgtaccggtttccggcgtgatggcagctcctagcgagt ccgggcataacacggttgaaaaacgagatgccaaaaacgttgttggcgttcaacagttggacttcagcgttctgaggggtga ttccttcgaaagtgcctcttcagagaacgtgcctcggcttgtgaggagagatgacacgctagaagctgagctaatcaaccag caatcattctacttgtcacgactgaaagttggatcacatcaagcggatattggaatcctagtggacacaggatcctctgatt tatgggtaatggactcggtaaacccatactgcagtagccgttcccgcgtgaagagagatatacacgatgagaagatcgccga atgggatcccatcaatctcaagaaaaatgaaacttctcagaataaaaatttttggggattggctcgttggaactagcactagt tctccttccaccgccacggcaactggtagtggtagtggtagtggtagtggtagtggtagtggtagtgctgccacagccgtat cggtaagttctgcacaggcaacattggattgctctacgtatggaacgtttgatcacgctgattcctcgacgttccatgacaa taatacagacttttttcatctcatacgctgataccacttttgcttcaggaatctggggttatgacgacgtcattatcgacggc atagaggtgaaagaacttttccttcgccgttgcagacatgaccaattcctctattggtgtgttaggtattggactgaaaggcc tagaatccacatatgctagtgcatcttcggtcagtgaaatgtatcagtatgacaatttgccagccaagatggtcaccgatgg gttgatcaacaaaaatgcatactccttgtacttgaactccaaggacgcctcaagtggttccatcctctttggaggtgtggat catgaaaaatattcgggacaattgttgacagttccagtcatcaacacactcgcttccagtggttacagagaggcaattcgtt tacaaattactttaaatggaatagatgtgaaaaagggttctgaccagggaactcttttacaagggagatttgctgcattatt ggactctggagctacgctaacgtatgctccttcttctgtttttaaattcaattggccggaacctgggcggctcctatgattcg tcaagacaagcttataccattcgttgtgtttctgcatcagataccacttctctggtattcaattttggggggtgctacagtgg aagtttccctgtacgatctacagattgcaacatattacaccggggggaagtgccacgcaatgtcttattggaatattcagctc tggaagtgatgagtttgtgctcggtgataccttcttgaggtcagcctacgtggtttacgatcttgatgggcttgaagtgtcg cttgcccaagccaacttcaacgaaaccgattctgatgttgaggctattacctccagtgtaccttccgctactcgtgcatccg gatacagttctcacatggtctggttctgccagcggtacagtttacacttcggttcagatggaatccggtgctgcttccagctc caactcttctggatcgaatatgggttcctcttcctcatcgtcctcttcatcgtcctcgacttccagtggagacgaagaagga gggagctccgccaacaggtcccccttcagctacctttctctctgtttggtagttattctcggcgtgtgtatagtatag |
| PAS_chr3_1157 | 2 | atgatcatcaaccacttggtattgacagccctcagcattgcactagcaagtgcgcaactccaatcgcctttcaaggctaaca agttgccattcaaaaagtttatcattccaacgacccaaaggaccgtttaattaagagagatgactacgagtccctcgacttg agacacatcggagtcttgtacactgcagagatccaaattggatctgacgaaactgaaattgaggtcattgtcgacactggtt ctgccgacttgtgggtcatcgattccgacgctgccgtctgtgagttatcctacgatgagattgaggcgcaatagcttttcctc ggcttctgccaaattcatggacaagatagctcctccatcacaaagagctcctggatgggctgagtgagtttggatttgctctc gatggtgaaatttctcaatacctagccgataaatctggacgtgtttcgaaaagagaggaaaatcaacaagatttcaacatta accgtgacgagcctgtgtgtgaacagtttggttccttcgattctagttcttccgacactttccaaagcaacaattcagcttt tggtattgcttaccttgatggaaccactgctaacggaacttgggtcagggacacagtccgcatcggcgactttgccatcagc caacagagttttgccttagtcaacatcacagataactacatgggaatcttgggtctcggtcctgctacccaacaaaccacca atagtaacccaattgcagcaaacagatttacttatgatggtgttgtgttggattcattgcggtcccaaggatttatcaattcagc |

TABLE 5-continued

SEQUENCE LISTING
Open reading frame nucleotide sequence for proteases targeted for deletion in *P. pastoris*

| Protease Gene Symbol/ Locus tag | SEQ ID NO: | Open reading frame nucleotide sequence (5' to 3') |
|---|---|---|
| | | atcgttttctgtttacttgtctccagatgaagataacgagcacgacgaattcagcgacggagaaattttatttggtgctatt gatagggccaagatagacgggccatttagactttcccatatgtcaatccttacaaaccagtttaccccgatcaatatactt cctacgttacagtgtccacaattgcggtgtcttcgtcagatgaaactctcattattgaaagacgtcctcgtttggcattaat cgatacaggtgccaccttctcctatttgccaacctacccattgattcgtttagcgttttccatccatggaggctttgaatat gtttctcaattgggactatttgtcattcgtacaagttctctgtctgttgctagaaataaggtgattgagttcaagtttggtg aagacgttgtgatccaatccccagtttctgatcatctattggacgtctcaggcctttttactgatggccaacaatactccgc attaactgtacgtgaaagtcttgacggactttccattctaggtgatacattcatcaaatcggcctacttattctttgacaat gaaaacagccagctgggtattggtcagatcaacgtcactgatgacgaggatattgaggtggtcggtgatttcactattgaac gagacccagcctactcctctacttggtctagcgatttacctcatgaaacacccactagggctttgagtactgcttcaggggg aggccttggtaccggaataaaacacggccacaagtcgtgcaagttctcgttccacatctggctctacttcacgaacttcttct acatctggctctgcttctggtacttcttcaggtgcatcttctgctactcaaaatgacgaaacatccactgatcttggagctc cagctgcatctttaagtgcaacgccatgtcttttgccatcttgctgctcatgttgtag |
| PAS_chr3_0299 | 3 | atgaaccctagcagccttaattctacttgcactcagcattggctactccattgctgagtcaaatttctcttttcaaacccagca agttacctctcaaaaaacatcgtgattcttcttccccgcatgaacgatttcttaaacgagatggaccctatcatccgctaga agccgacgcttacttttactacactacgtctatattggttggatcagaagaagaaaaagttgaagtaacagttgatttagga acctctgattatgggtcgtcgattacaacaccggtttatgtgatagatcctttgacgaaacctatcttaaacgtagtctgg atacttctgaggaagattattctgctggagatcttggctcctcagtcggtgtacgcagcgctagaaaattcttgcgcaaaag ggacaccaatcaaactgaggttaatgaagctaactatggtgcttgtccaaattcgattacctttcaatccagaaaactcgtct tctttccagagtaatgatactgctttcaatatcagctactttgatggaaccagtgctagtggttttttgggctactgatacaa tttactttggtgaccttgaggtcagcgagcaatttttttgggctggcaaacttaacaataagttatggaggagtcttaggtct tggcccttccaacctacaaacaaccaatgctaaccccaacggtgaggaattcattacagcggagtcttagattccatgcgt gatcaagggcttatcaactcggcttctttctcaatctatctcaatccagagaatttcagagatgaagataactattctaatg aaggagcgattttgttcggagcaattgataatgcgaagattgacgggtcattgaagctgttaccatacgtgacttcaggtgg acactctcagattgatgctaatttcacttacatcaccttgaataatattgccgtggctgacaatgatacagccctgatcgtt gagaccaacccccaattggcaatgttgaatccaaagtttatatacacctattttccaaacgaagtattgacccggctggtaa actctattgaatatgatcctgttgaggggttatatggaaggagaacaaacattaggggattattaacaaaaa aatcatagagtttcaatttggtgacgagattgtgatacattctcccttatcaaattatctgtctgatacatgggttccaagc acaaactacacctatttggagattcaggatagcagagaggagtttctttatccttggtaatgcattttttcaagtctgcgtatt tgtttttttgacaatgataacagtgaagtcggtattggccaactaaaggttaccgataaggaggacatcgttccagttggtga attttctttggatcaagattcagggtactcgtcaacctggtcaacgttctcctatgaaactggttcagctcccttgggtacg tcaactttcgaaacgagtacaaaaaactagttcagatggagctgccccgtcggtgtctcacattaacactagttcctacttat ttgcgtttgtactactttttcctttag |
| PAS_chr3_0303 | 4 | atgttgcccatccgcttatccaaacttctgcttttgctctccttaaagttgaaattgggtacagctgaagaaaaataccaaa agttggattttaaaaagaattgacaaagactattatgccgtcgatgtcaaagtcggctccgatgagcaggagatcaaagaggt actaatagatacgggttcatctgatttctggatcttggacaaatcgttctgtaattctccaacatcagaggaagaagagaac agtaacgggcgtagcaacaaggaaagctgtggagtctatggctcgttcgactccaacaagtcagagacatttcaggcaactg gccaagtatttgacgctgcttacggtgacaccacagcccgagtcgacaggatcttcaggagttcgaggaattgatcagctacg ggtaggagatattcatatagaagaactctattttggactagtgacaaacactacaagtttaccaccgttttaggaattgcc cagctttccgaagagttcagcaacaactcttatcctaactttccataccagatgaaagaggaaggtctgattgatgttgttg catactctctctccttgggccaaagtaaaggtgaactactgttcggggctatggaccactcaaaatataatggaacactatt gaaagcccctatattgcaggcgggcacaccaggaatgcaaatgtcttttaactgagtggccttacaaatggttcatcaagc gtcttcaatgagacagacaataaaggtttttatctactttgacagtgggactactgcttccactctgccatcagagcactttg atgatctttcaaccatcacggatgggcgtacgatggtgatacattgacatattcgattcaatgcgatagtgagggagaaaa atctttacttgacttcacttttagaatataccattgctggtaatattgtcatcaaagtaccatttgaagacattattatgaag aatgaaaatggagaatgcctctcaaccgtaatggtgcgaaccagacttctttttcatattccgatgacacacccttttt tcgttgctggagacgaagttctgttgaacgcttatgttgtttacaacctagaaacacaagagctggccattgctccagcagt ggataatccagaagatactgaagaagatattgagattatctccgcagactttgatattcagaagccagagattatagcgtt ggattagagttcagaaataccacaattccagctacaactgattacttgccttcctcgatgtcgtcaggttcagtcagcgaag agactggttccaagtctgagagctctacttctgaggactttgctgcagccacgttgaaaccatttacattttggggtttcgt cctttttttcttcacttttttgatttga |
| PAS_chr3_0866 | 5 | atgttagttgctgttgccctagtgttgttactgtctacaggctatgctggaatcgtcgccattgataccgaatatgagttca ccattggtttttcttagtacgatagaaatagggtttcccccacaaagcataacggctcaatgggatacaggatcgtctgacct cttggtcaattccgtgacaaattcacagtgtgctcaggacggatgtagctttggtgcgttcggccttcaacaaatccaccact tattccaatataacaaaccctaacaaccttcatgttcagttctccttttgcaagcggcagcgtggttgatgacaaacttgtga gtgacactatttttgtagattccaaggtaatcccacggttcaactttgcactggtatcgaagggagacctgtatggtgataa tatttttggtattggaccgagagggaaccagggaacattcgattccaatggaactccagctttctatgatagctttccttat cacttgaaggccctcggtttaatcaaacgactggcttactcattttacactgggcccaccaggggaaagggagtatttggag gggtggatcatggaaagtacgatgggtgcctggagaaactcgagattgtccatgacagtgcttttttacacactgcttgaggc aattgatgctgatgatacttccgtcttggatgagcaaattcatgtttttgtttgatactggtaccgccttgacactttttccc agctttattgctgaacaactggctgattttttgaaagctacatattcggacgaatacaatacgtttgtagttccctgcgacc aagatttgatttgaatacctcattttggtttttcgaaacattaagttgtcggtgcgcttttaaggatctgtttttttagtcat tgacgatagtgtttgtgctgtggggtttgatcaaggggcagatgcaaacaagataaccttgggtcttcacttttaagaaac tactacacgctttatgatctagattccaaagaaattttgattgctgacgtcaagcctgatggtccagacgatattgaaatat tatcgggtccagttcaacgaatttgtgatgaaaagggtgtcagtagcacttcattatggagtagtctgagtatagagtccac gataaacagacacttttaccactaagcctctatttcccagacacggtattcgactagctccattggacctcaaaacatt tctaactctttaggtgaatatccttcagtttccgtcactctcttctgaacaccatacaactacttccatagcctcaaattcct cattagaagggaaaccagcaactccaactgttacagaccagtcgtaccagaataataagactacctctaccgtaattgctgt gaatttgattacccattcaaccactcattcaaccactcattcacccacctattcaaccactcattctagtaatggatcacgc tcaactttagagtacacttcaaccaaggaatcctcggtgaaaatgccctgtgcgttgatcatctccgacacaattccgtaca atgcttccggtgggaatagtagttatggatcgttaatttcaacatctacggttaacaatgttgaagagaataattcaaacac |

TABLE 5-continued

SEQUENCE LISTING
Open reading frame nucleotide sequence for proteases targeted for deletion in *P. pastoris*

| Protease Gene Symbol/ Locus tag | SEQ ID NO: | Open reading frame nucleotide sequence (5' to 3') |
|---|---|---|
| | | tgttagaccaagaaaaagacagacctttcgtttcgggaaccacttccacgatactactctattcctcaactacgacccaagca tatcagatgttgtcctcaacttcaatcccccgaccatccataaaagccagttcaaatgctggtagccgcaaaacttcaaaga cattattaacatttatcatattgtatatttttttag |
| PAS_chr3_0394 | 6 | atgtaccaggcgttgttggttttgtctctgatatgcttttcgtcggctaattttgttaagctgcgaagcaacgctggtatgt tttatgatactatggctggagttccacgttcagatgaagagttctggttgcgtttggatattaaccaaggtctctcttggac tctggatagtagctactactcctgtaatggctcaaatgtttcgtcttccctgtgtttcaattctgctcaaaacgtttacgat gcttccaatagtccaactgcagatttcgttgatgtctacgcaaacacaactgtaaacaatacagatgaggcatcggccgaga gagtaaatcttacaaacaacttatttgctgatggcgtttatatggaagacaattttttacgtcacattgaataatggagcaag aatgactgctacagatctgaaattttttgaatgcccacaatagtagcgccgctgtggggtctttggcgttggggagttacacc tcacaggacgtgccaactttcttacaaagactccaaagcggtggtcttattgaatccaactcgttttcattggcattaaacg aaatcgattcttcatatggagagctctatttggggacaataaaactctaccaagtatgtcgagcctctggtagaattcgattt tattccggtgtcagatcccaatggagtttttggattcgattgggaagatacattccctacagttccgatcagcggattaagc atgtcttcgaatgacaaacagagaactgtcttttttccccaatgagtgaacaacacggtcttaacgggaacatacccacttc caatgatgttagattcaagaaacatctttatccatcttccattctcttcaatcatacatatagcagtgcagcttaatgcact gtatcttgatacacttcataaatgggccgtgaactgttctgttggtcaactggacgcaactttaaactttcacatgggtaac cttaccgttcatgctcctatcaaggagttgatttatccagcataccaaggagacaaaaggctgagctttgctaatggagaag atgtttgtattcttgccatggctcctgatgtttacattggttatccactgctaggaaccccctttttaaggaatgcagtggt tgccgttaatcatgattcaaaaaaggtcgccgttgccaatcttaatagagatagcattcctcccgcttcgaacgtttctgtt tcggaatcaatgggagtttatgttcctccacctgtttcaacttcaagaacatcggagagaccgtccacactagatgagacta gtacagccaattttgacaaaagggaagagtctgcaatatcatcaagttcagtcactaacagctcgtctagaaattcttcaac cataacttcttcaggaactcaaaccgagcgaaacatacaggcatagctaccatcgaaacagatagcataccaggagctctaggg aataatttaactgattattcaacgctgactctaacaatatacaccaattccgaagtggacgaactcaatcctaacatagcaa cagcattcatttccaatggttctatttattcagagccttaccccttttccggaactgcagttgctgaatcattcagtgcatc accttcacaggctgaaggatcgaactcatcgtcctcaggatcttctttagttttgtgtttctttacatcattggccagtctg ttgactgtgagctgtctactactgtaa |
| PAS_chr1-1_0379 | 7 | atgtttgtgatccagctggcattcctatgtctaggcgtcagcctaaccactgcacaacctagttcacctttcaaggcaaata agtttccttttaaaaaggttcactactcatcaaaccctagcgatcgcctatttaagcgagacaactataagaagcttgactt gagacatcttggcgtcttgtatactgcggaaattgaaattggttcaggcaaaactgaaatcgaagttattgttgacaccgga tctgcagatttgtgggtaattgactcaaatgcagccgtatgcgattgtcctatcttgagatacaaggtacaagtgtttccac ccttagtcaaactgccaacgtaacacccctatcaggtaaacttttgaatggacttcaagaaattggcattgtaactgatggc aaaatttccaaaaagtttcaggaaaaccatctcttttgaagagaaacgaggccttgaatttgatgtcgatctgaataagccca tttgtgatcaatttggatccttcaatccacagtcatcaagaacttttcaaagcaacgacacagcatttagtatcagatatct ggacaactcttttgccaatggatcgtgggtgagggatacggtttatgttggtgattttgaaattgaccagcaaagttttgca ttggttgatatcacaaataactacatgggaattctgggccttggtccttctagtcagcagacaacaatagtgatcctacag ataacagtttcacttatcttggtattctggattctttgcgggcccaaggattcattaattcagcctcgtactcggtttatct ggccccagatggtaagactgatgatactgatcacgatgatggtgagatcctgtttggtgctatcgacgaggctaaaattaat ggacagttgaagttgttccatatgtcaatccttataaatgcgtataccctgaccaatacgcttcatacatcaccgtttcca gtattactgtagccagttattttagtagccgcttggttgaaagaatccctcaattagctctcttttagacactggtgccacatt ttcttacttgccaacttatacgctgatacgtctcgcctatgccatccatcctggttttgagtatgtccgacaactgggttta tttattatagagtcaaacgtactctccagtgcgagacaaagtaccattgacttccggtttggcaaagacgtagtaattcgat ccaatgtttcagaccatctactcgacgtatcacaatacttcacatctggacattatcttgcacttaccatccatgaaagtgt cgatgggcttctcatttgggtgacacgtttatcaagtccacctacttattttttcgacaatgataacagtgaattgggtatt ggtcagatcaaaattaccaatgacgaggatattcaagaagttggtgaattcaccttagaacgcgattcagactattcttcta catggtccatttactcttatgaaacttctttggatcccttaagcactggcactggtacggggtcaacctattctcctactcg cagtactacagctagaagcgaaccgactacgtctcgacgctccaccaccctttcaacccagaacaactgtgattccttctatt gacaggctttcattgaacagcataactagtcatggttcctctactaacggaacctccccaactaatgagacttctttttgctg aggatggaggaactttgacacccgaagaagcttcttttgacaacttcactaaattctgctactatttctgagactactttgt cgatgttgaaacttctactaccaatggtgcttcagttgtatctttgagtgttggtccctgcattattgccttcctactactc atctcttaa |
| PAS chr1-10174 | 8 | atgagcatgggagctactgtttcaaaggagtccactgtagacctaacactgccgctgttgcagctgagtccaagactgttgt tcctgcctggagttgtctacaagacgactttcaagttccaggagggggtcaacatcttgctacgtttagagacctgttcga tgagtctttttctgaaagaaatgacgttctaggtgatattgcccgctcgcagaaggaacaacaggaaaacgattatgaccat atcccttttttgagcagcaagtgctaagaagagcataggtgtcctgaaagaccaacttgaactggtgggtgctgatgacaagt cacttccctgggttattgcctgtctccctgggtcgaccagtcagacaccaggactccattgccactacaatttgtcagataac tgaggtgtccgtcgttaaccaggatattgtactatccttcgaagcattaaccagaggatctttaaaatccaaaaagaccatc tccatgaatgaatcaaccatatctgtggaagtggatataccatttactgaggttgaccagaccatcagtaacaagctcatct tgacaaatattgataaggtgtctgcaactactggagaatatcaaacagtttctagtcaccatcaaaatgacatgatgaacct tgaagatactaccatggaaaagaactcccgtctaaagtctgcaatgatgatttttggctccgttgtctcacttgatctacgcc actgtctcatctcaagaatccactcatgcttatactagactatccaaccagtacaagtccgctaagaaggaattagattcaa ccaaaaacagaaagtctttactcaagaagattttgaaaactaatgatattctcacttcagtgttcccccttcagtatggttca aaaggtggatgtcttgggagctatttcaagttctacagacaggatccaaacaactatcgacgcgttggactttgccaatcca cttttcgaaacatatttgaacgttgattatgttctggagacatgaaaagattttgacactaagaacggcaaaattgctgcca atttgaccaggtctcaattagtatctaaccacttgaagggcctcagagtactgattgaagacatccaaggaacttcaagaag gcgggtcagtccttctcagagaactcgtttggcgccttcgcccaatacaaattctgcaaatcaggcaccgaaagctggagaa tcagacgacgaaataaagaattgcgtgattttatcaacaacctctccaaattgaaagatctcgagaggatggaaagaggctcg ttaccaaagatttcaacgaatgcatcaaatgcaaccaagttcatcggagtaccaactgctcagaacttatttagagattat tatggatatcccatgggaaacaaaaaatattgtaaaacaacaaattttttgatctagacaaggccaaagaaacactagatcag gaccattacggaatggactccgtcaaagataggatcttagagtatttagcagttcttaaactccacgatcacattaaaacgt ccaaccccaagcaagaagacgaggaaatcaaagccagagcacccattctcttactaacaggtccacctggtgttggtaaaac ttcgttaggaaaatctattgcaaaggctctgaacaaaaagttccagcgagtaagtcttggaggattgaaggatgagtccgaa |

TABLE 5-continued

SEQUENCE LISTING
Open reading frame nucleotide sequence for proteases targeted for deletion in *P. pastoris*

| Protease Gene Symbol/ Locus tag | SEQ ID NO: | Open reading frame nucleotide sequence (5' to 3') |
|---|---|---|
| | | attaagggacatcgcagaacttacgttggagcaatgccaggactattgacccaagcactgaggaaatctcaatcttttgatc cagtgatacttttggatgaaattgacaaggttgtcgatggatcccaaggccctggtagtcgtgtaaacggtgatccagctgc tgctttgcttgaagtgttagacccagagcaaaattctaacttctctgaccattatatcgggttcccacttgacttgtctcgt gttgtttttatctgtacgtccaacgatatgagcatgatcagtgccccattaagggatagaatggaggttattgaactgaatg gctacaattatttcgaaaaagtggagattgttaaacaattcttattaccaaagcagatcaaaagaaacggactgcctacgaa tgccgaatcaccatcggtggttattcctgacgaagtgattatgtacatcgctgtcaattatactcgggagccaggtattcgt aatttggaacggttaataggagtatctgtcgggtaaggctattgaatactctagcttgatgagtagtactcaagctccag gcgaaattccaaagggatacgtttccaaggtcacggtagataatctttcaaagtacattggaatacccccggaattgtctac aggcaagaatatgaggaatgattcagctatctctaaaaagtacggaatcgtgaacggcctcagttacaatagtagcggacat ggaagtaccctagtctttgaaatgaccggtatacctaatagtactaacactaacatgcctacgaccggcagattgggtgatg ttcttacagaaagtgtcaagatcgcaagaacaattataagatcgatgtttagtcacaacttactacaattaaaggatgacga aacttcaacttctgggatctttgaagaggtttgacactactcaggttcacatgcatgtgcccgctggtgctattcaaaaa gacggacccagtgctggaatcaccattacgctgtgccttctgtcggtgatgctagagaaacctgtaccaaggatttggcca tgactggagagattacttgagagggatggtactgccaattggaggtgttcatggagaagctactaggagcacatttaactgg aaccgttaaaagggtgatccttccaagaagtaatcgaagagatgtcattcaagacttttatctctaacttggaagccaataac agaagttctaggataagctactggtagatcttatcaaagaggaggagtcattactgtccaactcaaatatccgaacgaa ttggagtgttcgggcttcctgaaaaatgggttcaagagaagttgggacttcaagtgagctacgtggaagaattttgggatgt tatccagattgtctggaacgatcaggttgaaattgacagcaccaaattacacgagctagctactaaagagttcgcaaggcta tga |
| PAS chr1-10226 | 9 | atgcaattgcgtcattccgttggattggctatcttatctgccatagcagtccaaggattgctaattcctaacattgagtcat tacccagccagtttggtgctaatggtgacagtgaacaaggtgtattagcccaccatggtacaaacatcctaaagttgatatggc tcaccatggaaagcatcctaaaatcgctaaggattccaagggacaccctaagctttgccctgaagctttgaagaaagatgaaa gaaggccacccttcggctccagtcattactacccattccgcttctaaaaaacttaatcccttactcttatattatagtcttca agaagggtgtcacttcagaggatatcgacttccaccgtgacttatctccactcttcatgaagagtctgtgagcaaattaag agagtcagatccaaatcactcattttttcgtttctaatgagaatggcgaaacaggttacaccggtgacttctccgttggtgac ttgctcaagggttacaccggatacttcacggatgacactttagagcttatcagtaagcatccagcagttgctttcattgaaa gggattcgagagtatttgccaccgattttgaaactcaaaacggtgctccttggggttttggccagagtctctcacagaaagcc tctttccctaggcagcttcaacaagtacttatatgatggagctggtggtgaaggtgttacttcctatgttatcgatacaggt atccacgtcactcacaaagaattccagggtagagcatcttggggtaagaccattccagctggagacgttgatgacgatggaa acggtcacggaacctcactgtgctggtaccattgcttctgaaagtgttgccaagaaggctaatgttgttgccatcaa ggtcttgagatctaatggttctggttcgatgtcagatgttctgaagggtgttgagtatgccacccaatcccacttggatgct gttaaaaagggcaacaagaaatttaagggctctaccgctaacatgtcactgggtggtggtaaatctcctgctttggaccttg cagtcaatgctgctgttaagaatggtattcactttgccgttgcagcaggtaacgaaaaccaagatgcttgtaacacctcgcc agcagctgctgagaatggccatcaccgtcggtgcatcaaccttatcagacgctagcgagctactcaccttcttttctaactacggtaaatgt gttgacatttttcgctccaggtttaaacatttctttctacctacactggttcggatgacgcaactgctaccttgtctggtactt caatggcctctcctcacattgctggtctgttgacttacttcctatcattgcagcctgctgctggatctctctgtactctaacgg aggatctgagggtgtcacacctgctcaattgaaaaagaacctcctcaagtatgcatctgtcggagtattagaggatgttcca gaagacactccaaacctcttggtttacaatggtggtggacaaaacctttcttcttctgggaaaggagacagaagacaatg ttgcttcctccgacgatactggtgagtttcactcttttgtgaacaagcttgaatcagctgttgaaaacttggcccaagagtt tgcacattcagtgaaggagctggcttctgaacttatttag |
| PAS_chr3_1087 | 10 | atgatatttgacggtactacgatgtcaattgccattggtttgctctctactctaggtattggtgctgaagccaaagttcatt ctgctaagatacacaagcatccagtctcagaaactttaaaagaggccaattttgggcagtatgtctctgctctggaacataa atatgtttctctgttcaacgaacaaaatgctttgtccaagtcgaattttatgtctcagcaagatggtttttgccgttgaagct tcgcatgatgctccacttacaaactatcttaacgctcagtattttactgaggtatcattaggtaccctccacaatcgttca aggtgattcttgacacaggatcctccaatttatgggttcctagcaaagattgtggatcattagcttgcttcttgcatgctaa gtatgaccatgatgagtcttctacttataagaagaatggtagtagctttgaaattaggtatggatccggttccatggaaggg tatgtttctcaggatgtgttgcaaattggggatttgaccattcccaaagttgattttgctgaggccacatcggagccggggt tggccttcgcttttggcaaatttgacggaatttggggcttgcttatgattcaatatcagtaaataagattgttcctccaat ttacaaggctttggaattagatctccttgacgaaccaaaatttgccttctacttgggggatacggacaaagatgaatccgat ggcggtttggccacatttggtggtgtggacaaatctaagtatgaaggaaagatcacctggttgcctgtcagaagaaaggctt actgggaggtctcttttgatggtgtaggtttgggatccgaatatgctgaattgcaaaaaactggtgcagccatcgacactgg aacctcattgattgctttgcccagtggcctagctgaaattctcaatgcagaaattggtgctaccaagggttggtctggtcaa tacgctgtggactgtgacactagagactcttgccagacttaactttaacctcgccggttacaactttaccattactccat atgactatacttggaggtttctgggtcatgtattagtgcttcaccccatggactttcctgaaccaataggtcctttggc aatcattggtgactcgttcttgagaaaatattactcagtttatgacctaggcaaagatgcagtaggtttagccaagtctatt tag |
| PAS_chr3_0076 | 11 | atgaagctctccaccaatttgattctagctattgcagcagcttccgccgttgtctcagctgctccagttgctccagccgaag aggcagcaaaccacttgcacaagcgtgcttactacaccgacacaaccaagactcacactttcactgaggttgttactgtctta ccgaactttgaaaccgggcgaaagtatcccaactgactctctcaagccacggtggtaaaagtactaaaaagggtaagggtagt accactcactctggtgctccaggagctacctctggtgctccaactgacgacaccacttcgactagtggctcagtagggttac caactagcgcaacttcagttacctcttctacctcctctgcaagtacaacaagcagtggaacttcagccactagcactggtac cggtactagcactagcactagcactggtactggtactggtactacaggcacaggaaccactagttccagcactagctcttct gctacttcgactccaacatcggttctatcgacgctatcagccacagcaacttctggatactcacaatgataagacggtttgcacg gcgtcccagaccttacttggtctaccgaaccgctgactacgcccaaggttacgccgattcatacacttgtggctcttcatt agaacacacaggtggaccatacgtgaaaattgccctctggatactctcctgctggcagtgtagaagcatggtacaacgag atcagcgactacgatttctctaacccaggttattctgctggtaccggtcacttcacccaagttgtctggaaatcaactcac agctgggctgtggatacaaggagtgcagtaccgacagatactacatcatctgcgaatacgcacctcgtggaaatattgtttc tgccggctacttcgaagacaacgtcctgcctcctgtttga |

TABLE 5-continued

SEQUENCE LISTING
Open reading frame nucleotide sequence for proteases targeted for deletion in *P. pastoris*

| Protease Gene Symbol/ Locus tag | SEQ ID NO: | Open reading frame nucleotide sequence (5' to 3') |
|---|---|---|
| PAS_chr3_0691 | 12 | Atgactgtgcaaattttgattgtagttaccagtgttgctaagtatgaaagcggaaagctgccaacaggcttgtggttaagtg agttgacacatatgtatcatagtgcaaaagagaacggctatgatgtgacgattgcgagtccgcaaggcgggaaacattccgct tgaccctgaaagcttgaaatcaatgctgattgacaagctttcaaaggattatgagacaaaccaagactttatgaagttgttg caaaacacaaaaagtttgggtgaagtcacaggacaacagtttgacgttgtttatttggcaggtggacacggaacaatgtatg actttccgaacaacactgtttttacaaaacatcatcaaagaacactatgaggcgggcaaaattgttgccgctgtatgtcacgg agtttgtgggcttttgaacgtaaaactgtctgatggcgagtatctaatcaaagacaaggccattacaggatttaattggttt gaagaagctatagcaggacgcagaaaagaagtaccgttcaaccttgaagcagaattgaataaaaaaacttcaaaatacgaga aagctttttatcccaatgacgtcaaaagtggtcgtggacgggaacttaatcacaggacagaacccattcagttcaaaagaaat tgcgaaagtggtaatggaacaactgaagcaataa |
| PAS_chr3_0815 | 13 | atgattgatgagaagcaattgaatcaacccaaaaggagcgtcttaagacgtctccatatgctgtttctgccattactagcta tctccttttcctgatatatttaagtgatatcacacagcctctcttccgtgcccgaaaggaagacgaaaacccgttggaaat ttacttgaaggcattggaaacgaatgaagctcacaaatggtcaaaggtgtacacttcgcagcctcatttggccggaaccaac tacggattggttgagtttactaagtccaaatttgaagaatatggatttgaggccagtgtcgatgactacgatgtgtacctga gttaccctattgatcatagtttggaattgtatgagcattctgaggataaaaatgacaagctcttgtataaggcttcgctgca agaggacgttctctctgaagacccaactacttcaggcgacgacctgatccctaccttccttggttacggtgctaacggcaat gtatctgcagaatacatctacgctaactatggaaccaaagaggacttttgaggattggtggcccgtggtgttccaatcaagg ggaagatcgcagtcattagatatggtcaaatatttagaggcttaaaggtgaaattgcccaagaatatggcgcaatcggtgc tgtcatatacagtgacccaggcgacgattatggtatcaccccctgaaaatggttacaagccttaccctcatggtaaagccaga aacccaagctctgtgcaaagaggttctgcccaattttttgtctgtttatcccggtgacccaaccacgccaggagttggatcga agaagggagtagaaagagttgatcctcatgctacaacccccttccattccagtcttgcctttgagtttcaaagatgccttgcc aatttttgaagaaacttaataaggaaggattgtctgttcctgactcctggaaggaggtctcgagggagttgattacagtacc ggcccagctaaaaacattcatttgaacctttatagcgaacaaaactttactattacacctatttacaatgtctatggagaga tcaaaggtgagaatgctgacgaagttatcattattggtaaccatcgtgacgcttggattaagggaggtgcttctgaccctaa cagtggatctgctgctttgattgaacttagtagaggtttgcacgccctaaccaaaacaggatggaagccacaccgtactatt gtactagcttcctgggatgctgaggaatatggcttgactggatctactgagtttggagaacagtttgagaagttccttcaga agaaggtcgttgcctatttgaacgttgacgttgctgtagctggaactcatcttcatttgggtgcctcgccatctttgttcaa actattgaaggataatgccaaagaaatcactttcaagaattcaaccgagactttgtatgacaactatgttaaagatcatggc aacgacattatttcgaccttaggaagtggaagtgactacactgtcttttttggatcatttgggaattccttcgcttgatattg gtttcattgctggaaaaagtgaccccagtatatcactatcacttcaaactatgattcgtcaccactggatacgctactagtggtga tcctggatttgagtatcataatgtactggccaaatatttgggttcgttggttttgaatctctctgagagagaggtgttgtac ctgaagcttcatgattatgctaccgaattgctcaagtacctcttggaagcctacgcccaaatgccagaggaatgggacgatg aagtaattggtttcagatcttcctcgtgtcatcgtgcgaaagcatctcatcatggtaaggatcctcatcatgagggaagacg ccatcacggaaaaggattccattctaaaggagggcctcatcatgggaacgccatcacggaaaaaggattccacgctgaaggg ggaccccaccatgagaaaggaccgcatcacgaaaaagggctccacgtcgaaggagagcccccatcatcagaaaggacctcact ttgaaaaaggattccatcatgacatggagatgtaccataagaaattggctcatcacggtaaagaacccaagacgaagctaaa gcacttgaagaaacaagttgagagtttaatcatcgatttcgccaataccactcaaacatatgacgcttacactgacttcctt cagaagcaacatgagattaggggattctctttcattctgggaagaaatcaagctacattttaagatcaaggcagctaacttca aacttaaatattttgagcgagttttccttcatgaaaatggcttaaagaacagagaatggttcaaacatattgtatatgctgc aggaaggaacactggttacgccggacaaagactgcctggtcttgtgtggaagccattgaagacaagaatctgcatgatgcagta aaatggcttcacatccttttccaagaagattgatagtctacagaagtcattagagtag |
| PAS_chr1-4_0164 | 14 | atgagattacttcacatttcattgctatcaattatctcagtattgaccaaggccaacgctgaatgttgttacaccaacacac atactaccactgaagtctggtatactacagtatatgctcgagatgttagtgaagagacttcttccacactggctggtggaag tgcaactgtcagctcagaagtgagttcgacaattgaatctagcgttgccacttccgctaccaccgaatcttcaagtgagaca tcagggtccacatctgggtccacatctgccactgaatcatcaactggtagtagctcgctcagcaaccagttcatcgataacca gttcagagtcttccaccattacacaaaaccacaggacaagagtcaacaagcccaacccatcgtcctcagagacaggttcttc tactactactccctacgatataagtccaacggcaagttccgactttgatgctctttaaatatcaaattcttgatgaacacaac ataaaaagagctctacatggagttgacggattagagtgggatgaagaagtatatgctgccgcgcccaagcatatgctgacgcat acacttgtgacggaaccttggttcactctggaaatagtctgtacggagaaaacttagcgtatggttactcaaccagagggac tgttgatgcctggtacagttgaaattgaatattgatgactttaataccaaccaggttataccccaggtgttggacattttcactcaa gtagtttggaaaagcaccacaaagctcggctgcgcgcttcaagtactgcaatgactattacggagcctacggtgatgcaact actcaccaccaggaaattatgtcaacgagggatacttcgaagccaatgtgttaccactggtagattaa |
| PAS_chr3_0979 | 15 | atgagttatccccctaggtctgggtcgtacagcttataggttcatcccgaggtcaatctgttcaagacgatccatctcatccc atgcattacctccaacgccctccaactcaccaccagcaggagatttattcaccaaactgctgaacgaacgcatccatatattt agcaggaggcattgatgatgcgcaagcaacatctatcacggctcaattgctgtatctggaatcgcagtcaacgtcgaaacaa atcaacatttacatcaactcaccaggaggttcctgtcacggcagggctggccatctcacgacacaatccagtatatccgagcgc cagtttccacggtttgcttaggacaggcatgctccatggcatcccctcttgcttgcaagcggaacgcatggcaaacgtttgat cttgccaaacgctaccataatggtgcatcaaccatcttcggcaaacggaattaagggacaggccactgatatcgagatatat gcccgtcatatcatcaataccaaacagaaattgcaaactttatacctaaaacacatgtctccaaccatgacggtggatgaaa tcactgcacttttggagagagatcggttcatggagccagaggaggcagtgtctcttggactggcggaccgtgtattagagag gaaacccccggttgtatctgactaa |
| PAS_chr3_0803 | 16 | atgacagataccaaggagttagccacgttgctggagaacttgttgaaattgcaaaaatcaggaagtcttggtgaaattgtgg gtcaagcacagcgcatttatcatgacatttctgacctctcagtcctatctggattatcaaccccagaagtgctctctcctca cacatctccagatgtccccgagagagttccatctgaagtcaattccaattttagacaattcaatctgtcaactgatgtcaacgaaaag gagaagtattttgacgattttgcaaatgactacatcgagtttacctacaagaaccccaccacctaccattggtgcaatctg tggcggaattgttgaagaaaagcggattcgaatatcttcctgaagcagctgactggtccaaattattcgaccctgaaaagac gggagcgtatttcacaatccggaatggaacctctttagctgccttcacaattggtagtttctggtccccagccaagggagta ggagctatcggaagtcacatcgatgctctcacaactaagctgaagccagtctccaataagagtaaggttgatggctacgagt tgttgggagtttcccccctatgctggtgctttgtctgacgtctggtgggatagagatttgggtattggtggaagagtaatttta |

TABLE 5-continued

SEQUENCE LISTING
Open reading frame nucleotide sequence for proteases targeted for deletion in *P. pastoris*

| Protease Gene Symbol/ Locus tag | SEQ ID NO: | Open reading frame nucleotide sequence (5' to 3') |
|---|---|---|
| | | caaaaatgaatcttccggcaagctttccaccactttggttaacagtacacctcatcctgttgctcatattccaactttggcc cctcattttggtactccctccaacggtccattcaacaaggaaacccaagcagttcccgttgtaggattttctgacggaaacg acgaggagaaacccactgaggatgaacaaaagtctcctttgattggtaagcattctttaaaactactccgctacatatctaa gctagcaggagtgccagtgtcctccttgattgatttcgatttggacatattcgatgtccaaaaaggtactaggggcggtctt tccaatgagttcatttacgccccaagagtggatgatcgtatttgttcttactctgctctacaagcgcttatcagacgtcaca aggatcccgaatcctttgtcacagacgactctttcaatcttgttgccctttatgacaacgaggagatcggatctctctccag acagggagccaaggggtggtctacttgagtcgaccatttccagagcaatcgctgcattgaaaatttcagagccagggactctg caaagactatatgcaaattcagtgattctttctgcagatgtcacacatttgttaaatcccaatttcaccgaagtgtacttgg agcaccacaagccactgccaaacacagggattgcacttgcgctggattcgaatggccatatggccacagatttgttaggcaa ggtcgttgttgagcagctggctaaactcaatgatgataaagtgcagtacttccagattcggaacgattcaaggtctggaggg accattggacccagtatttccagtagtactggcgctagaaccattgatcttggaattccccaattgtccatgcacagtattc gtgctaccgtgggatacaaagatgttggcctcgctgtcaagttttttccaagggttctttaaaaattggagaaaagttgtcga cggcattgaagagttttaa |
| PAS_chr2-1_0366 | 17 | atgacttcggtattttttgggtgtttatagagcccatttgattaccaagctcaaaatgacgaagaactaactgtgcatgaga atgatctactatacgtattggaaaagtccgaaattgatgactggtggaaagttaaacaacgagttatcggagttaatgtcga ggaaccaataggtctggtacccagtacttatattgagcctgctacacctatcgggtcagctgttgcactgtatgattatgac agacaaacagaagaagaaattactttcaaggagaatgacacctttgacgtgtacgacaccgatcaggagtggatcttgg ttggcctgaacaatatccattttggtttcgtgcctgcaaactacatacaaatttcttgggtacgacggcacctgcttctaa caatccaccaatacttagtcccgccagcttccctccacctcctcaacggatcaacaactcctctgttccctctctcaaagat gctgaaccagcaagaaatctagaggacgataatgcttatgaagaggaggaagatgtacctccaccaatgccaacgcgaccaa ctgccactacagctacatctaatatctctgctcctcaggactctgaatccgaagaggaaccttctagtagtagcagaaggcc aagtggccgttcaagggcggatgatgattttgtaaaaggagactatttcacttgggatgttcaggaaatttaatggccgcaaa aagaggaaagctgtcctgggtatcggaaatggtagtatttatgtccaagcagagggacattcttctaagaaatgggatatca ggaatttgacaaatttcagtaacgaaaaaaagcacgtcttttttgacttaccaaccccctcggcatcctatgaacttcatgc aggctccaaggacgcagcagatgccatcctgtcaattgttggtgatttgaaaggtgcttcttcaatgcgtgctttgaaagag gtgaaggctgcatcttctgccccaaaaaccaagactggtaaagtcagttacaacttcgatgctgaaagtcccgatgagttgt cgattagggagggtgatgttgtctacatattgaacgataaagaatcctctgagtggtggatagttcaggacgttaatactaa caagaaaggtgttgttccagctagctacatagagttgattagcggggggtggatctcactttagccagcattggctcttctatt tccaaaggttctaagaaagcttttggatcctccagaaaacgtaaggaaaaagagcgtaagcatttggaagagcaacgtgccg ctaaaagagaaacccgaaaagggaacgtcaaagactgctccgatccaaggaaaagggataggctaagaaagttagatgaaaagga aagaaggaaaaagcaaaaagctactccacaggatgaagaccaacccgagactagcaaacctaatcctcatagagtgcgtacc tggattgacagttcaggatcctccaaagttgaagcagagtatttgggagttgttgacggtaagattcatctgcataaaacaa acggtgtaaagattgccgtagcggctcctaagttgtcactagaggatttagagtatgtggaaagaatcactggaatgtcgtt agaaaaatacaagccaaagccaaaatctagtggttcctattccagacctttccaaaaagccatcctctagagaatcttcacca aaggagtccagccgctccggagttaaacaatcagttcccaagattgatcctcccaaagacccagattatgattggtttcaat ttttcttgggttgcgatattgatccgaataattgtcagcgatacagtgtggtttttcattaatgaacaactggatgagagtag tttgcaagacctcactccatccctactaagatcgctagggttaagagaaggtgatattttgagagttcaaaaaattcttggat aacaagtttggtcgaaccaaagctcaagaatctggctaccaatggtggtttatttaccaagatgatgctacattgaagaaca ataggtccactgatgttctaacaagtacagttgtaacgcgagaaactttaagtcctactaaggccgaggctaagagcaaaag aattgatgacgaagcatgggctctcaaacccgctgccgaatctagctctcaaatggatcaattctccagacctgtcagtgca atgagcaaacaattgactggatccatacaagatctcgtcaacttgaaacctttggggggacaatgcaaacaacgcttcggtag cccacaaagctgaaacaccaaacactacccaggacaaacctttcctcctgtcttggaaacctgtgaagactggagctgcaag gggacctgtgcaagcgcaaccaacaagtggtggtttcgtcactgcacaacctactggtgctctagttgcaatgcctacaggt ttcatgcccattacgatggtgcccgtaaagacaggaggaactatagctcttcaacccactggtggattcgtttcgttgcaaa gaactggtggggtacttccgcaggttacaggggggacttgttcccgttcagactggtgggttagtaatgcctcagacctcatt tggtgtaactccaacttttgcagccaacaggagggattctacctgctcagaggacaggtgaggttggttcctgttcaaaggacg ggggggctaattccgtccaacaaactggaagattagttcctgttcaacaaactggaggattgattcctgttcaaaggactg gaggattagttcccgttcagagaactggaaacttacaacctgtacctacaacctcttttggaagtcaaccaacaggaacttt tgtgcctcaatcttcctttggtaatcagttggccaccaatttgaataacccgcaaaccacattcggctctcaaccaacagga ggtttccctcagacatcatttgcacaaaatcagtttagacaatcgacaggaggtttccagcagaccccaattgtgcaacaaa cagggggattccccaatactccgctgcaacagacggtaggattccctcagaactcttttggacagcagacaggaggaat tgcccaaaactcatttggacaacagacaggaggttatcaaacaggttttcaaggaaatggatcgattccaatgcccagtcc tcattcggtgcttcaaatctgggattcaatggtgctacgcagcagaactacaacattggcatgggccaatctttgccagcag cttctatccctcccttcaaccctcttacacctcatcactcaatggaatgtcaaacatgcttcagaacgtaagcatctctca gcagccacaacaagcccagccaatgacgacttttggagcacctgtggcccagcctccgttacaggctcaaccaactggcttt ggttttggtaactcgccctatggaggtcagaacccactccaatctcagcaacaggtaaaagagccaacttatcagcagcta ccgcagacaacccattcggcttctag |
| PAS_chr3_0842 | 18 | atgaccaaccaatcaacagtggtggatttacgcctttcatccaagagagttgttggcaaaccagtcaagttgcccacagtcc tagcgtgctcagggtcagattcttccggtggtgcagggatcgaagcagatatcaaatccatcacggcttttgggtgctatgc gctaacagcaattacatctttaactgcccagaataccaaaggtgtcaccagtatagaaaacaccgacccaaagttttcgaa gagatttagaggcaaattttgaggacattgaaatcgatgtggtgaaaactggactgttaaaccctgagtcatctcgtttat tgctgaaattttagataaataccacaaaaggaaagccatttgtcctggatccggtcttagtggctacgtctggttcaatgct tgcaatcaacacgaattagggttcaccattgattctcattttaagaaagctactatcattactccaaatttcgaagaggca tgtgtgatctactcttacttgaaaaagctgaagactgtagatgagttgggtgaaatagaaactttagaggatttgaaaggaa tggccaagttcatccagcaaactcacacattgcaactctgttcttcttaaaggtggccatattccctggaatagaaacgagca gttgttaaaaaaaggggaggagatccagcatacatcattactgatattctttatcagggtcatttggataaattcacggtaatc aagacagattactttgacaagttctggaactcatggttgtgggtgtacgattgctgcctcaattgctgcaaacattgcccgtt cgttgaagattgaggctgtgtaatttcttcgattagatacgttcatcaggcaatttttggagcagatgagacgctaggaca aggaaaaggccctttgaatcatgtgtttcatatttctcctcccattaacggcacaagtgctgagaataacttcttccgttc tatccaggtcacttcttagattacttactggagcatcctttggtgagtcccatctggaagaactacatcaaccacccatttt tagaaaacgtagcaacaaataagctggctaagaacagattcatccactacatttgtcaagattacgtgtatctagcttctta |

TABLE 5-continued

SEQUENCE LISTING
Open reading frame nucleotide sequence for proteases targeted for deletion in *P. pastoris*

| Protease Gene Symbol/ Locus tag | SEQ ID NO: | Open reading frame nucleotide sequence (5' to 3') |
|---|---|---|
| | | tgcccgtgtccacggcttagctgccggagttgcacctgatattgaaagcataaaggcagaagcccatataatcgactccatc atggaagaaatgcatagacataaagacgtattgaactctcgtggaattgtgaaactggatgaattaagaccctccaaggcct gcaaacagtattccgactacctcctaaacattgcgaagacatcagactgggtggccataaaaatcgccttagcaccatgcat ctttggctactattacgctgccatttatgctcggtcgtttatcaaggatgaagctgacgtggacgaagaattcttgaattgg atcaatacgtataccggtgattggtacaaagatgctgttgacgaggccagacagtcgctagaaagccatatgcaagctgttt ctcccgtccagtagcagagctagtcaagatcttgcagatgtctgtcaattggaggtgaacttctggacttcgccaatggaa actaccagaacaagatctatga |
| PAS_chr1-3_0195 | 19 | atgcctacagtggtgactaacgagtcctctctcttgcaaacaaccgtgagtgttgcaccattggtgcttttatctgttgttg atcactacgaacgagtggtgcaggcacccaacgccccaactaattcaaacgacaaaagagtcgtgggggtcattttgggaga caatacaaacaagaacttgatcaaggtaaccaactcatttgccatcccgtttgaagaagacgaaaagaacagggatatttgg tttttggatcacgacttcatcgaatcgatgatggaaatgttcaagaagattaatgccaaagaaagacttattggatggtacc actctggaccaaagttaaagtcatctgatctacaaatcaacgagttattcaagagattcactccaaatcctttgcttttgat tgtggatgtaaattccaccgatatagtcgatattcctacagactcatatttggcaattgaagaaattagagacgatggctca agtgcagaaaaaacgtttatccatttaccatccatcatccaggccgaagaagcagaagaaattggagtggagcatcttctga gggatatccgagaccaggcgtgcggaaatctgtccataagattgactaacaatttcaaatcgctgaagtctttaaacgatcg catagccaacattgtccaatatttgcgcaagattttaagtggagaattaccaataaatatgtaattcttggaaaattacag gacatattcaacttattgcccaacttggttgccgttcaaggtgatcccacaaaaccagccactgcaagtgctaaccaactag ccacatcattcaatgtgaagaccaatgatgaattaatgatggtttacatctctccagtttagtaagatccatcttggctttcca tgatttgatcgacaataagatcgagaacaagaagaacaacgagaaagataaggaattcacaccaacagaggaagaaccccaa caagcggctatagaatcgaaataa |
| PAS_chr1-4_0052 | 20 | atgacaatgtcaaccgaagatatcatcgccaggcataggaaggagaaaaagggaccaaattgcacttattacaaggatgaaga agcagagcactaagtcaaccaaaaaggaaatcatgaaacaatgctctctcttggaagaagagctacaggcaagacataagaa ggagttaggtgagtgcaagactgaaaattccgtcgagagaagtagtgagcctactgacgaaaaatcaaatggtggagaactt ttttcccctgaaaagttattatcaatgatgactttaaaacagcaaggaacttccaagtgagaatcaaggaaacgcaactgttc caaagagaaaacgcaataggcagaaggacagattagctagaagggaagttgccattaaagagatgcaagcagcagcagcaa agaggctaacctccaaacaaatttcaaagagatagaattgaacaacataagccaactgtgccaagttgctcacctggaacca tatgatatccgacctgatgggcattgcttgttgcatctataaaagatcagttggaggttcggcacaaaattgaaaatataa gtatacaagatcttcggtctctggctgcgagtcatattaaaaatgatcccgagacttatactcctttcctttttgatgagaa tactatgaaaatcagggacattgatgactatgcaaacgagcttgaaaaccacggcttatgggggaggtgatatggaaattttg gcattgagcaaagagtttgattgtccaatcagtgtaatgattagtggaagacctattcatcttgtcaatgccgacggttcta aagaggagttgaagttggtttattaccgtcatgtcatatggcctaggtgagcattacaactctttaagagatagatcagagat aagggagtcttgtatagttgagcaagaggaaaaagaagcggtagacgatggaaaatcatcttcttga |
| PAS_chr2-2_0057 | 21 | atgagacttaagatcaagcgttcaaatgaacagcggctaataacattgcctgacggggctacagtatcggatttacttaatg aaattggatcagcttctatcaatataaaggttgggtttcctcctcagacaattgatatctcagataccagcaagttgcttac tgatagtggaatcaagaatggtgaaatgatcattgtcactgatacccattgaaacagaagtgcctgtcaacaagaatgaggtt gcaattgccacctgtctcaaaccagaatgatgcgccctacgttcaaatagacgacatcttcctagtcttgcggaagattcccg atgataattcttgtttcttcaactctgtcggctactgtatatttggtcctgattcaatcaagtatccggattctcaacaaga actaagacaggccgtcgctaatgtaatcagagagaacaaccaaggtatttataactccgccatcttgggtggaaagtcaatc acagagtattctcagtggatccaaagcagtaattcctggggaggagccatcgaagcacagatattggcagaataccttgata tcagtatctggacagtggatattgagtctcttcaagtctacaaatttaatgatgaaatggcttcaaggttttgcgttattat gtatagtggtattcattacgacgctatggctctctaagctggacacatcattagatgaggaggactcacaaatttgtgtgtttt gataagttcagtgagttggggactttgattgaagacaacgttctcaaattaaccaaccatcttaagaaccagggctattata cgaatacttccacattcatactccaatgtcaaatatgtctcgcaacattgcaaggagaaaaagaagcaaatagccacgcaaa gaaaactggccacacaaattttggtgaagtcaattga |
| PAS_chr1-3_0150 | 22 | atgtcattgtctgatcctgaggacagcctaagacgtctacttgtgagtttaccctccaatgttaagtacgatgcggagtctt cggtattgaaaagccgactgaacctttgctctctatatttctcgctgacaaagagaggtgaatatctgggttccttggtaacgga cttgccaatggatttgccatcatcttattccgaaatcttagaggctgaagatgattcctactcaagattggctgaatcaatg tacaaatgccctaactataagcatcatggaacccttgtgcaaggcagttcaagcaaggagagccgcatataccggtgctacg aatgtggtttttgacgagacttgtgtaatgtgcatgcattgtttttaataagggagcaacatcgagaccacgaggtttccatttc aattgcttcgtcctccaacgatggtatctgtgattgtggagatcctcaggcatggaatatcgaattacactgccagagtgaa ctggaacaagatgaccattcaagttcagaagttaatccagattttaaatctgctataaaggggaaacaatggatattattttag attacattttggattgtactattcattctgcatctatgcttcctgctgttcaggacatgatgaaggaagaccccatccgacta tgaaatggctattcaatatgcttcagatagttcttctctgcccattgaaagatatggagtggaagacacgaatgttcagtcc tggaacgtagtcctgtggaacgacgaattccataattatgatgaggctattgattggcatccagcaagttagtagatgttcat tgtctaaaggacaagctgacgctcaaaagattaatgattttggatttttccatcataagaagaagtgaatccttgcctttact gatagaaggtgcgccaaggttgaagaatccgggtttactattacgattctttctctgatagagatgttacccgattgattatt attgatactattttttgattggttattgactctgttagaaaatttcaaggccggaaattcagactgctattagagaaagtttgt gtgaatctcttttggaagagtttcatgccgacattcacgaaggagattttttctaccgggaagatgaatattcagacacacg gggtttgctggatttcaaaaacagaattccagccccattggtggaggatgtaatgaacgagttgtctattgatgacttgaag aacagaaaactccagtttctcttaatgaacaaccttcagctctagtcggctcaagagtacagtatttcttctctatatggatc tgcggttctggaaaaaggcaagaaaatctttgaaattgctaacgacatctgttttggtttcaaacttggaatacaaaaagac ttttctgaacagtttgtgaaaatatactcgcatctgttgatattgatgcaaaggaagatagagagtggctctcagcaat gcgggcaatgctgtagtacaactcttacatgtcctaaaacatctctccatttattacaaccacaatatttcagaagcatca tcgtccccatcattttgttgttcgaatcttatactggaaaccatttgctgtggaaaacagacccatatctatcacctttaccg gaaaaggtctcaaattttggtttaatgcgttctttaactgatctagtgacgttaatcaccactgcccatcaatcagaagaacat ttggtacttttcagggtaagaacttcatttacataatcatgcttttaggatgttccagagtgccctgacattggtcagaa aggaaggagaacatattaccagggaatccactgaatttttaacctacctgcaaatatcttactacctaatgatgtcatcaa aggtattgttgaaattgcgcaggttcctgaaatacgtaaacctgaacattggaaagttgtggaaacaaacatacaaatattg gccactttaattttcatcagaacccttataagtttcatatggtgcacgaaaaacaacttattgaccatgacgtaacaaagaaac |

TABLE 5-continued

SEQUENCE LISTING
Open reading frame nucleotide sequence for proteases targeted for deletion in *P. pastoris*

| Protease Gene Symbol/ Locus tag | SEQ ID NO: | Open reading frame nucleotide sequence (5' to 3') |
|---|---|---|
| | | caacctctcttattaatccattgaatggattactgtctaacatgttaacaaccgtaagggccaattcttttttcattttaac |
| | | tcgtcaagtttctcagattaattttttggagtatcaatcccgaagtctcattttcagatgatttagactatctgaaactctca |
| | | tcgaagagtttagaagcaattactttgagttcacagataaaaattggccactggattagaaatggatccatgactagtaaac |
| | | aagcgcaattgtactgcacgaggttcactcaatatggttacatagccgacgttcatttgaaccaacttgctatactcgaaga |
| | | acgcgacgatgatcgtctattattaaacattttggatagattcaatctaatagattggttctataacgatcaggacgtgctt |
| | | ggtactgttttcgaagaacgatctttttacctaatgaatgaattggttaagtttctctttataaatatgtttttcacacagagtta |
| | | acttccagtttgaatcaaatttcacagagaaaacccagtatgaggtaacgcaatacattttatacacgctttgtaaaggatc |
| | | tttgtcattttcagatctgacagccgactttcctatctccgtggaagttactgttttttgacaagatccttgatgaggttgct |
| | | gtttacgaagagcccaaaactatgaatgattctggaaagtattctatcaagaaaagttattacaaaaagatggatccaatgt |
| | | ctatttatgtggactcgggtgatttcgatgatgtatcaacagcgatagtaaaggaactttcaattttaggaaaaaataaaaga |
| | | ggagaatgttgtaattgaacctcagatcagtggaccgaatgaatccaacagccgtgcttgagcagattgaaacggttcttc |
| | | attagcaaatctgtagtcaaactgttttataaattgttacaatctgctctttctgagagcaatgagacctacgtcattgaac |
| | | ttttacatttgattcaagcagtttttattagatgaacatgaattgtacagaatcgaagatccagtgcaatactttattcaaat |
| | | tcctgtgtgtgatctactgttatcagttgttgagcacaatgattttttcacgacctgtctgcaaaaaactgaagttctattga |
| | | attggttgatccagccgggacgagtcaatcattgactcattggttgattcttttggtgaaaagcacattgaaaactttaaaaa |
| | | atctaagggatctcaagttctggagactaaacgagctaaacaaaagcgtttagccaaggagagacaagagaagatcaaatca |
| | | cgatttgctaaacagcaaagtctttcatgaagcagaatttggacgcaaaaaagagtgcggaacatgtaactacacatttat |
| | | ccaaagacaatgaaggattaggtagttcctcccaggactctttcatgagtgcattctttgtcaacgtgctcaggagggcaa |
| | | cgagatgtttggaatccctgcatatgttgaaaaagtttccacgttttgggattttcaacctaaggatgagtcaacctatacg |
| | | gaaagatgcttaacaaccattgaaaatcaaatgaaacaattgcatgaagaaacggatgccaacaatgaggttagagaacatc |
| | | tttattatcaaaaagatactcctgtaaaaagcatggcaccgatatcttcaagacacattgttaagtcatgcgggcaccacat |
| | | gcattataaatgtttttctgagttactagaaaacagcaggaagtttagcacttgtccgctttgtcgctctgccattaatgct |
| | | tttgttccacaatttgccatgaaaaacgatgctagccctgcttttcaggaggctgcttcgaatattagtcactttgaaaagt |
| | | tgaatttgaatcaaattgtatcgaaatatcttctcaatgattccttcttgaaatttattgcggaagaaagtaaggaccagtt |
| | | catgtatttgaatgagtttaaagacattttgaaagacgccccagatgcttctgaccacatgttgagtgaagggttatttccc |
| | | tcattttttggccatgtcaacattattgggtaataccctagcaaatactgaaattcgtctcagattatcccccgagaagattc |
| | | cccagaaaggaaacttgaagagaaaagattcggaattaataacctcattacttcaatgtgtctcggttatctcaatcttatt |
| | | gaaacaatcttatcctgaagagcagtatctgtctccattttttgaataaaaccaaattcattaattattgatttttgccatttca |
| | | cttctacttggaaaagaagactcacttcaagaaactattgtgggcatttacaagcaaacaattctgcattcattgaatttac |
| | | tattgactaacgttggagataatgagcatttcagaaggatgctgagcggtgcaaactctattattaatgattcagaactggc |
| | | cattttcaaaaagtttgtgtcaacggccacttttacctctgatgtttcattcattacttgcaacgaacaattattggttgga |
| | | ctgtatattcttttggagaaaaccaccacagtgtatcttaaacagttgtttctgataatcagcatgtgcagacccttggact |
| | | tatgcctaaatcgtgactacgagaattccaatgattacgaccactatttgtttggccaactgtgcaaattttttttaacctttc |
| | | cagtataatcagttatttgggatctggaattcctggtggaaacctattggaggagcaaaatgatcttatattaaaaggacaa |
| | | tccactctcccttcaacaattgagtatccaggtctcgtttatcttgtgaatttgcctagagaactgaacactttttactttttt |
| | | caaaatatgacaccccaagatgcagttaatctaaacttttctgtttgtttaacgtgtggcaaaagagtgaaacatagcggtga |
| | | ttctgaaaatgaaattgaaaacttccctgggtacaatggtgttcctcttcactttgtttcaccatcataagaattgtcctttc |
| | | tctggatatggagaagcacaatgtatcttcttaacccccaaagttgaataaattgactgccttactaaagattcagcctccac |
| | | gaggaatttctgatcgctcgctatatcacagtacatttgcattcccattgagcagcccatatctaaccacacatggagagtc |
| | | acattctggtcatggaggcttgatacgcaaagcgttcctgaatagagatcgatttcgaaatctgaatgagctatggttggat |
| | | ggtgaactagctttgtatatttcccgaagccttgggggattctcaaattgtagcggaaccaatcaaccctgttatgattacaa |
| | | tgccgggaggtattcaggaggcattaaatcttgcgttcaccactttcctcggtgaccaagaacccgggggatgatgacttgga |
| | | agattatgagtatgacatactgttaaatagatga |
| PAS_chr1-3_0221 | 23 | atgtctgcctttggtgtgggttccgagtgtattaaacactggaaaccagatcaagcagaaaaacggaacgcttttcaagaaat |
| | | cttctggagtttacaataaacagcagcgggatcacaattccagggataaaaagcgatcagctcgtaaaacaaatacaccgcc |
| | | aacaccgactgagagtacttccgcaaagaagtcatcaactcaatcagacgacaaagtgagtcctgatattttacaattgtcg |
| | | catattgagattcaatatgtgggcccacttcttccaacccagaatctttgggatatgtgaaacaaaacaataataccaaaa |
| | | tcaagactccgaaatatttagtggatacagattcaaacctggtttttggtcctgatacaactaataaatgggatattgagaa |
| | | ccagcacaaaatgatcgaaatggaatcttcccatcaaggtgactggcaaggtatttatgaacaatttcaagaaatgaataaa |
| | | gtggagcgtcaaaaaatggaagatctgggcttggtggcaaaagagggacaaagcatggacctgacaaatgctatctcattca |
| | | aaggtagctgcgttgatatgtgtcccgttatgatagagtcaagagggaggtacagaggatgttgatccattggagagaga |
| | | tcctgccactggtaagatatctcgagagagagctttaaagaaatttgtgcgtccttcaggccaagcaccgcctcttccttct |
| | | gacgtaagacctcctcatattctggtaaaaagttaaactatattgtggataattgctggataaaattaccgcaaagtcatt |
| | | cattaatttgggatagaaacccgtagtatcagacaagattttacactacagagctactctggcttggaagcaattgagtgtaa |
| | | cgaaagaatttgtcgcatacatctactttgtgctcataaatgccgggttctgatcaatctgacttctccaagcagcaagaa |
| | | attgaacaattcacaaaatcattgaaaacattaacagacatatatgatgttgtcagatccaaaggaggaaaatgtgccaacg |
| | | aagctgaattcagggcttataattgctggtgcattttcgggacccaaatctaattcatgaaatccagaacttacctactcg |
| | | aattcttaaggacgaacgagttcaacttgctttaatgtttcgaagtctactattgaataataatttcaaagaataccagagg |
| | | aacattcctggttgctgggggtttttcagcagttttcaatatgtgttttgatccagccacccattcttaatcggatgtg |
| | | tgctggaacttaattttgaagagataagattttacgctttgaaatcgatctcacgttcttatcacaagaaatctgccctct |
| | | aacgacccagaagttagcatctatgctcggatttgattccgaggataagctcctaactttcactaattatttcaagactcct |
| | | acgtgtactaattctagaaatgaaacgtgcattgatatctcaaaacttagatacgagagttttacggatttggctgctccaa |
| | | agcagatttcaacttcaagattagacaacaaattaaaaggattcacctataaggatgttgttgatcaaggattaaataacac |
| | | atccttgcacatagctcaatttgaaagaaacaatggctcagaatcaacatattgcagtggagaaatteacccaatatctcattt |
| | | ccacaacatgctttgtcttctacccctttcgaagtagaatcaaagtcagacatagtcagatcttcttccggatcggctccgc |
| | | cccagactttgatcccaccgattcaagaaaaagtaataacttctcaaatacagccaccaataactcccgtcgttcccactga |
| | | agaaatccaaactcttccaaaaatagaggagcccaggttcaagatcttccaaatttgaaaatgcatgcaaagaggttttcc |
| | | tctatttaatcaagaagactatatctcctttgattgctcccatagtgaacaatcagctagaagagtacaaccggcgacaaa |
| | | cggttttaagggatcaggagagacaaaatcaaagaagacaacttttgatttcatcccttcaggaagaattgtactctgctttt |
| | | tatacgagaacaagtgtatattcaagtggttgatactcaagccaaagagtgctttaacaagaatctgaaacggcgaatattt |
| | | cagaaattcatcggggggtttaattacattgaaaaacaaacaaatgaataagaagagaaaacttgatgaaattcaagtcttca |
| | | agaataaggttgtttcctcaagtcaacttcggtattcagtttcaagaagtcaaacggaggacaattcaacgtcaaactcgag |

TABLE 5-continued

SEQUENCE LISTING
Open reading frame nucleotide sequence for proteases targeted for deletion in *P. pastoris*

| Protease Gene Symbol/ Locus tag | SEQ ID NO: | Open reading frame nucleotide sequence (5' to 3') |
|---|---|---|
| | | tgacgaggaagcatcagctgttcagatgaatattactctttcaccatctgtggatccactttggtcacccatagatattaag |
| | | tttatattagactccaatttaaagttgtttgaggataacaaggatataaatactggaatttcatgtttgcgattgccgattgga |
| | | ctattctaccaagcaaatggcttcgttacaaattccaacttcaaaaccccagtctcataaatactgttgaatcctcaaatta |
| | | caaagccaaattacgggctctacccagtgacaaacttcttacaagggaatacatggagcactgtcgattttggtatttcaa |
| | | gtcggaaaggttgatgaatcatcaaacctgaaagaatctttgttcagagactcacagtttattaaccgattaatgaaatatg |
| | | ccaagaagtactcgcaataccagattggagtacttgtcttatattatcatgaggatgactctttgataaacagaaaattat |
| | | tgatcttttgttattagaacaatacacaaataagttagtcaactcactcgagatagttgacatgaacaaactcacaaatgat |
| | | gaactgataaaagcattgaccacgctagtccacaactataaggataaaggtatcaacaaatcggtaccaacatcttccacca |
| | | aaggacacaccactagcattatggaacaggatatgacagtatacagctacagcacgtccaattccagggatgctaagcttaa |
| | | ttatattttgaagcaagcctacccccgcaggggggtttcacttgaaacaatga |
| PAS_FragD_0022 | 24 | atgtcagaatggccctcagcttttggaaaattttgtaagtcattgtttccagcgtgccaacattgagagctttccaccccggca |
| | | aaaaaaaagaactccaaaaacagttgacgcaaatcatcaatttagcaattcttgaaaacaaacttaattctaataactggtc |
| | | caaacaaagctaccaatatttggagaagcaagagagttagaattgggaaatgtttatcccaattactgtt |
| | | tctagtcgaagaagtgacttgatgcatcaagaggcagttcaaccatctgagcctttagttccctccgaaagccaacaaaaga |
| | | aaaagtctagagaattgcgatttaagatcactaaaaaaagttctgtatcacccgcaaatacaagttgcttgtgactt |
| | | gaattgtaaacttgtgggaactaacacctctatcgagaaagattattatagacttacatctcatccggatccttccatggta |
| | | agaccctttgcctattttaaagaaatcgttgcagcatctttacgccaaatatcaaagtctagaacgtttcaaagctctcagca |
| | | aggcagagtacagctatttttttgaatcaactgaaatccctaaggcaagacctcacagtgcaagacattcagaatcagttcac |
| | | tgttaaagtttacgaatttaatactcaattggcgattcaaaatgaagattttggtgagcttaatcaatgtttgactcagctg |
| | | gcgcaattgtacactgtatcaactatgggtcatacttattactattctgatactggcaaatacaaccaagagcacaactgtt |
| | | ttcttgccaaggatctttgtgaggatcgaaaccatatcaatatgttcaaatttacgagttatagaattttatattttcttct |
| | | catagacgcccctgggaattgctaaaaataaggcaggatttattcaaccgtggtcaacagtatgcaattcgtcacaacaaa |
| | | tttcttttgaagtcattcaagctttcggatctcataaccgccatggattatattcatatcaaggacgaatattcattcctcg |
| | | tgaatatggactcagatgtctgcaatttaaggacagtgtttgatgacgaacatatgactttgaaccaagacgactggttttt |
| | | ctataagatactctaccataagattttcttacgagaacagctgaaggccctgataactataagcaaatcttatcgacagata |
| | | tccctctacttgaaaaatctactgatggatttagtattcttggaaaagaataagttatctcgtttcattgagaatggtg |
| | | aggtatttaactgcacgagcgcaagatcattactgcttcaaatagagaagaagcagctatcaaagatagatatcaagggtca |
| | | ggtatga |
| PAS_chr2- 1_0159 | 25 | atggttgactcagagactatcaacaaaattcatagaagtaacgggagcctctgccttccaagcaattcagtacctagaggaga |
| | | ctgatgactttgaagcggcagtcaatgattattattcctctcaactggagaatgagaagggcaagggtaaatcagaacgtcc |
| | | agtcaatcaaacaaaggcttctgcagggcccaagatcagaactttcaacgacctaaatagcaactcaaatggggacaacaat |
| | | cttttcacaggtggtgaaaagtccggtcttcaagttgagaacccagacaaacgtggggacccttttgggttggtcaatgatc |
| | | ttttgaagaaagctgaggaaactggccaacaaccagatacaaggccccatgaagaagctcctgctagacaatttgttggaac |
| | | tggccacaagctgggcagtacggacagtccctccgaagttagtgtctgaccctgcctcaagaataagaagagctcagaaagt |
| | | cagccgacagataacatttttggaaggacggattccaagttgggagacggagatttatacagatatgatgacctgcaaacgca |
| | | agatatctagccgacttgaacgctggaagggcaccactggctcttctagatgtcgagattgggcaagaggtagatgtcacag |
| | | tgcataaaaagatagaaaaaaatttcactcctcctaagaaagcccgagttggctttcaaggtaaaggtcagagattagggtc |
| | | tccagtaccgggcgacataaagctcagtcaatctcctgaggtgcaacaagaaacacaagaggaagctgaggaggaaaagcaa |
| | | aaggaggaggccgagcagctgggaactggggattctcccgttcagattagactcgccaatggtcagagaattgttcatagat |
| | | tcaattctactgattctgttgctcaattatatgcatttgtcaatgaacatagtccctccgccagagaattgtgctttctct |
| | | agctttcccggtgaaacctattgagaacaatgaggacacactcaaggatgctggactcataaacgctgttgttgtccaaaga |
| | | tggaaataa |
| PAS_chr2- 1_0326 | 26 | atgggcgtgatacttccagacgatggtaagcaatcgggaggccaaccaaatagaagggctaaagtcctgagccgattttttac |
| | | caccagaacatcaaagacctttcaatcggcctcttcctgggacctttttactccagcagctgataatgagattgccctgtggac |
| | | ttgcattggcgctcagctctttagtgggctggcattgcttagaatgagccgaagatttgttttttcgcccgatcaatctgta |
| | | agaaggtttctctcttaagactttttcataatgtggtaggtgcagccctgatatttgggagcggattagaagggactaggatgc |
| | | ttctacctgaggatccttggaaagaagaagctagaaaagcaagaatattggcccaattgaaaggtgagcccgttagttggtg |
| | | gtatggacccaagagtttttattccttctggaaggttagaatacacaaaacagatgcagtttcacaactttgaagtcatgcat |
| | | aaatcaccctgaaaaaatagcccgagctctcatgattaaggacaaactcaaggaggaaacaaatacccttattcgtccattc |
| | | atgagaaagcggaacaacagactattcgactctctaaagatctacagaacaacgttccccctcaaagggggtaacgtcatatgt |
| | | tcctcaatttagcacttcaaatacggacaccaagttatatttgaaaaatgttagcttgaagacccatgccgacctggaaaag |
| | | gtctgggcagaacacaatccttgggacatcctggaagagaaaatttctccaatttccgtaattgcactgccaaagtttaacc |
| | | caattatatctgaggttgaacctgacaagcagcaaccatctacgggtgatatcaaatacattagtgacagaaaataa |
| PAS_chr1- 4_0611 | 27 | atgaaatatttgccactcgttgctaccctggcctcttcggccctcgctgctggcatcaacttcgcccaattactggaccaga |
| | | agccactggacattgccgataatgttaaatgggaattgaagcctgaggtcgactctgctgctcttcaaagtgcagtcaatga |
| | | gctagacttgaaaatcgaagcagctatttgtttgacattggttccgtcttcagaacggacatcctaccagagtc |
| | | atcggttctcctggtcactggtccacaatcaaccatgtcctcgacacattacataacttcaaacactactacgacgttgacg |
| | | ttcagccatttgaagcccttaccggtatccttaagtctttctcattgaccattaacggagttgcaccaaagtctgcagaagc |
| | | tttagatttaactcctcctactcctggcggttttccagtgaccggtccagtcgtttttagttgataattatggttgtcaagct |
| | | tctgactatccattcaacgtgactaacggaattgccttaattcaaaggggttcttgttcattcggtcaaaaatcagaacttg |
| | | ctggtatccgtggagccaaagccgctctcattacaacaacgtgccaggtagtgctaaggggaacttaggtgccccaactcc |
| | | tcatcaggtaccatcgttgtcacttttctcaggaagatggagaggccgtcaagcgtcagcttctgacttctggaagcgtaatt |
| | | gcaactgtcgctgtcgattcctacgttaagaagttcaaaaccaagaatgtgattgctaccactcgttacggtaatgatagca |
| | | acattgtagctaggtgacattcagactctgttgctgctgctggacaggtatcaatgacgagtggttggtaccatctctct |
| | | tttgaacgtggccaaatacctaactaaattcaaagttaataacaaaggttcgtttcgcttggtgggcagctgaagaagaagga |
| | | ttacttggatccgactactacgtttcaaagttaaccccccaaggagaaatctcagattcgtttgtttatggactacgatatga |
| | | tggcttcccctaactacgcctaccaggtctataatgccactaacagcgagaacccagttggatctgaggagcttaagaatttt |
| | | atacattgactggtacgttgaacagggtctgaactacactctagttccatttgatggccgatccgactatgatggattcatc |
| | | aagagcggtattcccggaggtggtattgctaccggagcagaaggtttgaagaccgaagaggaggctgaactatttggtggtg |

TABLE 5-continued

SEQUENCE LISTING
Open reading frame nucleotide sequence for proteases targeted for deletion in *P. pastoris*

| Protease Gene Symbol/ Locus tag | SEQ ID NO: | Open reading frame nucleotide sequence (5' to 3') |
|---|---|---|
| | | aagctggagttgcatatgacccatgttaccactctctttgtgacgatttggccaaccctgactatgttccatgggttgtcaa tactaaattaattgcccacagtgtcgccacttatgcaaagagcttggacggattcccattgcgtgaggagcctagcccattc aagatgactgcccagtcaaacttcaagtaccacggtccaaaacttgtcctttag |
| PAS_chr1-1_0274 | 28 | atgctcaaacactccttaaaaacagggttggtctttctcacttggataccggtgatttatacggtaaaggaacacctgatat acgttggaaaggtggaaggatcctcaatgtcacccactttgaatcccgttaaaggttattctgactatgtgatttttatggaa gttaaacttcaaagagtcactcaaagtgggagacgtggttttttataaggtctcctgtagatccagagaagttatatgctaaa cgtataaaggctgttcaaggggataccgttggtgactaggcatccataccccaaagacaaagtgtccattccaagaaaccatc tttgggtagaaggagacaatatacacagcgtggatagtaacaactttggtccgatatcgttgggccttgtattaggaagagc aactcacgtaattttttcccctgaacaggataggtaatatctctggtgaagggggtagagaagttagggaggattatttaaga gcggaggacagtccgatgtaa |
| PAS_chr4_0834 | 29 | atggtttctgaaattcagcttagattagctgttattatttatgatatactctgttcggcgtcttatgttctagtcatccatt tgagaccaaccagagccctccgcatcaacccatagaccgtaacaatcctctaacgattaaagaaaggtgccagcgagccag tgtgttgactgctacacatgtattattattgcctattcttttaaaagtgttgagactgttcagaaattgcggaaactacggcg aaacttggaatagtggtgggatatcacaaccagagctggtctttctctaacctccaagatgatattgtcagcattttcaaag ctttaggtttgaccatgattctcttttctggtcctattgtagattattttttactattcaaactcaacagaagtaatcaagca agatctggcgtatgtcgttagcctcgagggtatgcgtgatctacttgtgggacccatcactgaggaacttctttatcggtca tgttccatttcattaatgctagtagctaacgattacgccaacaaatttctgttcggccaacactggttaataatggtatcat cactctacttcggtatagcacatcttcatcatgctgttgaactgtatcattgtaaaagatattcattaactaccataaccat atcaactgccttccaatggtcatatacaacgttatttggaatatatgcaagctttctatacttgcgaacaggatctgtatgg tcagcaatagttgttcattcattttgcaacatgatggggtttccccggttgacatttggacgtgatgaagcgagagattgga aagtgggttactatgtgttgctcgctctaggttccgtcctattcaaaaagtttctttactctctaacagaatctaaccatac gcttcttctataa |
| PAS_chr3_0896 | 30 | atgtatcccgaacacaagtatcgggagtatcaacggagggtgccccttatggcagtactccctgttggtgattgtactgctat acgggtctcatttgcttatcagcaccatcaacttgatacactataaccacaaaaattatcatgcacaccagtcaatagtgg tatcgttcttaatgagtttgctgatgacgattcattctctcttgaatggcactctgaacttggagaactggagaaatggtacc tttttcccctaaatttcattccattcagtggaccgaaataggtcaggaagatgaccagggatattacattctctcttccaatt cctcttacatagtaaagtctttatccgacccagactttgaatctgttctattcaacgagtctacaatcacttacaacggtga agaacatcatgtggaagacgtcatagtgtccaataatcttcaatatgcattggtagttacggataagagacataattggcgc cattcttttttttgcgaattactggctgtataaagtcaacaatcctgaacaggttcagcctttgtttgatacagatctatcgt tgaatggtcttattagccttgtccattggtctccggattcttcccaagttgcatttgtgttggaaaataacatatatttgaa gcatcttaacaacttttctgattcaaggattgatcaactaacttatgatggaggcgaaaacatatttttatggcaaaccagat tgggtttatgaagaagaagtgtttgaaagcaaatctgctattggtggtctccaaatggaaagttttttatcaatattgcgaa ctaatgacacccaagtgcctgtctatcctattccatattttgttcagtctgatgctgaaacagctatcgatgaataccctct tctgaaacacataaaatacccaaaggcaggatttcccaatccagttgttgatgtgattgtatacgatgttcaacgccagcac atatctaggttacctgctggtgatcctttctacaacgatgagaacattaccaatgaggacagacttatcactgagatcatct gggttggtgattcacggttcctgaccaagattacgaacaggaaagtgacttgttagcatttttatctggtagacgctgaggc taacaatagtaagctggtaagattccaagatgctaagagcaccaagtcttggtttgaaattgaacacaacacattgtatatt cctaaggatacttcagtgggaagggcacaagatggctacatcgacaccatagatgttaacggctacaaccatttagcctatt tctcaccaccagacaacccagaccccaaggtcattcttacgcgtggtgattgggaagtcgttgacagtccatctgcatttga cttcaaaagaaatttggtttactttacagcaacaaagaaatctcaatagaaagacatgtttattgtgtttggatagacgggg aaacaattcaacaatgtaactgatgtttcatcagatggatactacagtacaagcttttcccctgggacaagatatgtattgc tatcacaccaaggtcccgtgtaccttatcaaaagatgatagatcttgtcaaaggcaccgaagaaataatcgaatctaacga agatttgaaagactccgttgctttatttgatttacctgatgtcaagtacggcgaaatcgagcttgaaaaaggtgtcaagtca aactacgttgagatcaggcctaagaacttcgatgaaagcaaaaagtatccggttttatttttttgtgtatggggggggccaggtt cccaattggtaacaaagacattttctaagagtttccagcatgttgtatcctctgagcttgacgtcattgttgttgtcaggtgga tggaagagggactggatttaaaggtagaaaatatagatccatagtgcgggacaacttgggtcattatgaatccctggaccaa atcacggcaggaaaaatttgggcagcaaagcccttacgttgatgagaatagactggccatttggggttggtcttatggaggtt acatgacgctaaaggttttagaacaggataaaggtgaaacattcaaatatggaatgtctgtttgcccctgtgacgaattggaa attctatgattctatctacacagaaagatacatgcacctcctcaggacaatccaaactattataattcgtcaatccatgag attgataattgaagggagtgaagaggttcttgctcaatgcacggaactggtgacgacaatgttcacttccaaaatacactca aagttctagatttatttgatttacatggtcttgaaaactatgatatccacgtgttccctgatagtgatcacagtattagata tcacaacggtaatgttatagtgtatgataagctattccattggattaggcgtgcattcaaggctggcaaataa |
| PAS_chr3_0561 | 31 | atgaaaccgtatcaccatgcaaaaagccgcccaataggcagctacctgtattttggggtgtttaccgtagcattgacatttc tgacgtggcttaaatatgacgcagagctgtttgctcagcaggttcactcgaaagacatttatgacccacagttcaacattac gttgccaattgatggcccaacatttaccccatcaaagaactattcaattagtgttcaaaatgcagcagtggcgtccgatata gaacaagttcaaaattaggtgtatctattctgcagcaaggtggcaatgcggccgattcagcagtcaccgtggccctgtgta tcggaacaatcaattcgtattcgtccggtatagggggaggaggattcattgtctctaagttaattgataatcctaccgctct gagttttgattgtcgagaaatggctcccttctaaaagtttcaaagaaatgttcaactatcatgaggagaaggccagagtaggt ggtttggctgtcgccattccaggagagttaaagggactctatgaactgtttcagcaccatggttctggtaatgttgagtgga aagatttgatttttgcccgttgctgagttgtatctcgaggtgggatggggactgtcgatccgctgtttctactgcattgaaatctat tgagcaccatatttacgagcattcatatgattgattccctttgcattgaatgaagacgggaaaaattaaaaaaagaggtgactgg attaatcgtcccatgttggctactacgttgaggggaatagctgaaagtggcaacgttgatcattctatgacccagagagcg atatagtacaaagcatggtgaatgctactagaaagtatgggaggaatcctttgaagcctcagactttgcaaaatatagagttcg aattgaagaatcgttgacattgcataatttcatatctgacggccctttacggttatacgtcaatgggcatctcaggggttg gtgctccttgctgggttgaagctcatggactttattcgaagatttcaaggaattttcatacataatgatttcggggctgttgagtctc aaaggcttgttgaaacgatgaagtggatggcttcagtaagaagcaacccttggagatttgaacatttactcaccaacgaaac tgaaattgacgatcataggaagagggtacgacagatacaaatcagatgagtgggcaatagaaactcatgccaaaattaatgat tcccacacacttccttcttggaaagattatgctccagcctttctacctaatgatcctcatggtacatctcatttcagtatcg ttgaccaatacggtaatgcggtggctatgacaaccactgttaaccttggatttggatctaaaatacacgatcctatatcagg |

TABLE 5-continued

SEQUENCE LISTING
Open reading frame nucleotide sequence for proteases targeted for deletion in *P. pastoris*

| Protease Gene Symbol/ Locus tag | SEQ ID NO: | Open reading frame nucleotide sequence (5' to 3') |
|---|---|---|
| | | gattattctaaatgatgaaatggacgattttttcagttccaacatcatctaatgcatttggtttgcatccatcaatctataat tgggtagagccttacaaaagacctctctcttcatgtgctcctaccgtaattgttgattctctgggagtacctcattttgtca tcggggcagcaggagggtccaagatcactaccacagtttttacaagcaattataagagtttaccattatcacctggatctttt agacgtcattgcatatccacgctttcatcatcaactacttccggaagaagttcttctggagtttccacgagataataaacta atacgccatctaaaagaaagagggcatgatgttagagtccaagcaccaatatccaccatgaatggtatcctacgaaaaagag gtggaagcctgatagcagttagtgatcactggagaaagcttggtcgaccttggggctttga |
| PAS_chr3_0633 | 32 | atgaaatcggttatttggagccttctatctttgctagcattgtcgcaggcattgactattccattgctggaagagcttcaac agcaaacattttttagcaagaaaaccgttcctcaacaagttgctgaattggtgggcacccattactctaaggatgagataat cagtctatggaaggacattgagctggtactacccagggaaagatccaagaggccttcgataagttcgtaaaacaatcaact gccacttcccccgttagaaatgaatttcccttgtctcagcaagattgggtgacagtgaccaacaccaagtttgataattatc aattgagggttaaaaaatcccaccctgaaaagctaaacattgataaggtaaagcaatcttcgggatacctggatatcattga tcaagataagcatctttttctattggttttttgaatcccgaaatgatccgtccacagacccaatcatcctatggttgaatggt ggaccggctgctcttctattacagggttgctattcgaaaagattggccccagttacatcaccaaagagattaagccggaac ataatccttattcatggaacaacaatgctagtgttatcttccttgagcaaccggttggagtaggattttcttactcttctaa gaaagtcggtgatactgcaactgctgccaaagatacatatgtgttttttggagcttttcttccaaaagtttcctcagttcctg acctctaatctgcacattgctggggaatcgtatgctggccattatttgcccaagattgcttctgagattgtgtctcacgcag acaagacgtttgacctttcaggagtcatgatcggtaatggtcttactgatcctctaattcagtataagtactatcagccaat ggcctgtggaaaaggtggctacaagcaggtcattttcggacgaggaatgtgatgaattggataggggtctatccaagatgtgaa cgtttaacgcgggcatgttatgagttccaaaattcagttacttgtgttccggcaacactttattgcgaccaaaagctactga agccgtacactgacactggcttgaatgtctatgatattcgtacaatgtgcgatgaagggactgatttgtgttacaaagaact ggaatacgtggagaagtacatgaaccagcctgaagtgcaggaagccgtgggcctctgaagtcagttcttacaaaaggttgtgac gatgatgtcttcttagattttttgtactctggcgatggatctaagccttccaccagtatatcacggatgttctcaatgcaa gtattccggttctgatttacgcaggtgataaagattatatctgtaattggctaggaaaccaagcttgggtcaatgagctaga atggaacttgtctgaggaattccaggcaactccgattcgaccgtggttcactttggacaataacgattatgcaggaaacgta caaacttatggaaacttttcctttctaagagtatttgatgctggtcacatggttccttacaatcaaccagtcaacgcacttg acatggttgtcagatggacacacggtgatttctcatttggttattaa |
| PAS_chr4_0013 | 33 | atgactcaattagatgtcgaatcattgattcaagaactcacactaaatgaaaaggttcaacttctgtccggatcagactttt ggcacaccacccccagttagacgtctaggaattccaaagatgagattatctgacggtcctaacggcgtccgaggaaccaagtt tttcaatggagttccaaccgcatgtttttccttgtggtactggattaggtgccactttcgataaagaacttctaaaagaagct ggctccttgatggcagacgaagctaaagcaaaagctgcctcggtagtttttgggtcctacagctaacattgctcgaggccca acggaggaagaggcttcgaatcttttggagaggatccagtggttaatggattatctagtgctgcaatgattaatggattgca aggtaaatatattgcggctaccatgaaacattatgtttgtaacgatttagagatggatccgtaattgcattgatgcacaggtg tctcacagagctctaagagaagtgtaccttcttccattccaaattgcggtaagagatgcaaatcctcgcgctatcatgactg cttataataaagcaaacggtgaacatgtatctcagtcaaagtttcttctagatgaggtttttgagaaaagaatgggctggga tggtttgttaatgtccgattggttcggtgtgtacgatgcaaagtcttctatcactaatggtcttgacctggaaatgcctggt ccacctcagtgcagagtccattcggcaaccgatcatgccatcaattctgggagatacacataaatgatgtcgatgagcgggg tgcgaagcctcttaagtttaattaactattgtcaccagagtggcgtcactgaggaggatccggagacatccgataacaacac cccagagaccatcgaaaaactcagaaaaatcagtagagaatcaatcgtcttgctgaaggatgatgacaggaacagaagtatc cttcctctgaagaagtcagataaaattgccgtgattggaaacaatgctaagcaggctgcatattgcggaggaggttctgctt ctgttctctcgtaccatactacaactcctttcgactctatcaaatcacgattggaagattcaaacactccagcttacaccat cggtgctgatgcttacaagaaccttccgccttgggccctcagatgacagacgcgatggaaaaccggggttcgacgccaaa ttttttgttggctcgcctacatctaaagatagaaagctgattgatcacttcagttgaccaattcacaagtcttcctggttg actactataatgaacagatccctgaaaacaaagagtttttacgtagacgttgaagggcaattcattcctgaggaagatggaac ctataactttggcttgaccgtattcggaacgggaagattattcgtggatgataagctggtttccgatagtagccaaaaccag accctggagattccttttttggactagcagctcaagaggttatcgggtccattcatttggtcaagggtaaagcatataaaa taaaggttctttatggatccagtgtcaccagaacatatgaaattgcagccagtgttgctttttgaaggaggagcatttacttt tggtgcagcaaaacaaagaaatgaagatgaagaaattgctagagctgtggaaattgctaaggcaaatgataaagtggtgttg tgcataggtctaaatcaagactttgaaagtgagggattcgacaggccggatatcaaaattcctggagcaaccaacaagatgg taagtgctgtttgaaggctaaccctaacactgtgatcgtcaaccaaacaggaaccccagtcgagatgccatgggccagtga cgctccagtgatcttgcaggcttggttttgggggtgctgaggcagggaccgctatagctgatgtactattcggtgactacaac cctagcggaaaactaacggttacttttcccttgagatttgaggataaccctgcatatctcaacttccaatccaataagcaag catgttggtatgggaagacgtttatgtgggctacagatattacgagaccatagacaggcctgtgttattcccatttggcca cggattgtcattcaccgaatttgatttaccgacatgtttgtcaggcttgaagaagaaaaccttgaagttgaggttgtagtc agaaacacaggaaagtatgatggtgctgaagttgtgcagttgtacgtagcaccagtatccccatccctgaaaaggcccatca aagaactcaaggaatatgctaagatttttcttagccagtggtgaggcaaaaacagttcacctgagcgttcctattaagtatgc cacttcgttctttgacgaatatcagaaagaaatggtgctccgagaaaggagagtacacaatcttactgggatccagctcagca gatattaaagtttcgcaatctattacttttagaaaaaacaacttttttggaaaggtttatag |
| PAS_chr2-1_0172 | 34 | atgttcctcaaaagtctccttagttttgcgtctatcctaacgctttgcaaggcctgggatctggaagatgtacaagatgcac caaagatcaaaggtaatgaagtacccggtcgctatatcattgagtatgaagaagcttccacttcagcatttgctacccaact gagagctgggggatatgactttaacatccaatacgactactcaactggttcccttttcaacgggagcatctgttcaaatcagc aacgataacaaaaccacttccaggatttgcaaagtttgcgtgcagtcaaaaatgtttacccagctactctcattacattag atgaaacattttgagcttgctgacacgaagccatggaaccctcatggaatttaccggtgtcgattctttgcatgagcaaggata tactggtagtggtgttgttattgcagttatcgatactggtgttgactatacacaccctgctctgggtggtggtatcggagat aatttccctatcaaagctggttatgatttgtcttccggtgatggtgtcatcacgaatgatcctatggattgtgacggtcatg gtacctttgtatcctccatcattgttgtgcaaataacaaagatatggttggtgttgcaccagatgtcagataatgatcagtaa agtgttccctgttctgatagtacttcgactgacatagttatggcgggtatgcaaaaggcctatgatgatgtcacaagatt atttcgctatcactgggatctgactcggggtttttccagtactccagcttcctaatggcagcaggattgctcaagacagag ttgttttggtggctgctggtaactctggagaacttggtccattctatgcctcctcccctgcttctgggaaacaagtcatttc agttggatctgttcaaaacgaacaatggacaacctttccagtaacctttacctcttcaaacggtgaatcaagggttttttcct tacctcgcttacaatggtgcacagattggatttgatgccgagcttgaggttgattttaccgaagaaagaggatgcgtctatg |

TABLE 5-continued

SEQUENCE LISTING
Open reading frame nucleotide sequence for proteases targeted for deletion in *P. pastoris*

| Protease Gene Symbol/ Locus tag | SEQ ID NO: | Open reading frame nucleotide sequence (5' to 3') |
|---|---|---|
| | | aaccagagatctccgcagataatgcgaataaagctattttgttaagaaggggcgtcggctgtgttgaaaacttggaattcaa |
| | | tttattgtctgtggctggttacaaggcttacttcttgtacaactcattttcaagaccatggagtctcttgaatatttctcca |
| | | ctgattgagctagacaacgcttactctcttgttgaagaggaagttggaatatgggtgaaaacccaaatcgacgccggtaaca |
| | | ccgtcaagttaaaggtgagcacgagtgaccaaatgttgccatctgataaagagtatttgggagttggaaagatggattatta |
| | | ctcctctcaaggacctgcttatgagcttgaattttttcccaacgatatccgctccaggtggagacagttggggcgcttggccc |
| | | ggtgggcaatacggtgttgcctcaggaacaagtttttgcttgcccctatgttgcaggtcttacagctctttatgaatcgcagt |
| | | ttggaattcaagatccccaggactatgtgagaaaattagtctccacagctaccgatcttcaattatttgactggaacgcagt |
| | | gaaacttgagacctctatgaatgctccacttattcaacagggagctggtctagtgaacgctcttggtttgtttgagactaag |
| | | actgtgatcgtgtctgctcctatttggagctcaatgacaccatcaatagagccagtgagtataccattcaaattaagaatg |
| | | agaactctgagactattacctatcaagttgttcacgttccgggaactactgtctactctagatcagcttctgggaacatccc |
| | | atacctggtcaatcaagatttttgcaccttacggtgatagtgatgctgcgacagttgctctatccacagaagagttggttttg |
| | | ggaccaggagaagttggtgaagtcactgtgatcttctctacagaagaaattgatcaagaaactgctccaattattcagggta |
| | | agattacattttatggtgatgtcataccgattgctgttccttatatgggagttgaagttgatattcattcctgggagcctct |
| | | cattgagaggccttatcagtgagaatgtatttggatgatggttccttagcatatgttgatgatgatcctgattatgagttc |
| | | aatgtgtatgactgggattctcctagattttattttaacctgagatatgcaaccaaagaagtatcgattgacttggtgcacc |
| | | ctgattatagcattgagaacgactacgaatggcctttagtttccggacacaacactattatggtcccgtgggatacgactac |
| | | gattatacctcgggtcaagcctttttgcctcgttactttcaacaacgtattaacgaacttggatatctttcttttttccagat |
| | | ttgctactttctgtagttcctgctggtgaatacaaagctctatttagagtttgctaccatatggagacttttggaacaa |
| | | agaagactggcaattgtttgaatccccagtgtttaacgtcctcgctccaccgaatgaagaaaacactactgaagagccaact |
| | | gaggaatccagcgaggagcctaccgaagagtcaacgtctgagtcaactgaagagccctcttctgagtcaactgagaaatcta |
| | | gcgaggtgccaactgaagaaattactgaagatgcaacatccacaattgatgatgatgaagcatccaccgaaagctctactga |
| | | agaaccaagtgctcagcccaccggtccttactctgatttgactgtcggtgaggccattaccgacgttagtgtcaccagtttg |
| | | aggacaactgaagcatttggatacacttccgactggttggttgtgtcttttcactttcaacactactgacagagatattactc |
| | | tcccaccttacgctgttgtacaagtaactatcccaaatgaacttcaattcattgctcatccagaatacgcccataccttga |
| | | gccctcattgcaagtttctctacactaagaatgaaagattaattatgactagtcagttcaactacgacaccagagtcatcgac |
| | | ttcaagtttgacaatcgagaccaagtaataactcaagtggagggagttgtttatttcacgatgaaactagaacaagatttca |
| | | tttctgcattggccccaggtgaatacgattttgaatttcatacatccgttgattcttatgcttcgacctttgactttattcc |
| | | attgattagatccgagccaatcaaattgatagcaggtgcaccagacgaagttgaatggtttattgatattccaagtgcatac |
| | | agcgatttggcaacgatagatattagttctgatatcgatactaatgataatttgcagcagtacttctatgattgctcaaagc |
| | | tcaagtacactattggaaaagagtttgatcagtggggtaattttacagctggatcagatggtaaccaatacagcaataccac |
| | | cgatgggtatgttccaattactgattctaccggctctccagtgccatctgtttaatggaaagtatctcattgagt |
| | | ttcacaaatactcttgctgaggatgaagtattggagagtgttcttcactcttctgcgtttagacgtggttcattcaccatgg |
| | | ccaacgtggtaaacgttgacattacagctggtggattggcaaaaagagaactcttctcttatatattggatgaaaattacta |
| | | tgctagtactggatctgaggggttggcatttgacgtatttgaagttgctgatcaggtcgaggagccaactgaggagtcaacc |
| | | tcagaggaatctactgaacaggaaacttccaccgaggaaactaccgaggaatcaactgaacctactgaggaatctacccagg |
| | | aacctactgaagagcccaccgacgagcctacttctgagtcaactgaggaacttctgaggagccaacttctgacgatctctc |
| | | aattgacccaactgctgtacctaccgatgaacctactgaagagccaactgaggagcctacttctgagtcaactgaggaacct |
| | | tctgaggagccaacttctgacgatctctcaattgacccaactgctgtacctaccgatgaacctactgaagagccaactgagg |
| | | agccgacctctgagactaccgatgatccatcgatagcacatcttctggacaatcggt |
| | | ggttactcaaaacactacagtcactcagactaccatcacttcagtcgtgtaatgtttgtgctgagacccctgtaacaatcact |
| | | tacactgcaccagttgtgactaagccagtttcttacaccaccgttacttcagtttgccatgtatgtgcagagacaccaatca |
| | | cagttaccttgacgttgccatgtgaaaccgaagacgtgacaaagactgccggccctaagactgtcacttacaccgaagtttg |
| | | caactcctgtgctgacaagcctatcacttacacctacatcgctccagagtacactcaaggtgccgaacgtacaacagttaca |
| | | tcggtttgcaacgtttgtgctgagacacctgtaacgctaacatacactgcgccgaaagccagtcgtcatcacagttccttcac |
| | | aatattcaagtgccggagagctcatttcatccaagggatcacgattcctactgttcctgcccgtccaactggtacttatag |
| | | taagtctgttgacactagccaacgtacactcgctaccattacaaaatcttcagatgagtctaacactgttaccactactcaa |
| | | gccacacaagttttgagcggtgaatccagtggaattcaagctgcttcaaacagcacgagcatctcagctccaactgtcacta |
| | | cagctgggaacgagaactctggatctagattttcgtttgctggactattcacagttctgcctcttatcttgttcgttatata |
| | | a |
| PAS_chr1-4_0251 | 35 | atgcagtttgcttccttactgcttctcttgtatattttcttggggcaaatttatcctactgaagcagcaaaatattttgttc |
| | | gtctgaagaagcctcacacactagacctcttgttcaaacaggatgaagcagatgcatctgctgagaaccgaatctctcttca |
| | | tggtttaagggaccgaatcaaaaaaaaagatctcttttggaacgttcgaaggttttgttggtgaattcacaacagaacttgta |
| | | gaaaaactaaaaaagaattcgttgattgcagacataactcctgacattatcgtctcatcttgcgatatcgaattgcagtccc |
| | | ccgctcctgatcacctggctaggttatccaaagaaggtgccgtaagagcacaagatcgtcttcttggaccggaatttttcta |
| | | cgatggtgactggactggagaaggcgtcaatgtatacggtgatagacaacgggtatcagggtaaatctagatgaatttgagggc |
| | | agagcatcatttggtgctgattttacaggcactgggaaagatgactctgttggtcatggaacccacgtagctggtcttattg |
| | | gctccaaaacttttggagtggccaaaaatatcaacttgatatccgtaaaagctctctctggtaatgggagcggttcgctttc |
| | | agaggtcctacaggcgattgaattcgcagtcaagcatatgaaagccagtcgtaagccaggtgttgctaacttgtctctaggt |
| | | gcaccaaaaaattcaatccttgaaaaagcgattgaagaggcatcaaggacattcaagaacggtttagtcatagtcagcagctggcaatg |
| | | ccttcgtggatgcctgtaacacatccctgcaaactctccatatgcaatcaccgttggagctataggtgatcacaacgatga |
| | | aataactagattttccaactggggagcctgtgtcgatcttttgtcaggaggggacacaattgtaagtgtaggacttctcaat |
| | | ggagtcgctgtccgcatgtctggaacttcgatgtctgctccaatagtcgcaggcttagccggaatattacttgaccagggtg |
| | | tggccccagaagatgtaaaaggtaagttaatagagctctgcagatgaaggaagatacaacgataatactggaattctaaagcc |
| | | gggaactccaaaccgaatagccaacaatgaattcgaaaaagtgattatgaagatcaaaaagaaaatgacaatgatgaagac |
| | | gatgaagacgggaagacaatctagaagacattgaagaggacgaggattattgggatgaagagagaaggtatagggaatatg |
| | | cggtatctagtttagtcttctaa |
| PAS_chr4_0874 | 36 | atgttcaacattatccaacggatacagagtttgagcaattttatttaacggttccattctattatgtattgttacaacag |
| | | ttgtctcaattattagtatgttcttggatgaaacgtccagtattcctgcccaattaagcaatgttgtaatatcaacaaattt |
| | | aaagtatagcagatcgtttggttcagtcggtggtagacctaaagaaaactccaagattttatttgatcttgatatggatctg |
| | | gctccattattcaattggaatactaaacaactgtttgtacaattggtagcagagtaccctacctctgttgccgatgatggtg |
| | | cgaaggtgacctattgggatagcataattactgagaaaaagtacgcaagagtgcatgtcaataagcagaggggaaaatactc |

TABLE 5-continued

SEQUENCE LISTING
Open reading frame nucleotide sequence for proteases targeted for deletion in *P. pastoris*

| Protease Gene Symbol/ Locus tag | SEQ ID NO: | Open reading frame nucleotide sequence (5' to 3') |
|---|---|---|
| | | agtttgggacgtgtcggactcctttcaaggccgcaatgctacggttaaactgaaatggaacttacagccctatgtcggctttctattctttggacaaactaagggagagattgaggtggcctatcctgcaacataa |
| PAS_chr3_0513 | 37 | atgagtgtcatagtgcatcctcttgcactattgacaataatcgacgagttccagagacgaggtcgcaacaacgattccataatattcggtgggttacttggtaaacatgatgaatccaccaaccaaatatctgttgttaacagctttgtgataccattgatcgataatcagttttttgaataaagagtacttgcaggacatgctactcaaattttctatcattaattccaactttcgattcgtaggttactatcacgttcaatctttaaacggtaccgaaactcaacagtatgacttgaacgctattaacctagtatgccaagatgataataggccttcgtcctttgtccattggatagtaacagatccaaaagagttcaaatcattctcgatgtattacttggatgattcaatggttcaactcgtcaattccaatattcaacattacattttctaaaccattgccctatgaatttaaaaaaccttctgtctgagaaaattgctatcgacacaatcctcaagcaatccaggctagaaaaagacttatccaccaaaaactcactgaagaaattaaacaatagttatatcgacattcattcctcactgaacgttctctataaatcagtcaataggcttattcgttacctcaaaaaatgctcaaaatcagaagtttcaattgactatgacacagttcaggaaatgaatactgtaatactgaaaattgaaaggcttaaattgatacccccaagtcaaggaggagtttgacttagtgactctttcactactggtagacaatcttgatcagatggatcatcttttgtatctccggaaacaagtggaacagtacaaaatatctgaatcaatgtatagttag |
| PAS_chr1-1_0127 | 38 | atgaaatttcactcgattgtcttcacattttcactcgttttgagttcactggcgttgtcgataccatgggtgtctgaccacatggtccagcatcttttttgccgacccttcaatcagtaaaggtcctgatgtagatctcgttgggctacataagcatttggtcagcatcaaatctcttcgggctatgaacaagaagtagtatcgtggttggccgattatctagccagtagggtcttactgtggagttgaacaaggtcgaggacgaaactgaacgttacaatttgtatgcttatttatttgggaaccaccgcaacactaaggttgtgctaacttctcacttagacacagttccccccttatcttccctacaaagttgaggaaggtggctatatctttggcagaggaagctgtgatgctaagggatcagttgcggcacaagtgattgccttcctaaatctcttggaagagggctccatcaaagaaggtgatgtcagtcttttgtacgtcgttggtgaagagattggaggtgatggaatgcgcacagctagcaagaccttgggtgctaaatgggacactgccattttggagaacctaccgagaacaagcttgccattggacacaaggaattgcactgtttgacctgaagattacaggaaaatcctgtcattctggataccctgagctgggaattgatgccgacgctatgttggtccagatttgcacaagttgcttttttgagacttcttggcctgtcagtgatttgctgggaaactccacagtcaacgcgggacagatcaacgaggagtagctgctaatgttatttcttcggaagcacatgccaaggtttttaatccgcgtggctaaagacattgacgctgtagagaagctgatctacgaggccattgccccccttcgaggagtatacagacattacctttcactccaaagaagatgctactttcttcttggattacaaggttgaaggggttcgagaactacattgcagcctacagtaccgatgtaccattcctagtgacgggctccaatttgaccagatatttgtacggaccaggaagcatcatggtggctcatgggcctgatgaaatggtcaaggtttcagacctgcaggatagtgttgacggatacaagcgattagtctccgtctcactttag |
| PAS_chr4_0686 | 39 | atgccagagaaaaagaaacaaaaaaaagagtcgacatctccattcaagggtaacctagttgggatctcattggtagctgtggcattgtttgccatctaccagtacctctacccaagctcgtttcctctcagcctgaaaccccagcccagtttcgatctgagcagtgaattagaagcattgtgtcccgtgtaccctgcagtcagatcttccgacttcgaaaaggatcgccccatcttagagagaattctgaacgatccctcatttagaatcgcttctgctcaaaaactgagtaaggctgttcagatcgataacccaagtgttcgacgaacaattggacgtggctcaagaccctgaagtttggaccaaattcgtcaagttccatgaatattggaggcaacttctccccaccgtttactcccaattgaaggtcgacaaaatcaacacctatggcttggttttcacttgggaaggctcagaccctagtctgaaaccactcatgttcttggctcaccaagacgtggttccagtccagaaagatactcttcaggattggtcatatcccccctttcgaaggacgtatcgccgatgacaggagtttggggacgtggatcagctgattgcaagagtttactgattgcattactggaaaccgtagaattgctggtagatgaagggtactcaccaaagagaggtgtcatcctccgcatttggattcgacgaagaagctcaggtacctacggtgctcacaatatctccaagttttttgcttgagaaatatgggccagatagtattgccctcattttggatgaaggtgaggctgtcagttacgtggacaagaaacaaactaccctcgttgcaaagattgctacgcaggaaaagggttaccttgacctagaggtcgcattgaccactgtaggaggccattcttctgtcccccctaagcacactgcaattggccttatttccaagttggtcacacatatcgaagatcatccattggacccagaaaattagtaccagaaatcctctggtacagttttcgaactgtcttggtgcagctggggcttttgagagatgacttcaagactgctcttgttgcatacagcaaggatccgtcgaacaacattgtcaaacaaggtgtgattaaaggtatttccaagattgcatttttcttcggttctttgattaccacaacacaagccaccgatcttattttcggtggagagaagatcaatgcttttgcctgaaagtgctagagtagttatcaaccatagagtggacgttgagcgtgattcagcccaaatcatagacagatgattcacttccacgttgttcctattgccaaggagcacggtttcaaggtcacttacagtgactatggtagtgacaaagttgaaactgtctacgagccagaaggagttgcctcattgggagaattccacgtttctcctttctccagagtctgggagcctgctccagaatctccatccgacgacaatgtctggtccatcatttctggtaccactcgtacgatatttgaggagtttgtggaccccctcggctaaacttattgcaagtccatacatgatgcctggtaacaccgacactcgacactactggccgctgacaaagaatatctatagatacgttccaggtattgtagatatttacaaggctaagatacactcggtagatgaatctaccgaggttgatgcccacttgcaagttatagcttttctaccacgagttcatcaaggttgccagcgaatgggagctttga |
| PAS_chr2-2_0056 | 40 | atgaaatcctctaaagaactatacaaggaggctctcaactatgaatactcttccgcggtttctttcaaggcctgggttcgaagtgctcaaatcattttgcgacatgcccggccagttgctgaacaaagatacatcagtgagtgctataagttgtctgttcgtttgtagacttgattgtgaacaagatggccacgcataaagagctcaagcaattgaagaaaataaatgcaccagtatatctcacctatttggatttggctacgaagaaagtcccagatgtcatcaaggaatgtgaggccttgaagacaatttgggatgatgagtaccaaagctacctcaaactgcaacaattgaaacgacagaagcagaaagaccaattgatccatcatcagaatcaggctcaaacgcataaattacgtagatcttcatcaatattgaaaagcatcatcaaccgctgttgatgaaagacgcgctgttgaaacaactacagcagttgacataccatgatcgtgaattcgcaaccgcaataacggagatgccaaattatccagagatcccccagctgagtatttcaacgaatcagaacactagatcagaggcaccccccacttccaccaagagtatcgcaggaacagtcattagcaccagtatcactagattcatcacaggcagatttacaaacacaaaactgttaacttcaccgaagctgggcaaccattacgaacagtatttatttcagatagactccaatctgagttccttagactagcggaacacaacacgatacaaaagctagagacttgtggcatcctttgtggaaagctcgtcagaaatgcattcttcatcaccccatttggttataccagatcaagaggtcgacaccaaacacatgtaatacaagaaatgaggaaaagttattcgacactatagatcagcttgatttatttgtccttggatggatcataccacccaacacaatcatgcttcctgtcttccatagacttacatacacagaattcgtaccagatcatgttaagcgaagcaattgccattgtgtgtgcaccagcactctcagttttctcatcattcttttggatgtttcggctaacccatcctccgggaattccaaccattacacaatgcactaggacgggatttcatcctcatgaggaacccaatctgtatgtgacttgtaatcgaaagaacatgggcgacgtgcaaggcggacacgttgtgatcaagaatcatttaccgtttgaaaaagcttgatctaagataa |
| PAS_chr2-2_0159 | 41 | atgactagttctgtagataaagtgagtcagaaggtcgctgacgtaaaactgggctcctccaagtcaacaaagaataacaagagcaaaggtaaaggaaaatccaacaagaatcaagtggttgaggatgatgatgaggatgattttgaaaaggccttggagcttgc |

TABLE 5-continued

SEQUENCE LISTING
Open reading frame nucleotide sequence for proteases targeted for deletion in *P. pastoris*

| Protease Gene Symbol/ Locus tag | SEQ ID NO: | Open reading frame nucleotide sequence (5' to 3') |
|---|---|---|
| | | aatgcaattagatgcacaaaaactagctcagaaaaaagctgatgatgtgcctcttgttgaagaagaagagaaaaaagttgag |
| | | gaaaagattgaacagcaatatgaccccatttccactttttaccctgatggaaactatccccaaggagaagttgtggattaca |
| | | aagatgacaacttgtaccgtactactgatgaagaaaagcgagctttggatcgagagaagaataacaagtggaatgaatttcg |
| | | taaaggtgctgaaattcataggagagttcgaaaactggcaaaggatgagatcaaaccgggaatgtcaatgatcgagatcgcc |
| | | gaactaatcgaaaacgcagttcgtggatatagtggtgaagacggactcaagggtggtatgggatttccttgtggtctttctt |
| | | tgaaccattgtgctgcgcgcactattctcctaatgctaacgacaaacttgtcttaaattatgaagacgtcatgaaagtagattt |
| | | tggtgtccatgtgaacggtcacattatcgatagtgcattcacgttaacattcgatgacaaatatgatgatctgttgaaagct |
| | | gtcaaggatgctaccaatactggtattcgtgaagcaggtattgatgtgagattgaccgacacttggtgaagccatccaagaag |
| | | taatggagtcctacgaagttactttagacggagaaacataccaagttaaacctatcaagaatctttgtggccataacatcgg |
| | | ccagtatagaattcatggtggtaagtctgttcccatagtgaagaattttgacaacaccaagatggaggaaggtgaaaccttt |
| | | gcaattgaaacctttggcagtacaggaaggggtcatgtgataggacaaggtgaatgctctcactacgccaagaatccagatg |
| | | cccccgccaatgctatctccagcattcgtgtgaaccgtgctaaacaattgctaaagactatcgatgagaacttggtactct |
| | | tccattctgtcgtcgctacatagatcgtcttggagaagaaaagtacttattggcattgaaccagttggttaaatctggagtt |
| | | gttagcgattatccacccttggtgatgtcaaggggtcatacactgcccaatacgagcacaccatcctttttgagacctaatg |
| | | ttaaggaagttgtatcccgcggtgaagactactag |
| PAS_chr3_0388 | 42 | atgattcacagctgtgctagtgctgagtgctcaaaagcgactgaatctaccttaaaatgtcccttgtgtctaaaacaaggtc |
| | | agatccaatattttgtaaccaaaaatgtttcaagaatggatggaagatccacaaagcggttcacgccaaagatggtgatat |
| | | agatggttcgtacaaccccctttcccaactttgcctacaccggtgagctcagaccagcatatcccttgtctgtgacgagag |
| | | gttccagagaacattactctcccagattatgctcttgatgggagtaccagtctcagaaatcaaaaataacagaatgaacaaga |
| | | tcaatttggtaacggagccagaagacctggccaagctaaaaaatgtttgccgtttagcacgagaggttctagatgctgcggc |
| | | tgcatctatcaaaccaggagttaccactgatgagatagatgaaacgttcatagtgaaacaatcaagagagaagcataccc |
| | | tcccctttaaattacttcaatttcccaaatctgtttgcacatccgttaatgaagtcatctgccacggtatacctgatcgta |
| | | gaccgctccaggatggtgacatcgtgaacctggatgttacccctttataaagatggattcatgcagatctgaatgaaacgta |
| | | ctatgttggagagaaggccaagactaacaaagatctggtcaacctcgtcgagacaaccagagaagctcttgctgaagctatc |
| | | cgtttagtgaaaccccggcatgccgttccgtcaaattggtactgttatcgaaaactatgtgactgaaagaggctgtgaaactg |
| | | ttcgttcttacactggtcatggtatcaatactttgttccaacactgaaccaaccattccgcattacgctcgtaacaaagctgt |
| | | tggagtagccaaaccaggagtggtattcactatcgaaccaatgttgactctgggcactcatcgtgacgtggtttggcccgac |
| | | aactggaccgccgttaccgctgatggaggaccaagtgcccaatttgaacatacccttttggttacggaagatggtgtggaga |
| | | ttctcactggcagaacggaaacttcgccaggcggtgccatctcaagactataa |
| PAS_chr3_0419 | 43 | atgctctataagaccaccttgtcaatagcacacacgagtgtgatattgttgtcattgataaccgccataagttgctttgagt |
| | | tgcatcttcctcagaaaggtttctcatatagtagacagtttacaatatacttgcggccaatttttgcaaaagcagcagatctt |
| | | tgcactctataacaagcaaaattcaccgaaatagtgaaccagaatatcaagggaatagaggagagagtttttgtctgagttg |
| | | cttgaagaaagattagagaatgaatcccagaatgattattataccgccaattctcaaaattggcctatcgacttggatcagt |
| | | actcagaatcatttgtaataaggatcacatctgaagatgagtttatcaagtacttgatcttcaaggaagctaaagctttgca |
| | | tatttccatatgggagcaatctgttggtttgatagatttgaaggttgaccgtgatcagatgcaccgcctactttacaacgtg |
| | | gagtcacgcatactggaacgaagaacgagaagtgttgacagtccagtttctgaatataaagtacaattgatgattggagatc |
| | | ttccacagcgaatctacgaaacatatccttcgacaaaagtgacatctttgcaagccctaggagagagttcccttcttttccagaa |
| | | cctaagtaatgcttttttttgaggattttagaacgctggaaactatatacgactggttcgaagaaatacagaaggaatttcct |
| | | aagctagtgtcgatcaactggattgggcaaacttatgaaggtcgtgatctgaaggctcttcacgttagagggaagcactctg |
| | | gcaacaaaacagtagtcgttacaggtggaatgcatgcgcgtgaatggatatcagtaaccagtgcatgctatgccgttcacaa |
| | | actgctccaaaactatgctgacggacaccacaaggaagcgaaatacctggacaagttggacttttttgtttgttccagtttttg |
| | | aatcctgatggatacgaatatagctttaacgaagacaggttgtggaggaagaacagacaagaaacttatatgccccgatgtt |
| | | ttggtatagacattgaccattcatttgattatcatttcgtgaaatcagaagacttacccgtggagaggaatattcgggtga |
| | | gtccccttctcgaaagtatagaaagtgaagtgtggaataatttcctgaacagaaccaaagaagaacataagatctacggctat |
| | | atcgacttacactcgtattcgcaaacggtgctgtatccctatgcgtactcatgcgaaatcttaccaagggacgaggaaaacc |
| | | tgattgagctaggttacggtattgcaagggccataagaaagagtacagggaaaaaatatcaagtgttgaaggcatgcgaaga |
| | | cagggatgcagatctattgcctgatttgggaggaggaaccgctttagattatatgtaccacaaccgtgcatactgggcgtttt |
| | | cagatcaaattgagggattccggtaatcatggctttctccttcccaaaaagtttatatacccagttggaacagaggtttatg |
| | | cctcaattcagtactttgttctttgtgctgaatttagaaggctaa |
| PAS_chr1- 3_0258 | 44 | atgaaattgaccataacacattagcccataacgatcaaatcttggacattgatgtgtccagtgaaatgctactatctgacctca |
| | | aagtcctgttggagttggaaacttccgtacttaaaaacgaccaacaattatttacaataacaacctgctcactggagatga |
| | | ctcgccactggaagattaggactcaaagataatgaactcataattctgagcaaagtcgaagcacatagtgatgtcaattca |
| | | cacttgaactctgttagagaacagttgatacaaaacccgctataccaggccagtttacctccaagtcttagagataagctcg |
| | | acgaccctcaaggcttcaaagaagaagtggaaaaactaatccaattggggcagtttggacaatacgggccttcccgtacttc |
| | | cgtccaacaggaattagacagactacaaagagatcctgacaatccacaaaatcagaaacgaattatggagctcattaacgaa |
| | | caagctatagaggaaaatatgaatactgcttttgaaatctcacctgaatctttcgtttccgtgaatatgctctatatataaatg |
| | | tggaaattaatggtgtccattgtaaagcattcgtcgatagtggagccataatgtgccctaaactcgcagagaa |
| | | atgcaaccttgcgaatctaattgataaaaaggttccgaggagtcgcacagggtgtaggaagttctgaaatcattggtcgtatc |
| | | cattctgctcccataaaaattcgaagatattattgttccctgctcattcactgtttttggataccaaggttgaccttctattcg |
| | | gacttgatatgttgagaagacatcagtgtgtgattgaccttaagaacaactgtttacaaattgcagacagaaagacagaatt |
| | | tttaggagaagcagacatcccaaaggaattcttaaccaaccaatggaagctccatccacagctcctgtcccaaaacctgta |
| | | caacctcctcaacaactcggtcagcggccggctggaagccctccctccacaattcaaagaccagcagtacaaccgccacctg |
| | | tggatataacctccagaaaaaatccagcagttgatcaaccttggattcggagaagaggagtcgaaagaagcacttattagatc |
| | | tagaggaaatgtggaagttgcagcggctttgttattcaactag |
| PAS_chr4_0913 | 45 | atgccaaacctttcttctagcttgaacaagatgactgctcaagccgtgaaatacgcaaacggtatgtcatctgccctctccc |
| | | gtgtttgagactctatccactaactttagattttatcaccttcctgaacaattcacctactccataccatgctgtcgactcc |
| | | gtaaagtccaaattggtagagtcggggtttaacgagctcagtgagagagtaattgggccggaaaagtcaagaagaatggcg |
| | | cttactttgtgactcgtaacaattcgtccattatagccttcactgttggcgggcactggcagccaggtaacggagtgtcaat |
| | | tgttggagcccatactgattcccaaccttgagaatcaaacccatatcccattcgactaaggagggatttaaccaagttgga |

TABLE 5-continued

<div style="text-align:center">

SEQUENCE LISTING

Open reading frame nucleotide sequence for proteases targeted for deletion in *P. pastoris*

</div>

| Protease Gene Symbol/ Locus tag | SEQ ID NO: | Open reading frame nucleotide sequence (5' to 3') |
|---|---|---|
| | | attgaaacttatggtggaggcttgtggcatacgtggtttgacagagatttaggagtagctggacgagtgtttattgaagaag aagaatctggtaacattgtgtccaagttagtcaagatcgataaaccagtattgagaatccccacactagccatacaccttac caaagagagagctaagtttgagtttaataaggaaactcaattccatccaatctcatcgcttgaaaactcctctgaaaaggag aaaaacaaagatgaggaacatgacgcttgtgcaggagaagatttgactacggaggagtttaagtcaattcaatctgttgtgg agagacacaacaaacaattgcttgatctggtggctgcagatcttgattgctctatatcccagatagtggactttgaattgat tcttttcgaccacaacaaaccagtactcggaggtttgaatgaagaatttgtgttctcaggaagattggacaacctaacttct tgtttctgtgccactgaagcgcttatataatgccagtaaagataccaacaggttagatctggatactaatattcaactgatct ctctgtttgaccacgaagagattggatcagtttctgctcaaggagctgattcttcatttctacctgacatacttcagcgtat aacaagactaactggtaatgaggttagcaccgatctggaaggacaaccaaattctttcttttttagagtcaatggccaaatct ttcctactatcttcagatatggcacatggtgcatcccaatcatggggaagtctatggagaagctaaataggccaagaatca acgagggaccagtgatcaaaataaaacgctaatcaaaggtacagcaccaattcccaggtattgtttgctcaagaagattgg tgagttgggaaaggtcccccttgcaattgtttgttgttagaaacgactctccctgtgggtcaacaattggtccaatgttgagt gctaaacttggacttcgaacgctggacctcgggaaccccccagctctccatgcattctatcagagaaactggaggtgctcgtg acgttaaaaagttggtcgatcttttcgaaagctattttgagaattattacaccttggagcctaagattaaggtataa |
| PAS_chr1-1_0066 | 46 | atgaacaaaggtccgaaagaattggagggccgcaagtatccagcaagagcccatgcactgacggtcaaaaatcactttatcc aaaagaaggctgacattttcaagtcgttctgcaatctttattagtggcgaagatctcaagttgtatccttactgtgaccaaac agctcctctcagacagaatcgttatttctttttatctgtcaggttgtaatatccctggatccccatgtccttttttgacttggac gccgaattgttaattctggtgctaccagaaattgattgggatgatgtcatgtggagtgggatgcctcttccgattgaagatg cctacaagacgtttgatgtggacaaggtggtatatctttaaagatttgcaaggcttttttgtcgtcgtttggaaaaatatatac aactgacatcaatgatgaaaattctaagtttggcaatctactaacagagaaagatcctgacttgttctgggctctggatgaa tccagattgatcaaagacgactatgaactcactctaatgagacatgcgtcaaaaatttctgacaattcccattacgctgtca tgtcggctcttccaattgaaactgacgaaggccatattcacgctgagtttgtttatcattcgttaagacagggatctaaatt tcaaagttatgacccgatttgttgcagtggaccaaactgtagtaccccttcattatgttaagaatgacgattctatggagaat aaacacaccgttctaatcgatgctggtgcagaatggaacaactatgctagtgacgttacaagatgtttttcccatcaatggag attggacgaaagagcatcttgagatctataatgctgtttttggatatgcaggaccaagttatgaagaagattaagcctgaagc ccattgggatgagctacaccttttggcacatcgtgttctcattaagcattttttgagcctcggcatatttcataacggaaca gaggatgagatatttgagagtggagtctcagtatcattctttcctcatgggctgggtcacctttttaggaatggatactcatg atgttggtgggcaccccaactatgatgatccaaaccctctattgagatacctaagattgagaagagtgttgaaagaaaatat ggtagttacgaacgaacctggaatctactttctctcccctatcttgttgaattgggactgaaggatgataataaggcaaaatat gtcaacaaggatgtactggaaaagtattggtatgtcggaggtgtgagaattgaagacgatattctttgttacgaaagatgggt atgaaaacttcaccaagattactagcgaccccgaagaaatttccaaaatcgttaaaaaggggttggagaagggtaaagacgg gttccataatgttgtatga |
| PAS_chr2-2_0310 | 47 | atgacatctcggacagctgagaacccgttcgatatagagcttcaagagaatctaagtccacgttcttccaattcgtccatat tggaaaacattaatgagtatgctagaagacatcgcaatgattcgctttcccaagaatgtgataatgaagatgagaacgaaaa tctcaattatactgataacttggccaagtttttcaaagtctggagtatcaagaaagagctgtatgctaatatttggtatttgc tttgttatctggctgtttctctcttgaccttgtatgcgagggacaatcgattttccaatttgaacgagtacgttccagattca aacagccacggaactgcttctgccaccacgtctaatcgttgaaccaaaacagactgaattacctgaaagcaaagattctaac actgattatcaaaaaggagctaaattgagccttagcggctggagatcaggtctgtacaatgtctatccaaaactgatctctc gtggtgaagatgacatatactatgaacacagttttcatcgtatagatgaaaagaggattacagactctcaacacggtcgaac tgtatttaactatgagaaaattgaagtaaatggaatcacgtatacagtgtcatttgtcaccatttctcccttacgattctgcc aaattcttagtcgcatgcgactatgaaaaaacactggagaacactctacgtttgcaaaatattttcatatatgataaggaaagcg accaagaggatagctttgtacctgtctacgatgacaaggcattgagcttcgttgaatggtcgccctcaggtgatcatgtagt attcgtttttgaaaacaatgtatacctcaaacaactctcaacttagaggttaagcaggtaacttttgatggtgatgagagt atttacaatggtaagcctgactggatctatgaagaggaagtttttaagtagcgacagagccatatggtggaatgacgatggat cgtactttacgttcttgagacttgacgcacaatgtcccaacctttaacttgcagcatttttttgaaagaaacaggctctgt gtcgaaatatccggtcattgatcgattgaaatatccaaaaccaggatttgacaaccccctggtttctttgtttagttacaac gttgccaagcaaaagttagaaaagctaaatattggagcagcagtttctttgggaagaacttcgtgcttacagtttaaaat ggatagacaattcttttttttcttgtcgaagttcacagaccgcacttcgaaaaaaatggaagttactctagtggacattgaagc caattctgcttcggtggtgagaaaacatgatgcaactgagtataacggctggttcactggagaattttctgtttatcctgtc gttggagataccattggttacattgatgtaatctattgatggagactacgatcacttggcttattatccagactgcacatccg ataagtatattgtgcttacgatggttcatgaatgttgttggacctggagtttagaagtgcttgaagatagagtctactt tatcggcaccaaagaatcatcaatggaacatcacttgtattatacatcattaacgggacccaagttaaggctgttatggat atcaaagaacctgggtactttgatgtaaacattaagggaaaatatgcttactatcttacagaggccccaaactcccatacc agaaattattgatctttctgaccctagtacaacagtcttgatgacattttatcgtctaatagaggaattgtcgaggttag tttagcaactcacagcgttcctgtttctacctatactaatgtaacacttgaggacggcgtcacactgaacatgattgaagtg ttgcctgccaattttaatcctagcaagaagtacccactgttggtcaacatttatggtggaccgggctcccagaagttagatg tgcagttcaacattgggtttgagcatattatttcttcgtcactggatgcaatagtgctttacatagatccgagaggtactgg aggtaaaagctgggcttttaaatcttacgctacagagaaaataggctactgggaaccacgaacatcactgcagtagttttcc aagtggattttcagatcactcatttgtgaatcctgacaaaactgcgatatgggggtggtcttacgtggggttcactacgctta agacattggaatatgattctggagaggttttcaaatatggtatggctgttgctccagtaactaattggcttttgtatgactc catctacactgaaagatacatgaacttccaaaggacaatgttgaaggctacagtgaacacagcgtcattaagaggtttcc aattttaagaatgtaaaccgattcttggtttgtcacgggactactgatgataacgtgcattttcagaacacactaaccttac tggaccagttcaatattaatggtggtgttgaattacgatcttcaggtgtatcccgacagtgaacatagcattgcccatcacaa cgcaaataaagtgatctacgagaggttattcaagtggttagagcgggcatttaacgatagattttttgtaa |
| PAS_chr1-3_0261 | 48 | atgacctgccaaagtgtagaagagctggatgctattgttgaatcaaagcttaggggggttgataataaagtttcgaacggaa atgttgacttcatcaaacaatatctgattcaggcgatgaactattatgacaagtatagatctgaaatcaaaaaaattggacc cacagaaaagaaccctaaatactattgttttcaagaggcagcgtatgttaactacaaagcttccaagctttactaagagag agaatacccaagctgcctggctttggaggatataaatctgcgtattcaaaaatctatcgtgaactgatagaaatggtagagg ggcaagaacatgagattgcccagataaaaaagcggcttaaggaaaaactttttgtgatgatacattagttcttcgactgagaag tttaaaatcaccatctgctactcagcccaaaagtttaccggattctacacccacttcacaatttaaaccaaaaccttcaaag |

TABLE 5-continued

SEQUENCE LISTING
Open reading frame nucleotide sequence for proteases targeted for deletion in *P. pastoris*

| Protease Gene Symbol/ Locus tag | SEQ ID NO: | Open reading frame nucleotide sequence (5' to 3') |
|---|---|---|
| | | cctttttagtatcacaatcaatgaggaatacatttcggttgaccaattgtcacgccttcttaaaacgaacccgaatgacatac<br>tcctcattgatctacggtctcgtcaagagtacgacgtgtatcacattgaagatggctccggggtggacatgtcaatatgtat<br>agaaccaatgagtatcagaaacggatacacagcagaggatctttatcaactttcaatggccgtcaatccagattatgaaagg<br>agattggttcaagaatcggtctcagtatgaactgttggtatgttatggtaattatgacaacgaggctactgttcaaatgttca<br>tgactatcatgaataaagatacttccctcaagaggcggagcgtctatttgaaatccggaattaagggctggaatcaggatct<br>gagtttttcaagattcgaaaccgaatgggtacttaactagtacgactgactacttcagtaacactccgaaacacacaattacg<br>cccaaatcatcaaaatcaagttcaaaacctactttaaaaactactgtcaactctgggcctgcccacactgttgggatcaata<br>atctaggaaatacatgttacatgaattgcatacttcaatgcctattagaaagtgataagtttgtttcatttttttttacaagg<br>cgattataagaaacatatcaatattaatagccgattaggctcgagaggtatattggctacaggatttcatttgttagtgcta<br>ttaatatccagatcatctggtaaaacagtgactccttcttcatttgccaaagatgtttcaacagtgaataagaattttaagt<br>taggagagcaacaggattgttttgaattttttagatttttctcctggatagtttacatgaagacctgaatgaatgtgggaatga<br>accaccaatcgcagaactcacacctgaagaggaaaagcttagggaagctttacctatcaggattgcttcgaccattgaatgg<br>gaaaggtatttaaaaaacaatttttagcatagtagaagatgtgtttcaagggcagtacttctccagattggaatgtacagtct<br>gtaaaagcacttcaactacttataactcattcagttcactgtccttgccaatcccattagatcgacaaaatgtcacactaga<br>tgactgtttccaggcttttttgttctgtagaagaattgaacggagatgacagatggcattgtccaagctgtaaaaaaaagcag<br>gtcgcttttaagaaacttggtatctctagactaccaagtgttctgatcgttcactttaaaaggtttcaggtcaagtgggaaa<br>caggtcatataatcaagatagacaagtttatcagttatccgttcaagctatcaatggacaaatattggcccaaagctcaatc<br>agaagaagaactaagaaacttggagaagctaccatcgagaaatcagaatcccccttcaattatcgattgacaggggtggct<br>aatcatttgggaccagaacatcatctggtcactacacatcatatgttcaaaaaggtggccaatggtattactttgacgata<br>gtgctgtgactagcaatgttgatcgtcataaaatcgtaaatgggaacgcctatgtttttattttatcgacgtagttag |
| PAS_chr2-1_0546 | 49 | atggaagccgtgaatttacaaaattgaatggattagacaggtgcctccagttactgtggctcttgtagcatccatgtcaatga<br>cctatttttttgcaacgcatagatgtattatcctcaaatatgttcgtgtttgaaagacatcgtgtgtttaatgagatggccta<br>ttctcgtttgatactaagtttcttcttcagcgcccattcgtttgttggattcttttggacattgtacacattatttcagaat<br>tcacaggcactcgagctgacctatgaaaactcaatcgattacctctactcattggtgataatagcaggtttgatcgtggcat<br>gggcctcatacttgggggggtccgttcatgctgggatgggttctagctgacgtcttgagaaccatatggtgcaaacagaatcc<br>caacgaaagaatgtctattttgggggctagtttccttcaagcaggatactttccatttgtaatacttgccatttcatggcta<br>gaaggaagttcaagaaatcttctattaatgctaattagccaaactgtcagtcaggcttatattttttggacaccatatgatgc<br>ccgaactacacgggatcgatctgtttctgcctatatggaaattccagtgtttcagacgtcagagacaaccaccaattcatca<br>gcatcaagactaa |
| PAS_chr2-2_0398 | 50 | atgtcaaaggtggtggtattcctaaatgggattattggcaataaccctttacgtttgaacttctctctgtttttaagcgtgccaa<br>tcaccaagcatatccaactttgttcttatcaaggatataagtttggcgtgtttggatattgcaccgagaataatatctgcac<br>aacgataggaatcggttatcatcgaaattcaatagacgaattgagaggctttttcattaccaagtaatgcaagaagctctata<br>tcaagcttgttggtggttcatttgattggctgtgtttgcacctttattttatgtggttctaagtctcatgttgaatatggata<br>gatttcacagatcattatggttcttattaacgtgtctagtatggacttgtgctttctttttttttttacattattctcccttcct<br>ggtagacgtgttactatttgtgccacacgttgcgtttggaggttggttgatgttggaagtactgtattttttggcatttaca<br>ggaaccatttttgtcatcatgcgaagaactgtcagctcaagaaaaactcatttgaagaactacaacgggggaagtacaagtt<br>tgatgcggctgacgtatatctccaatagctctagaggaagctctgtaaccaatgatgaatacgtctggtttcaagaaac<br>tccattacaagacctctaccccccagacaatcccaattacgacgacatctacggaacgactgaacacgaactaacccgcttg<br>gacacaatatctcttgaaaggccaagaataggcctttatcacaaacgaaaatgccagcggcgatggtggggtagtttccccac<br>cacagaatgacagtacacttctggaatcttcgggcagaattaggaatgggccactgggagaccgaagtgaatttcccaacgg<br>atcaacaagcgaactttctgcataa |
| PAS_chr4_0835 | 51 | atgaaatacagtgaccaattaatagaagagtacaaagaattatggttaacagcgacatctcaatgagcttactagagaatggt<br>gccagggaactctccacctgagcaaattatacgtttacttgacacaagacttaaagtattttgggggatggatttcgacttt<br>aggcaaaaccattcgttatgtcgccgtaggcaatcgcttgtgtcattaggcaaacatgtggggatgctcagtaatagtgag<br>aacacgtacttcgtgattgtattaacgatcttactgacagttattaagagatgggatgtacaatgctgaagaattagaag<br>aaatcagtggttaacgttacctgccgtgaaaggtacctttttattcatgagatcgatggtagagtcttctacaataactta<br>tgcagaaatgattactgtgatgtttgtaatggaacaagtctatctggattggtcaaataatggactgagaagtaaacctgac<br>aacttgcattggtggttcaatgaatggattgatatacatagtggggagaacttttgaaagctggtgccagtttttaaaggatg<br>aggtagaccgctgtatacaggagttgaaggatgctaatagatgatctcgtggcgagggttgaggagattttttagagaaac<br>attagaacttgaagtcgaattctttaaaagttgttacgatatcacggacgatgaatga |
| PAS_chr1-1_0491 | 52 | atgcactcgaaatttaggtgggtatgtgtcgatactcaattctgcacacaccaccaaaatctgtcgcctttctcttatatct<br>ccaacccgagtccaatgtcattttcttaccttgaaggcaacatcgatttttaaaggacagggaacttgcaaacaggatcactaa<br>aaaactaatcacatttggtgcaattattagttttctggtaggattttttgagtgacaacatcttatacactgtatacactttc<br>gcagcttttggtttattgactgcttcttggttattcccccttttagcttctacaaaaagaaccctgtaacatggttaccaa<br>agaaatccaaaatagagattcagcattga |
| PAS_chr2-1_0447 | 53 | atgacagactctgttaactctgatgattctgatctgaaatcatagaggtgactgagcctactccaaaagtggacctttttgg<br>cccccaatccagcatttaattttactgcccccataagcaacagtaacggcacaactccaataaggagaaaacttgatgacca<br>atccaactccaattcttttgccagactggaatcgttacgggaatcatcagtgaaaccacaagctagtacgttcaatagtagt<br>aggttcatccccccaagccgaccaattttccaataatcagaataatgaacttgataacaaatggattcgccgactggattt<br>ctaagtcccaacctgaatttccctttccacttaatgatggaccaaaaaagtccagcaatcaacctacaaatcaaattttga<br>agagatcatcgatttaactgaagatatcgagataaatacatctgtccccgcatctacatcatcttctaccccagttccctcc<br>agcacacagaatcagagccatcatatagccaacaacaacacagcacaagatgcgcatatcttccaagggaaacgacctctcc<br>aatcatattcagatgatgaagacgaaagatttgcaaattgtaggatccaatattgttcagcagcctctaggaattatgccagg<br>aacttttcaacgcccctgcaaacatactccattttgacggttcaaaccagaatgaacaagccagatggctggacttgcggata<br>aaagatttgttagataatcttcacaatcttcgagttcatgctcagtcgaatattatggagatcaataggttcatttccactt<br>tggggcatttaaacagagaagtttcagagctcaatctaagatatcaatctatcgtgaacaatcctcaggcgaccgctaataa<br>tcaaggatacctcactcagcttttgaacaggattcaggagcttactaatgaaaaagcgcacatatttagagagatggataca<br>tccaagataaaaacagcaggagattcacagaagaatccatgctctctcgtcaacaattgacaaactgaaaaaagatcgtgaac |

TABLE 5-continued

SEQUENCE LISTING
Open reading frame nucleotide sequence for proteases targeted for deletion in *P. pastoris*

| Protease Gene Symbol/ Locus tag | SEQ ID NO: | Open reading frame nucleotide sequence (5' to 3') |
|---|---|---|
| | | ttatctttcgaaatgctcaaaatgcttttcacggtgatatgaagaatgaagtttttggaaggccagtctttcatggatgcaat tcatagggcaaatagcttgggttatgcttcaaatatttattctcgttctgatgaagacgctggaagcttacaacggcttctt gaaaatatccagcccgatatggaggacaaagacgatgatgaattggctaaaactccgaaggagttcaatattcaactgctga agcatcagagagttgggttagattggctacttcggatggagaagtcaaccaacaaaggaggcattttagcagatgccatggg cctgggaaaaaccatccaggctattagtattatttacgcaaacaaatggaaaacacaagaagaagccgaagaggaggcaaaa cttgaagagaaggttagatccgaaaagtctacatcagaaacgaatggagaggtcagcaaaacgtcaacggcaaagtcggaaa agaaacccatccaggagacgaaggatatttcaaaactacgttaataatagcaccagtttctcttctacatcagtgggagtc tgaaatcttgttaaagacgaaaccagaatacaggctaaaagttttcatttatcacaagcaaaaaatgtcctcgtttgaagag ctccaacagtatgatatagtattaacatcgtatggaactctgtcttctcaaatgaagaagcattttgaagaggcaattaagg aggcagacctacagcccaacctcttcatccatatccagcagaagactctggaggcatatctttcaagtcaccattttttgcaaa agaaacaaagtttcttcgagtcattctagacgaagcccataagatcaaaggaaaaaatacaatcacttcgaaggcagtcgct ttggtgaagtctaaatacagatggtgtttaacgggcacaccgctacaaaataaaattgaagaactatggcctctacttcgat tcttgagaattaagccatattatgatgaaaagcgatttagaactggcatagtattacctataaagagttccatgtcaggcaa atatgattccacagacaagaagattgctatgaggaaatcttcatgccctacttaaagcaatcttgttgaaacgaaacaaagat tcgaagattgatggagagcccattctcaagttacccaagaagcatatcattgacacattcatagaaatggaagcaaaagagt tagacttttacaaggatctggaaggacagacagccaaaaaagccgaaaaagatgctaaacgctggaaaagggacaaggaaatca ttattctggtattcttatcttgctattgagactgagacaaacttgttgccaccatttcctcgtgaagttatctgagatgaag caagaagccaaattgaaacaggaagttgctaccaagatgccacaattggccacacaactatctcctgctgtggtaaggagaa ttaacattgaagcagaggccggatttacgtgtcctatatgtttggataacatcataaatgagaatgcttgtatattatacaa atgtggacatgttgtttgtcaagattgcaaagacgatttcttcaccaattatcaagagaatgaaactgatgacggtcttaga gtgtccaaatgtgtgacctgtcgtttgcctgtcaacgaaagcaatgtaatcagtttcccagtctacgacaagattgtgaacc agcatatttcagtgatggatatagttaaaagtgagtctccagtgttgtcaaaaattgaaatgattcaacaactgatccggga aacaaaggcgtcttcgaatcgtctgccaagatcgataaagcagtggaaatgatacaagagttactgagagacaatccaggg gagaagatcatagtttttagtcaattcacaactctcttcgatgtcatagaggtaatactcaaagagaacaacattaaattca ttagatatgacgggtcaatgtctcttagcaatagagatgctgccattcaagagttttatgagagtacggagaaaaacgtaat gcttcttctttgaaagcagggaacgtgggggttgacattgacttgcgcctcccgtgtcataataatggacccatttttggaac ccatatgtgaagaccaggccatggatagagcccatagaattggccagttaagagaagttttcgtctatcgaatgttgatca agaacaccgtcgaagatagaatttttgaccattcaaaatacgaaaagagaaatagttgaaaacgctctggataaccagagttt gaatacgatatccaagcttggcaggaacgagttggctttcttatttggtatcggcaattga |
| PAS_chr1- 3_0053 | 54 | atggagtgtaaaaaagtcaaagatcgcctagtcacggaatacttaaagattgaatgtagtcgacttaaccgaaggatacgct ccctgaaaaatccaaaagttgagcaagccctactgcaattcaagaactcacgtttggctcacatgagaaaggctcatctgga tggaataagaaaccacagtatacggatgacgccatctttcaggcattggaaaccatggattggaccacatatttgagaag gcaggtagtctttacaactcacagcaacaagatgaatcaaaaaaaagattccctggatgaaacagatttcaccgtggtggcgt tgctagattggttcaagaatgacttcttcaaatgggtaaacaggaccaccttgtcctgtttgccatagtgaagatgaaagccg cataagaatggtcggatctgcaaggcccactagtgaagaattgtcgtacggagcagggtcgtagaggtgtttaattgtgac cattgtagctgtgcaatcagatttccaagatataacgaccctaagaagctcctgagaactagagctggacgatgtggggaat ggaataactgttttctgttgtgtctaaaagccttgggtctgaaagctagatgtgtgaggaatgtggaagatcatgtatggag tgaatactactcggaacatctcaagcggtgggtccatctggatagttgcgagaatgccttttgatcaaccagaactatactgc aaaggttggggaaaaagatgagctattgttttgcttttgatgacactctcatagaagatgtgagtgccaagtacattactc aaggtagactgcctaaaatgctagacgacgaaaccatcagaatatgcttgtatttttcaaccaggaagctcttaagatggt gagtgaaaatccagaggcattctactccgctttggttaagtatcacagatgtctgtctgcgaatagaaaagagagcgggtca aaatcacgagccgtgaatgctagtttgacttcattgttaccacgacaatctggtagcgcatcctggacgtctgagagaggcg aaaacggactttag |
| PAS_chr3_0200 | 55 | atgcctataaaggggcggttcaccaaaaaagaagccaaaaaggaaagatgagccaaatcgaccgtcccccacccagttcatca aaaaaatagcctcattgaaaaagcagaccaggagagatgaggccctggatgtgctacacgaactagcagttgttgtgtcacc tttgatgaaagagaacggtttcactgttggattattatgcgaaatgttcccgaagaatgcctcttttattggggctgaatgtg aatatgggttcaaagatcatgatccgattgagacctagccacaacatgaacttgttttttgccaaaaagagagatcatcggta caatgctccatgagttaacccataatcgcttttcggcccatgatgtaaggtttttatgactttcttgagggtctcaagagcag gtttttttgagattcaggtgaaaggatctttacaaactacagggtatgttaactttagtgaagttctatctggtaatgcggcg agagggcaactgattcaaaaggaaaaagagaaagacaaaattgggtggtaataagcatgcaaaacctatgagagtcctaa tcttggaggcggccgagaagagaatgatagactctaaatggtgcggaggagctagcaatgaagtaggccttccaaaaattga agatctaatggacgatgaagaagctcaacactctgaactaaaggaagagaatacaaagaggtcagaaaaattgttcaacct agcaaaaagaaaattgtagatttggaaaacctaccgaatggcaagtccattattattgatctaactaatgacgatgactaa |
| PAS_chr1- 3_0105 | 56 | atggaacacaattgtctgaaagtcaatgaattggcgctccagttggctcaatcactgcagaacagcaaagtcagcacagctg atcctctaaagaagaggacaagcagctcacagaggcctgagtagcgagcctataatcacagaggaagaaccaacaatcaaggg cgactataatagattttacagtcagtcttcagataagcaagtattggacaataaaccatggttgcaggatggaaactatttc aagactgtatacatttcaacgatagcactactgaagatgatgtctcatgccggtccggtcggtgttcaattgagatattatgggca tgctgacaggtaaggtgtttgccaacacattagtcgtaatggattgctacttacttccggttgaaggtacagagacacgagt gaatgctcaagcggaaggatatgagttcatggtctcttatttggataacttaaaggaaatcaagcataacgagaatatcata ggatggtatcactctcatcctggttatgggtgctggttgagtggaattgatgttgccactcagaatttaaaccaaaagtttc aagatccctacctggcgatagtgattcctgaaagatcagtcagacaaggatttgttgagattggagcattcagaacgtt tgctgagccagccgttggaagatcgtcgtcgtcagtttcctctgcaagtggtgcaggaattagtgatgttgcgttttcttcc ggtagaaacagtgcatctggaatgtcctcagttctgagtgcaagtaatattagcattgccgaagagctaagcaaacaatcga tcacccaaaatgttttgacagaactactacaaagattcccaagggcaaaatgactgattttggagctcattcaggaaaata ttactcgctgaggttaaggttttcagatctccactggaggagaacactgatacgtttggttctaaaacctggattaaa ggttttaacgaactactccaacgttgttaatgccgaggaaactcaagtggagttaatgcataaaataatggaagccacggaga acttacggaaggaatctccttctaaattgccatctttggtgatgggaacctgatttattcaggtgcctctcaaggaacaac agggaacgcaagcgctcaatgtccaaatcttctatttattcgggtttacaagcttcatcgggtatacccagttctaggtat cctacgaagggaaaaaatgagtggatctcaattcaatgatgacccgctagcaagatcactggataaaataccgccagata gtccagatcaacagtacgatggcgcattatccattcaacaaccgaaaagagcatataatacacatacttctagagcaggtgg |

TABLE 5-continued

SEQUENCE LISTING
Open reading frame nucleotide sequence for proteases targeted for deletion in *P. pastoris*

| Protease Gene Symbol/ Locus tag | SEQ ID NO: | Open reading frame nucleotide sequence (5' to 3') |
|---|---|---|
| | | gttggccagcgttctgtcctctgggagtatggatcctcaaagttactccatggtaggacgaatgagtctaactaatcaatcg<br>ccggggacagctctgagaggcctaaatacacctcccaacaaacgaccgcagagaaaccctggtcatacaagctcaggtcaag<br>gaggaacgcctggaggagtcagtcggtccaaagagaaaattaacaagccaataggtataagcatgattagcaaggatttcaa<br>ggttgtcatctcacaacaggtcaaccagatgctacgtcgtcacgtccagaatgacctttttggatccaatagtccctaa |
| PAS_chr3_0635 | 57 | atggatcatgcccaacgattgctagaactaagttttttacaatcaaagtctgggcaaatcagtgatagcaaagaaatacagaa<br>tagaatcctctcgatatttgaatgaacaactggacaagtccttgacaagagataatgatctgattggattatgccgtatagc<br>attagacaacaagttgaccatatcagataagattatatggatgagctctcaagttgaagacaacttcttccgccagttttt<br>caaggcttgaagacgtatattgatagcgacgagatttatcaagagaaactttttaagcgtaccagcggattttgaaccaatag<br>ttgaatggaagagttgcacagagttgcccaatgaatggtcaaacaatggtgtggacaatttatttcaggattctttagatga<br>ctgttcgtttgtagcttcatttctatcctgcaacaatattggtatccctctcatgqataaagtcattccccacaaaaactcg<br>ttcaaatatgcggttagactgactttcaatggttgcgaaaggttggtgtttattgatagccgtttgcctttgcttaggaata<br>cttccaagactttacgagtgtcaagttttctaacaaagatctcttatggcctagcatcatcgaaaaagctttcctgaaaat<br>gtgtgatgatggtacaagtttcaggatcaaattcagccattgacaatatgctttgactggctggatccctgaagtcatt<br>aaaacttcttcatgtacaatagcagatattagccgattgcatgaggattttcggaacggaaacgtagtactatgcttgggaa<br>cgggcaatctgaccgagcgagaatgcaaacagtatggattgatccccaatcatgactatgctgtcactaaactatcatttac<br>gaatgattcagaatacaagtttgacattcgtaatccgtggactaaagggcagaaagcagtgacaattacagatctttcaacc<br>tttgaagttatctacgcaaacagaaatcctataatgtttttcgacatgaaccagctaagcggtatctgtcaaagtcaggtta<br>atgaagagttcatagatctaattcttaaccattcgcagtataccctaggcaatgacggtaattctacaattgatgtgattct<br>tttctttgaaagacattcgttaagaaagaaatcagtgcagagtctcgtattgagattttccaatcagaaggcgaaagacta<br>atctccagaagaaataaagcaagcaaggaatgtgtttctaataataccaactttcatttcataacaatcgaactgaaaccgt<br>tagaaaaggtaactgtggtaatagatatcggcgagtcttcgattcgaagccatccatttactctaaaggcttttgccaatga<br>ttcaactataactttgaacaaagcactttctagacctggttgtttcaagcaaatggacctagagctaacgcccttaaactct<br>ggtgggaattgggataattatgcttattacaaaaatccacaactcatagtcactcttcacggagattcaacggatgaagctc<br>catttgaatctgctgtttttcagcaaaagtgataagaccctatttacgtatacagtgtttttggaaaagtgacgatccagactt<br>tcctttcatcactgacgcaagcaagaacaagctcgtaagcacagacaataagtataaatacagatcatgtacaagatcaaga<br>gttgtttcttgcgacaaaagctatttgttcgtgctgagctcctacgaacctgatgcaattgagtctttcaaagtattttttc<br>aatgttcccacgattttttctatagagtgggctgagacgtcgcttgggctttttcacaaaggaagaaactttctcctggaagga<br>ccaattagtcaaggagttcattattcaagtctataacccttcaaagttgaaagttcacgcagtaaacaccaacaacaaacgc<br>agatcaaaactaaattgctctctctcattccaaaacacattaatcagctctttgcaagactacacagacaatctctatggat<br>gctttattagcgggaacttggagattcccggcaagtatctcattacaagttcataaaaaacattatatctaacgaagaatgttt<br>ggtcgaaattggatctagttcgtcatttgagttatgggaacatcattaa |
| PAS_chr4_0503 | 58 | atgttgaaaactcgatttcattccagaaagggttttgtaatctacagtggagatgatgaagagagtgacgaagagagtaaac<br>aatggatgtttcccgagtcgacctttgtaaccaatgggtttgaccaattgttcaaggtgagaaatgtcaataccattaatga<br>cgacgatgacggctaccaatcgttcgatcaaccggattgggcgcaagattaaccgcagatactcagtatcttgctttaggt<br>gacgaaggggagaatcatcgttcacaacaagagataggcaacaggaaaagagccaacaaaaagcaaaagaagccaactaaag<br>caaagacaaaacgtcaacaaagacgcacagccaaaaatgatcaatccacggaacgatctgccatttcacaaccttctaactt<br>aagtacactgaactccttactcaaatctgttcggtctgaacttccaattctgatgggagtccccacacattctacgatgta<br>tctctctatgaagaagatctgaacaacctagctgatgacgaatggttgaacgataataacgtctcgtttatctacgagtaca<br>ttgaaagattttacattacccgttgtttgagcgacaagcttcaattttcatcaaagaagatggtcaattctcaaataatact<br>cctccgaccttctatggttttttttgctggcacattcaactccaaaagatatccaggattttctcccaccgttggataagtct<br>ggctttatattccttcctctgaacgacaatgatgatcctggaaatggctgaaggtgatcccattggtgtctttagttgtag<br>ctgttcacgataacaaatgtttcctctatgactcattagagaatgccaatctcacagagtctgttgcgcttgtgtctaagct<br>gtccactctgctaaacaggcgaatacaactcgttgaaaatacacattgtcctcaacaactcaatggcagtgattgtggagta<br>atcacaacccaaattacagcactactggtatcccgactgctttgtgtttgccgggacatcctataaatttggatcttcaaa<br>atgtagctatcaacgcaataagcgggagaatcttcatgttaaaactcctccaacatgttctgaacaattaa |
| PAS_chr2-1_0569 | 59 | atggcaccaccagtccctgtatatacgagagatgaagtcaagatgcaatttccacagtacatgatgaaattttttgccttcaa<br>actgtgagctgtactccatcatccagaaccaatgtaccttctctgctgacgagataaatatgtgtgcccttcaagagggtgtt<br>tgccaaatgccggaggggaaaccaagaagccaagaggaacataataccagagaatggaggactgaatttaactggaaagaaa<br>ctaatcccaagagaatacacagtcattgaagttacggacctccctaacgaacaagtacgacaatagtagcctcatggacagat<br>tttttgaggcagaaaagagatttaatgataaaggtttcaagaatatgaggaacggaacagtaaggaaggagaaataaagtag |
| PAS_chr3_1223 | 60 | atgctcagacagtttgctggaagggagttcaagcgtcggttttctacgggaatcaagacgatgccaacaaagcttaccaaac<br>tgccaaatggtattcgtgtcgtaacggacgaaagtccgggccattttagtgccatgggcattttcgttgatgctggttcaag<br>atatgagagccagtttccagaattaaccggccactctcacatcatcgatagacttgcattcaaatcaacatccaaattcgat<br>gggaaatctatggtagaaaacaccaatcatttaggtggcaacttatgtgtgcctcttcaagagagtcattgatataccagg<br>cttcagtgttcaacaaagatgtggacaagatggctgaaatcctcagttctacagtcaaagaacctttatttactgaggagga<br>agtttctaatcagatagcaacagcaatatgatgagttgagtgtatggctgcaacctgacctaattcttcccgaattgtct<br>caacaggtagctctatggatcaaaaaatttgggttcccgctgctctgtccgaaggagtctttagcaaacatctcaagagaat<br>ccctttgaagtatcgtgaaatattttttagacctgagaacttggtcgttgctatgtgggagttccccacgagaaggcctt<br>ggaacttgttgataaaaatttaggcgtatgaaatctgtcggttccagtccagtggtcaaagaacctgctaaatatacagga<br>ggagaacttttcttgcctccagttcctcctatgggtgggctttcccgagtttcatcacatatatcttacatttgaaggtgtcc<br>ccgtggactctgacgatgtctactcactggctactttgcagatgctcgtcggtggtggatctttctctgctggtggtcc<br>aggaaaaggaatgtatgccagagcatacacgcgagttctgaatcagtacggtgtttattgaaagttgcaattcatatatacac<br>aatttctcagactcggggctgtttggtctctcaatttcaagcattccgcaggcaaataaagtgttcagaactcttaggtc<br>atgaactgagctgcttgttttctgaaaatccgggcaaaggtgctcttaccaatgccgaagtaaaccgtgccaaaaatcagct<br>acggtcttcttgttgatgaacttggagagcaagatggttcaattagaagaactaggaagacacattcaagtttatggcaga<br>aaagttgatgtcacagagatgtgtgataaaatcagcaaagttacaaaggaagatctagttgcaattgcaaagaaagtcttga<br>ccggaagcaacccgactatagttgttcaaggtgacagagaatcttatggagacattgagggtactttggcatcttttggagt<br>tggtttagatgccgcttccaaaagcttcaaagaaaaaaacgagaggttggttctaa |

TABLE 5-continued

SEQUENCE LISTING
Open reading frame nucleotide sequence for proteases targeted for deletion in *P. pastoris*

| Protease Gene Symbol/ Locus tag | SEQ ID NO: | Open reading frame nucleotide sequence (5' to 3') |
|---|---|---|
| PAS_chr2-1_0597 | 61 | atggcaattatcaagttcaacgcgcaggcaaagtcaagattgacgaggaaaccaagctttgtacacccttggcaacaagaggag<br>aaataatcgtccaattgtcggctgagggcgaagagtttttatgattttcaaatgggtccctactgagaacacagctggtgaagg<br>taaccagtcagagacattcttggtcattccgggcgatgtgacgtggaaacacgtcaaaagttgtaaagatggtagagtttttc<br>aaattgacattttttgagtagtggggcaaagagtttgttctggatgcaagatgataatggaaacgaggatgacccatcagagt<br>tgacaaccaaagataaggaaatttagtgaaaaaaattaccaagttgttcgacgaagaagagtga |
| PAS_chr1-1_0327 | 62 | atgaaacacttggctgtccataagtacaaggtaggagccatcgcagctggcttggttgtgtctcctataaaatcttttgcctacc<br>gcgctgcgtcttcctcctcctcaaacgtcatcaacttgaccaatatggcaaaaactccaatcactttaaaacccctcaggc<br>tccactccgctgggaccatactccagagcagatccttgccgaaactgataagtatatatctaccagtcaagaggttgacgat<br>tgggtggcaaacagctttgccactgccaatgtgacaccatcaagaaaatagccgccgctgagaatgaacaatacttgccac<br>tgtgtcaattgagtttttatcaacatatctcggataaccaggacgttcgtaatgccagtactgttagtgaggagaaaattga<br>taagttctccatcgaatccaaccttagagaagatgtgttcaaaacagtgaacaaagtgttcaaacaggttcaagaagattcg<br>gaactccaaaagaccttggacccagaatttaggcgtttactagaaaaattgaacctaggttacgtgagatctggtttagatt<br>tatcccaggagaagagagaccaagtcaagagtttgaaacaagaactatcaaccatttcaatcaagtttaataagaacttggg<br>agaggaaactgaacacatttggttcaccactgaggagttaaaaggtgttccagaatcagttgttgagcagtttgaaactaag<br>aatgagaatgatgttacttaccacaagatgacatacaagtatcctgacctgttcccggtactaaaatatgccgttaatccag<br>ctacgagacaaagagctttgtcgggatcaaaacaagatacctgaaaattcaggattacttgtgaaagccgtcaatttgag<br>aaacgaacttgcaaaagtttggttatgatacctatgctgactatatcctggaagtgaagatggccaagaactccaagaat<br>gtttttgaatttcttgatgatgtaaggaaaaactcagacctctcggagagaaggaactgcaaagaatgttgactctcaagg<br>ctaacgacccaaatgctgttgataaggaaaattactacgtctgggatcatcgttactatgataacaagcttcttgaatctga<br>atacaaagtggatgagcaaaagctggctgaatactttccaatggagtccaccattgaaaaaatgcttgccatttacgagcac<br>ttgttcaatttgcagtttcaacaagttgacgattcggagaaacaagtttggcatccagatgtaaaacaattctccgtttgga<br>aaatcgataaccctgattctcctgaatttgtgggctggatctattttgatttgcatccaagagaaggaaaatacggtcacgc<br>tgctaattttggaatcggtcctagttacatcaaagaagatgggagtaaaaattatcctgtcactgctttggtttgcaactttt<br>tctaaaccatcaaaggataagccatccctattgaagcacaatgagtcactacattcttccatgagctaggacatggtatcc<br>atgatttaattgggcaaactaggtatgctcgtttccatggtacttcagttgctcgtgatttcgttgaatgtccttcacagat<br>tctagagtactggacctggactagagatcaactcaagtctcttcccaacattacaagacaggagaagccctctccgatgaa<br>ctcattgattcgctagtcaagtccaagcatgtcaatggcgccattttcaatcttaggcagttacactttggtctctttgaca<br>tgaaactacatactgccaaagagcctgaatctttagatgtgacaaggttgtggaacgaattacgtgaggaagtcgctctggt<br>taagaatggtgaccaaattacgaaaggatacggttcatttggacacctaatgggcggttatgctgctggttactacggatac<br>ctgtattctcaagtgtttgccagtgacgcatttattacaaccttttcaaagctgatccaatgagtacagctcaaggtatcaagt<br>accgtgatatcattcttgccgagaggtggatcaagagaggagctagataatctcaaggaattacttggaagagagcctacatc<br>tgatgccttttatgactgagcttggagtagaaaatggtgcgtccaagttgtaa |
| PAS_chr2-2_0380 | 63 | atgcgtttttttggtctcatcctttcggcccttcagacatacaatttcgtcgcatatctcaatgggccaggctctgtctgcca<br>ttcgtgtatttcataaaaaattctcactcacgtacccaaggtttaaggcgccactctcactactgttgccaccgcaagataga<br>tatgagtacttctactaaacttccagagcgtcaattgctaccagccaatgttaggcctaccaaatatgatttgacattggag<br>cccttattttctaccttcaagtttaacggagaagagactatacatttagatgttcaggaggactccagttctattacgctac<br>acgctctagacatcgatctccaagattcactattgataacttcaaacaagtctaagactcccccgcttcatgtgacaagcaa<br>tgatgatgaccaatcgctcacttttcaattcaaagagggtactctagtaaaggagataaggtgcagctgcagttgaaattt<br>gttggtgaattgaatgataagatggccggtttttaccgctcttcatatgaagagaatggagaaactaaatatttggcaacta<br>cccagatggagccaacagattgtcgtcgtgctttcccttcctttgatgagccatcgctaaaagccgtattcaacattgccct<br>cattgctgatcagaaacttacttgtctctcaaacatggacgtgaaagaggaacaatctctcggagatagaaggaagaaggtg<br>atattcaatcccactccactaattctacttacctaattgctttattgttggtgattaaaatatattgaagccgactata<br>actatcgcattcctgtcagagtttatgccacccctggtttagagaagcagggtcgtttttctgtcgagcttgctgctaaaac<br>attagaattctttgagcaacagtttgatattgattatcctcttccaaagatggacatggtggcgattcatgatttcagtgca<br>ggagctatggaaaacttgggcttgttacctatagagttgtgatttgctgtacgatgaaaaaaattcaaatttggctacta<br>agcaacgtgttgcagaagttgtccaacacgaattggcgcatcagtggtttggtaatcttgtcacaatggagtggtgggaggg<br>cctttggctgaatgaaggctttgctacatggatgtcttggtactcttgtgacaagttttttccctgattggaaagtatgggaa<br>caatatgttacagattctttacaacaggctctggctctggacgctctacgtgcttctcaccctattgaagttcctgtgaaaa<br>gggccgacgagatcaatcaaatttttgacgcaatttcctattctaaaggatcctccttgctaaaaatgatctccaaatggct<br>cggagaggatgtgttcattaagggagtctccagttatttaaaaaagcacaggtatggtaatacgaaaaccaccgatttgtgg<br>gaatcgctttctgaggtgtctggaaaagatgtggtcaaagttatgagtatctggactggtaaaattggatttccaatcatct<br>cagtaactgaaaatgcaaaccgtatcacttttactcagaacagatatttaactactggtgatgtaactcctgaagaggatac<br>gacgatttatcctgtttttttgggactcaaaacagaaagctcaactgatgagtcgctggtccttgactcaaggtcaatgtca<br>gtagatatccagaattctgacttttttcaaagttaatgctgaacaagccggtatttacaggaccaattatgcaccgaagaat<br>ggatcaaacttggaaagcaacctcaccttctaagtgtagaagaccgtgctggtttggttgcggatgcgggcgctctggctag<br>ttctggtcactcatctacaaggaactttttgaaccttgtaaattcatggaaagatgagtctagctttgttgtctgggacgaa<br>ataacttcccgtgttgcagctttaaaagcagcttggttatttgaatcccaatctgacattgacgccctgaatgctttcgtaa<br>gagaccttatttctacgaagacataaaatatcggatgctcaatgataatgaaccattccttgaacaaagactaaagag<br>ccttctatatgctactgctgctggtcaaaagtaccaggagtagttaaatcagcattgataaactttcaaaaatacgttgct<br>ggtgataagactgccattcaccctaacataaaggcagttacgtttcaaactgttgcggcccaaggatctgaaaaggaatggg<br>atcagttactcgacatctacaagaaccctgtatctattgatgagaaaattattgctcttaggtctctcggaaggtttgaaga<br>tcccactctgacaaagaccctggcactgttatttgatggttccgtaaggtcacaagatatttacgtaccaatgcaaggc<br>cttcgtgcgactaagataggaggtagagtcacttttcaagtggttgactcttaattgggacaagatttataaattgcttccac<br>ctggtctgtcaatgcttggttctgtggttactatcagtacttctgggttcacttccttggatgatcaaaagcgtgtcaaaga<br>tttctttgcatcaaaggataccaaaggcttcgaccagggtttggcccaggcgttagacaccatccaatccaaggcaagttgg<br>gtacaacgtgactctaggaatgtatccgattggctacgtgagcagggatacaaaaaatag |
| PAS_chr3_0928 | 64 | atgataaggatatccttgctgaaaagagcactgtttccctacgggcgactaccaatgcataatggtaggtggtattcagaca<br>taggtggcggaaattcaaggaatcggaacgaacagaaaccaaaattgcctgtaccaactagtaatgaagttaaggacaatga<br>gtcaaacccggacttctttattaaaaaacggctttagatcagctgatattgcagagacatcctttgtgaaagacaagggtgct<br>acagtcgaagaggaacgtaatacatcggacagttcacacgaatctcctcaacttaattttaaggaaaccaacgacgaaacga |

TABLE 5-continued

| SEQUENCE LISTING | | |
| --- | --- | --- |
| Open reading frame nucleotide sequence for proteases targeted for deletion in *P. pastoris* | | |

| Protease Gene Symbol/ Locus tag | SEQ ID NO: | Open reading frame nucleotide sequence (5' to 3') |
| --- | --- | --- |
| | | attcaacgatccaaccaccagtggcaaaattacccaccccaaagcaattgaaacaatacctggataggttcatcgtgggaca |
| | | agagaagtgcaagaagataatgtcggtcgcagtttacactcattatgttcgaataaataaccaggctcagaaacggaatcag |
| | | aaggtcgattcctctgaagaaatgttgagaatgggtttccaaatgttactaaagaatttgaggacgaaaatgacccagatt |
| | | atgttccggattggagaaatcaaatgttcttttgctgggaccgtctggatcaggcaagaccctgattgctaagactctcgc |
| | | taaatgtctgcaggttccatttataattcaagattgtacctccttgacccaggctggttatgttggcgaggatattgagagc |
| | | tgtattgaaaagttgctaattgattcagactacgatattgaaaggtgtgaaaagggaattattgtgctggatgaaatagaca |
| | | agttggccaagccctctgtctatacaggaaccaaagatattgcaggagagggtgttcaacaaggccttttaaaactggttga |
| | | aggtactacagttacggttcaatgcaagaggagcaatgctcctgatcataatcagttcggattgaatggcaaagctacaaat |
| | | caggacaaggaaaattatatcgttgacactacaaatatcttattttttaaccctgggagcgtttgtgaacctagataagattg |
| | | ttgcttataggctgaagcagaactctattggattcgatactgatgagtcgaaagatatttctgaaacagactcagtttccga |
| | | caaatctacattagaatatgttacacttccagatggatcaaaagtttcagctctggaacttgtgtcttctacggatctacag |
| | | aattatgggttgattccagaactgatcggcaggcttccgattgtatcttcactttctcctttaacagttgatgatcttgtgg |
| | | ctgtcctgactgagcccaggaactcgatactaaagcaatatgtgcatttctttgacactgtcaatgtcaaacttgctatcac |
| | | ttccaaggcaatcagaaggatagccggagatctcgatcaagaatggtacaggtgcaagaggctctcagagccattttggagaaa |
| | | ctgctactcaatgccaagtatgattgccctggtagtgtatttcatttgtgttagttgatacagatgttataagtaagtcta |
| | | tcgatgagaataaggaaacggggggaattcgtcttcaaagtggtgagccaaagtattactcgcgtggagaattattttcctt |
| | | tttcaatgagttatcaaaagaagacgaaaaactcaagacatcaattgaaaagatgtgccaaataccactttccaagaatcgc |
| | | atagtttactccgaagaggagcaggcaaggttggattcttctaaacctctcgccgtgaagcactatgaacctttcatttga |
| PAS_chr1-3_0184 | 65 | atgagcttcaacctgctaagtgttcctttacgaacgtcaaagccgataccgttaggcgaaagcctaaaagagcttatcaaca |
| | | atcagtactaccagacatctgctgcgttcaaatcggatatcgaagagatcgaccaactaagaaatgatgtcctatcaataga |
| | | accaaacaatgatggacttgcattgctcaagagatacatgtacagttacgacagcattagccaaaaactccctgattatttt |
| | | atggagtatccctggtttggaacattaggataccaagtaactggccccgtagctctaaaatccctctatttcgaaagaatca |
| | | atatagcgtacaacatcgcagcgacgtattcaatcataggtttaaacgagcccagagctacaggagaaggcttgaaaaaatc |
| | | atgcatttattttcagtatagtagtggggcattcgaaagtgtactgaagctagtggagcaaaaaccgaaagagctgacactt |
| | | cccattgatcttagtgttaacattatgaaaaccctggctaaactcatgctggctcaggcccaggaatgttttttggcaaaagg |
| | | ctgtttctaacactttaaaagataacgttattgcaaggttggcctttcaagtatctcaattttacgatgaagctctgtctat |
| | | ggcttacaagtgcgatattttaaagtctgaatggatagaacatatgagttgcaagaagctgcattttaaggctgcggcccaa |
| | | tttagacttgcttgtgtggcagtcgctgcttctagacatggagaggaaatagcaagattaaggattgcaaataccatttgcg |
| | | aaacagcatctagagaagccaagtatccaccttccctctgtatcttccgatttggagagtctttcgaagataatcaaagactc |
| | | tttaagagaagtgaacgtgataatgatctaatatatctgcaggaagttcctaatgaatcagatcttcctccaattgttgca |
| | | gcatctatggttgaacctaagccaatagttgagttaaattcagctgaatgtgcgaaagatacaaagaaatacggcaaaatcc |
| | | tttccatgatcttatgccatacttagtgattgaaattgcacaggcatttagagagaggcaggattcttatgttgtaaagca |
| | | tatcaaggagcccatggagatgctgacaaagattcttcacacaatccttgctgaaaatggacttccggccgttgatagatacc |
| | | atacaaaggcctcaaagattgccaaccaacatccttgaacattgtcaaatactcaatgaaaggggtggcatggacaaactta |
| | | aggtatttttcgaagatatcagcaagctaagacacaaaagtgagcaagttctccaaaactgtgtcgaattgctacaaatgga |
| | | agagtccgaaaatgaggaaatgagaaggaagcatggatcacagaggtggaattttgctgactctaggaggcatcagcagat |
| | | gtcaggaaaagtgtacaggcactagagggctatttgaaacaggcccatgatggtgatcaagtgatctggaatgacttcgaac |
| | | aattgaagccactactaagcatgatgagtgctcctaattcaactaaattactggaagaatttgtaccaaattcaaaattcgt |
| | | cagacttcctccagaattgaaccgaatcgttaacgaattaagagctgatgttaatcaggtcaaaaagctcgcatcgcaaagg |
| | | gaaactttattaatacagttaaagtaaaaagcaccgacctgtccatattgcccttggtagtttcccatttataagaaattac |
| | | aacaaaacaacattaatacgatcacgacggaattgttcgaagaagtgttcagacgacaggttagcaacttcgattctgatat |
| | | cagatttgttcaaaaacacagggacaaccaaatcgagttagagaagcatattaaatctttggtccaacaattcaatcagctt |
| | | agagggaatatagatgcctcgcaagaacgccaaaatgcacttcagttgttggacgatgcctataacggataccttgatttgg |
| | | taaacaacctcacacagggacttagtttttacaatgatttcactggaaaggcaaatgatgtctatttgagatgtcaagaatt |
| | | ctacaactttcgtaaacaagaagccatgaagctggagcaggaaatatatgctgtatttgaacaaggtaaatctcctcagaaa |
| | | aaacaactagaagatcaggtttcagatcaaccaaaaagtgaagtcaagtcttcaaagggttattctaatgagctgtggaacc |
| | | ccgacgttggaattaaatttggctag |
| PAS_chr1-4_0286 | 66 | atggtggcctctcttcacattgtcaatccgaatttggcctccgctttcagtttgcctcccaggtcaaacactttgagcgttt |
| | | ccatacacgcttcggctttgttacagatcctggaatcaagttacttcgaccagaataagaatggtcgtatcataggaaccct |
| | | cctaggttctaggtctgaagagacaacggaggttcaagtcaagactctttcatagtttcccacacgcgaggacggagacgag |
| | | tttaccattgattcttctcaacgtgaatttgtcgccatccacaagaagtctagcccaagagactcagtcgtaggatggtttt |
| | | ccattaactctaaggtcgacagctttatcggactggtccatgactttttctcaaagggtccagatagcacacacccgtaccc |
| | | tgccatatatttgagtatccagttatgtgacgagagcggatccttcgtagagccagtttttcaaggcgtacgttgcctcccca |
| | | gtgggatgttatggagctctggcaagtcacttagaccttgaaaaagctggctcttttgtcttctctgaagtcccaaccaagg |
| | | tcatatactctgctaacgaaaaaagtctgctggctcatttcaagaacaacgttgtggaacccaaagtccaataccacaaaa |
| | | cgacacaaatcaactaatttcacaactcaacaaactcgacgtttccattgaccagttaatagactacgttgacaaagtcatt |
| | | tcaggatctctggatagaaatgatgtgaagaatgatgagattggccgtttcctgttgaccaacttagtttcccttccaactt |
| | | ctccttcaaaggaagagctttcatcttccataagctctcatatccaggactcactgatgatcgactacttggcctccgccgt |
| | | gaaaactcaattagatgttagctccaaattaatgaacctggtacaagatgataaatag |

TABLE 6

Polypeptide sequences of targeted proteases

| Protease Gene Symbol/Locus tag | SEQ ID NO: | Polypeptide sequence |
|---|---|---|
| PAS_chr4_0584 | 67 | 1 MLKDQFLLWV ALIASVPVSG VMAAPSESGH NTVEKRDAKN VVGVQQLDFS VLRGDSFESA<br>61 SSENVPRLVR RDDTLEAELI NQQSFYLSRL KVGSHQADIG ILVDTGSSDL WVMDSVNPYC<br>121 SSRSRVKRDI HDEKIAEWDP INLKKNETSQ NKNFWDWLVG TSTSSPSTAT ATGSGSGSGS<br>181 GSGSGSAATA VSVSSAQATL DCSTYGTFDH ADSSTFHDNN TDFFISYADT TFASGIWGYD<br>241 DVIIDGIEVK ELSFAVADMT NSSIGVLGIG LKGLESTYAS ASSVSEMYQY DNLPAKMVTD<br>301 GLINKNAYSL YLNSKDASSG SILFGGVDHE KYSGQLLTVP VINTLASSGY REAIRLQITL<br>361 NGIDVKKGSD QGTLLQGRFA ALLDSGATLT YAPSSVLNSI GRNLGGSYDS SRQAYTIRCV<br>421 SASDTTSLVF NFGGATVEVS LYDLQIATYY TGGSATQCLI GIFSSGSDEF VLGDTFLRSA<br>481 YVVYDLDGLE VSLAQANFNE TDSDVEAITS SVPSATRASG YSSTWSGSAS GTVYTSVQME<br>541 SGAASSSNSS GSNMGSSSSS SSSSSTSSG DEEGGSSANR VPFSYLSLCL VVILGVCIV |
| PAS_chr3_1157 | 68 | 1 MIINHLVLTA LSIALANDYE SLDLRHIGVL YTAEIQIGSD ETEIEVIVDT GSADLWVIDS<br>61 DAAVCELSYD EIEANSFSSA SAKFMDKIAP PSQELLDGLS EFGFALDGEI SQYLADKSGR<br>121 VSKREENQQD FNINRDEPVC EQFGSFDSSS SDTFQSNNSA FGIAYLDGTT ANGTWVRDTV<br>181 RIGDFAISQQ SFALVNITDN YMGILGLGPA TQQTTNSNPI AANRFTYDGV VDSLRSQGFI<br>241 NSASFSVYLS PDEDNEHDEF SDGEILFGAI DRAKIDGPFR LFPYVNPYKP VYPDQYTSYV<br>301 TVSTIAVSSS DETLIIERRP RLALIDTGAT FSYLPTYPLI RLAFSIHGGF EYVSQLGLFV<br>361 IRTSSLSVAR NKVIEFKFGE DVVIQSPVSD HLLDVSGLFT DGQQYSALTV RESLDGLSIL<br>421 GDTFIKSAYL FFDNENSQLG IGQINVTDDE DIEVVGDFTI ERDPAYSSTW SSDLPHETPT<br>481 RALSTASGGG LGTGINTATS RASSRSTSGS TSRTSSTSGS ASGTSSGASS ATQNDETSTD<br>541 LGAPAASLSA TPCLFAILLL ML |
| PAS_chr1-4_0289 | 69 | 1 MVASHVNNAS ASRSNTSVSH ASASSYDNKN GRGTGSRSTT VVKDSVSHTD GDTDSSRVAH<br>61 KKSSRDSVVG WSNSKVDSGV HDSKGDSTHY AYSCDSGSVV KAYVASVGCY GAASHDKAGS<br>121 VSVTKVYSAN KSAHKNNVVK VNDTNSNKDV SDDYVDKVSG SDRNDVKNDG RTNVSTSSKS<br>181 SSSSHDSMDY ASAVKTDVSS KMNVDDK |

TABLE 7

Forward (F) and Reverse (R) Primers for 5' and 3' homology arms (HA)
targeting protease ORF

| Description | SEQ ID NO: | 5' to 3' Sequence |
|---|---|---|
| PAS chr1-1 0174 5' HA F | 70 | ACCTATTGTTTACCTTCCTG |
| PAS chr1-1 0174 5' HA R | 71 | GAATTCTCTCACTTAATCTTTAGCTCCCATGCTCATCTTG |
| PAS chr1-1 0174 3' HA F | 72 | GCGGCCGCaagaagttgattGTTTATTTGTAGGCGGTGCC |
| PAS chr1-1 0174 3' HA R | 73 | GGGCTATCCGCCTTATCTTG |
| PAS chr1-1 0226 5' HA F | 74 | AATAACTTCATGACTGCATT |
| PAS chr1-1 0226 5' HA R | 75 | GAATTCTCTCACTTAATCTTAGTTTAAATAATATGGAGAT |
| PAS chr1-1 0226 3' HA F | 76 | GCGGCCGCaagaagttgattATTGGAGAAAAGGAATACAC |
| PAS chr1-1 0226 3' HA R | 77 | GGCATCTCCGTCTGGTGCAG |
| KO_PAS_chr3_1087 5' HA F | 78 | CAAGGTTCGAAACTGCAGCT |
| KO_PAS_chr3_1087 5' HA R | 79 | CTCACTTAATCTTCTGTACTCTGAAGAGAGAGCAAACCAATGGCAA |
| KO_PAS_chr3_1087 3' HA F | 80 | AGAAGTTGATTGAGACTTTCAACGAGGGTCCTTTGGCAATCATTGGT |
| KO_PAS_chr3_1087 3' HA R | 81 | ACCCCAGGACCAGGTATTTC |
| KO_PAS_chr4_0584 5' HA F | 82 | TACTACAGGCTGGCTGTTCC |
| KO_PAS_chr4_0584 5' HA R | 83 | CTCACTTAATCTTCTGTACTCTGAAGAAGTCCAACTGTTGAACGCC |
| KO_PAS_chr4_0584 3' HA F | 84 | AGAAGTTGATTGAGACTTTCAACGAGGGTCCCCTTCAGCTACCTTT |
| KO_PAS_chr4_0584 3' HA R | 85 | TCCCTGCTAAGCCCTAATCG |
| KO_PAS_chr3_0076 5' HA F | 86 | AAGTTGTATGGCCGTCCTCA |
| KO_PAS_chr3_0076 5' HA R | 87 | CTCACTTAATCTTCTGTACTCTGAAGTGAGTCTTGGTTGTGTCGGT |

TABLE 7-continued

| Description | SEQ ID NO: | 5' to 3' Sequence |
|---|---|---|
| Forward (F) and Reverse (R) Primers for 5' and 3' homology arms (HA) targeting protease ORF | | |
| KO_PAS_chr3_0076 3' HA F | 88 | AGAAGTTGATTGAGACTTTCAACGAGGCCTCCTGTTTGATCGGTTC |
| KO_PAS_chr3_0076 3' HA R | 89 | GTGCCATGGTGACGTTACAG |
| KO_PAS_chr3_0691 5' HA F | 90 | CGGAGTTATAGGGGACGCTT |
| KO_PAS_chr3_0691 5' HA R | 91 | CTCACTTAATCTTCTGTACTCTGAAGCGTCACATCATAGCCGTTCTC |
| KO_PAS_chr3_0691 3' HA F | 92 | AGAAGTTGATTGAGACTTTCAACGAGCGTCAAAAGTGGTCGTGGAC |
| KO_PAS_chr3_0691 3' HA R | 93 | TGGCCCAGTTACACGGAATA |
| KO_PAS_chr3_0303 5' HA F | 94 | GTCGATCGTTGGTGTGTGAC |
| KO_PAS_chr3_0303 5' HA R | 95 | CTCACTTAATCTTCTGTACTCTGAAGGAGCCGACTTTGACATCGAC |
| KO_PAS_chr3_0303 3' HA F | 96 | AGAAGTTGATTGAGACTTTCAACGAGAGCGAAGAGACTGGTTCCAA |
| KO_PAS_chr3_0303 3' HA R | 97 | AGCTGTTCTAACCGTCCTCA |
| KO_PAS_chr3_0815 5' HA F | 98 | CTTGGAATATCTGTGGGCGC |
| KO_PAS_chr3_0815 5' HA R | 99 | CTCACTTAATCTTCTGTACTCTGAAGTCATGACCAGCAGTTGTTCA |
| KO_PAS_chr3_0815 3' HA F | 100 | AGAAGTTGATTGAGACTTTCAACGAGATGCTGCAGGAAGGAACACT |
| KO_PAS_chr3_0815 3' HA R | 101 | CAAACTCTGCACCTCCAAGC |
| KO_PAS_chr3_1157 5' HA F | 102 | CTCTGATTGCACGAGAAGGC |
| KO_PAS_chr3_1157 5' HA R | 103 | CTCACTTAATCTTCTGTACTCTGAAGTGAAAGGCGATTGGAGTTGC |
| KO_PAS_chr3_1157 3' HA F | 104 | AGAAGTTGATTGAGACTTTCAACGAGCTGGCTCTGCTTCTGGTACT |
| KO_PAS_chr3_1157 3' HA R | 105 | GATGTTGAGGCGGGCATAAG |
| KO_PAS_chr1-4_0164 5' HA F | 106 | TTTCAACGGGGTTCTACGGA |
| KO_PAS_chr1-4_0164 5' HA R | 107 | CTCACTTAATCTTCTGTACTCTGAAGGTGGTAGTATGTGTGTTGGTGT |
| KO_PAS_chr1-4_0164 3' HA F | 108 | AGAAGTTGATTGAGACTTTCAACGAGCTGCGCTTTCAAGTACTGCA |
| KO_PAS_chr1-4_0164 3' HA R | 109 | TGTCTTCCTCGTCTTCCTCG |
| KO_PAS_chr3_0979 5' HA F | 110 | CGGGCAATAATCAGTGGAGC |
| KO_PAS_chr3_0979 5' HA R | 111 | CTCACTTAATCTTCTGTACTCTGAAGCGTTGGAGGTAATGCATGGG |
| KO_PAS_chr3_0979 3' HA F | 112 | AGAAGTTGATTGAGACTTTCAACGAGGGCGGACCGTGTATTAGAGA |
| KO_PAS_chr3_0979 3' HA R | 113 | TCAGAGAAGCCAGTGGAAGG |
| KO_PAS_chr3_0803 5' HA F | 114 | TTCCTCGGCCTCTTTATGCT |
| KO_PAS_chr3_0803 5' HA R | 115 | CTCACTTAATCTTCTGTACTCTGAAGCAACGTGGCTAACTCCTTGG |
| KO_PAS_chr3_0803 3' HA F | 116 | AGAAGTTGATTGAGACTTTCAACGAGGTTGTCGACGGCATTGAAGA |
| KO_PAS_chr3_0803 3' HA R | 117 | TCGGTTCAAAGCCCCTAAGT |
| KO_PAS_chr3_0394 5' HA F | 118 | AGGTGTGAAATGCGCTGATC |
| KO_PAS_chr3_0394 5' HA R | 119 | CTCACTTAATCTTCTGTACTCTGAAGAAACCAACAACGCCTGGTAC |
| KO_PAS_chr3_0394 3' HA F | 120 | AGAAGTTGATTGAGACTTTCAACGAGTCACAGGCTGAAGGATCGAA |
| KO_PAS_chr3_0394 3' HA R | 121 | CCATGGTGTGTTTTCCGGTT |
| KO_PAS_chr2-1_0366 5' HA F | 122 | TGAGGGACAAAGTAATGGGGT |
| KO_PAS_chr2-1_0366 5' HA R | 123 | CTCACTTAATCTTCTGTACTCTGAAGACCGAAGTCATGGTTGGAAA |
| KO_PAS_chr2-1_0366 3' HA F | 124 | AGAAGTTGATTGAGACTTTCAACGAGCTACCGCAGACAACCCATTC |

TABLE 7-continued

| | | |
|---|---|---|
| Forward (F) and Reverse (R) Primers for 5' and 3' homology arms (HA) targeting protease ORF | | |
| Description | SEQ ID NO: | 5' to 3' Sequence |
| KO_PAS_chr2-1_0366 3' HA R | 125 | CGCTCCCTCATCGAGTACTT |
| KO_PAS_chr3_0842 5' HA F | 126 | CAGACATCGTGGAAACTGCC |
| KO_PAS_chr3_0842 5' HA R | 127 | CTCACTTAATCTTCTGTACTCTGAAGTATCTGCTTCGATCCCTGCA |
| KO_PAS_chr3_0842 3' HA F | 128 | AGAAGTTGATTGAGACTTTCAACGAGTTCTCCCGTCCAGTTAGCAG |
| KO_PAS_chr3_0842 3' HA R | 129 | ATTTCAGAAGCTCCGCATCC |
| KO_PAS_chr1-3_0195 5' HA F | 130 | ACAAAAGCACGCGATTGAGA |
| KO_PAS_chr1-3_0195 5' HA R | 131 | CTCACTTAATCTTCTGTACTCTGAAGACACTCACGGTTGTTTGCAA |
| KO_PAS_chr1-3_0195 3' HA F | 132 | AGAAGTTGATTGAGACTTTCAACGAGAACCCCAACAAGCGGCTATA |
| KO_PAS_chr1-3_0195 3' HA R | 133 | ACCCGGATCTGCTAGTGAAG |
| KO_PAS_chr1-4_0052 5' HA F | 134 | CGTATGCTCGTGTGACTGTG |
| KO_PAS_chr1-4_0052 5' HA R | 135 | CTCACTTAATCTTCTGTACTCTGAAGTTCCTATGCCTGGCGATGAT |
| KO_PAS_chr1-4_0052 3' HA F | 136 | AGAAGTTGATTGAGACTTTCAACGAGAGGGAGTCTTGTATAGTTGAGCA |
| KO_PAS_chr1-4_0052 3' HA R | 137 | AGCAGGGGTATTTTCACGGA |
| KO_PAS_chr2-2_0057 5' HA F | 138 | AGCATGATTGTGTTGGGTGG |
| KO_PAS_chr2-2_0057 5' HA R | 139 | CTCACTTAATCTTCTGTACTCTGAAGAATCCGATACTGTAGCCCCG |
| KO_PAS_chr2-2_0057 3' HA F | 140 | AGAAGTTGATTGAGACTTTCAACGAGGCAAAGAAAACTGGCCACAC |
| KO_PAS_chr2-2_0057 3' HA R | 141 | GGAAGGCCCTATTCACGACT |
| KO_PAS_chr1-3_0150 5' HA F | 142 | CACCATTTCCCTGCTGTGTC |
| KO_PAS_chr1-3_0150 5' HA R | 143 | CTCACTTAATCTTCTGTACTCTGAAGTCAATACCGAAGACTCCGCA |
| KO_PAS_chr1-3_0150 3' HA F | 144 | AGAAGTTGATTGAGACTTTCAACGAGGGGAGGTATTCAGGAGGCAT |
| KO_PAS_chr1-3_0150 3' HA R | 145 | GCTCGATCAGATATTGTCCGC |
| KO_PAS_chr1-3_0221 5' HA F | 146 | AGCAGCTCTCCAATCAGTGT |
| KO_PAS_chr1-3_0221 5' HA R | 147 | CTCACTTAATCTTCTGTACTCTGAAGCTGGAATTGTGATCCCGCTG |
| KO_PAS_chr1-3_0221 3' HA F | 148 | AGAAGTTGATTGAGACTTTCAACGAGTTTTGAAGCAAGCCTACCCC |
| KO_PAS_chr1-3_0221 3' HA R | 149 | CAGGATCCAGCCGCTAAAAC |
| KO_PAS_FragD_0022 5' HA F | 150 | TGAACAAGCAGCCACATCAC |
| KO_PAS_FragD_0022 5' HA R | 151 | CTCACTTAATCTTCTGTACTCTGAAGTGAGGGCCATTCTGACATACT |
| KO_PAS_FragD_0022 3' HA F | 152 | AGAAGTTGATTGAGACTTTCAACGAGGTGAGGTATTTAACTGCACGAG |
| KO_PAS_FragD_0022 3' HA R | 153 | TCGCCTACATAGTCTGCACA |
| KO_PAS_chr2-1_0159 5' HA F | 154 | ACCTCATGCCATGTCTGTCA |
| KO_PAS_chr2-1_0159 5' HA R | 155 | CTCACTTAATCTTCTGTACTCTGAAGTTGACTGCCGCTTCAAAGTC |
| KO_PAS_chr2-1_0159 3' HA F | 156 | AGAAGTTGATTGAGACTTTCAACGAGCCGCCAGAGAATTTGTGCTT |
| KO_PAS_chr2-1_0159 3' HA R | 157 | TAGAGGTGAACGTTTGGCCT |
| KO_PAS_chr2-1_0326 5' HA F | 158 | AATCCATCACCTCCACCCAG |
| KO_PAS_chr2-1_0326 5' HA R | 159 | CTCACTTAATCTTCTGTACTCTGAAGGCTGCTGGAGTAAAAGGTCC |
| KO_PAS_chr2-1_0326 3' HA F | 160 | AGAAGTTGATTGAGACTTTCAACGAGCAAGCAGCAACCATCTACGG |
| KO_PAS_chr2-1_0326 3' HA R | 161 | AACCTCATCCACTGTCAGCA |

TABLE 7-continued

| Description | SEQ ID NO: | 5' to 3' Sequence |
|---|---|---|
| Forward (F) and Reverse (R) Primers for 5' and 3' homology arms (HA) targeting protease ORF | | |
| KO_PAS_chr2-2_0056 5' HA F | 162 | GGAAGACAAAGTTCGCTCCG |
| KO_PAS_chr2-2_0056 5' HA R | 163 | CTCACTTAATCTTCTGTACTCTGAAGTCATAGTTGAGAGCCTCCTTGT |
| KO_PAS_chr2-2_0056 3' HA F | 164 | AGAAGTTGATTGAGACTTTCAACGAGACAATGCACTAGGACGGGAT |
| KO_PAS_chr2-2_0056 3' HA R | 165 | CTTGAATCAGGCGACGTACC |
| KO_PAS_chr1-4_0611 5' HA F | 166 | CCCAGCTCTCTTTCACTCCA |
| KO_PAS_chr1-4_0611 5' HA R | 167 | CTCACTTAATCTTCTGTACTCTGAAGTTGAAGAGCAGCAGAGTCGA |
| KO_PAS_chr1-4_0611 3' HA F | 168 | AGAAGTTGATTGAGACTTTCAACGAGTTAATTGCCCACAGTGTCGC |
| KO_PAS_chr1-4_0611 3' HA R | 169 | ACCTTCCACAGTCGACGAAT |
| KO_PAS_chr1-1_0274 5' HA F | 170 | ACAAACAGTCAAATGCACGGA |
| KO_PAS_chr1-1_0274 5' HA R | 171 | CTCACTTAATCTTCTGTACTCTGAAGTCCTTCCACCTTTCCAACGT |
| KO_PAS_chr1-1_0274 3' HA F | 172 | AGAAGTTGATTGAGACTTTCAACGAGGGGGTAGAGAAGTTAGGGAGG |
| KO_PAS_chr1-1_0274 3' HA R | 173 | GGAACTACAACTGGAGGCCT |
| KO_PAS_chr4_0834 5' HA F | 174 | TAGTGCCGGTTCCATGGATT |
| KO_PAS_chr4_0834 5' HA R | 175 | CTCACTTAATCTTCTGTACTCTGAAGGGTCTATGGGTTGATGCGGA |
| KO_PAS_chr4_0834 3' HA F | 176 | AGAAGTTGATTGAGACTTTCAACGAGATGTGTTGCTCGCTCTAGGT |
| KO_PAS_chr4_0834 3' HA R | 177 | CGACAAACACACCAAGGTCC |
| KO_PAS_chr3_0896 5' HA F | 178 | GTTGTTGGAGTGAGCGATGG |
| KO_PAS_chr3_0896 5' HA R | 179 | CTCACTTAATCTTCTGTACTCTGAAGCCTCCGTTGATACTCCCGAT |
| KO_PAS_chr3_0896 3' HA F | 180 | AGAAGTTGATTGAGACTTTCAACGAGTGCATTCAAGGCTGGCAAAT |
| KO_PAS_chr3_0896 3' HA R | 181 | GCATATGGAGTGGTGTGCAG |
| KO_PAS_chr3_0561 5' HA F | 182 | CGGGTAGCATTGAACGTACG |
| KO_PAS_chr3_0561 5' HA R | 183 | CTCACTTAATCTTCTGTACTCTGAAGATGCTACGGTAAACACCCCA |
| KO_PAS_chr3_0561 3' HA F | 184 | AGAAGTTGATTGAGACTTTCAACGAGACTGGAGAAAGCTTGGTCGA |
| KO_PAS_chr3_0561 3' HA R | 185 | AGGCACCAGAAGAAAGAGCT |
| KO_PAS_chr3_0633 5' HA F | 186 | GGACACGTTTGGAGCTTCTT |
| KO_PAS_chr3_0633 5' HA R | 187 | CTCACTTAATCTTCTGTACTCTGAAGGCCCACCAATTCAGCAACTT |
| KO_PAS_chr3_0633 3' HA F | 188 | AGAAGTTGATTGAGACTTTCAACGAGGATGCTGGTCACATGGTTCC |
| KO_PAS_chr3_0633 3' HA R | 189 | AACCGCCAATAGTTTCAGCC |
| KO_PAS_chr4_0013 5' HA F | 190 | GGATGAGAAAGCGGCTTCTG |
| KO_PAS_chr4_0013 5' HA R | 191 | CTCACTTAATCTTCTGTACTCTGAAGGTGCCAAAAGTCTGATCCGG |
| KO_PAS_chr4_0013 3' HA F | 192 | AGAAGTTGATTGAGACTTTCAACGAGTGCCACTTCGTTCTTTGACG |
| KO_PAS_chr4_0013 3' HA R | 193 | ACGGATCAGTGATGGCGTAT |
| KO_PAS_chr1-1_0379 5' HA F | 194 | ATGGGATCTGGACGACGTTT |
| KO_PAS_chr1-1_0379 5' HA R | 195 | CTCACTTAATCTTCTGTACTCTGAAGAGCTGGATCACAAACATTCGG |
| KO_PAS_chr1-1_0379 3' HA F | 196 | AGAAGTTGATTGAGACTTTCAACGAGCTTTGAGTGTTGGTCCCTGC |
| KO_PAS_chr1-1_0379 3' HA R | 197 | CGGCTACCAAGTCAGACCTT |
| KO_PAS_chr2-1_0172 5' HA F | 198 | GTTGCCCATTACGTCCTGTG |

TABLE 7-continued

| Description | SEQ ID NO: | 5' to 3' Sequence |
|---|---|---|
| | Forward (F) and Reverse (R) Primers for 5' and 3' homology arms (HA) targeting protease ORF | |
| KO_PAS_chr2-1_0172 5' HA R | 199 | CTCACTTAATCTTCTGTACTCTGAAGCCTTTGATCTTTGGTGCATCTTG |
| KO_PAS_chr2-1_0172 3' HA F | 200 | AGAAGTTGATTGAGACTTTCAACGAGCACTACAGCTGGGAACGAGA |
| KO_PAS_chr2-1_0172 3' HA R | 201 | ACGGGTTGGAAAAGTTGAGC |
| KO_PAS_chr3_0866 5' HA F | 202 | AGTGGGGTTGGAGATTGGAG |
| KO_PAS_chr3_0866 5' HA R | 203 | CTCACTTAATCTTCTGTACTCTGAAGACGATTCCAGCATAGCCTGT |
| KO_PAS_chr3_0866 3' HA F | 204 | AGAAGTTGATTGAGACTTTCAACGAGCTGGTAGCCGCAAAACTTCA |
| KO_PAS_chr3_0866 3' HA R | 205 | GCGTTGAATCCTCCTCGTTC |
| KO_PAS_chr3_0299 5' HA F | 206 | CTGTGGGGTCTGAACATCCT |
| KO_PAS_chr3_0299 5' HA R | 207 | CTCACTTAATCTTCTGTACTCTGAAGAGCTGCTAGGGTTCATTGAGT |
| KO_PAS_chr3_0299 3' HA F | 208 | AGAAGTTGATTGAGACTTTCAACGAGCTCCCTTGGGTACGTCAACT |
| KO_PAS_chr3_0299 3' HA R | 209 | TGGCAGTCTTCACATGTCCT |
| KO_PAS_chr1-4_0251 5' HA F | 210 | AGCTGGTCAAGTCTGGTACC |
| KO_PAS_chr1-4_0251 5' HA R | 211 | CTCACTTAATCTTCTGTACTCTGAAGGAGGTCTAGTGTGTGAGGCT |
| KO_PAS_chr1-4_0251 3' HA F | 212 | AGAAGTTGATTGAGACTTTCAACGAGAGAAGGTATAGGGAATATGCGGT |
| KO_PAS_chr1-4_0251 3' HA R | 213 | TAGCCACAACCCTGATGACG |
| KO_PAS_chr4_0874 5' HA F | 214 | TACACTGGGACGCAGATGTT |
| KO_PAS_chr4_0874 5' HA R | 215 | CTCACTTAATCTTCTGTACTCTGAAGTGCTCAAACTCTGTATCCGTTG |
| KO_PAS_chr4_0874 3' HA F | 216 | AGAAGTTGATTGAGACTTTCAACGAGCTTTCAAGGCCGCAATGCTA |
| KO_PAS_chr4_0874 3' HA R | 217 | CTTCCTTTGCAGTTGGTGGT |
| KO_PAS_chr3_0513 5' HA F | 218 | GGGTCTTTGGCTTTGGTGAG |
| KO_PAS_chr3_0513 5' HA R | 219 | CTCACTTAATCTTCTGTACTCTGAAGCGTCTCTGGAACTCGTCGAT |
| KO_PAS_chr3_0513 3' HA F | 220 | AGAAGTTGATTGAGACTTTCAACGAGCCCCAAGTCAAGGAGGAGTT |
| KO_PAS_chr3_0513 3' HA R | 221 | GAGTCCAATCACGGCCAATC |
| KO_PAS_chr1-1_0127 5' HA F | 222 | TGCTTCTTCGGACAGATCGT |
| KO_PAS_chr1-1_0127 5' HA R | 223 | CTCACTTAATCTTCTGTACTCTGAAGTACTGATTGAAGGGTCGGCA |
| KO_PAS_chr1-1_0127 3' HA F | 224 | AGAAGTTGATTGAGACTTTCAACGAGTTGTACGGACCAGGAAGCAT |
| KO_PAS_chr1-1_0127 3' HA R | 225 | TTCCTCTGCCTCTTCCTTGG |
| KO_PAS_chr4_0686 5' HA F | 226 | AGCATGCAAACACGAGGTAC |
| KO_PAS_chr4_0686 5' HA R | 227 | CTCACTTAATCTTCTGTACTCTGAAGAGAGGAAAACGAGCTTGGGT |
| KO_PAS_chr4_0686 3' HA F | 228 | AGAAGTTGATTGAGACTTTCAACGAGATCAAGGTTGCCAGCGAATG |
| KO_PAS_chr4_0686 3' HA R | 229 | ACCCTACAGAACCGCAATGA |
| KO_PAS_chr2-2_0159 5' HA F | 230 | ACAGCCCAAATAGAGACGCA |
| KO_PAS_chr2-2_0159 5' HA R | 231 | CTCACTTAATCTTCTGTACTCTGAAGAGGAGCCCAGTTTTACGTCA |
| KO_PAS_chr2-2_0159 3' HA F | 232 | AGAAGTTGATTGAGACTTTCAACGAGTATCCCGCGGTGAAGACTAC |
| KO_PAS_chr2-2_0159 3' HA R | 233 | GTGTTGCTAAGCCTGTGGAC |
| KO_PAS_chr3_0388 5' HA F | 234 | TCCTCCTTTCGACGCTTCTT |
| KO_PAS_chr3_0388 5' HA R | 235 | CTCACTTAATCTTCTGTACTCTGAAGACAGCTGTGAATCATGAAGTTTT |

TABLE 7-continued

| Description | SEQ ID NO: | 5' to 3' Sequence |
|---|---|---|
| Forward (F) and Reverse (R) Primers for 5' and 3' homology arms (HA) targeting protease ORF | | |
| KO_PAS_chr3_0388 3' HA F | 236 | AGAAGTTGATTGAGACTTTCAACGAGATTCTCACTGGCAGAACGGA |
| KO_PAS_chr3_0388 3' HA R | 237 | TTTTCACGTTGAGGCCACTG |
| KO_PAS_chr3_0419 5' HA F | 238 | AGCTCCGCAGTAACAGGAAT |
| KO_PAS_chr3_0419 5' HA R | 239 | CTCACTTAATCTTCTGTACTCTGAAGTCAAAGCAACTTATGGCGGT |
| KO_PAS_chr3_0419 3' HA F | 240 | AGAAGTTGATTGAGACTTTCAACGAGCTCTTCGCAGCACCAGAAAG |
| KO_PAS_chr3_0419 3' HA R | 241 | TCGTTGTTGCTGGTGTTCTG |
| KO_PAS_chr1-3_0258 5' HA F | 242 | AGTTTGAAGGCACGTTGGTC |
| KO_PAS_chr1-3_0258 5' HA R | 243 | CTCACTTAATCTTCTGTACTCTGAAGACTCCAACAGGACTTTGAGGT |
| KO_PAS_chr1-3_0258 3' HA F | 244 | AGAAGTTGATTGAGACTTTCAACGAGAAATGTGGAAGTTGCAGCGG |
| KO_PAS_chr1-3_0258 3' HA R | 245 | AGGTTGATCGCCGTCTTGTA |
| KO_PAS_chr4_0913 5' HA F | 246 | TCTTCATGAGGTGGTAGGCG |
| KO_PAS_chr4_0913 5' HA R | 247 | CTCACTTAATCTTCTGTACTCTGAAGAGAGGGCAGATGACATACCG |
| KO_PAS_chr4_0913 3' HA F | 248 | AGAAGTTGATTGAGACTTTCAACGAGGAGAAACTGGAGGTGCTCGT |
| KO_PAS_chr4_0913 3' HA R | 249 | CAAGGCATTCAGTTGACCGT |
| KO_PAS_chr1-1_0066 5' HA F | 250 | ACCAACGAGCCTTACAGACA |
| KO_PAS_chr1-1_0066 5' HA R | 251 | CTCACTTAATCTTCTGTACTCTGAAGTTTTGACCGTCAGTGCATGG |
| KO_PAS_chr1-1_0066 3' HA F | 252 | AGAAGTTGATTGAGACTTTCAACGAGGTCGGAGGTGTGAGAATTGA |
| KO_PAS_chr1-1_0066 3' HA R | 253 | TGGGAACTATGTGGCTCCTC |
| KO_PAS_chr2-2_0310 5' HA F | 254 | CGAGCTATCAGTACTCCCGG |
| KO_PAS_chr2-2_0310 5' HA R | 255 | CTCACTTAATCTTCTGTACTCTGAAGGGTTCTCAGCTGTCCGAGAT |
| KO_PAS_chr2-2_0310 3' HA F | 256 | AGAAGTTGATTGAGACTTTCAACGAGTAGCATTGCCCATCACAACG |
| KO_PAS_chr2-2_0310 3' HA R | 257 | GTGGGAAGACTATTGATGCGA |
| KO_PAS_chr1-3_0261 5' HA F | 258 | GGGAAATCGCTGAGGTGTAC |
| KO_PAS_chr1-3_0261 5' HA R | 259 | CTCACTTAATCTTCTGTACTCTGAAGAGGTCATCTGGAAGCTTTGC |
| KO_PAS_chr1-3_0261 3' HA F | 260 | AGAAGTTGATTGAGACTTTCAACGAGGGTGGCCAATGGTATTACTTTGA |
| KO_PAS_chr1-3_0261 3' HA R | 261 | ATAAGAGCCCCGATACAGGC |
| KO_PAS_chr2-1_0546 5' HA F | 262 | CTTGACACACTTTGCTCCTGA |
| KO_PAS_chr2-1_0546 5' HA R | 263 | CTCACTTAATCTTCTGTACTCTGAAGAGTAGCTGACCTGTTGTGCC |
| KO_PAS_chr2-1_0546 3' HA F | 264 | AGAAGTTGATTGAGACTTTCAACGAGGGACACCATATGATGCCCGA |
| KO_PAS_chr2-1_0546 3' HA R | 265 | CAGATCAAGTCCAAGTCCGC |
| KO_PAS_chr2-2_0398 5' HA F | 266 | AGAGACTTTGCGAGAGTCCC |
| KO_PAS_chr2-2_0398 5' HA R | 267 | CTCACTTAATCTTCTGTACTCTGAAGTGCAATATCCAAACACGCCA |
| KO_PAS_chr2-2_0398 3' HA F | 268 | AGAAGTTGATTGAGACTTTCAACGAGACTTCTGGAATCTTCGGGCA |
| KO_PAS_chr2-2_0398 3' HA R | 269 | GGATGTTTGGGCCATTGTGA |
| KO_PAS_chr4_0835 5' HA F | 270 | CAATCTCTCGCTTCATCACG |
| KO_PAS_chr4_0835 5' HA R | 271 | CTCACTTAATCTTCTGTACTCTGAAGTCGCTGTTAACCATAATTCTTTG |
| KO_PAS_chr4_0835 3' HA F | 272 | AGAAGTTGATTGAGACTTTCAACGAGGCGAGGGTTGAGGAGATTTT |

TABLE 7-continued

| | | |
|---|---|---|
| Forward (F) and Reverse (R) Primers for 5' and 3' homology arms (HA) targeting protease ORF | | |
| Description | SEQ ID NO: | 5' to 3' Sequence |
| KO_PAS_chr4_0835 3' HA R | 273 | GGCCATGGCACTATTTTGTT |
| KO_PAS_chr1-1_0491 5' HA F | 274 | ACGTACTTCCCGCCCAATAA |
| KO_PAS_chr1-1_0491 5' HA R | 275 | CTCACTTAATCTTCTGTACTCTGAAGCCCACCTAAATTTCGAGTGCA |
| KO_PAS_chr1-1_0491 3' HA F | 276 | AGAAGTTGATTGAGACTTTCAACGAGACACTTTCGCAGCTTTTGGT |
| KO_PAS_chr1-1_0491 3' HA R | 277 | TCCTCCTTGCCATGAAGAGG |
| KO_PAS_chr2-1_0447 5' HA F | 278 | GCCTGATGAAGATGATGCCG |
| KO_PAS_chr2-1_0447 5' HA R | 279 | CTCACTTAATCTTCTGTACTCTGAAGAGGCTCAGTCACCTCTATGA |
| KO_PAS_chr2-1_0447 3' HA F | 280 | AGAAGTTGATTGAGACTTTCAACGAGTGATCAAGAACACCGTCGAAG |
| KO_PAS_chr2-1_0447 3' HA R | 281 | TCCCTTTGTTGGTCGTACGA |
| KO_PAS_chr1-3_0053 5' HA F | 282 | TGGTTCAACTTGTAGCGCAT |
| KO_PAS_chr1-3_0053 5' HA R | 283 | CTCACTTAATCTTCTGTACTCTGAAGGGGCTTGCTCAACTTTTGGA |
| KO_PAS_chr1-3_0053 3' HA F | 284 | AGAAGTTGATTGAGACTTTCAACGAGCGACAATCTGGTAGCGCATC |
| KO_PAS_chr1-3_0053 3' HA R | 285 | ATGCTCGTACAAAGACCCCA |
| KO_PAS_chr3_0200 5' HA F | 286 | TGAGATCTCCAAGTGCAGCA |
| KO_PAS_chr3_0200 5' HA R | 287 | CTCACTTAATCTTCTGTACTCTGAAGGACGGTCGATTTGGCTCATC |
| KO_PAS_chr3_0200 3' HA F | 288 | AGAAGTTGATTGAGACTTTCAACGAGTGAAGAAGCTCAACACTCTGAAC |
| KO_PAS_chr3_0200 3' HA R | 289 | TGATTGACGGCACCCTGTAT |
| KO_PAS_chr1-3_0105 5' HA F | 290 | CAATAATTCAGCTGCGCCCT |
| KO_PAS_chr1-3_0105 5' HA R | 291 | CTCACTTAATCTTCTGTACTCTGAAGCCTCTGTAGCTGCTTGTCCT |
| KO_PAS_chr1-3_0105 3' HA F | 292 | AGAAGTTGATTGAGACTTTCAACGAGAGGAGTCAGTCGGTCCAAAG |
| KO_PAS_chr1-3_0105 3' HA R | 293 | TGTGGGCTGGGATGTGTAAT |
| KO_PAS_chr3_0635 5' HA F | 294 | AGCACGGTCAAGTAAATCGC |
| KO_PAS_chr3_0635 5' HA R | 295 | CTCACTTAATCTTCTGTACTCTGAAGTGCTATCACTGATTTGCCCA |
| KO_PAS_chr3_0635 3' HA F | 296 | AGAAGTTGATTGAGACTTTCAACGAGGGAGATTCCCGGCAAGTATC |
| KO_PAS_chr3_0635 3' HA R | 297 | GGCTTTCTGACTACCTGGGT |
| KO_PAS_chr4_0503 5' HA F | 298 | AAAGGGAAGAAGGGTGCAGT |
| KO_PAS_chr4_0503 5' HA R | 299 | CTCACTTAATCTTCTGTACTCTGAAGAAGGTCGACTCGGGAAACAT |
| KO_PAS_chr4_0503 3' HA F | 300 | AGAAGTTGATTGAGACTTTCAACGAGTGGTATCCCGACTGCTTTGT |
| KO_PAS_chr4_0503 3' HA R | 301 | TGGAATGGCTCGAGAATGGT |
| KO_PAS_chr2-1_0569 5' HA F | 302 | ACCAACAGGCTGAACACTAGA |
| KO_PAS_chr2-1_0569 5' HA R | 303 | CTCACTTAATCTTCTGTACTCTGAAGTCGTCAGCAGAGAAGGTACA |
| KO_PAS_chr2-1_0569 3' HA F | 304 | AGAAGTTGATTGAGACTTTCAACGAGACGGACTCCCTAACGAACAA |
| KO_PAS_chr2-1_0569 3' HA R | 305 | TCTGATGGTTGGCTTTGCTT |
| KO_PAS_chr3_1223 5' HA F | 306 | CGGTTTGTGGCCCATCTATG |
| KO_PAS_chr3_1223 5' HA R | 307 | CTCACTTAATCTTCTGTACTCTGAAGAAAACCGACGCTTGAACTCC |
| KO_PAS_chr3_1223 3' HA F | 308 | AGAAGTTGATTGAGACTTTCAACGAGAAGTCTTGACCGGAAGCAAC |
| KO_PAS_chr3_1223 3' HA R | 309 | GGGCCTTAACAAACACCACA |

TABLE 7-continued

Forward (F) and Reverse (R) Primers for 5' and 3' homology arms (HA)
targeting protease ORF

| Description | SEQ ID NO: | 5' to 3' Sequence |
|---|---|---|
| KO_PAS_chr2-1_0597 5' HA F | 310 | TAGAGGCGGAAAGGAACGAG |
| KO_PAS_chr2-1_0597 5' HA R | 311 | CTCACTTAATCTTCTGTACTCTGAAGTTGCCAAGGGTGTACAAAGC |
| KO_PAS_chr2-1_0597 3' HA F | 312 | AGAAGTTGATTGAGACTTTCAACGAGACCAAGTTGTTCGACGAAGA |
| KO_PAS_chr2-1_0597 3' HA R | 313 | CAACACATACCAGGCGAAGG |
| KO_PAS_chr1-1_0327 5' HA F | 314 | CCCTCCTCCGCCATCATTAT |
| KO_PAS_chr1-1_0327 5' HA R | 315 | CTCACTTAATCTTCTGTACTCTGAAGTAGGAGACAACCAAGCCAGC |
| KO_PAS_chr1-1_0327 3' HA F | 316 | AGAAGTTGATTGAGACTTTCAACGAGGGAGTAGAAAATGGTGCGTCC |
| KO_PAS_chr1-1_0327 3' HA R | 317 | AATGGCTCCAAATCACAGGC |
| KO_PAS_chr2-2_0380 5' HA F | 318 | GCTTTGAGGAATGCGTGAAGA |
| KO_PAS_chr2-2_0380 5' HA R | 319 | CTCACTTAATCTTCTGTACTCTGAAGGTAGTGAGAGTGGCGCCTTA |
| KO_PAS_chr2-2_0380 3' HA F | 320 | AGAAGTTGATTGAGACTTTCAACGAGTGGGTACAACGTGACTCTAGG |
| KO_PAS_chr2-2_0380 3' HA R | 321 | ACACTCTTAAGGCTCGTCGT |
| KO_PAS_chr3_0928 5' HA F | 322 | CTCCTCCACTTCAGTATCCGT |
| KO_PAS_chr3_0928 5' HA R | 323 | CTCACTTAATCTTCTGTACTCTGAAGTTCCTTGAATTTCCGCCACC |
| KO_PAS_chr3_0928 3' HA F | 324 | AGAAGTTGATTGAGACTTTCAACGAGGAGCAGGCAAGGTTGGATTC |
| KO_PAS_chr3_0928 3' HA R | 325 | CTGGGCAGCAAATAACGGTT |
| PAS_chr1-3_0184 5' HA F | 326 | CCAAAGTTGGCTCCAGTAG |
| PAS_chr1-3_0184 5' HA R | 327 | CTCACTTAATCTTCTGTACTCTGAAGCCTAACGGTATCGGCTTTGA |
| PAS_chr1-3_0184 3' HA F | 328 | AGAAGTTGATTGAGACTTTCAACGAGGGCAAAATCCTTTTCCATGA |
| PAS_chr1-3_0184 3' HA R | 329 | GAAGAAGGCCAAGTGTGATA |
| KO_PAS_chr1-4_0289 5' HA F | 330 | GACGAGACGCTGTTCCTTTC |
| KO_PAS_chr1-4_0289 5' HA R | 331 | CTCACTTAATCTTCTGTACTCTGAAGTGTGAAGAGAGGCCACCATT |
| KO_PAS_chr1-4_0289 3' HA F | 332 | AGAAGTTGATTGAGACTTTCAACGAGTGATCGACTACTTGGCCTCC |
| KO_PAS_chr1-4_0289 3' HA R | 333 | AACAACATTCAAGCTGCCGT |

TABLE 8

Forward and reverse primers for amplifying modified sequences

| Description | SEQ ID NO: | Sequence (5' to 3') |
|---|---|---|
| KO_PAS_chr3_1087 Verification F | 334 | ATCGGCAAAGATGAAGCGAC |
| KO_PAS_chr3_1087 Verification R | 335 | GCTGGACACTTCTGAGCTCA |
| KO_PAS_chr4_0584 Verification F | 336 | ACTTGTCAGGACGATACGGA |
| KO_PAS_chr4_0584 Verification R | 337 | CCGGTCTCCCTGGAAATAGA |
| KO_PAS_chr3_0076 Verification F | 338 | GCGAGGTCCTTGTCAATGAG |
| KO_PAS_chr3_0076 Verification R | 339 | ACAAGAACTCGGGCTCCTTT |
| KO_PAS_chr3_0691 Verification F | 340 | TTGCAGCGCTCCATAATGTC |
| KO_PAS_chr3_0691 Verification R | 341 | GCTGATTCTGAGAACGCTGG |
| KO_PAS_chr3_0303 Verification F | 342 | GCCATTCTTCGGTGCAGTAG |

TABLE 8-continued

| Forward and reverse primers for amplifying modified sequences | | |
|---|---|---|
| Description | SEQ ID NO: | Sequence (5' to 3') |
| KO_PAS_chr3_0303 Verification R | 343 | TAGAGTTGTCCCAAACGGCA |
| KO_PAS_chr3_0815 Verification F | 344 | CGTGGTTCTCGAGGCTCTAT |
| KO_PAS_chr3_0815 Verification R | 345 | GGAGTTGGAACGTCGTAGGA |
| KO_PAS_chr3_1157 Verification F | 346 | AGTTGTCCGTCATTAGCCCT |
| KO_PAS_chr3_1157 Verification R | 347 | TGTTCCCTTTCGGCTAGACA |
| KO_PAS_chr1-4_0164 Verification F | 348 | ACGGTTGAGGGCATTACGTA |
| KO_PAS_chr1-4_0164 Verification R | 349 | TTGTCTTCCACCCCTTCGTT |
| KO_PAS_chr3_0979 Verification F | 350 | GGTTGGCCTTGGACATTGTT |
| KO_PAS_chr3_0979 Verification R | 351 | TGCTCTTCGGTACTCATGCT |
| KO_PAS_chr3_0803 Verification F | 352 | TTTGGCCATGCTGAGCTTTT |
| KO_PAS_chr3_0803 Verification R | 353 | AAGCCCGATCACTTGCATTT |
| KO_PAS_chr3_0394 Verification F | 354 | CACCTAATGTTTGGCACCCC |
| KO_PAS_chr3_0394 Verification R | 355 | ATCCCAGACTGACATCGCAA |
| KO_PAS_chr2-1_0366 Verification F | 356 | CCGCCAGAAATTCATGCCAT |
| KO_PAS_chr2-1_0366 Verification R | 357 | TCGTTTCACTGTACCATGCA |
| KO_PAS_chr3_0842 Verification F | 358 | ACCAGTCCGCATTTTCACTG |
| KO_PAS_chr3_0842 Verification R | 359 | GTGGACAGCTGCAATCGTAG |
| KO_PAS_chr1-3_0195 Verification F | 360 | CAACTGGGAAGCCTGCATTT |
| KO_PAS_chr1-3_0195 Verification R | 361 | CCTTGCATATCCGTTTGCCA |
| KO_PAS_chr1-4_0052 Verification F | 362 | GGAGGTTCAGGAGCAGGAAT |
| KO_PAS_chr1-4_0052 Verification R | 363 | CGGTTTCATCTGTTGCCTCC |
| KO_PAS_chr2-2_0057 Verification F | 364 | GTCGCCCATGTTCTTTCGAT |
| KO_PAS_chr2-2_0057 Verification R | 365 | CAAACAGGCTGGAAACCACA |
| KO_PAS_chr1-3_0150 Verification F | 366 | AATCTCCACGTTCAGTTGCG |
| KO_PAS_chr1-3_0150 Verification R | 367 | TCATCCCTTGAAAACCCCGA |
| KO_PAS_chr1-3_0221 Verification F | 368 | TTGTGGAGGGAGATTCAGGC |
| KO_PAS_chr1-3_0221 Verification R | 369 | AAGGTAAGGAACGTGCTTGC |
| KO_PAS_FragD_0022 Verification F | 370 | GTTCTACTGTTCACGTGCTCT |
| KO_PAS_FragD_0022 Verification R | 371 | ACCGGTTAGAATACATGCTGC |
| KO_PAS_chr2-1_0159 Verification F | 372 | CGAAAAGAAGCTGGACTCCG |
| KO_PAS_chr2-1_0159 Verification R | 373 | TTCCATCGTACGACCAGTGT |
| KO_PAS_chr2-1_0326 Verification F | 374 | AGCGATGAGGCCAACAGTAT |
| KO_PAS_chr2-1_0326 Verification R | 375 | TGTCCAGCCCAAAAGACTGA |
| KO_PAS_chr2-2_0056 Verification F | 376 | CTCCTGGGGCTCGTACTAAG |
| KO_PAS_chr2-2_0056 Verification R | 377 | CCTCAATAACGACGGCCTTG |
| KO_PAS_chr1-4_0611 Verification F | 378 | CCTTTTCCTGATCAGTGGGG |
| KO_PAS_chr1-4_0611 Verification R | 379 | TGTTGGGGAATGAAACACGA |
| KO_PAS_chr1-1_0274 Verification F | 380 | GAAGGACGAGTAGGGTTGCT |

TABLE 8-continued

| Forward and reverse primers for amplifying modified sequences | | |
|---|---|---|
| Description | SEQ ID NO: | Sequence (5' to 3') |
| KO_PAS_chr1-1_0274 Verification R | 381 | TCCTGATCTGGCTCGTTTGT |
| KO_PAS_chr4_0834 Verification F | 382 | ACCTCCAACTCCTGAAAGCA |
| KO_PAS_chr4_0834 Verification R | 383 | CCTCGAGTCTGGGCTTTACA |
| KO_PAS_chr3_0896 Verification F | 384 | GGAGAGATGCCAGACCAAGT |
| KO_PAS_chr3_0896 Verification R | 385 | AGCCTGTTCTACTGCATACGT |
| KO_PAS_chr3_0561 Verification F | 386 | CCATTTCTTGTACCCTGGGC |
| KO_PAS_chr3_0561 Verification R | 387 | GCAGAAAAGGCGCGAATTTC |
| KO_PAS_chr3_0633 Verification F | 388 | GGGAAAGGATGTGGACCAAC |
| KO_PAS_chr3_0633 Verification R | 389 | TGGCCAAGAGTGTCCAATTG |
| KO_PAS_chr4_0013 Verification F | 390 | TAACAGATGGCGCACGTAGA |
| KO_PAS_chr4_0013 Verification R | 391 | CCTTGCGTTCCCAGGTAAAG |
| KO_PAS_chr1-1_0379 Verification F | 392 | TGTGGTATGGTTTGGGGCTA |
| KO_PAS_chr1-1_0379 Verification R | 393 | ACTCCCGTTCCTCCATGTTC |
| KO_PAS_chr2-1_0172 Verification F | 394 | ACGGTACAAAAGGCGTTTCA |
| KO_PAS_chr2-1_0172 Verification R | 395 | AGTCAAACTCGGTGGTAGGT |
| KO_PAS_chr3_0866 Verification F | 396 | CGGTTATCATGTGCCTGCTC |
| KO_PAS_chr3_0866 Verification R | 397 | ATGTTGCTGCTCCGAAATCC |
| KO_PAS_chr3_0299 Verification F | 398 | GATCTGCTGGCCTTGAGAGT |
| KO_PAS_chr3_0299 Verification R | 399 | CTATGTCCTGGTGTTTGCCG |
| KO_PAS_chr1-4_0251 Verification F | 400 | GCCAATGATGATCTCGCAGG |
| KO_PAS_chr1-4_0251 Verification R | 401 | GCCTTTGATATGCCGTCGTT |
| KO_PAS_chr4_0874 Verification F | 402 | TCGAGTAATGCTTCCCACCA |
| KO_PAS_chr4_0874 Verification R | 403 | AGCTTTCACAACAGCGATCG |
| KO_PAS_chr3_0513 Verification F | 404 | TGATTGCTTCTGGGTTGCTG |
| KO_PAS_chr3_0513 Verification R | 405 | CAAAACCGGCGTAAAATGGC |
| KO_PAS_chr1-1_0127 Verification F | 406 | TTGTGCTGCATCTGTGTGAG |
| KO_PAS_chr1-1_0127 Verification R | 407 | AGCCTACAAGTGGTTACAGGT |
| KO_PAS_chr4_0686 Verification F | 408 | GGAAACCGACCAGCCTAAAG |
| KO_PAS_chr4_0686 Verification R | 409 | AGTCGCACCAGGTTATCACA |
| KO_PAS_chr2-2_0159 Verification F | 410 | GGAAAGCTGCCCAGAAACTC |
| KO_PAS_chr2-2_0159 Verification R | 411 | TGAGAGGATTCGTTGTGGCT |
| KO_PAS_chr3_0388 Verification F | 412 | CTATGTCGAAGTAGCGGTGC |
| KO_PAS_chr3_0388 Verification R | 413 | AGAGTGGCACTGCTATCGAA |
| KO_PAS_chr3_0419 Verification F | 414 | CGTACAAACTTGGCAGCTGT |
| KO_PAS_chr3_0419 Verification R | 415 | GCTGTGTTGTAAATTCCGGC |
| KO_PAS_chr1-3_0258 Verification F | 416 | ACAACCCGGAAGACAACTCT |
| KO_PAS_chr1-3_0258 Verification R | 417 | TGTCGTTGCCTTCCCGATAT |
| KO_PAS_chr4_0913 Verification F | 418 | GAAGATGGGAGAGGGTGCTT |

TABLE 8-continued

Forward and reverse primers for amplifying modified sequences

| Description | SEQ ID NO: | Sequence (5' to 3') |
|---|---|---|
| KO_PAS_chr4_0913 Verification R | 419 | CTTGTTGACGACGGTAGCAG |
| KO_PAS_chr1-1_0066 Verification F | 420 | CCCTAGTCTCGTTCGAAGGG |
| KO_PAS_chr1-1_0066 Verification R | 421 | GGCACAGCAGGTTTTCGTAT |
| KO_PAS_chr2-2_0310 Verification F | 422 | GGAGATTCTGATGCTACCCCA |
| KO_PAS_chr2-2_0310 Verification R | 423 | TGGAGCCATCAGATCAGGAC |
| KO_PAS_chr1-3_0261 Verification F | 424 | CCTGTTCTTGCAAGCCTTCA |
| KO_PAS_chr1-3_0261 Verification R | 425 | TAAGACATGCGACCACCAGA |
| KO_PAS_chr2-1_0546 Verification F | 426 | CATGGCCAATGTCGAACTGT |
| KO_PAS_chr2-1_0546 Verification R | 427 | AGCTGGCTGAAAAGGTGTTG |
| KO_PAS_chr2-2_0398 Verification F | 428 | CTCAGTGTTGGAAAGCACCC |
| KO_PAS_chr2-2_0398 Verification R | 429 | TAGGGAATCTTTGGTGGCGT |
| KO_PAS_chr4_0835 Verification F | 430 | GGAACCTAGAGCGAGCAACA |
| KO_PAS_chr4_0835 Verification R | 431 | CAGGCTCTATTGTCGACGTG |
| KO_PAS_chr1-1_0491 Verification F | 432 | GGAGGTGATGACAATGCCAC |
| KO_PAS_chr1-1_0491 Verification R | 433 | CTGTGAAGCTCCTCCTACGT |
| KO_PAS_chr2-1_0447 Verification F | 434 | GGACACTGCTGGACAAGAGA |
| KO_PAS_chr2-1_0447 Verification R | 435 | TACTGACGCCGAAGAGCTAG |
| KO_PAS_chr1-3_0053 Verification F | 436 | CCGATCGCAAAATAGTGGCA |
| KO_PAS_chr1-3_0053 Verification R | 437 | GTTGTGGTTGTATGCGGTCA |
| KO_PAS_chr3_0200 Verification F | 438 | CAATAACTCCACTGGTGCCG |
| KO_PAS_chr3_0200 Verification R | 439 | TCGTTATACTCCAGCGTGCT |
| KO_PAS_chr1-3_0105 Verification F | 440 | GGGCTCAAAATCTGGAACCA |
| KO_PAS_chr1-3_0105 Verification R | 441 | CAATGCAGTACTCACCGGTG |
| KO_PAS_chr3_0635 Verification F | 442 | AAGCTGACGACCCCTTAGAC |
| KO_PAS_chr3_0635 Verification R | 443 | CTATCGTGTCTGGGCTGCTA |
| KO_PAS_chr4_0503 Verification F | 444 | AAGGAGATTGCCGCAACTCT |
| KO_PAS_chr4_0503 Verification R | 445 | GTGGAGTCAGAGTCGAGAGG |
| KO_PAS_chr2-1_0569 Verification F | 446 | CCCAGCTTTTATACGGCTTGG |
| KO_PAS_chr2-1_0569 Verification R | 447 | CAGCAAAAGCTCGTGATCCA |
| KO_PAS_chr3_1223 Verification F | 448 | TGCGGGTAGTCGATTGATGT |
| KO_PAS_chr3_1223 Verification R | 449 | TCACGTATCTCAGCAACAGGA |
| KO_PAS_chr2-1_0597 Verification F | 450 | GGACCTAGGAAATACGCCCA |
| KO_PAS_chr2-1_0597 Verification R | 451 | ACTCCAGTTCCACAAGTCCA |
| KO_PAS_chr1-1_0327 Verification F | 452 | ACTGCCAACCGTTTACTCCA |
| KO_PAS_chr1-1_0327 Verification R | 453 | GCGCGGAAGATTAAAGTCGT |
| KO_PAS_chr2-2_0380 Verification F | 454 | TTGGACTCGATCGATGAGGG |
| KO_PAS_chr2-2_0380 Verification R | 455 | TGATGACTTCCAAGATGCGC |
| KO_PAS_chr3_0928 Verification F | 456 | TCACCTGGAGCAACTGATGT |

TABLE 8-continued

| Forward and reverse primers for amplifying modified sequences | | |
|---|---|---|
| Description | SEQ ID NO: | Sequence (5' to 3') |
| KO_PAS_chr3_0928 Verification R | 457 | GTTTGGTACGCTTGTAGGCC |
| PAS_chr1-3_0184 Verification F | 458 | GATGAGCAAGCATCCATTCA |
| PAS_chr1-3_0184 Verification R | 459 | AAAGACAGGAGCGTGAGCAT |
| KO_PAS_chr1-4_0289 Verification F | 460 | CTCAACTTCGCTTGCCCTTT |
| KO_PAS_chr1-4_0289 Verification R | 461 | TGGGAAACAGAACGATGAACT |

TABLE 9

| | | 18B Vector |
|---|---|---|
| Description | SEQ ID NO: | 5' to 3' Sequence |
| 18B silk-like polypeptide encoding sequence | 462 | ggtggttacg gtccaggcgc tggtcaacaa ggtccaggaa gtggtggtca acaaggacct   60<br>ggcggtcaag gaccctacgg tagtggccaa caaggtccag gtggagcagg acagcagggt  120<br>ccgggaggcc aaggacctta cggaccaggt gctgctgctg ccgccgctgc cgctgccgga  180<br>ggttacggtc caggagccgg acaacagggt ccaggtggac tggacaaca aggtccagga  240<br>tcacaaggtc ctggtggaca aggtccatac ggtcctggtg ctggtcaaca gggaccaggt  300<br>agtcaaggac ctggttcagg tggtcagcag ggtccaggag acagggtcc ttacggccct  360<br>tctgccgctg cagcagcagc cgctgccgca ggaggatacg gacctggtgc tggacaacga  420<br>tctcaaggac caggaggaca aggtccttat ggacctggcg ctggccaaca aggtccaggt  480<br>tctcagggtc caggttcagg aggccaacaa ggcccaggag gtcaaggacc atacggacca  540<br>tccgctgcgg cagctgcagc tgctgcaggt ggatatggcc caggagccgg acaacagggt  600<br>cctggttcac aaggtccagg atctggtggt caacaggac caggcggcca gggaccttat  660<br>ggtccaggag ccgctgcagc agcagcagct gttggaggtt acggccctgg tgccggtcaa  720<br>caaggcccag gatctcaggg tcctggatct ggaggacaac aaggtcctgg aggtcagggt  780<br>ccatacggac cttcagcagc agctgctgct gcagccgctg gtggttatgg acctggtgct  840<br>ggtcaacaag gaccgggttc tcaggtccg ggttcaggag gtcagcaggg ccctggtgga  900<br>caaggacctt atggacctag tgcggctgca gcagctgccg ccgcaggtgg ttacggtcca  960<br>ggcgctggtc aacaaggtcc aggaagtggt ggtcaacaag gacctggcgg tcaaggaccc 1020<br>tacggtagtg gccaacaagg tccaggtgga gcaggacagc agggtccggg aggccaagga 1080<br>ccttacggac caggtgctgc tgctgccgcc gctgccgctg ccggaggtta cggtccagga 1140<br>gccggacaac agggtccagg tggagctgga caacaaggtc caggatcaca aggtcctggt 1200<br>ggacaaggtc catacggtcc tggtgctggt caacaggac caggtagtca aggacctggt 1260<br>tcaggtggtc agcagggtcc aggaggacag ggtccttacg gcccttctgc cgctgcagca 1320<br>gcagccgctg ccgcaggagg atacggacct ggtgctggac aacgatctca aggaccagga 1380<br>ggacaaggtc cttatggacc tggcgctggc caacaaggac ctggttctca gggtccaggt 1440<br>tcaggggcc aacaaggccc aggaggtcaa ggaccatacg gaccatccgc tgcggcagct 1500<br>gcagctgctg caggtggata tggcccagga gccggacaac agggtcctgg ttcacaaggt 1560<br>ccaggatctg gtggtcaaca gggaccaggc ggccaggac cttatggtcc aggagccgct 1620<br>gcagcagcag cagctgttgg aggttacggc cctggtgccg gtcaacaagg cccaggatct 1680<br>cagggtcctg gatctggagg acaacaaggt cctggaggtc agggtccata cggaccttca 1740<br>gcagcagctg ctgctgcagc cgctggtggt tatggacctg gtgctggtca acaaggaccg 1800<br>ggttctcagg tccgggttc aggaggtcag cagggccctg gtggacaagg accttatgga 1860<br>cctagtgcg ctgcagcagc tgccgccgca ggtggttacg gtccaggcgc tggtcaacaa 1920<br>ggtccaggaa gtggtggtca acaaggacct ggcggtcaag gaccctacgg tagtggccaa 1980<br>caaggtccag gtggagcagg acagcagggt ccgggaggcc aaggacctta cggaccaggt 2040<br>gctgctgctg ccgccgctgc cgctgccgga ggttacggtc caggagccgg acaacagggt 2100<br>ccaggtggag ctggacaaca aggtccagga tcacaaggtc ctggtggaca aggtccatac 2160<br>ggtcctggtg ctggtcaaca gggaccaggt agtcaaggac ctggttcagg tggtcagcag 2220<br>ggtccaggag acagggtcc ttacggccct tctgccgctg cagcagcagc cgctgccgca 2280<br>ggaggatacg gacctggtgc tggacaacga tctcaaggac caggaggaca aggtccttat 2340<br>ggacctggcg ctggccaaca aggacctggt tctcagggtc caggttcagg aggccaacaa 2400<br>ggcccaggag gtcaaggacc atacggacca tccgctgcgg cagctgcagc agcagcagct 2460<br>ggatatggcc caggagccgg acaacagggt cctggttcac aaggtccagg atctggtgg atct 2520<br>caacagggac caggcggcca gggaccttat ggtccaggag ccgctgcagc agcagcagct 2580<br>gttggaggtt acggccctgg tgccggtcaa caaggcccag gatctcaggg tcctggatct 2640<br>ggaggacaac aaggtcctgg aggtcagggt ccatacggac cttcagcagc agctgctgct 2700<br>gcagccgctg gtggttatgg acctggtgct ggtcaacaag gaccgggttc tcaggtccg 2760<br>ggttcaggag gtcagcaggg ccctggtgga caaggacctt atgacctag tgcggctgca 2820<br>gcagctgccg ccgca   2835 |
| 18B polypeptide sequence | 463 | GGYGPGAGQQGPGSGGQQGPGGQGPYGSGQQGPGGAGQQGPGGQGPYGPGAAAAAAAAAG<br>GYGPGAGQQGPGGAGQQGPGSQGPGGQGPYGPGAGQQGPGSQGPGSGGQQGPGGQGPYGP<br>SAAAAAAAAAGGYGPGAGQRSQGPGGQGPYGPGAGQQGPGSQGPGSGGQQGPGGQGPYGP<br>SAAAAAAAAAGGYGPGAGQQGPGSQGPGSGGQQGPGGQGPYGPGAAAAAAAAVGGYGPGAGQ<br>QGPGSQGPGSGGQQGPGGQGPYGPSAAAAAAAAAGGYGPGAGQQGPGSQGPGSGGQQGPGG |

TABLE 9-continued

| | | 18B Vector |
|---|---|---|
| Description | SEQ ID NO: | 5' to 3' Sequence |
| | | QGPYGPSAAAAAAAAGGYGPGAGQQGPGSGGQQGPGGQGPYGSGQQGPGGAGQQGPGGQG |
| | | PYGPGAAAAAAAAAGGYGPGAGQQGPGGAGQQGPGSQGPGGQGPYGPGAGQQGPGSQGPG |
| | | SGGQQGPGGQGPYGPSAAAAAAAAAGGYGPGAGQRSQGPGGQGPYGPGAGQQGPGSQGPG |
| | | SGGQQGPGGQGPYGPSAAAAAAAAAGGYGPGAGQQGPGSQGPGSGGQQGPGGQGPYGPGAA |
| | | AAAAAVGGYGPGAGQQGPGSQGPGSGGQQGPGGQGPYGPSAAAAAAAAAGGYGPGAGQQGP |
| | | GSQGPGSGGQQGPGGQGPYGPSAAAAAAAAAGGYGPGAGQQGPGSGGQQGPGGQGPYGSGQ |
| | | QGPGGAGQQGPGGQGPYGPGAAAAAAAAAGGYGPGAGQQGPGGAGQQGPGSQGPGGQGPY |
| | | GPGAGQQGPGSQGPGSGGQQGPGGQGPYGPSAAAAAAAAAGGYGPGAGQRSQGPGGQGPY |
| | | GPGAGQQGPGSQGPGSGGQQGPGGQGPYGPSAAAAAAAAAGGYGPGAGQQGPGSQGPGSGG |
| | | QQGPGGQGPYGPGAAAAAAAVGGYGPGAGQQGPGSQGPGSGGQQGPGGQGPYGPSAAAAA |
| | | AAAGGYGPGAGQQGPGSQGPGSGGQQGPGGQGPYGPSAAAAAAAA |
| Repeat sequence of a silk-like polypeptide | 464 | GGYGPGAGQQGPGSGGQQGPGGQGPYGSGQQGPGGAGQQGPGGQGPYGPGAAAAAAAAAG |
| | | GYGPGAGQQGPGGAGQQGPGSQGPGGQGPYGPGAGQQGPGSQGPGSGGQQGPGGQGPYGP |
| | | SAAAAAAAAAGGYGPGAGQRSQGPGGQGPYGPGAGQQGPGSQGPGSGGQQGPGGQGPYGP |
| | | SAAAAAAAAGGYGPGAGQQGPGSQGPGSGGQQGPGGQGPYGPGAAAAAAAVGGYGPGAGQ |
| | | QGPGSQGPGSGGQQGPGGQGPYGPSAAAAAAAAAGGYGPGAGQQGPGSQGPGSGGQQGPGG |
| | | QGPYGPSAAAAAAAA |

TABLE 10

| | | Zeocin Cassette with HA arms for KU70 deletion in *P. pastoris* |
|---|---|---|
| Description | SEQ ID NO: | 5' to 3' Sequence |
| Plasmid sequence | 465 | ggagttgaatcacatcttactggatagcgagcttttttgacgaagtgaaaatttctaattttaaacaagaggaaggggtca |
| | | aaaacggagatatcttatacttggaaaaagagatgacaatcagtgatttcatcaattttgtatctagttggccttctgtg |
| | | ttttcgtggaagcagcaacgaggaaaggagggtatcctagatgattttttacaacgaactgaacgactgctttgagggggg |
| | | taacatgaaagtaatatggaactccgtcctagtatttgccaggaggaagcaaagggttgtataggctttagtacttatag |
| | | aggaaacgggggttacgtgcaagcgcgcatgcctgagctttgagggggggggactttcacatctcttcttctcacacttagc |
| | | cctaacacagagaataataaaaagcattgcaagatgagtgttgtcagcaagcaatacgacatccacgaaggcattatctt |
| | | tgtaattgaattgaccccggagcttcacgcgccggcttcagaagggaaatctcagctccagatcatcttagagaatgtca |
| | | gtgaggttatttctgagctaatcattaccttgcccggtacaggaataggggtgttaccttattaattacgacggtggtcaa |
| | | aacgacgaaatttaccccattttttgagttacaagacctgaatttggaaatgatgaaacaattgtaccaagtcttggagga |
| | | ccatgtaagtgggcttaatcctctcgagaagcaattcccaattgaacacagtaaaccgttatcagccactctgttctttc |
| | | acttaaggtctcttttttacatggcgaagactcataagcgtactggaagacattacaacttgaaaaagattttcttgttc |
| | | actaataacgataaaaccttacaatggaaactctcagctgagagttcccttgaagaaaaccctggctgattacaatgacgt |
| | | agacattactttgattccgtttcttctgaacaagccttcaggtgtcaagtttgacaagacggaatactcagaaattttgt |
| | | tctatgataaagatgcttgttcgatgtcaattgaggagatccgccaacgaatttctagacataaggagatcaagcgggtt |
| | | tacttcacctgtcctttgaaaatcgcaaataacttgtgcatttctgtgaaaggttattctatgttttatcatgaaactcc |
| | | aaggaagatcaaatttgtcgtcaatgagggttcaactttcaaagatgtggagacaaaatctcagtttgtcgatccaacat |
| | | ccggaaaagagtttttccagtgaacagctgatcaaagcatatcctctaggtgccgatgcttacattcctttaaaactcagag |
| | | caagtcaaaacaataaatcgatttaatgatatcatcaatatcccctctttggaaattctaggtttcagggatatatctaa |
| | | ttggttgccacagtatcagtttggcaaagcatcgttttttatcccctaataactatggtgattttacacattcgcagagaa |
| | | catttagttgtcttcagtaatgtcttgtttctttttgttgcagtggtgagccattttgacttcgtgaaagtttctttagaa |
| | | tagttgtttccagaggccaaacattccacccgtagtaaagtgcaagcgtaggaagaccaagactggcataaatcaggtat |
| | | aagtgtcgagcactggcaggtgatcttctgaaagtttctactagcagataagatccagtagtcatgcatatggcaacaat |
| | | gtaccgtgtggatctaagaacgcgtcctactaaccttcgttggtccagtttgttgttatcgatcaacgtgacaa |
| | | ggttgtcgattccgcgtaagcatgcatacccaaggacgcctgttgcaattccaagtgagccagttccaacaatctttgta |
| | | atattagagcacttcattgtgttgcgcttgaaagtaaaatgcgaacaaattaagagataatctcgaaaccgcgacttcaa |
| | | acgccaatatgatgtgcggcacacaataagcgttcatatccgctgggtgactttctcgctttaaaaaattatccgaaaaa |
| | | atttttgacggctagctcagtcctaggtacgctagcattaaagaggagaaatggctaaactgacctctgctgttccggt |
| | | tctgaccgccgtcgacgttgctggtgctgttgagttctggaccgaccgtctgggtttctctcgtgacttcgttgaagacg |
| | | acttcgctggtgttgttcgtgacgacgttaccctgttcatctctgctgttcaggaccaggttgttccggacaacaccctg |
| | | gcttgggtttggttcgtggtctggacgaactgtacgctgaatggtctgaagttgttctaccaacttccgtgacgcttc |
| | | tggtccggctatgaccgaaatcggtgaacagccgtggggtcgtgagttcgctctgcgtgaccggctggtaactgcgttc |
| | | acttcgttgctgaagaacaggactaacacgtccgacggccgacgtcccaggctccggagatccgtccccctttc |
| | | ctttgtcgatatcatgtaattagttatgtcacgcttacattcacgccctcccccacatccgctctaaccgaaaaggaag |
| | | gagttagacaacctgaagtctaggtcccctatttatttttttatagttatgttagtattaagaacgttatttatatttcaa |
| | | atttttcttttttttctgtacagacgcgtgtacgcatgtaacattatactgaaaaccttgcttgagaaggtttttgggacg |
| | | ctcgaaggcttttaatttgcaagctgtattagtttcacttttcagcaacctggtcggaaagatccacatcaagaatggata |
| | | ccaaccccaagagtatgaaaatccttccctacaattggcacttcaaaatgttacgtgacgattaccttcaattggaacacg |
| | | atatcgacatcagtgaccccctttgagaaacaaaagtacataaacagcctcgatgagacaaaaaccaagatcatgaaacta |
| | | cgggactatgtcaaggaaactgccgatgatgacgaccccttcacggcttgccaacactctcaaagagctcaaccaagagct |
| | | gaacaaaaatttccaactttgatatcatcgccaataagaagccaaagaccccacgacagtagaccctgttcctactgatg |

TABLE 10-continued

Zeocin Cassette with HA arms for KU70 deletion in *P. pastoris*

| Description | SEQ ID NO: | 5' to 3' Sequence |
|---|---|---|
| | | atgacatcatcaacgcctggaaggcaggaactctgaacggtttcaaggtggatcaattacgaaaatacgtaaggtcacga aacaactttctggagacggcctccaaaaaggcagatctcatcgccaacattgacaagtactttcagcagaagttcaaaga gactaaggcctgattcgtcgtgttccttactttttcctcgcaacgtgtttttttcccaccacattgcctatgttgtaatgcaa tgcagatgctggcccagttttttgacgattctcgaaaattggcattttcgtcgatgccattggccaaactgaaaattcaag acaaaatagattggattttatctgcaacgtcttccacctacacaaccactctacaaacttcagacaaacatgtttataaa agcagctactagatccaaaatgacaagttcgttattctctactacgtttgttgtggtgcatttggattggtggctagcaaca acctcttgccatgtcctgttgaccactctatgaataacgagactccgcaagaattgaaaccattgcaggctgaatcttct actagaaagttgaactcttccgcttaagtcaaataaaaactactgacacagatgatgcacagaaacaacggatcacgctct tgactgattagtcccgtcattttggttctcattttcttcacagtcacctatcaatgtatgatcacctggaaggatttccc tacgatacttcaaatctttttacttgataatattactcattatggctcaggaatgcagactgcctgattcaagacgctgct cttcttatttaacacttgtacactaaccccatggaagccagggaagggaataaccatctctctggtaataaatcggtctt tatttatgcatagaaaaggaatctattatatttcgttcatttggcactctgctaactgtagattaacgggtctcgtaaat tcaaaatcttcttccgatcaaaccgggggtgaaatattacttctcgtgcatagctaattttcaaataaccgtcctaaaatg aacggtcatttacctggactctcttgccaaatgggcaacaaaacataaagctgatcagaacgtaactagtctctcggaat ccat |
| HA F | 466 | ggagttgaatcacatcttactg |
| KU70 HA 1 | 467 | gacaactaaatgttctctgcgaatgtgtaaaatcaccatagttattaggggataaaaacgatgctttgccaaactgatac tgtggcaaccaattagatatatccctgaaacctagaatttccaaagagggagtattgatgatatcattaaaatcgatttat tgttttgacttgctctgagtttaaaggaatgtaagcatcggcacctagaggatatgctttgatcagctgttcactggaaa actctttccggatgttggatcgacaaactgagattttgtctccacatctttgaaagttgaaccctcattgacgacaaat ttgatcttccttggagtttcatgataaaacatagaataaccttcacagaaatgcacaagttatttgcgattttcaaagg acaggtgaagtaaacccgcttgatctccttatgtctagaaattcgttggcggatctcctcaattgacatcgaacaagcat ctttatcatagaacaaaatttctgagtattccgtcttgtcaaacttgacacctgaaggcttgttcagaagaaacggaatc aaagtaatgtctacgtcattgtaatcagccagggtttcttcaagggaactctcagctgagagtttccattgtaaggttt atcgttattagtgaacaagaaaatctttttcaagttgtaatgtcttccagtacgcttatgagtcttcgccatgtaaaaaa gagaccttaagtgaaagaacagagtggctgataacgagtttactgtgttcaattgggaattgcttctcgagaggattaagc ccacttacatggtcctccaagacttggtacaattgtttcatcatttccaaattcaggtcttgtaactcaaaaatggggta aatttcgtcgtttgaccaccgtcgtaattaataaggtaacaccctattcctgtaccgggcaaggtaatgattagctcag aaataacctcactgacattctctaagatgatctggagctgagatttcccttctgaagccggcgcgtgaagctccgggggtc aattcaattacaaagataatgccttcgtggatgtcgtattgcttgctgacaacactcat |
| KU70 HA 2 | 468 | tcaggccttagtctctttgaacttctgctgaaagtacttgtcaatgttggcgatgagatctgcctttttggaggccgtct ccagaaagttgtttcgtgaccttacgtattttcgtaattgatccaccttgaaaccgttcagagttcctgccttccaggcg ttgatgatgtcatcatcagtaggaacagggtctactgtcgtggggggtctttggcttcttattggcgatgatatcaaagtt ggaaattttgttcagctcttggttgagctctttgagagtgttggcaagccgtgaagggtcgtcatcatcggcagtttcct tgacatagtcccgtagtttcatgatcttggttttttgtctcatcgaggctgtttatgtacttttgtttctcaaggggtca ctgatgtcgatatcgtgttccaattgaaggtaatcgtcacgtaacattttgaagtgccattgtagggaaggattttcata ctcttggggttggtatccattcttgatgtggatctttccgaccaggttgctgaaaagtgaaactaatac |
| pILV5 | 469 | ttcagtaatgtcttgtttcttttgttgcagtggtgagccattttgacttcgtgaaagtttctttagaatagttgtttcca gaggccaaacattccaccgtagtaaagtgcaagcgtaggaagaccaagactggcataaatcaggtatagtgtcgagca ctggcaggtgatcttctgaaagtttctactagcagataagatccagtagtcatgcatatggcaacaatgtaccgtgtgga tctaagaacgcgtcctactaaccttcgcattcgttggtccagtttgttgttatcgatcaacgtgacaaggttgtcgattc cgcgtaagcatgcatacccaaggacgcctgttgcaattccaagtgagccagttccaacaatctttgtaatattagagcac ttcattgtgttgcgcttgaaagtaaaatgcgaacaaattaagagataatctcgaaaccgcgacttcaaacgccaatatga tgtgcggcacacaataagcgttcatatccgctgggtgactttctcgctttaaaaaattatccgaaaaaattt |
| RM2734; testR | 470 | cagaggccaaacattccacc |
| pproRBS | 471 | ttaaagaggagaaa |
| Sh ble (codon optimized) | 472 | atggctaaactgacctctgctgttccggttctgaccgctcgtgacgttgctggtgctgttgagttctggaccgaccgtct gggtttctctcgtgacttcgttgaagacgacgttcgctggtgttgttcgtgacgacgttaccctgttcatctctgctgttc aggaccaggttgttccggacaacaccctggctcgtgggtttgggttcgtggtctggacgaactgtacgctgaatggtctgaa gttgtttctaccaacttccgtgacgcttctggtccggctatgaccgaaatcggtgaacagccgtggggtcgtgagttcgc tctgcgtgaccccggctggtaactgcgttcacttcgttgctgaagaacaggactaa |
| CYC1 terminator | 473 | cacgtccgacggcggcccacgggtcccaggcctcggagatccgtcccccttttccttgtcgatatcatgtaattagtta tgtcacgcttacattcacgccctcccccacatccgctctaaccgaaaaggaaggagttagacaacctgaagtctaggtc cctatttatttttttatagttatgttagtattaagaacgttatttatatttcaaattttcttttttttttctgtacagacg cgtgtacgcatgtaacattatactgaaaaccttgcttgagaaggttttgggacgctcgaaggctttaatttgcaagct |
| Rm3386; F test oligo | 474 | aggagttagacaacctgaag |
| HA R | 475 | gtaactagtctctcggaatccat |

TABLE 11

Nourseothricin Cassette for protease deletion in *P. pastoris*

| Description | SEQ ID NO: | 5' to 3' Sequence |
|---|---|---|
| Plasmid sequence | 476 | cttcagagtacagaagattaagtgagagaattctaccgttcgtatagcatacattatacgaagttatttcagtaatgtct tgtttctttgttgcagtggtgagccattttgacttcgtgaaagtttctttagaatagttgtttccagaggccaaacatt ccaccgtagtaaagtgcaagcgtaggaagaccaagactggcataaatcaggtataagtgtcgagcactggcaggtgatc ttctgaaagtttctactagcagataagatccagtagtcatgcatatggcaacaatgtaccgtgtggatctaagaacgcgt cctactaaccttcgcattcgttggtccagtttgttgttatcgatcaacgtgacaaggttgtcgattccgcgtaagcatgc atacccaaggacgcctgttgcaattccaagtgagccagttccaacaatctttgtaatattagagcacttcattgtgttgc gcttgaaagtaaaatgcgaacaaattaagagataatctcgaaaccgcgacttcaaacgccaatatgatgtgcggcacaca ataagcgttcatatccgctgggtgactttctcgctttaaaaaattatccgaaaaaattttttgacggctagctcagtccta ggtacgctagcattaaagaggagaaaatgactactcttgatgacacagcctacagatataggacatcagttccgggtgac gcagaggctatcgaagccttggacggttcattcactactgatacggtgtttagagtcaccgctacaggtgatggcttcac cttgagagaggttcctgtagacccacccttaacgaaagtttccctgatgacgaatcggatgacgagtctgatgctggtg aggacggtgaccctgattccagaacatttgtcgcatacggagatgatggtgacctggctggctttgttgttggtgtcctac agcggatggaatcgtagactcacagttgaggacatcgaagttgcacctgaacatcgtggtcacggtgttggtcgtgcact gatgggactggcaacagagtttgctagagaaagaggagccggacatttgtggttagaagtgaccaatgtcaacgctcctg ctattcacgcatataggcgaatgggtttcactttgtgcggtcttgatactgctttgtatgacggaactgcttctgatggt gaacaagctctttacatgagtatgccatgtccatagccatacgacgtcccacgggcccacgggcccacgggcccaggcctcggagatccgt ccccctttttcctttgtcgatatcatgtaattagttatgtcacgcttacattcacgcctcccccccacatccgctctaacc gaaaaggaaggagttagacaacctgaagtctaggtccctatttatttttttatagttatgttagtattaagaacgttatt tatatttcaaattttttctttttttttctgtacagacgcgtgtacgcatgtaacattatactgaaaaccttgcttgagaagg ttttgggacgctcgaaggctttaatttgcaagctataacttcgtatagcatacattataccttgttatgcggccgcaaga agttgattgagactttcaacgag |
| AOX1 pA terminator | 477 | cttcagagtacagaagattaagtgaga |
| Lox71 F | 478 | taccgttcgtatagcatacattatacgaagttat |
| pILV5 | 479 | ttcagtaatgtcttgtttctttgttgcagtggtgagccattttgacttcgtgaaagtttctttagaatagttgtttcca gaggccaaacattccaccgtagtaaagtgcaagcgtaggaagaccaagactggcataaatcaggtataagtgtcgagca ctggcaggtgatcttctgaaagtttctactagcagataagatccagtagtcatgcatatggcaacaatgtaccgtgtgga tctaagaacgcgtcctactaaccttcgcattcgttggtccagtttgttgttatcgatcaacgtgacaaggttgtcgattc cgcgtaagcatgcatacccaaggacgcctgttgcaattccaagtgagccagttccaacaatctttgtaatattagagcac ttcattgtgttgcgcttgaaagtaaaatgcgaacaaattaagagataatctcgaaaccgcgacttcaaacgccaatatga tgtgcggcacacaataagcgttcatatccgctgggtgactttctcgctttaaaaaattatccgaaaaaattt |
| pproRBS | 480 | ttaaagaggagaaa |
| nat (Nourseothricin resistance) | 481 | atgactactcttgatgacacagcctacagatataggacatcagttccgggtgacgcagaggctatcgaagccttggacgg ttcattcactactgatacggtgtttagagtcaccgctacaggtgatggcttcaccttgagagaggttcctgtagacccac ccttaacgaaagtttccctgatgacgaatcggatgacgagtctgatgctggtgaggacggtgaccctgattccagaaca tttgtcgcatacggagatgatggtgacctggctggctttgttgttggtgtcctacagtgaggacatcgaagttgcacctgaacatcgtggtcacggtgttggtcgtgcactgatgggactggcaacagagtttgcta gagaaagaggagccggacatttgtggttagaagtgaccaatgtcaacgctcctgctattcacgcatataggcgaatgggt ttcactttgtgcggtcttgatactgctttgtatgacggaactgcttctgatggtgaacaagctctttacatgagtatgcc atgtccatag |
| CYC1 terminator | 482 | cacgtccgacggcggcccacgggcccaggcctcggagatccgtccccctttttcctttgtcgatatcatgtaattagtta tgtcacgcttacattcacgcctcccccccacatccgctctaaccgaaaaggaaggagttagacaacctgaagtctaggtc cctatttatttttttatagttatgttagtattaagaacgttatttatatttcaaattttttctttttttttctgtacagacg cgtgtacgcatgtaacattatactgaaaaccttgcttgagaaggttttgggacgctcgaaggctttaatttgcaagct |
| LoxKR3 F | 483 | ataacttcgtatagcatacattataccttgttat |
| HSP82 | 484 | gcggccgcaagaagttgattgagactttcaacgag |

TABLE 12

Exemplary nourseothricin cassettes with HA arms for protease deletion in *P. pastoris*

| Description | SEQ ID NO: | 5' to 3' Sequence |
|---|---|---|
| Nourseothricin cassette with homology arms targeting PAS_chr4_0584 | 485 | tactacaggctggctgttcctcgcatggtgtttaatgtcctgactgggttttcgtttatcggtattaccggagccaccttg actgtaagggaacgatactggactaagagagtaatgcgaaaggcaacagcgtttctggcgaacctaatcaatgacggttac gagtttactactcctaaagccagtcttattttgctagagcgagtcaacgcttacttaaagggccagggacctaattatgac atcgattttgacgagcaggaggcgttcattaaagaaatggaggagttgaggacctctggtggatatgagaacagatactca tattcaggaaccgatgaaacacccagagatccgggttgcctgtttcttcccattgctttaaataaatggcacttttgatgtg ctagactgcctgaggatatacggtactcaggaagatctggaatctaaattattaagtgttcagcaattggtgttacaatgt tgcatgaagcacagtggcatgactccagacatggtctttgcaacggaagtagctcagaagccgaccttcgaagacgacata gtttgtgatgatattgacgcttatgcccaggggggtgattgtctagattattgttacacgccaagcaattactccagaact ttagaaattcatggcaagattgctaccttacaacgagagctggggctatgctataatattctcggaattttggaccgtttt |

TABLE 12-continued

Exemplary nourseothricin cassettes with HA arms for protease deletion in *P. pastoris*

| Description | SEQ ID NO: | 5' to 3' Sequence |
|---|---|---|
| | | tccgattaaggtttttagctccattgcgccaaccccgctctccagactccttcgttatccagcattcagcatggacaggt<br>tcaaaaaataaaatttcttgatatgggtccacttcaaacatgcgcctacctgtaggaaaaaaaaagagaacataaatatgc<br>cgcgaacagaaaacgtaatgtactgttctatatataaactgttcagatcaatcataaattctcagtttcaaactttccgct<br>cagccagatttttattcgtaaagaacgcatcattggctctatgttgaaggatcagttcttgttatgggttgctttgatagcg<br>agcgtaccggtttccggcgtgatggcagctcctagcgagtccgggcataacacggttgaaaaacgagatgccaaaaacgtt<br>gttggcgttcaacagttggacttcttcagagtacagaagattaagtgagagaattctaccgttcgtatagcatacattata<br>cgaagttatttcagtaatgtcttgtttctttgttgcagtggtgagccattttgacttcgtgaaagtttctttagaatagt<br>tgtttccagaggccaaacattccaccgtagtaaagtgcaagcgtaggaagaccaagactggcataaatcaggtataagtg<br>tcgagcactggcaggtgatcttctgaaagtttctactagcagataagatccagtagtcatgcatatggcaacaatgtaccg<br>tgtggatctaagaacgcgtcctactaaccttcgcattcgttggtccagtttgttgttatcgatcaacgtgacaaggttgtc<br>gattccgcgtaagcatgcataccaaggacgcctgttgcaattccaagtgagccagttccaacaatcttgtaatattaga<br>gcacttcattgtgttgcgcttgaaagtaaaatgcgaacaaattaagagataatctcgaaaccgcgacttcaaacgccaata<br>tgatgtgcggcacacaataagcgttcatatccgctgggtgactttctcgctttaaaaaattatccgaaaaaatttttgacg<br>gctagctcagtcctaggtacgctagcattaaagaggagaaaatgactactcttgatgacacagcctacagatataggacat<br>cagttccgggtgacgcagaggctatcgaagccttggacggttcattcactactgatacggtgttagagtcaccgctacag<br>gtgatggcttcaccttgagagaggttcctgtagacccacccttaacgaaagttttccctgatgacgaatcggatgacgagt<br>ctgatgctggtgaggacggtgaccctgattccagaacatttgtcgcatacggagatgatggtgacctggctggctttgttg<br>tggtgtcctacagcggatggaatcgtagactcacagttgaggacatcgaagttgcacctgaacatcgtggtcacggtgttg<br>gtcgtgcactgatgggacctggcaacagagtttgctagagaaagaggagccggacatttgtggttagaagtgaccaatgtca<br>acgctcctgctattcacgcatataggcgaatgggtttcacttgtgcggtcttgatactgctttgtatgacggaactgctt<br>ctgatggtgaacaagctcttacatgagtatgccatgtccatagcacgtccgacggcggcccacgggtcccaggcctcgga<br>gatccgtccccctttcctttgtcgatatcatgtaattagttatgtcacgcttacattcacgccctccccccacatccgct<br>ctaaccgaaaaggaaggagttagacaacctgaagtctaggtccctatttatttttttatagttatgttagtattaagaacg<br>ttatttatatttcaaattttctctttttttctgtacagacgcgtgtacgcatgtaacattatactgaaaaccttgcttgag<br>aaggttttgggacgctcgaaggctttaatttgcaagctataacttcgtatagcatacattatacctgttatgcggccgca<br>agaagttgattgagacttcaacgagggtcccccttcagctacctttctctctgtttggtagttattctcggcgtgtgtata<br>gtatagtatataaagggcctacattggataggcttcaacattcctcaataaacaaacatccaacatcgcgcattccgcattt<br>cgcatttcacatttcgcgcctgccttccttaggttcttttgaatcatcatcaatcgtcgccgtctacatcagagcaggact<br>tatctttgccttccccaaaaattgccactccgtcaaatagattctttttgaatccttgactattttgcctaaataggtttt<br>tgttagtttttcttcaaagcccaaaagaaactctatttagattcatccagaaacaatcttttctcaccccatttcgaagt<br>gccgtggagcacagacataaaaagatgactaccgttcaacctacagggccagacaggctcaccctgccgcatattctactg<br>gaattcaacgatggctcctcgcagcatgcagtgatcagttgattaagctaagcatgaacgagggggattaatatatccaccccatgagtgg<br>aatccatccactaatgagcaatcgccacgggaagagagagcaccaccccaacaatccaatccatcgcatcatccagaatca<br>tcgaacatagctactcaaagtcccgctcaggaaaccgagactcagcccggcattccaggactagataggcctgcctttgat<br>acctcggcaacggggtcgtcagaacaggttgacccagtacagggaaggatcctggatgatattataggccaatcattaagg<br>acttccgagagaagacgaatcccgcccagaatccgcccagaagaacattatgatcaccgtgaattacttgtac<br>gcagacgacacaaattccagaagtgctaatacaaacaaccagacgcccaataacacttctagaacttccgacagtgaacgt<br>gtgggctccttatcgttgcacgttccggatctaccagataatgccgacgattactatatcgatgtactcattaaactaacc<br>acaagcattgccctcagcgtcatcacgtccatgatcaagaaacgattagggcttagcaggga |
| PAS_chr4_0584 Homology Arm 1 | 486 | tactacaggctggctgttcctcgcatggtgtttaatgtcctgactgggttttcgtttatcggtattaccggagccaccttg<br>actgtaagggaacgatactggactaagagagtaatgcgaaaggcaacagcgtttctggcgaacctaatcaatgacggttac<br>gagtttactactcctaaagccagtcttatttgctagagcgagtcaacgcttacttaaagggcagggacctaattatgac<br>atcgattttgacgagcaggaggcgttcattaaagaaatggaggagttgacgacctctggtggatatgagaacagatactca<br>tattcaggaaccgatgaaacacccagagatccgggttgcctgtttcttcccattgctttaaataaatggcactttgatgtg<br>ctagactgcctgaggatatacggtactcaggaagatctggaatctaaattattaagtgttcagcaattggtgttacaatgt<br>tgcatgaagcacagtggcatgactccagacatggtctttgcaacggaagtagctcagaagccgaccttcgaagacgacata<br>gtttgtgatgatattgacgcttatgcccaggggggtgattgtctagattattgttacacgccaagcaattactccagaact<br>ttagaaattcatggcaagattgctaccttacaacgagagctggggctatgctataatattctcggaattttggaccgtttt<br>tccgattaaggtttttagctccattgcgccaaccccgctctccagactccttcgttatccagcattcagcatggacaggt<br>tcaaaaaataaaatttcttgatatgggtccacttcaaacatgcgcctacctgtaggaaaaaaaaagagaacataaatatgc<br>cgcgaacagaaaacgtaatgtactgttctatatataaactgttcagatcaatcataaattctcagtttcaaactttccgct<br>cagccagatttttattcgtaaagaacgcatcattggctctatgttgaaggatcagttcttgttatgggttgctttgatagcg<br>agcgtaccggtttccggcgtgatggcagctcctagcgagtccgggcataacacggttgaaaaacgagatgccaaaaacgtt<br>gttggcgttcaacagttggactt |
| PAS_chr4_0584 Homology Arm 2 | 487 | ggtccccttcagctacctttctctctgtttggtagttattctcggcgtgtgtatagtatagtatataaagggcctacattgg<br>ataggcttcaacattcctcaataaacaaacatccaacatcgcgcattccgcatttcgcatttcacatttcgcgcctgcctt<br>cctttaggttcttttgaatcatcatcaatcgtcgccgtctacatcagagcaggacttatctttgccttccccaaaaattgcc<br>actccgtcaaatagattctttttgaatccttgactattttgcctaaataggtttttgttagtttttcttcaaagcccaaaa<br>gaaactctatttagattcatccagaaacaatcttttctcaccccatttcgaagtgccgtggagcacagacataaaaagat<br>gactaccgttcaacctacagggccagacaggctcaccctgccgcatattctactggaattcaacgatggctcctcgcagca<br>tgcagtgatcgagctaagcatgaacgagggggattaatatatccaccccatgagtggaatccatccactaatgagcaatcgcc<br>acgggaagagagagcaccaccccaacaatccaatccatcgcatcatccagaatcatcgaacatagctactcaaagtcccgc<br>tcaggaaaccgagactcagcccggcattccaggactagataggcctgcctttgatacctcggcaacggggtcgtcagaaca<br>ggttgacccagtacagggaaggatcctggatgatattataggccaatcattaaggacttccgaagaagacgataccgaatc<br>ccgccagagaccacgagaccagaagaacattatgatcaccgtgaattacttgtacgcagacgacacaaattccagaagtgc<br>taatacaaacaaccagacgcccaataacacttctagaacttccgacagtgaacgtgtgggctccttatcgttgcacgttcc<br>ggatctaccagataatgccgacgattactatatcgatgtactcattaaactaaccacaagcattgccctcagcgtcatcac<br>gtccatgatcaagaaacgattagggcttagcaggga |
| Nourseothricin cassette with homology arms | 488 | gccttctcgtgcaatcagagctgttgaaagagagaagagggcacacggaagctgctgttcaattgtgtgaattgaccggat<br>tacaacctgctggagtgataggagagctggttcgtgacgaggacggctctatgatgcgattagacgactgtgttcagtttg<br>gtctccgccacaacgtaaaaattatcaaccttgaccagatcattgaatacatggattccaagaacagctagatacgatgga |

TABLE 12-continued

Exemplary nourseothricin cassettes with HA arms for protease deletion in *P. pastoris*

| Description | SEQ ID NO: | 5' to 3' Sequence |
|---|---|---|
| targeting PAS_chr3_1157 | | taggaatacagagatatcatgattgaggaacgtaagagcttttttcgaaagtgtgagtttgtggtgagggccaggcggtggg gaggtggtggggagcctccttggtcgaatgtagatatagtaagcaagacacaagagcgcgcgaagtcttcaacgaggcggc gttgggtcttgtacgcaacgtaatgactacacagttgagcttgtcgcgaaccggtcgacattttgatcatgcatactatgt tgagacaccatctcgtactattgcggcaaccagctgtaaatttgactaattaaagctgatgaaggatgcagggcgtcgtca atttttttgattgattgcatttaattgtttgagccattcaaggctgaatgcccggcaccctagacccttcttgtgagtacta taaacccgcaggcagggtacccttggccttctgcgagactaccagtcataacgtatatccacaatgtactagtaatagccc cggaaaactctaatcccacagaacgtctaacgcctcctatgtcatcgataccccattcgcactactgccatggccccccttta cgtgatcatttcacttactcccgcctaagcttcgcccacatgcctgcgttttgccaagatttactgacgagtttggtttac tcatcctctatttataactactagactttcaccattcttcaccaccctcgtgccaatgatcatcaaccacttggtattgac agccctcagcattgcactagcaagtcgcgaactccaatcgcctttcacttcagagtacagaagattaagtgagagaattct accgttcgtatagcatacattatacgaagttatttcagtaatgtcttgtttcttttgtcagtggtgagccattttgact tcgtgaaagtttctttagaatagttgtttccagaggccaaacattccacccgtagtaaagtgcaagcgtaggaagaccaag actggcataaatcaggtataagtgtcgagcactggcaggtgatcttctgaaagtttctactagcagataagatccagtagt catgcatatggcaacaatgtaccgtgtgggatctaagaacgcgtcctactaaccttcgcattcgttggtccagtttgttgtt atcgatcaacgtgcaaggttgtcgattccgcgtaagcatgcataccccaaggacgcctgttgcaattccaagtgagccagt tccaacaatctttgtaatattagagcacttcattgtgttgcgcttgaaagtaaaatgcgaacaaattaagagataatctcg aaaccgcgacttcaaacgccaatatgatgtgcggcacacaataagcgttcatatccgctgggtgactttctcgctttaaaa aattatccgaaaaaatttttgacggctagctcagtcctaggtacgctagcattaaagaggagaaaatgactactcttgatg acacagcctacagatataggacatcagttccgggtgacgcagaggctatcgaagccttggacggttcattcactactgata cggtgtttagagtcaccgctacaggtgatggcttcaccttgagagaggttcctgtagacccaccctaacgaaagttttcc ctgatgacgaatcggatgacgagtctgatgctggtgaggacggtgaccctgattccagaacatttgtcgcatacggagatg atggtgacctggctggctttgttgtggtgtcctacagcggatggaatcgtagactcacagttgaggacatcgaagttgcac ctgaacatcgtggtcacggtgttggtcgtgcactgatgggactggcaacagagtttgctagagaaagaggagccggacatt tgtggttagaagtgaccaatgtcaacgctcctgctattcacgcatataggcgaatgggtttcactttgtgcggtcttgata ctgctttgtatgacggaactgcttctgatggtgaacaagctctttacatgagtatgccatgtccatagcacgtccgacggc ggcccacgggtcccaggcctcggagatccgtcccccttttccttgtcgatatcatgtaattagttatgtcacgcttacat tcacgccctccccccacatccgctctaaccgaaaaggaaggagttagacaacctgaagtctaggtccctatttattttttt atagttatgttagtattaagaacgttatttatatttcaaatttttcttttttttctgtacagacgcgcgtgtgacgcatgtaac attatactgaaaaccttgcttgagaaggttttgggacgctcgaaggctttaatttgcaagctataacttcgtatagcatac attataccttgttatgcggccgcaagaagttgattgagactttcaacgagctggctctgcttctggtacttcttcaggtgc atcttctgctactcaaaatgacgaaacatccactgatcttggagctccagctgcatctttaagtgcaacgccatgtctttt tgccatcttgctgctcatgttgtagtagacttttttttttcactgagttttatgtactactgattacattgtgtaggtgtaatgatgtgcactataatactaatatagtcaaaatgctacagaggaaagtgcaggttgcctgtggtggtttttcttattagc accctctgaacactctttacctctaacatcctcagccatgctaatcgcgcataaaatataaatcttcgaactttttttccattt tatgctcataaagcttccttactgtcaccttatcaaaagagcttttgccactaaagtagtcacacccagaattgctcccga atatcgtccaacaatgctaggatctgtggaaagtttgacaaataatttgaacaatattgttgagacctttcttgcagttcttttttttaacacatcggttctgtacaagttggtgatatctgatgctctggagagaggcgatgactttggtgcacttcctctaggaaagggacaaaaagtta tatccaaggctcctttccagaaagtaacccagtggaccttttgagaaactacatcactcaagaacttagtaaaaatttctgg agttgacaaagaattgattttcccagccttggaatggggtaccacactggaaaaaggtgatctttttgatcccagttcctcg tctgagaataaagggtgctaatcctaaagatttagccgaacaatgggctgctgcattcccaaagggtggatatcttaaaga cgttattgcgcaaggaccctttcttcgagttcttttttaacacatcggttctgtacaagttggtgatatctgatgctctgga gagaggcgatgactttggtgcacttcctctaggaaagggacaaaaagttatagtggagtttttcttctccaaatattgccaa acctttccacgctggccatcttagaagtacaatcatcggtggtttttatttccaatctgtatgaaaagctgggtcatgaagt tatgaggatgaattatttgggagactggggaaaacaattggttgttcttgcagtaggatttgagcgttacggtgatgaggc aaaattaaagactgatccaatcaacccatttgtttgaggtctatgttaaaatcaaccaaagtattaaggctcaatcagagtc tactgaggagattgcagaagggcaatcattagatgaccaggcaagagctctttttcaagaaaatggaaaatggcgacgaatc ggctgtaagcttgtggaaaagattccgtgagttatccattgagaagtacattgatacttatgcccgcctcaacatc |
| PAS_chr3_1157 Homology Arm 1 | 489 | gccttctcgtgcaatcagagctgttgaaagagagaagagggcacacggaagctgctgttcaattgtgtgaattgaccggat tacaacctgctggagtgataggagagctggttcgtgacgaggacggctctatgatgcgattagacgactgtgttcagtttg gtctccgccacaacgtaaaaattatcaaccttgaccagatcattgaatacatggattccaagaacagctagatacgatgga taggaatacagagatatcatgattgaggaacgtaagagcttttttcgaaagtgtgagtttgtggtgagggccaggcggtggg gaggtggtggggagcctccttggtcgaatgtagatatagtaagcaagacacaagagcgcgcgaagtcttcaacgaggcggc gttgggtcttgtacgcaacgtaatgactacacagttgagcttgtcgcgaaccggtcgacattttgatcatgcatactatgt tgagacaccatctcgtactattgcggcaaccagctgtaaatttgactaattaaagctgatgaaggatgcagggcgtcgtca atttttttgattgattgcatttaattgtttgagccattcaaggctgaatgcccggcaccctagaccccttcttgtgagtacta taaacccgcaggcagggtacccttggccttctgcgagactaccagtcataacgtatatccacaatgtactagtaatagccc cggaaaactctaatcccacagaacgtctaacgcctcctatgtcatcgataccccattcgcactactgccatggccccccttta cgtgatcatttcacttactcccgcctaagcttcgcccacatgcctgcgttttgccaagatttactgacgagtttggtttac tcatcctctatttataactactagactttcaccattcttcaccaccctcgtgccaatgatcatcaaccacttggtattgac agccctcagcattgcactagcaagtcgcgaactccaatcgcctttca |
| PAS_chr3_1157 Homology Arm 2 | 490 | ctggctctgcttctggtacttcttcaggtgcatcttctgctactcaaaatgacgaaacatccactgatcttggagctccag ctgcatctttaagtgcaacgccatgtctttttgccatcttgctgctcatgttgtagtagacttttttttttcactgagttttt tatgtactactgattacattgtgtaggtgtaatgatgtgcactataatactaatatagtcaaaatgctacagaggaaagtg caggttgcctgtggtggtttttcttattagcaccctctgaacactctttacctctaacatcctcagccatgctaatcgcgc ataaaatataaatcttcgaactttttttccatttttatgctcataaagcttccttactgtcaccttatcaaaagagcttttgcca ctaaagtagtcacacccagaattgctcccgaatatcgtccaacaatgctaggatctgtggaaagtttgacaaataatttga acacctgagcttgaagcttcctgaagttaatatccaaggctcctttccagaaagtaacccagtggaccttttgagaaact acatcactcaagaacttagtaaaaatttctggagttgacaaagaattgattttcccagccttggaatggggtaccacactgg aaaaaggtgatctttttgatcccagttcctcgtctgagaataaagggtgctaatcctaaagatttagccgaacaatgggct gctgcattcccaaagggtggatatcttaaagacgttattgcgcaaggaccctttcttcgagttcttttttaacacatcggttc tgtacaagttggtgatatctgatgctctggagagaggcgatgactttggtgcacttcctctaggaaagggacaaaaagtta tagtggagtttttcttctccaaatattgccaaacctttccacgctggccatcttagaagtacaatcatcggtggtttttatttt ccaatctgtatgaaaagctgggtcatgaagttatgaggatgaattatttgggagactggggaaaacaatttggtgttcttg |

TABLE 12-continued

Exemplary nourseothricin cassettes with HA arms for protease deletion in *P. pastoris*

| Description | SEQ ID NO: | 5' to 3' Sequence |
|---|---|---|
| | | cagtaggatttgagcgttacggtgatgaggcaaaattaaagactgatccaatcaaccatttgtttgaggtctatgttaaaa tcaaccaagatattaaggctcaatcagagtctactgaggagattgcagaagggcaatcattagatgaccaggcaagagctt ttttcaagaaaatggaaaatggcgacgaatcggctgtaagcttgtggaaaagattccgtgagttatccattgagaagtaca ttgatacttatgcccgcctcaacatc |
| Nourseothricin cassette with homology arms targeting PAS_chr1-4_0289 | 491 | gacgagacgctgttcctttcaacttgtccacttggactgacaagtcaacacctgttactaattcttttgtcatctctcagt atgaagacacgcgtgttcctcaatcagccaccagttctacacatccaaacatacctaaacacgccaaagagtatccgttag caaatgggccacctgggtggtgttggaattcccattccagtatgtcgacagaccaaccaatatatccaggacaccaatatc caccaccgcttcagcagcactaccactttgcttcacccaggcaactatcaaactctagctctgggacgtcatccgttcctt tccaaccacccccctgctggtcaattacaaccacaaggtaattctatgttcatacacatgccattttcgctaaatggcccac cagctgctggacagcaattgataccaccccaaggactagcctcaatacctgtcggcccggcaacaacagttccctattgg ttagccaaggtgcacctggcggctattctttagcttcaccagcgttgtcaccggtagatgcgacctcgaagatcccgtca agagactgcccaaaaagcggacaaaaactggatgtctcacttgccgtaagagacgaatcaaatgtgacgaacgcaagccgt tctgtttcaactgtgaaaaaagcaaaaaggtgtgtactggttttacgcatctattcaaagatcccctagcaaatcctacc ctcccagttcagatggtgcctcccctgttgccaatgaccaccctgtcccccaaggcaaaactttggtgaattgaggggca gtctgaattcatcatcaactagaagaatgcttattcctttctctactgtataatcacgacgttatgtcctttaatataa gaaacgacaattaaaccactttaggtggacataatccatttctggatgctgttcgatgtgtagtgtctaaaccgatactga gatttctctttctcttttctcttttttttttttttttcctaccatttccttcaagaaaatacacctttcgacagatcatcataa atggtggcctctcttctcacacttcagagtacagaagattaagtgagagaattctaccgttcgtatagcatacattatacgaa gttatttcagtaatgtcttgtttctttttgttgcagtggtgagccattttgacttcgtgaaagtttctttagaatagttgtt tccagaggccaaacattccacccgtagtaaagtgcaagcgtaggaagaccaagactggcataaatcaggtataagtgtcga gcactggcaggtgatcttctgaaagtttctactagcagataagatccagtagtcatgcatatggcaacaatgtaccgtgtg gatctaagaacgcgtcctactaaccttcgcattcgttggtccagtttgttgttatcgatcaacgtgacaaggttgtcgatt ccgcgtaagcatgcatacccaaggacgccctgttgcaattccaagtgagccagttccaacaatctttgtaatattagagcac ttcattgtgttgcgcttgaaagtaaaatgcgaacaaattaagagataatctcgaaaccgcgacttcaaacgccaatatgat gtgcggcacacaataagcgttcatatccgctgggtgactttctcgctttaaaaaattatccgaaaaaatttttgacggcta gctcagttcctaggtacgctagcattaaagaggagaaaatgactactcttgatgacacagcctacagatataggacatcagt tccgggtgacgcagaggctatcgaagccttggacggttcattcactactgatacggtgttagagtcacccgctacaggtga tggcttcaccttgagagaggttcctgtagacccacccttaacgaaagtttttccctgatgacgaatcggatgacgagtctga tgctggtgaggacggtgaccctgattccagaacattgtcgcatacggagatgatggtgacctggctggctttgttgtggt gtcctacagcggatggaatcgtagactcacagttgaggacatcgaagttgcacctgaacatcgtggtcacggtgttggtcg tgcactgatgggactggcaacagagtttgctagagaaaggagcccgacatttgtggttagaagtgaccaatgtcaacgc tcctgctattcacgcatataggcgaatgggtttcactttgtgcggtcttgatactgctttgtatgacggaactgcttctga tggtgaacaagctcttacatgagtatgccatgtccatagcacgtccgacggcggcccacgggtcccaggcctcggagatc cgtcccccttttcctttgtcgatatcatgtaattagttatgtcacgcttacattcacgccctccccccacatccgctcaa ccgaaaaggaaggagttagacaacctgaagtctaggtccctatttattttttttatagttatgttagtattaagaacgttat ttatatttcaaatttttcttttttttctgtacagacgcgtgtacgcatgtaacattatactgaaaaccttgcttgagaagg ttttgggacgctcgaaggctttaatttgcaagctataacttcgtatagcatacattataccttgttatgcggccgcaagaa gttgattgagactttcaacgagtgatcgactacttggcctccgccgtgaaaactcaattagatgttagctccaaattaatg aacctggtacaagatgataaataggaactcaaatacaaagcctaccattaatgactgtttttattttttatactaaagtagct aaagggtgattatcaaggagtggttaacgatctattcctagcagggcactcagctcatcgatctttccaatatcggcgtat aacgcttccacttctatcaacgtatcttcgttaaaaagaccacctctggtgggaactaatccttctgctgccgcctctgct aaactctgtcttcgaatccgtttctttcttactaacatcagcttcgacagataagccactcttcttttatctttttcttagatcct gttttgaatctcagggacttttactggtgccataacctcctgttccagtacctgttcttcttactctttttttggtatt aaagaatgtcccgccttgagtcctcgatcatccttggccatactcaatcgtctagtagtgctgttgaaatgctgtaaagaa gaggaatatcttcttaaatggttggtatctttttcagcaaccacacctttgtttcggaaagcggataatggcacattgctt ggattgatagaagaagctataaaagcccatcctgcgtttggagcagtttgattgctctgagttactatgttcaactgtgta ttggcaaaagccttagagtcggtcgtctgattcggcttatattgagtaaatcatccaggtccaatagaggaacagaaccagtc tgcttccctttggtttttgtacgatccctaattgcacccttcacagaaagttctacccgtttggactttatactgtctttg ttctctgatactgatcgcattgaaaacccatcaataatctcaaagggtttgccacagtccgaggtggtccaaattccaatc actggagggataggatccactttggaagatgccagaacttcttttgcaattttggtaccaatttttttattggatgtttttg ggaagagcttcatcttcatcagtggagttgctgcttcgttgtcatctacttttggtcatcttctagttcgtcgtcgtct gaagcaatagcatctgaggaggacgcatctccttcacctttgaaaaagtaattaaataggtaggagtcatcatcagaatct tgttcttggtctgatcccctttcgacggcagcttgaatgttgtt |
| PAS_chr1-4_0289 Homology Arm 1 | 492 | gacgagacgctgttcctttcaacttgtccacttggactgacaagtcaacacctgttactaattcttttgtcatctctcagt atgaagacacgcgtgttcctcaatcagccaccagttctacacatccaaacatacctaaacacgccaaagagtatccgttag caaatgggccacctgggtggtgttggaattcccattccagtatgtcgacagaccaaccaatatatccaggacaccaatatc caccaccgcttcagcagcactaccactttgcttcacccaggcaactatcaaactctagctctgggacgtcatccgttcctt tccaaccacccccctgctggtcaattacaaccacaaggtaattctatgttcatacacatgccattttcgctaaatggcccac cagctgctggacagcaattgataccaccccaaggactagcctcaatacctgtcggcccggcaacaacagttccctattgg ttagccaaggtgcacctggcggctattctttagcttcaccagcgttgtcaccggtagatgcgacctcgaagatcccgtca agagactgcccaaaaagcggacaaaaactggatgtctcacttgccgtaagagacgaatcaaatgtgacgaacgcaagccgt tctgtttcaactgtgaaaaaagcaaaaaggtgtgtactggttttacgcatctattcaaagatcccctagcaaatcctacc ctcccagttcagatggtgcctcccctgttgccaatgaccaccctgtcccccaaggcaaaactttggtgaattgaggggca gtctgaattcatcatcaactagaagaatgcttattcctttctctactgtataatcacgacgttatgtcctttaatataa gaaacgacaattaaaccactttaggtggacataatccatttctggatgctgttcgatgtgtagtgtctaaaccgatactga gatttctctttctcttttctcttttttttttttttttcctaccatttccttcaagaaaatacacctttcgacagatcatcataa atggtggcctctcttcaca |
| PAS_chr1-4_0289 Homology Arm 2 | 493 | tgatcgactacttggcctccgccgtgaaaactcaattagatgttagctccaaattaatgaacctggtacaagatgataaat aggaactcaaatacaaagcctaccattaatgactgtttttattttttatactaaagtagctaaagggtgattatcaaggagtg gttaacgatctattcctagcagggcactcagctcatcgatctttccaatatcggcgtataacgcttccacttctatcaacg tatcttcgttaaaaagaccacctctggtgggaactaatccttctgctgccgcctctgctaaactctgtcttcgaatccgtt |

TABLE 12-continued

| | | |
|---|---|---|
| | | Exemplary nourseothricin cassettes with HA arms for protease deletion in *P. pastoris* |
| Description | SEQ ID NO: | 5' to 3' Sequence |
| | | tcttactaacatcagcttcgacagataagccactcttctttatcttttttcttagatcctgttttgaatctcagggacttta ctggtgccataacaacttcctgttccagtaccttgttcttcttactctttttttggtattaaagaatgtcccgccttgagtc ctcgatcatccttggccatactcaatcgtctagtagtgctgttgaaatgctgtaaagaagaggaatatcttcttaaatggt tggtatcttttttcagcaaccacacctttgtttcggaaagcggataatggcacattgcttggattgatagaagaagctataa aagcccatcctgcgtttggagcagtttgattgctctgagttactatgttcaactgtgtattggcaaaagccttagagtcgc tgtctgattcgcttatattgagtaaatcatccaggtccaatagaggaacagaaccagtctgcttcccttttggttttgtac gatccctaattgcacccttcacagaaagttctacccgtttggactttatactgtctttgttctctgatactgatcgcattg aaaacccatcaataatctcaaagggtttgccacagtccgaggtggtccaaattccaatcactggagggataggatccactt tggaagatgccagaacttcttttgcaattttggtaccaatttttttattggatgtttgggaagagcttcatcttcatcag tggagttgctgctttcgttgtcatctacttttttggtcatcttctagttcgtcgtcgtctgaagcaatagcatctgaggagg acgcatctccttcacctttgaaaaagtaattaaataggtaggagtcatcatcagaatcttgttcttggtctgatccccttt cgacggcagcttgaatgttgtt |

The invention claimed is:

1. A *Pichia pastoris* microorganism, in which the activities of a YPS1-1 protease comprising a polypeptide sequence having at least 95% sequence identity to SEQ ID NO: 67, a YPS1-2 protease comprising a polypeptide sequence having at least 95% sequence identity to SEQ ID NO; 68 and a MKC7 protease comprising a polypeptide sequence having at least 95% sequence identity to the full-length polypeptide sequence encoded by SEQ ID NO: 7 have been attenuated or eliminated as compared to an otherwise identical *Pichia pastoris* microorganism whose YPS1-1, YPS1-2, and MKC7 protease activities have not been attenuated or eliminated, wherein each of said polypeptide sequences has a protease activity before said attenuation or elimination, and wherein said microorganism expresses a recombinant protein.

2. The microorganism of claim 1, wherein the polypeptide sequence of said YPS1-1 protease comprises SEQ ID NO: 67.

3. The microorganism of claim 1, wherein said YPS1-1 protease is encoded by a YPS1-1 gene comprising a polynucleotide sequence having at least 95% sequence identity to SEQ ID NO: 1.

4. The microorganism of claim 3, wherein said YPS1-1 gene comprises SEQ ID NO: 1.

5. The microorganism of claim 1, wherein the polypeptide sequence of said YPS1-2 protease comprises SEQ ID NO: 68.

6. The microorganism of claim 1, wherein said YPS1-2 protease is encoded by a YPS1-2 gene comprising a polynucleotide sequence having at least 95% sequence identity to SEQ ID NO: 2.

7. The microorganism of claim 6, wherein said YPS1-2 gene comprises SEQ ID NO: 2.

8. The microorganism of claim 1, wherein said MKC7 protease is encoded by a MKC7 gene comprising a polynucleotide sequence having at least 95% sequence identity to SEQ ID NO: 7.

9. The microorganism of claim 1, wherein said MKC7 gene comprises SEQ ID NO: 7.

10. The microorganism of claim 1, wherein said YPS1-1 protease is encoded by a YPS1-1 gene, wherein said YPS1-2 protease is encoded by a YPS1-2 gene, and wherein said MKC7 protease is encoded by a MKC7 gene, and wherein said YPS1-1 gene, said YPS1-2 gene, and said MKC7 gene have been mutated or knocked out.

11. The microorganism of claim 1, wherein said recombinant protein is a silk-like polypeptide comprising one or more repeat sequences {GGY-[GPG-X$_1$]$_{n1}$-GPS-(A)$_{n2}$}$_{n3}$, wherein $$X_1 = SGGQQ, \quad \text{(SEQ ID NO: 515)}$$

$$GAGQQ, \quad \text{(SEQ ID NO: 516)}$$

$$GQGPY, \quad \text{SEQ ID NO: 517)}$$

$$AGQQ, \quad \text{(SEQ ID NO: 518)}$$
$$or$$

$$SQ;$$

n1 is from 4 to 8;
n2 is from 6 to 20; and
n3 is from 2 to 20.

12. The microorganism of claim 11, wherein the polypeptide sequence of said silk-like polypeptide comprises SEQ ID NO: 463.

13. The microorganism of claim 1, wherein the activity of one or more additional proteases has been attenuated or eliminated as compared to an otherwise identical *Pichia pastoris* microorganism whose one or more additional protease activities has not been attenuated or eliminated.

14. The microorganism of claim 13, wherein the activity of one or more additional proteases comprises activity of a YPS1-5 protease.

15. The microorganism of claim 13, wherein the activity of one or more additional proteases comprises activity of a YPS1-3 protease.

16. An engineered *Pichia pastoris* microorganism comprising a mutation or deletion of a YPS1-1 gene comprising SEQ ID NO: 1 and encoding a YPS-1 protease, a mutation or deletion of a YPS1-2 gene comprising SEQ ID NO: 2 and encoding a YPS1-2 protease, and a mutation or deletion of a MKC7 gene comprising SEQ ID NO: 7 and encoding a MKC7 protease, wherein the activities of the YPS1-1 protease, the YPS1-2 protease, and the MKC7 protease of the engineered microorganism are reduced as compared to an otherwise identical *Pichia pastoris* microorganism whose YPS1-1, YPS1-2, and MKC7 genes have not been mutated or deleted, and wherein said microorganism further comprises a recombinantly expressed protein comprising the polypeptide sequence of SEQ ID NO: 463.

17. A cell culture comprising the microorganism of claim 1.

18. The cell culture of claim 17, wherein said recombinant protein is less degraded than a cell culture comprising an otherwise identical *Pichia pastoris* microorganism whose YPS1-1, YPS1-2, and MKC7 protease activities have not been attenuated or eliminated.

19. A method of producing a recombinant protein with a reduced degradation, comprising:

culturing the microorganism of claim 1 in a culture medium under conditions suitable for expression of the recombinant protein; and isolating the recombinant protein from the microorganism or the culture medium.

20. The method of claim 19, wherein said recombinant protein is secreted from said microorganism, and wherein isolating said recombinant protein comprises collecting a culture medium comprising said secreted recombinant protein.

21. The method of claim 19, wherein said recombinant protein has a decreased level of degradation as compared to said recombinant protein produced by an otherwise identical microorganism whose YPS1-1, YPS1-2, and MKC7 protease activities have not been attenuated or eliminated.

22. A method of making the *Pichia pastoris* of claim 1, comprising knocking out or mutating a gene encoding the YPS1-1 protease, knocking out or mutating a gene encoding the YPS1-2 protease, knocking out or mutating a gene encoding the MKC7 protease, and transformation with a polynucleotide encoding the recombinant protein.

23. The method of claim 22, wherein said recombinant protein comprises a polyA sequence comprising at least 2, 3, 4, 5, 6, 7, 8, 9, or 10 contiguous alanine residues (SEQ ID NO: 519).

24. The method of claim 22, wherein said recombinant protein comprises a silk-like polypeptide.

25. The method of claim 24, wherein said silk-like polypeptide comprises one or more repeat sequences {GGY-[GPG-$X_1$]$_{n1}$-GPS-(A)$_{n2}$}$_{n3}$, wherein $X_1$ = SGGQQ, (SEQ ID NO: 515)

GAGQQ, (SEQ ID NO: 516)

GQGPY, SEQ ID NO: 517)

AGQQ, (SEQ ID NO: 518)

or

SQ;

n1 is from 4 to 8;

n2 is from 6 to 20; and n3 is from 2 to 20.

26. The method of claim 22, wherein the polypeptide sequence of said recombinant protein comprises SEQ ID NO: 463.

27. A *Pichia pastoris* microorganism, in which the activities of a YPS1-1 protease comprising a polypeptide sequence having at least 95% sequence identity to SEQ ID NO: 67, a YPS1-2 protease comprising a polypeptide sequence having at least 95% sequence identity to SEQ ID NO 68, and a MKC7 protease comprising a polypeptide sequence having at least 95% sequence identity to the full-length polypeptide sequence encoded by SEQ ID NO: 7 have been attenuated or eliminated as compared to an otherwise identical *Pichia pastoris* microorganism whose YPS1-1, YPS1-2, and MKC7 protease activities have not been attenuated or eliminated, wherein each of said polypeptide sequences has a protease activity before said attenuation or elimination.

* * * * *